(12) United States Patent
Li et al.

(10) Patent No.: US 9,815,853 B2
(45) Date of Patent: Nov. 14, 2017

(54) BRIDGED BICYCLIC KALLIKREIN INHIBITORS

(71) Applicant: GLOBAL BLOOD THERAPEUTICS, INC., South San Francisco, CA (US)

(72) Inventors: Zhe Li, San Diego, CA (US); Manuel Zancanella, San Mateo, CA (US); Chul Yu, San Ramon, CA (US); Lina Setti, Fremont, CA (US); Hing Sham, Palo Alto, CA (US); Qing Xu, Foster City, CA (US); Calvin Yee, Daly City, CA (US); Ming Yu, Foster City, CA (US)

(73) Assignee: Global Blood Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 15/177,641

(22) Filed: Jun. 9, 2016

(65) Prior Publication Data

US 2016/0362427 A1    Dec. 15, 2016

Related U.S. Application Data

(60) Provisional application No. 62/174,769, filed on Jun. 12, 2015, provisional application No. 62/277,387, filed on Jan. 11, 2016.

(51) Int. Cl.

| | | |
|---|---|---|
| *C07D 519/00* | (2006.01) | |
| *C07D 405/12* | (2006.01) | |
| *C07D 307/81* | (2006.01) | |
| *C07D 491/18* | (2006.01) | |
| *C07D 401/12* | (2006.01) | |
| *C07D 493/08* | (2006.01) | |
| *C07D 213/73* | (2006.01) | |
| *C07B 59/00* | (2006.01) | |
| *C07D 487/08* | (2006.01) | |
| *C07D 471/08* | (2006.01) | |

(52) U.S. Cl.
CPC .......... *C07D 519/00* (2013.01); *C07B 59/002* (2013.01); *C07D 213/73* (2013.01); *C07D 307/81* (2013.01); *C07D 401/12* (2013.01); *C07D 405/12* (2013.01); *C07D 471/08* (2013.01); *C07D 487/08* (2013.01); *C07D 491/18* (2013.01); *C07D 493/08* (2013.01); *C07B 2200/05* (2013.01)

(58) Field of Classification Search
CPC .. C07D 519/00; C07D 405/12; C07D 307/81; C07D 491/18; C07D 401/12
USPC ...................................... 546/284.1
See application file for complete search history.

(56) References Cited

FOREIGN PATENT DOCUMENTS

| | | |
|---|---|---|
| WO | WO 2005/057171 | 6/2005 |
| WO | WO 2007/070818 | 6/2007 |
| WO | WO 2014/153037 | 9/2014 |
| WO | WO 2014/206954 | 12/2014 |
| WO | WO 2015/022546 | 2/2015 |

OTHER PUBLICATIONS

Barluenga et al., Organic Letters (2008), 10(4), 677-679.*
Kitamura et al., "Efficient generation and trapping of acylbenzynes from hypervalent iodine compounds" Tet. Lett. (2006) 47(11):1709-1712.
International Search Report and Written Opinion mailed Oct. 20, 2016 for PCT Application No. PCT/US2016/036610, filed Jun. 9, 2016.
Clermont et al, "Effects of Plasma Kallikrein on Retinal Vascular Functions in Diabetes" Abstract 5035-0883, ARVO 2010, Fort Lauderdale, Florida.
Fieser, M., Fieser and Fieser's Reagents for Organic Synthesis, vols. 1-17 (1991) ** Ed., John Wiley & Sons, New York, New York, Cover and Table of Contents.
Gennaro, AR., Remington's Pharmaceutical Sciences, (1985) 17th Ed., Mack Publishing Co., Easton, PA, Cover and Table of Contents.
Gennaro, AR., Remington's Pharmaceutical Sciences, (2013) 22nd Ed., Mack Publishing Co., Easton, PA, Cover and Table of Contents.
Greene, et al., Protective Groups in Organic Synthesis, (1999) 3rd. Ed., John Wiley & Sons, Cover and Table of Contents.
Larock, R.C., Comprehensive Organic Transformations (1989) 2nd Ed., VCH Publishers, New York, NY, Cover and Table of Contents.
March, J., Advanced Organic Chemistry (1992) 4th Ed., John Wiley and Sons, New York, New York, Cover and Table of Contents.
Nzeako et al., "Hereditary Angioedema, A Broad Review for Clinicians" Arch Intern Med., (2001) 161(20): 2417-2429 and 2406.
Phipps et al, "Plasma Kallikrein Mediates Angiotensin II Type 1 Receptor—Stimulated Retinal Vascular Permeability" Hypertension (2009) 53(2):175-181.
Sainsbury et al., Rodd's Chemistry of Carbon Compounds vols. 1-5 and Supplementals (1989) 2nd Ed., Elsevier Science & Technology, Oxford, United Kingdom, Cover and Table of Contents.
Spicer et al., "Inhibition of the pore-forming protein perforin by a series of aryl-substituted isobenzofuran-1(3H)-ones" Bioorg. Med. Chem., (2012) 20(3):1319-1336.
Storoni et. al., "Selective Inhibition of Plasma Kallikrein Protects Brain from Reperfusion Injury" JPET (2006) 318(2), 849-954.

* cited by examiner

*Primary Examiner* — Niloofar Rahmani
(74) *Attorney, Agent, or Firm* — Knobbe, Martens, Olson & Bear, LLP

(57) ABSTRACT

Provided herein are kallikrein modulating compounds, pharmaceutical compositions comprising the same, and uses thereof.

16 Claims, No Drawings

BRIDGED BICYCLIC KALLIKREIN INHIBITORS

FIELD

This application relates generally to kallikrein modulating compounds, pharmaceutical compositions comprising the same, and uses thereof.

BACKGROUND

Plasma prekallikrein (PK) is a serine protease zymogen in blood that is converted to its catalytically active form, plasma kallikrein (PK), by coagulation factor XIIa, and contributes to the innate inflammatory response and intrinsic cascade of blood coagulation. The mechanisms that lead to the activation of this pathway in vivo include interactions with poly-phosphates released from activated platelets and deficiency of C1 inhibitor (C1-INH), the primary physiological inhibitor of plasma kallikrein. PK-mediated cleavage of high-molecular weight kininogen generates the nonapeptide bradykinin (BK), which activates the bradykinin 2 receptor. Subsequent cleavage of BK by carboxypeptidases generates des-Arg9-BK, which activates the B1 receptor. Both B1 and B2 receptors are expressed by vascular, glial, and neuronal cell types, with the highest levels of retinal expression detected in the ganglion cell layer and inner and outer nuclear layers. Activation of B1 and B2 receptors causes vasodilation and increases vascular permeability. Bradykinin and its binding to B2 receptor are reportedly responsible for many symptoms of hereditary angioedema (HAE).

Kallikrein is also associated with Hereditary Angioedema (HAE), an autosomal dominant disease characterized by painful, unpredictable, recurrent attacks of inflammation affecting the hands, feet, face, abdomen, urogenital tract, and the larynx. Prevalence for HAE is uncertain but is estimated to be approximately 1 case per 50,000 persons without known differences among ethnic groups. HAE is caused by deficient (Type I) or dysfunctional (Type II) levels of C1-Inhibitor (C1-INH), a naturally occurring molecule that is known to inhibit kallikrein, bradykinin, and other serine proteases in the blood. If left untreated, HAE can result in a mortality rate as high as 40% primarily due to upper airway obstruction.

SUMMARY

In a first aspect, provided is a compound of formula (I):

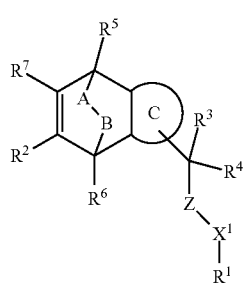

(I)

wherein:
one of A and B is a bond, O, CO, $S(O)_p$, $NCOR^b$, $NCONHR^c$, $NSO_2R^d$, or $CR^8R^9$, and the other of A and B is a bond, $NR^a$, or $CR^{10}R^{11}$, wherein p is 0, 1, or 2, $R^a$ is hydrogen, $C_1$-$C_6$alkyl, $C_1$-$C_6$alkoxy, hydroxy, or $C_3$-$C_6$cycloalkyl, $R^b$, $R^c$ and $R^d$ are independently $C_1$-$C_6$alkyl, $C_1$-$C_6$alkoxy, $C_3$-$C_6$cycloalkyl, mono or bicyclic heteroaryl, monocyclic heterocyclyl, or mono or bicyclic aryl (wherein the aforementioned mono or bicyclic aryl, mono or bicyclic heteroaryl, and monocyclic heterocyclyl are optionally substituted with one, two, or three substituents independently selected from $C_1$-$C_6$alkyl, $C_1$-$C_6$alkoxy, hydroxy, halo, halo$C_1$-$C_6$alkyl, halo$C_1$-$C_6$alkoxy, and cyano), and $R^8$, $R^9$, $R^{10}$ and $R^{11}$ are independently hydrogen, OH, $C_1$-$C_6$alkoxy, $C_1$-$C_6$alkyl, or $C_3$-$C_6$cycloalkyl, and provided that A and B are not each a bond or each a heteroatom simultaneously;

ring C is phenyl, monocyclic heteroaryl, monocyclic heterocyclyl, or $C_5$-$C_6$cycloalkyl, wherein ring C, in addition to —$CR^3R^4$—Z—$X^1$—$R^1$, is optionally substituted with one or two substituents independently selected from $C_1$-$C_6$alkyl, $C_1$-$C_6$alkoxy, hydroxy, halo, halo$C_1$-$C_6$alkyl, halo$C_1$-$C_6$alkoxy, amino, $C_1$-$C_6$alkylamino, di$C_1$-$C_6$alkylamino, and cyano;

$R^3$ and $R^4$ are independently hydrogen, fluoro, or $C_1$-$C_6$alkyl; or $R^3$ and $R^4$ together with the carbon they are attached form C=O, C=$NR^{12}$ (wherein $R^{12}$ is hydrogen, $C_1$-$C_6$alkyl, $C_1$-$C_6$alkoxy, or hydroxy), or $C_3$-$C_6$cycloalkyl, provided that when $R^3$ and $R^4$ together form C=$NR^{12}$, then Z is $NR^{13}$;

Z is a bond, $NR^{13}$, or $CR^{14}R^{15}$ wherein $R^{13}$, $R^{14}$, and $R^{15}$ are independently hydrogen or $C_1$-$C_6$alkyl;

$X^1$ is bond, —C=$NR^8$, $CR^{16}R^{17}$, O, or $S(O)_q$, wherein q is 0, 1, or 2, $R^8$ is as defined above, and $R^{16}$ and $R^{17}$ are independently hydrogen, deuterium, or $C_1$-$C_6$alkyl, or $R^{16}$ and $R^{17}$ together with the carbon atom they are attached form $C_3$-$C_6$cycloalkyl, C=NH, or C=O, provided that when $R^3$ and $R^4$ together form C=O, then $X^1$ is not O;

$R^1$ is mono or bicyclic aryl, mono or bicyclic heteroaryl, $C_3$-$C_6$cycloalkyl, monocyclic heterocyclyl, or fused heterocyclyl, wherein each of the aforementioned ring(s) is optionally substituted with $R^e$, $R^f$ or $R^g$ independently selected from $C_1$-$C_6$alkyl, $C_2$-$C_6$alkenyl, $C_3$-$C_6$cycloalkyl, $C_1$-$C_6$alkoxy, hydroxy, halo, halo$C_1$-$C_6$alkyl, halo$C_1$-$C_6$alkoxy, amino, $C_1$-$C_6$alkylamino, di$C_1$-$C_6$alkylamino, amino$C_1$-$C_6$alkyl, aminocarbonyl, amidino$C_1$-$C_6$alkyl, —C(=$NR^h$)$NHR^i$ (wherein $R^h$ and $R^i$ are independently hydrogen, hydroxy, $C_1$-$C_6$alkoxy, benzyloxy, acyl, —C(O)O$C_1$-$C_6$alkyl, a natural or an unnatural amino acid residue, a dipeptidic residue, —CO(ethylene)$SO_2R^u$ (wherein $R^u$ is $C_1$-$C_6$alkyl, optionally substituted monocyclic heteroaryl, optionally substituted phenyl, or optionally substituted monocyclic heterocyclyl), or —$CO(CH_2)_{2-3}OR^v$ (wherein $R^v$ is hydrogen, $C_1$-$C_6$alkoxy$C_{1-3}$alkyl, or optionally substituted monocyclic heterocyclyl)), cyano, monocyclic heteroaryl (wherein the monocyclic heteroaryl is optionally substituted with one, two or three substituents independently selected from $C_1$-$C_6$alkyl, $C_3$-$C_6$cycloalkyl, $C_1$-$C_6$alkoxy, hydroxy, halo, halo$C_1$-$C_6$alkyl, halo$C_1$-$C_6$alkoxy, amino, $C_1$-$C_6$alkylamino, di$C_1$-$C_6$alkylamino, and cyano) and monocyclic heterocyclyl (wherein the monocyclic heterocyclyl is optionally substituted with one, two or three substituents independently selected from $C_1$-$C_6$alkyl, $C_3$-$C_6$cycloalkyl, $C_1$-$C_6$alkoxy, hydroxy, halo, halo$C_1$-$C_6$alkyl, halo$C_1$-$C_6$alkoxy, amino, $C_1$-$C_6$alkylamino, and di$C_1$-$C_6$alkylamino);

$R^5$ and $R^6$ independently are hydrogen, $C_1$-$C_6$alkyl, $C_3$-$C_6$cycloalkyl, halo, hydroxy, carboxy, $C_1$-$C_6$alkoxycarbonyl, or $C_1$-$C_6$alkoxy;

$R^2$ and $R^7$ are independently hydrogen, halo, $C_1$-$C_6$alkyl, halo$C_1$-$C_6$alkyl, halo$C_1$-$C_6$alkoxy, hydroxy$C_1$-$C_6$alkyl, $C_1$-$C_6$alkoxy$C_1$-$C_6$alkyl, $C_3$-$C_6$cycloalkyl, mono or bicyclic aryl, mono or bicyclic heteroaryl, monocyclic heterocyclyl, fused heterocyclyl, mono or bicyclic aryl$C_1$-$C_6$alkyl, mono or bicyclic heteroaryl$C_1$-$C_6$alkyl, monocyclic heterocyclyl$C_1$-$C_6$alkyl (wherein the alkylene chain in mono or bicyclic aryl$C_1$-$C_6$alkyl, mono or bicyclic heteroaryl$C_1$-$C_6$alkyl, or monocyclic heterocyclyl$C_1$-$C_6$alkyl is optionally substituted with deuterium), spiroheterocycloamino, bridged heterocycloamino, —$NR^{18}R^{19}$, —$OR^{20}$, —$CHFR^{21}$, —$CF_2R^{22}$, $SR^{23}$, $SOR^{24}$, $SO_2R^{25}$, —$C(=O)R^{26}$, —$C(=O)NR^{27}R^{28}$, or —$NR^{18}C(=O)R^{29}$ wherein $R^{18}$, $R^{19}$, $R^{20}$, $R^{21}$, $R^{22}$, $R^{23}$, $R^{24}$, $R^{25}$, $R^{26}$, $R^{27}$, $R^{28}$, and $R^{29}$ are independently hydrogen, $C_1$-$C_6$alkyl, $C_3$-$C_6$cycloalkyl, $C_3$-$C_6$cycloalkyl$C_1$-$C_6$alkyl, mono or bicyclic aryl, mono or bicyclic heteroaryl, or monocyclic heterocyclyl; or $R^{18}$ and $R^{19}$ or $R^{27}$ and $R^{28}$ together with the nitrogen atom they are attached form heterocycloamino or mono or bicyclic heteroaryl, and wherein each of the aforementioned ring in $R^2$ and $R^7$, by itself or as part of another group, is optionally substituted with $R^j$, $R^k$ or $R^l$ independently selected from $C_1$-$C_6$alkyl, $C_2$-$C_6$alkenyl, $C_3$-$C_6$cycloalkyl, $C_1$-$C_6$alkoxy, hydroxy, halo, halo$C_1$-$C_6$alkyl, halo$C_1$-$C_6$alkoxy, $C_1$-$C_6$alkylthio, $C_1$-$C_6$alkylsulfonyl, amino, $C_1$-$C_6$alkylamino, di$C_1$-$C_6$alkylamino, amino$C_1$-$C_6$alkyl, cyano, monocyclic heteroaryl (wherein the monocyclic heteroaryl is optionally substituted with one, two or three substituents independently selected from $C_1$-$C_6$alkyl, $C_3$-$C_6$cycloalkyl, $C_1$-$C_6$alkoxy, hydroxy, halo, halo$C_1$-$C_6$alkyl, halo$C_1$-$C_6$alkoxy, amino, $C_1$-$C_6$alkylamino, di$C_1$-$C_6$alkylamino, and cyano) and monocyclic heterocyclyl (wherein the monocyclic heterocyclyl is optionally substituted with one, two or three substituents independently selected from $C_1$-$C_6$alkyl, $C_3$-$C_6$cycloalkyl, $C_1$-$C_6$alkoxy, hydroxy, halo, halo$C_1$-$C_6$alkyl, halo$C_1$-$C_6$alkoxy, amino, $C_1$-$C_6$alkylamino, and di$C_1$-$C_6$alkylamino); or $R^2$ and $R^7$ together with the atom to which each is attached form ring D:

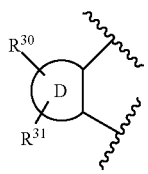

wherein ring D is phenyl, mono or bicyclic heteroaryl, monocyclic heterocyclyl, fused heterocyclyl, or $C_5$-$C_6$cycloalkyl; and $R^{30}$ and $R^{31}$ are independently hydrogen, halo, $C_1$-$C_6$alkyl, halo$C_1$-$C_6$alkyl, halo$C_1$-$C_6$alkoxy, cyano, hydroxy$C_1$-$C_6$alkyl, $C_1$-$C_6$alkoxy$C_1$-$C_6$alkyl, $C_3$-$C_6$cycloalkyl, mono or bicyclic aryl, mono or bicyclic heteroaryl, monocyclic heterocyclyl, fused heterocyclyl, mono or bicyclic aryl$C_1$-$C_6$alkyl, mono or bicyclic heteroaryl$C_1$-$C_6$alkyl, monocyclic heterocyclyl$C_1$-$C_6$alkyl (wherein the alkylene chain in mono or bicyclic aryl$C_1$-$C_6$alkyl, mono or bicyclic heteroaryl$C_1$-$C_6$alkyl, or monocyclic heterocyclyl$C_1$-$C_6$alkyl is optionally substituted with deuterium), spiro heterocycloamino, bridged heterocycloamino, —$NR^{32}R^{33}$, —$OR^{34}$, —$CHFR^{35}$, —$CF_2R^{36}$, $SR^{37}$, $SOR^{38}$, $SO_2R^{39}$, —$C(=O)R^{40}$, —$C(=O)NR^{41}R^{42}$, or —$NR^{43}C(=O)R^{44}$ wherein $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, and $R^{44}$ are independently hydrogen, $C_1$-$C_6$alkyl, mono or bicyclic aryl, mono or bicyclic heteroaryl, or monocyclic heterocyclyl, or $R^{32}$ and $R^{33}$ or $R^{41}$ and $R^{42}$ together with the nitrogen atom they are attached form heterocycloamino or mono or bicyclic heteroaryl, and wherein each of the aforementioned ring in $R^{30}$ and $R^{31}$, whether by itself or part of another group, is optionally substituted with $R^m$, $R^n$ or $R^o$ independently selected from $C_1$-$C_6$alkyl, $C_2$-$C_6$alkenyl, $C_3$-$C_6$cycloalkyl, $C_3$-$C_6$cycloalkyoxy, $C_3$-$C_6$cycloalkyl$C_{1-6}$alkoxy, $C_1$-$C_6$alkoxy, hydroxy, halo, halo$C_1$-$C_6$alkyl, halo$C_1$-$C_6$alkoxy, $C_1$-$C_6$alkylthio, $C_1$-$C_6$alkylsulfonyl, amino, $C_1$-$C_6$alkylamino, di$C_1$-$C_6$alkylamino, aminocarbonyl, acyl, amino$C_1$-$C_6$alkyl, cyano, monocyclic heteroaryl (wherein the monocyclic heteroaryl is optionally substituted with one, two or three substituents independently selected from $C_1$-$C_6$alkyl, $C_3$-$C_6$cycloalkyl, $C_1$-$C_6$alkoxy, hydroxy, halo, halo$C_1$-$C_6$alkyl, halo$C_1$-$C_6$alkoxy, amino, $C_1$-$C_6$alkylamino, di$C_1$-$C_6$alkylamino, and cyano) and monocyclic heterocyclyl (wherein the monocyclic heterocyclyl is optionally substituted with one, two or three substituents independently selected from $C_1$-$C_6$alkyl, $C_3$-$C_6$cycloalkyl, $C_1$-$C_6$alkoxy, hydroxy, halo, halo$C_1$-$C_6$alkyl, halo$C_1$-$C_6$alkoxy, amino, $C_1$-$C_6$alkylamino, and di$C_1$-$C_6$alkylamino); or a pharmaceutically acceptable salt thereof.

Also provided are compounds of Formula (I) where $R^h$ and $R^i$ in —$C(=NR^h)NHR^i$ in group $R^1$ can also be —OC(O)R where R is $C_1$-$C_6$alkyl or amino$C_1$-$C_6$alkyl as defined herein.

Definitions for Compound of Formula (I):

For compounds of Formula (I) and embodiments (a)-(pp) (see Embodiment D below) thereof disclosed herein, the following terms used in the specification and the claims are defined for the purposes of this Application and have the following meaning unless stated otherwise. If not defined, all technical and scientific terms used herein have the same meaning as commonly understood by one of ordinary skill in the art to which this application belongs.

As used herein, $C_m$-$C_n$, such as $C_1$-$C_6$, $C_1$-$C_4$ etc., when used before a group refers to that group containing m to n carbon atoms.

"$C_1$-$C_6$alkyl" means a linear saturated monovalent hydrocarbon radical of one to six carbon atoms or a branched saturated monovalent hydrocarbon radical of three to six carbon atoms, e.g., methyl, ethyl, n-propyl, 2-propyl, n-butyl, iso-butyl, t-butyl, pentyl (linear and branched), and the like.

"Alkylene" means a linear saturated divalent hydrocarbon radical of one to six carbon atoms or a branched saturated divalent hydrocarbon radical of three to six carbon atoms unless otherwise stated e.g., methylene, ethylene, propylene, 1-methylpropylene, 2-methylpropylene, butylene, pentylene, and the like.

"$C_1$-$C_6$alkenyl" means a linear monovalent hydrocarbon radical of two to six carbon atoms or a branched monovalent hydrocarbon radical of three to six carbon atoms containing a double bond, e.g., propenyl, butenyl, and the like.

"$C_1$-$C_6$alkylthio" means a —SR radical where R is $C_1$-$C_6$alkyl as defined above, e.g., methylthio, ethylthio, and the like.

"$C_1$-$C_6$lkylsulfonyl" means a —$SO_2R$ radical where R is $C_1$-$C_6$alkyl as defined above, e.g., methylsulfonyl, ethylsulfonyl, and the like.

"Amino" means a —$NH_2$.

"$C_1$-$C_6$alkylamino" means a —NHR radical where R is $C_1$-$C_6$alkyl as defined above, e.g., methylamino, ethylamino, propylamino, or 2-propylamino, and the like.

"AminoC$_1$-C$_6$alkyl" means a linear monovalent hydrocarbon radical of one to six carbon atoms or a branched monovalent hydrocarbon radical of three to six carbons substituted with —NR'R" where R' and R" are independently hydrogen or C$_1$-C$_6$alkyl as defined above, e.g., aminomethyl, aminoethyl, methylaminomethyl, and the like.

"Aminocarbonyl" means a —CONRR' group where R and R' are independently hydrogen or C$_{1-6}$alkyl defined herein.

"AmidinoC$_1$-C$_6$alkyl" means a linear monovalent hydrocarbon radical of one to six carbon atoms or a branched monovalent hydrocarbon radical of three to six carbons substituted with —C(=NR')NR"R'" where R, R", and R'" are independently hydrogen, hydroxy, C$_1$-C$_6$alkoxy, acyl, —C(O)OC$_1$-C$_6$alkyl, a natural or an unnatural amino acid residue, or a dipeptidic residue, or R' and R" together with the nitrogen atom to which they are attached may join together to form a 5 to 6 membered ring optionally containing one or two heteroatoms independently selected from N (nitrogen), O (oxygen), and S(O), where n is an integer from 0 to 2, and additionally, one or two ring carbon atoms in the ring can optionally be replaced by a —CO group, and wherein each aforementioned term is as defined herein.

"C$_1$-C$_6$alkoxy" means a —OR radical where R is C$_1$-C$_6$alkyl as defined above, e.g., methoxy, ethoxy, propoxy, or 2-propoxy, n-, iso-, or tert-butoxy, and the like.

"C$_1$-C$_6$alkoxyC$_1$-C$_6$alkyl" means a linear monovalent hydrocarbon radical of one to six carbon atoms or a branched monovalent hydrocarbon radical of three to six carbons substituted with at least one alkoxy group, such as one or two alkoxy groups, as defined above, e.g., 2-methoxyethyl, 1-, 2-, or 3-methoxypropyl, 2-ethoxyethyl, and the like.

"C$_1$-C$_6$alkoxycarbonyl" means a —C(O)OR radical where R is C$_1$-C$_6$alkyl as defined above, e.g., methoxycarbonyl, ethoxycarbonyl, and the like.

"Acyl" means a —C(O)R radical where R is C$_1$-C$_6$alkyl, C$_3$-C$_6$cycloalkyl, monocyclic heterocyclyl, monocyclic heteroaryl, or phenyl and unless stated otherwise, each ring may be optionally substituted with halo, cyano, haloC$_1$-C$_6$alkyl, haloC$_1$-C$_6$alkoxy, carboxy, C$_1$-C$_6$alkoxycarbonyl, as defined herein. Examples of acyl groups include methylcarbonyl, ethylcarbonyl, and the like.

"Bicyclic aryl" means naphthyl.

"Bicyclic arylC$_1$-C$_6$alkyl" means a -(alkylene)-R radical where R is naphthyl and alkylene is as defined herein. Examples of bicyclic arylC$_1$-C$_6$alkyl include naphthylmethyl and the like.

"Bicyclic heteroaryl" means a monovalent bicyclic aromatic radical of 9 or 10 ring atoms, unless otherwise stated, where one or more, (in one embodiments, one, two, three, or four), ring atoms are heteroatom selected from N, N-oxide, O, and S, the remaining ring atoms being carbon. Representative examples include, but are not limited to, indolyl, isoindolyl, benzothiazolyl, benzoxazolyl, quinolinyl, isoquinolinyl, pyrrolopyrimidine, azaindolyl, and the like.

"Bicyclic heteroarylC$_1$-C$_6$alkyl" means a -(alkylene)-R radical where R is bicyclic heteroaryl and where alkylene and bicyclic heteroaryl are as defined herein. Examples of bicyclic heteroarylC$_1$-C$_6$alkyl include benzofuranylmethyl, indolylmethyl, and the like.

"Bridged heterocycloamino" means a saturated or unsaturated bicyclic ring (provided that when the bicyclic ring includes unsaturated bonds, a fully delocalized pi-electron system does not occur throughout all the rings) having 7 to 10 ring atoms with two or more atoms in common and in which one, two, or three ring atoms are heteroatom selected from N, N-oxide, O, and S(O)$_n$, where n is an integer from 0 to 2, the remaining ring atoms being carbon, and provided at least one ring atom is N. Examples of bridged heterocycloamino include octahydropyrrolo[3,4-c]pyrrolyl, 2-azabicyclo[2.2.1]-heptanyl, 7-azabicyclo[4.2.0]octane, octahydro-1H-pyrrolo[3,4-c]pyridine, or decahydro-2,6-naphthyridine, and the like.

"C$_3$-C$_8$cycloalkyl" means a cyclic saturated monovalent hydrocarbon radical of three to eight carbon atoms, e.g., cyclopropyl, cyclobutyl, cyclopentyl, or cyclohexyl, and the like.

"C$_3$-C$_8$cycloalkyloxy" means a —OR radical where R is C$_3$-C$_8$cycloalkyl as defined above, e.g., cyclopropyloxy, cyclobutyloxy, cyclopentyloxy, or cyclohexyloxy, and the like.

"C$_3$-C$_6$cycloalkylC$_1$-C$_6$alkyl" means a -(alkylene)-R radical where R is cycloalkyl, and cycloalkyl and alkylene are as defined above, e.g., cyclopropylmethyl, cyclohexylmethyl, and the like.

"C$_3$-C$_6$cycloalkylC$_1$-C$_6$alkyloxy" means a —(O)—R radical where R is C$_3$-C$_6$cycloalkylC$_1$-C$_6$alkyl as defined above, e.g., cyclopropylmethyloxy, cyclohexylmethyloxy, and the like. "Carboxy" means —COOH.

"DiC$_1$-C$_6$alkylamino" means a —NRR' radical where R and R' are C$_1$-C$_6$alkyl as defined herein, e.g., dimethylamino, methylethylamino, and the like.

"Dipeptidic residue" means a group of formula —C(O)CH(R)NHCOCH(R')NH$_2$ or —O—C(O)CH(R)NHCOCH(R')NH$_2$ where R and R' are independently the side chain of a natural amino acid, such as valine, glycine, leucine, isoleucine, phenylalanine, alanine, tyrosine, lysine, threonine, glutamic acid, aspartic acid, methionine, serine, methionine, lysine, tryptophan, asparagine, arginine, histidine, cysteine, and glutamine. For example, the side chain R for valine is —CH(CH$_3$)$_2$), and for glycine is H.

"Fused heterocyclyl" means a monocyclic heterocyclyl as defined herein that is fused to a monocyclic aryl, a monocyclic heteroaryl, or C$_3$-C$_6$cycloalkyl each as defined herein. The fused heterocyclyl can be attached to the rest of the molecule at any of the ring atoms e.g., tetrahydrobenzofuranyl, tetrahydroindolyl, isoindol-5-yl, 2,3-dihydrobenzo[b][1,4]dioxine, and the like.

"Halo" means fluoro, chloro, bromo, or iodo, preferably fluoro or chloro.

"HaloC$_1$-C$_6$alkyl" means C$_1$-C$_6$alkyl radical as defined above, which is substituted with one or more halogen atoms, such as one to five halogen atoms, such as fluorine or chlorine, including those substituted with different halogens, e.g., —CH$_2$Cl, —CF$_3$, —CHF$_2$, —CH$_2$CF$_3$, —CF$_2$CF$_3$, —CF(CH$_3$)$_2$, and the like. When the alkyl is substituted with only fluoro, it can be referred to in this application as fluoroalkyl.

"HaloC$_1$-C$_6$alkoxy" means a —OR radical where R is haloC$_1$-C$_6$alkyl as defined above e.g., —OCF$_3$, —OCHF$_2$, and the like. When R is haloalkyl where the alkyl is substituted with only fluoro, it is referred to in this application as fluoroalkoxy.

"HydroxyC$_1$-C$_6$alkyl" means a linear monovalent, saturated hydrocarbon radical of one to six carbon atoms or a branched saturated monovalent hydrocarbon radical of three to six carbons substituted with one or two hydroxy groups, provided that if two hydroxy groups are present they are not both on the same carbon atom. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-

2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

"Heterocycloamino" means a saturated or unsaturated monovalent monocyclic group of 4 to 8 ring atoms in which one or two ring atoms are heteroatom selected from N, N-oxide, O, and $S(O)_n$, where n is an integer from 0 to 2, the remaining ring atoms being C, and provided that at least one of the ring atoms is N. When the ring is unsaturated, a fully delocalized pi-electron system does not occur in the ring. Additionally, one or two ring carbon atoms in the heterocycloamino ring can optionally be replaced by a —CO group. Unless otherwise stated, the heterocycloamino ring can optionally be substituted with one, two, or three substituents independently selected from $C_1$-$C_6$alkyl, hydroxy, $C_1$-$C_6$alkoxy, amino, $C_1$-$C_6$alkylamino, and di$C_1$-$C_6$alkylamino.

"Natural amino acid residue" means a group of formula —C(O)CHRNH$_2$ or —OCOCHR—NH$_2$ where R is the side chain of a natural amino acid, such as valine, glycine, leucine, isoleucine, phenylalanine, alanine, tyrosine, lysine, threonine, glutamic acid, aspartic acid, methionine, serine, lysine, tryptophan, asparagine, arginine, histidine, cysteine, and glutamine.

"Mono or monocyclic heteroaryl" means a monovalent aromatic radical of 5 or 6 ring atoms, unless otherwise stated, where one or more, (in one embodiment, one, two, three, or four), ring atoms are heteroatom selected from N, N-oxide, O, and S, and the remaining ring atoms being carbon. Representative examples include, but are not limited to, pyrrolyl, thienyl, thiazolyl, imidazolyl, furanyl, oxazolyl, isoxazolyl, pyridinyl, pyrimidinyl, pyrazinyl, pyridazinyl, triazolyl, tetrazolyl, and the like.

"Monocyclic heteroaryl$C_1$-$C_6$alkyl" means a -(alkylene)-R radical where R is monocyclic heteroaryl, and alkylene and monocyclic heteroaryl are as defined herein. Examples of monocyclic heteroaryl$C_1$-$C_6$alkyl include pyridinylmethyl, furanmethyl, pyrazolylmethyl, and the like.

"Monocyclic aryl" means phenyl.

"Monocyclic aryl$C_1$-$C_6$alkyl" means a -(alkylene)-phenyl where alkylene is as defined herein. Examples of monocyclic aryl$C_1$-$C_6$alkyl include benzyl, phenethyl, and the like.

"Monocyclic heterocyclyl" means a saturated or unsaturated monovalent monocyclic group of 4 to 8 ring atoms in which one three ring atoms are heteroatom selected from N, N-oxide, O, and $S(O)_n$, where n is an integer from 0 to 2, the remaining ring atoms being C, and provided that when the ring is unsaturated, the ring is not aromatic. Additionally, one or two ring carbon atoms in the heterocyclyl ring can optionally be replaced by a —CO group. Examples of heterocyclyls include rings such as pyrrolidino, piperidino, homopiperidino, 2-oxopyrrolidinyl, 2-oxopiperidinyl, morpholino, piperazino, tetrahydro-pyranyl, thiomorpholino, and the like.

"Mono or monocyclic heterocyclyl$C_1$-$C_6$alkyl" or "heterocycloalkyl" means a -(alkylene)-R radical where R is monocyclic heterocyclyl ring, and monocyclic heterocyclyl and alkylene are as defined above e.g., tetraydrofuranylmethyl, piperazinylmethyl, morpholinylethyl, and the like.

The present disclosure also includes protected derivatives of compounds of the compounds of Formula (I). For example, when compounds of Formula (I) contain groups such as hydroxy, carboxy, thiol or any group containing a nitrogen atom(s), these groups can be protected with a suitable protecting groups. A comprehensive list of suitable protective groups can be found in T. W. Greene, *Protective Groups in Organic Synthesis*, John Wiley & Sons, Inc. (1999), the disclosure of which is incorporated herein by reference in its entirety. The protected derivatives of compounds of Formula (I) can be prepared by methods well known in the art.

The compounds of Formula (I) also includes polymorphic forms, amorphous forms, hydrates and solvates.

A "pharmaceutically acceptable salt" of a compound of Formula (I) means a salt that is pharmaceutically acceptable and that possesses the desired pharmacological activity of the parent compound. Such salts include:

acid addition salts, formed with inorganic acids such as hydrochloric acid, hydrobromic acid, sulfuric acid, nitric acid, phosphoric acid, and the like; or formed with organic acids such as formic acid, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It is understood that the pharmaceutically acceptable salts are non-toxic. Additional information on suitable pharmaceutically acceptable salts can be found in *Remington's Pharmaceutical Sciences,* 17th ed., Mack Publishing Company, Easton, Pa., 1985, which is incorporated herein by reference in its entirety.

The compounds of Formula (I) may have asymmetric centers. Compounds of Formula (I) containing an asymmetrically substituted atom may be isolated in optically active or racemic forms. It is well known in the art how to prepare optically active forms, such as by resolution of materials. All chiral, diastereomeric, all mixtures of chiral or diasteromeric forms, and racemic forms are within the scope of this disclosure, unless the specific stereochemistry or isomeric form is specifically indicated. It will also be understood by a person of ordinary skill in the art that when a compound is denoted as (R) stereoisomer, it may contain the corresponding (S) stereoisomer as an impurity and vice versa.

Certain compounds of Formula (I) can exist as tautomers and/or geometric isomers. All possible tautomers and cis and trans isomers, as individual forms and mixtures thereof are within the scope of this disclosure. Additionally, as used herein the term alkyl includes all the possible isomeric forms of said alkyl group albeit only a few examples are set forth. Furthermore, when the cyclic groups such as aryl, heteroaryl, heterocyclyl are substituted, they include all the positional isomers albeit only a few examples are set forth.

The phrase " . . . wherein each of the aforementioned ring in $R^2$ and $R^7$, by itself or as part of another group, is optionally substituted with $R^j$, $R^k$ or $R^l$ independently selected from . . . " in the definition of groups $R^2$ and $R^7$ (and similar language elsewhere in the claim and specification e.g., groups R³⁰ and R³¹) include groups in the definition of R² and R⁷ where R² and R⁷ are rings such as mono or bicyclic aryl, mono or bicyclic heteroaryl, monocyclic heterocyclyl, etc, as well as groups arylC₁-C₆alkyl, NR¹⁸R¹⁹, —OR²⁰, etc where R¹⁸, R¹⁹, and R²⁰ are rings.

"Oxo" or "carbonyl" means C(O).

"Optional substituted phenyl, optionally substituted monocyclic heteroaryl or optionally substituted monocyclic heterocyclyl" means phenyl, monocyclic heteroaryl, or monocyclic heterocyclyl as defined herein that are optionally substituted with one, two, or three substituents independently selected from halo, cyano, haloC₁-C₆alkyl, haloC₁-C₆alkoxy, carboxy, and C₁-C₆alkoxycarbonyl, unless alternatives substituents are specified, and wherein each term is as defined above.

"Optional" or "optionally" means that the subsequently described event or circumstance may but need not occur, and that the description includes instances where the event or circumstance occurs and instances in which it does not. For example, "heterocyclyl group optionally substituted with an alkyl group" means that the alkyl may but need not be present, and the description includes situations where the heterocyclyl group is substituted with an alkyl group and situations where the heterocyclyl group is not substituted with alkyl.

"Spiroheterocycloamino" means a saturated bicyclic ring having 6 to 10 ring atoms in which one, two, or three ring atoms are heteroatom selected from N, N-oxide, O, and S(O)ₙ where n is an integer from 0 to 2, the remaining ring atoms being C, provided that at least one ring atom is N, and the rings are connected through only one atom. The connecting atom is also called the spiroatom, and is most often a quaternary carbon ("spiro carbon"). Representative examples include, but are not limited to, 2,6-diazaspiro[3.3]heptane, 2,6-diazaspiro[3.4]octane, 2-azaspiro[3.4]octane, 2-azaspiro[3.5]nonane, 2,7-diazaspiro[4.4]nonane, and the like.

"Unnatural amino acid residue" means a group of formula —C(O)CHRNH₂ or —OC(O)CHRNH₂ where R is a group selected from C₃-C₇cycloalkyl, C₃-C₇cycloalkylCH₂, C₃-C₇cycloalkylC₂H₅, monocyclic heterocyclyl, C₃-C₇heterocyclylmethylene, C₃-C₇heterocyclylethylene, mono- and bicyclic aryl (optionally substituted with 1-4 substituents independently selected from halo, hydroxy, CN, amino, C₁-C₆alkylamino, diC₁-C₆alkylamino, and C₁-C₆alkoxy), mono- and bicyclic heteroaryl (optionally substituted with 1-4 substituents independently selected from halo, hydroxy, CN, amino, C₁-C₆alkylamino, diC₁-C₆alkylamino, and C₁-C₆alkoxy), mono- and bicyclic arylC₁₋₂alkyl (optionally substituted with 1-4 substituents independently selected from halo, hydroxy, CN, amino, C₁-C₆alkylamino, diC₁-C₆alkylamino, and C₁-C₆alkoxy) or mono- and bicyclic heteroarylC₁₋₂alkyl (optionally substituted with 1-4 substituents independently selected from halo, hydroxy, CN, amino, C₁-C₆alkylamino, diC₁-C₆alkylamino, and C₁-C₆alkoxy).

It is to be understood that where compounds disclosed herein have unfilled valencies, then the valencies are to be filled with hydrogens.

Where a range of values is provided, it is understood that the upper and lower limit, and each intervening value between the upper and lower limit of the range is encompassed within the embodiments.

The indefinite article "a" or "an" does not exclude a plurality.

In a second aspect, provided herein is a compound of Formula (A1) or (B1):

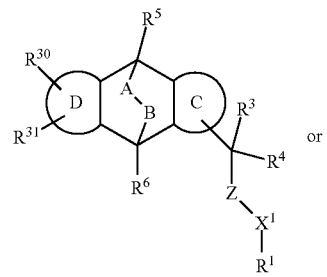

(A1)

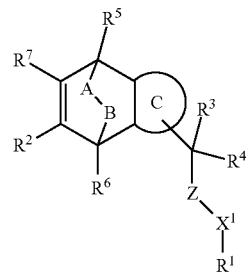

(B1)

or a tautomer thereof, or a pharmaceutically acceptable salt of each thereof, or a solvate of each of the foregoing, wherein A is a bond, O, S(O)$_p$, substituted NH, preferably NCOR$^b$, NCONHR$^c$, or NSO₂R$^d$, or CR⁸R⁹ where p is 0, 1, or 2; and R$^b$, R$^c$ and R$^d$ are independently hydrogen, optionally substituted C₁-C₆alkyl, optionally substituted C₃-C₈cycloalkyl, optionally substituted heteroaryl, preferably 5-10 membered heteroaryl, optionally substituted, heterocyclyl, preferably 4-10 membered heterocyclyl, or optionally substituted aryl, preferably 6-10 membered aryl;

B is O, S(O)$_p$, NR$^a$, or CR¹⁰R¹¹, provided that when one of A and B is O or S(O)$_p$, the other excludes O or S(O)$_p$, preferably, -A-B— excludes two heteroatoms bonded to each other such as —O—O—, —S—S—, —N—O—, etc.;

R³ and R⁴ are each hydrogen, or R³ and R⁴ together with the carbon they are attached form C=O or C=NR¹², wherein R¹² is hydrogen or C₁-C₆alkyl, preferably NH or NMe, more preferably, when R³ and R⁴ together form C=NR¹², Z is NR¹³;

Z is NR¹³ or CR¹⁴R¹⁵ wherein R¹³, R¹⁴ and R¹⁵ are independently hydrogen or C₁-C₆alkyl, preferably CR¹⁴R¹⁵ is CH₂;

R⁵ and R⁶ independently are hydrogen, optionally substituted, preferably optionally substituted with 1-3 substituents, C₁-C₆alkyl or more preferably C₁-C₄alkyl, optionally substituted C₃-C₈cycloalkyl, halo, preferably, F, or C₁-C₆alkoxy, preferably OMe or OEt;

ring C is optionally substituted heteroaryl, optionally substituted heterocyclyl, optionally substituted aryl, or optionally substituted cycloalkyl;

X¹ is CR¹⁶R¹⁷, O, S(O)$_q$ where q is 0, 1, or 2, NR⁸, or a bond;

R$^a$, R⁸, R⁹, R¹⁰, and R¹¹ are independently hydrogen, OH, C₁-C₆alkoxy, preferably, OMe, optionally substituted C₁-C₆alkyl, or optionally substituted C₃-C₈cycloalkyl; provided that R⁸ and R⁹ and R¹⁰ and R¹¹ are not OH at the same time;

R¹⁶ and R¹⁷ independently are hydrogen, deuterium, or C₁-C₆alkyl, preferably C₁-C₄alkyl, or R¹⁶ and R¹⁷ together with the carbon atom form an optionally substituted C₃-C₆cycloalkyl, preferably a cyclopropyl ring;

$R^1$ is optionally substituted heteroaryl or optionally substituted aryl;

$R^2$ and $R^7$ independently are hydrogen, halo, optionally substituted $C_1$-$C_6$alkyl, preferably substituted with an optionally substituted 5-6 membered heteroaryl or heterocyclyl, optionally substituted $C_6$-$C_{10}$ aryl, optionally substituted heteroaryl, optionally substituted heterocyclyl, —$NR^{18}R^{19}$, —$OR^{20}$, —$CF_2R^{22}$, —$C(=O)R^{26}$, or —$C(=O)NR^{27}R^{28}$, or $R^2$ and $R^7$ together with the atoms they are bonded to form a 5-10 membered optionally substituted heteroaryl or a 6-10 membered optionally substituted aryl;

where each $R^{18}$, $R^{19}$, $R^{20}$, $R^{22}$, $R^{26}$, $R^{27}$, and $R^{28}$ is optionally substituted aryl, optionally substituted heteroaryl, or optionally substituted $C_1$-$C_6$alkyl, or $R^{18}$ and $R^{19}$ or $R^{27}$ and $R^{28}$ together with the nitrogen atom they are bonded to form an optionally substituted heterocycle or optionally substituted heteroaryl;

ring D is optionally substituted heteroaryl, optionally substituted heterocyclyl, optionally substituted aryl, or optionally substituted $C_5$-$C_{10}$cycloalkyl;

$R^{30}$ and $R^{31}$ independently are hydrogen, halo, optionally substituted $C_1$-$C_6$alkyl, preferably substituted with an optionally substituted 5-6 membered heteroaryl or heterocyclyl, optionally substituted $C_6$-$C_{10}$ aryl, optionally substituted heteroaryl, optionally substituted heterocyclyl, —$NR^{32}R^{33}$, —$OR^{34}$, —$CF_2R^{36}$, —$C(=O)R^{40}$, or —$C(=O)NR^{41}R^{42}$;

or $R^{30}$ and $R^{31}$ together with the atoms they are bonded to form a 5-10 membered optionally substituted heteroaryl or a 6-10 membered optionally substituted aryl;

where $R^{32}$, $R^{33}$, —$R^{34}$, $R^{36}$, $R^{40}$, $R^{41}$, and $R^{42}$ independently are optionally substituted aryl, optionally substituted heteroaryl, or optionally substituted $C_1$-$C_6$alkyl, or $R^{32}$ and $R^{33}$ or $R^{41}$ and $R^{42}$ together with the nitrogen atom they are bonded to form an optionally substituted heterocycle or optionally substituted heteroaryl.

In a third aspect, provided herein is a pharmaceutical composition comprising a compound of Formula (I), (A1), or (B1) (or any embodiments thereof provided herein), and optionally at least one pharmaceutically acceptable excipient.

In a fourth aspect, provided herein is a method for inhibiting plasma kallikrein activity in a patient, the method comprising administering to the patient a therapeutically effective amount of a compound of Formula (I), (A1), or (B1) (or any embodiments thereof provided herein), or a pharmaceutical composition comprising a therapeutically effective amount of a compound of Formula (I), (A1), or (B1) (or any embodiments thereof provided herein) and a pharmaceutically acceptable excipient.

In a fifth aspect, provided herein is a method for treating a disorder or a disease in a patient mediated by plasma kallikrein, comprising administering therapeutically effective amount of a compound of Formula (I), (A1), or (B1) (or any embodiments thereof provided herein) or a pharmaceutical composition comprising a therapeutically effective amount of a compound of Formula (I), (A1), or (B1) (or any embodiments thereof provided herein) and a pharmaceutically acceptable excipient to the patient in need thereof.

In a sixth aspect, provided herein is a method of treating hereditary angioedema, comprising administering to a patient in need thereof a therapeutically effective amount of a compound of Formula (I), (A1), or (B1) (or any embodiments thereof disclosed herein) or a pharmaceutically acceptable composition comprising a therapeutically effective amount of a compound of Formula (I), (A1), or (B1) (or any embodiments thereof provided herein) provided herein and a pharmaceutically acceptable excipient.

Definitions

The following terms are used for compounds of Formula (AI) and (B1) of the second aspect (and embodiments thereof disclosed herein), and in the third and fourth aspects, in the specification for the purposes of this application and have the following meaning unless stated otherwise. If not defined, all technical and scientific terms used herein have the same meaning as commonly understood by one of ordinary skill in the art.

It must be noted that as used herein and in the appended claims, the singular forms "a", "an", and "the" include plural referents unless the context clearly dictates otherwise. Thus, for example, reference to "an excipient" includes a plurality of excipients.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s). "Consisting of" shall mean excluding more than trace elements of other ingredients and substantial method steps. Embodiments defined by each of these transition terms are within the scope of this invention.

The term "about" when used before a numerical designation, e.g., temperature, time, amount, and concentration, including range, indicates approximations which may vary by (+) or (−) 10%, 5% or 1%.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations. Each numerical parameter should at least be construed in light of the number of reported significant digits and by applying ordinary rounding techniques.

As used herein, $C_m$-$C_n$, such as $C_1$-$C_{10}$, $C_1$-$C_6$, or $C_1$-$C_4$ when used before a group refers to that group containing m to n carbon atoms.

The term "alkyl" refers to monovalent saturated aliphatic hydrocarbyl groups having from 1 to 25 carbon atoms (i.e., $C_1$-$C_{25}$ alkyl) or 1 to 6 carbon atoms (i.e., $C_1$-$C_6$ alkyl), or 1 to 4 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—). Alkyl substituted with a substituent refers to an alkyl group that is substituted with up to 5, preferably up to 4, and still more preferably up to 3 substituents, and includes alkyl groups substituted with 1 or 2 substituents. The term "alkyl" encompasses the term "cycloalkyl" described below.

"Substituted alkyl" refers to an alkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein.

The terms "alkylene" alone or as part of another substituent means a divalent radical derived from an alkyl or cycloalkyl group as exemplified by —$CH_2CH_2CH_2CH_2$—. For alkylene groups, no orientation of the linking group is implied.

The term "alkenyl" refers to monovalent aliphatic hydrocarbyl groups having from 2 to 25 carbon atoms or 2 to 6 carbon atoms and 1 or more, preferably 1, carbon carbon double bond. Examples of alkenyl include vinyl, allyl, dimethyl allyl, and the like.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein, and with the proviso that any hydroxy or thiol substitution is not attached to a vinyl (unsaturated) carbon atom.

"Alkynyl" refers to straight or branched monovalent hydrocarbyl groups having from 2 to 6 carbon atoms and preferably 2 to 3 carbon atoms and having at least 1 and preferably from 1 to 2 sites of acetylenic (—C≡C—) unsaturation. Examples of such alkynyl groups include acetylenyl (—C≡CH), and propargyl (—$CH_2$C≡CH). $C_x$ alkynyl refers to an alkynyl group having x number of carbon atoms.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein, and with the proviso that any hydroxy or thiol substitution is not attached to an acetylenic carbon atom.

The term "alkoxy" refers to —O-alkyl, where alkyl is as defined above.

"Substituted alkoxy" refers to the group —O-(substituted alkyl) wherein substituted alkyl is defined herein. Preferred substituted alkyl groups in —O-(substituted alkyl) include halogenated alkyl groups and particularly halogenated methyl groups such as trifluoromethyl, difluoromethyl, fluoromethyl and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein. Acyl includes the "acetyl" group $CH_3C$(O)—.

"Acylamino" refers to the groups —$NR^{300}$C(O)alkyl, —$NR^{300}$C(O)substituted alkyl, —$NR^{300}$C(O)cycloalkyl, —$NR^{300}$C(O)substituted cycloalkyl, —$NR^{300}$C(O)alkenyl, —$NR^{300}$C(O)substituted alkenyl, alkoxy, substituted-alkoxy-$NR^{300}$C(O)— alkynyl, —$NR^{300}$C(O)substituted alkynyl, —$NR^{300}$C(O)aryl, —$NR^{300}$C(O)substituted aryl, —$NR^{300}$C(O)heteroaryl, —$NR^{300}$C(O)substituted heteroaryl, —$NR^{300}$C(O)heterocyclic, and —$NR^{300}$C(O)substituted heterocyclic wherein $R^{300}$ is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Substituted amino" refers to the group —$NR^{310}R^{320}$ where $R^{310}$ and $R^{320}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, substituted heterocyclic, and substituted sulfonyl, and wherein $R^{310}$ and $R^{320}$ are optionally joined, together with the nitrogen bound thereto to form a heterocyclic or substituted heterocyclic group, provided that $R^{310}$ and $R^{320}$ are both not hydrogen, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic, and substituted heterocyclic are as defined herein. When $R^{310}$ is hydrogen and $R^{320}$ is alkyl, the substituted amino group is sometimes referred to herein as alkylamino. When $R^{310}$ and $R^{320}$ are alkyl, the substituted amino group is sometimes referred to herein as dialkylamino. When referring to a monosubstituted amino, it is meant that either $R^{310}$ or $R^{320}$ is hydrogen but not both. When referring to a disubstituted amino, it is meant that neither $R^{310}$ nor $R^{320}$ are hydrogen.

"Aminocarbonyl" refers to the group —C(O)NR$^{330}$R$^{340}$ where $R^{330}$ and $R^{340}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl heteroaryl, substituted heteroaryl, heterocyclic, and substituted heterocyclic, and wherein $R^{330}$ and $R^{340}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonyl" refers to the group —C(S)NR$^{330}$R$^{340}$ where $R^{330}$ and $R^{340}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic, and wherein $R^{330}$ and $R^{340}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonylamino" refers to the group —NR$^{300}$C(O)NR$^{330}$R$^{340}$ where $R^{300}$ is hydrogen or alkyl and $R^{330}$ and $R^{340}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic, and wherein $R^{330}$ and $R^{340}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonylamino" refers to the group —NR$^{300}$C(S)NR$^{330}$R$^{340}$ where $R^{300}$ is hydrogen or alkyl and $R^{330}$ and $R^{340}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic, and wherein $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonyloxy" refers to the group —O—C(O)NR$^{330}$R$^{340}$ where $R^{330}$ and $R^{340}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic, and wherein $R^{330}$ and $R^{340}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonyl" refers to the group —SO$_2$NR$^{330}$R$^{340}$ where $R^{330}$ and $R^{340}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic, and wherein $R^{330}$ and $R^{340}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonyloxy" refers to the group —O—SO$_2$NR$^{330}$R$^{340}$ where $R^{330}$ and $R^{340}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic, and wherein $R^{330}$ and $R^{340}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonylamino" refers to the group —NR$^{300}$—SO$_2$NR$^{330}$R$^{340}$ where $R^{300}$ is hydrogen or alkyl and $R^{330}$ and $R^{340}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic, and wherein $R^{330}$ and $R^{340}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Amidino" refers to the group —C(=NR$^{35}$)NR$^{330}$R$^{340}$ where $R^{330}$, $R^{340}$, and $R^{350}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic, and wherein $R^{330}$ and $R^{340}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

The term "aryl" refers to a monovalent, aromatic mono- or bicyclic ring having 6-10 ring carbon atoms. Examples of aryl include phenyl and naphthyl. The condensed ring may or may not be aromatic provided that the point of attachment is at an aromatic carbon atom. For example, and without limitation, the following is an aryl group:

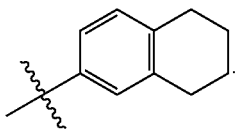 [SMILES: *c1ccc2c(c1)CCCC2]

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein.

"Aryloxy" refers to the group —O-aryl, where aryl is as defined herein, that includes, by way of example, phenoxy and naphthoxy.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group —S-(substituted aryl), where substituted aryl is as defined herein.

"Carbonyl" refers to the divalent group —C(O)— which is equivalent to —C(=O)—.

"Carboxy" or "carboxyl" refers to —COOH or salts thereof.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"(Carboxyl ester)amino" refers to the group —NR$^{300}$—C(O)O-alkyl, —NR$^{300}$—C(O)O-substituted alkyl, —NR$^{300}$—C(O)O-alkenyl, —NR$^{300}$—C(O)O-substituted alkenyl, —NR$^{300}$—C(O)O-alkynyl, —NR$^{300}$—C(O)O-substituted alkynyl, —NR$^{300}$—C(O)O-aryl, —NR$^{300}$—C(O)O-substituted aryl, —NR$^{300}$—C(O)O-cycloalkyl, —NR$^{300}$—C(O)O-substituted cycloalkyl, —NR$^{300}$—C(O)O-heteroaryl, —NR$^{300}$—C(O)O-substituted heteroaryl, —NR$^{300}$—C(O)O-heterocyclic, and —NR$^{300}$—C(O)O-substituted heterocyclic wherein $R^{300}$ is alkyl or hydrogen, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"(Carboxyl ester)oxy" refers to the group —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted-alkynyl, —O—C(O)O-aryl, —O—C(O)O-substituted aryl, —O—C(O)O-cycloalkyl, —O—C(O)O-substituted cycloalkyl, —O—C(O)O-heteroaryl, —O—C(O)O-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "cycloalkyl" refers to a monovalent, preferably saturated, hydrocarbyl mono-, bi-, or tricyclic ring having 3-12 ring carbon atoms. While cycloalkyl, refers preferably to saturated hydrocarbyl rings, as used herein, it also includes rings containing 1-2 carbon-carbon double bonds. Nonlimiting examples of cycloalkyl include cyclopropyl, cyclobutyl, cyclopentyl, cyclohexyl, cycloheptyl, adamentyl, and the like. The condensed rings may or may not be non-aromatic hydrocarbyl rings provided that the point of attachment is at a cycloalkyl carbon atom. For example, and without limitation, the following is a cycloalkyl group:

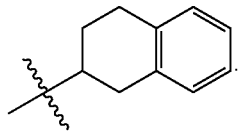 [SMILES: *C1CCc2ccccc2C1]

"Cycloalkyloxy" refers to —O-cycloalkyl.

"Substituted cycloalkyloxy" refers to —O-(substituted cycloalkyl).

"Cycloalkylthio" refers to —S-cycloalkyl.

"Substituted cycloalkylthio" refers to —S-(substituted cycloalkyl).

"Guanidino" refers to the group —NHC(=NH)NH$_2$.

"Substituted guanidino" refers to —NR$^{360}$C(=NR$^{360}$)N(R$^{360}$)$_2$ where each R$^{360}$ is independently selected from the group consisting of hydrogen, alkyl, substituted alkyl, aryl, substituted aryl, heteroaryl, substituted heteroaryl, heterocyclic, and substituted heterocyclic, and two R$^{360}$ groups attached to a common guanidino nitrogen atom are optionally joined together with the nitrogen bound thereto to form a heterocyclic or substituted heterocyclic group, provided that at least one $R^{360}$ is not hydrogen, and wherein said substituents are as defined herein.

The term "heteroaryl" refers to a monovalent, aromatic mono-, bi-, or tricyclic ring having 2-16 ring carbon atoms and 1-8 ring heteroatoms selected preferably from N, O, S, and P and oxidized forms of N, S, and P, provided that the ring contains at least 5 ring atoms. Nonlimiting examples of heteroaryl include furan, imidazole, oxadiazole, oxazole, pyridine, quinoline, and the like. The condensed rings may or may not be a heteroatom containing aromatic ring provided that the point of attachment is a heteroaryl atom. For example, and without limitation, the following is a heteroaryl group:

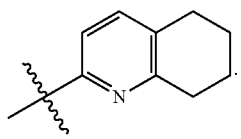 [SMILES: *c1ccc2c(n1)CCCC2]

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryloxy" refers to the group —O-(substituted heteroaryl).

"Heteroarylthio" refers to the group —S-heteroaryl.

"Substituted heteroarylthio" refers to the group —S-(substituted heteroaryl).

The term "heterocyclyl" or heterocycle refers to a non-aromatic, mono-, bi-, or tricyclic ring containing 2-12 ring carbon atoms and 1-8 ring heteroatoms selected preferably from N, O, S, and P and oxidized forms of N, S, and P, provided that the ring contains at least 3 ring atoms. While heterocyclyl preferably refers to saturated ring systems, it also includes ring systems containing 1-3 double bonds, provided that the ring is non-aromatic. Nonlimiting examples of heterocyclyl include, azalactones, oxazoline, piperidinyl, piperazinyl, pyrrolidinyl, tetrahydrofuranyl, and tetrahydropyranyl. The condensed rings may or may not contain a non-aromatic heteroatom containing ring provided that the point of attachment is a heterocyclyl group. For example, and without limitation, the following is a heterocyclyl group:

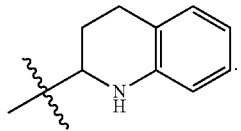 [SMILES: *C1CCc2ccccc2N1]

"Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl.

"Heterocyclyloxy" refers to the group —O-heterocyclyl.

"Substituted heterocyclyloxy" refers to the group —O-(substituted heterocyclyl).

"Heterocyclylthio" refers to the group —S-heterocyclyl.

"Substituted heterocyclylthio" refers to the group —S-(substituted heterocyclyl).

Non-limiting examples of heterocycle and heteroaryl include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

The term "hydrolyzing" refers to breaking an $R^H$—O—CO—, $R^H$—O—CS—, or an $R^H$—O—SO_2— moiety to an $R^H$—OH, preferably by adding water across the broken bond. A hydrolyzing is performed using various methods well known to the skilled artisan, non-limiting examples of which include acidic and basic hydrolysis.

The terms "alkenylene" and "arylene" alone or as part of another substituent means a divalent radical derived from an alkenyl or aryl group, respectively. For, alkenylene and arylene linking groups are contemplated to be used together with, or instead of, alkylene linking groups in some embodiments; no orientation of the linking group is implied.

The term "halo" refers to F, Cl, Br, and I.

The term "nitro" refers to —NO_2.

The term "cyano" refers to —CN.

The term "oxo" refers to a C=O group, and to a substitution of 2 geminal hydrogen atoms with a C=O group.

"Spiro ring systems" refers to bicyclic ring systems that have a single ring carbon atom common to both rings.

"Sulfinyl" refers to the divalent group —SO—.

"Sulfonyl" refers to the divalent group —S(O)_2—.

"Substituted sulfonyl" refers to the group —SO_2-alkyl, —SO_2-substituted alkyl, —SO_2—OH, —SO_2-alkenyl, —SO_2-substituted alkenyl, —SO_2-cycloalkyl, —SO_2-substituted cycloalkyl, —SO_2-aryl, —SO_2-substituted aryl, —SO_2-heteroaryl, —SO_2-substituted heteroaryl, —SO_2-heterocyclic, —SO_2-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein. Substituted sulfonyl includes groups such as methyl-SO_2—, phenyl-SO_2—, and 4-methylphenyl-SO_2—. Preferred substituted alkyl groups on the substituted alkyl-SO_2— include halogenated alkyl groups and particularly halogenated methyl groups such as trifluoromethyl, difluoromethyl, fluoromethyl and the like.

"Substituted sulfinyl" refers to the group —SO-alkyl, —SO-substituted alkyl, —SO-alkenyl, —SO-substituted alkenyl, —SO-cycloalkyl, —SO-substituted cycloalkyl, —SO-aryl, —SO-substituted aryl, —SO-heteroaryl, —SO-substituted heteroaryl, —SO-heterocyclic, —SO-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein. Substituted sulfinyl includes groups such as methyl-SO—, phenyl-SO—, and 4-methylphenyl-SO—. Preferred substituted alkyl groups on the substituted alkyl-SO— include halogenated alkyl groups and particularly halogenated methyl groups such as trifluoromethyl, difluromethyl, fluoromethyl and the like.

"Sulfonyloxy" or "substituted sulfonyloxy" refers to the group —OSO$_2$-alkyl, —OSO$_2$-substituted alkyl, —OSO$_2$-OH, —OSO$_2$-alkenyl, —OSO$_2$-substituted alkenyl, —OSO$_2$-cycloalkyl, —OSO$_2$-substituted cycloalkyl, —OSO$_2$-aryl, —OSO$_2$-substituted aryl, —OSO$_2$-heteroaryl, —OSO$_2$-substituted heteroaryl, —OSO$_2$-heterocyclic, —OSO$_2$-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Mercapto" or "thiol" refers to the group —SH.

"Formyl" refers to the group —C(O)H.

"Thiocarbonyl" refers to the divalent group —C(S)— which is equivalent to —C(=S)—.

"Thione" refers to the atom (=S).

"Alkylthio" refers to the group —S-alkyl wherein alkyl is as defined herein.

"Substituted alkylthio" refers to the group —S-(substituted alkyl) wherein substituted alkyl is as defined herein. Preferred substituted alkyl groups on —S-(substituted alkyl) include halogenated alkyl groups and particularly halogenated methyl groups such as trifluoromethyl, difluoromethyl, fluoromethyl and the like.

"Stereoisomer" or "stereoisomers" refer to compounds that differ in the chirality of one or more stereocenters. Stereoisomers include enantiomers and diastereomers.

"Tautomer" refer to alternate forms of a compound that differ in the position of a proton, such as enol-keto and imine-enamine tautomers, or the tautomeric forms of heteroaryl groups containing a ring atom attached to both a ring —NH— moiety and a ring=N— moiety such as pyrazoles, imidazoles, benzimidazoles, triazoles, and tetrazoles.

An "amino-protecting group," as used herein, is attached to a nitrogen atom. An amino protecting group is well known in the art and includes those described in detail in *Protecting Groups in Organic Synthesis*, T. W. Greene and P. G. M. Wuts, 3$^{rd}$ edition, John Wiley & Sons, 1999, the entirety of which is incorporated herein by reference. Suitable amino protecting groups include carbamates such as methyl carbamate, ethyl carbamate, 9-fluorenylmethyl carbamate (Fmoc), benzyl carbamate (Cbz), t-butyl carbamate (BOC), 9-(2-sulfo)fluorenylmethyl carbamate, 9-(2,7-dibromo)fluorenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc); amides such as formamide, acetamide, chloroacetamide, trichloroacetamide, trifluoroacetamide, phenylacetamide; N-phthalimide, N-dithiasuccinimide (Dts), N-2,3-diphenylmaleimide, N-2,5-dimethylpyrrole, N-benzylamine, N-triphenylmethylamine (Tr); eneamines such as N-1,1-dimethylthiomethyleneamine, N-benzylideneamine, N-p-methoxybenzylideneamine; enamides such as benzenesulfenamide, o-nitrobenzenesulfenamide (Nps), 2,4-dinitrobenzenesulfenamide, pentachlorobenzenesulfenamide; and sulfonamides such as p-toluenesulfonamide (Ts), benzenesulfonamide, 2,3,6,-trimethyl-4-methoxybenzene-sulfonamide (Mtr).

The terms "optional" or "optionally" as used throughout the specification means that the subsequently described event or circumstance may but need not occur, and that the description includes instances where the event or circumstance occurs and instances in which it does not. For example, "the nitrogen atom is optionally oxidized to provide for the N-oxide (N→O) moiety" means that the nitrogen atom may but need not be oxidized, and the description includes situations where the nitrogen atom is not oxidized and situations where the nitrogen atom is oxidized.

The term "optionally substituted" refers to a substituted or unsubstituted group. The group may be substituted with one or more substituents, such as e.g., 1, 2, 3, 4 or 5 substituents. Preferably, the substituents are selected from the functional groups provided herein. In certain more preferred embodiments, "optionally substituted" refers to a substituted or unsubstituted group. The group may be substituted with one or more substituents, such as e.g., 1, 2, 3, 4 or 5 substituents. Preferably, the substituents are selected from the group consisting of oxo, halo, —CN, NO$_2$, —N$_2$+, —CO$_2$R$^{100}$, —OR$^{100}$, —SR$^{100}$, —SOR$^{100}$, —SO$_2$R$^{100}$, —NR$^{101}$R$^{102}$, —CONR$^{101}$R$^{102}$, —SO$_2$NR$^{101}$R$^{102}$, C$_1$-C$_6$alkyl, C$_1$-C$_6$ haloalkyl, C$_1$-C$_6$alkoxy, —CR$^{100}$=C(R$^{100}$)$_2$, —CCR$^{100}$, C$_3$-C$_{10}$cycloalkyl, C$_3$-C$_{10}$ heterocyclyl, C$_6$-C$_{12}$ aryl and C$_2$-C$_{12}$ heteroaryl, wherein each R$^{100}$ independently is hydrogen or C$_1$-C$_5$alkyl; C$_3$-C$_{12}$cycloalkyl; C$_3$-C$_{10}$ heterocyclyl; C$_6$-C$_{12}$ aryl; or C$_2$-C$_{12}$ heteroaryl; wherein each alkyl, cycloalkyl, heterocyclyl, aryl, or heteroaryl is optionally substituted 1-3 times with halo, 1-3 times with C$_1$-C$_6$alkyl, 1-3 times with C$_1$-C$_6$ haloalkyl or 1-3 times with C$_1$-C$_6$alkoxy groups. Preferably, the substituents are selected from the group consisting of chloro, fluoro, —OCH$_3$, methyl, ethyl, iso-propyl, cyclopropyl, vinyl, ethynyl, —CO$_2$H, —CO$_2$CH$_3$, —OCF$_3$, —CF$_3$, and —OCHF$_2$.

R$^{101}$ and R$^{102}$ independently is hydrogen; C$_1$-C$_8$alkyl, optionally substituted with —CO$_2$H or an ester thereof, C$_1$-C$_6$alkoxy, oxo, —CR$^{103}$=C(R$^{103}$)$_2$, —CCR, C$_3$-C$_{10}$cycloalkyl, C$_3$-C$_{10}$ heterocyclyl, C$_6$-C$_{12}$ aryl, or C$_2$-C$_{12}$ heteroaryl, wherein each R$^{103}$ independently is hydrogen or C$_1$-C$_8$alkyl; C$_3$-C$_{12}$cycloalkyl; C$_3$-C$_{10}$heterocyclyl; C$_6$-C$_{12}$aryl; or C$_2$-C$_{12}$heteroaryl; wherein each cycloalkyl, heterocyclyl, aryl, or heteroaryl is optionally substituted 1-3 times with alkyl groups or 1-3 times with halo groups, or R$^{101}$ and R$^{102}$ together with the nitrogen atom they are attached to form a 5-7 membered heterocycle.

Unless indicated otherwise, the nomenclature of substituents that are not explicitly defined herein are arrived at by naming the terminal portion of the functionality followed by the adjacent functionality toward the point of attachment. For example, the substituent "alkoxycarbonylalkyl" refers to the group (alkoxy)-C(O)-(alkyl)-.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to -substituted aryl-(substituted aryl)-substituted aryl.

It is understood that the above definitions are not intended to include impermissible substitution patterns (e.g., methyl substituted with 5 fluoro groups). Such impermissible substitution patterns are well known to the skilled artisan.

The term "pharmaceutically acceptable" refers to generally safe and non-toxic for in vivo, preferably, human administration. The term "pharmaceutically acceptable salt" refers to a salt that is pharmaceutically acceptable. The term "salt" refers to an ionic compound formed between an acid and a base. When the compound provided herein contains an acidic functionality, such salts include, without limitation, alkali metal, alkaline earth metal, and ammonium salts. As used herein, ammonium salts include, salts containing protonated nitrogen bases and alkylated nitrogen bases. Exemplary, and non-limiting cations useful in pharmaceutically acceptable salts include Na, K, Rb, Cs, $NH_4$, Ca, Ba, imidazolium, and ammonium cations based on naturally occurring amino acids. When the compounds utilized herein contain basic functionality, such salts include, without limitation, salts of organic acids, such as carboxylic acids and sulfonic acids, and mineral acids, such as hydrogen halides, sulfuric acid, phosphoric acid, and the likes. Exemplary and non-limiting anions useful in pharmaceutically acceptable salts include oxalate, maleate, acetate, propionate, succinate, tartrate, chloride, sulfate, bisulfate, mono-, di-, and tribasic phosphate, mesylate, tosylate, and the likes.

A "pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable carrier/excipient" as used in the specification and claims includes both one and more than one such excipient.

As used herein, the term "treatment" or "treating" means any treatment of a disease or condition in a patient, including one or more of:
preventing or protecting against the disease or condition, that is, causing the clinical symptoms not to develop, for example, in a subject at risk of suffering from such a disease or condition, thereby substantially averting onset of the disease or condition;
inhibiting the disease or condition, that is, arresting or suppressing the development of clinical symptoms; and/or
relieving the disease or condition that is, causing the regression of clinical symptoms.

A "therapeutically effective amount" means the amount of a compound of the present disclosure and/or a pharmaceutically acceptable salt thereof that, when administered to a patient for treating a disease, is sufficient to effect such treatment for the disease. The "therapeutically effective amount" will vary depending on the compound, the disease and its severity and the age, weight, etc., of the mammal to be treated.

In a seventh aspect, provided is an intermediate of Formula (A):

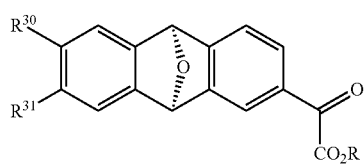

wherein:
$R^{30}$ is hydrogen, ethyl, or cyclopropyl;
$R^{31}$ is ethyl, cyclopropyl, 2-F-phenyl, 4-F-phenyl, or 2,4-diF-phenyl; and
R is hydrogen or $C_1$-$C_6$alkyl; or
a alkali salt thereof.

In one embodiment of the seventh aspect, R is methyl or ethyl.

In another embodiment of the seventh aspect, R is hydrogen.

In yet another embodiment of the seventh aspect, R is Na+.

In yet another embodiment of the seventh aspect and embodiments thereof above $R^{30}$ is hydrogen and $R^{31}$ is 2-F-phenyl, 4-F-phenyl, or 2,4-diF-phenyl.

In yet another embodiment of the seventh aspect and embodiments thereof above $R^{30}$ is ethyl, or cyclopropyl and $R^{31}$ is ethyl or cyclopropyl.

In an eighth aspect, provided is a process of making a compound of Formula:

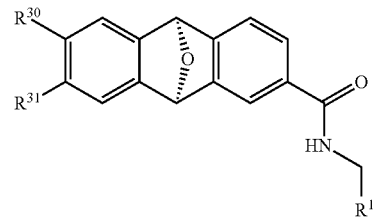

wherein:
$R^{30}$ is hydrogen, ethyl, or cyclopropyl;
$R^{31}$ is ethyl, cyclopropyl, 2-F-phenyl, 4-F-phenyl, or 2,4-diF-phenyl; and
$R^1$ is 4-carbamimidoylphenyl, 4-(N'-hydroxycarbamimidoyl)phenyl, 4-(N'-methoxycarbamimidoyl)phenyl, 4-carbamimidoyl-2-fluorophenyl, 2-fluoro-4-(N'-hydroxycarbamimidoyl)phenyl, 4-(N'-ethoxycarbamimidoyl)phenyl, or 2-fluoro-4-(N'-methoxycarbamimidoyl)phenyl;

comprising:
reacting a compound for Formula (A):

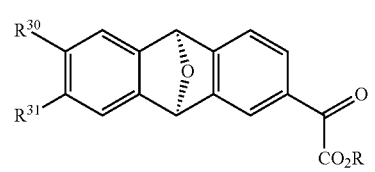

wherein:
$R^{30}$ is hydrogen, ethyl, or cyclopropyl;
$R^{31}$ is ethyl, cyclopropyl, 2-F-phenyl, 4-F-phenyl, or 2,4-diF-phenyl; and
R is hydrogen or $C_1$-$C_6$alkyl; or
a alkali salt thereof;

with an amine of formula:

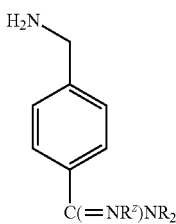

where $R^z$ is hydrogen, hydroxyl, or methoxy;
under amino acid coupling conditions.

EMBODIMENTS

Embodiment (A)

In embodiment A, provided is a compound of Formula (A1) or (B1):

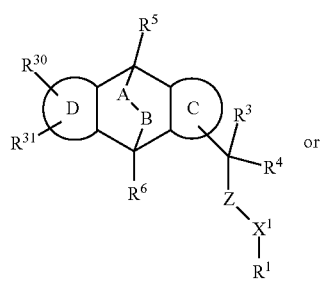

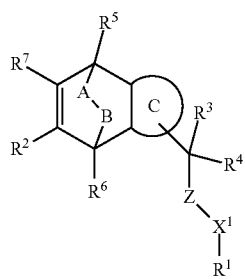

or a tautomer thereof, or a pharmaceutically acceptable salt of each thereof, or a solvate of each of the foregoing, wherein A is a bond or O, $S(O)_p$, substituted NH, preferably $NCOR^b$, $NCONHR^c$, $NSO_2R^d$, or $CR^8R^9$;

p is 0, 1, or 2; $R^b$, $R^c$, and $R^d$ are independently hydrogen, optionally substituted $C_1$-$C_6$alkyl, optionally substituted $C_3$-$C_8$cycloalkyl, optionally substituted heteroaryl, optionally substituted, heterocyclyl, or optionally substituted aryl; provided that when bonded to a $SO_2$, $R^d$ is not H;

B is O, $S(O)_p$, $NR^a$, or $CR^{10}R^{11}$, provided that when one of A and B is O or $S(O)_p$, the other excludes O or $S(O)_p$, preferably, -A-B— excludes two heteroatoms bonded to each other such as —O—O—, —S—S—, —N—O—, etc.;

$R^3$ and $R^4$ are hydrogen, or $R^3$ and $R^4$ together with the carbon they are attached form C=O or C=$NR^{12}$, wherein $R^{12}$ is hydrogen or $C_1$-$C_6$alkyl, preferably NH or NMe, more preferably, when $R^3$ and $R^4$ together with the carbon they are attached form $NR^{12}$, Z is $NR^{13}$;

Z is $NR^{13}$ or $CR^{14}R^{15}$ wherein $R^{13}$, $R^{14}$ and $R^{15}$ are independently hydrogen or $C_1$-$C_6$alkyl, preferably $CR^{14}R^{15}$ is $CH_2$, more preferably, Z is $NR^{13}$;

$R^5$ and $R^6$ independently are hydrogen, optionally substituted, preferably optionally substituted with 1-3 substituents $C_1$-$C_6$alkyl, or $C_1$-$C_4$alkyl, or optionally substituted $C_3$-$C_8$cycloalkyl;

ring C is 5-10 membered optionally substituted heteroaryl, 4-10 membered optionally substituted heterocyclyl, or 6-10 membered optionally substituted aryl, or $C_5$-$C_6$cycloalkyl;

$X^1$ is $CR^{16}R^{17}$, O, $S(O)_q$ where q is 0, 1, or 2, $NR^8$; or a bond;

$R^a$, $R^8$, $R^9$, $R^{10}$ and $R^{11}$ are independently hydrogen, OH, $C_1$-$C_6$alkoxy, preferably OMe, optionally substituted $C_1$-$C_6$alkyl, or optionally substituted $C_3$-$C_8$cycloalkyl; provided that $R^8$ and $R^9$ and $R^{10}$ and $R^{11}$ are not OH at the same time;

$R^{16}$ and $R^{17}$ independently are hydrogen, deuterium, or $C_1$-$C_6$alkyl, preferably $C_1$-$C_4$alkyl, or $R^{16}$ and $R^{17}$ together with the carbon atom they are attached form an optionally substituted $C_3$-$C_6$cycloalkyl, preferably a cyclopropyl ring;

$R^1$ is 5-10 membered optionally substituted heteroaryl or 6-10 membered optionally substituted aryl;

ring D is 5-10 membered optionally substituted heteroaryl, 4-10 membered optionally substituted heterocyclyl, 6-10 membered optionally substituted aryl, or $C_5$-$C_{10}$cycloalkyl;

$R^2$ and $R^7$ independently are hydrogen, halo, optionally substituted $C_1$-$C_6$alkyl, preferably substituted with a 5-6 membered heteroaryl or heterocyclyl, optionally substituted $C_6$-$C_{10}$ aryl, 5-10 membered optionally substituted heteroaryl, 4-10 membered optionally substituted heterocyclyl, —$NR^{18}R^{19}$, —$OR^{20}$, —C(=O)$R^{26}$, —C(=O)$NR^{27}R^{28}$, or —$CF_2R^{22}$;

or $R^2$ and $R^7$ together with the atoms they are bonded to form a 5-10 membered optionally substituted heteroaryl or a 6-10 membered optionally substituted aryl;

$R^{18}$, $R^{19}$, $R^{20}$, $R^{22}$, $R^{26}$, $R^{27}$, and $R^{28}$ independently are optionally substituted aryl, optionally substituted heteroaryl, or optionally substituted $C_1$-$C_6$alkyl, or $R^{18}$ and $R^{19}$ and $R^{27}$ and $R^{28}$ together with the nitrogen atom they are bonded to form an optionally substituted heterocycle or heteroaryl;

$R^{30}$ and $R^{31}$ independently is hydrogen, halo, optionally substituted $C_1$-$C_6$alkyl, preferably substituted with an optionally substituted 5-6 membered heteroaryl or heterocyclyl, optionally substituted $C_6$-$C_{10}$aryl, optionally substituted heteroaryl, optionally substituted heterocyclyl, —$NR^{32}R^{33}$, —$OR^{34}$, —$CF_2R^{36}$, —C(=O)$R^{40}$, or —C(=O)$NR^{41}R^{42}$;

or $R^{30}$ and $R^{31}$ together with the atoms they are bonded to form a 5-10 membered optionally substituted heteroaryl or a 6-10 membered optionally substituted aryl;

where $R^{32}$, $R^{33}$, —$R^{34}$, $R^{36}$, $R^{40}$, $R^{41}$, and $R^{42}$ independently are optionally substituted aryl, optionally substituted heteroaryl, or optionally substituted $C_1$-$C_6$alkyl, or $R^{32}$ and $R^{33}$ or $R^{41}$ and $R^{42}$ together with the nitrogen atom they are bonded to form an optionally substituted heterocycle or optionally substituted heteroaryl.

Embodiment (B)

(i) Embodiment (B)(i) provides embodiments within compounds of Formula (A1) and (B1):

In one embodiment, provided herein is a compound of Formula (A2) or (B2):

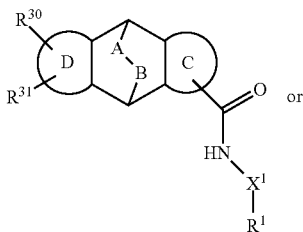

(A2)

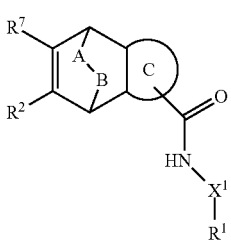

(B2)

wherein the substituents are defined as in the second aspect or any embodiment thereof provided herein.

(ii) Embodiment (B)(i) provides embodiments within compound of Formula (A1), (B1), (A2) and (B2):

In one embodiment, provided herein is a compound of Formula (A2).

In another embodiment, provided herein is a compound of Formula (B2).

In another embodiment, A is a bond. In another embodiment, B is O and A is a bond. In another embodiment, B is O.

In another embodiment, ring C is optionally substituted aryl, preferably a 6 membered aryl ring. In another embodiment, ring C is optionally substituted heteroaryl, preferably a 6 membered heteroaryl, more preferably, containing 1-3 nitrogen atoms.

In another embodiment, $R^1$ is an optionally substituted 6-10 membered heteroaryl comprising an —C=(N)NH$_2$ moiety. In another embodiment, $R^1$ is an optionally substituted 6-10 membered heteroaryl comprising an —NH— moiety.

In another embodiment, $R^1$ is a 6 member aryl substituted with 1-4 substituents. In some embodiments, suitable substituents are selected from $C_1$-$C_6$alkyl, $C_3$-$C_6$cycloalkyl, $C_1$-$C_6$alkoxy, halo, 5-6 member heteroaryl, and heterocycle (such as 4-6 membered heterocycle).

In another embodiment, ring D is an aryl, preferably 6 membered aryl. In another embodiment, ring D is a heterocycle, preferably a 5-6 membered monocyclic heterocycle. In another embodiment, ring D is bicyclic heterocycle, preferably a 6-10 membered heterocycle. In another embodiment, ring D is a heteroaryl, preferably a 6 membered heteroaryl, more preferably containing up to 3 nitrogen atoms. In another embodiment, ring D is a bicyclic heteroaryl, preferably a 6-9 membered bicyclic heteroaryl.

In another embodiment, one of $R^2$ and $R^7$ is hydrogen, and one of $R^{30}$ and $R^{31}$ is hydrogen.

In another embodiment, one of $R^2$ and $R^7$ and one of $R^{30}$ and $R^{31}$ is are methyl substituted with a 5-6 membered heteroaryl optionally substituted with 1-3 substituents, selected preferably from: $C_1$-$C_6$alkyl, preferably, $C_1$-$C_3$alkyl; $C_1$-$C_6$alkoxy, preferably $C_1$-$C_3$alkoxy; and halo, preferably, fluoro, chloro, and bromo.

In another embodiment, one of $R^2$ and $R^7$ is methyl, and one of $R^{30}$ and $R^{31}$ is methyl, wherein each methyl is substituted with a 4-6 membered heterocyclyl optionally substituted with 1-3 substituents, selected preferably from: $C_1$-$C_6$alkyl, preferably, $C_1$-$C_3$alkyl; $C_1$-$C_6$alkoxy, preferably $C_1$-$C_3$alkoxy; and halo, preferably, fluoro, chloro, and bromo.

In another embodiment, one of $R^2$ and $R^7$ is 5-10 membered heteroaryl, and one of $R^{30}$ and $R^{31}$ is 5-10 membered heteroaryl, wherein each 5-10 membered heteroaryl is optionally substituted 1-3 times with: $C_1$-$C_6$alkyl, preferably, $C_1$-$C_3$alkyl; $C_1$-$C_6$alkoxy, preferably $C_1$-$C_3$alkoxy; and halo, preferably, fluoro, chloro, and bromo.

In another embodiment, one of $R^2$ and $R^7$ is phenyl, and one of $R^{30}$ and $R^{31}$ is phenyl, wherein each phenyl is optionally substituted with 1-3 substituents, selected preferably from: $C_1$-$C_6$alkyl, preferably, $C_1$-$C_3$alkyl; $C_1$-$C_6$alkoxy, preferably $C_1$-$C_3$alkoxy; and halo, preferably, fluoro, chloro, and bromo.

In another embodiment, $R^2$ or $R^7$ is $OR^{20}$, and $R^{30}$ or $R^{31}$ is $OR^{34}$, wherein $R^{20}$ and $R^{34}$ are independently hydrogen, optionally substituted $C_1$-$C_6$alkyl, optionally substituted $C_3$-$C_8$cycloalkyl, optionally substituted $C_6$-$C_{10}$ aryl, optionally substituted 5-10 membered heteroaryl, or 4-10 membered heterocycle. In another embodiment, $R^2$ or $R^7$ is $NR^{18}R^{19}$, and $R^{30}$ or $R^{31}$ is $NR^{32}R^{33}$. In another embodiment, $R^2$ or $R^7$ is $NHR^{19}$, and $R^{30}$ or $R^{31}$ is $NHR^{33}$. In another embodiment, $R^{18}$ and $R^{19}$, and $R^{32}$ and $R^{33}$ together with the nitrogen atom form optionally substituted 5-10 membered heteroaryl or 4-10 membered heterocycle.

In another embodiment, provided herein is a compound of Formula (II) or (III)

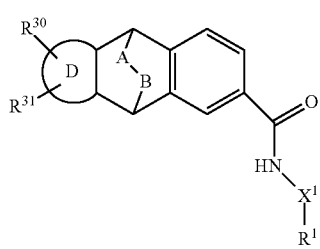

(II)

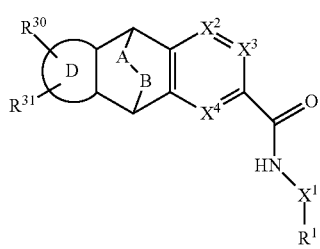

(III)

wherein each $X^2$, $X^3$ and $X^4$ independently is N, CH or CH optionally substituted with an optionally substituted $C_1$-$C_6$alkyl, provided that at least one of $X^2$, $X^3$ and $X^4$ is N.

In another embodiment, provided herein is a compound of Formula (IV), (V), or (VI):

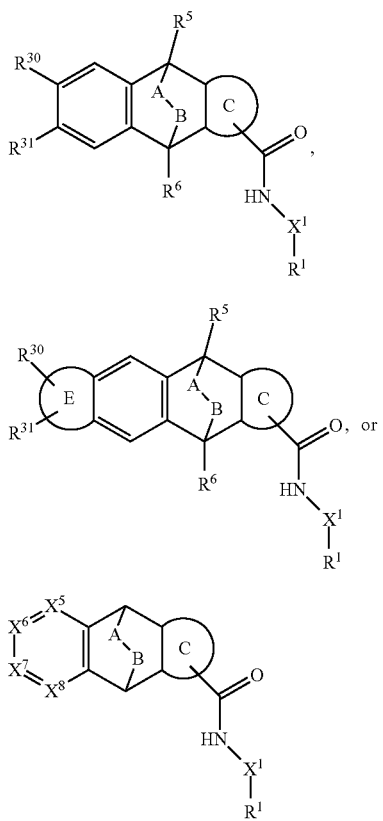

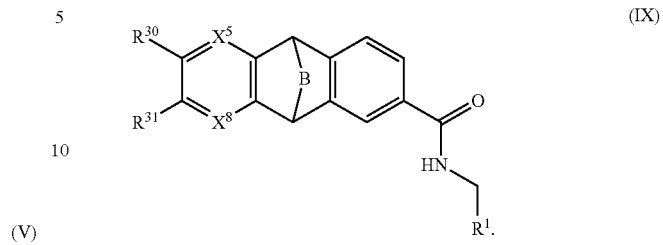

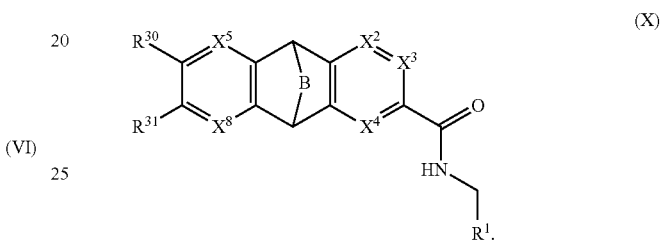

wherein each $X^5$-$X^8$ is independently N, CH, or $CR^{31}$, provided that at least one of $X^5$-$X^8$ is N, and also provided that at least one of $X^5$-$X^8$ is $CR^{31}$.

In another embodiment, provided herein is a compound of Formula (VII):

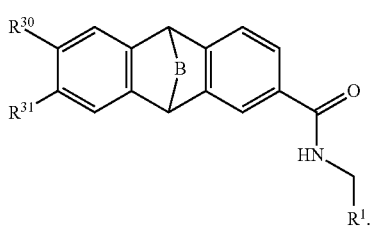

In another embodiment, provided herein is a compound of Formula (VIII):

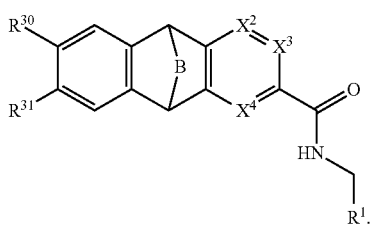

In another embodiment, provided herein is a compound of Formula (IX):

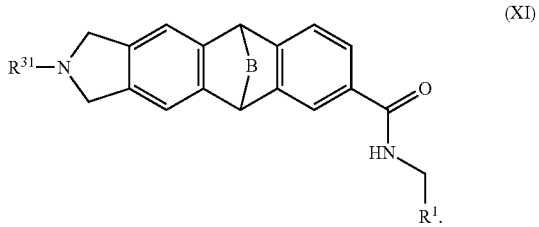

In another embodiment, provided herein is a compound of Formula (X):

In another embodiment, provided herein is a compound of Formula (XI):

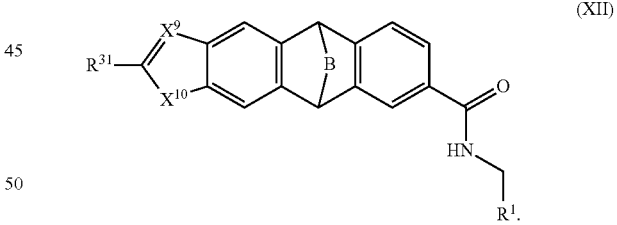

In another embodiment, provided herein is a compound of Formula (XII):

In another embodiment, provided herein is a compound of Formula (XIII):

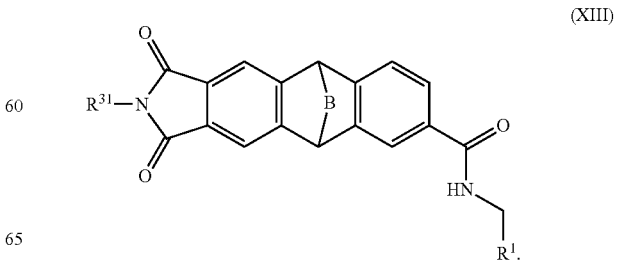

In another embodiment, provided herein is a compound of Formula (XIV):

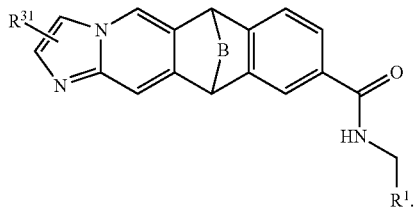

(XIV)

In another embodiment, provided herein is a compound of Formula (XV):

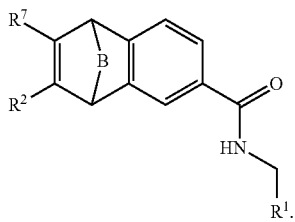

(XV)

In another embodiment, provided herein is a compound of Formula (XVI):

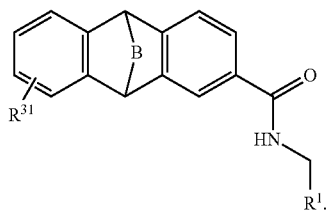

(XVI)

In another embodiment, provided herein is a compound of Formula (XVII):

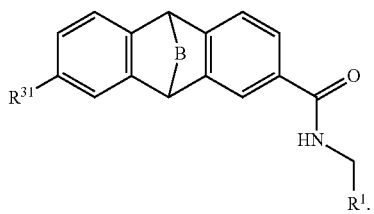

(XVII)

In another embodiment, provided herein is a compound of Formula (XVIII):

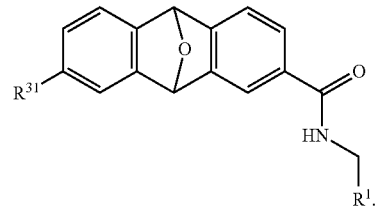

(XVIII)

In another embodiment, provided herein is a compound of Formula (XIX):

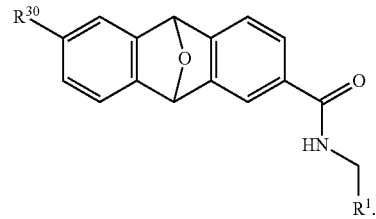

(XIX)

In another embodiment, provided herein is a compound of Formula (XX):

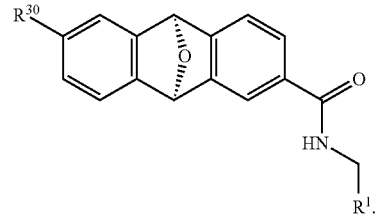

(XX)

In another embodiment, provided herein is a compound of Formula (XXI):

(XXI)

In another embodiment, $X^1$ is $CR^{16}R^{17}$. In another embodiment, $X^1$ is $CH_2$. In another embodiment, $X^1$ is O. In another embodiment, $X^1$ is $S(O)_q$. In another embodiment, $X^1$ is $NR^8$.

In another embodiment, $R^8$ is hydrogen. In another embodiment, $R^8$ is optionally substituted $C_1$-$C_6$alkyl. In another embodiment, $R^8$ is optionally substituted $C_3$-$C_8$cycloalkyl.

In another embodiment, $R^{16}$ is hydrogen. In another embodiment, $R^{16}$ is deuterium. In another embodiment, $R^{16}$ is $C_1$-$C_6$alkyl, preferably $C_1$-$C_4$alkyl. In another embodiment, $R^{17}$ is hydrogen. In another embodiment, $R^{17}$ is deuterium. In another embodiment, $R^{17}$ is $C_1$-$C_6$alkyl, preferably $C_1$-$C_4$alkyl. In another embodiment, $R^{16}$ and $R^{17}$ together with the carbon atom to which they are attached form an optionally substituted $C_3$-$C_6$cycloalkyl, preferably a cyclopropyl ring.

In another embodiment, $R^1$ is:

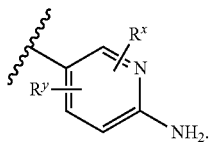

In another embodiment, $R^1$ is:

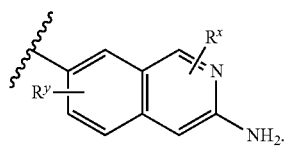

In another embodiment, $R^1$ is:

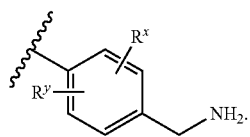

In another embodiment, $R^1$ is:

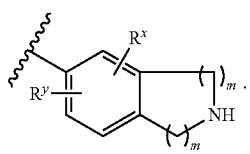

In another embodiment, $R^1$ is:

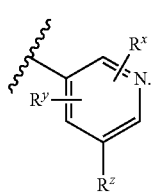

In another embodiment, $R^1$ is:

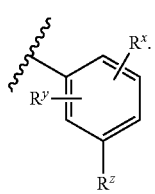

In another embodiment, $R^1$ is:

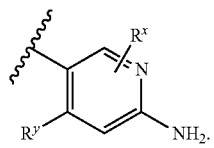

In another embodiment, $R^1$ is:

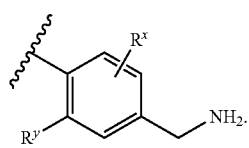

In another embodiment, $R^1$ is:

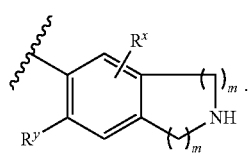

In another embodiment, $R^1$ is:

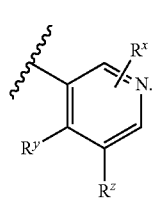

In another embodiment, $R^1$ is:

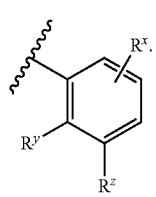

In another embodiment, $R^1$ is selected from:

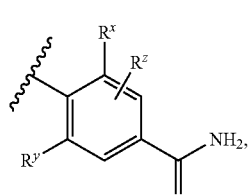

-continued

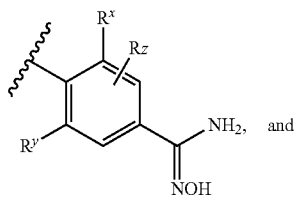

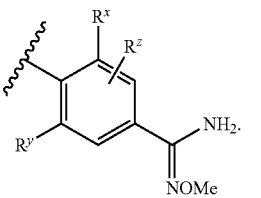

In another embodiment, $R^1$ is selected from:

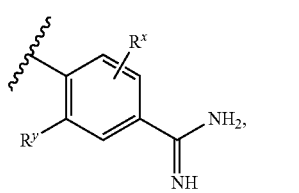

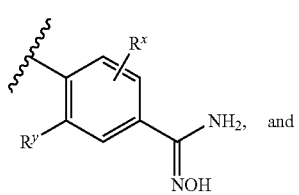

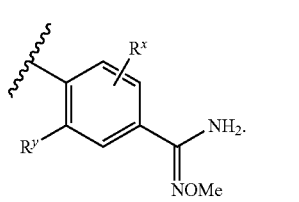

In another embodiment, $R^1$ is selected from:

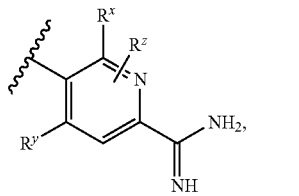

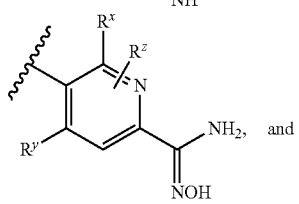

-continued

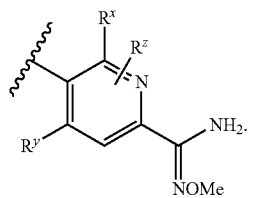

In another embodiment, $R^1$ is selected from:

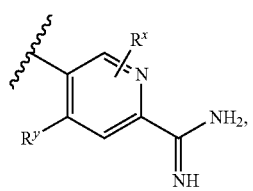

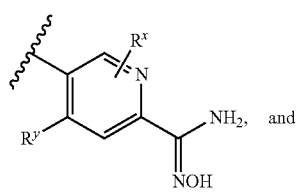

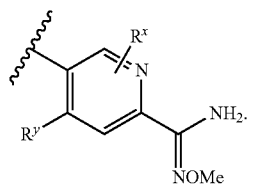

In various embodiments, as provided herein above, $R^x$, $R^y$ and $R^z$ are independently optionally substituted $C_1$-$C_3$alkyl, halo, optionally substituted $C_1$-$C_3$alkoxy, —CN, or a 5 membered optionally substituted heteroaryl preferably containing 3-4 nitrogen atoms; and each m independently is 1 or 2, preferably 1.

In another embodiment, $R^1$ is selected from:

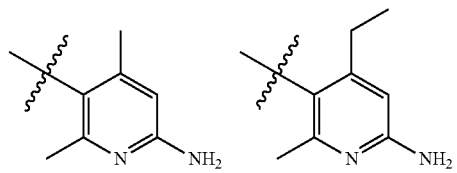

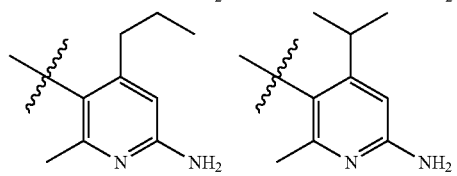

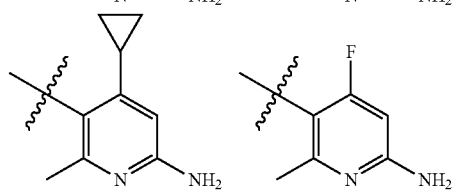

-continued
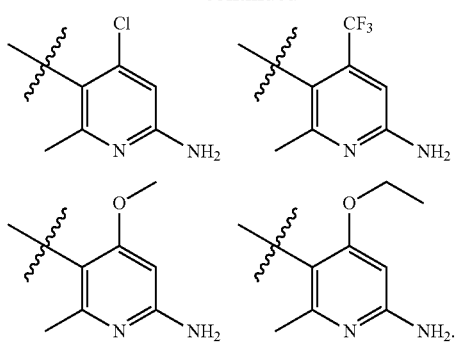
In another embodiment, $R^1$ is selected from:
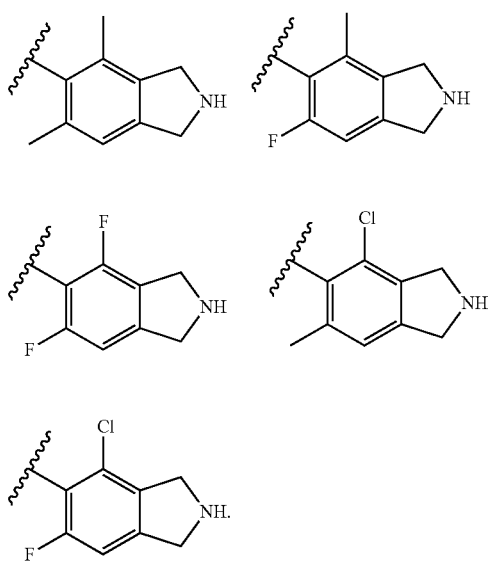
In another embodiment, $R^1$ is:
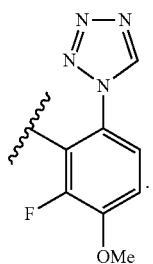
In another embodiment, $R^1$ is selected from:
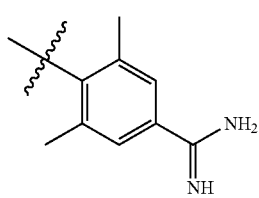
-continued
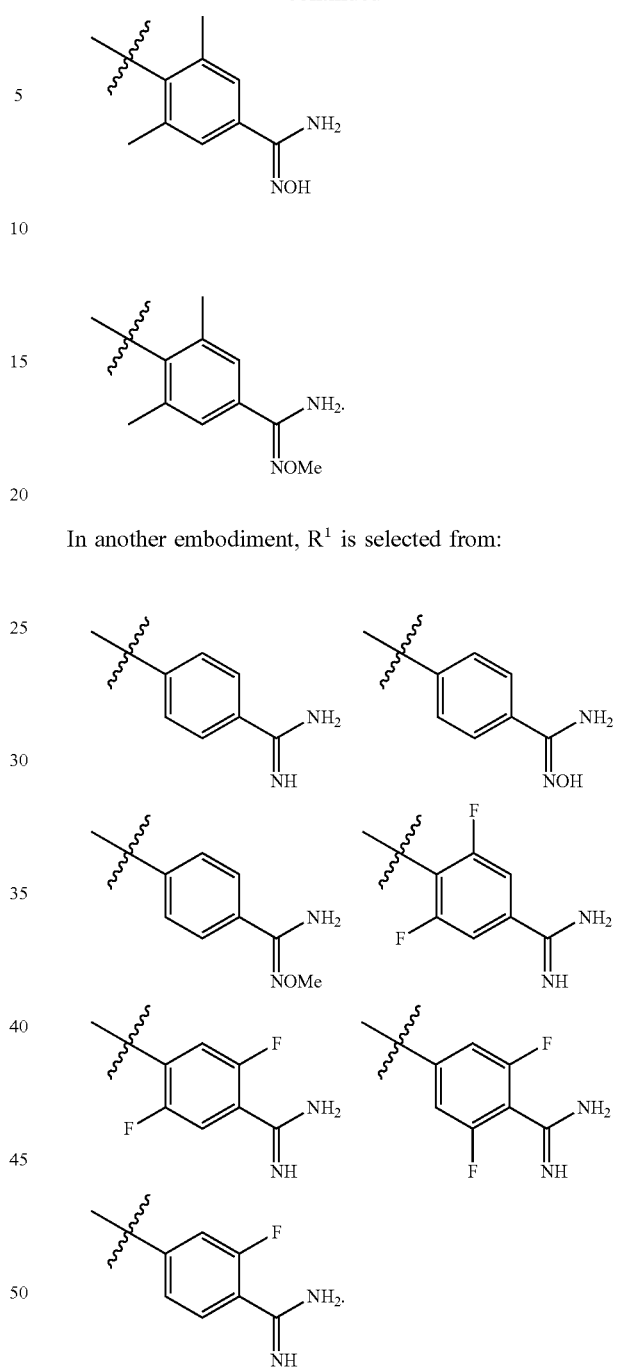
In another embodiment, $R^1$ is selected from:
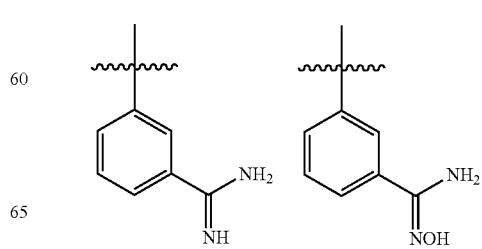

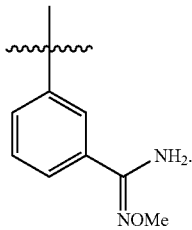

In another embodiment, $R^1$ is selected from:

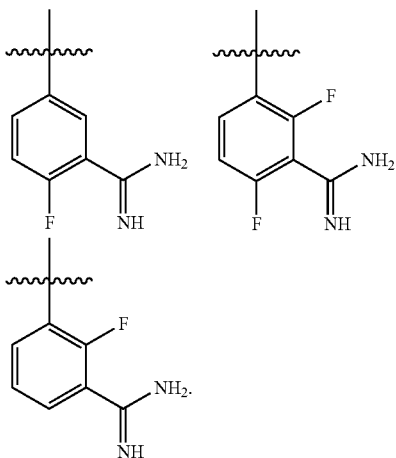

In another embodiment, $R^1$ is selected from:

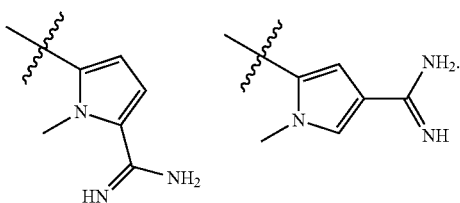

In another embodiment, $R^2$, $R^{30}$, or $R^{31}$ is a 5-6 member monocyclic heteroaryl optionally substituted 1-3 times, preferably 2 times, more preferably 1 time with substituent selected from: $C_1$-$C_3$alkyl; halo, preferably fluoro, chloro, or bromo; $C_1$-$C_3$alkoxy; and hydroxy.

In another embodiment, $R^2$, $R^{30}$, or $R^{31}$ is a 9-10 member bicyclic heteroaryl optionally substituted 1-3 times, preferably, 2 times, more preferably 1 time with substituent selected from: $C_1$-$C_3$alkyl; halo, preferably fluoro, chloro, or bromo; $C_1$-$C_3$alkoxy; and hydroxy.

In another embodiment, $R^2$, $R^{30}$, or $R^{31}$ is a 5-6 member monocyclic heterocyclyl optionally substituted 1-3 times, preferably, 2 times, more preferably 1 time with substituent selected from: $C_1$-$C_3$alkyl; halo, preferably fluoro, chloro, or bromo; $C_1$-$C_3$alkoxy; and hydroxy.

In another embodiment, $R^2$, $R^{30}$, or $R^{31}$ is a 7-10 membered bicyclic heterocycle optionally substituted 1-3 times, preferably, 2 times, more preferably 1 times with substituent selected from: $C_1$-$C_3$alkyl; halo, preferably fluoro, chloro, or bromo; $C_1$-$C_3$alkoxy; and hydroxy.

In another embodiment, $R^2$, $R^{30}$, or $R^{31}$ is —$CH_2$—$R^{50}$, wherein $R^{50}$ is a 5-membered monocyclic heteroaryl optionally substituted 1-3 times with $C_1$-$C_3$alkyl or halo; a 5 membered heterocyclyl that is optionally substituted 1-3 times with $C_1$-$C_3$alkyl or halo; or a 6 membered aryl optionally substituted 1-3 times with $C_1$-$C_3$alkyl or halo.

In another embodiment, $R^2$, $R^{30}$, or $R^{31}$ is —$CR^{50}R^{51}$—$R^{52}$, wherein $R^{50}$ is defined as above, and $R^{51}$ and $R^{52}$ independently are hydrogen, deuterium, $C_1$-$C_3$alkyl, cyclopropyl, or $R^{51}$ and $R^{52}$ together with the carbon atom they are bonded form a $C_3$-$C_8$cycloalkyl that is optionally substituted with 1-6 deuterium and/or 1-3 times with $C_1$-$C_3$alkyl. In another embodiment, $CR^{51}R^{52}$ is $CD_2$, $CMe_2$, $CHMe$, or

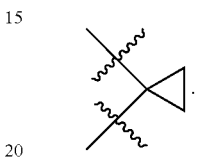

In another embodiment, $R^{51}$ and $R^{52}$ independently are hydrogen, deuterium, $C_1$-$C_4$alkyl, such as methyl.

In another embodiment, $R^2$ is $NR^{18}R^{19}$ and $R^{30}$ or $R^{31}$ is $NR^{32}R^{33}$ wherein $R^{18}$ and $R^{32}$ independently are a 5-membered monocyclic heteroaryl optionally substituted 1-3 times with $C_1$-$C_3$alkyl or halo; a 5 membered heterocyclyl that is optionally substituted 1-3 times with $C_1$-$C_3$alkyl or halo; or a 6 membered aryl optionally substituted 1-3 times with $C_1$-$C_3$alkyl or halo.

In one embodiment, $R^{20}$ and $R^{34}$ independently are optionally substituted $C_1$-$C_6$alkyl. In one embodiment, $R^{20}$ and $R^{34}$ independently are optionally substituted $C_3$-$C_8$cycloalkyl. In one embodiment, $R^{20}$ and $R^{34}$ independently are optionally substituted $C_6$-$C_{10}$ aryl. In one embodiment, $R^{20}$ and $R^{34}$ independently are optionally substituted 5-10 membered heteroaryl. In one embodiment, $R^{20}$ and $R^{34}$ independently are 4-10 membered heterocycle.

In another embodiment, $R^2$ is O—$R^{20}$ and $R^{30}$ or $R^{31}$ is $R^{34}$ wherein $R^{34}$ is a 5-membered monocyclic heteroaryl optionally substituted 1-3 times with $C_1$-$C_3$alkyl or halo; a 5 membered heterocyclyl that is optionally substituted 1-3 times with $C_1$-$C_3$alkyl or halo; or a 6 membered aryl optionally substituted 1-3 times with $C_1$-$C_3$alkyl or halo.

In another embodiment, $R^2$, $R^{30}$, or $R^{31}$ is selected from:

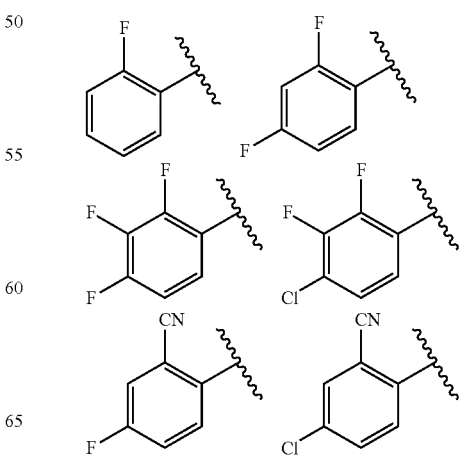

-continued
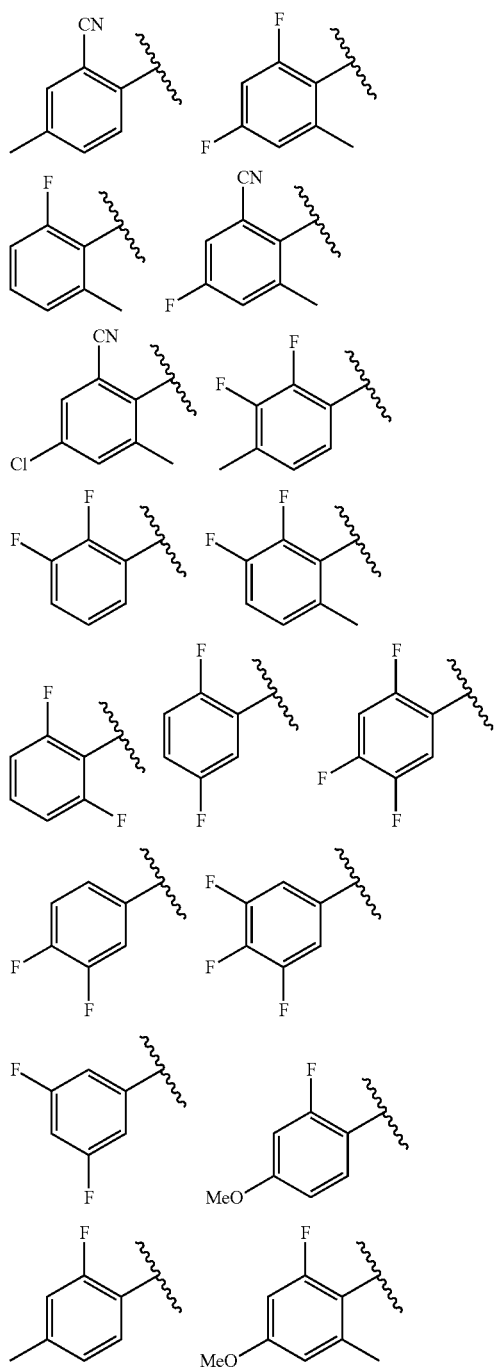
In another embodiment, R², R³⁰, or R³¹ is selected from:
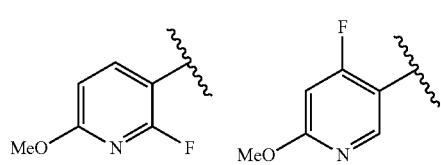
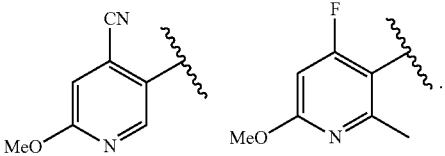
In another embodiment, R², R³⁰, or R³¹ is selected from:
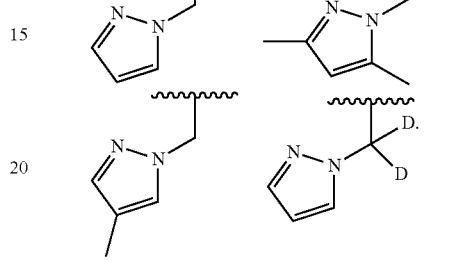
In another embodiment, R², R³⁰, or R³¹ is selected from:
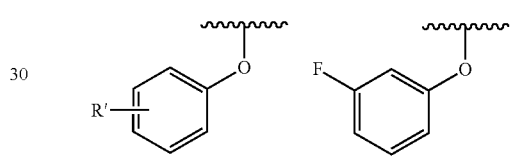
wherein R' is a substituent as defined herein.
Embodiment (C)
In embodiment (C) provided herein are embodiments 1-28 below:
1. In embodiment 1, provided is a compound of Formula (A1), or (B1):
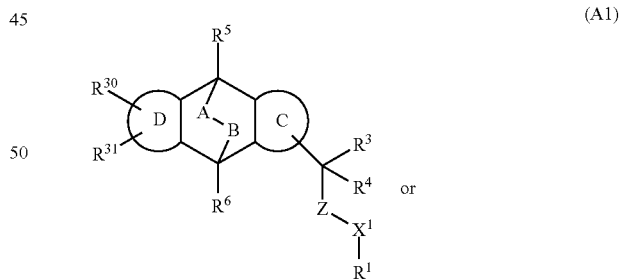
(A1)
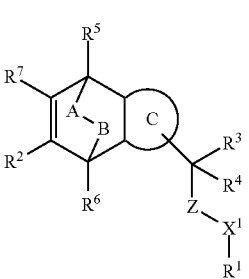
(B1)

or a tautomer thereof, or a pharmaceutically acceptable salt of each thereof, or a solvate of each of the foregoing, wherein A is a bond, O, S(O)$_p$, substituted NH, preferably NCOR$^b$, NCONHR$^c$, or NSO$_2$R$^d$, or CR$^8$R$^9$, wherein p is 0, 1, or 2, and R$^b$, R$^c$ and R$^d$ are independently hydrogen, optionally substituted C$_1$-C$_6$alkyl, optionally substituted C$_3$-C$_8$cycloalkyl, optionally substituted heteroaryl, optionally substituted, heterocyclyl, or optionally substituted aryl;

B is O, S(O)$_p$, NR$^a$, or CR$^{10}$R$^{11}$, provided that when one of A and B is O or S(O)$_p$, the other excludes O or S(O)$_p$;

R$^3$ and R$^4$ are each hydrogen, or R$^3$ and R$^4$ together with the carbon they are attached form C=O, C=NR$^{12}$, wherein R$^{12}$ is hydrogen or C$_1$-C$_6$alkyl, preferably NH or NMe, more preferably, when R$^3$ and R$^4$ together form C=NR$^{12}$, Z is also NR$^{13}$;

Z is NR$^{13}$ or CR$^{14}$R$^{15}$, wherein R$^{13}$, R$^{14}$ and R$^{15}$ are independently hydrogen or C$_1$-C$_6$alkyl;

R$^5$ and R$^6$ independently are hydrogen, C$_1$-C$_6$alkyl, preferably C$_1$-C$_4$alkyl, optionally substituted C$_3$-C$_8$cycloalkyl, halo, preferably, F, or C$_1$-C$_6$alkoxy.

ring C is 5-10 membered optionally substituted heteroaryl, 4-10 membered optionally substituted heterocyclyl, or 6-10 membered optionally substituted aryl;

X$^1$ is CR$^{16}$R$^{17}$, O, S(O)$_q$ wherein q is 0, 1, or 2, NR$^8$, or a bond;

R$^a$, R$^8$, R$^9$, R$^{10}$, and R$^{11}$ are independently hydrogen, OH, C$_1$-C$_6$alkoxy, optionally substituted C$_1$-C$_6$alkyl, or optionally substituted C$_3$-C$_8$cycloalkyl, provided that R$^8$ and R$^9$ and R$^{10}$ and R$^{11}$ are not OH at the same time;

R$^{16}$ and R$^{17}$ independently are hydrogen, deuterium, C$_1$-C$_6$alkyl, preferably C$_1$-C$_4$alkyl, or R$^{16}$ and R$^{17}$ together with the carbon atom they are attached form an optionally substituted C$_3$-C$_6$cycloalkyl, preferably a cyclopropyl ring;

R$^1$ is 5-10 membered optionally substituted heteroaryl or 6-10 membered optionally substituted aryl;

R$^2$ and R$^7$ independently are hydrogen, halo, optionally substituted C$_1$-C$_6$alkyl, 6-10 membered optionally substituted C$_6$-C$_{10}$ aryl, 5-10 membered optionally substituted heteroaryl, 4-10 membered optionally substituted heterocyclyl, —NR$^{18}$R$^{19}$, —OR$^{20}$, —CF$_2$R$^{22}$, —C(=O)R$^{26}$, or —C(=O)NR$^{27}$R$^{28}$, or R$^2$ and R$^7$ together with the atoms they are bonded form a 5-10 membered optionally substituted heteroaryl or a 6-10 membered optionally substituted aryl;

R$^{18}$, R$^{19}$, or R$^{20}$, R$^{22}$, R$^{26}$, R$^{27}$, and R$^{28}$ are independently optionally substituted aryl, optionally substituted heteroaryl, or optionally substituted C$_1$-C$_6$alkyl, or R$^{18}$ and R$^{19}$ or R$^{27}$ and R$^{28}$ together with the nitrogen atom they are bonded form an optionally substituted heterocycle or optionally substituted heteroaryl;

ring D is 5-10 membered optionally substituted heteroaryl, 4-10 membered optionally substituted heterocyclyl, 6-10 membered optionally substituted aryl, or optionally substituted C$_5$-C$_{10}$cycloalkyl;

R$^{30}$ and R$^{31}$ independently are hydrogen, halo, optionally substituted C$_1$-C$_6$alkyl, 6-10 membered optionally substituted C$_6$-C$_{10}$ aryl, 5-10 membered optionally substituted heteroaryl, 4-10 membered optionally substituted heterocyclyl, —NR$^{32}$R$^{33}$, —OR$^{34}$, —CF$_2$R$^{36}$, —C(=O)R$^{40}$, or —C(=O)NR$^{41}$R$^{42}$; or R$^{30}$ and R$^{31}$ together with the atoms they are bonded form a 5-10 membered optionally substituted heteroaryl or a 6-10 membered optionally substituted aryl;

R$^{32}$, R$^{33}$, and R$^{34}$, R$^{36}$, R$^{40}$, R$^{41}$, and R$^{42}$ independently are optionally substituted aryl, optionally substituted heteroaryl, or optionally substituted C$_1$-C$_6$alkyl, or R$^{32}$ and R$^{33}$ or R$^{41}$ and R$^{42}$ together with the nitrogen atom they are bonded form an optionally substituted heterocycle or optionally substituted heteroaryl.

2. The compound of embodiment 1 wherein the compound is of Formula (A2) or (B2):

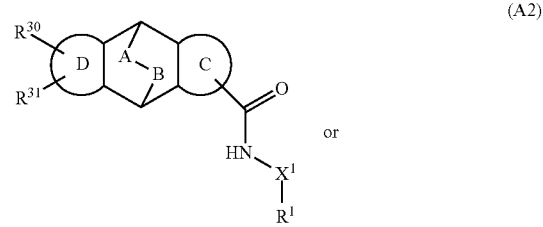

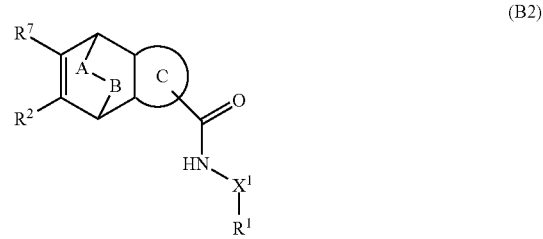

3. The compound of embodiment 2 wherein the compound is of Formula (A2).

4. The compound of embodiment 2 wherein the compound is of Formula (B2).

5. The compound of embodiment 1, wherein A is a bond.

6. The compound of embodiment 2 wherein the compound is of Formula (A2), wherein ring C is optionally substituted 6 membered aryl or optionally substituted 6 member heteroaryl containing 1-3 nitrogen atoms.

7. The compound of embodiment 1, wherein R$^1$ is:
an optionally substituted 6-10 membered heteroaryl comprising an —C=N(—NH$_2$) moiety, or an —NH— moiety; or
a 6 member aryl substituted with 1-4 substituents selected from C$_1$-C$_6$alkyl, C$_3$-C$_6$cycloalkyl, C$_1$-C$_6$alkoxy, halo, 5-6 member heteroaryl, and 4-6 membered heterocycle.

8. The compound of embodiment 1, wherein ring D is:
a 6 membered aryl; or
a 5-6 membered monocyclic heterocycle; or
a 6-10 membered bicyclic heterocycle; or
a 6 membered heteroaryl containing up to 3 nitrogen atoms; or
a 6-9 membered bicyclic heteroaryl.

9. The compound of embodiment 1, wherein one of R$^2$ and R$^7$ and one of R$^{30}$ and R$^{31}$ is hydrogen.

10. The compound of embodiment 1, wherein one of R$^2$ and R$^7$ and one of R$^{30}$ and R$^{31}$ is:
methyl substituted with a 5-6 membered heteroaryl, which heteroaryl is optionally substituted with 1-3: C$_1$-C$_6$alkyl, preferably, C$_1$-C$_3$alkyl; C$_1$-C$_6$alkoxy, preferably C$_1$-C$_3$alkoxy; and halo, preferably, fluoro, chloro, and bromo; or
methyl substituted with a 4-6 membered heterocyclyl optionally substituted with 1-3: C$_1$-C$_6$alkyl, preferably, C$_1$-C$_3$alkyl; C$_1$-C$_6$alkoxy, preferably C$_1$-C$_3$alkoxy; and halo, preferably, fluoro, chloro, and bromo; or
5-10 membered heteroaryl, optionally substituted with 1-3: C$_1$-C$_6$alkyl, preferably, C$_1$-C$_3$alkyl; C$_1$-C$_6$alkoxy, preferably C$_1$-C$_3$alkoxy; and halo, preferably, fluoro, chloro, and bromo;

phenyl, optionally substituted with 1-3: $C_1$-$C_6$alkyl, preferably, $C_1$-$C_3$alkyl; $C_1$-$C_6$alkoxy, preferably $C_1$-$C_3$alkoxy; and halo, preferably, fluoro, chloro, and bromo; or $OR^{20}$ (when $R^2$ or $R^7$) or $OR^{34}$ (when $R^{30}$ or $R^{31}$); or $NR^{18}R^{19}$ (when $R^2$ or R) or $NR^{32}R^{33}$ (when $R^{30}$ or $R^{31}$) wherein $R^{18}$, $R^{19}$, $R^{32}$ and $R^{34}$ are independently hydrogen, optionally substituted $C_1$-$C_6$alkyl, optionally substituted $C_3$-$C_8$cycloalkyl, optionally substituted $C_6$-$C_{10}$aryl, optionally substituted 5-10 membered heteroaryl, or 4-10 membered heterocycle, or $R^{18}$ and $R^{19}$ and $R^{32}$ and together with the nitrogen atom they are attached form optionally substituted 5-10 membered heteroaryl or optionally substituted 4-10 membered heterocycle.

11. The compound of embodiment 1 wherein the compound is of Formula (II) or (III)

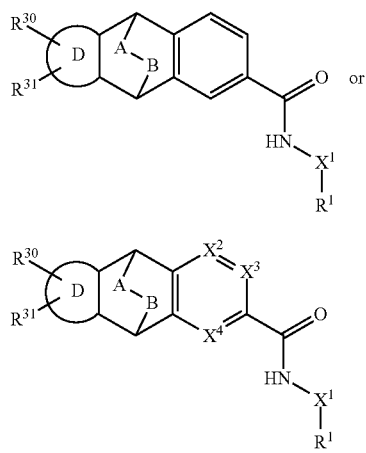

wherein $X^2$, $X^3$ and $X^4$ independently is N, CH or CH optionally substituted with an optionally substituted $C_1$-$C_6$alkyl, provided that at least one of $X^2$, $X^3$ and $X^4$ is N.

12. The compound of embodiment 11, wherein A is a bond.

13. The compound of embodiment 1, wherein the compound is of Formula (IV), (V), or (VI):

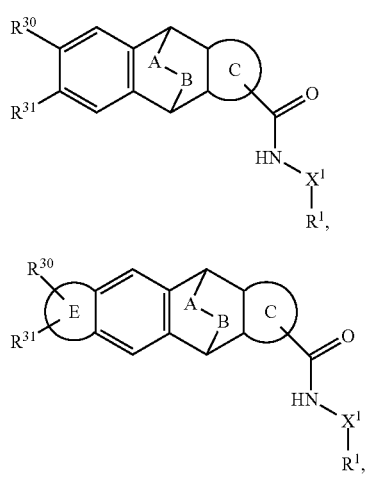

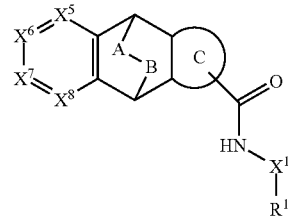

wherein $X^5$-$X^8$ is independently N, CH, or $CR^{31}$, provided that at least one of $X^5$-$X^8$ is N, and also provided that at least one of $X^5$-$X^8$ is $CR^{31}$.

14. The compound of embodiment 13, wherein A is a bond.

15. The compound of embodiment 1, wherein the compound is selected from:

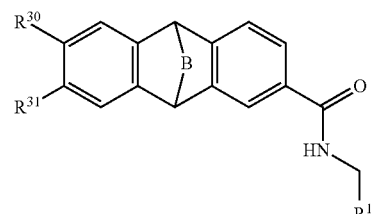

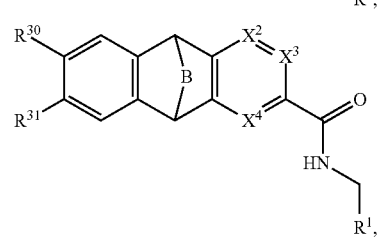

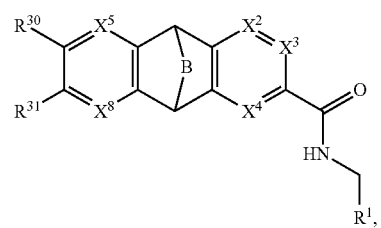

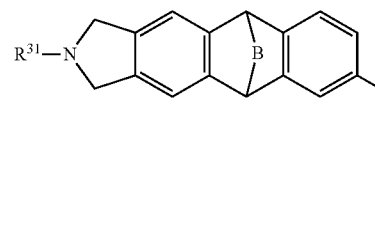

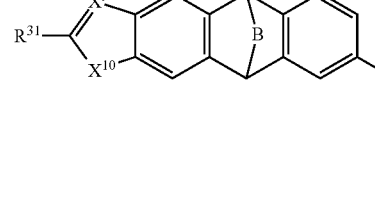

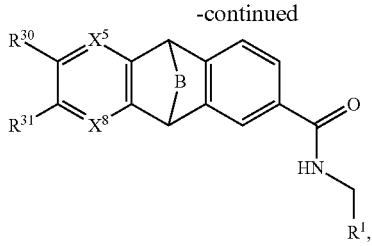

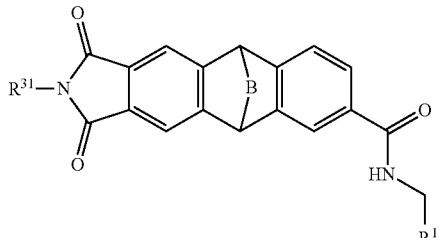

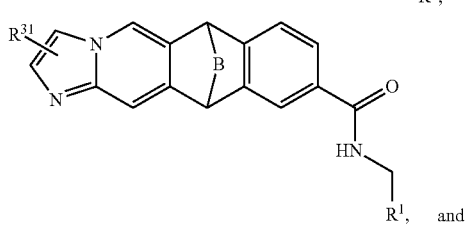

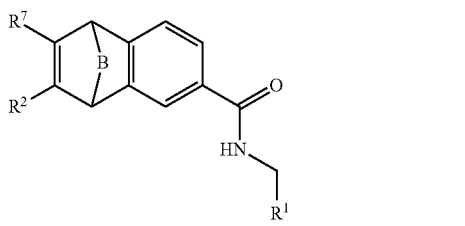

wherein:

$X^2$, $X^3$ and $X^4$ are independently is N, CH or CH optionally substituted with an optionally substituted $C_1$-$C_6$alkyl, provided that at least one of $X^2$, $X^3$ and $X^4$ is N;

$X^5$ and $X^8$ are independently N, CH, or $CR^{31}$, provided that at least one of $X^5$-$X^8$ is N, and also provided that at least one of $X^5$-$X^8$ is $CR^{31}$; and $X^9$ or $X^{10}$ having a double bond is optionally substituted CH or N, and the $X^9$ or $X^{10}$ joined only by single bonds is O, $S(O)_s$ wherein s is 0, 1 or 2, or is optionally substituted $CH_2$.

16. The compound of embodiment 1 wherein the compound is of formula:

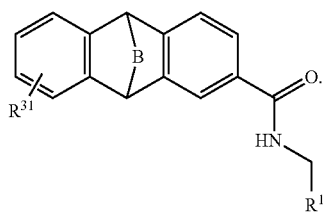

17. The compound of embodiment 1 wherein the compound is of formula:

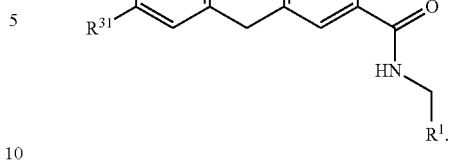

18. The compound of embodiment 1 wherein the compound is of formula:

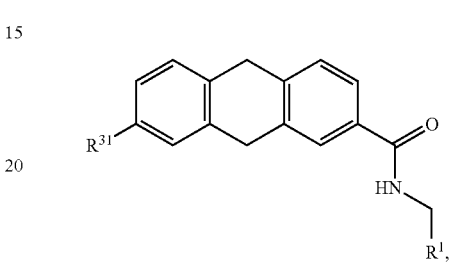

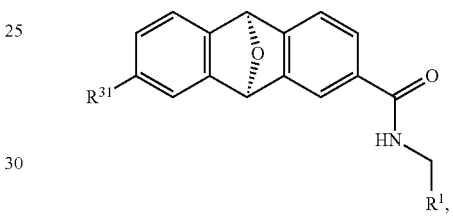

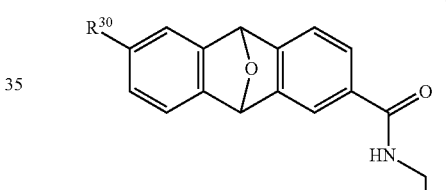

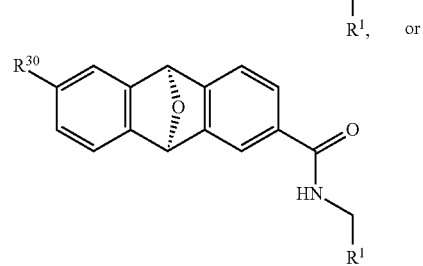

19. The compound of embodiment 1, wherein $R^1$ is selected from:

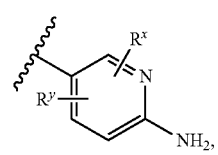

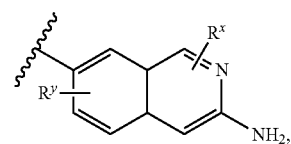

-continued

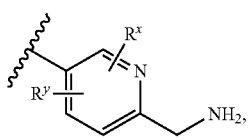

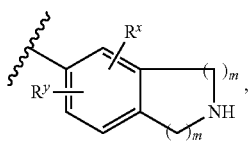

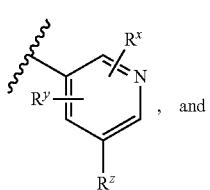, and

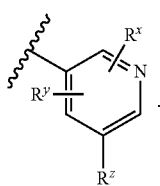.

wherein each $R^x$, $R^y$ or $R^z$ are independently optionally substituted $C_1$-$C_3$alkyl, halo, optionally substituted $C_1$-$C_3$alkoxy, —CN, or a 5 membered optionally substituted heteroaryl preferably containing 3-4 nitrogen atoms; and each m independently is 1 or 2, preferably 1.

20. The compound of embodiment 1, wherein $R^1$ is selected from:

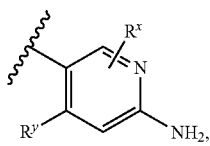

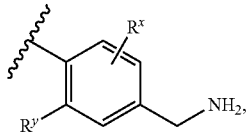

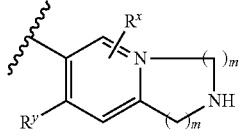

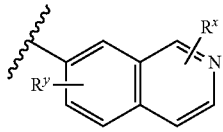

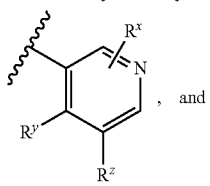, and

-continued

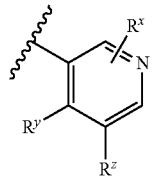

wherein each $R^x$, $R^y$ and $R^z$ are independently optionally substituted $C_1$-$C_3$alkyl, halo, optionally substituted $C_1$-$C_3$alkoxy, —CN, or a 5 membered optionally substituted heteroaryl preferably containing 3-4 nitrogen atoms; and each m independently is 1 or 2, preferably 1.

21. The compound of embodiment 1, wherein $R^1$ is selected from:

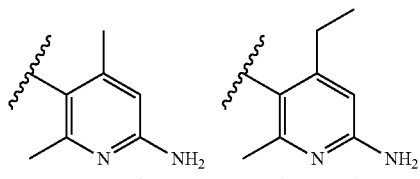

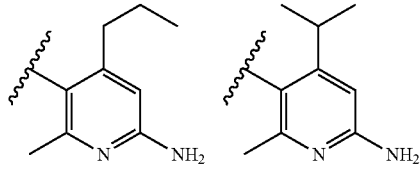

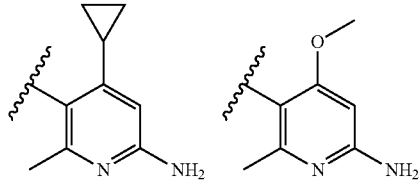

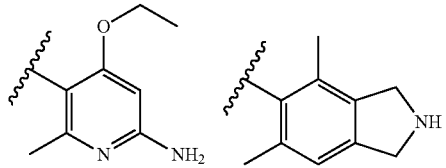

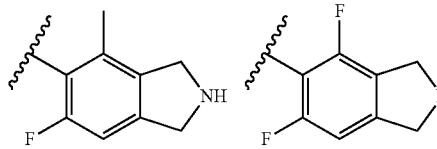

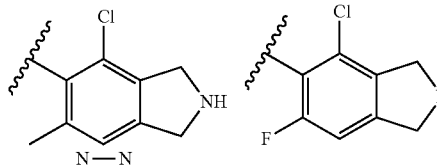

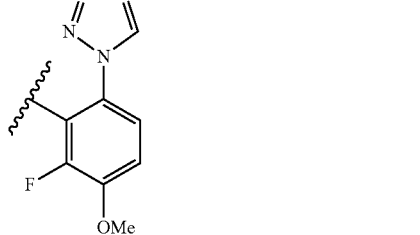

22. The compound of embodiment 1, wherein one of $R^2$ and $R^7$ and one of $R^{30}$ and $R^{31}$ is:

a 5-6 member monocyclic heteroaryl optionally substituted with 1-3: preferably 2, more preferably 1 substituent selected from: $C_1$-$C_3$alkyl; halo, preferably fluoro, chloro, or bromo; $C_1$-$C_3$alkoxy; and hydroxy;

a 9-10 member bicyclic heteroaryl optionally substituted with 1-3: preferably, 2, more preferably 1 substituent selected from: $C_1$-$C_3$alkyl; halo, preferably fluoro, chloro, or bromo; $C_1$-$C_3$alkoxy; and hydroxy;

a 5-6 member monocyclic heterocyclyl optionally substituted with 1-3: preferably 2, more preferably 1 substituent selected from: $C_1$-$C_3$alkyl; halo, preferably fluoro, chloro, or bromo; $C_1$-$C_3$alkoxy; and hydroxy;

a 7-10 membered bicyclic heterocycle optionally substituted with 1-3: preferably 2, more preferably 1 substituent selected from: $C_1$-$C_3$alkyl; halo, preferably fluoro, chloro, or bromo; $C_1$-$C_3$alkoxy; and hydroxy;

—$CH_2$—$R^{50}$ wherein $R^{50}$ is a 5-membered monocyclic heteroaryl optionally substituted with 1-3 $C_1$-$C_3$alkyl or halo, a 5 membered heterocyclyl that is optionally substituted with 1-3 $C_1$-$C_3$alkyl or halo, or a 6 membered aryl optionally substituted with 1-3 $C_1$-$C_3$alkyl or halo; or —$CR^{50}R^{51}R^{52}$ wherein $R^{50}$ is defined as above, and $R^{51}$ and $R^{52}$ independently are deuterium, $C_1$-$C_3$alkyl, cyclopropyl, or $R^{51}$ and $R^{52}$ together with the carbon atom they are attached form a $C_3$-$C_8$cycloalkyl that is optionally substituted with 1-6 deuterium and/or 1-3 times with $C_1$-$C_3$alkyl groups, or —$NR^{18}$—$R^{19}$ (when $R^2$) or $NR^{32}R^{33}$ (when $R^7$) or $OR^{20}$ (when $R^2$) or $OR^{34}$ (when $R^7$), wherein $R^{18}$, $R^{32}$, $R^{20}$ and $R^{34}$ are independently a 5-membered monocyclic heteroaryl optionally substituted with 1-3 $C_1$-$C_3$alkyl or halo; a 5 membered heterocyclyl that is optionally substituted with 1-3 $C_1$-$C_3$alkyl or halo; or a 6 membered aryl optionally substituted with 1-3 $C_1$-$C_3$alkyl or halo, and $R^{19}$ and $R^{33}$ are independently optionally substituted $C_1$-$C_6$alkyl, optionally substituted $C_3$-$C_8$cycloalkyl, optionally substituted $C_6$-$C_{10}$aryl, optionally substituted 5-10 membered heteroaryl, or 4-10 membered heterocycle.

23. The compound of embodiment 1, wherein one of $R^2$ and $R^7$ and one of $R^{30}$ and $R^{31}$ is selected from:

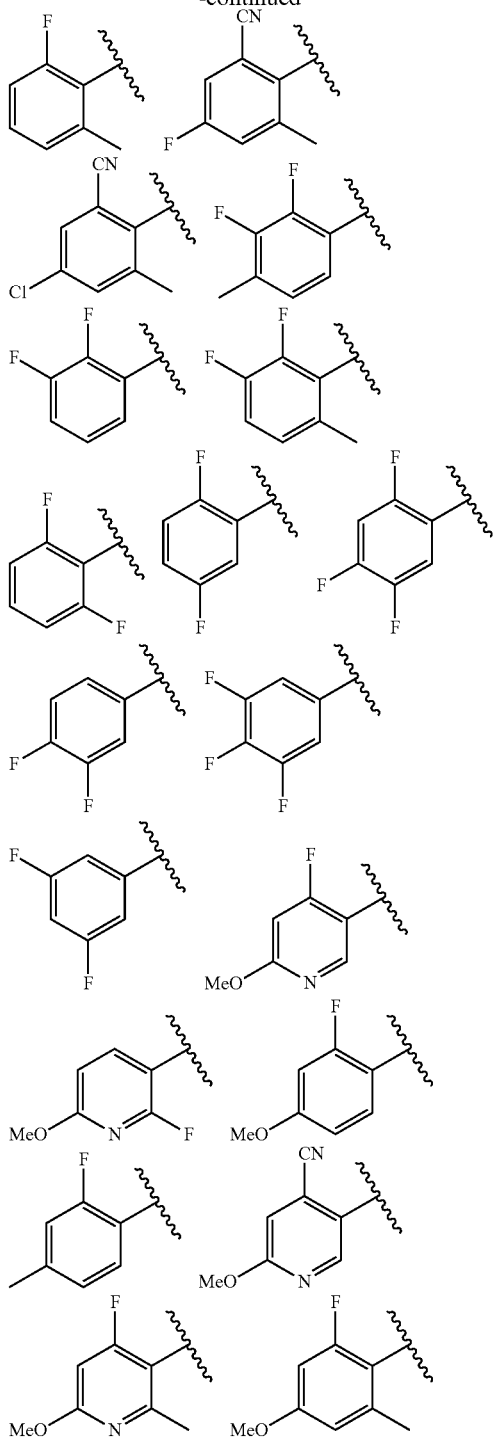

24. The compound of embodiment 1, wherein one of $R^2$ and $R^7$ and one of $R^{30}$ and $R^{31}$ is selected from:

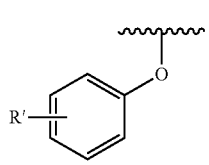

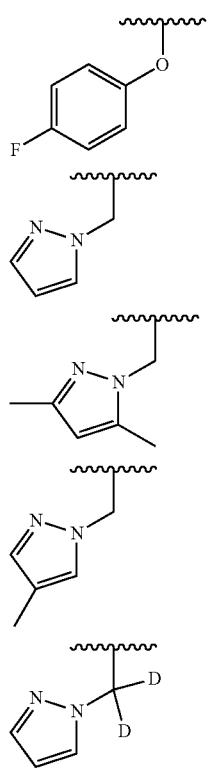
25. The compound of embodiment 1, wherein B is O, and A is a bond.
26. The compound of embodiment 1, wherein B is O.
27. A compound selected from:
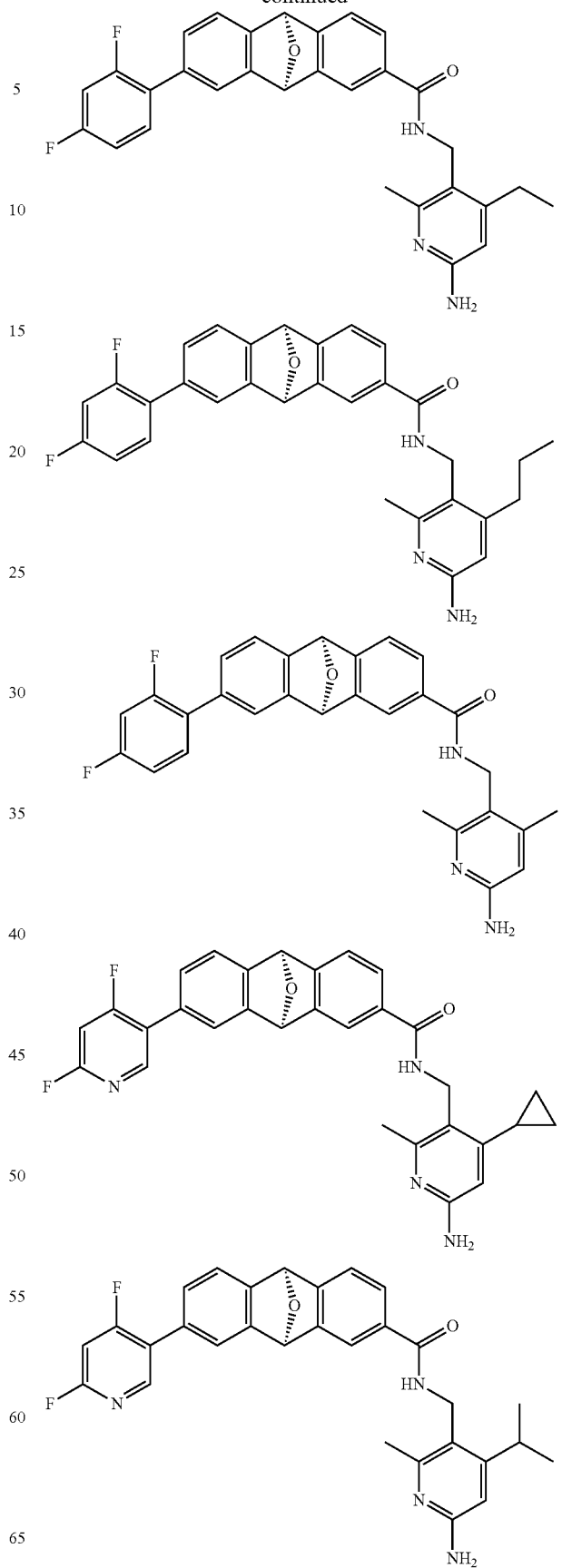

55
-continued
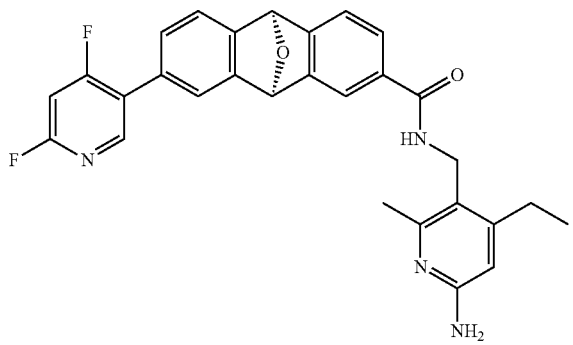
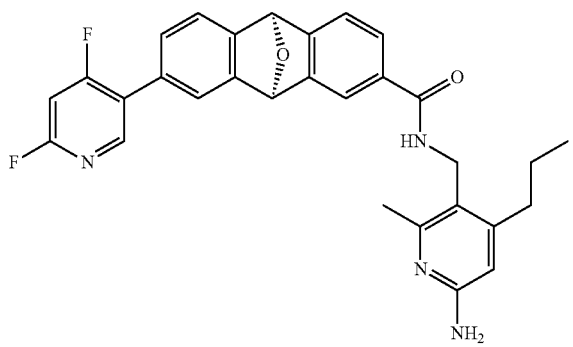
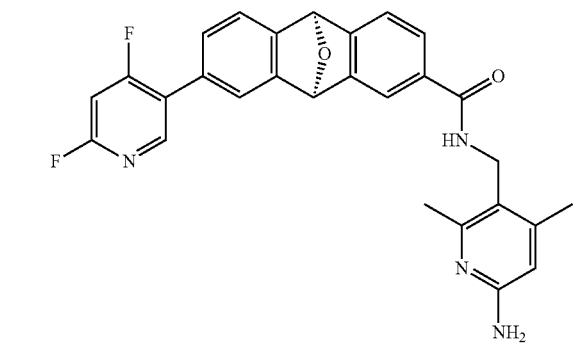
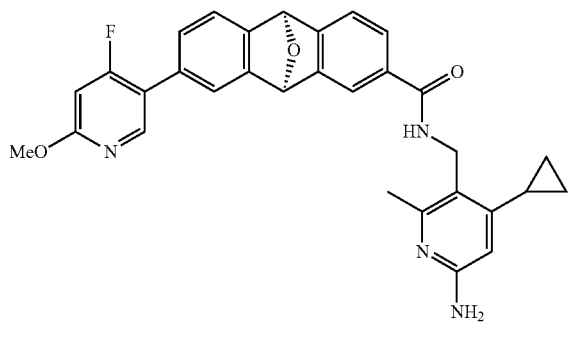
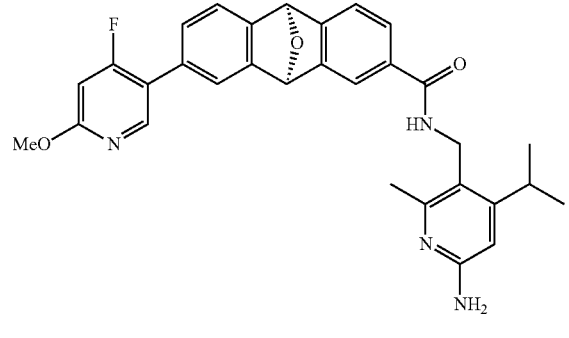
56
-continued
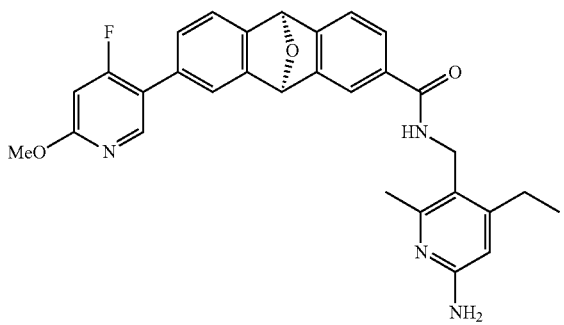
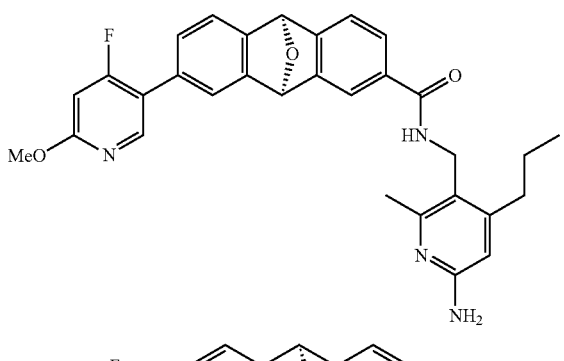
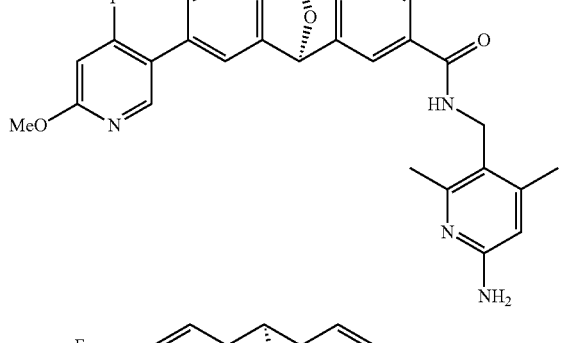
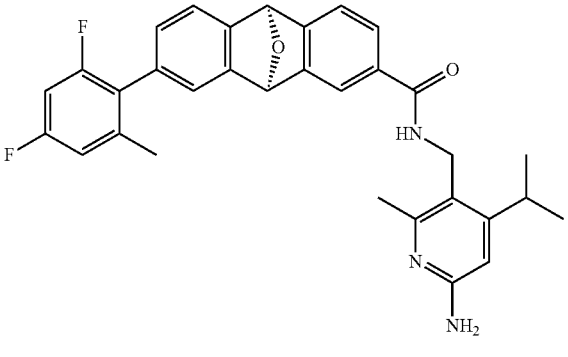

57
-continued
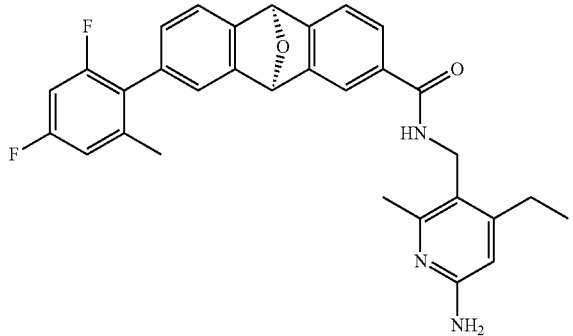
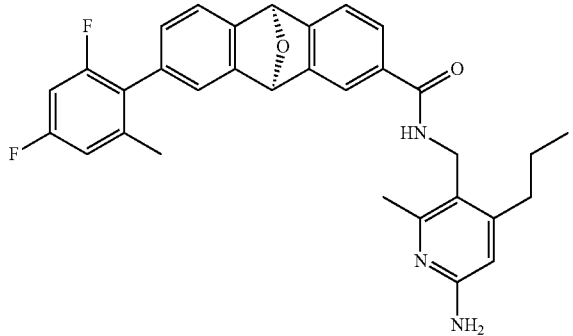
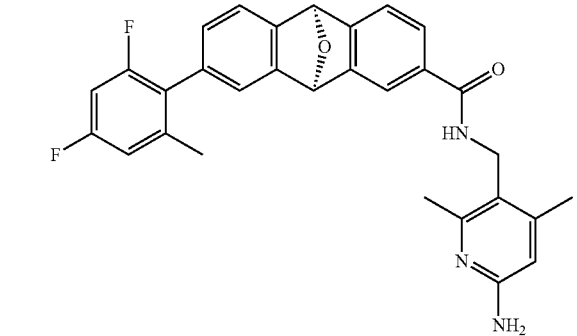
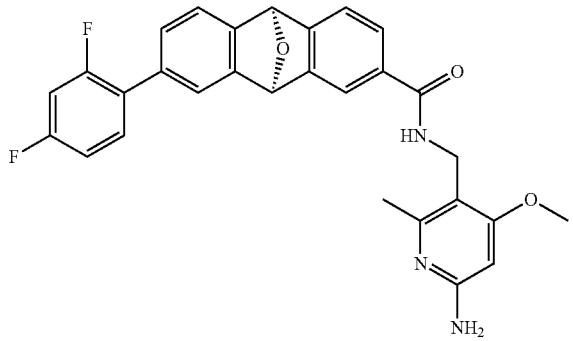
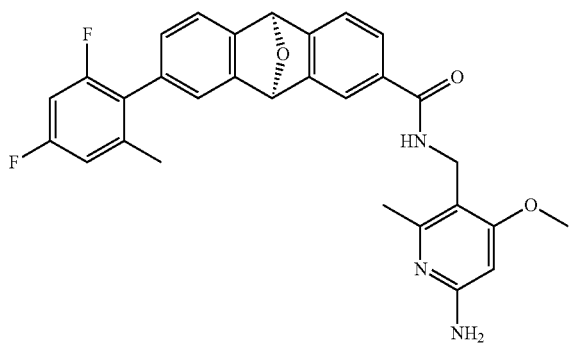
58
-continued

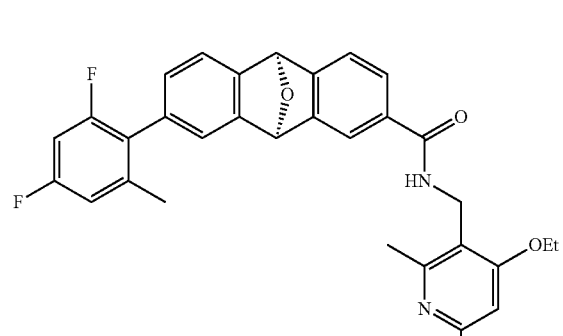
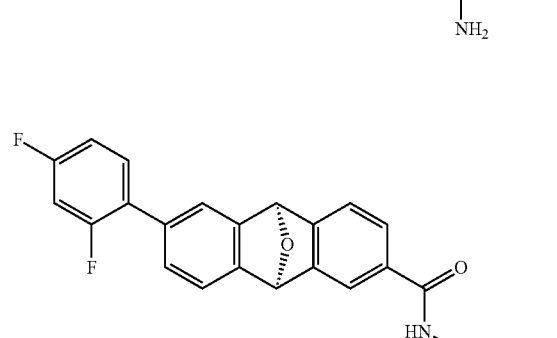
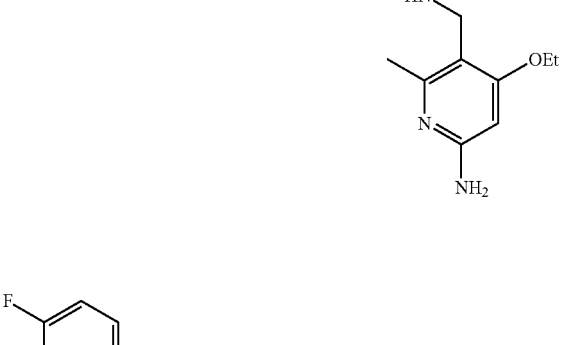
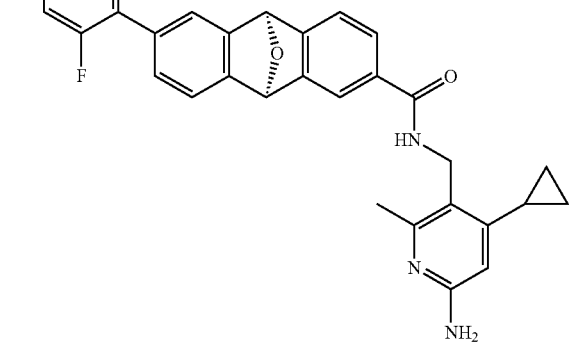

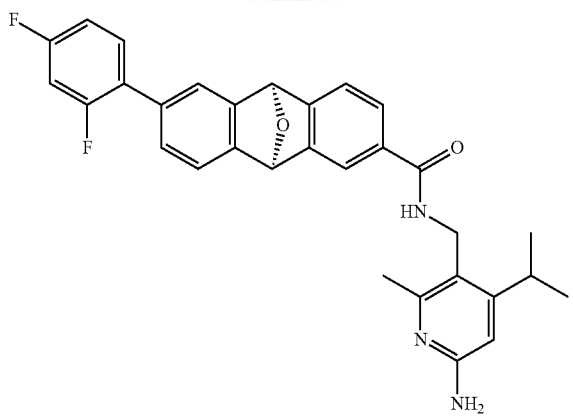
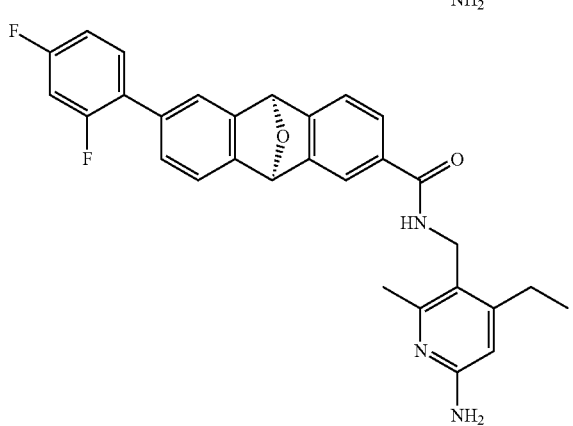
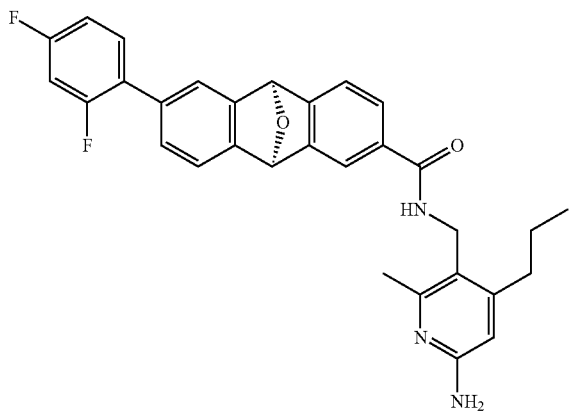
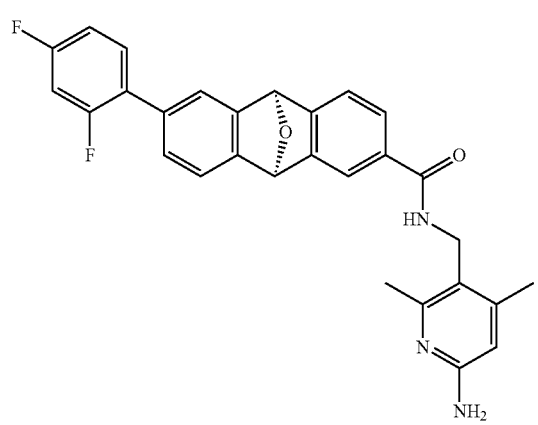
28. A compound selected from:
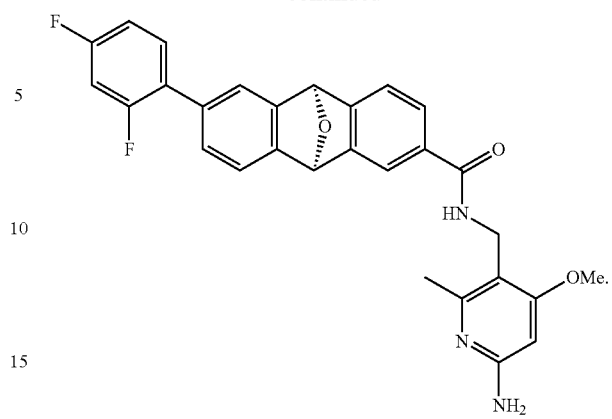
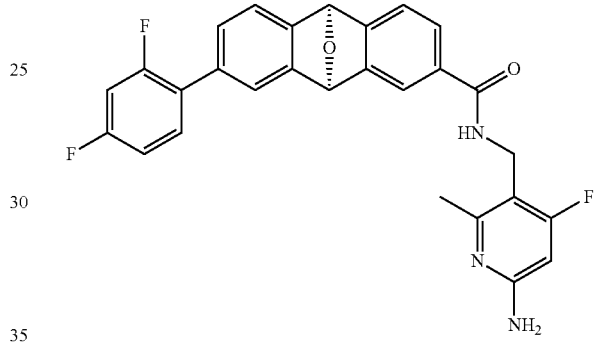
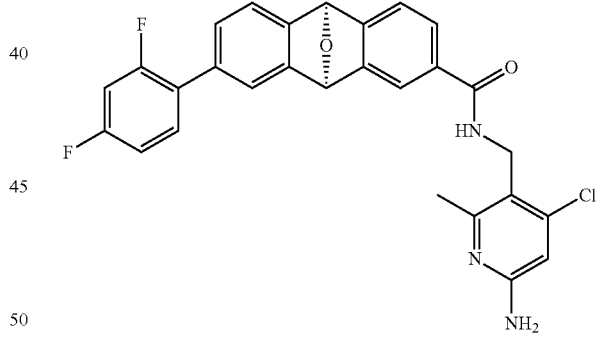
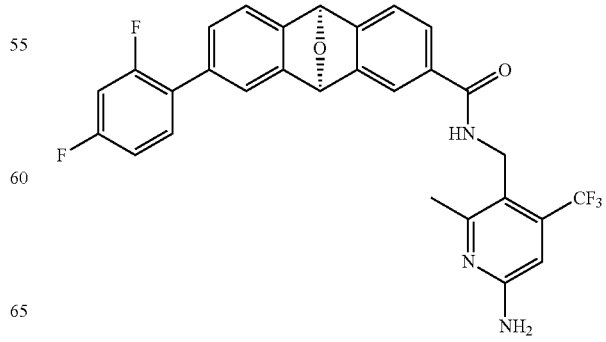

61
-continued
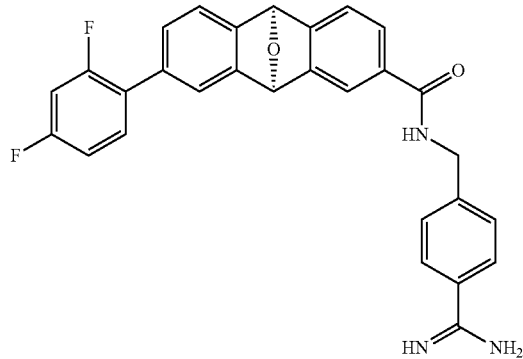
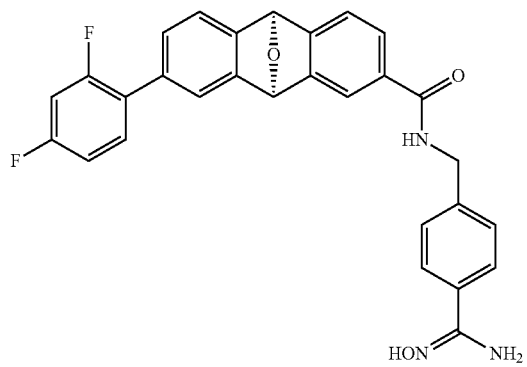
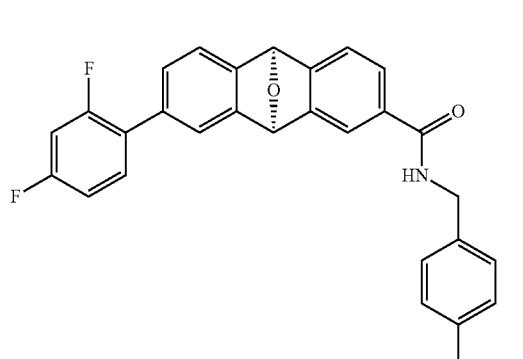
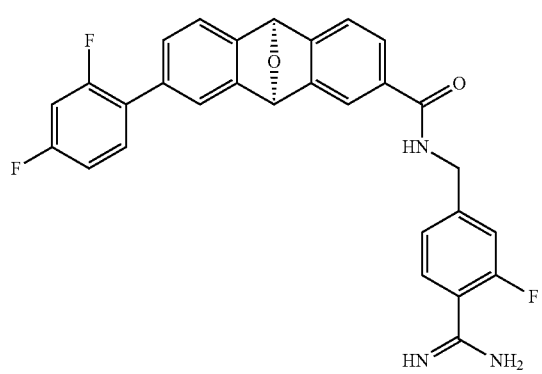
62
-continued
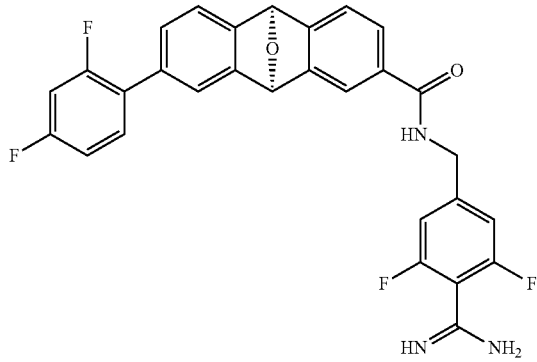
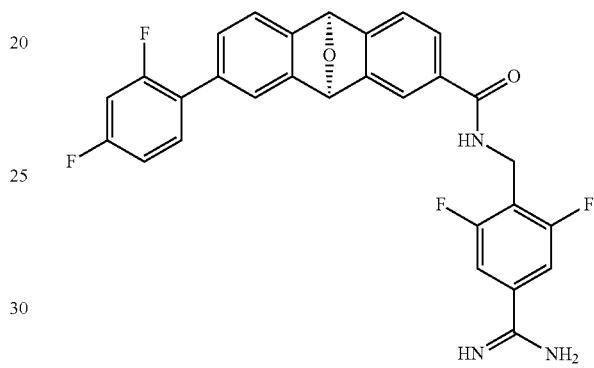
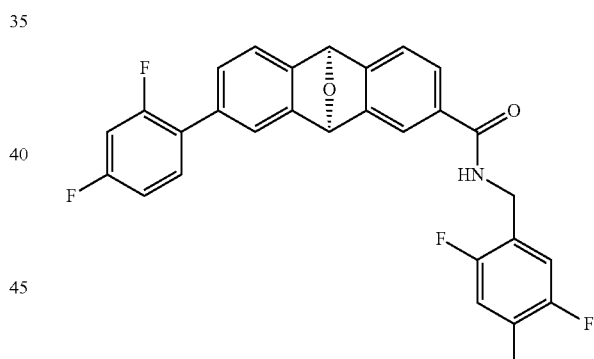
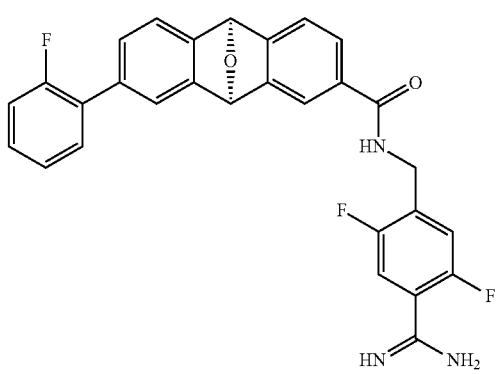

63

-continued

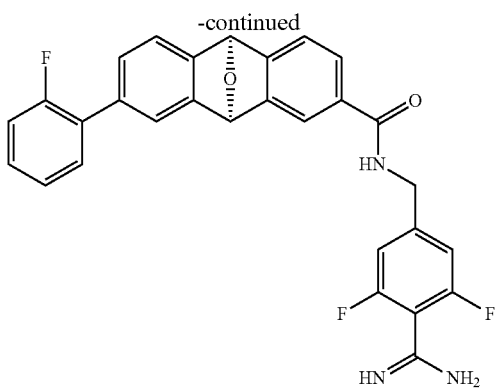

Embodiment (D)

In embodiment (D) provided herein are embodiments (a)-(pp) below.

(a) In embodiment (a), provided is a compound of Formula (I) and (IZ) as described in the first aspect in the Summary, or a pharmaceutically acceptable salt thereof.

(b) The compound of embodiment (a), or a pharmaceutically acceptable salt thereof, wherein $R^2$ and $R^7$ are independently hydrogen, halo, $C_1$-$C_6$alkyl, halo$C_1$-$C_6$alkyl, halo$C_1$-$C_6$alkoxy, hydroxy$C_1$-$C_6$alkyl, $C_1$-$C_6$alkoxy$C_1$-$C_6$alkyl, $C_3$-$C_6$cycloalkyl, mono or bicyclic aryl, mono or bicyclic heteroaryl, monocyclic heterocyclyl, fused heterocyclyl, mono or bicyclic aryl$C_1$-$C_6$alkyl, mono or bicyclic heteroaryl$C_1$-$C_6$alkyl, monocyclic heterocyclyl$C_1$-$C_6$alkyl (wherein the alkylene chain in mono or bicyclic aryl$C_1$-$C_6$alkyl, mono or bicyclic heteroaryl$C_1$-$C_6$alkyl or monocyclic heterocyclyl$C_1$-$C_6$alkyl is optionally substituted with deuterium), spiroheterocycloamino, bridged heterocycloamino, —$NR^{18}R^{19}$, —$OR^{20}$, —$CHFR^{21}$, —$CF_2R^{22}$, $SR^{23}$, $SOR^{24}$, —$C(=O)R^{26}$, —$C(=O)NR^{27}R^{28}$, or —$NR^{18}C(=O)R^{29}$, wherein $R^{18}$, $R^{19}$, $R^{20}$, $R^{21}$, $R^{22}$, $R^{23}$, $R^{24}$, $R^{26}$, $R^{27}$, $R^{28}$, and $R^{29}$ are independently hydrogen, $C_1$-$C_6$alkyl, $C_3$-$C_6$cycloalkyl, $C_3$-$C_6$cycloalkyl$C_1$-$C_6$alkyl, mono or bicyclic aryl, mono or bicyclic heteroaryl, or monocyclic heterocyclyl; or $R^{18}$ and $R^{19}$ or $R^{27}$ and $R^{28}$ together with the nitrogen atom they are attached form heterocycloamino, or mono or bicyclic heteroaryl wherein each of the aforementioned ring in $R^2$ and $R^7$, by itself or as part of another group, is optionally substituted with $R^j$, $R^k$ or $R^l$ independently selected from $C_1$-$C_6$alkyl, $C_2$-$C_6$alkenyl, $C_3$-$C_6$cycloalkyl, $C_1$-$C_6$alkoxy, hydroxy, halo, halo$C_1$-$C_6$alkyl, halo$C_1$-$C_6$alkoxy, $C_1$-$C_6$alkylthio, $C_1$-$C_6$alkylsulfonyl, amino, $C_1$-$C_6$alkylamino, di$C_1$-$C_6$alkylamino, amino$C_1$-$C_6$alkyl, cyano, monocyclic heteroaryl (wherein monocyclic heteroaryl is optionally substituted with one, two or three substituents independently selected from $C_1$-$C_6$alkyl, $C_3$-$C_6$cycloalkyl, $C_1$-$C_6$alkoxy, hydroxy, halo, halo$C_1$-$C_6$alkyl, halo$C_1$-$C_6$alkoxy, amino, $C_1$-$C_6$alkylamino, di$C_1$-$C_6$alkylamino, and cyano) and monocyclic heterocyclyl (wherein the monocyclic heterocyclyl is optionally substituted with one, two or three substituents independently selected from $C_1$-$C_6$alkyl, $C_3$-$C_6$cycloalkyl, $C_1$-$C_6$alkoxy, hydroxy, halo, halo$C_1$-$C_6$alkyl, halo$C_1$-$C_6$alkoxy, amino, $C_1$-$C_6$alkylamino, and di$C_1$-$C_6$alkylamino).

(c). The compound of embodiment (a), or a pharmaceutically acceptable salt thereof, wherein $R^2$ and $R^7$ together with the atoms they are bonded to form ring D:

64

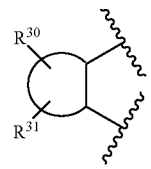

where ring D is phenyl, mono or bicyclic heteroaryl, monocyclic heterocyclyl, fused heterocyclyl, or $C_5$-$C_6$cycloalkyl. In one embodiment, ring D is phenyl or monocyclic heteroaryl. In another embodiment, ring D is phenyl.

(d). The compound of any one of embodiments (a)-(c), or a pharmaceutically acceptable salt thereof, wherein $R^5$ and $R^6$ are each hydrogen.

(e). The compound of any one of embodiments (a)-(c), or a pharmaceutically acceptable salt thereof, wherein $R^5$ and $R^6$ are independently hydrogen or methyl.

(f). The compound of any one of embodiments (a)-(c), or a pharmaceutically acceptable salt thereof, wherein $R^5$ and $R^6$ are independently hydrogen or fluoro.

(g). The compound of any one of embodiments (a)-(f), or a pharmaceutically acceptable salt thereof, wherein B is bond, O, $NCOR^b$, $NSO_2R^d$ or $CR^8R^9$, and A is a bond, $NR^a$, or $CR^{10}R^{11}$, preferably $R^a$ is hydrogen, $C_1$-$C_3$alkyl, or $C_3$-$C_4$cycloalkyl, $R^b$ and $R^d$ are independently $C_1$-$C_3$alkyl, $C_3$-$C_4$cycloalkyl, or $C_3$-$C_4$heterocyclyl, and $R^8$, $R^9$, $R^{10}$, and $R^{11}$ are independently hydrogen or methyl, more preferably hydrogen.

(h). The compound of embodiment (g), or a pharmaceutically acceptable salt thereof, wherein B is bond, O or $CR^8R^9$, and A is a bond, $NR^a$ or $CR^{10}R^{11}$.

(i). The compound of embodiment (g), or a pharmaceutically acceptable salt thereof, wherein B is O or $CR^8R^9$, and A is a bond or $CR^{10}R^{11}$.

(j). The compound of embodiment (g), or a pharmaceutically acceptable salt thereof, wherein B is O or $CR^8R^9$, and A is a bond.

(k). The compound of any one of embodiments (a)-(f), or a pharmaceutically acceptable salt thereof, wherein B is O or $CR^8R^9$, and A is a bond or $CR^{10}R^{11}$, provided B is not O when A is $CR^{10}R^{11}$, preferably $R^8$, $R^9$, $R^{10}$, and $R^{11}$ are independently hydrogen or methyl, more preferably hydrogen.

(l). The compound of any one of embodiments (a)-(f), or a pharmaceutically acceptable salt thereof, wherein B is O, and A is a bond.

(m). The compound of any one of embodiments (a)-(f), or a pharmaceutically acceptable salt thereof, wherein B is bond, and A is $NR^a$ wherein $R^a$ is $C_1$-$C_6$alkyl.

(n). The compound of any one of embodiments (a)-(f), or a pharmaceutically acceptable salt thereof, wherein B is $CR^8R^9$, and A is a bond, and preferably $R^8$ and $R^9$ are hydrogen.

(o). The compound of any one of embodiments (a)-(n), or a pharmaceutically acceptable salt thereof, wherein ring C is phenyl optionally substituted, in addition to —$CR^3R^4$—Z—$X^1$—$R^1$, with a substituent selected from $C_1$-$C_6$alkyl, $C_1$-$C_6$alkoxy, hydroxy, halo, halo$C_1$-$C_6$alkyl, halo$C_1$-$C_6$alkoxy and cyano. In one embodiment the substituent is fluoro or methyl.

(p). The compound of any one of embodiments (a)-(n), or a pharmaceutically acceptable salt thereof, wherein ring C is phenyl.

(q). The compound of embodiment (o) or (p), or a pharmaceutically acceptable salt thereof, wherein the —CR³R⁴—Z—X¹—R¹ group is attached to the carbon in the phenyl ring as shown in the structures (I') or (I") below:

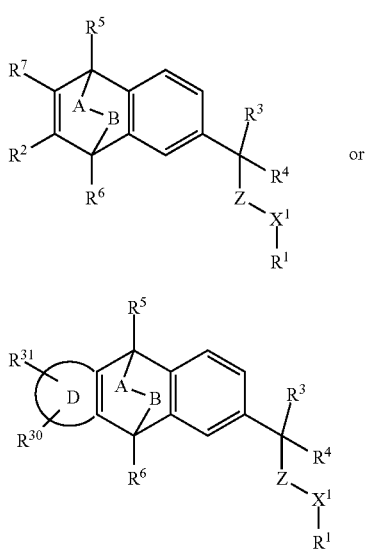

(r). The compound of any one of embodiments (a)-(n), or a pharmaceutically acceptable salt thereof, wherein ring C is monocyclic heteroaryl ring optionally substituted, in addition to —CR³R⁴—Z—X¹—R¹, with a substituent selected from $C_1$-$C_6$alkyl, $C_1$-$C_6$alkoxy, hydroxy, halo, halo$C_1$-$C_6$alkyl, halo$C_1$-$C_6$alkoxy, and cyano. In one embodiment, the monocyclic heteroaryl ring is pyridinyl. In another embodiment, ring C is pyridinyl wherein the —CR³R⁴—Z—X¹—R¹ group is attached to the carbon on the pyridinyl ring that corresponds to the carbon in the phenyl ring in the structures shown in embodiment (q) above.

(s). The compound of any one of embodiments (a)-(n), or a pharmaceutically acceptable salt thereof, wherein ring C is monocyclic heteroaryl ring, preferably the heteroaryl ring is pyridinyl. In one embodiment, the compound has the structure (I''') below:

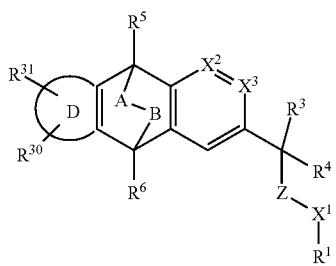

where $X^2$ or $X^3$ is N, preferably $X^3$ is N.

(t) The compound of any one of embodiments (a)-(s), or a pharmaceutically acceptable salt thereof, wherein R³ and R⁴ together with the carbon atom to which they are attached form C=O.

(u) The compound of any one of embodiments (a)-(s), or a pharmaceutically acceptable salt thereof, wherein R³ and R⁴ are independently hydrogen, fluoro, or $C_1$-$C_6$alkyl.

(v) The compound of any one of embodiments (a)-(s), or a pharmaceutically acceptable salt thereof, wherein R³ and R⁴ are independently hydrogen or methyl.

(w) The compound of any one of embodiments (a)-(s), or a pharmaceutically acceptable salt thereof, wherein R³ and R⁴ together with the carbon atom to which they are attached form $C_3$-$C_6$cycloalkyl, preferably cyclopropylene.

(x) The compound of any one of embodiments (a)-(s), or a pharmaceutically acceptable salt thereof, wherein R³ and R⁴ together with the carbon atom to which they are attached form C=NR¹² (wherein R¹² is hydrogen, $C_1$-$C_6$alkyl, $C_1$-$C_6$alkoxy, or hydroxy, preferably R¹² is hydrogen, methyl, methoxy, ethoxy or hydroxy)

(y) The compound of any one of embodiments (a)-(w), or a pharmaceutically acceptable salt thereof, wherein Z is a bond.

(z) The compound of any one of embodiments (a)-(v) and (x), or a pharmaceutically acceptable salt thereof, wherein Z is NR¹³, preferably R¹³ is hydrogen.

(aa) The compound of any one of embodiments (a)-(w), or a pharmaceutically acceptable salt thereof, wherein Z is CR¹⁴R¹⁵.

(bb) The compound of any one of embodiments (a)-(aa), or a pharmaceutically acceptable salt thereof, wherein X¹ is bond.

(cc) The compound of any one of embodiments (a)-(aa), or a pharmaceutically acceptable salt thereof, wherein X¹ is C=NR⁸.

(dd) The compound of any one of embodiments (a)-(aa), or a pharmaceutically acceptable salt thereof, wherein X¹ is CR¹⁶R¹⁷, preferably R¹⁶ and R¹⁷ are independently hydrogen, deuterium, or $C_1$-$C_6$alkyl; more preferably R¹⁶ and R¹⁷ are each hydrogen.

(ee) The compound of any one of embodiments (a)-(aa), or a pharmaceutically acceptable salt thereof, wherein X¹ is O or S(O)$_q$.

(ff) The compound of any one of embodiments (a)-(s), or a pharmaceutically acceptable salt thereof, wherein —(CR³R⁴)—Z—X¹— is —CONHCH₂—.

(gg) The compound of any one of embodiments (a)-(ff), or a pharmaceutically acceptable salt thereof, wherein R¹ is mono or bicyclic aryl optionally substituted with R$^e$, R$^f$, or R$^g$ independently selected from $C_1$-$C_6$alkyl, $C_2$-$C_6$alkenyl, $C_3$-$C_6$cycloalkyl, $C_1$-$C_6$alkoxy, hydroxy, halo, halo$C_1$-$C_6$alkyl, halo$C_1$-$C_6$alkoxy, amino, $C_1$-$C_6$alkylamino, di$C_1$-$C_6$alkylamino, amino$C_1$-$C_6$alkyl, aminocarbonyl, amidino$C_1$-$C_6$alkyl, —C(=NR$^h$)NHR$^i$ (where R$^h$ and R$^i$ are independently hydrogen, hydroxy, $C_1$-$C_6$alkoxy, acyl, —C(O)O$C_1$-$C_6$alkyl, a natural or an unnatural amino acid residue, a dipeptidic residue, —CO(ethylene)SO₂R$^u$ (where R$^u$ is $C_1$-$C_6$alkyl, optionally substituted monocyclic heteroaryl, optionally substituted phenyl, or optionally substituted monocyclic heterocyclyl), or —CO(CH₂)$_{2-3}$OR$^v$ (where R$^v$ is hydrogen, $C_1$-$C_6$alkoxy$C_{1-3}$alkyl, or optionally substituted monocyclic heterocyclyl)), cyano, monocyclic heteroaryl (wherein the monocyclic heteroaryl is optionally substituted with one, two or three substituents independently selected from $C_1$-$C_6$alkyl, $C_3$-$C_6$cycloalkyl, $C_1$-$C_6$alkoxy, hydroxy, halo, halo$C_1$-$C_6$alkyl, halo$C_1$-$C_6$alkoxy, amino, $C_1$-$C_6$alkylamino, di$C_1$-$C_6$alkylamino, and cyano) and monocyclic heterocyclyl (wherein the monocyclic heterocyclyl is optionally substituted with one, two or three substituents independently selected from $C_1$-$C_6$alkyl, $C_3$-$C_6$cycloalkyl, $C_1$-$C_6$alkoxy, hydroxy, halo, halo$C_1$-$C_6$alkyl, halo$C_1$-$C_6$alkoxy, amino, $C_1$-$C_6$alkylamino, and di$C_1$-$C_6$alkylamino).

In one embodiment, R$^1$ is phenyl optionally substituted with R$^e$, R$^f$, or R$^g$ independently selected from methyl, ethyl, isopropyl, n-propyl, cyclopropyl, methoxy, ethoxy, hydroxy, trifluoromethyl, trifluoromethoxy, difluoromethyl, difluoromethoxy, fluoro, chloro, amino, aminomethyl, —CONH$_2$, —CONHCH$_3$, tetrahydropyran-4-yl, 3,6-dihydro-2H-pyran-4-yl, 2,4-dihydrofuran-3-yl, tetrazol-1-yl, amidinoC$_1$-C$_6$alkyl, —C(=NR$^h$)NHR$^i$ (where R$^h$ and R$^i$ are independently hydrogen, hydroxy, C$_1$-C$_6$alkoxy, acyl, —C(O)OC$_1$-C$_6$alkyl, a natural or an unnatural amino acid residue, —CO(ethylene)SO$_2$R$^u$ (where R$^u$ is C$_1$-C$_6$alkyl, optionally substituted monocyclic heteroaryl, optionally substituted phenyl, or optionally substituted monocyclic heterocyclyl), or —CO(CH$_2$)$_{2-3}$OR$^v$ (where R$^v$ is hydrogen, C$_1$-C$_6$alkoxyC$_{1-3}$alkyl, or optionally substituted monocyclic heterocyclyl)), cyano, or 1,2,4-oxadiazol-5(4H)-one-3-yl. In another embodiment, R$^e$ and R$^f$ are attached to the carbon atoms of the phenyl ring that are ortho to the carbon of the phenyl ring attached to X$^1$.

In yet another embodiment, R$^1$ is phenyl optionally substituted with R$^e$ and R$^f$ independently selected from methyl, ethyl, isopropyl, n-propyl, cyclopropyl, methoxy, ethoxy, hydroxy, trifluoromethyl, trifluoromethoxy, difluoromethyl, difluoromethoxy, fluoro, chloro, —CONH$_2$, —CONHCH$_3$, tetrahydropyran-4-yl, 3,6-dihydro-2H-pyran-4-yl, 2,4-dihydrofuran-3-yl, tetrazol-1-yl, and cyano, and is substituted with R$^g$ wherein R$^g$ is amino, aminomethyl, amidinoC$_1$-C$_6$alkyl, —C(=NR$^h$)NHR$^i$ (where R$^h$ and R$^i$ are independently hydrogen, hydroxy, C$_1$-C$_6$alkoxy, acyl, —C(O)OC$_1$-C$_6$alkyl, a natural or an unnatural amino acid residue, —CO(ethylene)SO$_2$R$^u$ (where R$^u$ is C$_1$-C$_6$alkyl, optionally substituted monocyclic heteroaryl, optionally substituted phenyl, or optionally substituted monocyclic heterocyclyl), or —CO(CH$_2$)$_{2-3}$OR$^v$ (where R$^v$ is hydrogen, C$_1$-C$_6$alkoxyC$_{1-3}$alkyl, or optionally substituted monocyclic heterocyclyl)) or 1,2,4-oxadiazol-5(4H)-one-3-yl.

In yet another embodiment, R$^1$ is phenyl optionally substituted with R$^e$ and R$^f$ independently selected from methyl, ethyl, isopropyl, n-propyl, cyclopropyl, methoxy, ethoxy, hydroxy, trifluoromethyl, trifluoromethoxy, difluoromethyl, difluoromethoxy, fluoro, chloro, —CONH$_2$, —CONHCH$_3$, tetrahydropyran-4-yl, 3,6-dihydro-2H-pyran-4-yl,2,4-dihydrofuran-3-yl, tetrazol-1-yl, and cyano (Preferably, R$^e$ and R$^f$ are attached to the carbon atoms of the phenyl ring that are ortho to the carbon of the phenyl ring attached to X$^1$) and is substituted with R$^g$ where R$^g$ is amino, aminomethyl, —C(=NR$^h$)NHR$^i$ (where R$^h$ and R$^i$ are independently hydrogen, hydroxy, methoxy, ethoxy, isopropoxy, tert-butoxy, methylcarbonyl, methoxycarbonyl, ethoxycarbonyl, tert-butoxycarboxy, a natural or an unnatural amino acid residue, —CO(ethylene)SO$_2$R$^u$ (where R$^u$ is C$_1$-C$_6$alkyl, optionally substituted monocyclic heteroaryl, optionally substituted phenyl, or optionally substituted monocyclic heterocyclyl), or —CO(CH$_2$)$_2$R$^v$ (where R$^v$ is hydrogen, C$_1$-C$_6$alkoxyC$_{1-3}$alkyl, or optionally substituted monocyclic heterocyclyl)) or 1,2,4-oxadiazol-5(4H)-one-3-yl, and R$^g$ is located at the carbon of the phenyl ring that is para to the carbon of the phenyl ring attached to X$^1$.

In yet another embodiment, R$^1$ is 4-amidino-2,6-dimethylphenyl, 4-aminomethyl-2,6-dimethylphenyl, 4-amidino-2,6-difluorophenyl, 4-amidinophenyl, 3-fluoro-4-amidinophenyl, 4-N'-hydroxyamidinophenyl, 4-N'-hydroxyamidino-2,6-difluorophenyl, 4-N'-methoxyamidino-2,6-difluorophenyl, 4-N'-methoxycarbonylamidino-2,6-difluorophenyl, or 4-N'-methoxyamidinophenyl. In yet another embodiment, R$^1$ is 4-amidino-2,6-dimethylphenyl, 4-amidino-2,6-difluorophenyl, 4-amidinophenyl, 3-fluoro-4-amidinophenyl, 4-N'-hydroxyamidinophenyl, 4-N'-hydroxyamidino-2,6-difluorophenyl, 4-N'-methoxyamidino-2,6-difluorophenyl, 4-N'-methoxycarbonylamidino-2,6-difluorophenyl, 4-N'-ethoxycarbonylamidino-2,6-difluorophenyl, 4-N'-ethoxycarbonylamidinophenyl, 4-N'-methoxyamidinophenyl, or

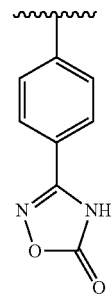

(gg) The compound of any one of embodiments (a)-(ff), or a pharmaceutically acceptable salt thereof, wherein R$^1$ is mono or bicyclic heteroaryl optionally substituted with R$^e$, R$^f$ or R$^g$ independently selected from C$_1$-C$_6$alkyl, C$_2$-C$_6$alkenyl, C$_3$-C$_6$cycloalkyl, C$_1$-C$_6$alkoxy, hydroxy, halo, haloC$_1$-C$_6$alkyl, haloC$_1$-C$_6$alkoxy, amino, C$_1$-C$_6$alkylamino, diC$_1$-C$_6$alkylamino, aminoC$_1$-C$_6$alkyl, aminocarbonyl, amidinoC$_1$-C$_6$alkyl, —C(=NR$^h$)NHR$^i$ (where R$^h$ and R$^i$ are independently hydrogen, hydroxy, C$_1$-C$_6$alkoxy, acyl, —C(O)OC$_1$-C$_6$alkyl, a natural or an unnatural amino acid residue, a dipeptidic residue, —CO(ethylene)SO$_2$R$^u$ (where R$^u$ is C$_1$-C$_6$alkyl, optionally substituted monocyclic heteroaryl, optionally substituted phenyl, or optionally substituted monocyclic heterocyclyl), or —CO(CH$_2$)$_{2-3}$OR$^v$ (where R$^v$ is hydrogen, C$_1$-C$_6$alkoxyC$_{1-3}$alkyl, or optionally substituted monocyclic heterocyclyl)), cyano, monocyclic heteroaryl (wherein the monocyclic heteroaryl is optionally substituted with one, two or three substituents independently selected from C$_1$-C$_6$alkyl, C$_3$-C$_6$cycloalkyl, C$_1$-C$_6$alkoxy, hydroxy, halo, haloC$_1$-C$_6$alkyl, haloC$_1$-C$_6$alkoxy, amino, C$_1$-C$_6$alkylamino, diC$_1$-C$_6$alkylamino, and cyano) and monocyclic heterocyclyl (wherein monocyclic heterocyclyl is optionally substituted with one, two or three substituents independently selected from C$_1$-C$_6$alkyl, C$_3$-C$_6$cycloalkyl, C$_1$-C$_6$alkoxy, hydroxy, halo, haloC$_1$-C$_6$alkyl, haloC$_1$-C$_6$alkoxy, amino, C$_1$-C$_6$alkylamino, and diC$_1$-C$_6$alkylamino).

In one embodiment, R$^1$ is pyridinyl, pyrimidinyl, pyazinyl, pyridazinyl, isoquinolinyl, benzpyrazolyl, or benzisoxazolyl optionally substituted with R$^e$, R$^f$ or R$^g$ independently selected from methyl, ethyl, isopropyl, n-propyl, cyclopropyl, methoxy, ethoxy, hydroxy, trifluoromethyl, trifluoromethoxy, difluoromethyl, difluoromethoxy, fluoro, chloro, amino, aminomethyl, —CONH$_2$, —CONHCH$_3$, tetrahydropyran-4-yl, 3,6-dihydro-2H-pyran4-yl, 2,4-dihydrofuran-3-yl, tetrazol-1-yl, amidinoC$_1$-C$_6$alkyl, —C(=NR$^h$)NHR$^i$ (where R$^h$ and R$^i$ are independently hydrogen, hydroxy, C$_1$-C$_6$alkoxy, acyl, —C(O)OC$_1$-C$_6$alkyl, a natural or an unnatural amino acid residue, —CO(ethylene)SO$_2$R$^u$ (where R$^u$ is C$_1$-C$_6$alkyl, optionally substituted monocyclic heteroaryl, optionally substituted phenyl, or optionally substituted monocyclic heterocyclyl), or —CO(CH$_2$)$_{2-3}$OR$^v$ (where R$^v$ is hydrogen, C$_1$-C$_6$alkoxyC$_{1-3}$alkyl, or optionally substituted monocyclic heterocyclyl)), cyano, and 1,2,4-oxadiazol-5(4H)-one-3-yl.

In another embodiment, $R^1$ is pyridinyl, pyrimidinyl, pyazinyl, pyridazinyl, isoquinolinyl, benzpyrazolyl, or benzisoxazolyl optionally substituted with $R^e$ and $R^f$ independently selected from methyl, ethyl, isopropyl, n-propyl, cyclopropyl, methoxy, ethoxy, hydroxy, trifluoromethyl, trifluoromethoxy, difluoromethyl, difluoromethoxy, fluoro, chloro, —$CONH_2$, —$CONHCH_3$, tetrahydropyran-4-yl, 3,6-dihydro-2H-pyran4-yl, 2,4-dihydrofuran-3-yl, tetrazol-1-yl, and cyano, and substituted with $R^g$ wherein $R^g$ is amino, aminomethyl, amidino$C_1$-$C_6$alkyl, —C(=N$R^h$)NH$R^i$ (where $R^h$ and $R^i$ are independently hydrogen, hydroxy, $C_1$-$C_6$alkoxy, acyl, —C(O)O$C_1$-$C_6$alkyl, a natural or an unnatural amino acid residue, —CO(ethylene)$SO_2R^u$ (where $R^u$ is $C_1$-$C_6$alkyl, optionally substituted monocyclic heteroaryl, optionally substituted phenyl, or optionally substituted monocyclic heterocyclyl), or —CO$(CH_2)_{2-3}OR^v$ (where $R^v$ is hydrogen, $C_1$-$C_6$alkoxy$C_{1-3}$alkyl, or optionally substituted monocyclic heterocyclyl)) or 1,2,4-oxadiazol-5(4H)-one-3-yl.

In yet one embodiment, $R^1$ is pyridin-3-yl optionally substituted with $R^e$ and $R^f$ independently selected from methyl, ethyl, isopropyl, n-propyl, cyclopropyl, methoxy, ethoxy, hydroxy, trifluoromethyl, trifluoromethoxy, difluoromethyl, difluoromethoxy, fluoro, chloro, —$CONH_2$, —$CONHCH_3$, tetrahydropyran-4-yl, 3,6-dihydro-2H-pyran-4-yl, 2,4-dihydrofuran-3-yl, tetrazol-1-yl, and cyano, and wherein $R^e$ and $R^f$ are attached to the C-2 and C4 position of the pyridine-3-yl ring and the pyridine-3-yl ring is substituted with $R^g$ wherein $R^g$ is amino, aminomethyl, —C(=N$R^h$)NH$R^i$ (where $R^h$ and $R^i$ are independently hydrogen, hydroxy, methoxy, ethoxy, isopropoxy, tert-butoxy, methylcarbonyl, methoxycarbonyl, ethoxycarbonyl, tert-butoxycarbonyl, a natural or an unnatural amino acid residue, —CO(ethylene)$SO_2R^u$ (where $R^u$ is $C_1$-$C_6$alkyl, optionally substituted monocyclic heteroaryl, optionally substituted phenyl, or optionally substituted monocyclic heterocyclyl), or —CO$(CH_2)_{2-3}OR^v$ (where $R^v$ is hydrogen, $C_1$-$C_6$alkoxy$C_{1-3}$alkyl, or optionally substituted monocyclic heterocyclyl)) or 1,2,4-oxadiazol-5(4H)-one-3-yl, and is attached to the C-6 position of the pyridin-3-yl ring (i.e., $R^1$ is

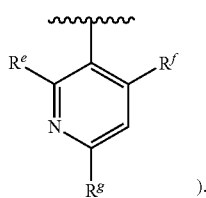

).

In yet one embodiment, $R^1$ is 6-amino-2,4-dimethylpyridin-3-yl, 6-amino-2,5-dimethylpyridin-3-yl, 6-amino-4-isopropyl-2-methyl-pyridin-3-yl, 6-amino-4-methoxy-2-methylpyridin-3-yl, 6-amino-4-ethoxy-2-methylpyridin-3-yl, 6-amino-4-ethyl-2-methylpyridin-3-yl, 6-amidinopyridin-3-yl, 6-amino-2-methyl-4-(tetrahydropyran-4-yl)pyridin-3-yl, 6-amino-2-methyl-4-n-propylpyridin-3-yl, 6-amino-4-cyclopropyl-2-methyl-pyridin-3-yl, 6-amino-2-methyl-4-propen-2-ylpyridin-3-yl, 1-aminoisoquinolin-5-yl, 6-amino-2-methyl-4-(3,6-dihydro-2H-pyran-4-yl)pyridin-3-yl, 6-amino-2-methyl-4-(2,5-dihydrofuran-3-yl)pyridin-3-yl, 6-amino-4-chloro-2-methyl-pyridin-3-yl, 3-aminobenzisoxazol-6-yl, 6-amino-2,4-diethyl-pyridin-3-yl, 6-amino-4,5-dimethylpyridin-3-yl, 1-aminoisoquinolin-7-yl, 1-aminoisoquinolin-4-yl, 3-aminobenzpyrazol-6-yl, 3-aminobenzisoxazol-5-yl, 3-aminobenzisoxazol-7-yl, 1-aminoisoquinolin-6-yl, 2-aminopyridin-4-yl, 2-amino-4,6-dimethylpyrimidin-5-yl, or 6-amino-2,4-dicyclopropylpyridin-3-yl.

In yet one embodiment, $R^1$ is 7-chloroquinolin-2-yl, 5-chloro-1H-indazol-3-yl, 6-amino-4-chloropyridin-3-yl, 6-amino-2-methyl-4-trifluoromethylpyridin-3-yl, 1-amino-6-chloroisoquinolin-6-yl, 1-amino-6-methylisoquinolin-6-yl, 1-amino-6-methylisoquinolin-7-yl, 6-aminopyridin-3-yl, 5-amidinopyridin-2-yl, 5-N'-methoxyamidinopyridin-2-yl, or 6-N'-methoxyamidinopyridin-3-yl.

(hh) The compound of any one of embodiments (a)-(ff), or a pharmaceutically acceptable salt thereof, wherein $R^1$ is fused heterocyclyl optionally substituted with $R^e$, $R^f$, or $R^g$ independently selected from $C_1$-$C_6$alkyl, $C_2$-$C_6$alkenyl, $C_3$-$C_6$cycloalkyl, $C_1$-$C_6$alkoxy, hydroxy, halo, halo$C_1$-$C_6$alkyl, halo$C_1$-$C_6$alkoxy, amino, $C_1$-$C_6$alkylamino, di$C_1$-$C_6$alkylamino, amino$C_1$-$C_6$alkyl, aminocarbonyl, amidino$C_1$-$C_6$alkyl, —C(=N$R^h$)NH$R^i$ (where $R^h$ and $R^i$ are independently hydrogen, hydroxy, $C_1$-$C_6$alkoxy, acyl, —C(O)O$C_1$-$C_6$alkyl, a natural or an unnatural amino acid residue, a dipeptidic residue, —CO(ethylene)$SO_2R^u$ (where $R^u$ is $C_1$-$C_6$alkyl, optionally substituted monocyclic heteroaryl, optionally substituted phenyl, or optionally substituted monocyclic heterocyclyl), or —CO$(CH_2)_{2-3}OR^v$ (where $R^v$ is hydrogen, $C_1$-$C_6$alkoxy$C_{1-3}$alkyl, or optionally substituted monocyclic heterocyclyl)), cyano, monocyclic heteroaryl (wherein the monocyclic heteroaryl is optionally substituted with one, two or three substituents independently selected from $C_1$-$C_6$alkyl, $C_3$-$C_6$cycloalkyl, $C_1$-$C_6$alkoxy, hydroxy, halo, halo$C_1$-$C_6$alkyl, halo$C_1$-$C_6$alkoxy, amino, $C_1$-$C_6$alkylamino, di$C_1$-$C_6$alkylamino, and cyano) and monocyclic heterocyclyl (wherein the monocyclic heterocyclyl is optionally substituted with one, two or three substituents independently selected from $C_1$-$C_6$alkyl, $C_3$-$C_6$cycloalkyl, $C_1$-$C_6$alkoxy, hydroxy, halo, halo$C_1$-$C_6$alkyl, halo$C_1$-$C_6$alkoxy, amino, $C_1$-$C_6$alkylamino, and di$C_1$-$C_6$alkylamino).

In one embodiment, $R^1$ is isoindolin-5-yl, optionally substituted with $R^e$, $R^f$, and $R^g$ independently selected from methyl, ethyl, isopropyl, n-propyl, cyclopropyl, methoxy, ethoxy, hydroxy, trifluoromethyl, trifluoromethoxy, difluoromethyl, difluoromethoxy, fluoro, and chloro.

(ii) The compound of any one of embodiments (a) and (c)-(hh), or a pharmaceutically acceptable salt thereof, wherein ring D is phenyl.

(jj) The compound of any one of embodiments (a) and (c)-(hh), or a pharmaceutically acceptable salt thereof, wherein ring D is monocyclic heteroaryl. In one embodiment, ring D is pyridinyl.

(kk) The compound of any one of embodiments (a) and (c)-(hh), or a pharmaceutically acceptable salt thereof, wherein the compound has the structure shown below:

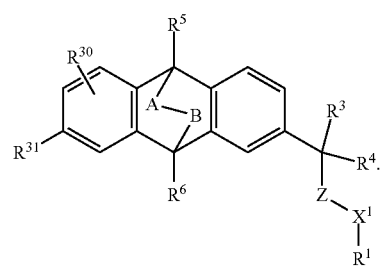

In one embodiment, the compound has the structure:

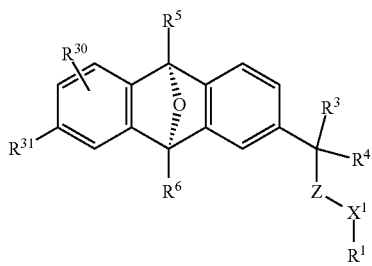

In another embodiment, the compound has the structure:

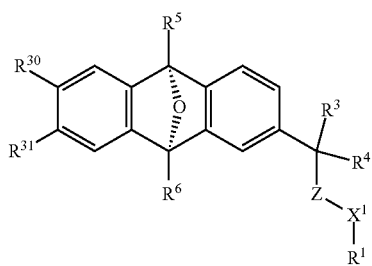

(ll) The compound of any one of embodiment (a)-(kk) or a pharmaceutically acceptable salt thereof wherein:

$R^7$ and $R^{30}$ are independently hydrogen, halo, $C_1$-$C_6$alkyl, $C_1$-$C_6$haloalkyl, $C_1$-$C_6$haloalkoxy, or $C_3$-$C_6$cycloalkyl. In one embodiment, $R^7$ and $R^{30}$ are independently hydrogen, fluoro, methyl, ethyl, propyl, isopropyl, trifluoromethyl, trifluoromethoxy, or cyclopropyl. In another embodiment, $R^7$ and $R^{30}$ are each hydrogen.

(mm) The compound of any one of embodiment (ll), or a pharmaceutically acceptable salt thereof, wherein $R^2$ and $R^{31}$ are independently halo, $C_1$-$C_6$alkyl, $C_1$-$C_6$haloalkyl, $C_1$-$C_6$haloalkoxy, hydroxy$C_1$-$C_6$alkyl, $C_3$-$C_6$cycloalkyl, monocyclic aryl, mono or bicyclic heteroaryl, monocyclic heterocyclyl, fused heterocyclyl, monocyclic aryl$C_1$-$C_6$alkyl, monocyclic heteroaryl$C_1$-$C_6$alkyl, monocyclic heterocyclyl$C_1$-$C_6$alkyl (wherein the alkylene chain in monocyclic aryl$C_1$-$C_6$alkyl, monocyclic heteroaryl$C_1$-$C_6$alkyl or monocyclic heterocyclyl$C_1$-$C_6$alkyl is optionally substituted with deuterium), —$NR^{32}R^{33}$, —$OR^{34}$, —$CHFR^{35}$, —$CF_2R^{36}$, $SR^{37}$, $SO_2R^{39}$, —$C(=O)R^{40}$, —$C(=O)NR^{41}R^{42}$, or —$NR^{43}C(=O)R^{44}$, wherein $R^{32}$, $R^{33}$, $R^{34}$, $R^{35}$, $R^{36}$, $R^{37}$, $R^{39}$, $R^{40}$, $R^{41}$, $R^{42}$, $R^{43}$, and $R^{44}$ are independently hydrogen, $C_1$-$C_6$alkyl, mono or bicyclic aryl, mono or bicyclic heteroaryl, or monocyclic heterocyclyl, or $R^{32}$ and $R^{33}$ or $R^{41}$ and $R^{42}$ together with the nitrogen atom they are bonded to form heterocycloamino wherein each of the aforementioned ring, whether by itself or part of another group, is optionally substituted with $R'''$, $R''$ or $R°$ independently selected from $C_1$-$C_6$alkyl, $C_3$-$C_6$cycloalkyl, $C_1$-$C_6$alkoxy, hydroxy, halo, halo$C_1$-$C_6$alkyl, halo$C_1$-$C_6$alkoxy, amino, $C_1$-$C_6$alkylamino, di$C_1$-$C_6$alkylamino, and cyano.

(nn) The compound of any one of embodiment (ll), or a pharmaceutically acceptable salt thereof, wherein $R^2$ and $R^{31}$ are independently methyl, ethyl, propyl, isopropyl, cyclopropyl, cyclobutyl, cyclopentyl, cyano, bromo, pyrazolyl-1-ylmethyl, 4-methylpyrazolyl-1-ylmethyl, 3,5-dimethylpyrazol-1-ylmethyl, phenyl, 2-fluorophenyl, 4-fluorophenyl, 2,4-difluorophenyl, 2,6-difluorophenyl, 2,3-difluoro-4-chlorophenyl, 2,3,4-trifluorophenyl, 2,4-difluoro-6-methylphenyl, 3-fluorobenzoyl, or 3-fluorophenoxy.

(oo) The compound of any one of embodiment (ll), or a pharmaceutically acceptable salt thereof, wherein $R^2$ and $R^{31}$ are independently bromo, benzofuran-3-yl, phenyl, 4-fluorophenyl, pyrazol-1-ylmethyl, 6-methoxypyridin-3-yl, 3,5-dimethyl-1,2-oxazol-4-yl, pyridin-2-yl, isoquinolin-1-yl, 3-fluorophenyl, 2-ethoxy-5-fluoropyridin-4-yl, 5-fluoro-2-(propan-2-yloxy)pyridin-4-yl, furan-2-yl, (4-bromo-1H-pyrazol-1-yl)methyl, 2-fluorophenyl, (4-methyl-1H-pyrazol-1-yl)methyl, 2-methoxyphenyl, 1H-1,3-benzodiazol-4-yl, 1,3-benzoxazol-7-yl, 2-oxo-1,2-dihydropyridin-1-yl, pyrrolidin-1-ylmethyl, (3,5-dimethyl-1H-pyrazol-1-yl)methyl, (3,5-dimethyl-1H-pyrazol-1-yl)methyl, 4-fluoropyridin-3-yl, 2,6-difluorophenyl, 2,4-difluorophenyl, 3-fluoropyridin-4-yl, morpholin-4-ylmethyl, (1-methyl-1H-pyrazol-3-yl)amino, (1-methyl-1H-pyrazol-5-yl)amino, 3,5-difluorophenyl, 2,3-difluorophenyl, 2-chlorophenyl, 3,4-difluorophenyl, 2-(trifluoromethyl)phenyl, 5-chloro-2-fluorophenyl, 2-fluoro-5-methylphenyl, 5-chlorothiophen-2-yl, 4-benzoylpiperazin-1-yl, 2-fluoro-4-methoxyphenyl, 4-cyano-2-fluorophenyl, 2-cyano-4-fluorophenyl, 2H-1,3-benzodioxol-4-yl, 2-aminocarbonylphenyl, (3-cyanophenyl)methyl, (2-fluorophenyl)amino, (3-fluoropyridin-2-yl)amino, 3-fluorophenoxy, 2-cyano-4-methylphenyl, 2-cyano-4-methoxyphenyl, pyridin-2-yl, 2,4-difluorophenyl, 2,3-dihydro-1,4-benzodioxin-5-yl, 2-cyanophenyl, (2-phenyl-1,3-oxazol-4-yl)methyl, 2-cyano-6-methylphenyl, 6-(cyclopropyl-methoxy)pyridin-3-yl, 6-methoxy-4-methylpyridin-3-yl, pyrimidin-2-yl, 2-methanesulfonylphenyl, 1,3-oxazol-4-ylmethyl, 5-methylfuran-2-yl, 3-oxomorpholin-4-yl, 2-fluoro-4-(trifluoromethyl)phenyl, 4-chloro-2-cyanophenyl, 2,3,4-trifluorophenyl, 2-cyano-4-methylphenyl, 4-chloro-2,3-difluorophenyl, 1,3-thiazol-2-yl, 4-chloro-2,3-difluorophenyl, 3-fluoropyridin-2-yl, 2-fluoro-6-methylphenyl, 2-cyanophenoxy, 3,5-difluoropyridin-2-yl, 2,3-difluoro-4-methylphenyl, 2,3-difluoro-4-(trifluoromethyl)phenyl, 2,4-difluorophenoxy, 4-fluoro-3-(trifluoromethyl)phenyl, 1H-1,3-benzodiazol-5-yl, 2,4-difluoro-6-methylphenyl, pyridin-3-yloxy, 2-chloro-4,6-difluorophenyl, 4-oxo-1,4-dihydropyridin-1-yl, 6-methoxypyridin-3-yl)oxy, 2-cyano-5-methylphenyl, 2-cyano-6-methylpyridin-3-yl, 2-cyano-3-(trifluoromethyl) phenyl, 3-methylphenoxy, phenylsulfanyl, benzenesulfonyl, 4-methoxypyridin-3-yl, 2,4,5-trifluorophenyl, 4-chloro-2-fluorophenyl, 2-chloro-4-fluorophenyl, 2-fluoro-6-methoxypyridin-3-yl, 4-fluoro-1H-pyrazol-1-yl, 4-chloro-1H-pyrazol-1-yl)methyl, 1-methyl-1H-pyrazol-3-yl)oxy, 2-methyl-5-oxo-2,5-dihydro-1H-pyrazol-1-yl, benzoyl, phenyl, N4-methyl-N4-phenylaminocarbonyl, N4-(4-fluorophenyl)-N4-methylaminocarbonyl, 2-methylpyridin-3-yl, 2-methoxypyridin-3-yl, 5-fluoro-pyridin-2-yl, 4-methylpyridin-3-yl, 5-chlorothiophen-2-yl, (3-fluorophenyl) (methyl)amino, 5-methylfuran-2-yl, (2-oxo-1,2-dihydropyridin-1-yl)methyl, 3-fluorobenzoyl, benzoylamino, ethyl (3-fluorophenyl)amino, ethyl, N-ethylbenzoylamino, 3-methyl-2-oxo-1,3-diazinan-1-yl)methyl, pyrrolidin-1-yl, ethyl(2-fluorophenyl)amino, N-methylbenzoylamino, (3-fluorophenyl)-(propan-2-yl)amino, (3-fluorophenyl)(propyl)amino, imidazo[1,2-a]pyridin-2-yl, benzyl, cyclopropyl, (3-chlorophenyl)(methyl)amino, 1,3-thiazol-2-yl, 2-hydroxypropan-2-yl, 5-methyl-furan-2-carbonyl, 1,1-difluoroethyl, 2-fluoropropan-2-yl, 1H-pyrazol-1-yl, 3-fluoropyridin-2-yl, 5-fluoropyridin-2-yl, 3,3,3-trifluoropropyl, 2H-1,2,3-triazol-2-yl, propan-2-yl, 6-aminopyridin-3-ylaminocarbonyl, 3,3-difluoroazetidin-1-yl, methyl, 4-aminopyridin-2-ylaminocarbonyl, ethyl, methoxy, or 1,1-dioxo-1λ$^6$-thiomorpholin-4-yl.

(pp). The compound of embodiment (a) wherein the compound is selected from Table 1 below, or an individual regioisomer thereof;

or an individual stereoisomer of any of the foregoing compounds;

or an E or Z isomer thereof of any of the foregoing compounds;

or a pharmaceutically acceptable salt of any of the foregoing compounds.

Representative compound of the disclosure are provide in Table 1 below. Chemical names were generated by J. Chem. from ChemAxon.

TABLE 1

| Cpd. No | Structure | Compound Type | KLKB1 pIC$_{50}$ | IUPAC Name |
|---|---|---|---|---|
| 1 | 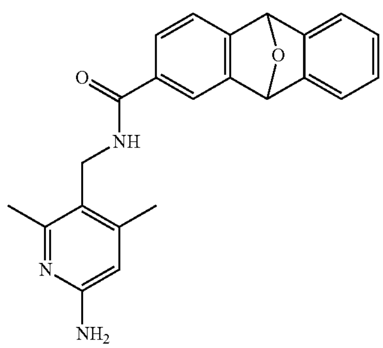 [SMILES: Cc1cc(N)nc(C)c1CNC(=O)c1ccc2c(c1)C1OC2c2ccccc21] | Racemic mixture | 5.2 | (±)-N-[(6-amino-2,4-dimethylpyridin-3-yl)methyl]-15-oxatetra-cyclo[6.6.1.0$^2$,$^7$.0$^9$,$^{14}$]-pentadeca-2,4,6,9,11,13-hexaene-4-carboxamide |
| 2 | | Racemic mixture | 5.6 | (±)-N-[(6-amino-2,4-dimethylpyridin-3-yl)methyl]-10-(1-benzofuran-3-yl)tricycle-[6.2.1.0$^2$,$^7$]undeca-2,4,6,9-tetraene-4-carboxamide and (±)-N-[(6-amino-2,4-dimethylpyridin-3-yl)methyl]-9-(1-benzofuran-3-yl)tricycle-[6.2.1.0$^2$,$^7$]undeca-2,4,6,9-tetraene-4-carboxamide |

TABLE 1-continued

| Cpd. No | Structure | Compound Type | KLKB1 pIC$_{50}$ | IUPAC Name |
|---|---|---|---|---|
| 3 | 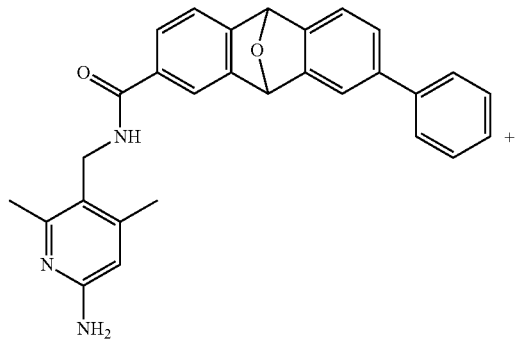 [SMILES: Cc1cc(N)nc(C)c1CNC(=O)c1ccc2c(c1)C1OC2c2ccc(C3=CC=[C+]C=C3)cc21] | Racemic mixture | 6.4 | (±)-N-[(6-amino-2,4-dimethylpyridin-3-yl)methyl]-12-phenyl-15-oxatetracyclo-[6.6.1.0$^2$,$^7$.0$^9$, $^{14}$]pentadeca-2,4,6,9,11,13-hexaene-4-carboxamide and N-[(6-amino-2,4-dimethyl-pyridin-3-yl)methyl]-11-phenyl-15-oxatetra-cyclo[6.6.1.0$^2$,$^7$.0$^9$, $^{14}$]pentadeca-2,4,6,9,11,13-hexaene-4-carboxamide |
| 4 | 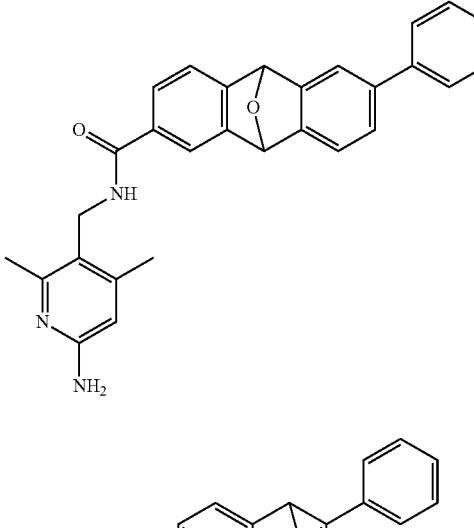 | Racemic mixture | 4.58 | (±)-N-[(6-amino-2,4-dimethylpyridin-3-yl)methyl]-9-phenyl-11-oxatricyclo-[6.2.1.0$^2$,$^7$]undeca-2,4,6,9-tetraene-4-carboxamide and (±)-N-[(6-amino-2,4-dimethylpyridin-3-yl)methyl]-10-phenyl-11-oxatricyclo-[6.2.1.0$^2$,$^7$]undeca-2,4,6,9-tetraene-4-carboxamide |

TABLE 1-continued

| Cpd. No | Structure | Compound Type | KLKB1 pIC$_{50}$ | IUPAC Name |
|---|---|---|---|---|
| 5 | 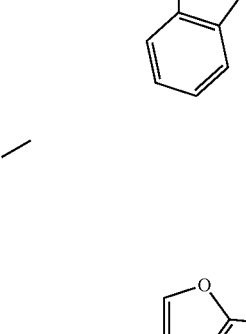 | Racemic mixture | 3 | (±)-10-(1-benzofuran-3-yl)-N-[(6-chloro-2-fluoro-3-methoxyphenyl)methyl]tricycle-[6.2.1.0$^{2,7}$]undeca-2,4,6,9-tetraene-4-carboxamide and (±)-9-(1-benzofuran-3-yl)-N-[(6-chloro-2-fluoro-3-methoxyphenyl)methyl]tricycle-[6.2.1.0$^{2,7}$]undeca-2,4,6,9-tetraene-4-carboxamide |
| 6 | 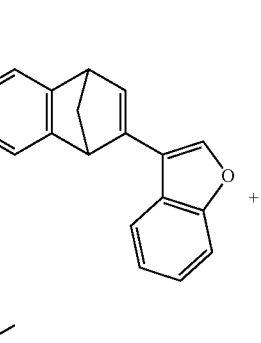 | Racemic mixture | 3 | (±)-10-(1-benzofuran-3-yl)-N-[(2,6-difluoro-3-methoxyphenyl)methyl]tricycle-[6.2.1.0$^{2,7}$]undeca-2,4,6,9-tetraene-4-carboxamide and (±)-9-(1-benzofuran-3-yl)-N-[(2,6-difluoro-3-methoxyphenyl)methyl]tricyclo[6.2.1.0$^{2,7}$]-undeca-2,4,6,9-tetraene-4-carboxamide |

TABLE 1-continued

| Cpd. No | Structure | Compound Type | KLKB1 pIC$_{50}$ | IUPAC Name |
|---|---|---|---|---|
| 7 | 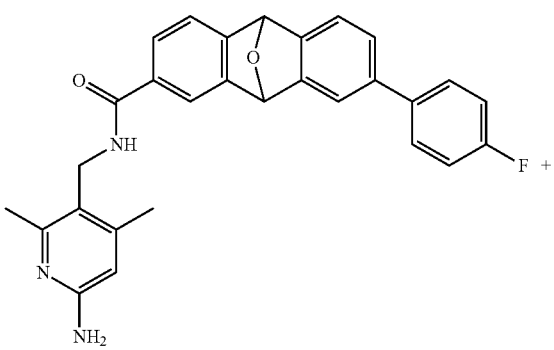 [SMILES: Cc1cc(N)nc(C)c1CNC(=O)c1ccc2c(c1)C1OC2c2ccc(-c3ccc(F)cc3)cc21] | Racemic mixture | 6.66 | (±)-N-[(6-amino-2,4-dimethylpyridin-3-yl)methyl]-12-(4-fluorophenyl)-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(4-fluorophenyl)-15-oxatetracyclo[6.6.1.0$^{2,7}$.0$^{9,14}$]pentadeca-2,4,6,9,11,13-hexaene-4-carboxamide |
| 8 | 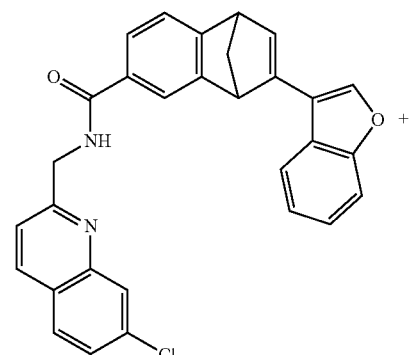 | Racemic mixture | 3 | (±)-10-(1-benzofuran-3-yl)-N-[(7-chloroquinolin-2-yl)methyl]tricyclo[6.2.1.0$^{2,7}$]undeca-2,4,6,9-tetraene-4-carboxamide and (±)-9-(1-benzofuran-3-yl)-N-[(7-chloroquinolin-2-yl)methyl]tricycle-[6.2.1.0$^{2,7}$]undeca-2,4,6,9-tetraene-4-carboxamide |

TABLE 1-continued

| Cpd. No | Structure | Compound Type | KLKB1 pIC$_{50}$ | IUPAC Name |
|---|---|---|---|---|
| 9 | 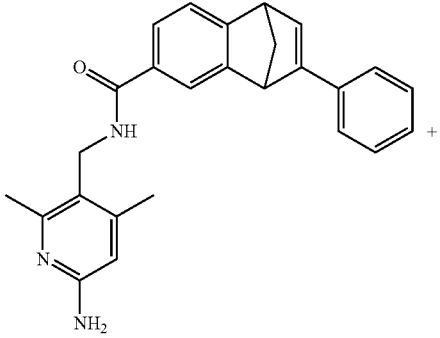 | Racemic mixture | 4.89 | (±)-N-[(6-amino-2,4-dimethylpyridin-3-yl)-methyl]-10-phenyltricyclo[6.2.1.0$^{2,7}$]undeca-2,4,6,9-tetraene-4-carboxamide and (±)-N-[(6-amino-2,4-dimethylpyridin-3-yl)methyl]-9-phenyltricyclo[6.2.1.0$^{2,7}$]undeca-2,4,6,9-tetraene-4-carboxamide |
| 10 | 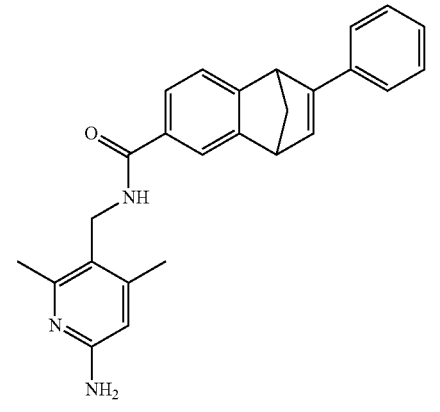 [SMILES: Cc1cc(N)nc(C)c1CNC(=O)c1ccc2c(c1)C1C=C(c3ccccc3)C2C1] | Racemic mixture | 7.76 | (±)-N-[(6-amino-2,4-dimethylpyridin-3-yl)methyl]-12-[(1H-pyrazol-1-yl)methyl]-15-oxatetracyclo[6.6.1.0$^{2,7}$.0$^{9,14}$]pentadeca-2,4,6,9,11,13-hexaene-4-carboxamide (±)-N-[(6-amino-2,4-dimethylpyridin-3-yl)methyl]-11-[(1H-pyrazol-1-yl)methyl]-15-oxatetracyclo-[6.6.1.0$^{2,7}$.0$^{9,14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 11 | 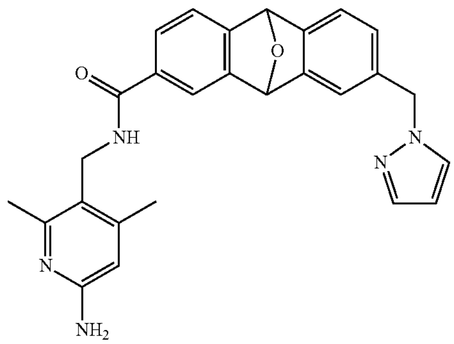 [SMILES: Cc1cc(N)nc(C)c1CNC(=O)c1ccc2c(c1)C1OC2c2ccc(Cn3cccn3)cc21] | Racemic mixture | 7.63 | (±)-N-[(6-amino-2,4-dimethylpyridin-3-yl)-methyl]-12-[(1H-pyrazol-1-yl)methyl]-15-oxatetracyclo[6.6.1.0$^{2,7}$.0$^{9,14}$]pentadeca-2,4,6,9,11,13-hexaene-4-carboxamide |
| 12 | | Racemic mixture | 7.29 | (±)-N-[(6-amino-2,4-dimethylpyridin-3-yl)methyl]-12-[(1H-pyrazol-1-yl)($^2$H$_2$)methyl]-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-[(1H-pyrazol-1-yl)($^2$H$_2$)methyl]-15-oxatetra-cyclo[6.6.1.0$^{2,7}$.0$^{9,14}$]pentadeca-2,4,6,9,11,13-hexaene-4-carboxamide |
| 13 | 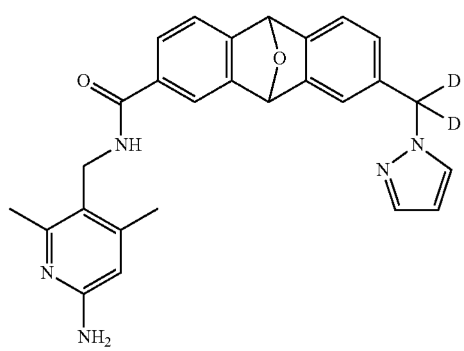 [SMILES: [2H]C([2H])(c1ccc2c(c1)C1OC2c2ccc(C(=O)NCc3c(C)cc(N)nc3C)cc21)n1cccn1] | Racemic mixture | 8.32 | (±)-N-[(6-amino-2,4-dimethylpyridin-3-yl)-methyl]-12-[(1H-pyrazol-1-yl)($^2$H$_2$)methyl]-15-oxatetracyclo[6.6.1.0$^{2,7}$.0$^{9,14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 14 | 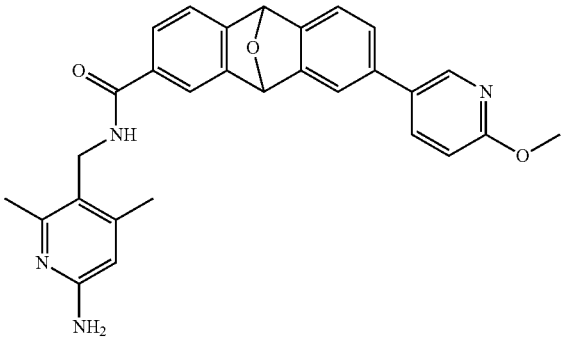 | Racemic mixture | 6.73 | (±)-N-[(6-amino-2,4-dimethylpyridin-3-yl)methyl]-12-(6-methoxypyridin-3-yl)-15-oxatetracyclo[6.6.1.0$^2$,$^7$.0$^9$,$^{14}$]pentadeca-2,4,6,9,11,13-hexaene-4-carboxamide and (±)-N-[(6-amino-2,4-dimethylpyridin-3-yl)methyl]-11-(6-methoxypyridin-3-yl)-15-oxatetracyclo-[6.6.1.0$^2$,$^7$.0$^9$,$^{14}$]pentadeca-2,4,6,9,11,13-hexaene-4-carboxamide |
| 15 | 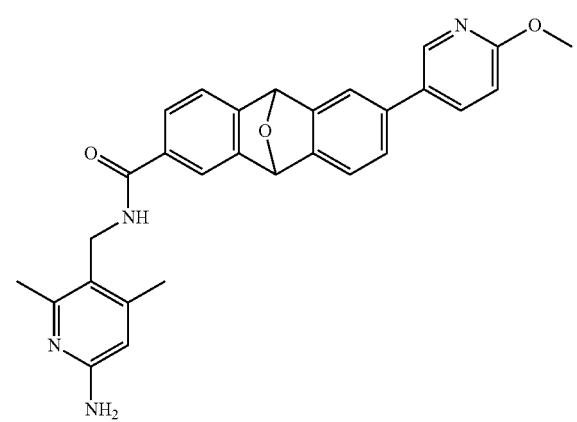 | Racemic mixture | 5.96 | (±)-N-[(6-amino-2,4-dimethylpyridin-3-yl)methyl]-12-(3,5-dimethyl-1,2-oxazol-4-yl)-15-oxatetracyclo[6.6.1.0$^2$,$^7$.0$^9$,$^{14}$]pentadeca-2,4,6,9,11,13-hexaene-4-carboxamide and (±)-N-[(6-amino-2,4-dimethylpyridin-3-yl)methyl]-11-(3,5-dimethyl-1,2-oxazol-4-yl)-15-oxatetracyclo-[6.6.1.0$^2$,$^7$.0$^9$,$^{14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 16 | 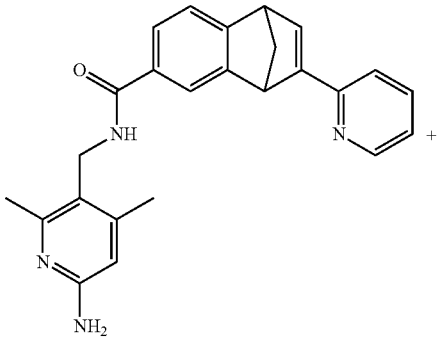 | Racemic mixture | 4.84 | (±)-N-[(6-amino-2,4-dimethylpyridin-3-yl)methyl]-10-(pyridin-2-yl)tricyclo[6.2.1.0$^{2,7}$]-undeca-2,4,6,9-tetraene-4-carboxamide and (±)-N-[(6-amino-2,4-dimethylpyridin-3-yl)methyl]-9-(pyridin-2-yl)tricyclo[6.2.1.0$^{2,7}$]undeca-2,4,6,9-tetraene-4-carboxamide |
| 17 | 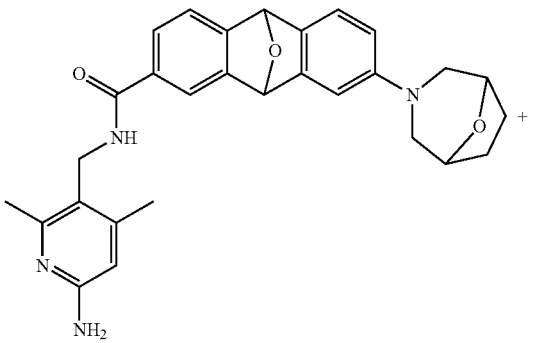 | Racemic mixture | 6.36 | (±)-N-[(6-amino-2,4-dimethylpyridin-3-yl)methyl]-12-{8-oxa-3-azabicyclo[3.2.1]octan-3-yl}-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-{8-oxa-3-azabicyclo[3.2.1]octan-3-yl}-15-oxatetracyclo[6.6.1.0$^{2,7}$.0$^{9,14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 18 | 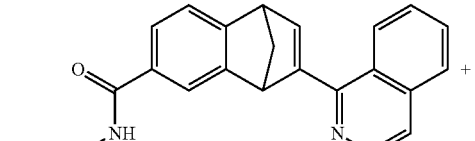 | Racemic mixture | 5.01 | (±)-N-[(6-amino-2,4-dimethylpyridin-3-yl)methyl]-10-(isoquinolin-1-yl)tricycle-[6.2.1.0$^{2,7}$]undeca-2,4,6,9-tetraene-4-carboxamide and (±)-N-[(6-amino-2,4-dimethyl-pyridin-3-yl)methyl]-9-(isoquinolin-1-yl)tricycle-[6.2.1.0$^{2,7}$]undeca-2,4,6,9-tetraene-4-carboxamide |
| 19 | 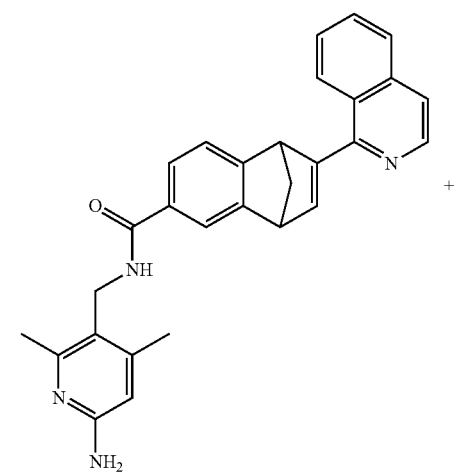 [SMILES: Cc1cc(N)nc(C)c1CNC(=O)c1ccc2c(c1)C1C=C(c3nccc4ccccc34)C2C1] | Racemic mixture | 4.72 | (±)-N-[(6-amino-2,4-dimethylpyridin-3-yl)methyl]-11-methyl-10-phenyl-11-azatricyclo-[6.2.1.0$^{2,7}$]undeca-2,4,6,9-tetraene-4-carboxamide and (±)-N-[(6-amino-2,4-dimethylpyridin-3-yl)methyl]-11-methyl-9-phenyl-11-azatricyclo-[6.2.1.0$^{2,7}$]undeca-2,4,6,9-tetraene-4-carboxamide |

TABLE 1-continued

| Cpd. No | Structure | Compound Type | KLKB1 pIC$_{50}$ | IUPAC Name |
|---|---|---|---|---|
| 20 | 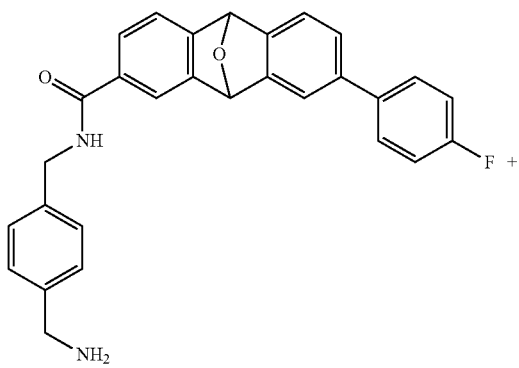 [SMILES: NCc1ccc(CNC(=O)c2ccc3c(c2)C2OC3c3ccc(-c4ccc(F)cc4)cc32)cc1] | Racemic mixture | 5.46 | (±)-N-{[4-(aminomethyl)phenyl]methyl}-12-(4-fluorophenyl)-15-oxatetracyclo-[6.6.1.0$^{2,7}$.0$^{9,14}$]-pentadeca-2,4,6,9,11,13-hexaene-4-carboxamide and (±)-N-{[4-(aminomethyl)phenyl]methyl}-11-(4-fluorophenyl)-15-oxatetracyclo-[6.6.1.0$^{2,7}$.0$^{9,14}$]-pentadeca-2,4,6,9,11,13-hexaene-4-carboxamide |
| 21 | 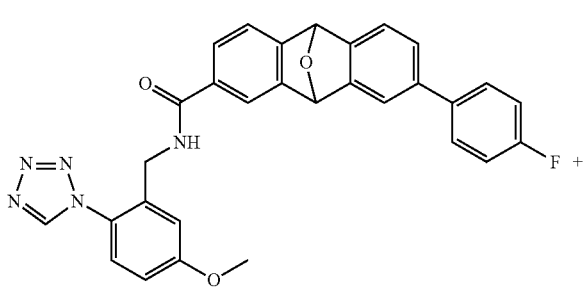 [SMILES: COc1ccc(-n2cnnn2)c(CNC(=O)c2ccc3c(c2)C2OC3c3ccc(-c4ccc(F)cc4)cc32)c1] | Racemic mixture | 5.93 | (±)-12-(4-fluorophenyl)-N-{[5-methoxy-2-(1H-1,2,3,4-tetrazol-1-yl)phenyl]methyl}-15-oxatetracyclo[6.6.1.0$^{2,7}$.0$^{9,14}$]pentadeca-2,4,6,9,11,13-hexaene-4-carboxamide and (±)-11-(4-fluorophenyl)-N-{[5-methoxy-2-(1H-1,2,3,4-tetrazol-1-yl)phenyl]methyl}-15-oxatetracyclo[6.6.1.0$^{2,7}$.0$^{9,14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 22 | 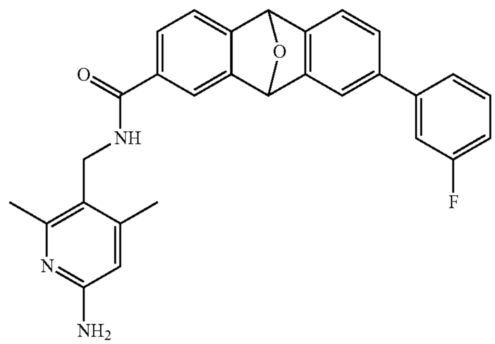 | Racemic mixture | 6.48 | (±)-N-[(6-amino-2,4-dimethylpyridin-3-yl)methyl]-12-(3-fluorophenyl)-15-oxatetracyclo-[6.6.1.0$^2$,$^7$.0$^9$,1$^4$]pentadeca-2,4,6,9,11,13-hexaene-4-carboxamide and (±)-N-[(6-amino-2,4-dimethylpyridin-3-yl)methyl]-11-(3-fluorophenyl)-15-oxatetracyclo[6.6.1.0$^2$,$^7$.0$^9$,1$^4$]-pentadeca-2,4,6,9,11,13-hexaene-4-carboxamide |
| 23 | 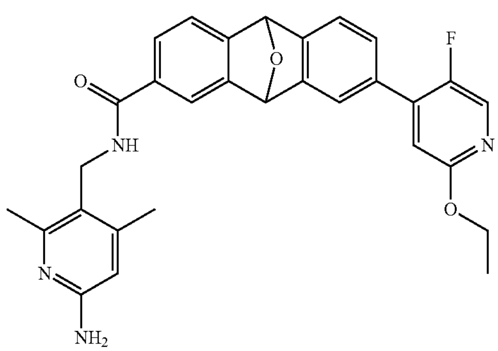 | Racemic mixture | 6.26 | (±)-N-[(6-amino-2,4-dimethylpyridin-3-yl)methyl]-12-(2-ethoxy-5-fluoropyridin-4-yl)-15-oxatetracyclo[6.6.1.0$^2$,$^7$.0$^9$,1$^4$]pentadeca-2,4,6,9,11,13-hexaene-4-carboxamide and (±)-N-[(6-amino-2,4-dimethylpyridin-3-yl)methyl]-11-(2-ethoxy-5-fluoropyridin-4-yl)-15-oxatetracyclo[6.6.1.0$^2$,$^7$.0$^9$,1$^4$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 24 | 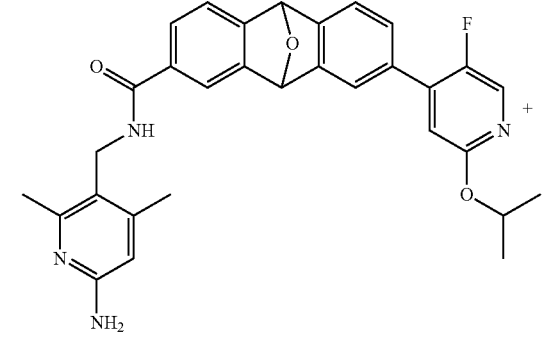 [SMILES: Cc1cc(N)nc(C)c1CNC(=O)c1ccc2c(c1)C1OC2c2ccc(-c3cc(OC(C)C)ncc3F)cc21] | Racemic mixture | 5.99 | (±)-N-[(6-amino-2,4-dimethylpyridin-3-yl)-methyl]-12-[5-fluoro-2-(propan-2-yloxy)pyridin-4-yl]-15-oxatetracyclo[6.6.1.0$^2$,$^7$.0$^9$,$^{14}$]pentadeca-2,4,6,9,11,13-hexaene-4-carboxamide (±)-N-[(6-amino-2,4-dimethylpyridin-3-yl)methyl]-11-[5-fluoro-2-(propan-2-yloxy)pyridin-4-yl]-15-oxatetracyclo[6.6.1.0$^2$,$^7$.0$^9$,$^{14}$]pentadeca-2,4,6,9,11,13-hexaene-4-carboxamide |
| 25 | 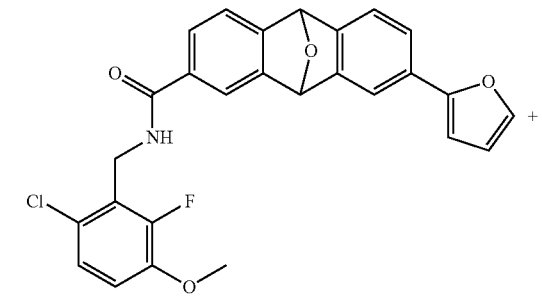 [SMILES: COc1ccc(Cl)c(CNC(=O)c2ccc3c(c2)C2OC3c3ccc(C4=CC=[C+]O4)cc32)c1F] | Racemic mixture | 4.47 | (±)-N-[(6-chloro-2-fluoro-3-methoxyphenyl)methyl]-12-(furan-2-yl)-15-oxatetracyclo-[6.6.1.0$^2$,$^7$.0$^9$,$^{14}$]-pentadeca-2,4,6,9,11,13-hexaene-4-carboxamide and (±)-N-[(6-chloro-2-fluoro-3-methoxyphenyl)methyl]-11-(furan-2-yl)-15-oxatetracyclo-[6.6.1.0$^2$,$^7$.0$^9$,$^{14}$]-pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 26 | 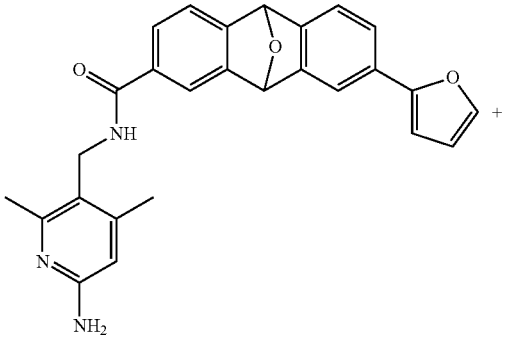 [SMILES: Cc1cc(N)nc(C)c1CNC(=O)c1ccc2c(c1)C1OC2c2ccc(C3=CC=[C+]O3)cc21] | Racemic mixture | 6.74 | (±)-N-[(6-amino-2,4-dimethylpyridin-3-yl)methyl]-12-(furan-2-yl)-15-oxatetracyclo-[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(furan-2-yl)-15-oxatetracyclo[6.6.1.0$^{2,7}$.0$^{9,14}$]pentadeca-2,4,6,9,11,13-hexaene-4-carboxamide |
| 27 | 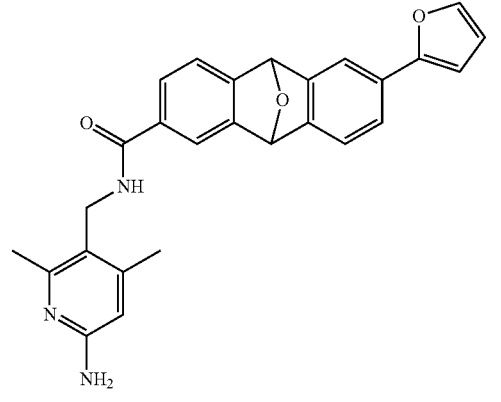 [SMILES: Cc1cc(N)nc(C)c1CNC(=O)c1ccc2c(c1)C1OC2c2cc(-c3ccco3)ccc21] | Racemic mixture | 7.62 | (±)-N-[(6-amino-2,4-dimethylpyridin-3-yl)methyl]-12-[(4-bromo-1H-pyrazol-1-yl)methyl]-15-oxatetracyclo[6.6.1.0$^{2,7}$.0$^{9,14}$]-pentadeca-2,4,6,9,11,13-hexaene-4-carboxamide and (±)-N-[(6-amino-2,4-dimethylpyridin-3-yl)methyl]-11-[(4-bromo-1H-pyrazol-1-yl)methyl]-15-oxatetracyclo[6.6.1.0$^{2,7}$.0$^{9,14}$]-pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 28 | 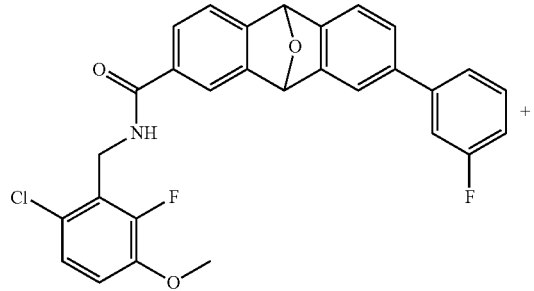 [SMILES: COc1ccc(Cl)c(CNC(=O)c2ccc3c(c2)C2OC3c3ccc(-c4cccc(F)c4)cc32)c1F] | Racemic mixture | 3 | (±)-N-[(6-chloro-2-fluoro-3-methoxyphenyl)-methyl]-12-(3-fluorophenyl)-15-oxatetracyclo-[6.6.1.0$^2$,$^7$.0$^9$,$^{14}$]pentadeca-2,4,6,9,11,13-hexaene-4-carboxamide and (±)-N-[(6-chloro-2-fluoro-3-methoxyphenyl)methyl]-11-(3-fluorophenyl)-15-oxatetracyclo[6.6.1.0$^2$,$^7$.0$^9$,$^{14}$]pentadeca-2,4,6,9,11,13-hexaene-4-carboxamide |
| 29 | 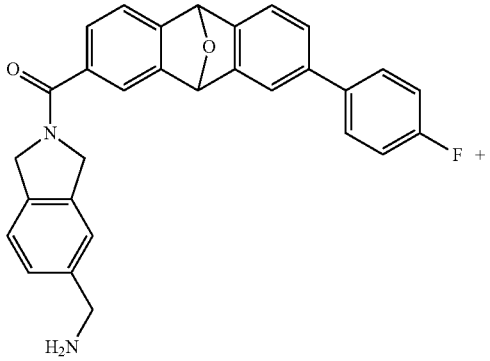 [SMILES: NCc1ccc2c(c1)CN(C(=O)c1ccc3c(c1)C1OC3c3ccc(-c4ccc(F)cc4)cc31)C2] | Racemic mixture | 4.41 | (±)-{2-[12-(4-fluorophenyl)-15-oxatetracyclo-[6.6.1.0$^2$,$^7$.0$^9$,$^{14}$]pentadeca-2,4,6,9,11,13-hexaene-4-carbonyl]-2,3-dihydro-1H-isoindol-5-yl}methanamine and (±)-{2-[11-(4-fluorophenyl)-15-oxatetracyclo[6.6.1.0$^2$,$^7$.0$^9$,$^{14}$]pentadeca-2,4,6,9,11,13-hexaene-4-carbonyl]-2,3-dihydro-1H-isoindol-5-yl}methanamine |

TABLE 1-continued

| Cpd. No | Structure | Compound Type | KLKB1 pIC$_{50}$ | IUPAC Name |
|---|---|---|---|---|
| 30 | | Racemic mixture | 6.75 | (±)-N-[(6-amino-2,4-dimethylpyridin-3-yl)-methyl]-12-(2-fluorophenyl)-15-oxatetracyclo-[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(2-fluoro-phenyl)-15-oxatetracyclo[6.6.1.0$^{2,7}$.0$^{9,14}$]-pentadeca-2,4,6,9,11,13-hexaene-4-carboxamide |
| 31 | 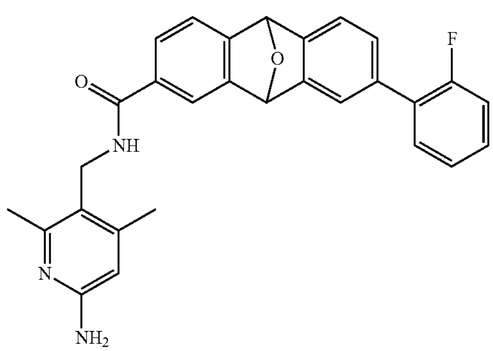 [SMILES: Cc1cc(N)nc(C)c1CNC(=O)c1ccc2c(c1)C1OC2c2ccc(-c3ccccc3F)cc21] | Racemic mixture | 6.91 | (±)-N-[(6-amino-2,4-dimethylpyridin-3-yl)-methyl]-12-(2-fluorophenyl)-15-oxatetra-cyclo[6.6.1.0$^{2,7}$.0$^{9,14}$]pentadeca-2,4,6,9,11,13-hexaene-4-carboxamide |
| 32 | 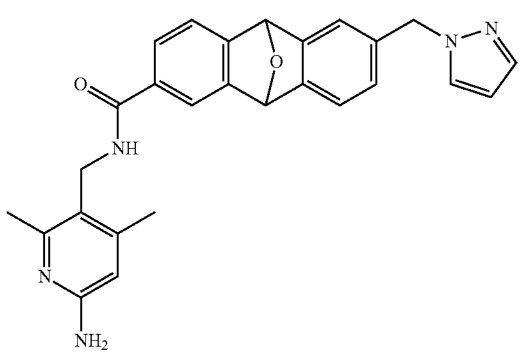 [SMILES: Cc1cc(N)nc(C)c1CNC(=O)c1ccc2c(c1)C1OC2c2cc(Cn3cccn3)ccc21] | Racemic mixture | 7.06 | (±)-N-[(6-amino-2,4-dimethylpyridin-3-yl)-methyl]-11-[(1H-pyrazol-1-yl)methyl]-15-oxatetracyclo[6.6.1.0$^{2,7}$.0$^{9,14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 33 | 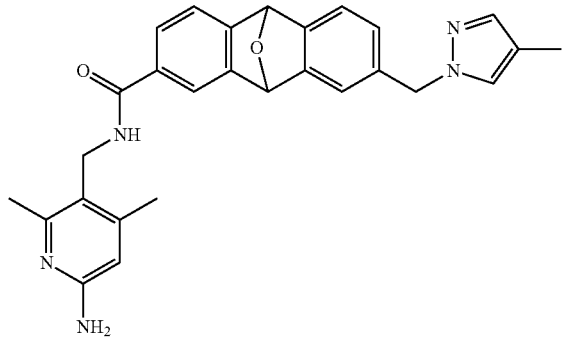 | Racemic mixture | 7.96 | (±)-N-[(6-amino-2,4-dimethylpyridin-3-yl)methyl]-12-[(4-methyl-1H-pyrazol-1-yl)methyl]-15-oxatetracyclo[6.6.1.0$^2$,$^7$.0$^9$,$^{1^4}$]-pentadeca-2,4,6,9,11,13-hexaene-4-carboxamide and (±)-N-[(6-amino-2,4-dimethylpyridin-3-yl)methyl]-11-[(4-methyl-1H-pyrazol-1-yl)methyl]-15-oxatetracyclo[6.6.1.0$^2$,$^7$.0$^9$,$^{1^4}$]-pentadeca-2,4,6,9,11,13-hexaene-4-carboxamide |
| 34 | 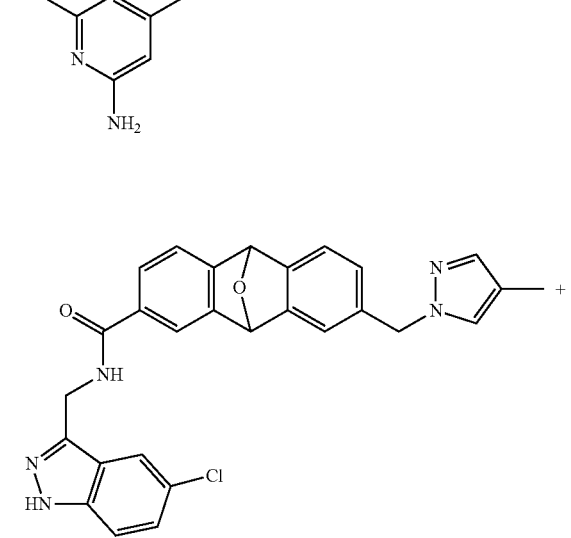 | Racemic mixture | 6.65 | (±)-N-[(5-chloro-1H-indazol-3-yl)methyl]-12-[(4-methyl-1H-pyrazol-1-yl)methyl]-15-oxatetra-cyclo[6.6.1.0$^2$,$^7$.0$^9$,$^{1^4}$] pentadeca-2,4,6,9,11,13-hexaene-4-carboxamide and (±)-N-[(5-chloro-1H-indazol-3-yl)methyl]-11-[(4-methyl-1H-pyrazol-1-yl) methyl]-15-oxatetracyclo[6.6.1.0$^2$,$^7$.0$^9$,$^{1^4}$]-pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 35 | | Racemic mixture | 6.39 | (±)-N-[(6-amino-2,4-dimethylpyridin-3-yl)methyl]-12-(2-methoxyphenyl)-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(2-methoxyphenyl)-15-oxatetracyclo-[6.6.1.0$^{2,7}$.0$^{9,14}$]-pentadeca-2,4,6,9,11,13-hexaene-4-carboxamide |
| 36 | | Racemic mixture | 6.47 | (±)-N-[(6-amino-2,4-dimethylpyridin-3-yl)methyl]-12-(1H-1,3-benzodiazol-4-yl)-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(1H-1,3-benzodiazol-4-yl)-15-oxatetracyclo-[6.6.1.0$^{2,7}$.0$^{9,14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 37 | | Racemic mixture | 3 | (±)-12-(1H-1,3-benzodiazol-4-yl)-N-[(6-chloro-2-fluoro-3-methoxyphenyl)methyl]-15-oxatetracyclo[6.6.1.0$^{2,7}$.0$^{9,14}$]pentadeca-2,4,6,9,11,13-hexaene-4-carboxamide and (±)-11-(1H-1,3-benzodiazol-4-yl)-N-[(6-chloro-2-fluoro-3-methoxyphenyl)methyl]-15-oxatetracyclo-[6.6.1.0$^{2,7}$.0$^{9,14}$]pentadeca-2,4,6,9,11,13-hexaene-4-carboxamide |
| 38 | | Racemic mixture | 6.28 | (±)-N-[(6-amino-2,4-dimethylpyridin-3-yl)methyl]-12-(1,3-benzoxazol-7-yl)-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(1,3-benzoxazol-7-yl)-15-oxatetracyclo-[6.6.1.0$^{2,7}$.0$^{9,14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
| --- | --- | --- | --- | --- |
| 39 | | Racemic mixture | 6.37 | (±)-N-[(6-amino-2,4-dimethylpyridin-3-yl)methyl]-12-(2-oxo-1,2-dihydropyridin-1-yl)-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(2-oxo-1,2-dihydropyridin-1-yl)-15-oxatetracyclo[6.6.1.0$^{2,7}$.0$^{9,14}$]pentadeca-2,4,6,9,11,13-hexaene-4-carboxamide |
| 40 | | Racemic mixture | 4.92 | (±)-N-[(1-aminoisoquinolin-6-yl)methyl]-12-(2-fluorophenyl)-15-oxatetracyclo[6.6.1.0$^{2,7}$.0$^{9,14}$]-pentadeca-2,4,6,9,11,13-hexaene-4-carboxamide and (±)-N-[(1-aminoisoquinolin-6-yl)methyl]-11-(2-fluorophenyl)-15-oxatetracyclo-[6.6.1.0$^{2,7}$.0$^{9,14}$]-pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 41 | | Racemic mixture | 6.88 | (±)-N-[(6-amino-2,4-dimethylpyridin-3-yl)methyl]-12-[(pyrrolidin-1-yl)methyl]-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-[(pyrrolidin-1-yl)methyl]-15-oxatetracyclo-[6.6.1.0$^{2,7}$.0$^{9,14}$]pentadeca-2,4,6,9,11,13-hexaene-4-carboxamide |
| 42 | | Racemic mixture | 7.74 | (±)-12-[(3,5-dimethyl-1H-pyrazol-1-yl)methyl]-N-{[5-methoxy-2-(1H-1,2,3,4-tetrazol-1-yl)phenyl]methyl}-15-oxatetracyclo-[6.6.1.0$^{2,7}$.0$^{9,14}$]pentadeca-2,4,6,9,11,13-hexaene-4-carboxamide and (±)-11-[(3,5-dimethyl-1H-pyrazol-1-yl)methyl]-N-{[5-methoxy-2-(1H-1,2,3,4-tetrazol-1-yl)phenyl]methyl}-15-oxatetracyclo[6.6.1.0$^{2,7}$.0$^{9,14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 43 | | Racemic mixture | 7.77 | (±)-N-[(6-amino-2,4-dimethylpyridin-3-yl)methyl]-12-[(3,5-dimethyl-1H-pyrazol-1-yl)methyl]-15-oxatetracyclo[6.6.1.0$^2$,$^7$.0$^9$,$^{14}$]-pentadeca-2,4,6,9,11,13-hexaene-4-carboxamide and (±)-N-[(6-amino-2,4-dimethylpyridin-3-yl)methyl]-11-[(3,5-dimethyl-1H-pyrazol-1-yl)methyl]-15-oxatetracyclo[6.6.1.0$^2$,$^7$.0$^9$,$^{14}$]-pentadeca-2,4,6,9,11,13-hexaene-4-carboxamide |
| 44 | | Racemic mixture | 6.75 | (±)-N-[(6-amino-2,4-dimethylpyridin-3-yl)methyl]-12-(4-fluoropyridin-3-yl)-15-oxatetracyclo[6.6.1.0$^2$,$^7$.0$^9$,$^{14}$]pentadeca-2,4,6,9,11,13-hexaene-4-carboxamide and (±)-N-[(6-amino-2,4-dimethylpyridin-3-yl)methyl]-11-(4-fluoropyridin-3-yl)-15-oxatetracyclo-[6.6.1.0$^2$,$^7$.0$^9$,$^{14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 45 | | Racemic mixture | 7.02 | (±)-N-[(6-amino-2,4-dimethylpyridin-3-yl)methyl]-12-(1,3-benzoxazol-4-yl)-15-oxatetracyclo[6.6.1.0$^2$,$^7$.0$^9$,$^{14}$]pentadeca-2,4,6,9,11,13-hexaene-4-carboxamide and (±)-N-[(6-amino-2,4-dimethylpyridin-3-yl)methyl]-11-(1,3-benzoxazol-4-yl)-15-oxatetracyclo[6.6.1.0$^2$,$^7$.0$^9$,$^{14}$]pentadeca-2,4,6,9,11,13-hexaene-4-carboxamide |
| 46 | | Racemic mixture | 6.61 | (±)-N-[(6-amino-2,4-dimethylpyridin-3-yl)methyl]-12-(2,6-difluorophenyl)-15-oxatetracyclo[6.6.1.0$^2$,$^7$.0$^9$,$^{14}$]pentadeca-2,4,6,9,11,13-hexaene-4-carboxamide and (±)-N-[(6-amino-2,4-dimethylpyridin-3-yl)methyl]-11-(2,6-difluorophenyl)-15-oxatetracyclo[6.6.1.0$^2$,$^7$.0$^9$,$^{14}$]-pentadeca-2,4,6,9,11,13-hexaene-4-carboxamide |

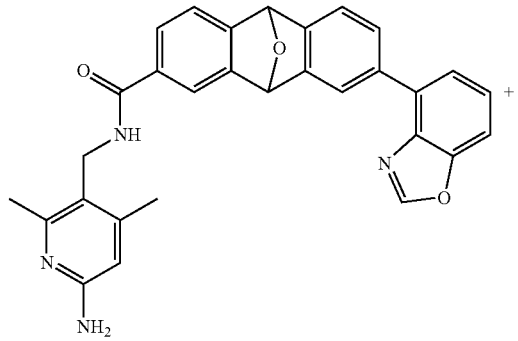 [SMILES: Cc1cc(N)nc(C)c1CNC(=O)c1ccc2c(c1)C1OC2c2ccc(C3=c4ncoc4=C[C+]=C3)cc21]
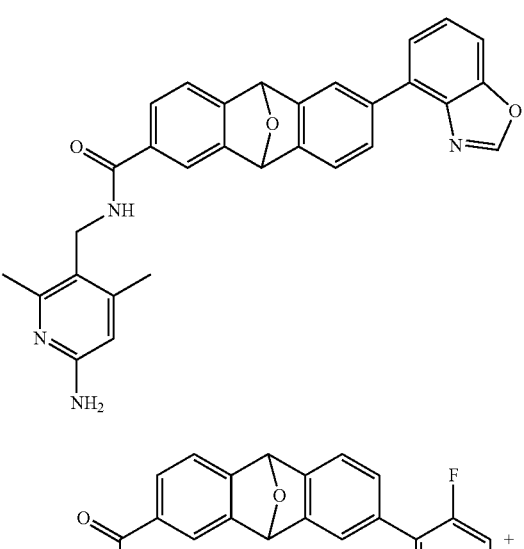

TABLE 1-continued

| Cpd. No | Structure | Compound Type | KLKB1 pIC$_{50}$ | IUPAC Name |
|---|---|---|---|---|
| 47 | | Racemic mixture | 6.93 | (±)-N-[(6-amino-2,4-dimethylpyridin-3-yl)methyl]-12-(2,4-difluorophenyl)-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(2,4-difluoro-phenyl)-15-oxatetracyclo[6.6.1.0$^{2,7}$.0$^{9,14}$]-pentadeca-2,4,6,9,11,13-hexaene-4-carboxamide |
| 48 | 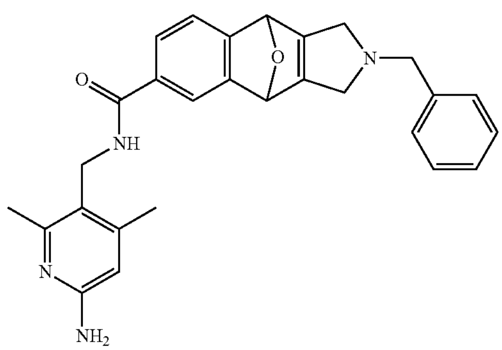 [SMILES: Cc1cc(N)nc(C)c1CNC(=O)c1ccc2c(c1)C1OC2C2=C1CN(Cc1ccccc1)C2] | Racemic mixture | 4.87 | (±)-N-[(6-amino-2,4-dimethylpyridin-3-yl)methyl]-11-benzyl-14-oxa-11-azatetracyclo-[6.5.1.0$^{2,7}$.0$^{9,13}$]tetradeca-2,4,6,9(13)-tetraene-4-carboxamide |
| 49 | 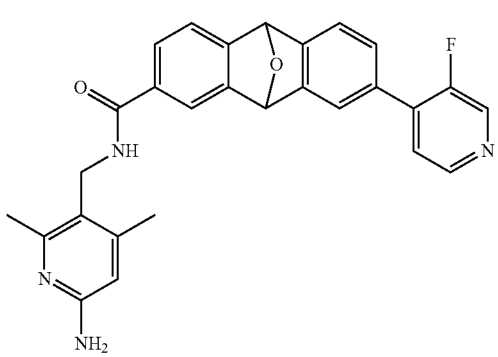 | Racemic mixture | 6.35 | (±)-N-[(6-amino-2,4-dimethylpyridin-3-yl)methyl]-12-(3-fluoropyridin-4-yl)-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(3-fluoropyridin-4-yl)-15-oxatetracyclo-[6.6.1.0$^{2,7}$.0$^{9,14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| | | | | |
| 50 | 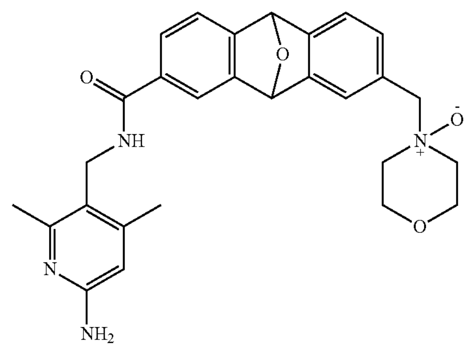 | Racemic mixture | 5.45 | (±)-4-[(12-{[(6-amino-2,4-dimethylpyridin-3-yl)methyl]carbamoyl}-15-oxatetracyclo-[6.6.1.0$^{2,7}$.0$^{9,14}$]pentadeca-2,4,6,9,11,13-hexaen-4-yl)methyl]morpholin-4-ium-4-olate |
| 51 | 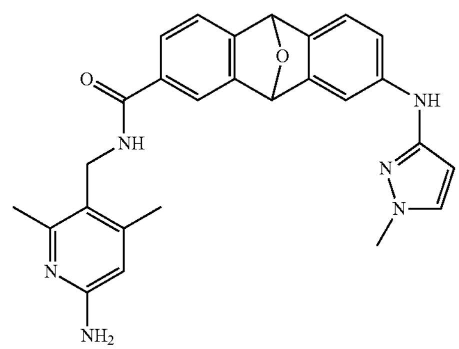 [SMILES: Cc1cc(N)nc(C)c1CNC(=O)c1ccc2c(c1)C1OC2c2ccc(Nc3ccn(C)n3)cc21] | Racemic mixture | 6.03 | (±)-N-[(6-amino-2,4-dimethylpyridin-3-yl)-methyl]-12-[(1-methyl-1H-pyrazol-3-yl)amino]-15-oxatetracyclo[6.6.1.0$^{2,7}$.0$^{9,14}$]-pentadeca-2,4,6,9,11,13-hexaene-4-carboxamide |
| 52 | 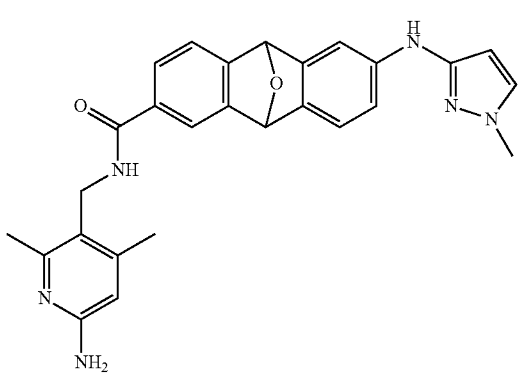 [SMILES: Cc1cc(N)nc(C)c1CNC(=O)c1ccc2c(c1)C1OC2c2cc(Nc3ccn(C)n3)ccc21] | Racemic mixture | 5.82 | (±)-N-[(6-amino-2,4-dimethylpyridin-3-yl)methyl]-11-[(1-methyl-1H-pyrazol-3-yl)amino]-15-oxatetracyclo[6.6.1.0$^{2,7}$.0$^{9,14}$]-pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 53 | 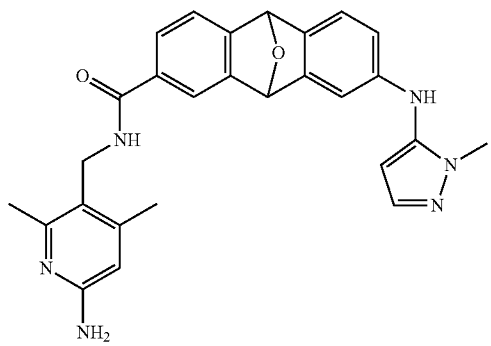 | Racemic mixture | 4.62 | (±)-N-[(6-amino-2,4-dimethylpyridin-3-yl)methyl]-12-[(1-methyl-1H-pyrazol-5-yl)amino]-15-oxatetracyclo[6.6.1.0$^2$,$^7$.0$^9$,$^{14}$]-pentadeca-2,4,6,9,11,13-hexaene-4-carboxamide |
| 54 | 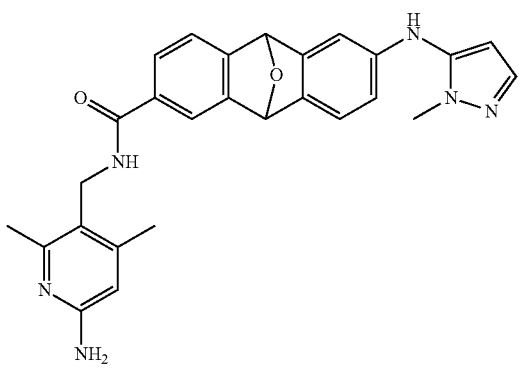 [SMILES: Cc1cc(N)nc(C)c1CNC(=O)c1ccc2c(c1)C1OC2c2cc(Nc3ccnn3C)ccc21] | Racemic mixture | 6.34 | (±)-N-[(6-amino-2,4-dimethylpyridin-3-yl)methyl]-11-[(1-methyl-1H-pyrazol-5-yl)amino]-15-oxatetracyclo[6.6.1.0$^2$,$^7$.0$^9$,$^{14}$]-pentadeca-2,4,6,9,11,13-hexaene-4-carboxamide |
| 55 | | Racemic mixture | 6.44 | (±)-N-[(6-amino-2,4-dimethylpyridin-3-yl)methyl]-12-(3,5-difluorophenyl)-15-oxatetra-cyclo[6.6.1.0$^2$,$^7$.0$^9$,$^{14}$]pentadeca-2,4,6,9,11,13-hexaene-4-carboxamide and (±)-N-[(6-amino-2,4-dimethylpyridin-3-yl)methyl]-11-(3,5-difluorophenyl)-15-oxatetracyclo-[6.6.1.0$^2$,$^7$.0$^9$,$^{14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 56 | | Racemic mixture | 6.98 | (±)-N-[(6-amino-2,4-dimethylpyridin-3-yl)methyl]-12-(2,3-difluorophenyl)-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(2,3-difluorophenyl)-15-oxatetracyclo-[6.6.1.0$^{2,7}$.0$^{9,14}$]pentadeca-2,4,6,9,11,13-hexaene-4-carboxamide |
| 57 | | Racemic mixture | 5.55 | (±)-N-[(6-amino-2,4-dimethylpyridin-3-yl)methyl]-12-(2-chlorophenyl)-15-oxatetra-cyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(2-chloro-phenyl)-15-oxatetracyclo[6.6.1.0$^{2,7}$.0$^{9,14}$]-pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 58 | | Racemic mixture | 6.4 | (±)-N-[(6-amino-2,4-dimethylpyridin-3-yl)methyl]-12-(3,4-difluorophenyl)-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(3,4-difluorophenyl)-15-oxatetracyclo[6.6.1.0$^{2,7}$.0$^{9,14}$]pentadeca-2,4,6,9,11,13-hexaene-4-carboxamide |
| 59 | | Racemic mixture | 5.84 | (±)-N-[(6-amino-2,4-dimethylpyridin-3-yl)methyl]-12-[2-(trifluoromethyl)phenyl]-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-[2-(trifluoromethyl)phenyl]-15-oxatetracyclo[6.6.1.0$^{2,7}$.0$^{9,14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 60 | | Racemic mixture | 6.31 | (±)-N-[(6-amino-2,4-dimethylpyridin-3-yl)methyl]-12-(5-chloro-2-fluorophenyl)-15-oxatetracyclo[6.6.1.0$^2$,$^7$.0$^9$,1$^4$]pentadeca-2,4,6,9,11,13-hexaene-4-carboxamide and (±)-N-[(6-amino-2,4-dimethylpyridin-3-yl)methyl]-11-(5-chloro-2-fluorophenyl)-15-oxatetracyclo-[6.6.1.0$^2$,$^7$.0$^9$,1$^4$]pentadeca-2,4,6,9,11,13-hexaene-4-carboxamide |
| 61 | | Racemic mixture | 5.76 | (±)-N-[(6-amino-2,4-dimethylpyridin-3-yl)methyl]-12-(2-fluoro-5-methylphenyl)-15-oxatetracyclo[6.6.1.0$^2$,$^7$.0$^9$,1$^4$]pentadeca-2,4,6,9,11,13-hexaene-4-carboxamide and (±)-N-[(6-amino-2,4-dimethylpyridin-3-yl)methyl]-11-(2-fluoro-5-methylphenyl)-15-oxatetracyclo-[6.6.1.0$^2$,$^7$.0$^9$,1$^4$]pentadeca-2,4,6,9,11,13-hexaene-4-carboxamide |

| Cpd. No | Structure | Compound Type | KLKB1 pIC$_{50}$ | IUPAC Name |
|---|---|---|---|---|
| 62 | 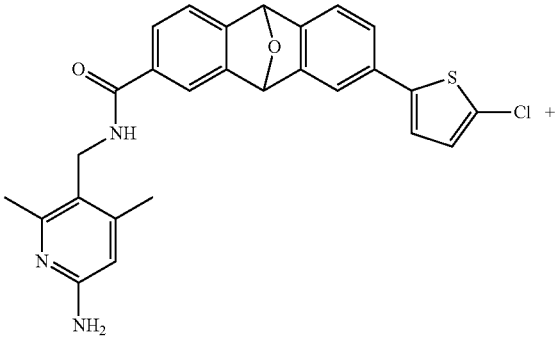 [SMILES: Cc1cc(N)nc(C)c1CNC(=O)c1ccc2c(c1)C1OC2c2ccc(-c3ccc(Cl)s3)cc21] | Racemic mixture | 6.45 | (±)-N-[(6-amino-2,4-dimethylpyridin-3-yl)methyl]-12-(5-chlorothiophen-2-yl)-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(5-chlorothiophen-2-yl)-15-oxatetracyclo-[6.6.1.0$^{2,7}$.0$^{9,14}$]pentadeca-2,4,6,9,11,13-hexaene-4-carboxamide |
| 63 | 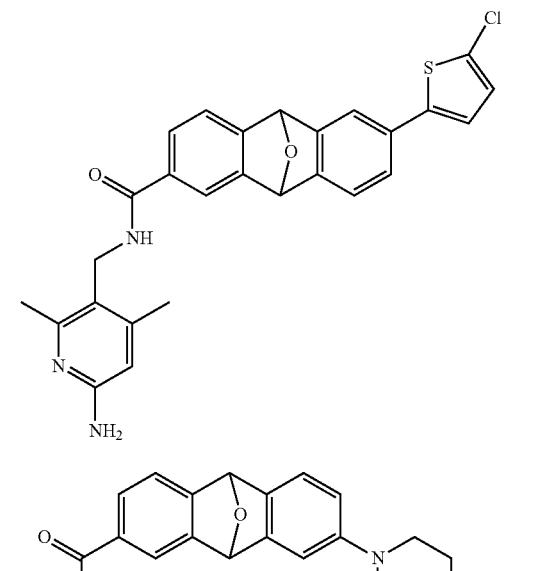 | Racemic mixture | 6.34 | (±)-N-[(6-amino-2,4-dimethylpyridin-3-yl)-methyl]-12-(4-benzoylpiperazin-1-yl)-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(4-benzoylpiperazin-1-yl)-15-oxatetracyclo-[6.6.1.0$^{2,7}$.0$^{9,14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 64 | 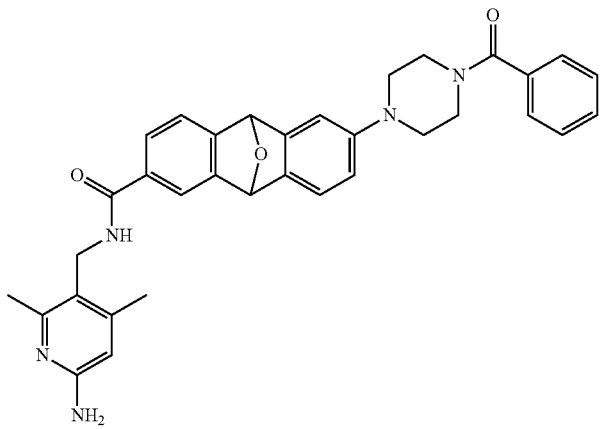 [SMILES: Cc1cc(N)nc(C)c1CNC(=O)c1ccc2c(c1)C1OC2c2cc(N3CCN(C(=O)c4ccccc4)CC3)ccc21] | Racemic mixture | 6.55 | (±)-N-[(6-amino-2,4-dimethylpyridin-3-yl)methyl]-11-(4-benzoylpiperazin-l-yl)-15-oxatetracyclo[6.6.1.0$^{2,7}$.0$^{9,14}$]pentadeca-2,4,6,9,11,13-hexaene-4-carboxamide |
| 65 | 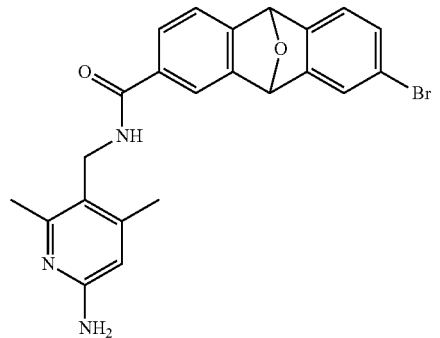 [SMILES: Cc1cc(N)nc(C)c1CNC(=O)c1ccc2c(c1)C1OC2c2ccc(Br)cc21] | Racemic mixture | 6 | (±)-N-[(6-amino-2,4-dimethylpyridin-3-yl)-methyl]-12-bromo-15-oxatetracyclo-[6.6.1.0$^{2,7}$.0$^{9,14}$]pentadeca-2,4,6,9,11,13-hexaene-4-carboxamide |
| 66 | 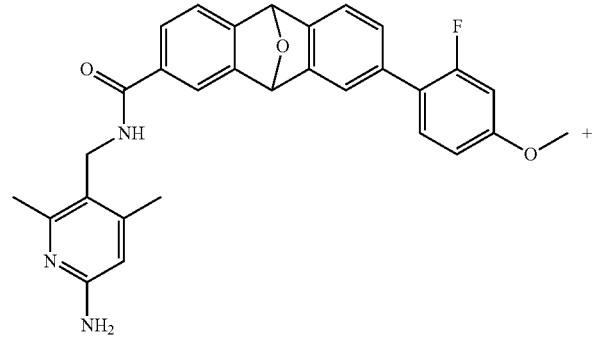 | Racemic mixture | 6.5 | (±)-N-[(6-amino-2,4-dimethylpyridin-3-yl)-methyl]-12-(2-fluoro-4-methoxyphenyl)-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(2-fluoro-4-methoxyphenyl)-15-oxatetracyclo[6.6.1.0$^{2,7}$.0$^{9,14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 67 | 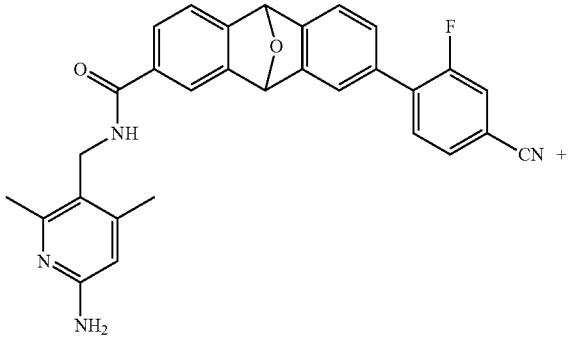 [SMILES: Cc1cc(N)nc(C)c1CNC(=O)c1ccc2c(c1)C1OC2c2ccc(-c3ccc(C#N)cc3F)cc21] | Racemic mixture | 6.57 | (±)-N-[(6-amino-2,4-dimethylpyridin-3-yl)-methyl]-12-(4-cyano-2-fluorophenyl)-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(4-cyano-2-fluorophenyl)-15-oxatetracyclo-[6.6.1.0$^{2,7}$.0$^{9,14}$]pentadeca-2,4,6,9,11,13-hexaene-4-carboxamide |
| 68 | 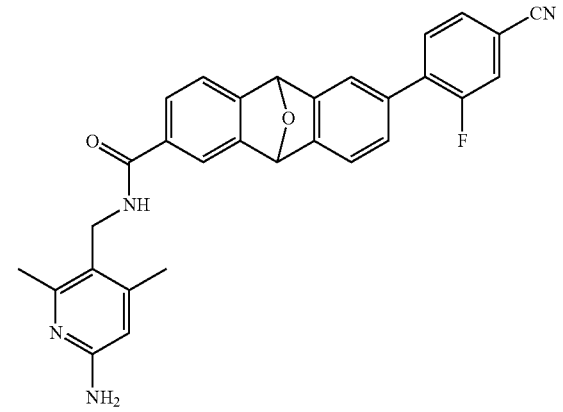 [SMILES: Cc1cc(N)nc(C)c1CNC(=O)c1ccc2c(c1)C1OC2c2cc(-c3ccc(C#N)cc3F)ccc21] | Racemic mixture | 7.65 | (±)-N-[(6-amino-2,4-dimethylpyridin-3-yl)methyl]-12-(2-cyano-4-fluorophenyl)-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(2-cyano-4-fluorophenyl)-15-oxatetracyclo-[6.6.1.0$^{2,7}$.0$^{9,14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 69 | 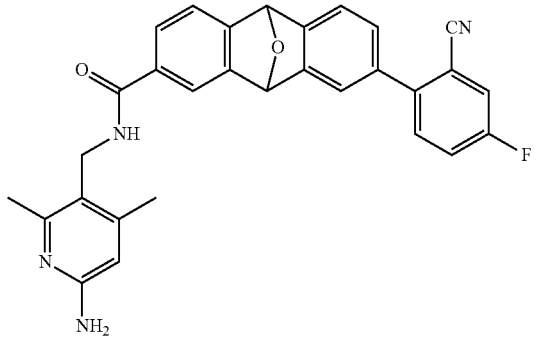 [SMILES: Cc1cc(N)nc(C)c1CNC(=O)c1ccc2c(c1)C1OC2c2ccc(-c3ccc(F)cc3C#N)cc21] | Racemic mixture | 8.2 | (±)-N-[(6-amino-2,4-dimethylpyridin-3-yl)-methyl]-12-(2-cyano-4-fluorophenyl)-15-oxatetracyclo[6.6.1.0$^2$,$^7$.0$^9$,$^{14}$]pentadeca-2,4,6,9,11,13-hexaene-4-carboxamide |
| 70 | 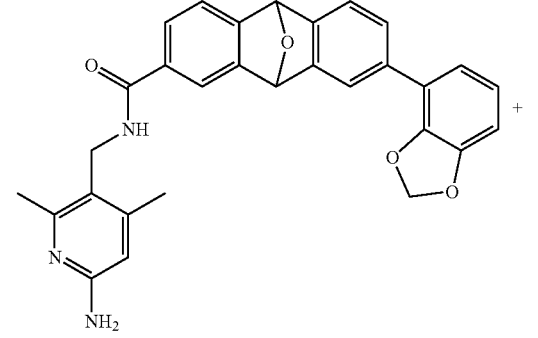 | Racemic mixture | 6.57 | (±)-N-[(6-amino-2,4-dimethylpyridin-3-yl)-methyl]-12-(2H-1,3-benzodioxol-4-yl)-15-oxatetracyclo[6.6.1.0$^2$,$^7$.0$^9$,$^{14}$]pentadeca-2,4,6,9,11,13-hexaene-4-carboxamide |
| 71 | 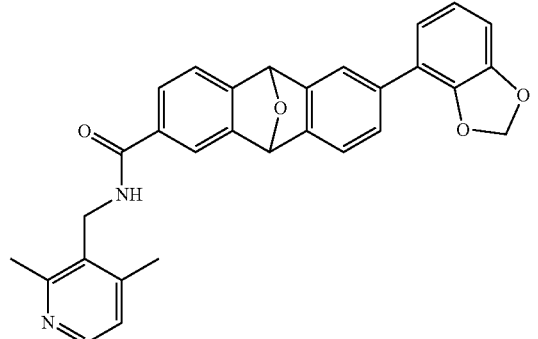 | Racemic mixture | 5.09 | (±)-N-[(6-amino-2,4-dimethylpyridin-3-yl)-methyl]-12-(2-carbamoylphenyl)-15-oxatetracyclo[6.6.1.0$^2$,$^7$.0$^9$,$^{14}$]pentadeca-2,4,6,9,11,13-hexaene-4-carboxamide and (±)-N-[(6-amino-2,4-dimethylpyridin-3-yl)methyl]-11-(2-carbamoylphenyl)-15-oxatetracyclo[6.6.1.0$^2$,$^7$.0$^9$,$^{14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| | | | | |
| 72 | | Racemic mixture | 5.65 | (±)-N-[(6-amino-2,4-dimethylpyridin-3-yl)-methyl]-12-[(3-cyanophenyl)methyl]-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-[(3-cyanophenyl)methyl]-15-oxatetracyclo-[6.6.1.0$^{2,7}$.0$^{9,14}$]pentadeca-2,4,6,9,11,13-hexaene-4-carboxamide |
| 73 | 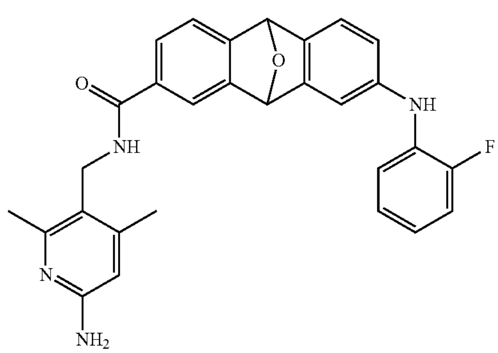 | Racemic mixture | 5.28 | (±)-N-[(6-amino-2,4-dimethylpyridin-3-yl)methyl]-12-[(2-fluorophenyl)amino]-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-[(2-fluorophenyl)amino]-15-oxatetracyclo-[6.6.1.0$^{2,7}$.0$^{9,14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| | 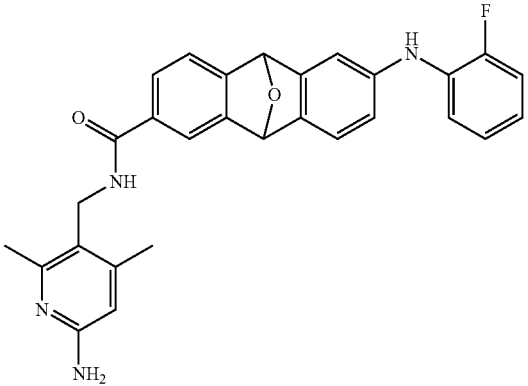 [SMILES: Cc1cc(N)nc(C)c1CNC(=O)c1ccc2c(c1)C1OC2c2cc(Nc3ccccc3F)ccc21] | | | |
| 74 | 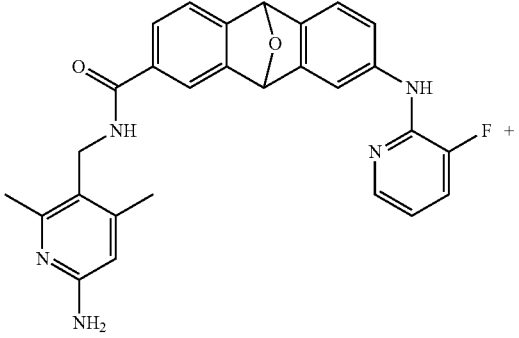 [SMILES: Cc1cc(N)nc(C)c1CNC(=O)c1ccc2c(c1)C1OC2c2ccc(Oc3cccc(F)c3)cc21] | Racemic mixture | 5.47 | (±)-N-[(6-amino-2,4-dimethylpyridin-3-yl)methyl]-12-[(3-fluoropyridin-2-yl)amino]-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-[(3-fluoropyridin-2-yl)amino]-15-oxatetracyclo[6.6.1.0$^{2,7}$.0$^{9,14}$]pentadeca-2,4,6,9,11,13-hexaene-4-carboxamide |
| 75 | 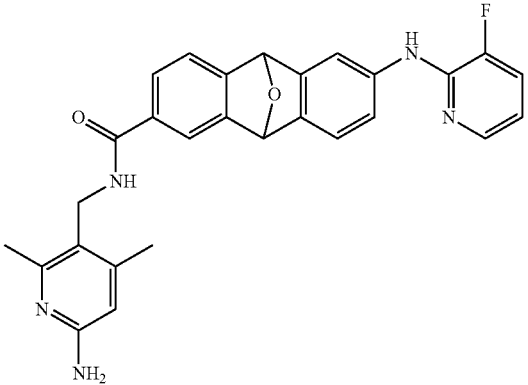 | Racemic mixture | 7.03 | (±)-N-[(6-amino-2,4-dimethylpyridin-3-yl)-methyl]-12-(3-fluorophenoxy)-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(3-fluorophenoxy)-15-oxatetracyclo-[6.6.1.0$^{2,7}$.0$^{9,14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| | | | | |
| 76 | | Racemic mixture | 7.66 | (±)-N-[(6-amino-2,4-dimethylpyridin-3-yl)-methyl]-12-(2-cyano-4-methylphenyl)-15-oxatetracyclo[6.6.1.0$^2$,$^7$.0$^9$,$^{14}$]pentadeca-2,4,6,9,11,13-hexaene-4-carboxamide and (±)-N-[(6-amino-2,4-dimethylpyridin-3-yl)methyl]-11-(2-cyano-4-methylphenyl)-15-oxatetracyclo-[6.6.1.0$^2$,$^7$.0$^9$,$^{14}$]pentadeca-2,4,6,9,11,13-hexaene-4-carboxamide |
| 77 | 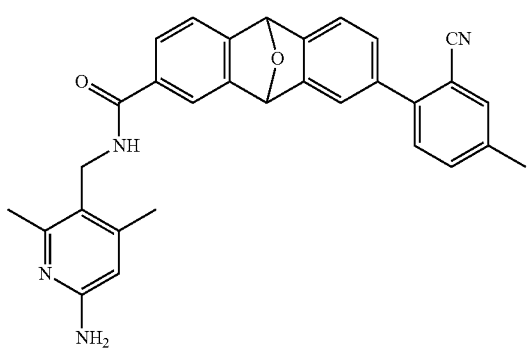 | Racemic mixture | 8.1 | (±)-N-[(6-amino-2,4-dimethylpyridin-3-yl)-methyl]-12-(2-cyano-4-methylphenyl)-15-oxatetracyclo[6.6.1.0$^2$,$^7$.0$^9$,$^{14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 78 | 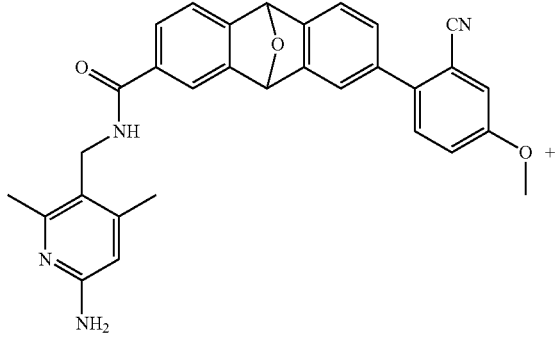 | Racemic mixture | 6.59 | (±)-N-[(6-amino-2,4-dimethylpyridin-3-yl)-methyl]-12-(2-cyano-4-methoxyphenyl)-15-oxatetracyclo[6.6.1.0$^{2,7}$.0$^{9,14}$]pentadeca-2,4,6,9,11,13-hexaene-4-carboxamide |
| 79 | 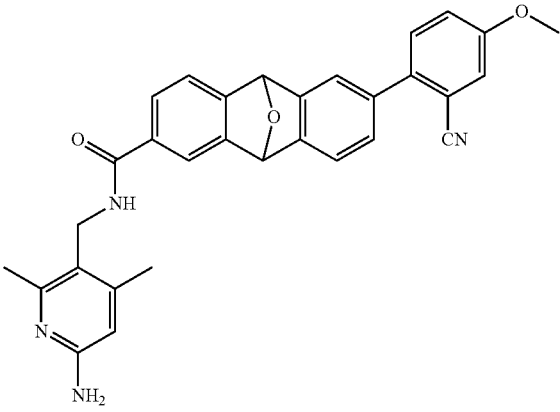 | Racemic mixture | 6.47 | (±)-N-[(6-amino-2,4-dimethylpyridin-3-yl)methyl]-12-(pyridin-2-yl)-15-oxatetra-cyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(pyridin-2-yl)-15-oxatetracyclo[6.6.1.0$^{2,7}$.0$^{9,14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 80 | 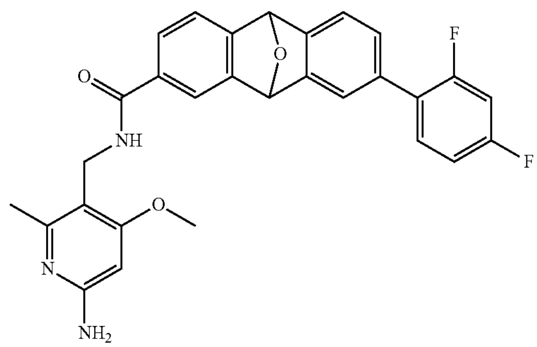 | Racemic mixture | 7.57 | (±)-N-[(6-amino-4-methoxy-2-methylpyridin-3-yl)methyl]-12-(2,4-difluorophenyl)-15-oxatetra-cyclo[6.6.1.0$^{2,7}$.0$^{9,14}$]pentadeca-2,4,6,9,11,13-hexaene-4-carboxamide |
| 81 | | Racemic mixture | 5.8 | (±)-N-[(6-amino-2,4-dimethylpyridin-3-yl)-methyl]-12-(2,3-dihydro-1,4-benzodioxin-5-yl)-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(2,3-dihydro-1,4-benzodioxin-5-yl)-15-oxatetracyclo[6.6.1.0$^{2,7}$.0$^{9,14}$]pentadeca-2,4,6,9,11,13-hexaene-4-carboxamide |
| 82 | 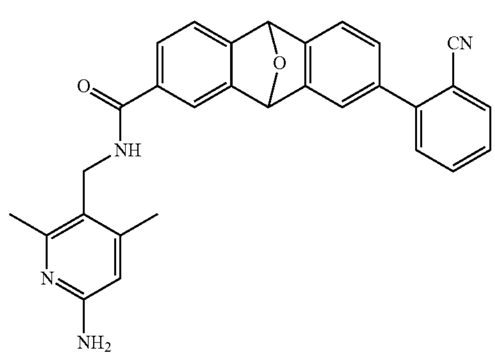 | Racemic mixture | 7.37 | (±)-N-[(6-amino-2,4-dimethylpyridin-3-yl)-methyl]-12-(2-cyanophenyl)-15-oxatetra-cyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(2-cyanophenyl)-15-oxatetracyclo[6.6.1.0$^{2,7}$.0$^{9,14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 83 | | Racemic mixture | 5.58 | (±)-N-[(6-amino-2,4-dimethylpyridin-3-yl)-methyl]-12-[(2-phenyl-1,3-oxazol-4-yl)methyl]-15-oxatetracyclo[6.6.1.0$^{2,7}$.0$^9$,1$^4$]pentadeca-2,4,6,9,11,13-hexaene-4-carboxamide and (±)-N-[(6-amino-2,4-dimethylpyridin-3-yl)methyl]-11-[(2-phenyl-1,3-oxazol-4-yl)methyl]-15-oxatetracyclo[6.6.1.0$^{2,7}$.0$^9$,1$^4$]pentadeca-2,4,6,9,11,13-hexaene-4-carboxamide |
| 84 | 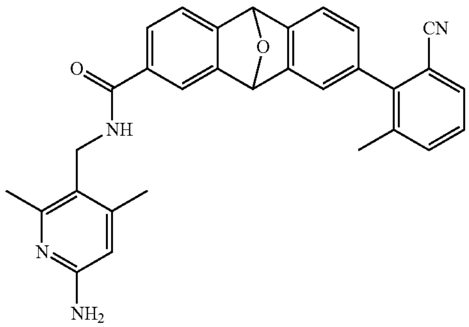 | Racemic mixture | 6.75 | (±)-N-[(6-amino-2,4-dimethylpyridin-3-yl)-methyl]-12-(2-cyano-6-methylphenyl)-15-oxatetracyclo[6.6.1.0$^{2,7}$.0$^9$,1$^4$]pentadeca-2,4,6,9,11,13-hexaene-4-carboxamide and (±)-N-[(6-amino-2,4-dimethylpyridin-3-yl)methyl]-11-(2-cyano-6-methylphenyl)-15-oxatetra-cyclo[6.6.1.0$^{2,7}$.0$^9$,1$^4$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 85 | | Racemic mixture | 6.58 | (±)-N-[(6-amino-2,4-dimethylpyridin-3-yl)-methyl]-12-[6-(cyclopropylmethoxy)pyridin-3-yl]-15-oxatetracyclo[6.6.1.0$^{2,7}$.0$^{9,14}$]pentadeca-2,4,6,9,11,13-hexaene-4-carboxamide (±)-N-[(6-amino-2,4-dimethylpyridin-3-yl)methyl]-11-[6-(cyclopropylmethoxy)pyridin-3-yl]-15-oxatetracyclo[6.6.1.0$^{2,7}$.0$^{9,14}$]pentadeca-2,4,6,9,11,13-hexaene-4-carboxamide |
| 86 | 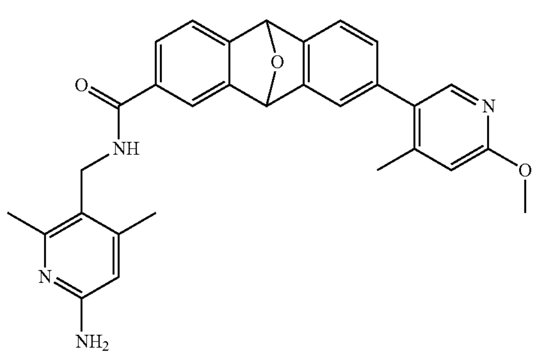 | Racemic mixture | 6.41 | (±)-N-[(6-amino-2,4-dimethylpyridin-3-yl)-methyl]-12-(6-methoxy-4-methylpyridin-3-yl)-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(6-methoxy-4-methylpyridin-3-yl)-15-oxatetracyclo[6.6.1.0$^{2,7}$.0$^{9,14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 87 | | Racemic mixture | 5.8 | (±)-N-[(6-amino-2,4-dimethylpyridin-3-yl)-methyl]-12-(pyrimidin-2-yl)-15-oxatetra-cyclo[6.6.1.0$^2$,$^7$.0$^9$,$^{14}$]pentadeca-2,4,6,9,11,13-hexaene-4-carboxamide and (±)-N-[(6-amino-2,4-dimethylpyridin-3-yl)methyl]-11-(pyrimidin-2-yl)-15-oxatetracyclo[6.6.1.0$^2$,$^7$.0$^9$,$^{14}$]pentadeca-2,4,6,9,11,13-hexaene-4-carboxamide |
| 88 | 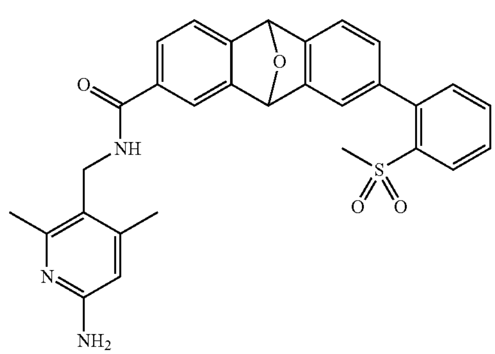 | Racemic mixture | 5.57 | (±)-N-[(6-amino-2,4-dimethylpyridin-3-yl)-methyl]-12-(2-methanesulfonylphenyl)-15-oxatetra-cyclo[6.6.1.0$^2$,$^7$.0$^9$,$^{14}$]pentadeca-2,4,6,9,11,13-hexaene-4-carboxamide and (±)-N-[(6-amino-2,4-dimethylpyridin-3-yl)methyl]-11-(2-methanesulfonylphenyl)-15-oxatetra-cyclo[6.6.1.0$^2$,$^7$.0$^9$,$^{14}$]pentadeca-2,4,6,9,11,13-hexaene-4-carboxamide |

| Cpd. No | Structure | Compound Type | KLKB1 pIC$_{50}$ | IUPAC Name |
|---|---|---|---|---|
| | | | | |
| 89 | 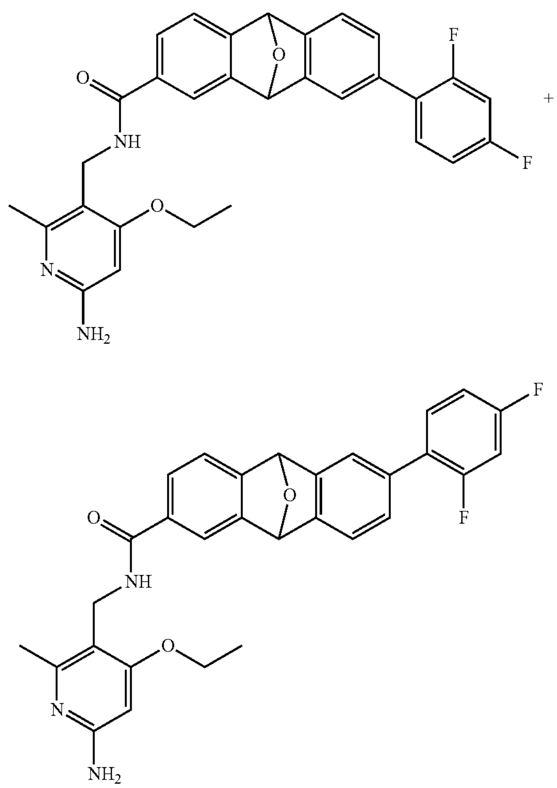 | Racemic mixture + | 7.47 | (±)-N-[(6-amino-4-ethoxy-2-methylpyridin-3-yl)-methyl]-12-(2,4-difluorophenyl)-15-oxatetracyclo[6.6.1.0$^2$,$^7$.0$^9$,$^{14}$]pentadeca-2,4,6,9,11,13-hexaene-4-carboxamide and (±)-N-[(6-amino-4-ethoxy-2-methylpyridin-3-yl)methyl]-11-(2,4-difluorophenyl)-15-oxatetracyclo-[6.6.1.0$^2$,$^7$.0$^9$,$^{14}$]pentadeca-2,4,6,9,11,13-hexaene-4-carboxamide |
| 90 | 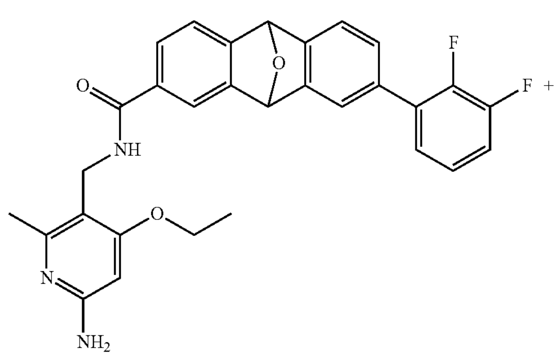 [SMILES: CCOc1cc(N)nc(C)c1CNC(=O)c1ccc2c(c1)C1OC2c2ccc(-c3cccc(F)c3F)cc21] | Racemic mixture + | 7.14 | (±)-N-[(6-amino-4-ethoxy-2-methylpyridin-3-yl)methyl]-12-(2,3-difluorophenyl)-15-oxatetracyclo[6.6.1.0$^2$,$^7$.0$^9$,$^{14}$]pentadeca-2,4,6,9,11,13-hexaene-4-carboxamide and (±)-N-[(6-amino-4-ethoxy-2-methylpyridin-3-yl)methyl]-11-(2,3-difluorophenyl)-15-oxatetracyclo[6.6.1.0$^2$,$^7$.0$^9$,$^{14}$]-pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 91 | 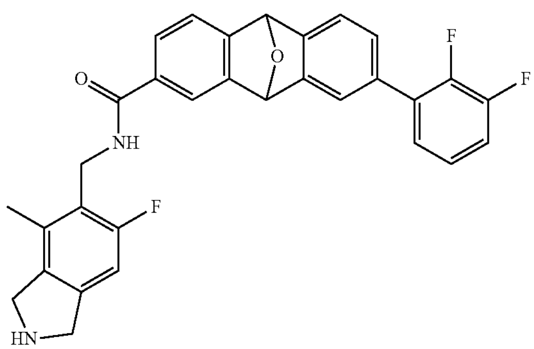 [SMILES: Cc1c(CNC(=O)c2ccc3c(c2)C2OC3c3ccc(-c4cccc(F)c4F)cc32)c(F)cc2c1CNC2] | Racemic mixture | 5 | (±)-12-(2,3-difluorophenyl)-N-[(6-fluoro-4-methyl-2,3-dihydro-1H-isoindol-5-yl)methyl]-15-oxatetracyclo[6.6.1.0$^2$,$^7$.0$^9$,$^1$$^4$]pentadeca-2,4,6,9,11,13-hexaene-4-carboxamide |
| 92 | | Racemic mixture | 6.81 | (±)-N-[(6-amino-2,4-dimethylpyridin-3-yl)methyl]-12-[(1,3-oxazol-4-yl)methyl]-15-oxatetracyclo[6.6.1.0$^2$,$^7$.0$^9$,$^1$$^4$]pentadeca-2,4,6,9,11,13-hexaene-4-carboxamide and (±)-N-[(6-amino-2,4-dimethylpyridin-3-yl)methyl]-11-[(1,3-oxazol-4-yl)methyl]-15-oxatetracyclo-[6.6.1.0$^2$,$^7$.0$^9$,$^1$$^4$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 93 | 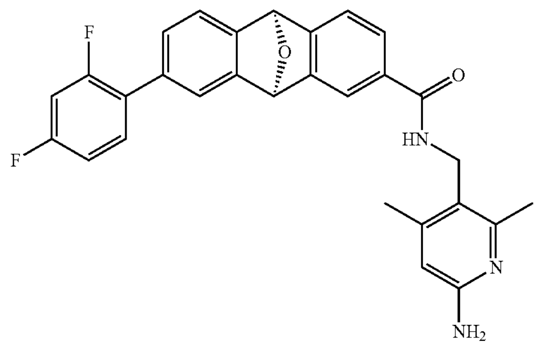 [SMILES: Cc1cc(N)nc(C)c1CNC(=O)c1ccc2c(c1)[C@@H]1O[C@H]2c2ccc(-c3ccc(F)cc3F)cc21] | Single enantiomer | 7.73 | (1R,8S)-N-[(6-amino-2,4-dimethylpyridin-3-yl)methyl]-12-(2,4-difluorophenyl)-15-oxatetra-cyclo[6.6.1.0$^2$,$^7$.0$^9$,$^{14}$]pentadeca-2,4,6,9,11,13-hexaene-4-carboxamide |
| 94 | 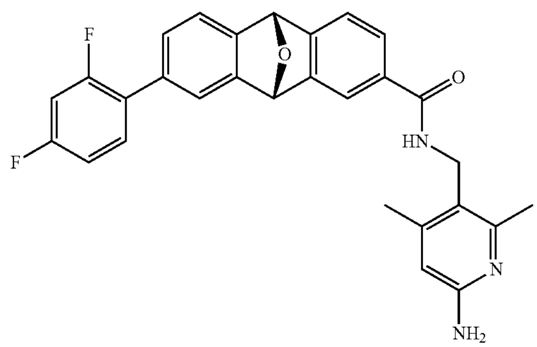 [SMILES: Cc1cc(N)nc(C)c1CNC(=O)c1ccc2c(c1)[C@H]1O[C@@H]2c2ccc(-c3ccc(F)cc3F)cc21] | Single enantiomer | 4.44 | (1S,8R)-N-[(6-amino-2,4-dimethylpyridin-3-yl)-methyl]-12-(2,4-difluorophenyl)-15-oxatetracyclo-[6.6.1.0$^2$,$^7$.0$^9$,$^{14}$]pentadeca-2,4,6,9,11,13-hexaene-4-carboxamide |
| 95 | | Racemic mixture | 6.34 | (±)-N-[(6-amino-2,4-dimethylpyridin-3-yl)-methyl]-12-(5-methylfuran-2-yl)-15-oxatetra-cyclo[6.6.1.0$^2$,$^7$.0$^9$,$^{14}$]pentadeca-2,4,6,9,11,13-hexaene-4-carboxamide and (±)-N-[(6-amino-2,4-dimethylpyridin-3-yl)methyl]-11-(5-methylfuran-2-yl)-15-oxatetracyclo[6.6.1.0$^2$,$^7$.0$^9$,$^{14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 96 | | Racemic mixture | 6.51 | (±)-N-{[4-(aminomethyl)-2,6-dimethylphenyl]-methyl}-12-(2-cyano-4-fluorophenyl)-15-oxatetracyclo[6.6.1.0$^2$,$^7$.0$^9$,1$^4$]pentadeca-2,4,6,9,11,13-hexaene-4-carboxamide and (±)-N-{[4-(aminomethyl)-2,6-dimethylphenyl]methyl}-11-(2-cyano-4-fluorophenyl)-15-oxatetracyclo-[6.6.1.0$^2$,$^7$.0$^9$,1$^4$]pentadeca-2,4,6,9,11,13-hexaene-4-carboxamide |
| 97 | | Racemic mixture | 5.65 | (±)-N-[(6-amino-2,4-dimethylpyridin-3-yl)-methyl]-12-{2-oxa-6-azaspiro[3.3]heptan-6-yl}-15-oxatetracyclo[6.6.1.0$^2$,$^7$.0$^9$,1$^4$]pentadeca-2,4,6,9,11,13-hexaene-4-carboxamide and (±)-N-[6-amino-2,4-dimethylpyridin-3-yl)methyl]-11-{2-oxa-6-azaspiro[3.3]heptan-6-yl}-15-oxatetracyclo[6.6.1.0$^2$,$^7$.0$^9$,1$^4$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 98 | 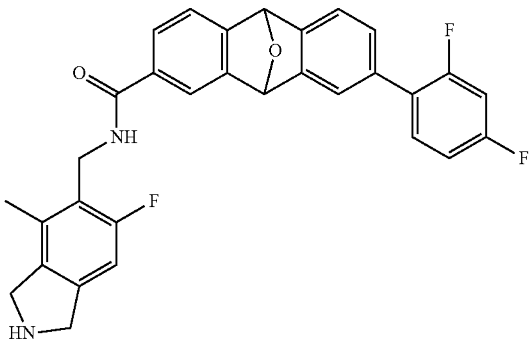 [SMILES: Cc1c(CNC(=O)c2ccc3c(c2)C2OC3c3ccc(-c4ccc(F)cc4F)cc32)c(F)cc2c1CNC2] | Racemic mixture | 6.99 | (±)-12-(2,4-difluorophenyl)-N-[(6-fluoro-4-methyl-2,3-dihydro-1H-isoindol-5-yl)methyl]-15-oxatetracyclo[6.6.1.0$^2$,$^7$.0$^9$,$^{14}$]pentadeca-2,4,6,9,11,13-hexaene-4-carboxamide |
| 99 | 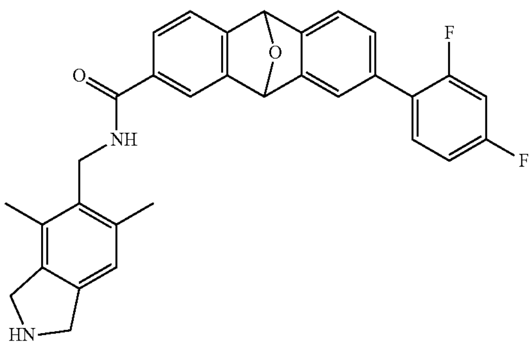 [SMILES: Cc1cc2c(c(C)c1CNC(=O)c1ccc3c(c1)C1OC3c3ccc(-c4ccc(F)cc4F)cc31)CNC2] | Racemic mixture | 6.5 | (±)-12-(2,4-difluorophenyl)-N-[(4,6-dimethyl-2,3-dihydro-1H-isoindol-5-yl)methyl]-15-oxatetra-cyclo[6.6.1.0$^2$,$^7$.0$^9$,$^{14}$]pentadeca-2,4,6,9,11,13-hexaene-4-carboxamide |
| 100 | 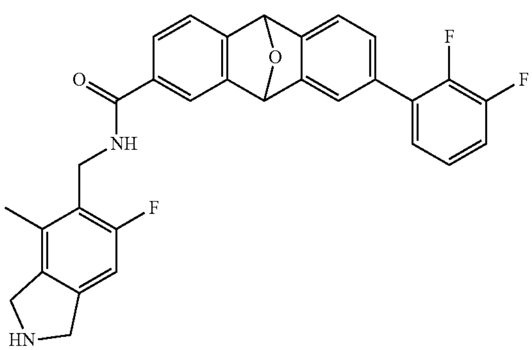 [SMILES: Cc1c(CNC(=O)c2ccc3c(c2)C2OC3c3ccc(-c4cccc(F)c4F)cc32)c(F)cc2c1CNC2] | Racemic mixture | 5.21 | (±)-12-(2,3-difluorophenyl)-N-[(4,6-dimethyl-2,3-dihydro-1H-isoindol-5-yl)methyl]-15-oxatetra-cyclo[6.6.1.0$^2$,$^7$.0$^9$,$^{14}$]pentadeca-2,4,6,9,11,13-hexaene-4-carboxamide |
| 101 | 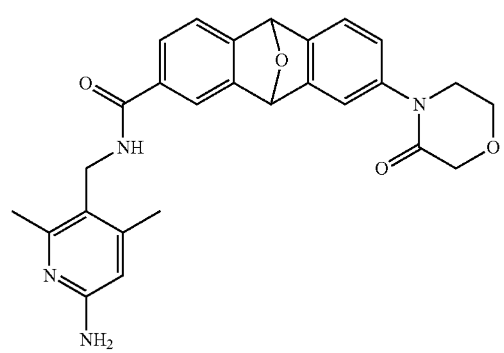 | Racemic mixture | 5.8 | (±)-N-[(6-amino-2,4-dimethylpyridin-3-yl)methyl]-12-(3-oxomorpholin-4-yl)-15-oxatetracyclo[6.6.1.0$^2$,$^7$.0$^9$,$^{14}$]pentadeca-2,4,6,9,11,13-hexaene-4-carboxamide and (±)-N-[(6-amino-2,4-dimethylpyridin-3-yl)methyl]-11-(3-oxomorpholin-4-yl)-15-oxatetracyclo-[6.6.1.0$^2$,$^7$.0$^9$,$^{14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| | | | | |
| 102 | 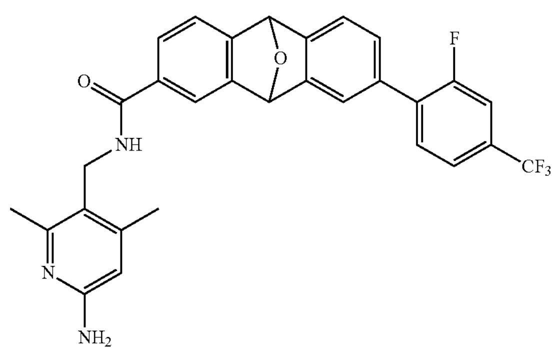 [SMILES: Cc1cc(N)nc(C)c1CNC(=O)c1ccc2c(c1)C1OC2c2ccc(-c3ccc(C(F)(F)F)cc3F)cc21] | Racemic mixture | 6.27 | (±)-N-[(6-amino-2,4-dimethylpyridin-3-yl)methyl]-12-[2-fluoro-4-(trifluoromethyl)phenyl]-15-oxatetracyclo[6.6.1.0$^2$,$^7$.0$^9$,$^{14}$]-pentadeca-2,4,6,9,11,13-hexaene-4-carboxamide |
| 103 | 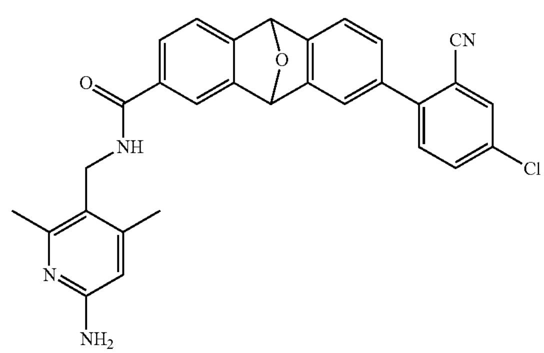 [SMILES: Cc1cc(N)nc(C)c1CNC(=O)c1ccc2c(c1)C1OC2c2ccc(-c3ccc(Cl)cc3C#N)cc21] | Racemic mixture | 8.05 | (±)-N-[(6-amino-2,4-dimethylpyridin-3-yl)-methyl]-12-(4-chloro-2-cyanophenyl)-15-oxatetracyclo[6.6.1.0$^2$,$^7$.0$^9$,$^{14}$]pentadeca-2,4,6,9,11,13-hexaene-4-carboxamide |
| 104 | 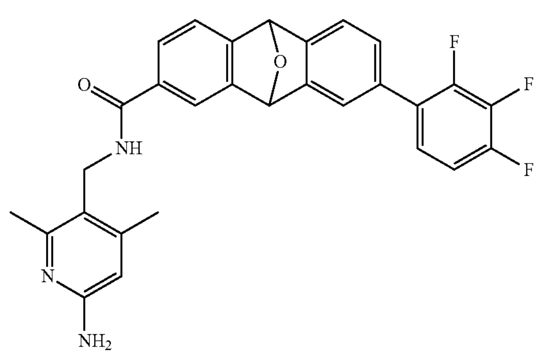 | Racemic mixture | 7.55 | (±)-N-[(6-amino-2,4-dimethylpyridin-3-yl)-methyl]-12-(2,3,4-trifluorophenyl)-15-oxatetracyclo[6.6.1.0$^2$,$^7$.0$^9$,$^{14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 105 | 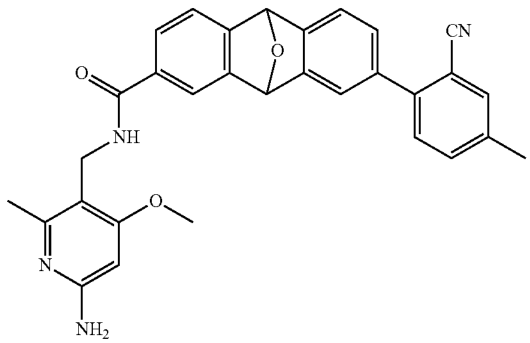 | Racemic mixture | 7.82 | (±)-N-[(6-amino-4-methoxy-2-methylpyridin-3-yl)methyl]-12-(2-cyano-4-methylphenyl)-15-oxatetra-cyclo[6.6.1.0$^2$,$^7$.0$^9$,$^{14}$]pentadeca-2,4,6,9,11,13-hexaene-4-carboxamide |
| 106 | 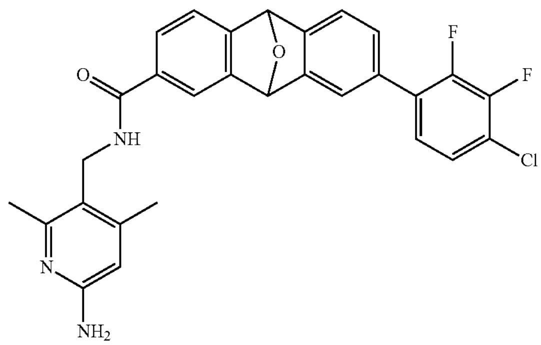 | Racemic mixture | 7.64 | (±)-N-[(6-amino-2,4-dimethylpyridin-3-yl)-methyl]-12-(4-chloro-2,3-difluorophenyl)-15-oxatetracyclo[6.6.1.0$^2$,$^7$.0$^9$,$^{14}$]pentadeca-2,4,6,9,11,13-hexaene-4-carboxamide |
| 107 | 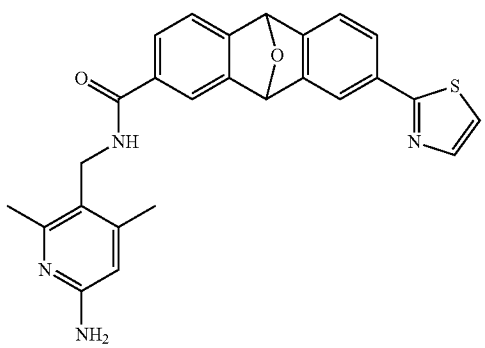 | Racemic mixture | 6.13 | (±)-N-[(6-amino-2,4-dimethylpyridin-3-yl)-methyl]-12-(1,3-thiazol-2-yl)-15-oxatetra-cyclo[6.6.1.0$^2$,$^7$.0$^9$,$^{14}$]pentadeca-2,4,6,9,11,13-hexaene-4-carboxamide and (±)-N-[(6-amino-2,4-dimethylpyridin-3-yl)methyl]-11-(1,3-thiazol-2-yl)-15-oxatetracyclo[6.6.1.0$^2$,$^7$.0$^9$,$^{14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 108 | 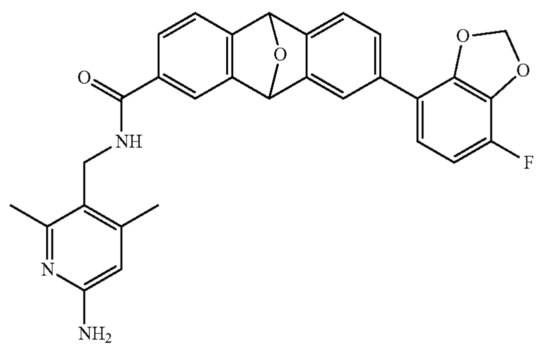 [SMILES: Cc1cc(N)nc(C)c1CNC(=O)c1ccc2c(c1)C1OC2c2ccc(-c3ccc(F)c4c3OCO4)cc21] | Racemic mixture | 7.59 | (±)-N-[(6-amino-2,4-dimethylpyridin-3-yl)-methyl]-12-(7-fluoro-2H-1,3-benzodioxol-4-yl)-15-oxatetracyclo[6.6.1.0$^{2,7}$.0$^{9,14}$]pentadeca-2,4,6,9,11,13-hexaene-4-carboxamide |
| 109 | 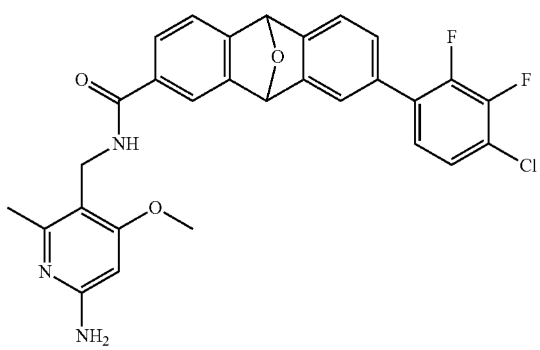 [SMILES: COc1cc(N)nc(C)c1CNC(=O)c1ccc2c(c1)C1OC2c2ccc(-c3ccc(Cl)c(F)c3F)cc21] | Racemic mixture | 7.59 | (±)-N-[(6-amino-4-methoxy-2-methylpyridin-3-yl)methyl]-12-(4-chloro-2,3-difluorophenyl)-15-oxatetracyclo[6.6.1.0$^{2,7}$.0$^{9,14}$]pentadeca-2,4,6,9,11,13-hexaene-4-carboxamide |
| 110 | 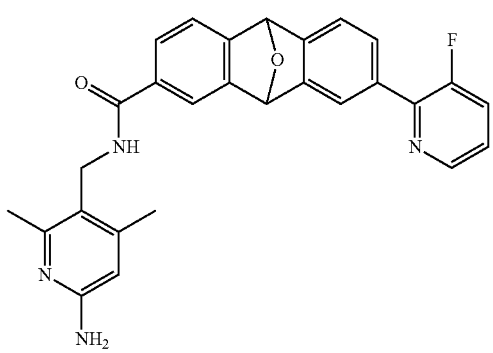 [SMILES: Cc1cc(N)nc(C)c1CNC(=O)c1ccc2c(c1)C1OC2c2ccc(-c3ncccc3F)cc21] | Racemic mixture | 6.79 | (±)-N-[(6-amino-2,4-dimethylpyridin-3-yl)-methyl]-12-(3-fluoropyridin-2-yl)-15-oxatetracyclo[6.6.1.0$^{2,7}$.0$^{9,14}$]pentadeca-2,4,6,9,11,13-hexaene-4-carboxamide |
| 111 | 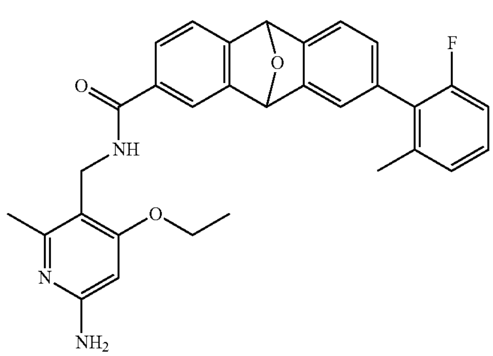 [SMILES: CCOc1cc(N)nc(C)c1CNC(=O)c1ccc2c(c1)C1OC2c2ccc(-c3c(C)cccc3F)cc21] | Racemic mixture | 6.91 | (±)-N-[(6-amino-4-ethoxy-2-methylpyridin-3-yl)-methyl]-12-(2-fluoro-6-methylphenyl)-15-oxatetra-cyclo[6.6.1.0$^{2,7}$.0$^{9,14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 112 | 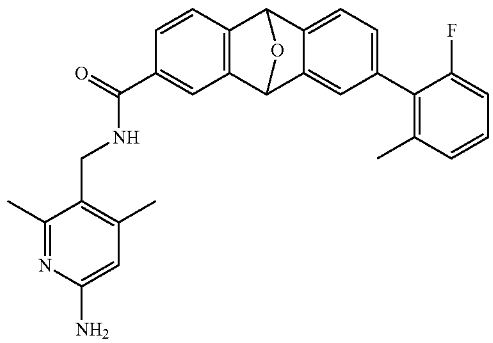 | Racemic mixture | 6.82 | (±)-N-[(6-amino-2,4-dimethylpyridin-3-yl)-methyl]-12-(2-fluoro-6-methylphenyl)-15-oxatetracyclo[6.6.1.0$^2$,$^7$.0$^9$,$^{14}$]pentadeca-+n12,4,6,9,11,13-hexaene-4-carboxamide |
| 113 | 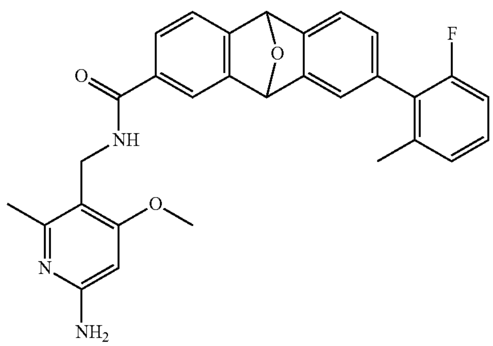 [SMILES: COc1cc(N)nc(C)c1CNC(=O)c1ccc2c(c1)C1OC2c2ccc(-c3c(C)cccc3F)cc21] | Racemic mixture | 6.89 | (±)-N-[(6-amino-4-methoxy-2-methylpyridin-3-yl)methyl]-12-(2-fluoro-6-methylphenyl)-15-oxatetracyclo[6.6.1.0$^2$,$^7$.0$^9$,$^{14}$]pentadeca-2,4,6,9,11,13-hexaene-4-carboxamide |
| 114 | 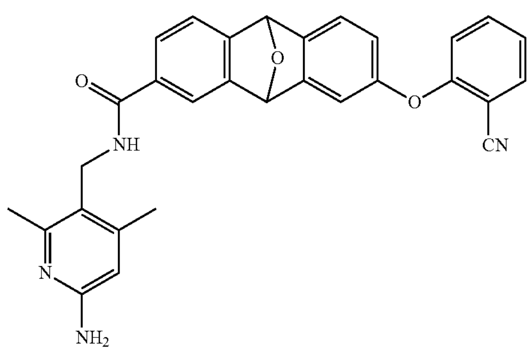 [SMILES: Cc1cc(N)nc(C)c1CNC(=O)c1ccc2c(c1)C1OC2c2ccc(Oc3ccccc3C#N)cc21] | Racemic mixture | 6.24 | (±)-N-[(6-amino-2,4-dimethylpyridin-3-yl)-methyl]-12-(2-cyanophenoxy)-15-oxatetracyclo[6.6.1.0$^2$,$^7$.0$^9$,$^{14}$]pentadeca-2,4,6,9,11,13-hexaene-4-carboxamide |
| 115 | 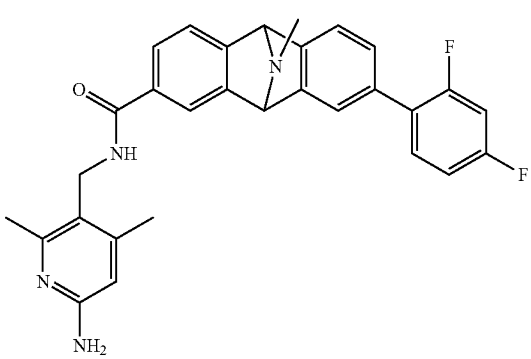 | Racemic mixture | 4 | (±)-N-[(6-amino-2,4-dimethylpyridin-3-yl)-methyl]-12-(2,4-difluorophenyl)-15-methyl-15-azatetracyclo[6.6.1.0$^2$,$^7$.0$^9$,$^{14}$]pentadeca-2,4,6,9,11,13-hexaene-4-carboxamide and (±)-N-[(6-amino-2,4-dimethylpyridin-3-yl)methyl]-11-(2,4-difluorophenyl)-15-methyl-15-azatetra-cyclo[6.6.1.0$^2$,$^7$.0$^9$,$^{14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| | | | | |
| 116 | 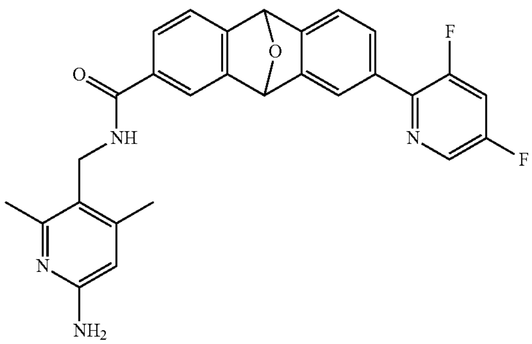 [SMILES: Cc1cc(N)nc(C)c1CNC(=O)c1ccc2c(c1)C1OC2c2ccc(-c3ncc(F)cc3F)cc21] | Racemic mixture | 7.34 | (±)-N-[(6-amino-2,4-dimethylpyridin-3-yl)-methyl]-12-(3,5-difluoropyridin-2-yl)-15-oxatetracyclo[6.6.1.0$^{2,7}$.0$^{9,14}$]pentadeca-2,4,6,9,11,13-hexaene-4-carboxamide |
| 117 | 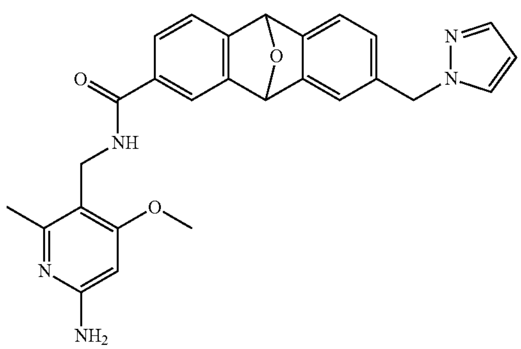 [SMILES: COc1cc(N)nc(C)c1CNC(=O)c1ccc2c(c1)C1OC2c2ccc(Cn3cccn3)cc21] | Racemic mixture | 8.4 | (±)-N-[(6-amino-4-methoxy-2-methylpyridin-3-yl)methyl]-12-[(1H-pyrazol-1-yl)methyl]-15-oxatetracyclo[6.6.1.0$^{2,7}$.0$^{9,14}$]pentadeca-2,4,6,9,11,13-hexaene-4-carboxamide |
| 118 | 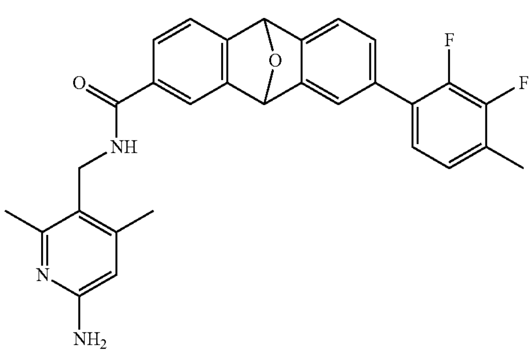 | Racemic mixture | 7.19 | (±)-N-[(6-amino-2,4-dimethylpyridin-3-yl)-methyl]-12-(2,3-difluoro-4-methylphenyl)-15-oxatetracyclo[6.6.1.0$^{2,7}$.0$^{9,14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 119 | 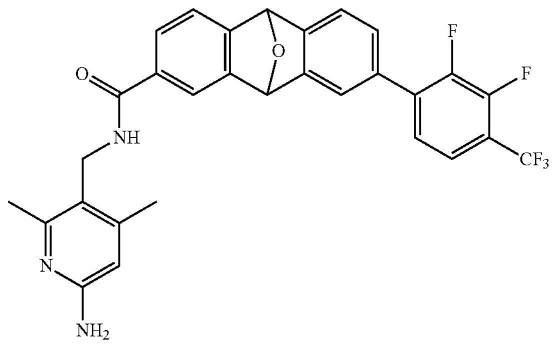 [SMILES: Cc1cc(N)nc(C)c1CNC(=O)c1ccc2c(c1)C1OC2c2ccc(-c3ccc(C(F)(F)F)c(F)c3F)cc21] | Racemic mixture | 6.37 | (±)-N-[(6-amino-2,4-dimethylpyridin-3-yl)-methyl]-12-[2,3-difluoro-4-(trifluoromethyl)-phenyl]-15-oxatetracyclo[6.6.1.0$^2$,$^7$.0$^9$,$^{14}$]-pentadeca-2,4,6,9,11,13-hexaene-4-carboxamide |
| 120 | 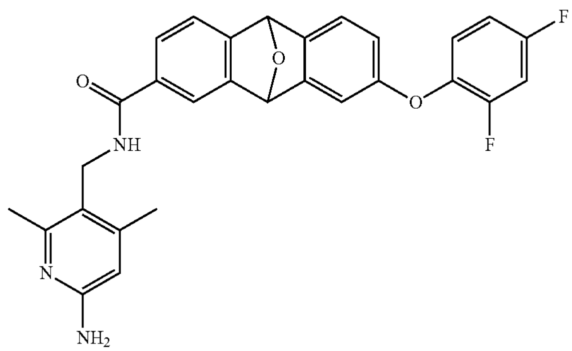 [SMILES: Cc1cc(N)nc(C)c1CNC(=O)c1ccc2c(c1)C1OC2c2ccc(Oc3ccc(F)cc3F)cc21] | Racemic mixture | 6.17 | (±)-N-[(6-amino-2,4-dimethylpyridin-3-yl)-methyl]-12-(2,4-difluorophenoxy)-15-oxatetra-cyclo[6.6.1.0$^2$,$^7$.0$^9$,$^{14}$]pentadeca-2,4,6,9,11,13-hexaene-4-carboxamide |
| 121 | 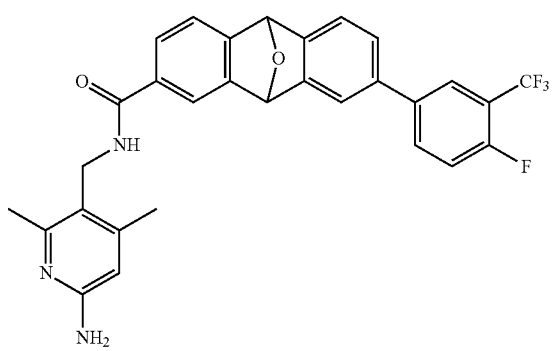 [SMILES: Cc1cc(N)nc(C)c1CNC(=O)c1ccc2c(c1)C1OC2c2ccc(-c3ccc(F)c(C(F)(F)F)c3)cc21] | Racemic mixture | 6.36 | (±)-N-[(6-amino-2,4-dimethylpyridin-3-yl)-methyl]-12-[4-fluoro-3-(trifluoromethyl)phenyl]-15-oxatetracyclo[6.6.1.0$^2$,$^7$.0$^9$,$^{14}$]pentadeca-2,4,6,9,11,13-hexaene-4-carboxamide |
| 122 | 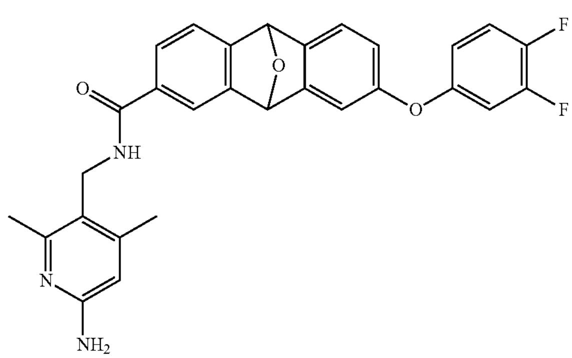 [SMILES: Cc1cc(N)nc(C)c1CNC(=O)c1ccc2c(c1)C1OC2c2ccc(Oc3ccc(F)c(F)c3)cc21] | Racemic mixture | 6.83 | (±)-N-[(6-amino-2,4-dimethylpyridin-3-yl)-methyl]-12-(3,4-difluorophenoxy)-15-oxatetracyclo[6.6.1.0$^2$,$^7$.0$^9$,$^{14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 123 | 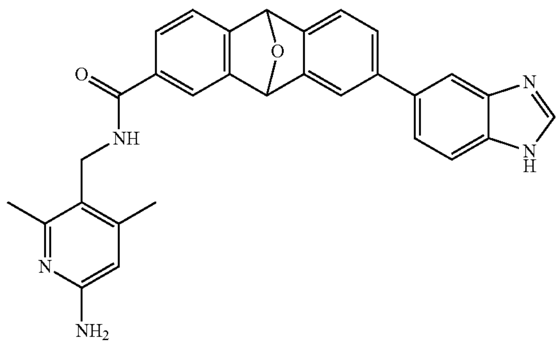 [SMILES: Cc1cc(N)nc(C)c1CNC(=O)c1ccc2c(c1)C1OC2c2ccc(-c3ccc4[nH]cnc4c3)cc21] | Racemic mixture | 6.55 | (±)-N-[(6-amino-2,4-dimethylpyridin-3-yl)-methyl]-12-(1H-1,3-benzodiazol-5-yl)-15-oxatetracyclo[6.6.1.0$^{2,7}$.0$^{9,14}$]pentadeca-2,4,6,9,11,13-hexaene-4-carboxamide |
| 124 | 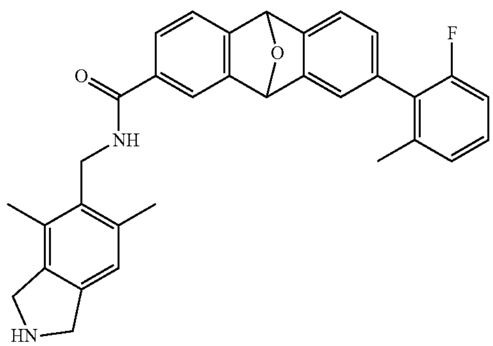 [SMILES: Cc1cc2c(c(C)c1CNC(=O)c1ccc3c(c1)C1OC3c3ccc(-c4c(C)cccc4F)cc31)CNC2] | Racemic mixture | 4.94 | (±)-N-[(4,6-dimethyl-2,3-dihydro-1H-isoindol-5-yl)methyl]-12-(2-fluoro-6-methylphenyl)-15-oxatetracyclo[6.6.1.0$^{2,7}$.0$^{9,14}$]pentadeca-2,4,6,9,11,13-hexaene-4-carboxamide |
| 125 | 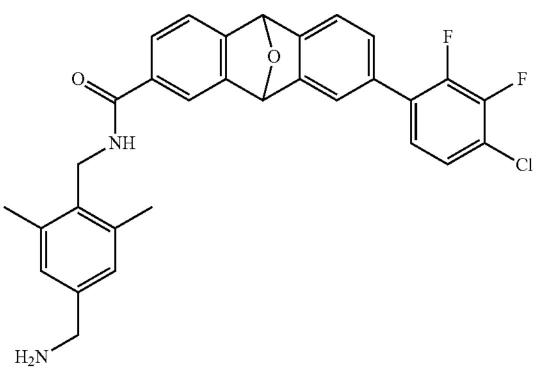 [SMILES: Cc1cc(CN)cc(C)c1CNC(=O)c1ccc2c(c1)C1OC2c2ccc(-c3ccc(Cl)c(F)c3F)cc21] | Racemic mixture | 6.18 | (±)-N-{[4-(aminomethyl)-2,6-dimethylphenyl]-methyl}-12-(4-chloro-2,3-difluorophenyl)-15-oxatetracyclo-[6.6.1.0$^{2,7}$.0$^{9,14}$]pentadeca-2,4,6,9,11,13-hexaene-4-carboxamide |
| 126 | 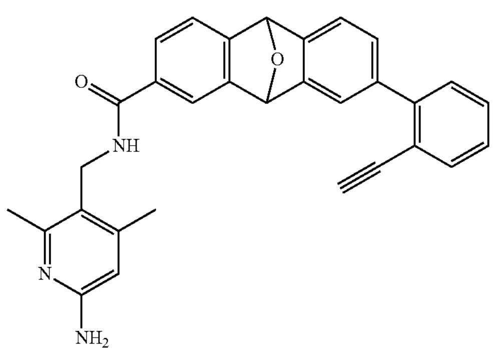 [SMILES: C#Cc1ccccc1-c1ccc2c(c1)C1OC2c2ccc(C(=O)NCc3c(C)cc(N)nc3C)cc21] | Racemic mixture | 5.2 | (±)-N-[(6-amino-2,4-dimethylpyridin-3-yl)-methyl]-12-(2-ethynylphenyl)-15-oxatetra-cyclo[6.6.1.0$^{2,7}$.0$^{9,14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 127 | 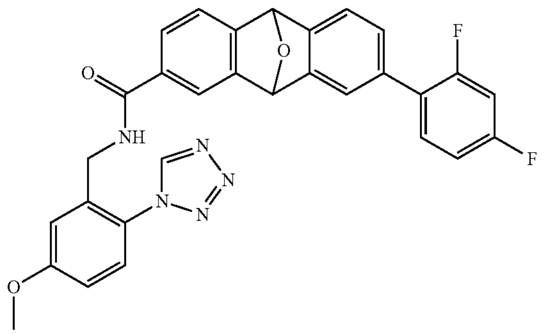 [SMILES: COc1ccc(-n2cnnn2)c(CNC(=O)c2ccc3c(c2)C2OC3c3ccc(-c4ccc(F)cc4F)cc32)c1] | Racemic mixture | 6.01 | (±)-12-(2,4-difluorophenyl)-N-{[5-methoxy-2-(1H-1,2,3,4-tetrazol-1-yl)phenyl]methyl}-15-oxatetracyclo[6.6.1.0$^{2,7}$.0$^{9,14}$]pentadeca-2,4,6,9,11,13-hexaene-4-carboxamide |
| 128 | 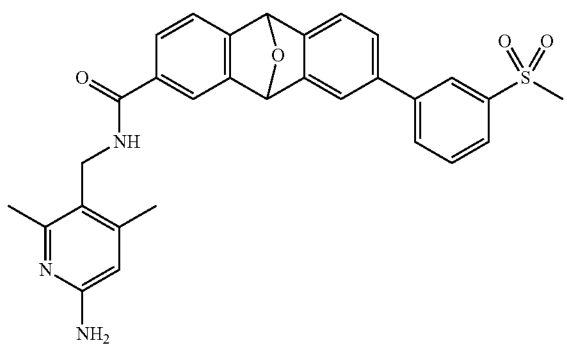 | Racemic mixture | 6.03 | (±)-N-[(6-amino-2,4-dimethylpyridin-3-yl)methyl]-12-(3-methanesulfonylphenyl)-15-oxatetracyclo[6.6.1.0$^{2,7}$.0$^{9,14}$]pentadeca-2,4,6,9,11,13-hexaene-4-carboxamide |
| 129 | 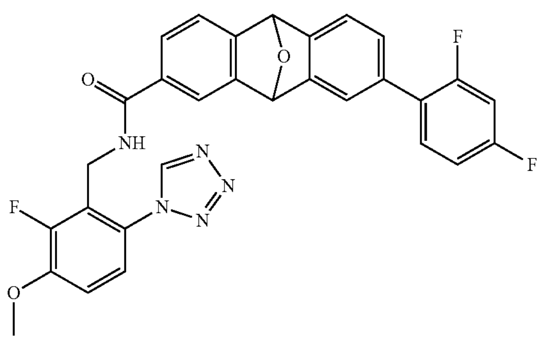 [SMILES: COc1ccc(-n2cnnn2)c(CNC(=O)c2ccc3c(c2)C2OC3c3ccc(-c4ccc(F)cc4F)cc32)c1F] | Racemic mixture | 6.63 | (±)-12-(2,4-difluorophenyl)-N-{[2-fluoro-3-methoxy-6-(1H-1,2,3,4-tetrazol-1-yl)phenyl]methyl}-15-oxatetracyclo[6.6.1.0$^{2,7}$.0$^{9,14}$]pentadeca-2,4,6,9,11,13-hexaene-4-carboxamide |
| 130 | 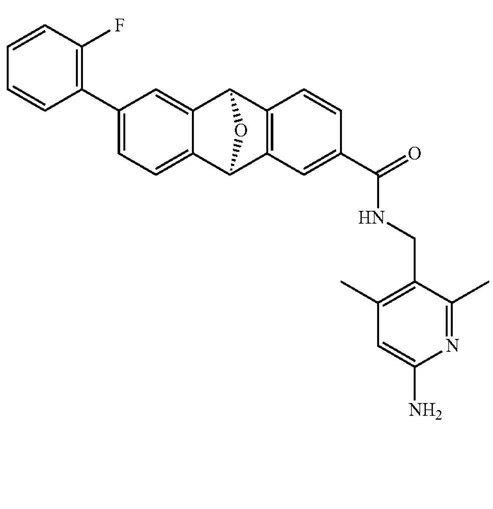 [SMILES: Cc1cc(N)nc(C)c1CNC(=O)c1ccc2c(c1)[C@@H]1O[C@H]2c2cc(-c3ccccc3F)ccc21] | Single enantiomer | 6.71 | (1R,8R)-N-[(6-amino-2,4-dimethylpyridin-3-yl)methyl]-11-(2-fluorophenyl)-15-oxatetracyclo-[6.6.1.0$^{2,7}$.0$^{9,14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 131 | 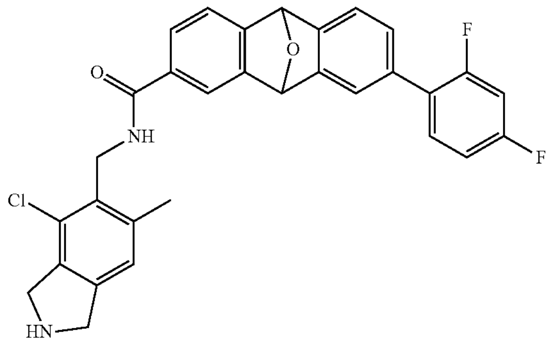 [SMILES: Cc1cc2c(c(Cl)c1CNC(=O)c1ccc3c(c1)C1OC3c3ccc(-c4ccc(F)cc4F)cc31)CNC2] | Racemic mixture | 5.13 | (±)-N-[(4-chloro-6-methyl-2,3-dihydro-1H-isoindol-5-yl)methyl]-12-(2,4-difluorophenyl)-15-oxatetracyclo[6.6.1.0$^2$,$^7$.0$^9$,$^{14}$]pentadeca-2,4,6,9,11,13-hexaene-4-carboxamide |
| 132 | 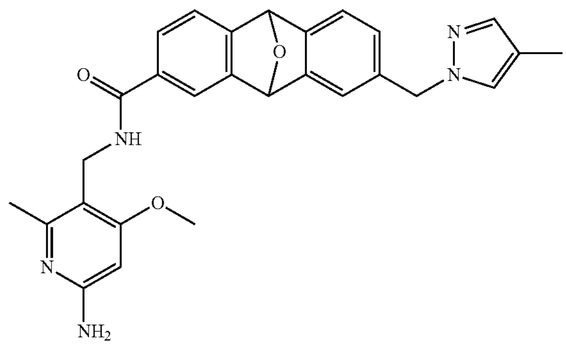 | Racemic mixture | 8.7 | (±)-N-[(6-amino-4-methoxy-2-methylpyridin-3-yl)methyl]-12-[(4-methyl-1H-pyrazol-1-yl)methyl]-15-oxatetracyclo[6.6.1.0$^2$,$^7$.0$^9$,$^{14}$]-pentadeca-2,4,6,9,11,13-hexaene-4-carboxamide |
| 133 | 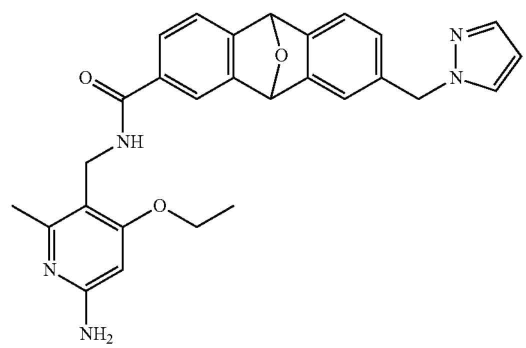 [SMILES: CCOc1cc(N)nc(C)c1CNC(=O)c1ccc2c(c1)C1OC2c2ccc(Cn3cccn3)cc21] | Racemic mixture | 7.96 | (±)-N-[(6-amino-4-ethoxy-2-methylpyridin-3-yl)methyl]-12-[(1H-pyrazol-1-yl)methyl]-15-oxatetracyclo[6.6.1.0$^2$,$^7$.0$^9$,$^{14}$]pentadeca-2,4,6,9,11,13-hexaene-4-carboxamide |
| 134 | 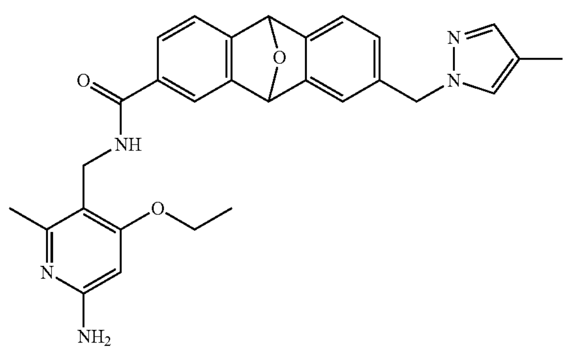 | Racemic mixture | 87 | (±)-N-[(6-amino-4-ethoxy-2-methylpyridin-3-yl)methyl]-12-[(4-methyl-1H-pyrazol-1-yl)methyl]-15-oxatetracyclo[6.6.1.0$^2$,$^7$.0$^9$,$^{14}$]-pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 135 | 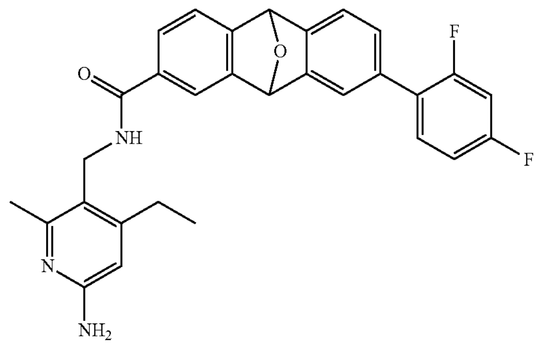 [SMILES: CCc1cc(N)nc(C)c1CNC(=O)c1ccc2c(c1)C1OC2c2ccc(-c3ccc(F)cc3F)cc21] | Racemic mixture | 7.71 | (±)-N-[(6-amino-4-ethyl-2-methylpyridin-3-yl)methyl]-12-(2,4-difluorophenyl)-15-oxatetracyclo[6.6.1.0$^{2,7}$.0$^{9,14}$]pentadeca-2,4,6,9,11,13-hexaene-4-carboxamide |
| 136 | 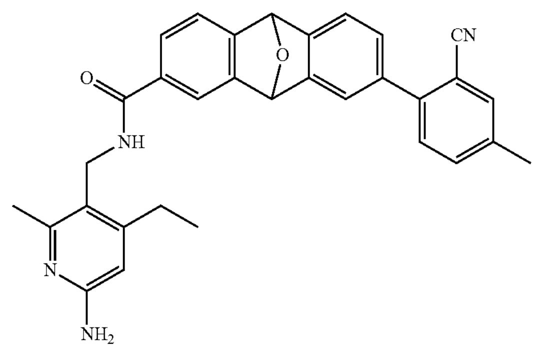 | Racemic mixture | 8.4 | (±)-N-[(6-amino-4-ethyl-2-methylpyridin-3-yl)methyl]-12-(2-cyano-4-methylphenyl)-15-oxatetracyclo[6.6.1.0$^{2,7}$.0$^{9,14}$]pentadeca-2,4,6,9,11,13-hexaene-4-carboxamide |
| 137 | 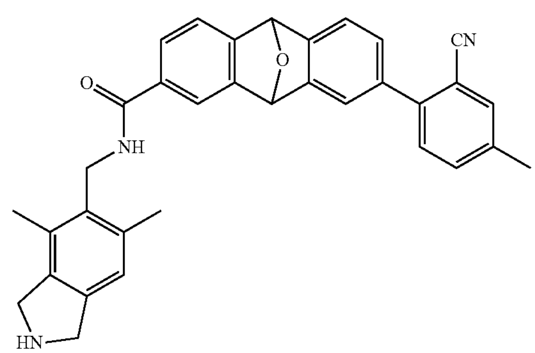 | Racemic mixture | 6.36 | (±)-12-(2-cyano-4-methylphenyl)-N-[(4,6-dimethyl-2,3-dihydro-1H-isoindol-5-yl)methyl]-15-oxatetracyclo[6.6.1.0$^{2,7}$.0$^{9,14}$]pentadeca-2,4,6,9,11,13-hexaene-4-carboxamide |
| 138 | 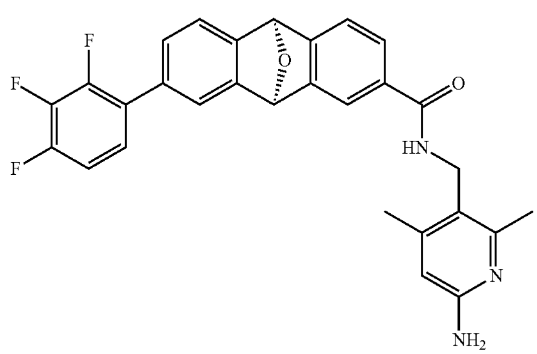 | Single enantiomer | 7.62 | (1R,8S)-N-[(6-amino-2,4-dimethylpyridin-3-yl)methyl]-12-(2,3,4-trifluorophenyl)-15-oxatetracyclo[6.6.1.0$^{2,7}$.0$^{9,14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 139 | 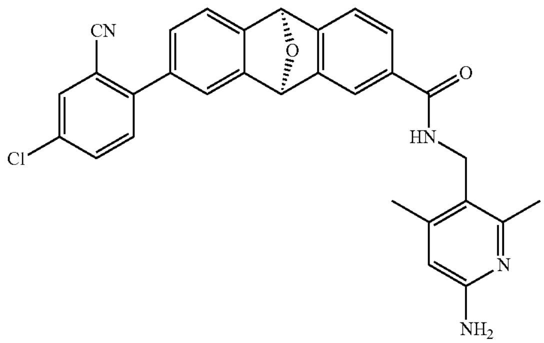 | Single enantiomer | 8.52 | (1R,8S)-N-[(6-amino-2,4-dimethylpyridin-3-yl)-methyl]-12-(4-chloro-2-cyanophenyl)-15-oxatetracyclo[6.6.1.0$^{2,7}$.0$^{9,14}$]pentadeca-2,4,6,9,11,13-hexaene-4-carboxamide |
| 140 | 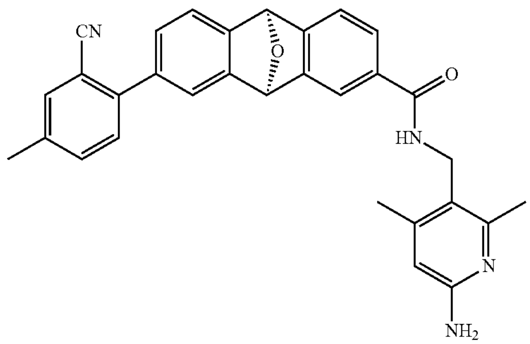 | Single enantiomer | 8.3 | (1R,8S)-N-[(6-amino-2,4-dimethylpyridin-3-yl)-methyl]-12-(2-cyano-4-methylphenyl)-15-oxatetracyclo[6.6.1.0$^{2,7}$.0$^{9,14}$]pentadeca-2,4,6,9,11,13-hexaene-4-carboxamide |
| 141 | 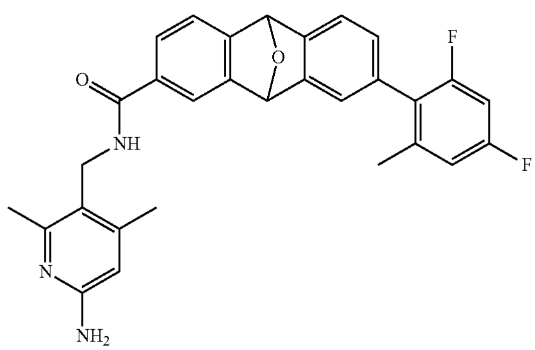 [SMILES: Cc1cc(N)nc(C)c1CNC(=O)c1ccc2c(c1)C1OC2c2ccc(-c3c(C)cc(F)cc3F)cc21] | Racemic mixture | 6.98 | (±)-N-[(6-amino-2,4-dimethylpyridin-3-yl)-methyl]-12-(2,4-difluoro-6-methylphenyl)-15-oxatetracyclo[6.6.1.0$^{2,7}$.0$^{9,14}$]pentadeca-2,4,6,9,11,13-hexaene-4-carboxamide |
| 142 | 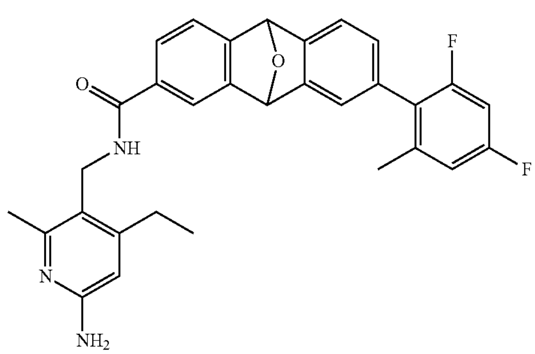 [SMILES: CCc1cc(N)nc(C)c1CNC(=O)c1ccc2c(c1)C1OC2c2ccc(-c3c(C)cc(F)cc3F)cc21] | Racemic mixture | 5.79 | (±)-N-[(6-amino-4-ethyl-2-methylpyridin-3-yl)-methyl]-12-(2,4-difluoro-6-methylphenyl)-15-oxatetracyclo[6.6.1.0$^{2,7}$.0$^{9,14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 143 | 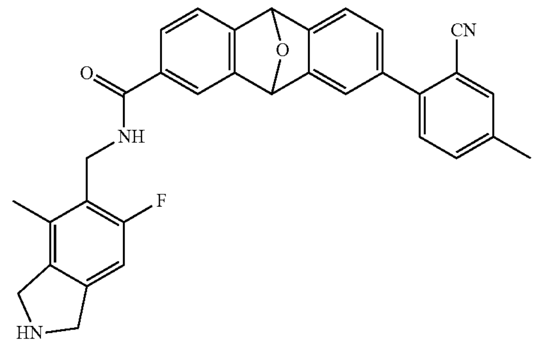 | Racemic mixture | 6.54 | (±)-12-(2-cyano-4-methylphenyl)-N-[(6-fluoro-4-methyl-2,3-dihydro-1H-isoindol-5-yl)methyl]-15-oxatetracyclo[6.6.1.0$^{2,7}$.0$^{9,14}$]pentadeca-2,4,6,9,11,13-hexaene-4-carboxamide |
| 144 | 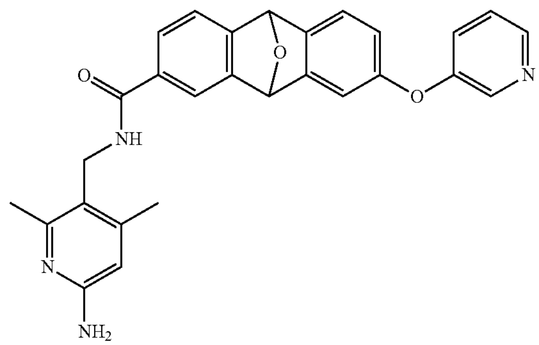 [SMILES: Cc1cc(N)nc(C)c1CNC(=O)c1ccc2c(c1)C1OC2c2ccc(Oc3cccnc3)cc21] | Racemic mixture | 5.2 | (±)-N-[(6-amino-2,4-dimethylpyridin-3-yl)methyl]-12-(pyridin-3-yloxy)-15-oxatetracyclo[6.6.1.0$^{2,7}$.0$^{9,14}$]pentadeca-2,4,6,9,11,13-hexaene-4-carboxamide |
| 145 | 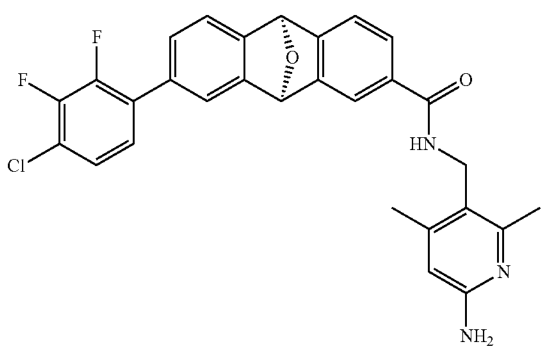 [SMILES: Cc1cc(N)nc(C)c1CNC(=O)c1ccc2c(c1)[C@@H]1O[C@H]2c2ccc(-c3ccc(Cl)c(F)c3F)cc21] | Single enantiomer | 7.76 | (1R,8S)-N-[(6-amino-2,4-dimethylpyridin-3-yl)methyl]-12-(4-chloro-2,3-difluorophenyl)-15-oxatetracyclo[6.6.1.0$^{2,7}$.0$^{9,14}$]pentadeca-2,4,6,9,11,13-hexaene-4-carboxamide |
| 146 | 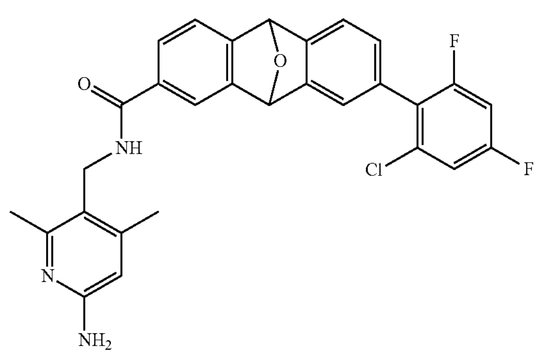 [SMILES: Cc1cc(N)nc(C)c1CNC(=O)c1ccc2c(c1)C1OC2c2ccc(-c3c(F)cc(F)cc3Cl)cc21] | Racemic mixture | 6.83 | (±)-N-[(6-amino-2,4-dimethylpyridin-3-yl)methyl]-12-(2-chloro-4,6-difluorophenyl)-15-oxatetracyclo[6.6.1.0$^{2,7}$.0$^{9,14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 147 | 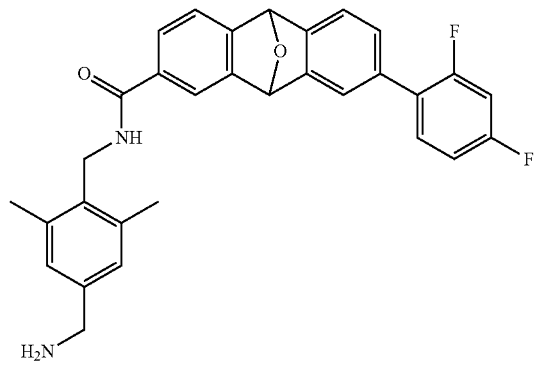 [SMILES: Cc1cc(CN)cc(C)c1CNC(=O)c1ccc2c(c1)C1OC2c2ccc(-c3ccc(F)cc3F)cc21] | Racemic mixture | 6.43 | (±)-N-{[4-(aminomethyl)-2,6-dimethylphenyl]-methyl}-12-(2,4-difluorophenyl)-15-oxatetracyclo[6.6.1.0$^{2,7}$.0$^{9,14}$]pentadeca-2,4,6,9,11,13-hexaene-4-carboxamide |
| 148 | 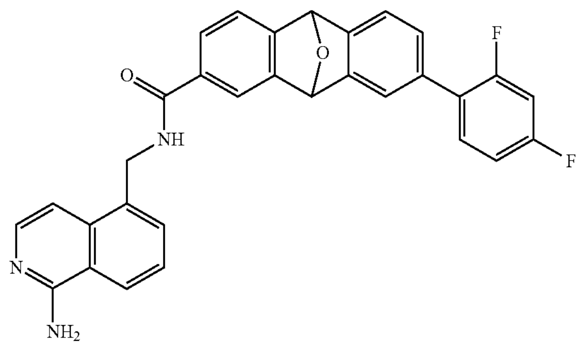 [SMILES: Nc1nccc2c(CNC(=O)c3ccc4c(c3)C3OC4c4ccc(-c5ccc(F)cc5F)cc43)cccc12] | Racemic mixture | 7.07 | (±)-N-[(1-aminoisoquinolin-5-yl)methyl]-12-(2,4-difluorophenyl)-15-oxatetracyclo[6.6.1.0$^{2,7}$.0$^{9,14}$]-pentadeca-2,4,6,9,11,13-hexaene-4-carboxamide |
| 149 | 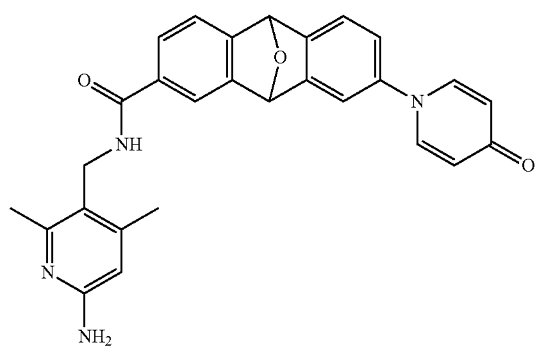 [SMILES: Cc1cc(N)nc(C)c1CNC(=O)c1ccc2c(c1)C1OC2c2ccc(-n3ccc(=O)cc3)cc21] | Racemic mixture | 5.23 | (±)-N-[(6-amino-2,4-dimethylpyridin-3-yl)-methyl]-12-(4-oxo-1,4-dihydropyridin-1-yl)-15-oxatetra-cyclo[6.6.1.0$^{2,7}$.0$^{9,14}$]pentadeca-2,4,6,9,11,13-hexaene-4-carboxamide |
| 150 | 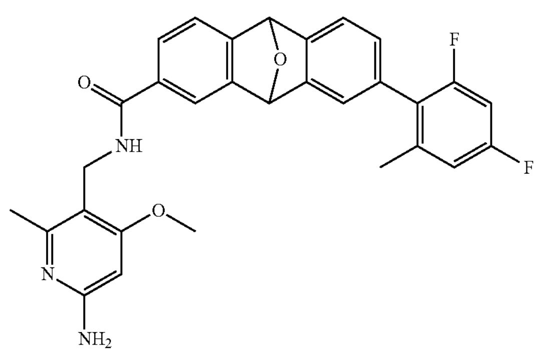 [SMILES: COc1cc(N)nc(C)c1CNC(=O)c1ccc2c(c1)C1OC2c2ccc(-c3c(C)cc(F)cc3F)cc21] | Racemic mixture | 7.46 | (±)-N-[(6-amino-4-methoxy-2-methylpyridin-3-yl)methyl]-12-(2,4-difluoro-6-methylphenyl)-15-oxatetracyclo[6.6.1.0$^{2,7}$.0$^{9,14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 151 | 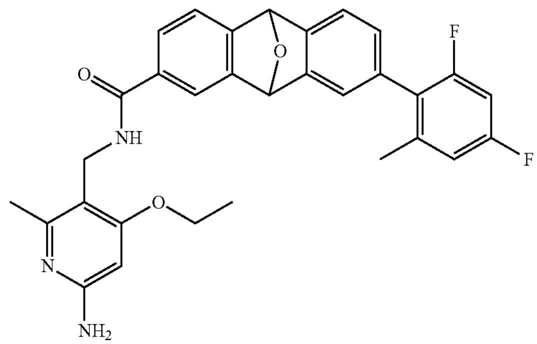 [SMILES: CCOc1cc(N)nc(C)c1CNC(=O)c1ccc2c(c1)C1OC2c2ccc(-c3c(C)cc(F)cc3F)cc21] | Racemic mixture | 6.71 | (±)-N-[(6-amino-4-ethoxy-2-methylpyridin-3-yl)methyl]-12-(2,4-difluoro-6-methylphenyl)-15-oxatetracyclo[6.6.1.0$^{2,7}$.0$^{9,14}$]pentadeca-2,4,6,9,11,13-hexaene-4-carboxamide |
| 152 | 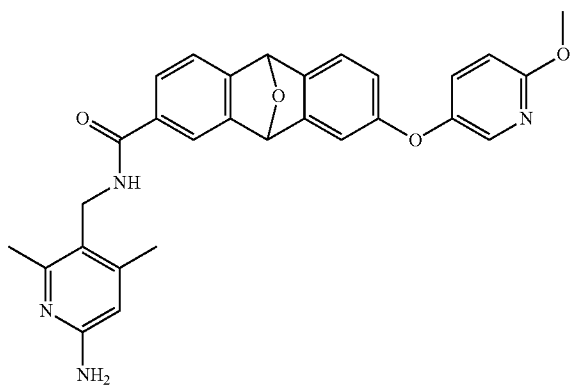 | Racemic mixture | 5.9 | (±)-N-[(6-amino-2,4-dimethylpyridin-3-yl)methyl]-12-[(6-methoxypyridin-3-yl)oxy]-15-oxatetracyclo[6.6.1.0$^{2,7}$.0$^{9,14}$]pentadeca-2,4,6,9,11,13-hexaene-4-carboxamide |
| 153 | 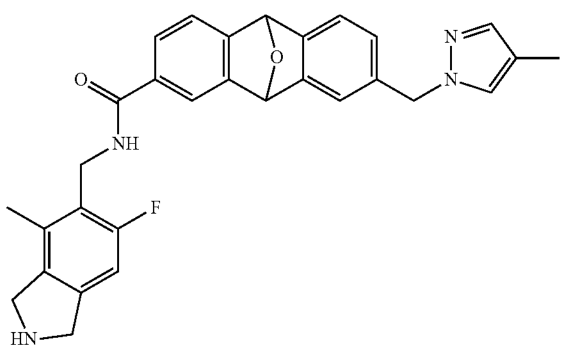 | Racemic mixture | 6.69 | (±)-N-[(6-fluoro-4-methyl-2,3-dihydro-1H-isoindol-5-yl)methyl]-12-[(4-methyl-1H-pyrazol-1-yl)methyl]-15-oxatetracyclo[6.6.1.0$^{2,7}$.0$^{9,14}$]pentadeca-2,4,6,9,11,13-hexaene-4-carboxamide |
| 154 | 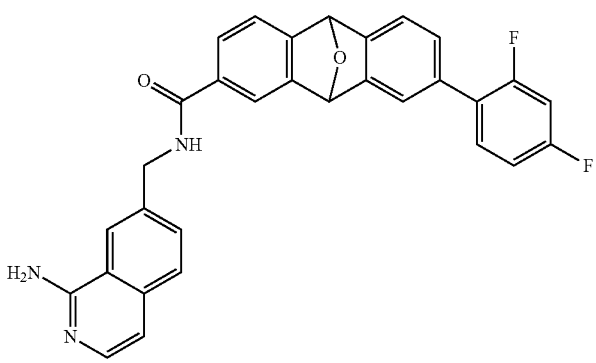 [SMILES: Nc1nccc2ccc(CNC(=O)c3ccc4c(c3)C3OC4c4ccc(-c5ccc(F)cc5F)cc43)cc12] | Racemic mixture | 5.43 | (±)-N-[(1-aminoisoquinolin-7-yl)methyl]-12-(2,4-difluorophenyl)-15-oxatetracyclo[6.6.1.0$^{2,7}$.0$^{9,14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 155 | 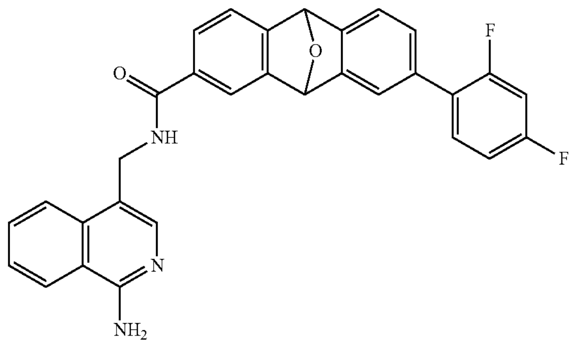 [SMILES: Nc1ncc(CNC(=O)c2ccc3c(c2)C2OC3c3ccc(-c4ccc(F)cc4F)cc32)c2ccccc12] | Racemic mixture | 5.39 | (±)-N-[(1-aminoisoquinolin-4-yl)methyl]-12-(2,4-difluorophenyl)-15-oxatetracyclo[6.6.1.0$^{2,7}$.0$^{9,14}$]-pentadeca-2,4,6,9,11,13-hexaene-4-carboxamide |
| 156 | 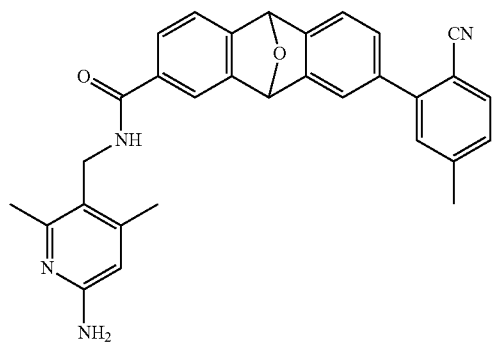 [SMILES: Cc1ccc(C#N)c(-c2ccc3c(c2)C2OC3c3ccc(C(=O)NCc4c(C)cc(N)nc4C)cc32)c1] | Racemic mixture | 7.03 | (±)-N-[(6-amino-2,4-dimethylpyridin-3-yl)-methyl]-12-(2-cyano-5-methylphenyl)-15-oxatetra-cyclo[6.6.1.0$^{2,7}$.0$^{9,14}$]pentadeca-2,4,6,9,11,13-hexaene-4-carboxamide |
| 157 | 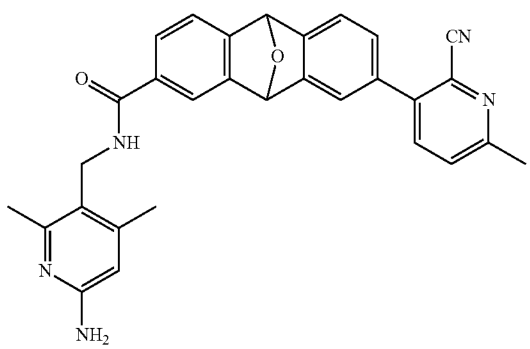 | Racemic mixture | 7.64 | (±)-N-[(6-amino-2,4-dimethylpyridin-3-yl)-methyl]-12-(2-cyano-6-methylpyridin-3-yl)-15-oxatetracyclo[6.6.1.0$^{2,7}$.0$^{9,14}$]pentadeca-2,4,6,9,11,13-hexaene-4-carboxamide |
| 158 | 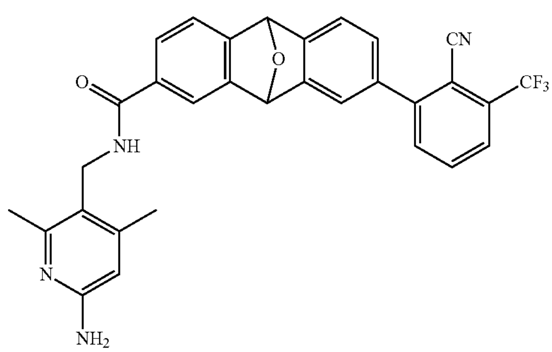 [SMILES: Cc1cc(N)nc(C)c1CNC(=O)c1ccc2c(c1)C1OC2c2ccc(-c3cccc(C(F)(F)F)c3C#N)cc21] | Racemic mixture | 6.95 | (±)-N-[(6-amino-2,4-dimethylpyridin-3-yl)-methyl]-12-[2-cyano-3-(trifluoromethyl)phenyl]-15-oxatetracyclo[6.6.1.0$^{2,7}$.0$^{9,14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
| --- | --- | --- | --- | --- |
| 159 | 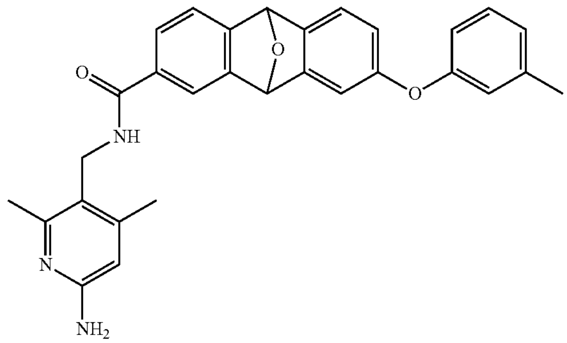 | Racemic mixture | 5.73 | (±)-N-[(6-amino-2,4-dimethylpyridin-3-yl)-methyl]-12-(3-methylphenoxy)-15-oxatetracyclo[6.6.1.0$^2$,$^7$.0$^9$,$^{14}$] pentadeca-2,4,6,9,11,13-hexaene-4-carboxamide |
| 160 | 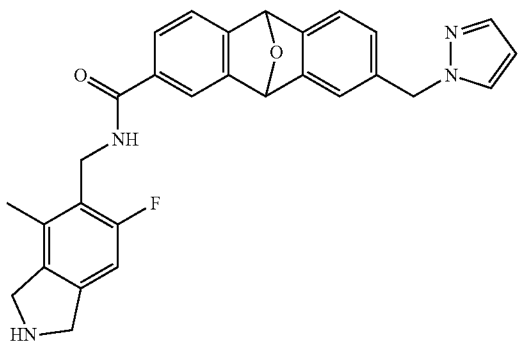 [SMILES: Cc1c(CNC(=O)c2ccc3c(c2)C2OC3c3ccc(Cn4cccn4)cc32)c(F)cc2c1CNC2] | Racemic mixture | 6.92 | (±)-N-[(6-fluoro-4-methyl-2,3-dihydro-1H-isoindol-5-yl)methyl]-12-[(1H-pyrazol-1-yl)methyl]-15-oxatetracyclo[6.6.1.0$^2$,$^7$.0$^9$,$^{14}$]-pentadeca-2,4,6,9,11,13-hexaene-4-carboxamide |
| 161 | 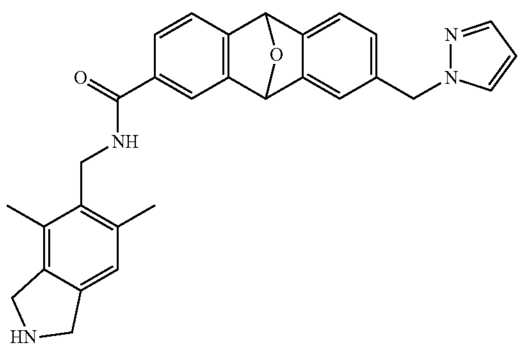 [SMILES: Cc1cc2c(c(C)c1CNC(=O)c1ccc3c(c1)C1OC3c3ccc(Cn4cccn4)cc31)CNC2] | Racemic mixture | 5.89 | (±)-N-[(4,6-dimethyl-2,3-dihydro-1H-isoindol-5-yl)methyl]-12-[(1H-pyrazol-1-yl)methyl]-15-oxatetra-cyclo[6.6.1.0$^2$,$^7$.0$^9$,$^{14}$] pentadeca-2,4,6,9,11,13-hexaene-4-carboxamide |
| 162 | 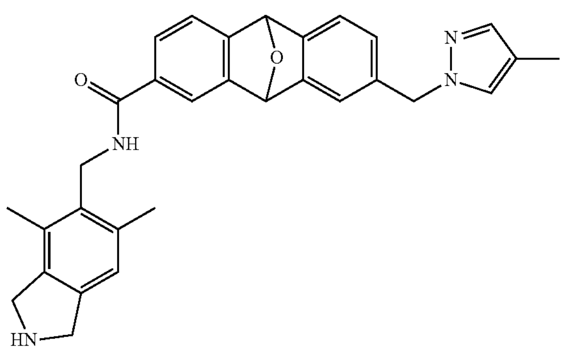 | Racemic mixture | 7.14 | (±)-N-[(4,6-dimethyl-2,3-dihydro-1H-isoindol-5-yl)methyl]-12-[(4-methyl-1H-pyrazol-1-yl)methyl]-15-oxatetracyclo[6.6.1.0$^2$,$^7$.0$^9$,$^{14}$]-pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 163 | 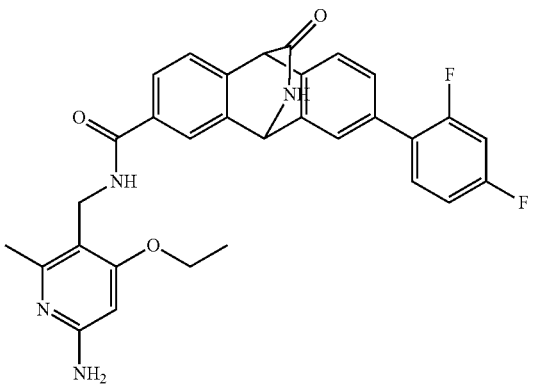 | Racemic mixture | 6.11 | (±)-N-[(6-amino-4-ethoxy-2-methylpyridin-3-yl)methyl]-12-(2,4-difluorophenyl)-16-oxo-15-azatetracyclo[6.6.1.0$^2$,$^7$.0$^9$,$^{14}$] hexadeca-2,4,6,9,11,13-hexaene-4-carboxamide and (±)-N-[(6-amino-4-ethoxy-2-methylpyridin-3-yl)methyl]-11-(2,4-difluorophenyl)-16-oxo-15-azatetracyclo[6.6.1.0$^2$,$^7$.0$^9$,$^{14}$] hexadeca-2,4,6,9,11,13-hexaene-4-carboxamide |
| 164 | 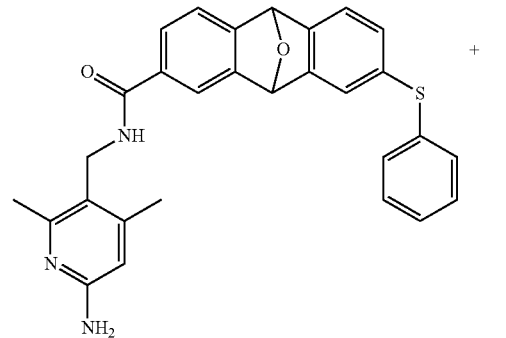 [SMILES: Cc1cc(N)nc(C)c1CNC(=O)c1ccc2c(c1)C1OC2c2ccc(Sc3ccccc3)cc21] | Racemic mixture | 6.86 | (±)-N-[(6-amino-2,4-dimethylpyridin-3-yl)methyl]-12-(phenylsulfanyl)-15-oxatetracyclo[6.6.1.0$^2$,$^7$.0$^9$,$^{14}$] pentadeca-2,4,6,9,11,13-hexaene-4-carboxamide (±)-N-[(6-amino-2,4-dimethylpyridin-3-yl)methyl]-11-(phenylsulfanyl)-15-oxatetracyclo[6.6.1.0$^2$,$^7$.0$^9$,$^{14}$] pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 165 | 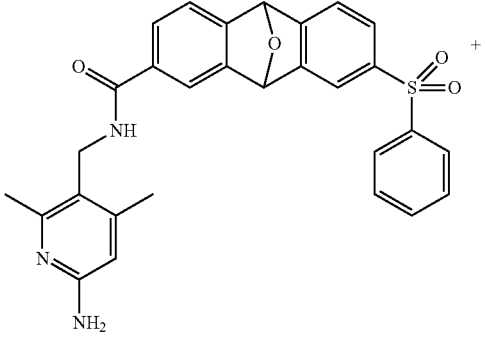 [SMILES: Cc1cc(N)nc(C)c1CNC(=O)c1ccc2c(c1)C1OC2c2ccc(S(=O)(=O)c3ccccc3)cc21] | Racemic mixture | 5.99 | (±)-N-[(6-amino-2,4-dimethylpyridin-3-yl)methyl]-12-(benzenesulfonyl)-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(benzenesulfonyl)-15-oxatetracyclo-[6.6.1.0$^{2,7}$.0$^{9,14}$]pentadeca-2,4,6,9,11,13-hexaene-4-carboxamide |
| 166 | 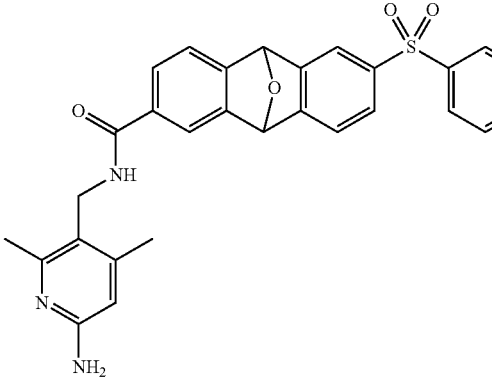 | Racemic mixture | 5.17 | (±)-N-[(6-amino-2,5-dimethylpyridin-3-yl)-methyl]-12-(2,4-difluorophenyl)-15-oxatetracyclo[6.6.1.0$^{2,7}$.0$^{9,14}$]pentadeca-2,4,6,9,11,13-hexaene-4-carboxamide |
| 167 | 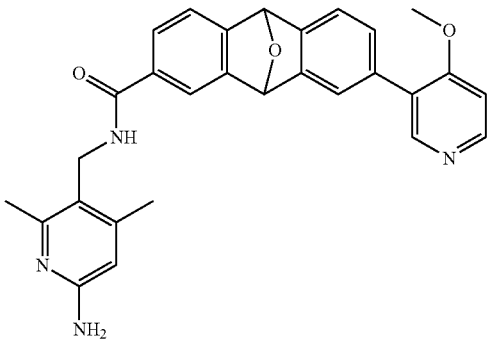 [SMILES: COc1ccncc1-c1ccc2c(c1)C1OC2c2ccc(C(=O)NCc3c(C)cc(N)nc3C)cc21] | Racemic mixture | 6.94 | (±)-N-[(6-amino-2,4-dimethylpyridin-3-yl)-methyl]-12-(4-methoxypyridin-3-yl)-15-oxatetracyclo[6.6.1.0$^{2,7}$.0$^{9,14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 168 | 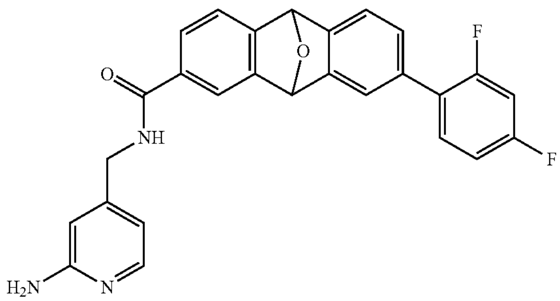 [SMILES: Nc1cc(CNC(=O)c2ccc3c(c2)C2OC3c3ccc(-c4ccc(F)cc4F)cc32)ccn1] | Racemic mixture | 4.7 | (±)-N-[(2-aminopyridin-4-yl)methyl]-12-(2,4-difluorophenyl)-15-oxatetracyclo[6.6.1.0$^2$,$^7$.0$^9$,$^{14}$]-pentadeca-2,4,6,9,11,13-hexaene-4-carboxamide |
| 169 | 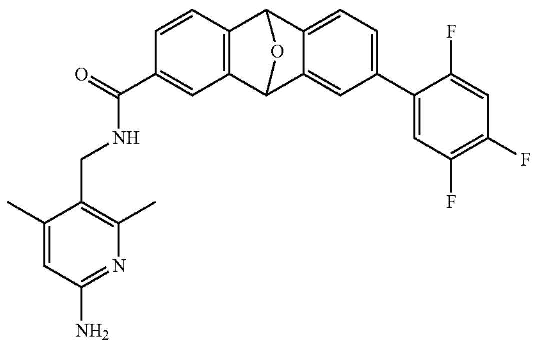 [SMILES: Cc1cc(N)nc(C)c1CNC(=O)c1ccc2c(c1)C1OC2c2ccc(-c3cc(F)c(F)cc3F)cc21] | Racemic mixture | 7.46 | (±)-N-[(6-amino-2,4-dimethylpyridin-3-yl)-methyl]-12-(2,4,5-trifluorophenyl)-15-oxatetra-cyclo[6.6.1.0$^2$,$^7$.0$^9$,$^{14}$] pentadeca-2,4,6,9,11,13-hexaene-4-carboxamide |
| 170 | 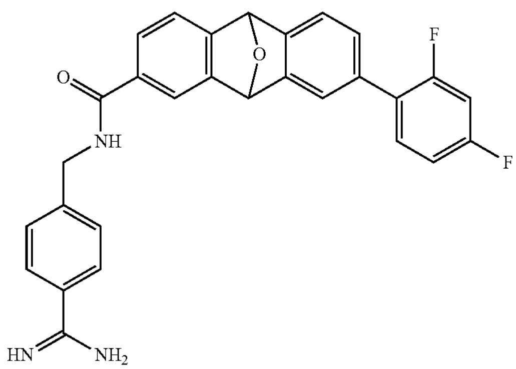 [SMILES: N=C(N)c1ccc(CNC(=O)c2ccc3c(c2)C2OC3c3ccc(-c4ccc(F)cc4F)cc32)cc1] | Racemic mixture | 9 | (±)-N-[(4-carbamimidoylphenyl)methyl]-12-(2,4-difluorophenyl)-15-oxatetracyclo[6.6.1.0$^2$,$^7$.0$^9$,$^{14}$]-pentadeca-2,4,6,9,11,13-hexaene-4-carboxamide |
| 171 | 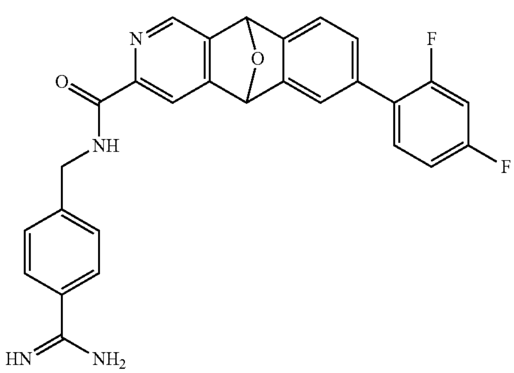 | Racemic mixture | + | (±)-N-[(4-carbamimidoylphenyl)methyl]-11-(2,4-difluorophenyl)-15-oxa-4-azatetracyclo-[6.6.1.0$^2$,$^7$.0$^9$,$^{14}$] pentadeca-2(7),3,5,9,11,13-hexaene-5-carboxamide and (±)-N-[(4-carbamimidoylphenyl)methyl]-12-(2,4-difluorophenyl)-15-oxa-4-azatetracyclo-[6.6.1.0$^2$,$^7$.0$^9$,$^{14}$] pentadeca-2(7),3,5,9,11,13-hexaene-5-carboxamide |

TABLE 1-continued

| Cpd. No | Structure | Compound Type | KLKB1 pIC$_{50}$ | IUPAC Name |
|---|---|---|---|---|
| | 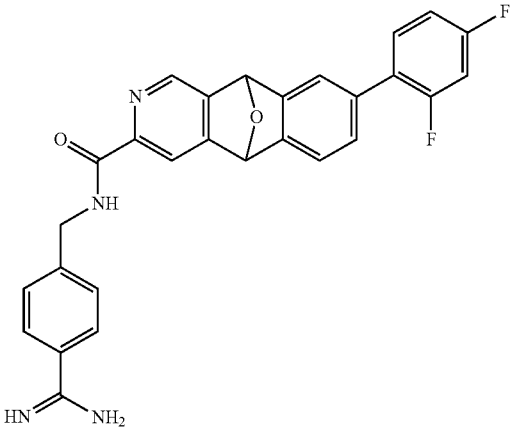 [SMILES: N=C(N)c1ccc(CNC(=O)c2cc3c(cn2)C2OC3c3ccc(-c4ccc(F)cc4F)cc32)cc1] | | | |
| 172 | 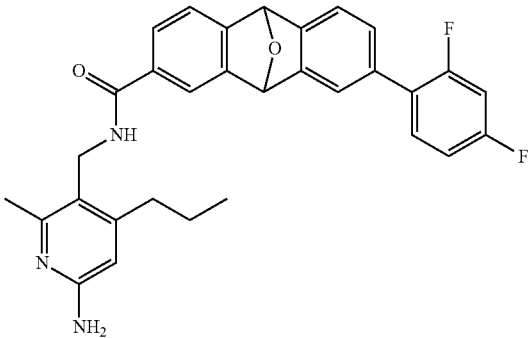 [SMILES: CCCc1cc(N)nc(C)c1CNC(=O)c1ccc2c(c1)C1OC2c2ccc(-c3ccc(F)cc3F)cc21] | Racemic mixture | 8 | (±)-N-[(6-amino-2-methyl-4-propylpyridin-3-yl)methyl]-12-(2,4-difluorophenyl)-15-oxatetracyclo[6.6.1.0$^2$,$^7$.0$^9$,$^{14}$]pentadeca-2,4,6,9,11,13-hexaene-4-carboxamide |
| 173 | 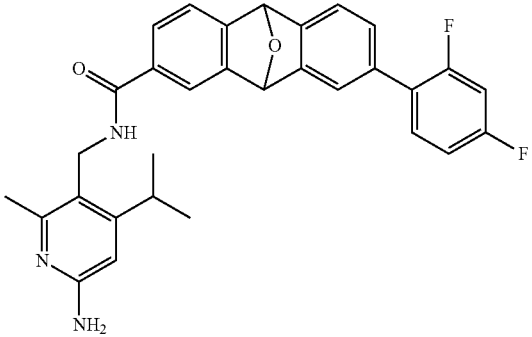 [SMILES: Cc1nc(N)cc(C(C)C)c1CNC(=O)c1ccc2c(c1)C1OC2c2ccc(-c3ccc(F)cc3F)cc21] | Racemic mixture | 8.52 | (±)-N-{[6-amino-2-methyl-4-(propan-2-yl)pyridin-3-yl]methyl}-12-(2,4-difluorophenyl)-15-oxatetracyclo[6.6.1.0$^2$,$^7$.0$^9$,$^{14}$]pentadeca-2,4,6,9,11,13-hexaene-4-carboxamide |
| 174 | 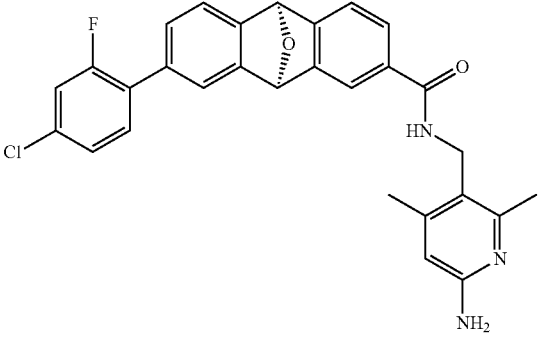 | Single enantiomer | 7.33 | (1R,8S)-N-[(6-amino-2,4-dimethylpyridin-3-yl)-methyl]-12-(4-chloro-2-fluorophenyl)-15-oxatetracyclo[6.6.1.0$^2$,$^7$.0$^9$,$^{14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 175 | 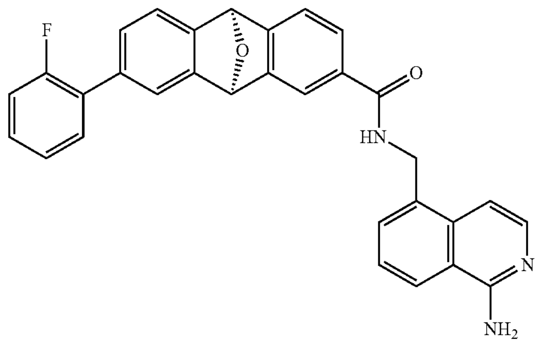 [SMILES: Nc1nccc2c(CNC(=O)c3ccc4c(c3)[C@@H]3O[C@H]4c4ccc(-c5ccccc5F)cc43)cccc12] | Single enantiomer | 7.26 | (1R,8S)-N-[(1-aminoisoquinolin-5-yl)methyl]-12-(2-fluorophenyl)-15-oxatetracyclo-[6.6.1.0$^{2,7}$.0$^{9,14}$] pentadeca-2,4,6,9,11,13-hexaene-4-carboxamide |
| 176 | 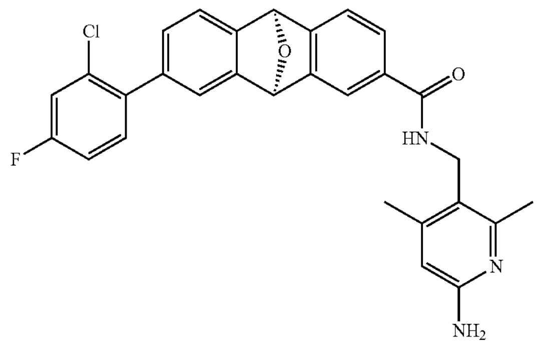 | Single enantiomer | 7.17 | (1R,8S)-N-[(6-amino-2,4-dimethylpyridin-3-yl)-methyl]-12-(2-chloro-4-fluorophenyl)-15-oxatetracyclo[6.6.1.0$^{2,7}$.0$^{9,14}$] pentadeca-2,4,6,9,11,13-hexaene-4-carboxamide |
| 177 | 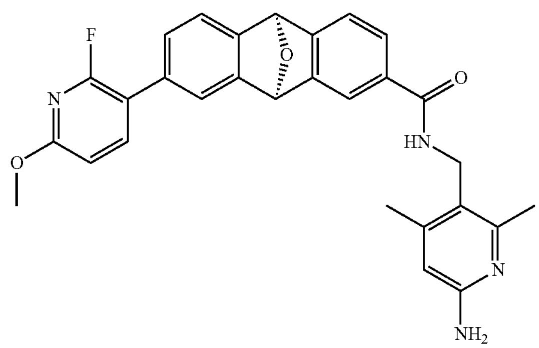 [SMILES: COc1ccc(-c2ccc3c(c2)[C@H]2O[C@@H]3c3ccc(C(=O)NCc4c(C)cc(N)nc4C)cc32)c(F)n1] | Single enantiomer | 6.93 | (1R,8S)-N-[(6-amino-2,4-dimethylpyridin-3-yl)-methyl]-12-(2-fluoro-6-methoxypyridin-3-yl)-15-oxatetracyclo[6.6.1.0$^{2,7}$.0$^{9,14}$] pentadeca-2,4,6,9,11,13-hexaene-4-carboxamide |
| 178 | 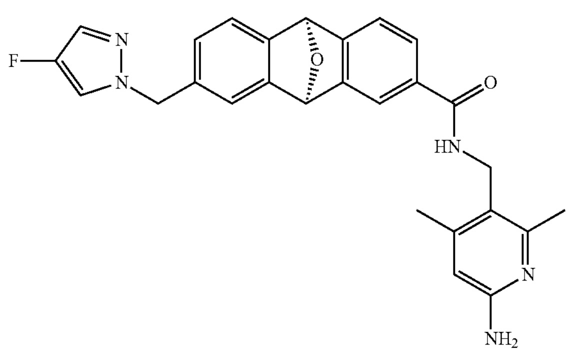 [SMILES: Cc1cc(N)nc(C)c1CNC(=O)c1ccc2c(c1)[C@@H]1O[C@H]2c2ccc(Cn3cc(F)cn3)cc21] | Single enantiomer | 9 | (1R,8S)-N-[(6-amino-2,4-dimethylpyridin-3-yl)methyl]-12-[(4-fluoro-1H-pyrazol-1-yl)methyl]-15-oxatetracyclo[6.6.1.0$^{2,7}$.0$^{9,14}$] pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 179 | 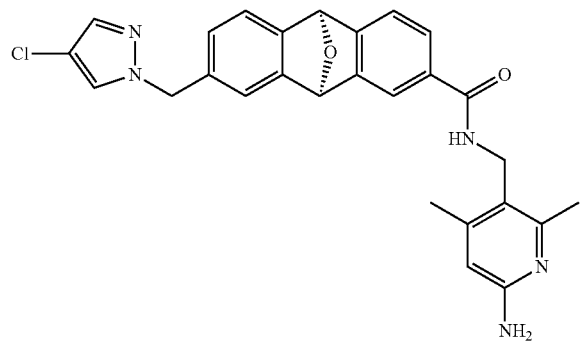 [SMILES: Cc1cc(N)nc(C)c1CNC(=O)c1ccc2c(c1)[C@@H]1O[C@H]2c2ccc(Cn3cc(Cl)cn3)cc21] | Single enantiomer | 9 | (1R,8S)-N-[(6-amino-2,4-dimethylpyridin-3-yl)methyl]-12-[(4-chloro-1H-pyrazol-1-yl)methyl]-15-oxatetracyclo[6.6.1.0$^2$,$^7$.0$^9$,$^{14}$]-pentadeca-2,4,6,9,11,13-hexaene-4-carboxamide |
| 180 | 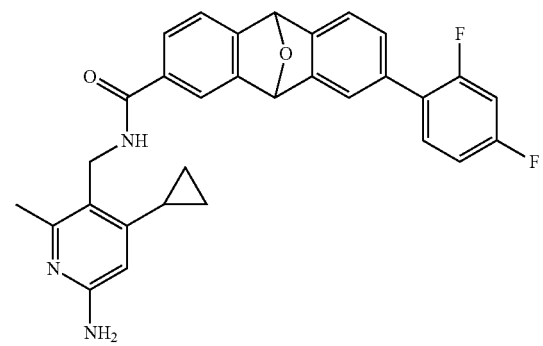 [SMILES: Cc1nc(N)cc(C2CC2)c1CNC(=O)c1ccc2c(c1)C1OC2c2ccc(-c3ccc(F)cc3F)cc21] | Racemic mixture | 7.96 | (±)-N-[(6-amino-4-cyclopropyl-2-methylpyridin-3-yl)methyl]-12-(2,4-difluorophenyl)-15-oxatetracyclo[6.6.1.0$^2$,$^7$.0$^9$,$^{14}$] pentadeca-2,4,6,9,11,13-hexaene-4-carboxamide |
| 181 | 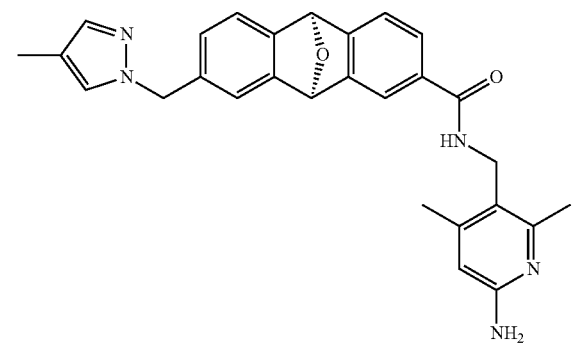 | Single enantiomer | 9 | (1R,8S)-N-[(6-amino-2,4-dimethylpyridin-3-yl)methyl]-12-[(4-methyl-1H-pyrazol-1-yl)methyl]-15-oxatetracyclo[6.6.1.0$^2$,$^7$.0$^9$,$^{14}$]-pentadeca-2,4,6,9,11,13-hexaene-4-carboxamide |
| 182 | 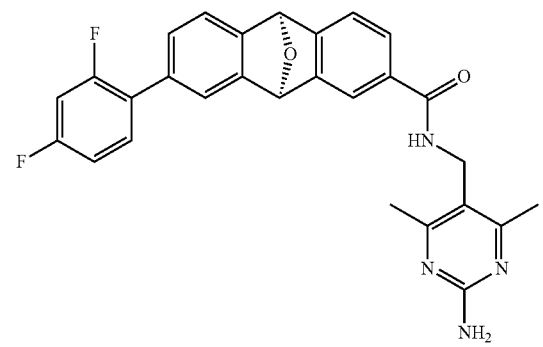 | Single enantiomer | 4.67 | (1R,8S)-N-[(2-amino-4,6-dimethylpyrimidin-5-yl)methyl]-12-(2,4-difluorophenyl)-15-oxatetracyclo[6.6.1.0$^2$,$^7$.0$^9$,$^{14}$] pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 183 | 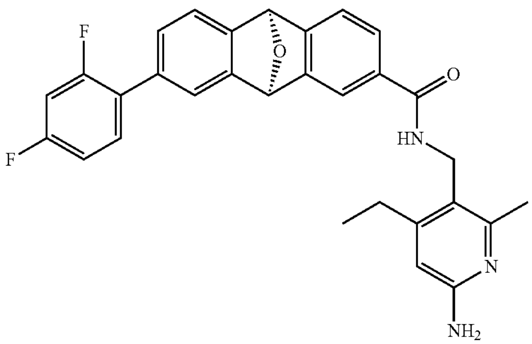 [SMILES: CCc1cc(N)nc(C)c1CNC(=O)c1ccc2c(c1)[C@@H]1O[C@H]2c2ccc(-c3ccc(F)cc3F)cc21] | Single enantiomer | 7.92 | (1R,8S)-N-[(6-amino-4-ethyl-2-methylpyridin-3-yl)methyl]-12-(2,4-difluorophenyl)-15-oxatetracyclo[6.6.1.0$^{2,7}$.0$^{9,14}$]pentadeca-2,4,6,9,11,13-hexaene-4-carboxamide |
| 184 | 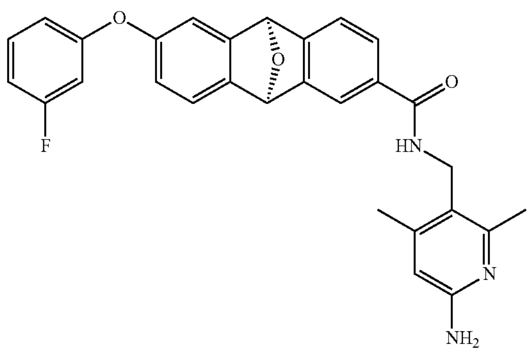 [SMILES: Cc1cc(N)nc(C)c1CNC(=O)c1ccc2c(c1)[C@@H]1O[C@H]2c2cc(Oc3cccc(F)c3)ccc21] | Single enantiomer | 7.12 | (1R,8R)-N-[(6-amino-2,4-dimethylpyridin-3-yl)-methyl]-11-(3-fluorophenoxy)-15-oxatetracyclo[6.6.1.0$^{2,7}$.0$^{9,14}$]pentadeca-2,4,6,9,11,13-hexaene-4-carboxamide |
| 185 | 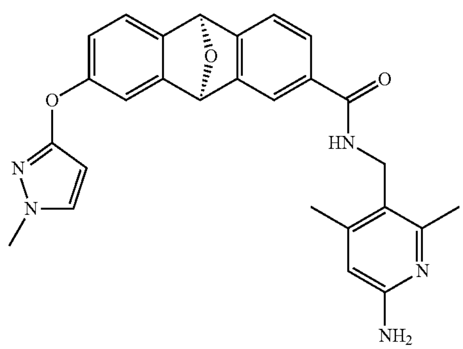 | Single enantiomer | 5.65 | (1S,8R)-N-[(6-amino-2,4-dimethylpyridin-3-yl)-methyl]-12-[(1-methyl-1H-pyrazol-3-yl)oxy]-15-oxatetracyclo[6.6.1.0$^{2,7}$.0$^{9,14}$]pentadeca-2,4,6,9,11,13-hexaene-4-carboxamide |
| 186 | 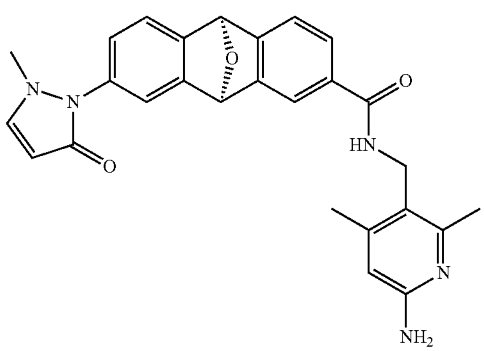 [SMILES: Cc1cc(N)nc(C)c1CNC(=O)c1ccc2c(c1)[C@@H]1O[C@H]2c2ccc(-n3c(=O)ccn3C)cc21] | Single enantiomer | 5.74 | (1S,8R)-N-[(6-amino-2,4-dimethylpyridin-3-yl)-methyl]-12-(2-methyl-5-oxo-2,5-dihydro-1H-pyrazol-1-yl)-15-oxatetracyclo[6.6.1.0$^{2,7}$.0$^{9,14}$]-pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 187 | 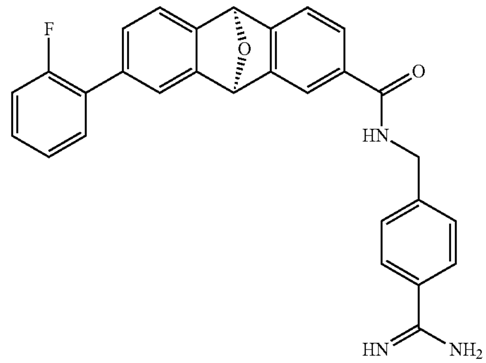 [SMILES: N=C(N)c1ccc(CNC(=O)c2ccc3c(c2)[C@@H]2O[C@H]3c3ccc(-c4ccccc4F)cc32)cc1] | Single enantiomer | 8.76 | (1R,8S)-N-[(4-carbamimidoyl-phenyl)methyl]-12-(2-fluorophenyl)-15-oxatetracyclo-[6.6.1.0$^2$,$^7$.0$^9$,$^{14}$]pentadeca-2,4,6,9,11,13-hexaene-4-carboxamide |
| 188 | 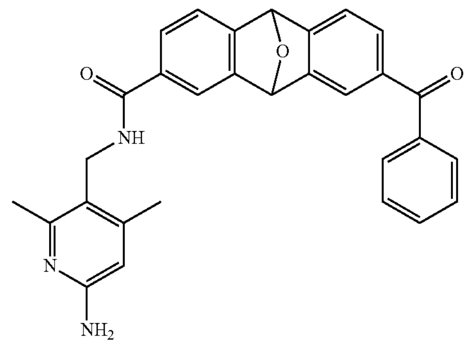 [SMILES: Cc1cc(N)nc(C)c1CNC(=O)c1ccc2c(c1)C1OC2c2ccc(C(=O)c3ccccc3)cc21] | Racemic mixture | 8 | (±)-N-[(6-amino-2,4-dimethylpyridin-3-yl)methyl]-12-benzoyl-15-oxatetra-cyclo-[6.6.1.0$^2$,$^7$.0$^9$,$^{14}$]pentadeca-2,4,6,9,11,13-hexaene-4-carboxamide |
| 189 | 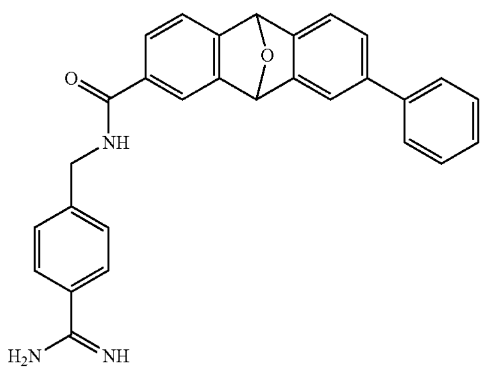 [SMILES: N=C(N)c1ccc(CNC(=O)c2ccc3c(c2)C2OC3c3ccc(-c4ccccc4)cc32)cc1] | Racemic mixture | 8.34 | (±)-N-[(4-carbamimidoyl-phenyl)methyl]-12-phenyl-15-oxatetracyclo[6.6.1.0$^2$,$^7$.0$^9$,$^{14}$]-pentadeca-2,4,6,9,11,13-hexaene-4-carboxamide |
| 190 | 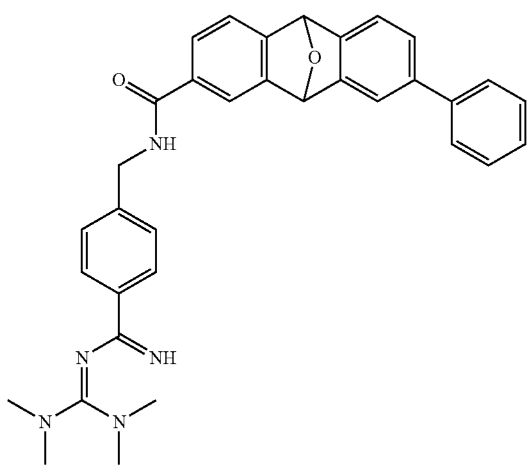 [SMILES: CN(C)C(=NC(=N)c1ccc(CNC(=O)c2ccc3c(c2)C2OC3c3ccc(-c4ccccc4)cc32)cc1)N(C)C] | Racemic mixture | 6.89 | (±)-N-{[4-({[bis(dimethylamino)methylidene]-amino}methanimidoyl)phenyl]methyl}-12-phenyl-15-oxatetracyclo[6.6.1.0$^2$,$^7$.0$^9$,$^{14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 191 | 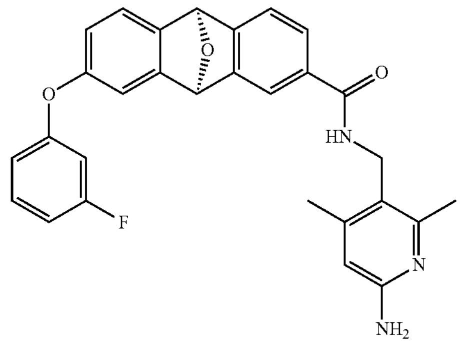 [SMILES: Cc1cc(N)nc(C)c1CNC(=O)c1ccc2c(c1)[C@@H]1O[C@H]2c2ccc(Oc3cccc(F)c3)cc21] | Single enantiomer | 6.98 | (1S,8R)-N-[(6-amino-2,4-dimethylpyridin-3-yl)methyl]-12-(3-fluorophenoxy)-15-oxatetracyclo[6.6.1.0$^2$,$^7$.0$^9$,$^{14}$]pentadeca-2,4,6,9,11,13-hexaene-4-carboxamide |
| 192 | 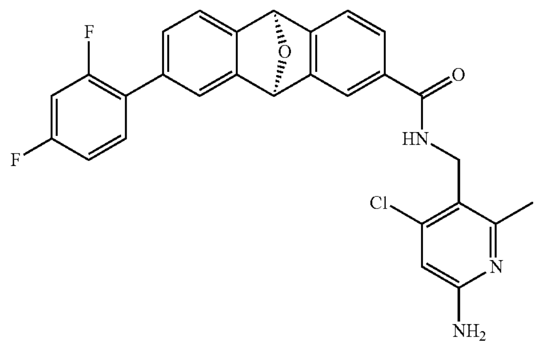 [SMILES: Cc1nc(N)cc(Cl)c1CNC(=O)c1ccc2c(c1)[C@@H]1O[C@H]2c2ccc(-c3ccc(F)cc3F)cc21] | Single enantiomer | 6.01 | (1R,8S)-N-[(6-amino-4-chloro-2-methylpyridin-3-yl)methyl]-12-(2,4-difluorophenyl)-15-oxatetracyclo[6.6.1.0$^2$,$^7$.0$^9$,$^{14}$]pentadeca-2,4,6,9,11,13-hexaene-4-carboxamide |
| 193 | 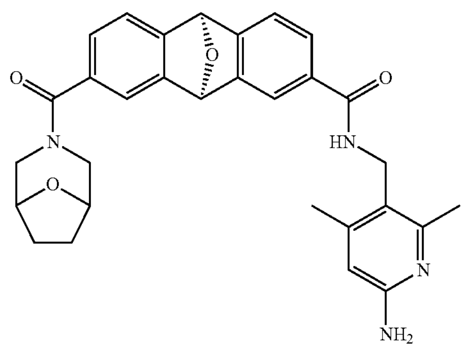 [SMILES: Cc1cc(N)nc(C)c1CNC(=O)c1ccc2c(c1)[C@@H]1O[C@H]2c2ccc(C(=O)N3CC4CCC(C3)O4)cc21] | Single enantiomer | 5.8 | (1S,8R)-N-[(6-amino-2,4-dimethylpyridin-3-yl)-methyl]-12-{8-oxa-3-azabicyclo[3.2.1]octane-3-carbonyl}-15-oxatetracyclo[6.6.1.0$^2$,$^7$.0$^9$,$^{14}$]-pentadeca-2,4,6,9,11,13-hexaene-4-carboxamide |
| 194 | 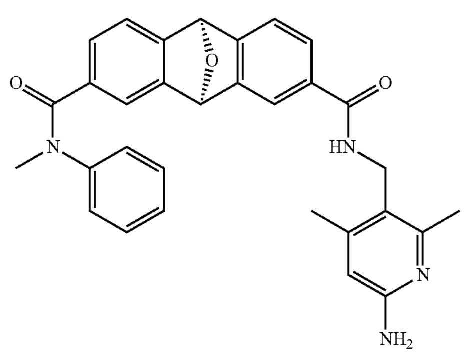 [SMILES: Cc1cc(N)nc(C)c1CNC(=O)c1ccc2c(c1)[C@@H]1O[C@H]2c2ccc(C(=O)N(C)c3ccccc3)cc21] | Single enantiomer | 5.78 | (1S,8R)-N12-[(6-amino-2,4-dimethylpyridin-3-yl)methyl]-N4-methyl-N4-phenyl-15-oxatetra-cyclo[6.6.1.0$^2$,$^7$.0$^9$,$^{14}$]pentadeca-2,4,6,9,11,13-hexaene-4,12-dicarboxamide |

TABLE 1-continued

| Cpd. No | Structure | Compound Type | KLKB1 pIC$_{50}$ | IUPAC Name |
|---|---|---|---|---|
| 195 | 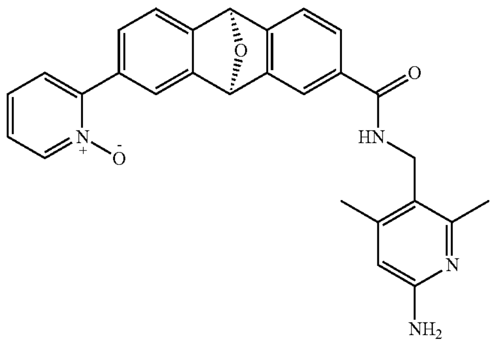 | Single enantiomer | 5.98 | 2-[(1R,8S)-12-{[(6-amino-2,4-dimethylpyridin-3-yl)methyl]carbamoyl}-15-oxatetracyclo-[6.6.1.0$^{2,7}$.0$^{9,14}$]pentadeca-2,4,6,9,11,13-hexaen-4-yl]pyridin-1-ium-1-olate |
| 196 | 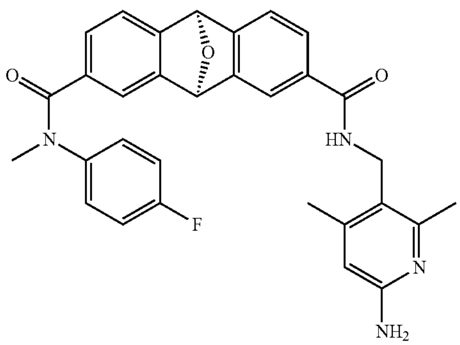 | Single enantiomer | 5.33 | (1S,8R)-N12-[(6-amino-2,4-dimethylpyridin-3-yl)methyl]-N4-(4-fluorophenyl)-N4-methyl-15-oxatetra-cyclo[6.6.1.0$^{2,7}$.0$^{9,14}$]pentadeca-2,4,6,9,11,13-hexaene-4,12-dicarboxamide |
| 197 | 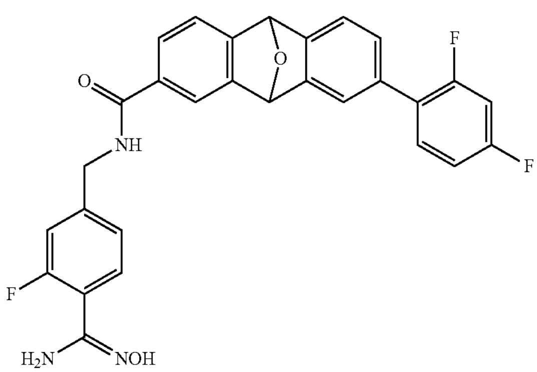 | Racemic mixture | 4 | (±)-12-(2,4-difluorophenyl)-N-({3-fluoro-4-[N'-hydroxycarbamimidoyl]phenyl}methyl)-15-oxatetracyclo[6.6.1.0$^{2,7}$.0$^{9,14}$]pentadeca-2,4,6,9,11,13-hexaene-4-carboxamide |
| 198 | 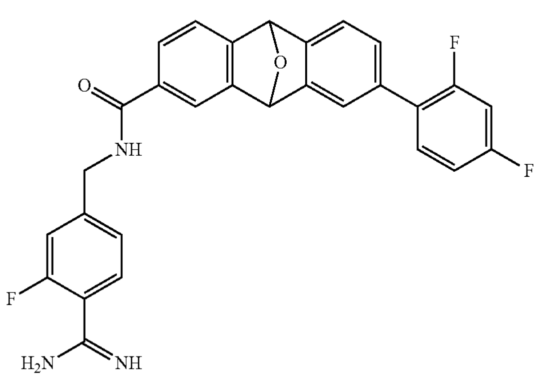 [SMILES: N=C(N)c1ccc(CNC(=O)c2ccc3c(c2)C2OC3c3ccc(-c4ccc(F)cc4F)cc32)cc1F] | Racemic mixture | 7.68 | (±)-N-[(4-carbamimidoyl-3-fluorophenyl)methyl]-12-(2,4-difluorophenyl)-15-oxatetracyclo-[6.6.1.0$^{2,7}$.0$^{9,14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 199 | 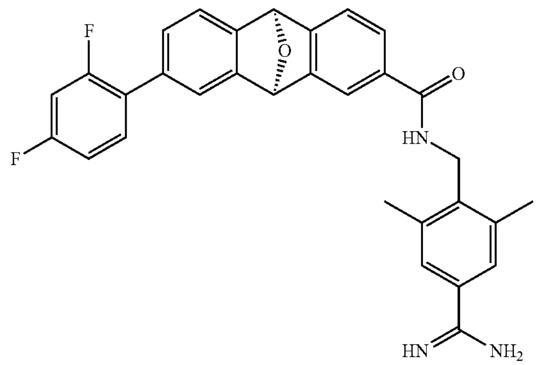 [SMILES: Cc1cc(C(=N)N)cc(C)c1CNC(=O)c1ccc2c(c1)[C@@H]1O[C@H]2c2ccc(-c3ccc(F)cc3F)cc21] | Single enantiomer | 9.13 | (1R,8S)-N-[(4-carbamimidoyl-2,6-dimethyl-phenyl)methyl]-12-(2,4-difluorophenyl)-15-oxatetracyclo[6.6.1.0$^{2,7}$.0$^{9,14}$]pentadeca-2,4,6,9,11,13-hexaene-4-carboxamide |
| 200 | 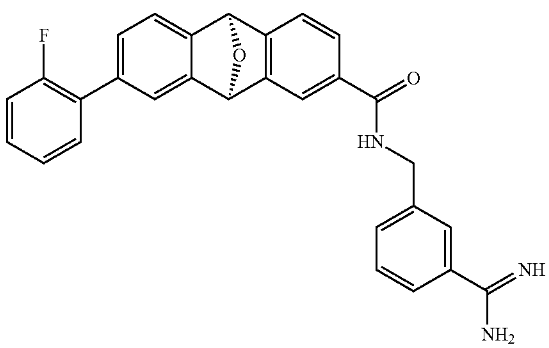 [SMILES: N=C(N)c1cccc(CNC(=O)c2ccc3c(c2)[C@@H]2O[C@H]3c3ccc(-c4ccccc4F)cc32)c1] | Single enantiomer | 5.91 | (1R,8S)-N-[(3-carbamimidoylphenyl)methyl]-12-(2-fluorophenyl)-15-oxatetracyclo-[6.6.1.0$^{2,7}$.0$^{9,14}$]pentadeca-2,4,6,9,11,13-hexaene-4-carboxamide |
| 201 | 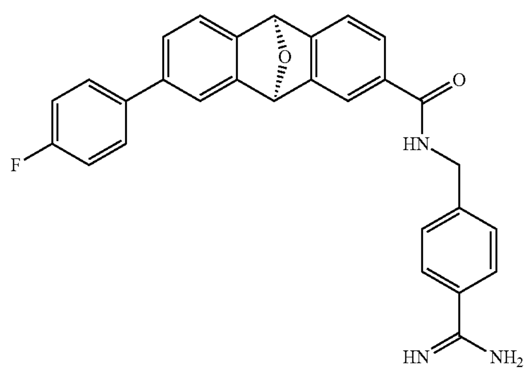 [SMILES: N=C(N)c1ccc(CNC(=O)c2ccc3c(c2)[C@@H]2O[C@H]3c3ccc(-c4ccc(F)cc4)cc32)cc1] | Single enantiomer | 9 | (1R,8S)-N-[(4-carbamimidoylphenyl)methyl]-12-(4-fluorophenyl)-15-oxatetracyclo-[6.6.1.0$^{2,7}$.0$^{9,14}$]pentadeca-2,4,6,9,11,13-hexaene-4-carboxamide |
| 202 | 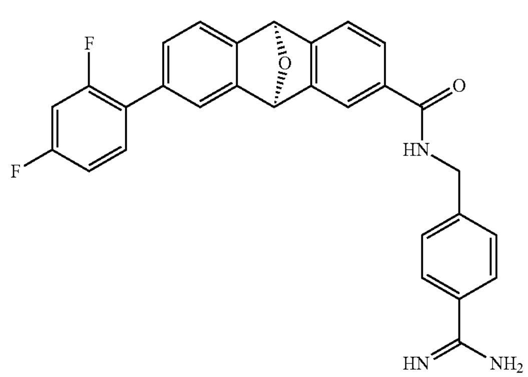 [SMILES: N=C(N)c1ccc(CNC(=O)c2ccc3c(c2)[C@@H]2O[C@H]3c3ccc(-c4ccc(F)cc4F)cc32)cc1] | Single enantiomer | 9 | (1R,8S)-N-[(4-carbamimidoylphenyl)methyl]-12-(2,4-difluorophenyl)-15-oxatetracyclo-[6.6.1.0$^{2,7}$.0$^{9,14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 203 | 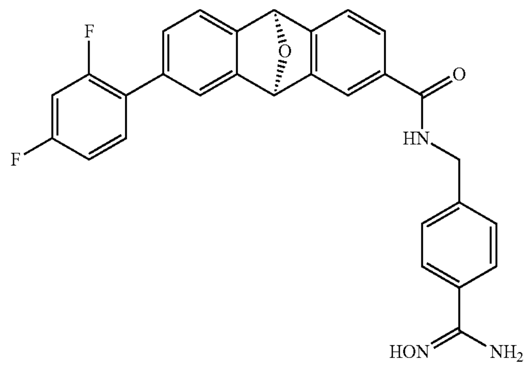 | Single enantiomer | 5.98 | (1R,8S)-12-(2,4-difluorophenyl)-N-{[4-(N'-hydroxycarbamimidoyl)phenyl]methyl}-15-oxatetracyclo[6.6.1.0$^{2,7}$.0$^{9,14}$]pentadeca-2,4,6,9,11,13-hexaene-4-carboxamide |
| 204 | 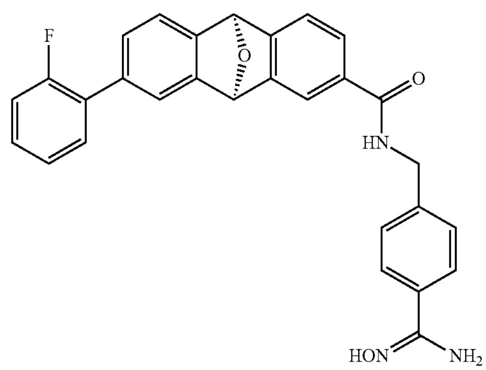 | Single enantiomer | 6.03 | (1R,8S)-12-(2-fluorophenyl)-N-{[4-(N'-hydroxycarbamimidoyl)phenyl]methyl}-15-oxatetracyclo[6.6.1.0$^{2,7}$.0$^{9,14}$]pentadeca-2,4,6,9,11,13-hexaene-4-carboxamide |
| 205 | 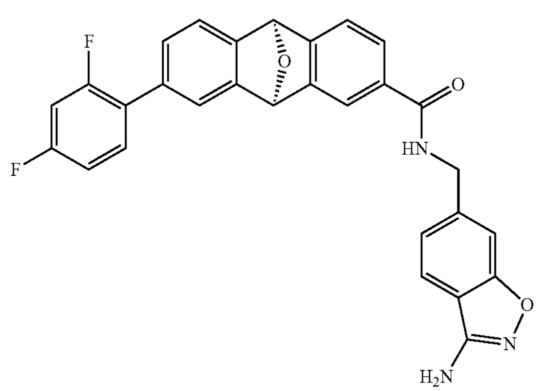 [SMILES: Nc1noc2cc(CNC(=O)c3ccc4c(c3)[C@@H]3O[C@H]4c4ccc(-c5ccc(F)cc5F)cc43)ccc12] | Single enantiomer | 6 | (1R,8S)-N-[(3-amino-1,2-benzoxazol-6-yl)-methyl]-12-(2,4-difluorophenyl)-15-oxatetracyclo[6.6.1.0$^{2,7}$.0$^{9,14}$]pentadeca-2,4,6,9,11,13-hexaene-4-carboxamide |
| 206 | 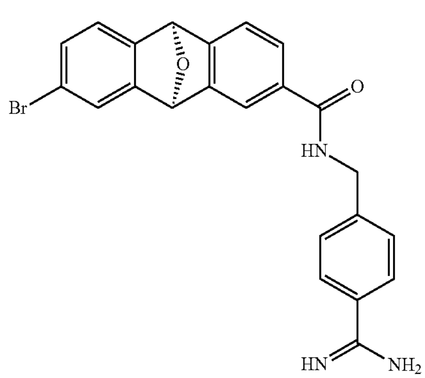 [SMILES: N=C(N)c1ccc(CNC(=O)c2ccc3c(c2)[C@@H]2O[C@H]3c3ccc(Br)cc32)cc1] | Single enantiomer | 7.43 | (1S,8R)-12-bromo-N-[(4-carbamimidoylphenyl)methyl]-15-oxatetracyclo[6.6.1.0$^{2,7}$.0$^{9,14}$]-pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 207 | 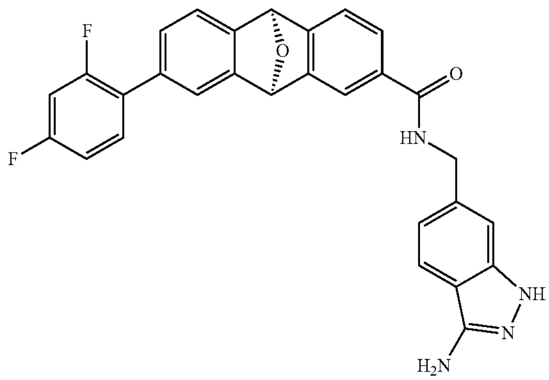 [SMILES: Nc1n[nH]c2cc(CNC(=O)c3ccc4c(c3)[C@@H]3O[C@H]4c4ccc(-c5ccc(F)cc5F)cc43)ccc12] | Single enantiomer | 5.31 | (1R,8S)-N-[(3-amino-1H-indazol-6-yl)methyl]-12-(2,4-difluorophenyl)-15-oxatetracyclo-[6.6.1.0$^2$,$^7$.0$^9$,$^{14}$] pentadeca-2,4,6,9,11,13-hexaene-4-carboxamide |
| 208 | 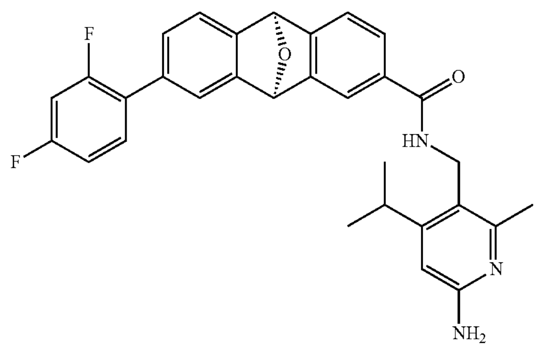 [SMILES: Cc1nc(N)cc(C(C)C)c1CNC(=O)c1ccc2c(c1)[C@@H]1O[C@H]2c2ccc(-c3ccc(F)cc3F)cc21] | Single enantiomer | 9 | (1R,8S)-N-{[6-amino-2-methyl-4-(propan-2-yl)-pyridin-3-yl]methyl}-12-(2,4-difluorophenyl)-15-oxatetracyclo[6.6.1.0$^2$,$^7$.0$^9$,$^{14}$] pentadeca-2,4,6,9,11,13-hexaene-4-carboxamide |
| 209 | | Racemic mixture | 5.46 | (±)-15-acetyl-N-[(6-amino-2,4-dimethylpyridin-3-yl)methyl]-12-(2,4-difluorophenyl)-15-azatetracyclo[6.6.1.0$^2$,$^7$.0$^9$,$^{14}$] pentadeca-2,4,6,9,11,13-hexaene-4-carboxamide and (±)-15-acetyl-N-[(6-amino-2,4-dimethylpyridin-3-yl)methyl]-11-(2,4-difluorophenyl)-15-azatetracyclo[6.6.1.0$^2$,$^7$.0$^9$,$^{14}$] pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 210 | 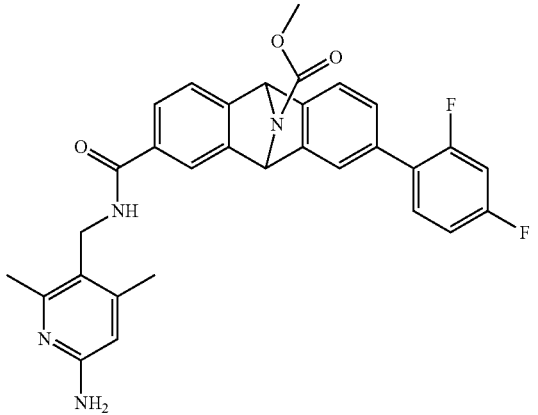 | Mixture of 4 compounds | 4.87 | (±)-methyl 4-{[(6-amino-2,4-dimethylpyridin-3-yl)methyl]carbamoyl}-12-(2,4-difluorophenyl)-15-azatetracyclo[6.6.1.0$^2$,$^7$.0$^9$,$^{14}$]pentadeca-2,4,6,9,11,13-hexaene-15-carboxylate (±)-methyl 4-{[(6-amino-2,4-dimethylpyridin-3-yl)methyl]carbamoyl}-11-(2,4-difluorophenyl)-15-azatetracyclo[6.6.1.0$^2$,$^7$.0$^9$,$^{14}$]pentadeca-2,4,6,9,11,13-hexaene-15-carboxylate |
| 211 | 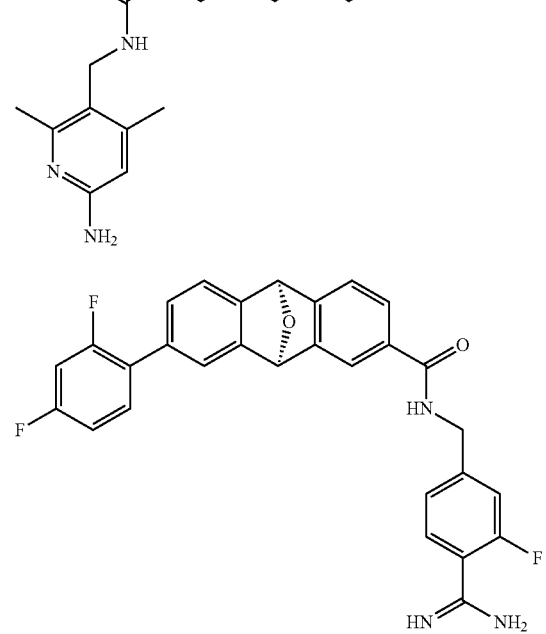 | Single enantiomer | 7.93 | (1R,8S)-N-[(4-carbamimidoyl-3-fluorophenyl)-methyl]-12-(2,4-difluorophenyl)-15-oxatetracyclo[6.6.1.0$^2$,$^7$.0$^9$,$^{14}$]pentadeca-2,4,6,9,11,13-hexaene-4-carboxamide |
| 212 | 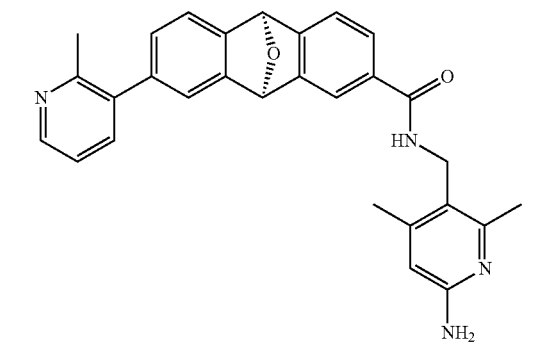 | Single enantiomer | 7.15 | (1R,8S)-N-[(6-amino-2,4-dimethylpyridin-3-yl)-methyl]-12-(2-methylpyridin-3-yl)-15-oxatetracyclo[6.6.1.0$^2$,$^7$.0$^9$,$^{14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 213 | 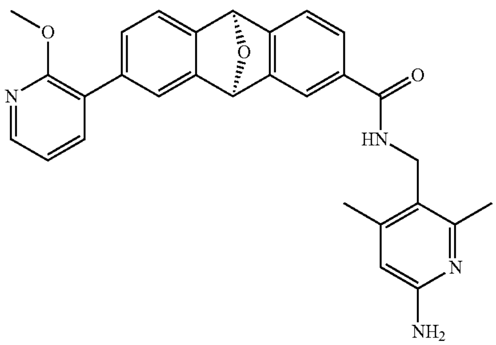 [SMILES: COc1ncccc1-c1ccc2c(c1)[C@H]1O[C@@H]2c2ccc(C(=O)NCc3c(C)cc(N)nc3C)cc21] | Single enantiomer | 6.7 | (1R,8S)-N-[(6-amino-2,4-dimethylpyridin-3-yl)methyl]-12-(2-methoxypyridin-3-yl)-15-oxatetracyclo[6.6.1.0$^2$,$^7$.0$^9$,$^{14}$]pentadeca-2,4,6,9,11,13-hexaene-4-carboxamide |
| 214 | 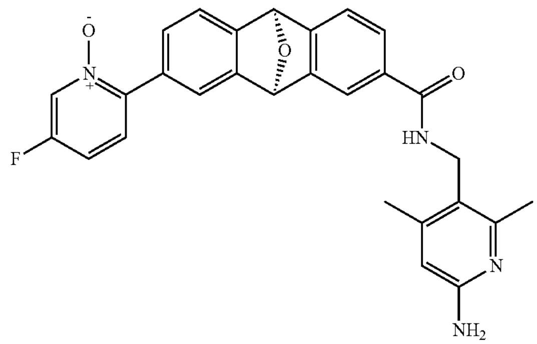 | Single enantiomer | 7.08 | 2-[(1R,8S)-12-{[(6-amino-2,4-dimethylpyridin-3-yl)methyl]carbamoyl}-15-oxatetracyclo-[6.6.1.0$^2$,$^7$.0$^9$,$^{14}$]pentadeca-2,4,6,9,11,13-hexaen-4-yl]-5-fluoropyridin-1-ium-1-olate |
| 215 | 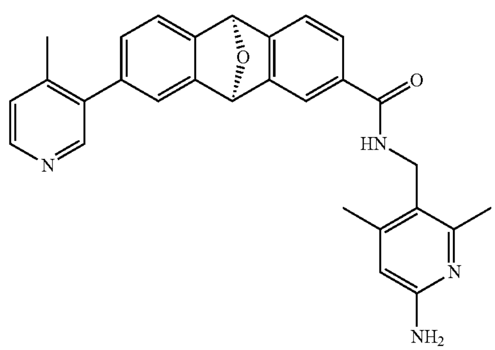 [SMILES: Cc1ccncc1-c1ccc2c(c1)[C@H]1O[C@@H]2c2ccc(C(=O)NCc3c(C)cc(N)nc3C)cc21] | Single enantiomer | 7.1 | (1R,8S)-N-[(6-amino-2,4-dimethylpyridin-3-yl)methyl]-12-(4-methylpyridin-3-yl)-15-oxatetracyclo[6.6.1.0$^2$,$^7$.0$^9$,$^{14}$]pentadeca-2,4,6,9,11,13-hexaene-4-carboxamide |
| 216 | 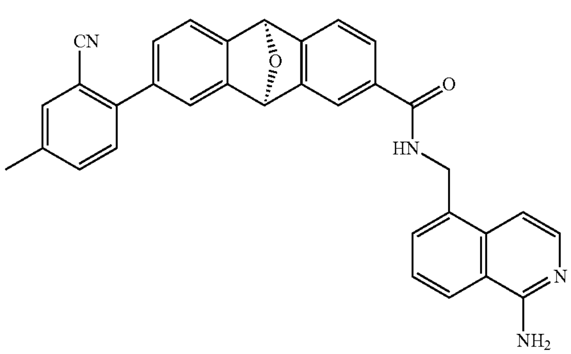 [SMILES: Cc1ccc(-c2ccc3c(c2)[C@H]2O[C@@H]3c3ccc(C(=O)NCc4cccc5c(N)nccc45)cc32)c(C#N)c1] | Single enantiomer | 7.8 | (1R,8S)-N-[(1-aminoisoquinolin-5-yl)methyl]-12-(2-cyano-4-methylphenyl)-15-oxatetracyclo-[6.6.1.0$^2$,$^7$.0$^9$,$^{14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 217 | 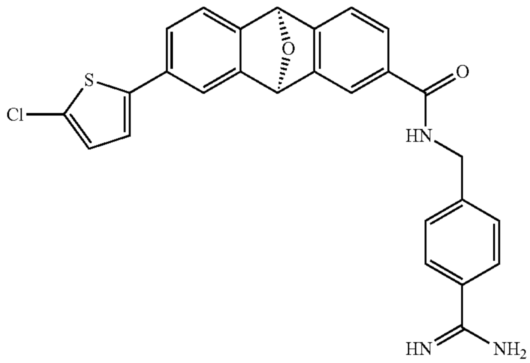 [SMILES: N=C(N)c1ccc(CNC(=O)c2ccc3c(c2)[C@@H]2O[C@H]3c3ccc(-c4ccc(Cl)s4)cc32)cc1] | Single enantiomer | 8.7 | (1S,8R)-N-[(4-carbamimidoylphenyl)methyl]-12-(5-chlorothiophen-2-yl)-15-oxatetracyclo-[6.6.1.0$^{2,7}$.0$^{9,14}$]pentadeca-2,4,6,9,11,13-hexaene-4-carboxamide |
| 218 | 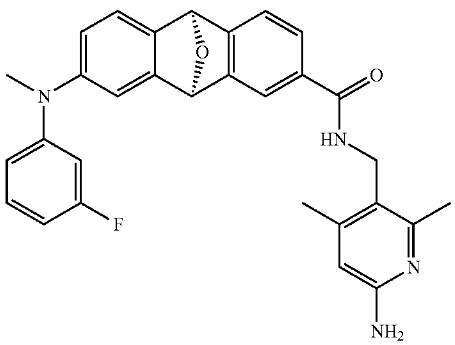 | Single enantiomer | 7.57 | (1S,8R)-N-[(6-amino-2,4-dimethylpyridin-3-yl)methyl]-12-[(3-fluorophenyl)(methyl)amino]-15-oxatetracyclo[6.6.1.0$^{2,7}$.0$^{9,14}$]pentadeca-2,4,6,9,11,13-hexaene-4-carboxamide |
| 219 | 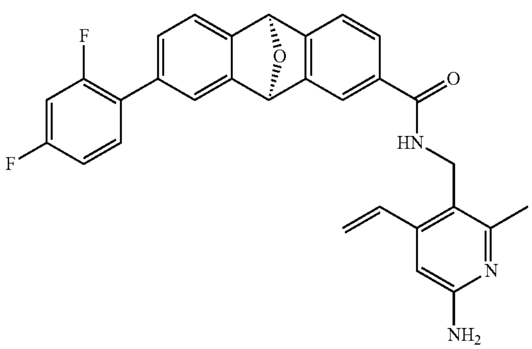 [SMILES: C=Cc1cc(N)nc(C)c1CNC(=O)c1ccc2c(c1)[C@@H]1O[C@H]2c2ccc(-c3ccc(F)cc3F)cc21] | Single enantiomer | 7.77 | (1R,8S)-N-[(6-amino-4-ethenyl-2-methylpyridin-3-yl)methyl]-12-(2,4-difluorophenyl)-15-oxatetracyclo[6.6.1.0$^{2,7}$.0$^{9,14}$]pentadeca-2,4,6,9,11,13-hexaene-4-carboxamide |
| 220 | 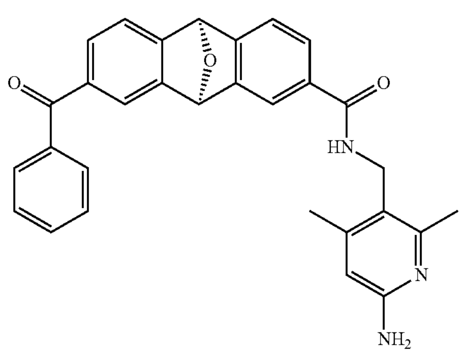 [SMILES: Cc1cc(N)nc(C)c1CNC(=O)c1ccc2c(c1)[C@@H]1O[C@H]2c2ccc(C(=O)c3ccccc3)cc21] | Single enantiomer | 7.92 | (1R,8S)-N-[(6-amino-2,4-dimethylpyridin-3-yl)methyl]-12-benzoyl-15-oxatetracyclo-[6.6.1.0$^{2,7}$.0$^{9,14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 221 | 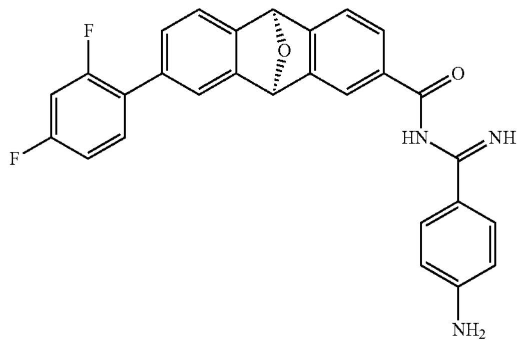 [SMILES: N=C(NC(=O)c1ccc2c(c1)[C@@H]1O[C@H]2c2ccc(-c3ccc(F)cc3F)cc21)c1ccc(N)cc1] | Single enantiomer | 5 | (1R,8S)-N-(4-aminobenzene-carboximidoyl)-12-(2,4-difluorophenyl)-15-oxatetracyclo-[6.6.1.0$^{2,7}$.0$^{9,14}$]pentadeca-2,4,6,9,11,13-hexaene-4-carboxamide |
| 222 | 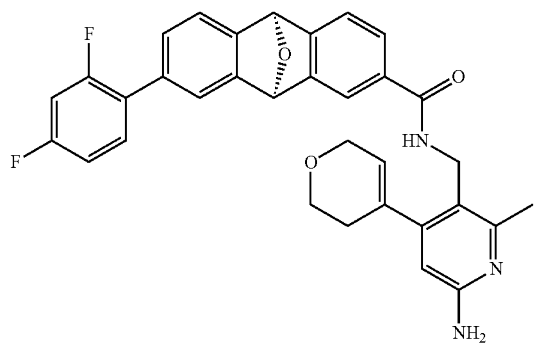 [SMILES: Cc1nc(N)cc(C2=CCOCC2)c1CNC(=O)c1ccc2c(c1)[C@@H]1O[C@H]2c2ccc(-c3ccc(F)cc3F)cc21] | Single enantiomer | 7.55 | (1R,8S)-N-{[6-amino-4-(3,6-dihydro-2H-pyran-4-yl)-2-methylpyridin-3-yl]methyl}-12-(2,4-difluorophenyl)-15-oxatetracyclo[6.6.1.0$^{2,7}$.0$^{9,14}$]-pentadeca-2,4,6,9,11,13-hexaene-4-carboxamide |
| 223 | 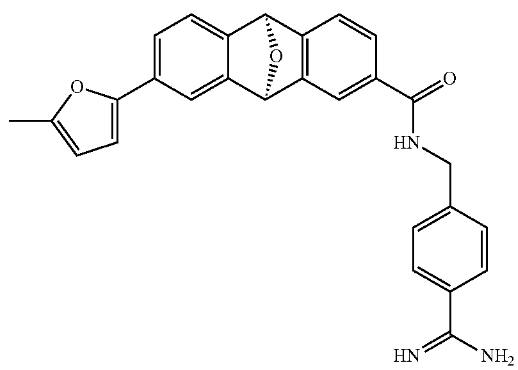 [SMILES: Cc1ccc(-c2ccc3c(c2)[C@H]2O[C@@H]3c3ccc(C(=O)NCc4ccc(C(=N)N)cc4)cc32)o1] | Single enantiomer | 7.47 | (1R,8S)-N-[(4-carbamimidoylphenyl)methyl]-12-(5-methylfuran-2-yl)-15-oxatetracyclo-[6.6.1.0$^{2,7}$.0$^{9,14}$]pentadeca-2,4,6,9,11,13-hexaene-4-carboxamide |
| 224 | 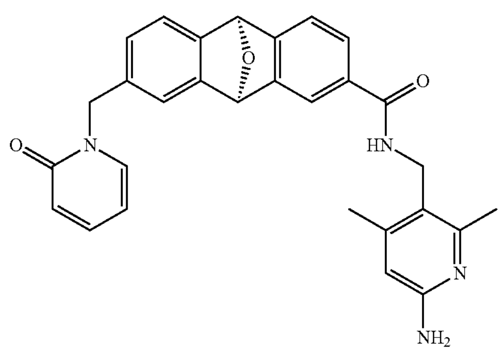 [SMILES: Cc1cc(N)nc(C)c1CNC(=O)c1ccc2c(c1)[C@@H]1O[C@H]2c2ccc(Cn3ccccc3=O)cc21] | Single enantiomer | 9 | (1R,8S)-N-[(6-amino-2,4-dimethylpyridin-3-yl)methyl]-12-[(2-oxo-1,2-dihydropyridin-1-yl)methyl]-15-oxatetracyclo[6.6.1.0$^{2,7}$.0$^{9,14}$]-pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 225 | 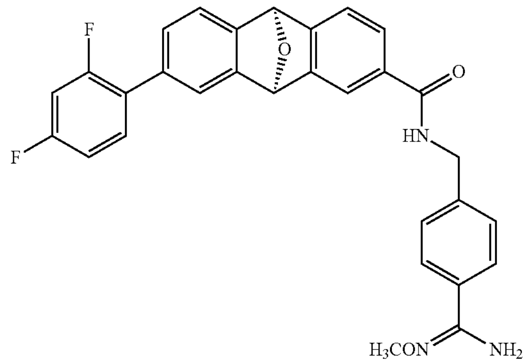 | Single enantiomer | 5 | (1R,8S)-12-(2,4-difluorophenyl)-N-{[4-(N'-methoxy-carbamimidoyl)phenyl]methyl}-15-oxatetracyclo[6.6.1.0$^2$,$^7$.0$^9$,$^{14}$]pentadeca-2,4,6,9,11,13-hexaene-4-carboxamide |
| 226 | 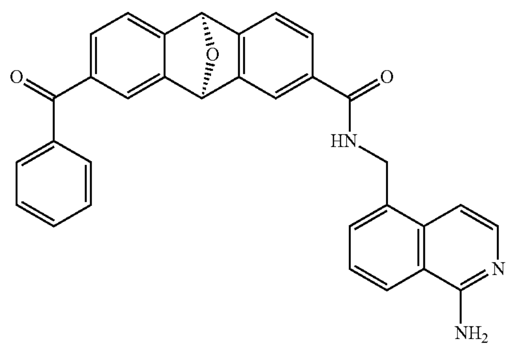 [SMILES: Nc1nccc2c(CNC(=O)c3ccc4c(c3)[C@@H]3O[C@H]4c4ccc(C(=O)c5ccccc5)cc43)cccc12] | Single enantiomer | 7.44 | (1R,8S)-N-[(1-aminoisoquinolin-5-yl)methyl]-12-benzoyl-15-oxatetracyclo[6.6.1.0$^2$,$^7$.0$^9$,$^{14}$]-pentadeca-2,4,6,9,11,13-hexaene-4-carboxamide |
| 227 | 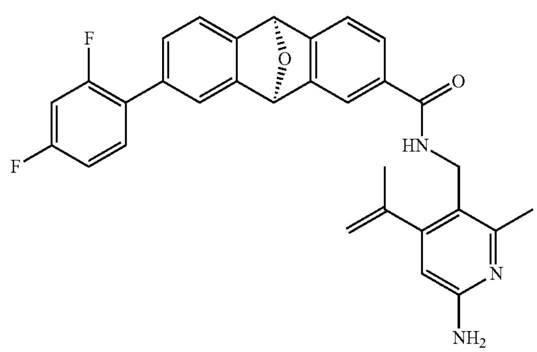 [SMILES: C=C(C)c1cc(N)nc(C)c1CNC(=O)c1ccc2c(c1)[C@@H]1O[C@H]2c2ccc(-c3ccc(F)cc3F)cc21] | Single enantiomer | 7.92 | (1R,8S)-N-{[6-amino-2-methyl-4-(prop-1-en-2-yl)pyridin-3-yl]methyl}-12-(2,4-difluorophenyl)-15-oxatetracyclo[6.6.1.0$^2$,$^7$.0$^9$,$^{14}$]pentadeca-2,4,6,9,11,13-hexaene-4-carboxamide |
| 228 | 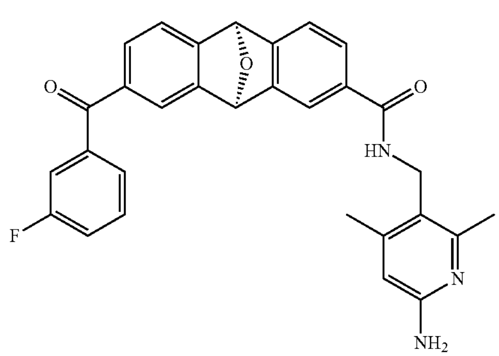 [SMILES: Cc1cc(N)nc(C)c1CNC(=O)c1ccc2c(c1)[C@@H]1O[C@H]2c2ccc(C(=O)c3cccc(F)c3)cc21] | Single enantiomer | 7.92 | (1R,8S)-N-[(6-amino-2,4-dimethylpyridin-3-yl)methyl]-12-(3-fluorobenzoyl)-15-oxatetracyclo[6.6.1.0$^2$,$^7$.0$^9$,$^{14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 229 | 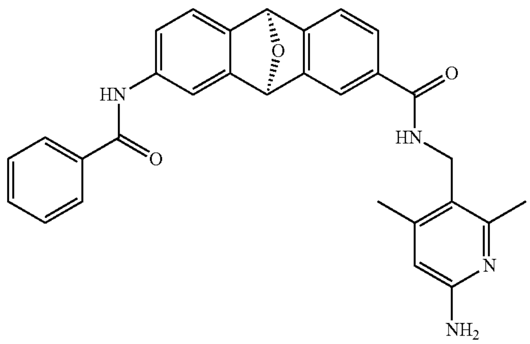 [SMILES: Cc1cc(N)nc(C)c1CNC(=O)c1ccc2c(c1)[C@@H]1O[C@H]2c2ccc(NC(=O)c3ccccc3)cc21] | Single enantiomer | 5 | (1S,8R)-N-[(6-amino-2,4-dimethylpyridin-3-yl)methyl]-12-benzamido-15-oxatetracyclo-[6.6.1.0$^2$,$^7$.0$^9$,$^{14}$]pentadeca-2,4,6,9,11,13-hexaene-4-carboxamide |
| 230 | 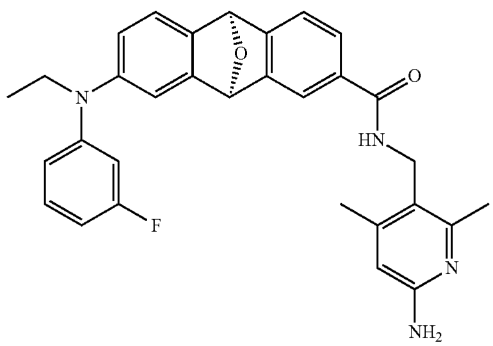 [SMILES: CCN(c1cccc(F)c1)c1ccc2c(c1)[C@H]1O[C@@H]2c2ccc(C(=O)NCc3c(C)cc(N)nc3C)cc21] | Single enantiomer | 7.92 | (1S,8R)-N-[(6-amino-2,4-dimethylpyridin-3-yl)methyl]-12-[ethyl(3-fluorophenyl)amino]-15-oxatetracyclo[6.6.1.0$^2$,$^7$.0$^9$,$^{14}$]pentadeca-2,4,6,9,11,13-hexaene-4-carboxamide |
| 231 | 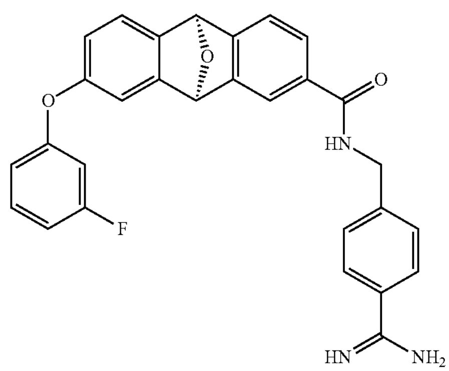 [SMILES: N=C(N)c1ccc(CNC(=O)c2ccc3c(c2)[C@@H]2O[C@H]3c3ccc(Oc4cccc(F)c4)cc32)cc1] | Single enantiomer | 7.47 | (1S,8R)-N-[(4-carbamimidoylphenyl)methyl]-12-(3-fluorophenoxy)-15-oxatetracyclo-[6.6.1.0$^2$,$^7$.0$^9$,$^{14}$]pentadeca-2,4,6,9,11,13-hexaene-4-carboxamide |
| 232 | 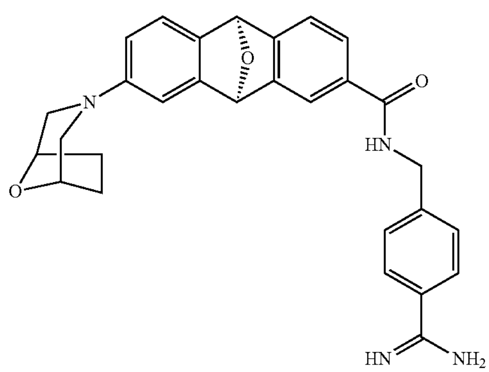 [SMILES: N=C(N)c1ccc(CNC(=O)c2ccc3c(c2)[C@@H]2O[C@H]3c3ccc(N4CC5CCC(C4)O5)cc32)cc1] | Single enantiomer | 7.41 | (1S,8R)-N-[(4-carbamimidoylphenyl)methyl]-12-{8-oxa-3-azabicyclo[3.2.1]octan-3-yl}-15-oxatetracyclo[6.6.1.0$^2$,$^7$.0$^9$,$^{14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 233 | 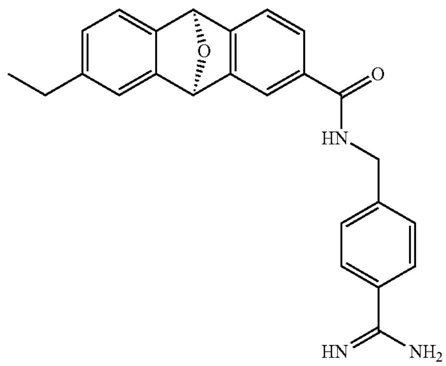 [SMILES: CCc1ccc2c(c1)[C@H]1O[C@@H]2c2ccc(C(=O)NCc3ccc(C(=N)N)cc3)cc21] | Single enantiomer | 8.15 | (1R,8S)-N-[(4-carbamimidoylphenyl)methyl]-12-ethyl-15-oxatetracyclo[6.6.1.0$^{2,7}$.0$^{9,14}$]pentadeca-2,4,6,9,11,13-hexaene-4-carboxamide |
| 234 | 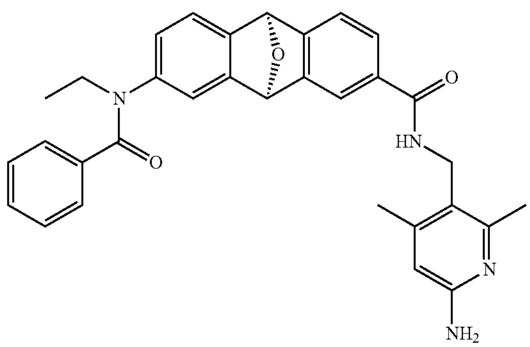 | Single enantiomer | 5 | (1S, 8R)-N-[(6-amino-2,4-dimethylpyridin-3-yl)methyl]-12-(N-ethylbenzamido)-15-oxatetracyclo[6.6.1.0$^{2,7}$.0$^{9,14}$]pentadeca-2,4,6,9,11,13-hexaene-4-carboxamide |
| 235 | 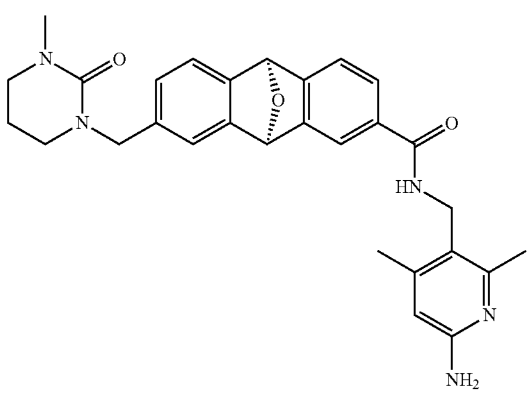 [SMILES: Cc1cc(N)nc(C)c1CNC(=O)c1ccc2c(c1)[C@@H]1O[C@H]2c2ccc(CN3CCCN(C)C3=O)cc21] | Single enantiomer | 7.89 | (1R,8S)-N-[(6-amino-2,4-dimethylpyridin-3-yl)methyl]-12-[(3-methyl-2-oxo-1,3-diazinan-1-yl)methyl]-15-oxatetracyclo[6.6.1.0$^{2,7}$.0$^{9,14}$]-pentadeca-2,4,6,9,11,13-hexaene-4-carboxamide |
| 236 | 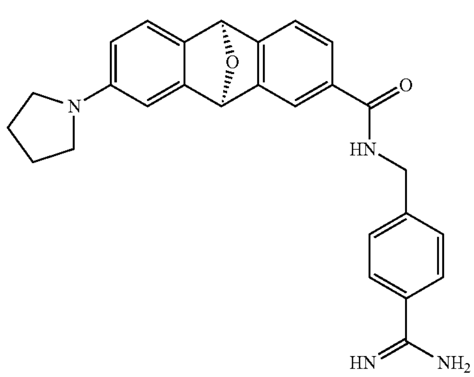 [SMILES: N=C(N)c1ccc(CNC(=O)c2ccc3c(c2)[C@@H]2O[C@H]3c3ccc(N4CCCC4)cc32)cc1] | Single enantiomer | 8.7 | (1S,8R)-N-[(4-carbamimidoylphenyl)methyl]-12-(pyrrolidin-1-yl)-15-oxatetracyclo-[6.6.1.0$^{2,7}$.0$^{9,14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 237 | 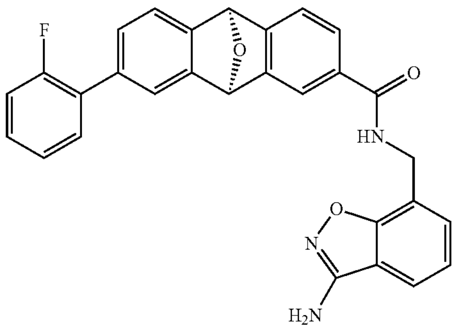 [SMILES: Nc1noc2c(CNC(=O)c3ccc4c(c3)[C@@H]3O[C@H]4c4ccc(-c5ccccc5F)cc43)cccc12] | Single enantiomer | 5 | (1R,8S)-N-[(3-amino-1,2-benzoxazol-7-yl)-methyl]-12-(2-fluorophenyl)-15-oxatetracyclo-[6.6.1.0$^2$,$^7$.0$^9$,1$^4$] pentadeca-2,4,6,9,11,13-hexaene-4-carboxamide |
| 238 | 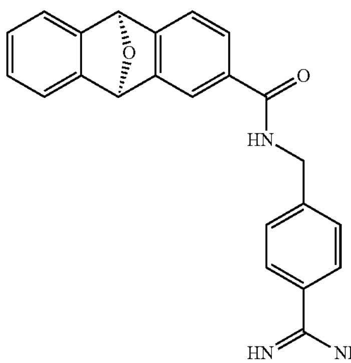 | Single enantiomer | 6.49 | (1R,8S)-N-[(4-carbamimidoyl-phenyl)methyl]-15-oxatetracyclo[6.6.1.0$^2$,$^7$.0$^9$,1$^4$] pentadeca-2,4,6,9,11,13-hexaene-4-carboxamide |
| 239 | 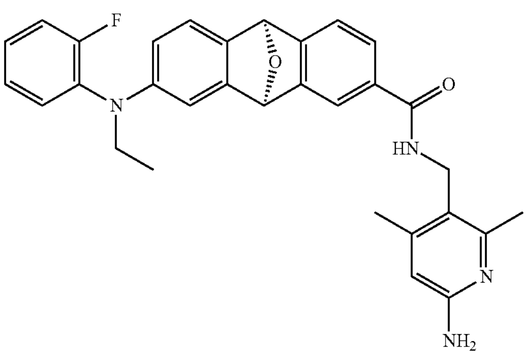 [SMILES: CCN(c1ccc2c(c1)[C@H]1O[C@@H]2c2ccc(C(=O)NCc3c(C)cc(N)nc3C)cc21)c1ccccc1F] | Single enantiomer | 6.63 | (1S,8R)-N-[(6-amino-2,4-dimethylpyridin-3-yl)methyl]-12-[ethyl(2-fluorophenyl)amino]-15-oxatetracyclo[6.6.1.0$^2$,$^7$.0$^9$,1$^4$] pentadeca-2,4,6,9,11,13-hexaene-4-carboxamide |
| 240 | 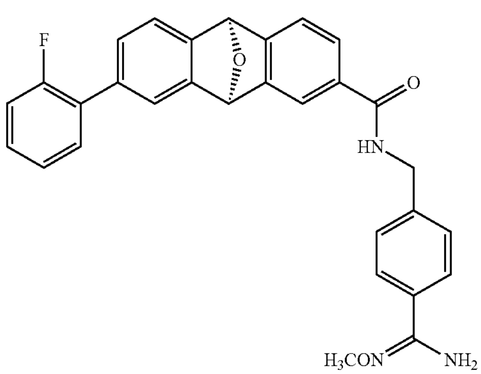 | Single enantiomer | 4 | (1R,8S)-12-(2-fluorophenyl)-N-{[4-(N'-methoxy-carbamimidoyl)phenyl] methyl}-15-oxatetracyclo-[6.6.1.0$^2$,$^7$.0$^9$,1$^4$] pentadeca-2,4,6,9,11,13-hexaene-4-carboxamide |

| Cpd. No | Structure | Compound Type | KLKB1 pIC$_{50}$ | IUPAC Name |
|---|---|---|---|---|
| 241 | 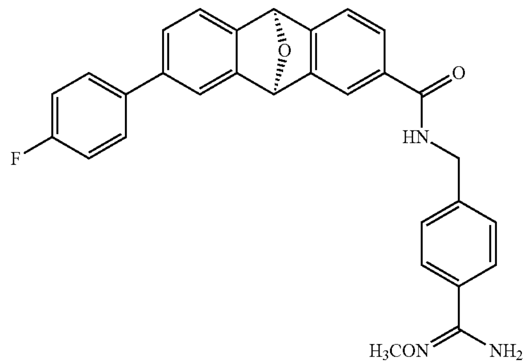 | Single enantiomer | 4 | (1R,8S)-12-(4-fluorophenyl)-N-{[4-(N'-methoxy-carbamimidoyl)phenyl]methyl}-15-oxatetracyclo-[6.6.1.0$^{2,7}$.0$^{9,14}$]pentadeca-2,4,6,9,11,13-hexaene-4-carboxamide |
| 242 | 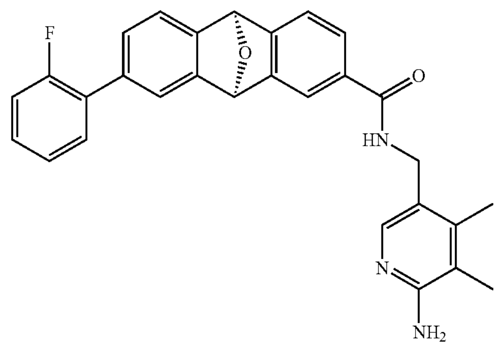 [SMILES: Cc1c(CNC(=O)c2ccc3c(c2)[C@@H]2O[C@H]3c3ccc(-c4ccccc4F)cc32)cnc(N)c1C] | Single enantiomer | 5.56 | (1R,8S)-N-[(6-amino-4,5-dimethylpyridin-3-yl)methyl]-12-(2-fluorophenyl)-15-oxatetra-cyclo[6.6.1.0$^{2,7}$.0$^{9,14}$]pentadeca-2,4,6,9,11,13-hexaene-4-carboxamide |
| 243 | 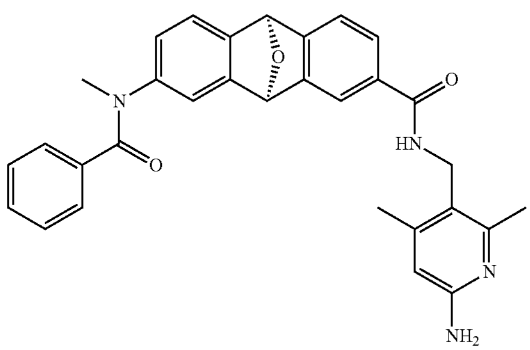 [SMILES: Cc1cc(N)nc(C)c1CNC(=O)c1ccc2c(c1)[C@@H]1O[C@H]2c2ccc(N(C)C(=O)c3ccccc3)cc21] | Single enantiomer | 5.91 | (1S,8R)-N-[(6-amino-2,4-dimethylpyridin-3-yl)methyl]-12-(N-methylbenzamido)-15-oxatetracyclo[6.6.1.0$^{2,7}$.0$^{9,14}$]pentadeca-2,4,6,9,11,13-hexaene-4-carboxamide |
| 244 | 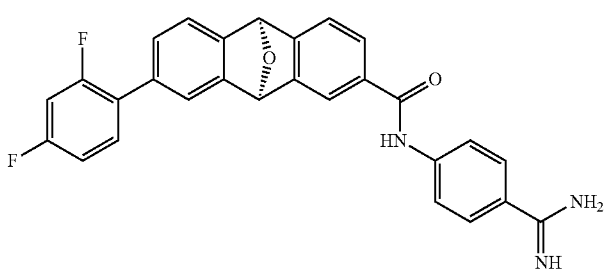 [SMILES: N=C(N)c1ccc(NC(=O)c2ccc3c(c2)[C@@H]2O[C@H]3c3ccc(-c4ccc(F)cc4F)cc32)cc1] | Single enantiomer | 4.97 | (1R,8S)-N-(4-carbamimidoyl-phenyl)-12-(2,4-difluorophenyl)-15-oxatetracyclo[6.6.1.0$^{2,7}$.0$^{9,14}$]-pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 245 | 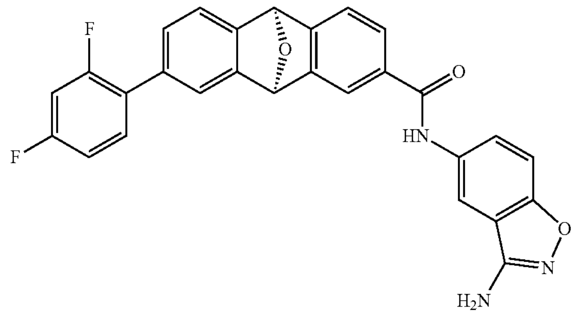 [SMILES: Nc1noc2ccc(NC(=O)c3ccc4c(c3)[C@@H]3O[C@H]4c4ccc(-c5ccc(F)cc5F)cc43)cc12] | Single enantiomer | 5 | (1R,8S)-N-(3-amino-1,2-benzoxazol-5-yl)-12-(2,4-difluorophenyl)-15-oxatetracyclo-[6.6.1.0$^2$,$^7$.0$^9$,$^{14}$] pentadeca-2,4,6,9,11,13-hexaene-4-carboxamide |
| 246 | 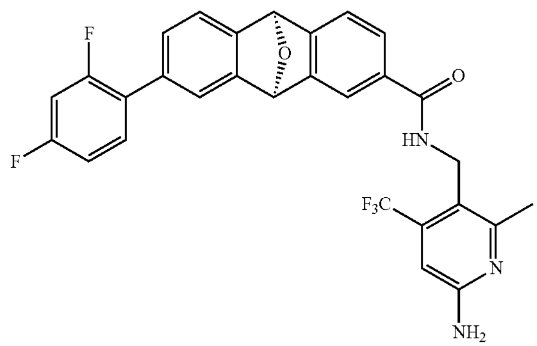 [SMILES: Cc1nc(N)cc(C(F)(F)F)c1CNC(=O)c1ccc2c(c1)[C@@H]1O[C@H]2c2ccc(-c3ccc(F)cc3F)cc21] | Single enantiomer | 4.97 | (1R,8S)-N-{[6-amino-2-methyl-4-(trifluoro-methyl)pyridin-3-yl]methyl}-12-(2,4-difluorophenyl)-15-oxatetracyclo[6.6.1.0$^2$,$^7$.0$^9$,$^{14}$]-pentadeca-2,4,6,9,11,13-hexaene-4-carboxamide |
| 247 | 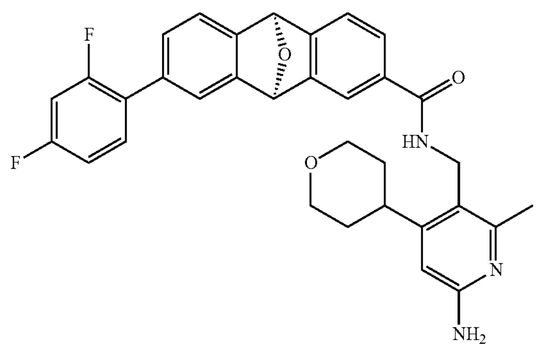 [SMILES: Cc1nc(N)cc(C2CCOCC2)c1CNC(=O)c1ccc2c(c1)[C@@H]1O[C@H]2c2ccc(-c3ccc(F)cc3F)cc21] | Single enantiomer | 8.3 | (1R,8S)-N-{[6-amino-2-methyl-4-(oxan-4-yl)pyridin-3-yl]methyl}-12-(2,4-difluorophenyl)-15-oxatetracyclo[6.6.1.0$^2$,$^7$.0$^9$,$^{14}$] pentadeca-2,4,6,9,11,13-hexaene-4-carboxamide |
| 248 | 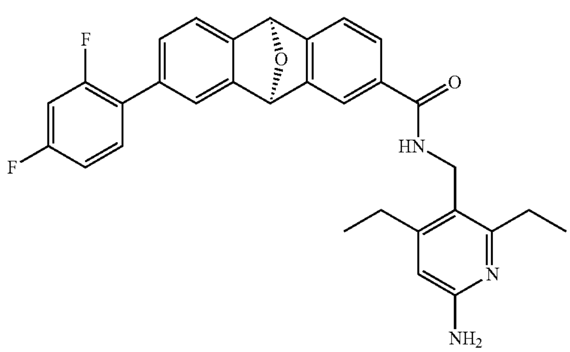 [SMILES: CCc1cc(N)nc(CC)c1CNC(=O)c1ccc2c(c1)[C@@H]1O[C@H]2c2ccc(-c3ccc(F)cc3F)cc21] | Single enantiomer | 5.59 | (1R,8S)-N-[(6-amino-2,4-diethylpyridin-3-yl)methyl]-12-(2,4-difluorophenyl)-15-oxatetracyclo[6.6.1.0$^2$,$^7$.0$^9$,$^{14}$] pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 249 | 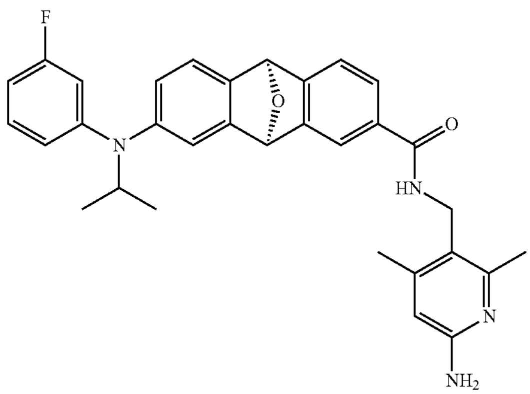 [SMILES: Cc1cc(N)nc(C)c1CNC(=O)c1ccc2c(c1)[C@@H]1O[C@H]2c2ccc(N(c3cccc(F)c3)C(C)C)cc21] | Single enantiomer | 7.03 | (1S,8R)-N-[(6-amino-2,4-dimethylpyridin-3-yl)methyl]-12-[(3-fluorophenyl)(propan-2-yl)amino]-15-oxatetracyclo[6.6.1.0$^{2,7}$.0$^{9,14}$]-pentadeca-2,4,6,9,11,13-hexaene-4-carboxamide |
| 250 | 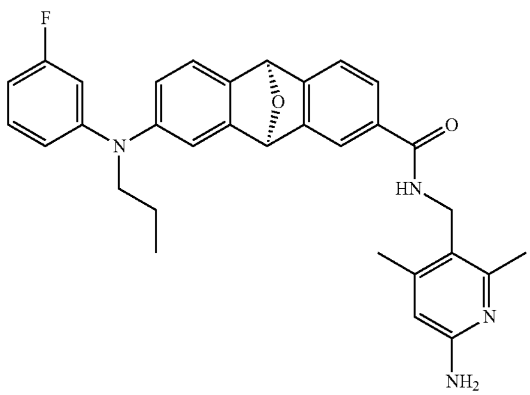 [SMILES: CCCN(c1cccc(F)c1)c1ccc2c(c1)[C@H]1O[C@@H]2c2ccc(C(=O)NCc3c(C)cc(N)nc3C)cc21] | Single enantiomer | 7.48 | (1S,8R)-N-[(6-amino-2,4-dimethylpyridin-3-yl)methyl]-12-[(3-fluorophenyl)(propyl)amino]-15-oxatetracyclo[6.6.1.0$^{2,7}$.0$^{9,14}$]pentadeca-2,4,6,9,11,13-hexaene-4-carboxamide |
| 251 | 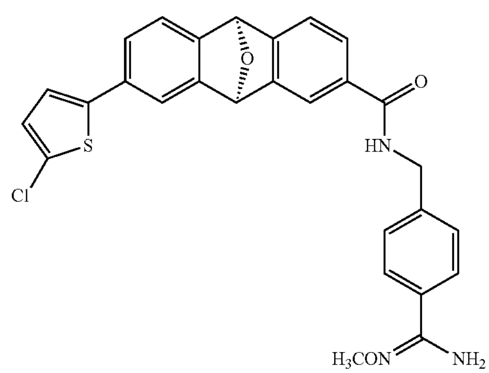 | Single enantiomer | 4 | (1S,8R)-12-(5-chlorothiophen-2-yl)-N-({4-[N'-methoxy-carbamimidoyl]phenyl}methyl)-15-oxatetracyclo[6.6.1.0$^{2,7}$.0$^{9,14}$]pentadeca-2,4,6,9,11,13-hexaene-4-carboxamide |
| 252 | 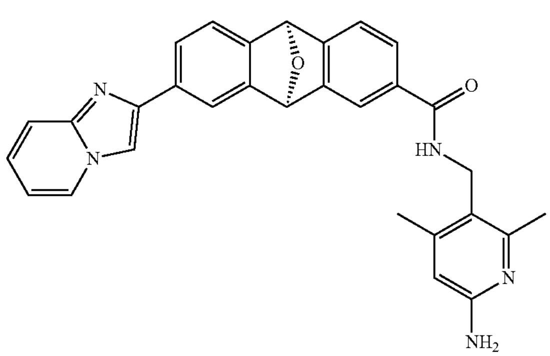 [SMILES: Cc1cc(N)nc(C)c1CNC(=O)c1ccc2c(c1)[C@@H]1O[C@H]2c2ccc(-c3cn4ccccc4n3)cc21] | Single enantiomer | 7.03 | (1R,8S)-N-[(6-amino-2,4-dimethylpyridin-3-yl)methyl]-12-{imidazo[1,2-a]pyridin-2-yl}-15-oxatetracyclo[6.6.1.0$^{2,7}$.0$^{9,14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 253 | 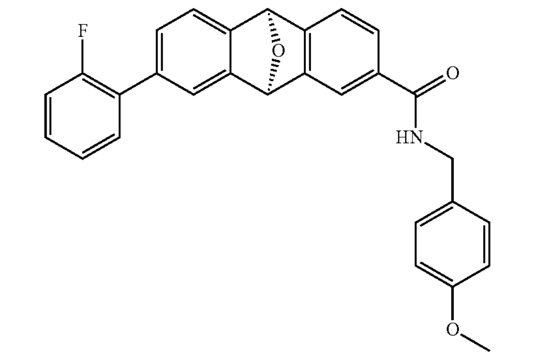 [SMILES: COc1ccc(CNC(=O)c2ccc3c(c2)[C@@H]2O[C@H]3c3ccc(-c4ccccc4F)cc32)cc1] | Single enantiomer | 4 | (1R,8S)-12-(2-fluorophenyl)-N-[(4-methoxy-phenyl)methyl]-15-oxatetracyclo[6.6.1.0$^2$,$^7$.0$^9$,$^{14}$]-pentadeca-2,4,6,9,11,13-hexaene-4-carboxamide |
| 254 | 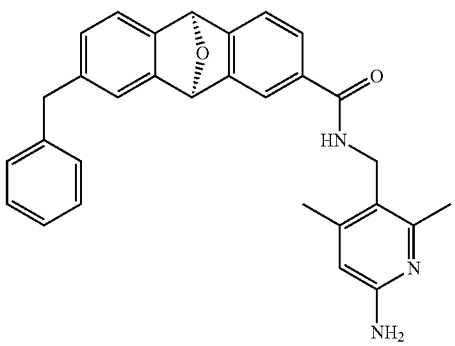 [SMILES: Cc1cc(N)nc(C)c1CNC(=O)c1ccc2c(c1)[C@@H]1O[C@H]2c2ccc(Cc3ccccc3)cc21] | Single enantiomer | 7.72 | (1R,8S)-N-[(6-amino-2,4-dimethylpyridin-3-yl)methyl]-12-benzyl-15-oxatetracyclo-[6.6.1.0$^2$,$^7$.0$^9$,$^{14}$]pentadeca-2,4,6,9,11,13-hexaene-4-carboxamide |
| 255 | 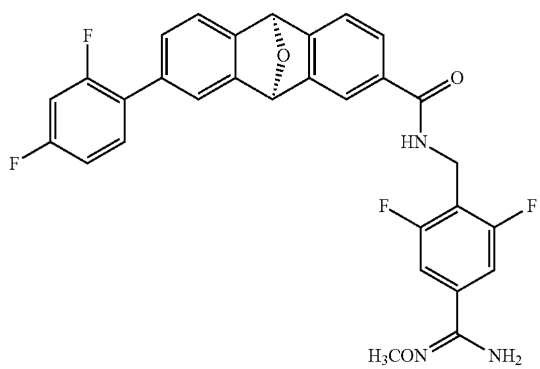 | Single enantiomer | 6.18 | (1R,8S)-N-({2,6-difluoro-4-[N'-methoxy-carbamimidoyl]phenyl}methyl)-12-(2,4-difluorophenyl)-15-oxatetra-cyclo[6.6.1.0$^2$,$^7$.0$^9$,$^{14}$]-pentadeca-2,4,6,9,11,13-hexaene-4-carboxamide |
| 256 | 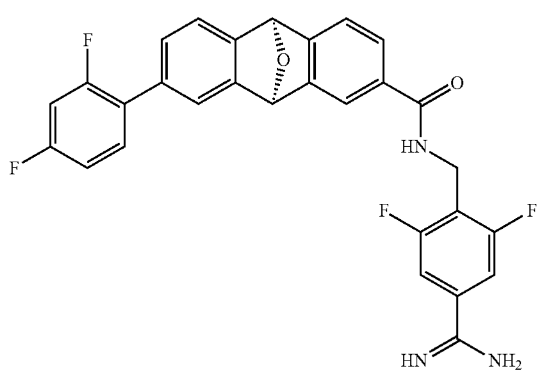 [SMILES: N=C(N)c1cc(F)c(CNC(=O)c2ccc3c(c2)[C@@H]2O[C@H]3c3ccc(-c4ccc(F)cc4F)cc32)c(F)c1] | Single enantiomer | 9.12 | (1R,8S)-N-[(4-carbamimidoyl-2,6-difluoro-phenyl)methyl]-12-(2,4-difluorophenyl)-15-oxatetracyclo[6.6.1.0$^2$,$^7$.0$^9$,$^{14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 257 | 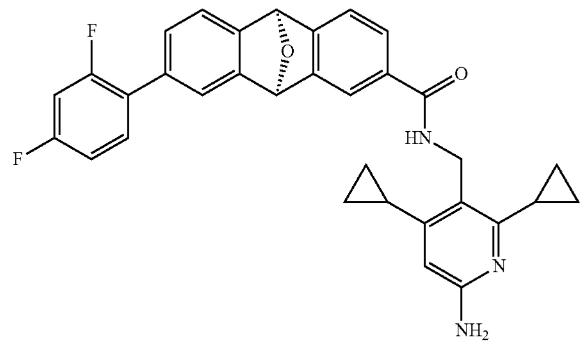 [SMILES: Nc1cc(C2CC2)c(CNC(=O)c2ccc3c(c2)[C@@H]2O[C@H]3c3ccc(-c4ccc(F)cc4F)cc32)c(C2CC2)n1] | Single enantiomer | 3.7 | (1R,8S)-N-[(6-amino-2,4-dicyclopropylpyridin-3-yl)methyl]-12-(2,4-difluorophenyl)-15-oxatetracyclo[6.6.1.0$^2$,$^7$.0$^9$,$^{14}$]pentadeca-2,4,6,9,11,13-hexaene-4-carboxamide |
| 258 | 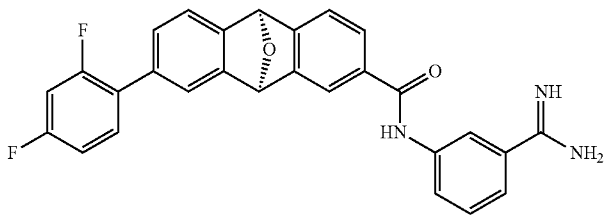 [SMILES: N=C(N)c1cccc(NC(=O)c2ccc3c(c2)[C@@H]2O[C@H]3c3ccc(-c4ccc(F)cc4F)cc32)c1] | Single enantiomer | 5 | (1R,8S)-N-(3-carbamimidoyl-phenyl)-12-(2,4-difluorophenyl)-15-oxatetracyclo[6.6.1.0$^2$,$^7$.0$^9$,$^{14}$]-pentadeca-2,4,6,9,11,13-hexaene-4-carboxamide |
| 259 | 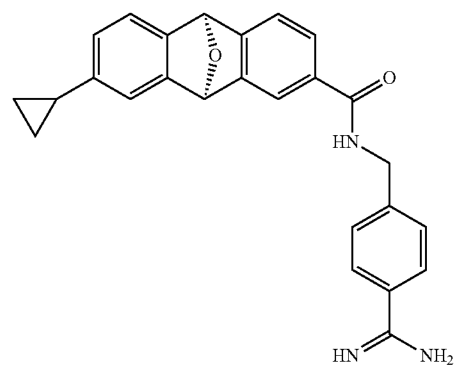 [SMILES: N=C(N)c1ccc(CNC(=O)c2ccc3c(c2)[C@@H]2O[C@H]3c3ccc(C4CC4)cc32)cc1] | Single enantiomer | 8.7 | (1R,8S)-N-[(4-carbamimidoyl-phenyl)methyl]-12-cyclopropyl-15-oxatetracyclo[6.6.1.0$^2$,$^7$.0$^9$,$^{14}$]-pentadeca-2,4,6,9,11,13-hexaene-4-carboxamide |
| 260 | 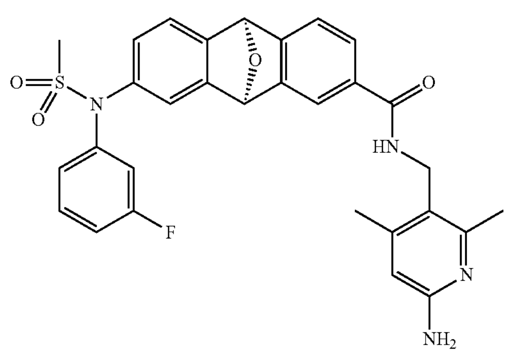 [SMILES: Cc1cc(N)nc(C)c1CNC(=O)c1ccc2c(c1)[C@@H]1O[C@H]2c2ccc(N(c3cccc(F)c3)S(C)(=O)=O)cc21] | Single enantiomer | 6.73 | (1S,8R)-N-[(6-amino-2,4-dimethylpyridin-3-yl)methyl]-12-[N-(3-fluorophenyl)methane-sulfonamido]-15-oxatetracyclo[6.6.1.0$^2$,$^7$.0$^9$,$^{14}$]-pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 261 | 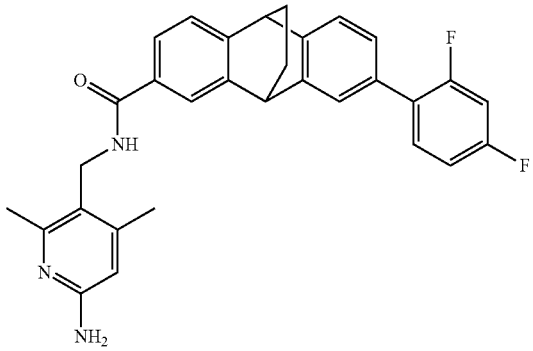 | Racemic mixture | 6.32 | (±)-N-[(6-amino-2,4-dimethylpyridin-3-yl)methyl]-12-(2,4-difluorophenyl) tetracyclo-[6.6.2.0$^2$,$^7$.0$^9$,1$^4$] hexadeca-2,4,6,9,11,13-hexaene-4-carboxamide and (±)-N-[(6-amino-2,4-dimethylpyridin-3-yl) methyl]-11-(2,4-difluorophenyl) tetracyclo[6.6.2.0$^2$,$^7$.0$^9$,1$^4$] hexadeca-2,4,6,9,11,13-hexaene-4-carboxamide |
| 262 | 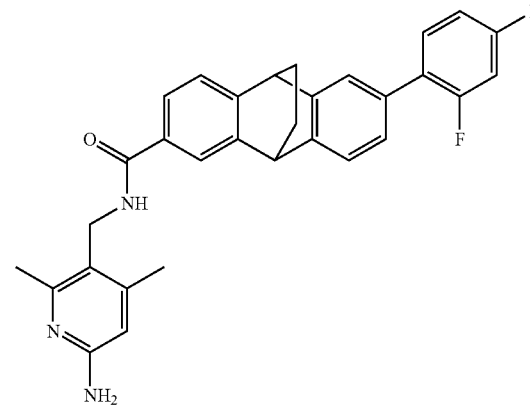 | Single enantiomer | 8.05 | (1S,8R)-N-[(6-amino-2,4-dimethylpyridin-3-yl)methyl]-12-[(3-chlorophenyl) (methyl)amino]-15-oxatetracyclo[6.6.1.0$^2$,$^7$.0$^9$,1$^4$] pentadeca-2,4,6,9,11,13-hexaene-4-carboxamide |
| 263 | 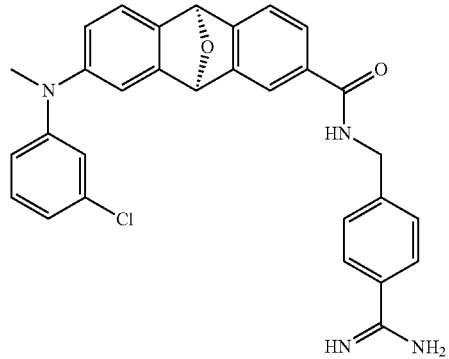 [SMILES: CN(c1cccc(Cl)c1)c1ccc2c(c1)[C@H]1O[C@@H]2c2ccc(C(=O)NCc3ccc(C(=N)N)cc3)cc21] | Single enantiomer | 9 | (1S,8R)-N-[(4-carbamimidoyl-phenyl)methyl]-12-[(3-chlorophenyl) (methyl)amino]-15-oxatetracyclo[6.6.1.0$^2$,$^7$.0$^9$,1$^4$] pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 264 | 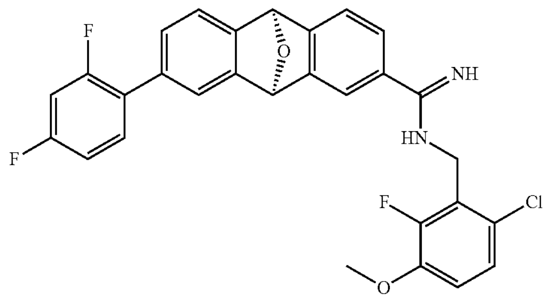 [SMILES: COc1ccc(Cl)c(CNC(=N)c2ccc3c(c2)[C@@H]2O[C@H]3c3ccc(-c4ccc(F)cc4F)cc32)c1F] | Single enantiomer | 5.62 | (1R,8S)-N-[(6-chloro-2-fluoro-3-methoxyphenyl)-methyl]-12-(2,4-difluorophenyl)-15-oxatetracyclo[6.6.1.0$^2$,$^7$.0$^9$,$^{14}$]pentadeca-2,4,6,9,11,13-hexaene-4-carboximidamide |
| 265 | 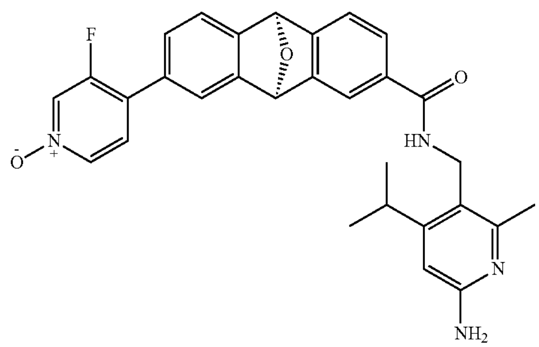 | Single enantiomer | 7.04 | 4-[(1R,8S)-12-({[6-amino-2-methyl-4-(propan-2-yl)pyridin-3-yl]methyl}carbamoyl)-15-oxatetracyclo[6.6.1.0$^2$,$^7$.0$^9$,$^{14}$]pentadeca-2,4,6,9,11,13-hexaen-4-yl]-3-fluoropyridin-1-ium-1-olate |
| 266 | 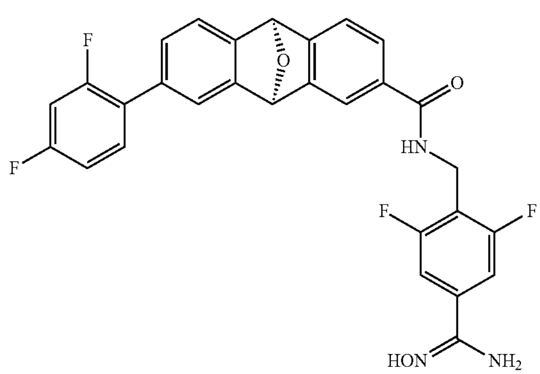 | Single enantiomer | 6.99 | (1R,8S)-N-({2,6-difluoro-4-[N'-hydroxy-carbamimidoyl]phenyl}methyl)-12-(2,4-difluorophenyl)-15-oxatetracyclo[6.6.1.0$^2$,$^7$.0$^9$,$^{14}$]-pentadeca-2,4,6,9,11,13-hexaene-4-carboxamide |
| 267 | 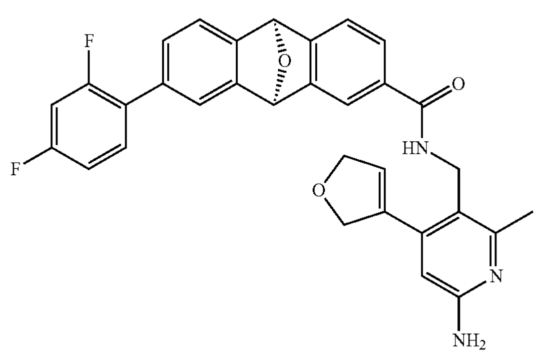 [SMILES: Cc1nc(N)cc(C2=CCOC2)c1CNC(=O)c1ccc2c(c1)[C@@H]1O[C@H]2c2ccc(-c3ccc(F)cc3F)cc21] | Single enantiomer | 7.01 | (1R,8S)-N-{[6-amino-4-(2,5-dihydrofuran-3-yl)-2-methylpyridin-3-yl]methyl}-12-(2,4-difluoro-phenyl)-15-oxatetracyclo[6.6.1.0$^2$,$^7$.0$^9$,$^{14}$]-pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 268 | 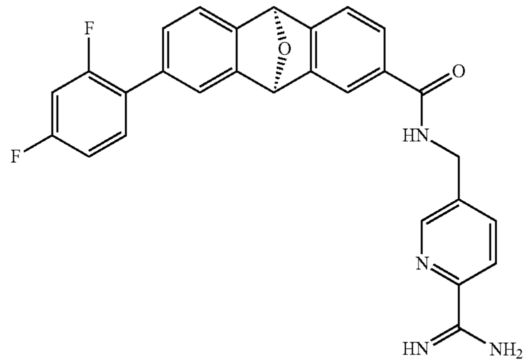 | Single enantiomer | 8.3 | (1R,8S)-N-[(6-carbamimidoylpyridin-3-yl)-methyl]-12-(2,4-difluorophenyl)-15-oxatetracyclo[6.6.1.0$^2$,$^7$.0$^9$,$^{14}$]pentadeca-2,4,6,9,11,13-hexaene-4-carboxamide |
| 269 | 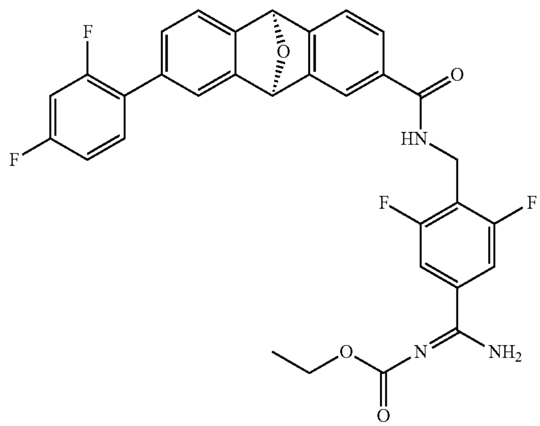 [SMILES: CCOC(=O)N=C(N)c1cc(F)c(CNC(=O)c2ccc3c(c2)[C@@H]2O[C@H]3c3ccc(-c4ccc(F)cc4F)cc32)c(F)c1] | Single enantiomer | 5.91 | ethyl N-[amino[4-({[(1R,8S)-12-(2,4-difluoro-phenyl)-15-oxatetracyclo[6.6.1.0$^2$,$^7$.0$^9$,$^{14}$]-pentadeca-2,4,6,9,11,13-hexaen-4-yl]formamido}-methyl)-3,5-difluorophenyl]methylidene]-carbamate |
| 270 | 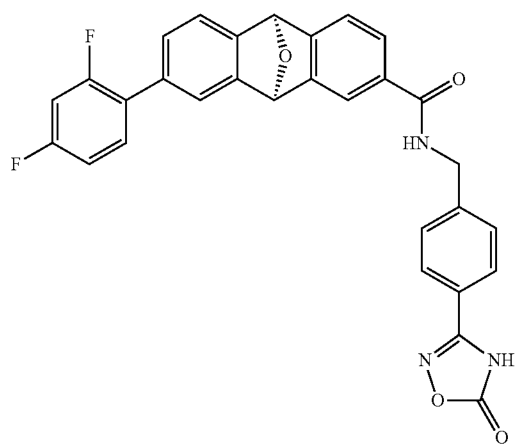 [SMILES: O=C(NCc1ccc(-c2noc(=O)[nH]2)cc1)c1ccc2c(c1)[C@@H]1O[C@H]2c2ccc(-c3ccc(F)cc3F)cc21] | Single enantiomer | 4 | (1R,8S)-12-(2,4-difluorophenyl)-N-{[4-(5-oxo-4,5-dihydro-1,2,4-oxadiazol-3-yl)phenyl]methyl}-15-oxatetracyclo[6.6.1.0$^2$,$^7$.0$^9$,$^{14}$]pentadeca-2,4,6,9,11,13-hexaene-4-carboxamide |
| 271 | 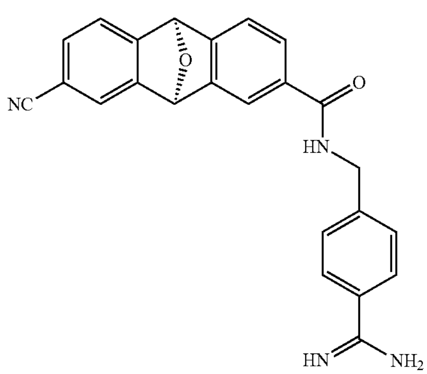 [SMILES: N#Cc1ccc2c(c1)[C@H]1O[C@@H]2c2ccc(C(=O)NCc3ccc(C(=N)N)cc3)cc21] | Single enantiomer | 6.86 | (1R,8S)-N-[(4-carbamimidoyl-phenyl)methyl]-12-cyano-15-oxatetracyclo[6.6.1.0$^2$,$^7$.0$^9$,$^{14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 272 | 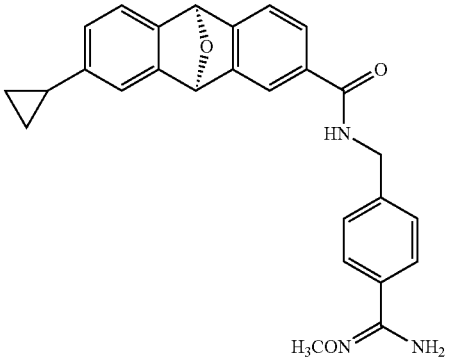 | Single enantiomer | 5.61 | (1R,8S)-12-cyclopropyl-N-({4-[N'-methoxy-carbamimidoyl]phenyl}methyl)-15-oxatetracyclo[6.6.1.0$^2$,$^7$.0$^9$,$^{14}$]pentadeca-2,4,6,9,11,13-hexaene-4-carboxamide |
| 273 | 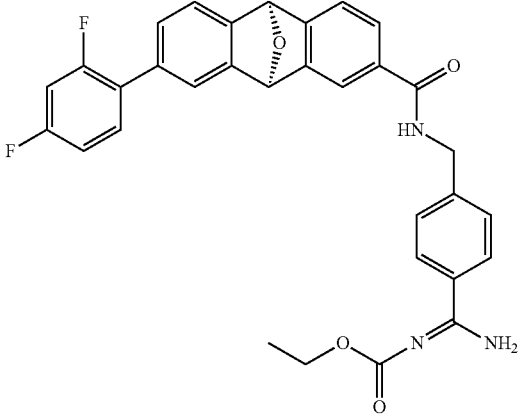 [SMILES: CCOC(=O)N=C(N)c1ccc(CNC(=O)c2ccc3c(c2)[C@@H]2O[C@H]3c3ccc(-c4ccc(F)cc4F)cc32)cc1] | Single enantiomer | 5.22 | ethyl N-[amino[4-({[(1R,8S)-12-(2,4-difluorophenyl)-15-oxatetracyclo[6.6.1.0$^2$,$^7$.0$^9$,$^{14}$]-pentadeca-2,4,6,9,11,13-hexaen-4-yl]formamido}-methyl)phenyl]methylidene]carbamate |
| 274 | 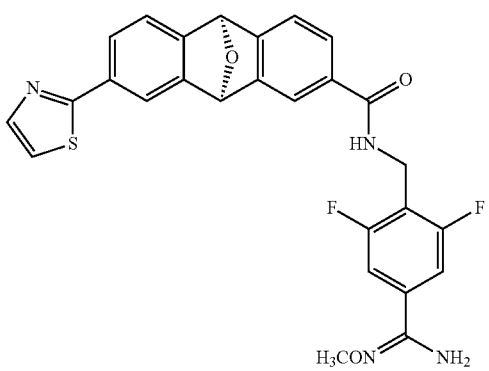 | Single enantiomer | 5.86 | (1S,8R)-N-({2,6-difluoro-4-[N'-methoxy-carbamimidoyl]phenyl}methyl)-12-(1,3-thiazol-2-yl)-15-oxatetracyclo[6.6.1.0$^2$,$^7$.0$^9$,$^{14}$]pentadeca-2,4,6,9,11,13-hexaene-4-carboxamide |
| 275 | 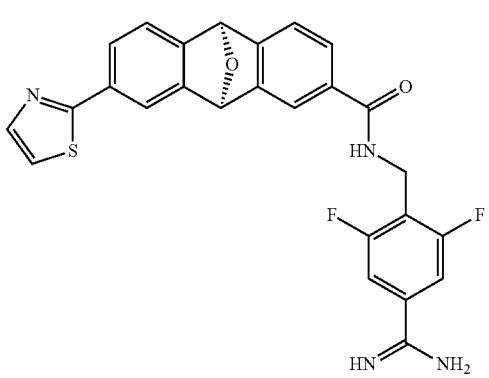 [SMILES: N=C(N)c1cc(F)c(CNC(=O)c2ccc3c(c2)[C@@H]2O[C@H]3c3ccc(-c4nccs4)cc32)c(F)c1] | Single enantiomer | 8.7 | (1S,8R)-N-[(4-carbamimidoyl-2,6-difluoro-phenyl)methyl]-12-(1,3-thiazol-2-yl)-15-oxatetracyclo[6.6.1.0$^2$,$^7$.0$^9$,$^{14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 276 | 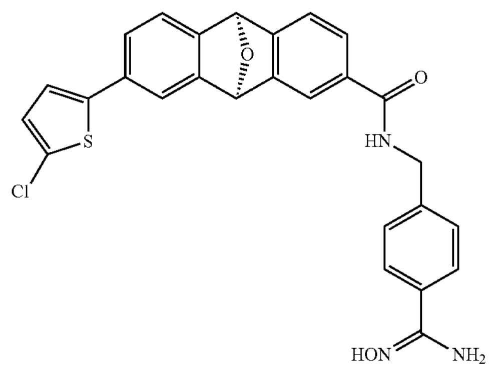 | Single enantiomer | 4 | (1S,8R)-12-(5-chlorothiophen-2-yl)-N-{[4-(N'-hydroxycarbamimidoyl)phenyl]methyl}-15-oxatetracyclo[6.6.1.0$^2$,$^7$.0$^9$,$^{14}$]pentadeca-2,4,6,9,11,13-hexaene-4-carboxamide |
| 277 | 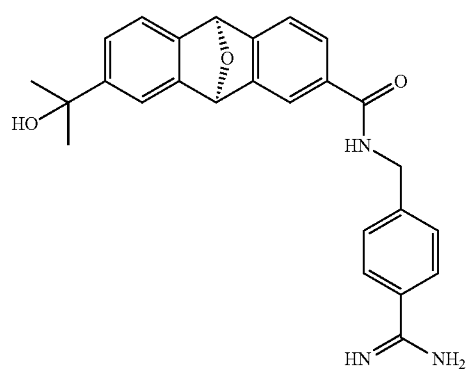 [SMILES: CC(C)(O)c1ccc2c(c1)[C@H]1O[C@@H]2c2ccc(C(=O)NCc3ccc(C(=N)N)cc3)cc21] | Single enantiomer | 7.45 | (1R,8S)-N-[(4-carbamimidoyl-phenyl)methyl]-12-(2-hydroxypropan-2-yl)-15-oxatetracyclo-[6.6.1.0$^2$,$^7$.0$^9$,$^{14}$]pentadeca-2,4,6,9,11,13-hexaene-4-carboxamide |
| 278 | 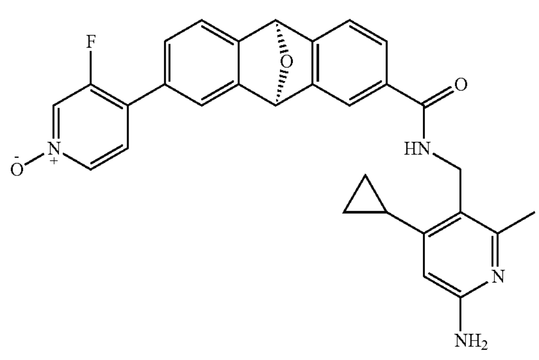 | Single enantiomer | 7.46 | 4-[(1R,8S)-12-{[(6-amino-4-cyclopropyl-2-methylpyridin-3-yl)methyl]carbamoyl}-15-oxatetracyclo[6.6.1.0$^2$,$^7$.0$^9$,$^{14}$]pentadeca-2,4,6,9,11,13-hexaen-4-yl]-3-fluoropyridin-1-ium-1-olate |
| 279 | 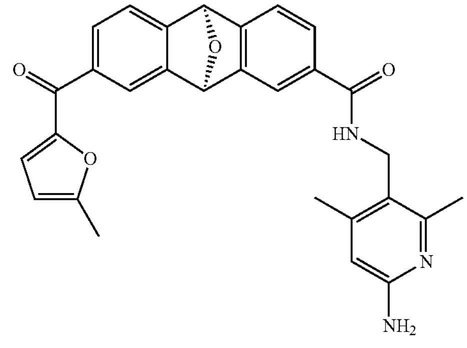 [SMILES: Cc1ccc(C(=O)c2ccc3c(c2)[C@H]2O[C@@H]3c3ccc(C(=O)NCc4c(C)cc(N)nc4C)cc32)o1] | Single enantiomer | 7.64 | (1R,8S)-N-[(6-amino-2,4-dimethylpyridin-3-yl)methyl]-12-(5-methylfuran-2-carbonyl)-15-oxatetracyclo[6.6.1.0$^2$,$^7$.0$^9$,$^{14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 280 | 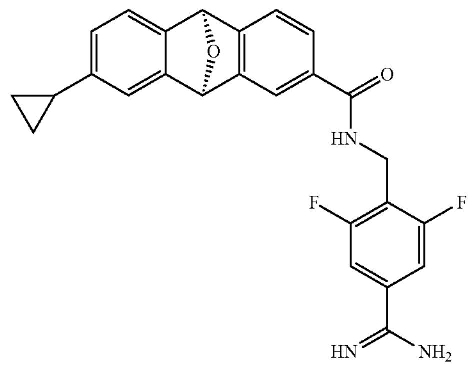 [SMILES: N=C(N)c1cc(F)c(CNC(=O)c2ccc3c(c2)[C@@H]2O[C@H]3c3ccc(C4CC4)cc32)c(F)c1] | Single enantiomer | 9.12 | (1R,8S)-N-[(4-carbamimidoyl-2,6-difluoro-phenyl)methyl]-12-cyclopropyl-15-oxatetracyclo[6.6.1.0$^2$,$^7$.0$^9$,$^{14}$]pentadeca-2,4,6,9,11,13-hexaene-4-carboxamide |
| 281 | 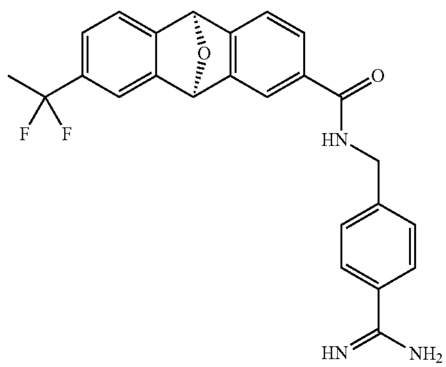 [SMILES: CC(F)(F)c1ccc2c(c1)[C@H]1O[C@@H]2c2ccc(C(=O)NCc3ccc(C(=N)N)cc3)cc21] | Single enantiomer | 8 | (1S,8R)-N-[(4-carbamimidoyl-phenyl)methyl]-12-(1,1-difluoroethyl)-15-oxatetracyclo-[6.6.1.0$^2$,$^7$.0$^9$,$^{14}$]pentadeca-2,4,6,9,11,13-hexaene-4-carboxamide |
| 282 | 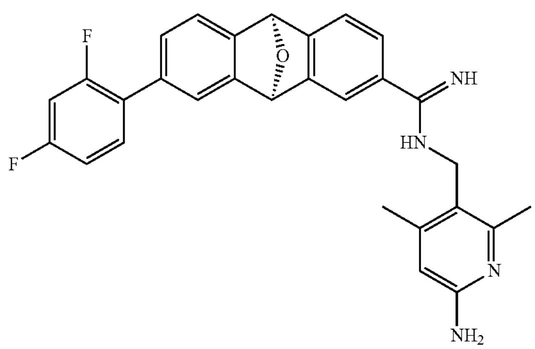 | Single enantiomer | 5.53 | (1R,8S)-N-[(6-amino-2,4-dimethylpyridin-3-yl)methyl]-12-(2,4-difluorophenyl)-15-oxatetracyclo[6.6.1.0$^2$,$^7$.0$^9$,$^{14}$]pentadeca-2,4,6,9,11,13-hexaene-4-carboximidamide |
| 283 | 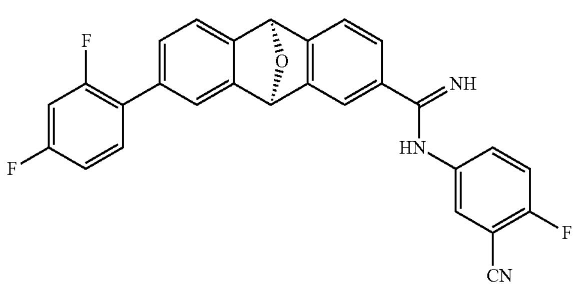 [SMILES: N#Cc1cc(NC(=N)c2ccc3c(c2)[C@@H]2O[C@H]3c3ccc(-c4ccc(F)cc4F)cc32)ccc1F] | Single enantiomer | 4 | (1R,8S)-N-(3-cyano-4-fluorophenyl)-12-(2,4-difluorophenyl)-15-oxatetracyclo[6.6.1.0$^2$,$^7$.0$^9$,$^{14}$]-pentadeca-2,4,6,9,11,13-hexaene-4-carboximidamide |

TABLE 1-continued

| Cpd. No | Structure | Compound Type | KLKB1 pIC$_{50}$ | IUPAC Name |
|---|---|---|---|---|
| 284 | 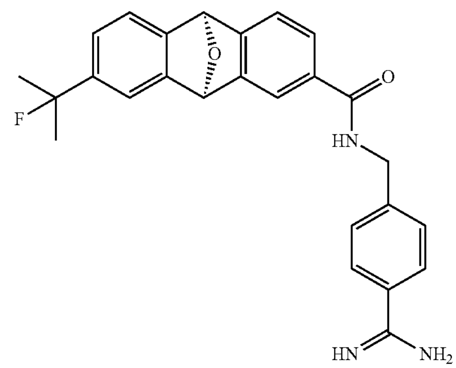 [SMILES: CC(C)(F)c1ccc2c(c1)[C@H]1O[C@@H]2c2ccc(C(=O)NCc3ccc(C(=N)N)cc3)cc21] | Single enantiomer | 8.2 | (1S,8R)-N-[(4-carbamimidoyl-phenyl)methyl]-12-(2-fluoropropan-2-yl)-15-oxatetracyclo-[6.6.1.0$^{2,7}$.0$^{9,14}$] pentadeca-2,4,6,9,11,13-hexaene-4-carboxamide |
| 285 | 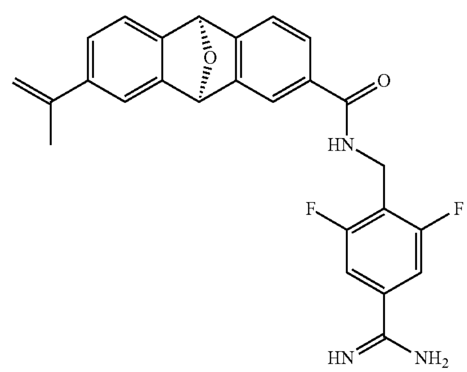 [SMILES: C=C(C)c1ccc2c(c1)[C@H]1O[C@@H]2c2ccc(C(=O)NCc3c(F)cc(C(=N)N)cc3F)cc21] | Single enantiomer | 9 | (1R,8S)-N-[(4-carbamimidoyl-2,6-difluoro-phenyl)methyl]-12-(prop-1-en-2-yl)-15-oxatetracyclo[6.6.1.0$^{2,7}$.0$^{9,14}$] pentadeca-2,4,6,9,11,13-hexaene-4-carboxamide |
| 286 | 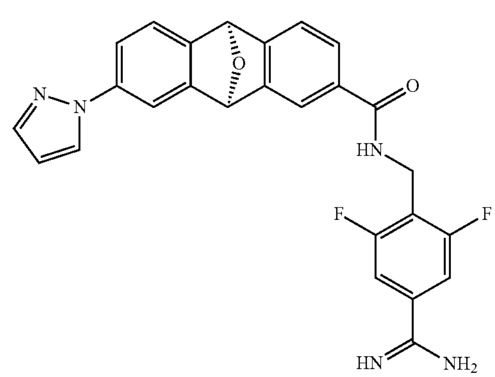 [SMILES: N=C(N)c1cc(F)c(CNC(=O)c2ccc3c(c2)[C@@H]2O[C@H]3c3ccc(-n4cccn4)cc32)c(F)c1] | Single enantiomer | 8.61 | (1S,8R)-N-[(4-carbamimidoyl-2,6-difluoro-phenyl)methyl]-12-(1H-pyrazol-1-yl)-15-oxatetracyclo[6.6.1.0$^{2,7}$.0$^{9,14}$] pentadeca-2,4,6,9,11,13-hexaene-4-carboxamide |
| 287 | 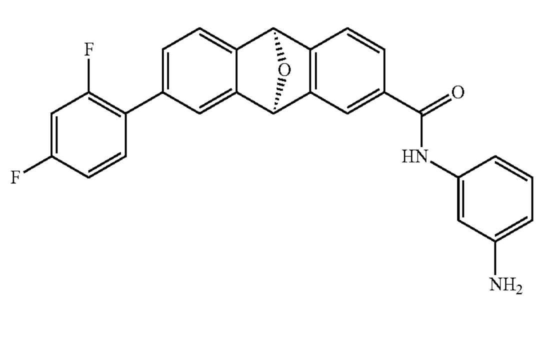 [SMILES: Nc1cccc(NC(=O)c2ccc3c(c2)[C@@H]2O[C@H]3c3ccc(-c4ccc(F)cc4F)cc32)c1] | Single enantiomer | 5 | (1R,8S)-N-(3-aminophenyl)-12-(2,4-difluoro-phenyl)-15-oxatetracyclo[6.6.1.0$^{2,7}$.0$^{9,14}$]-pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 288 | 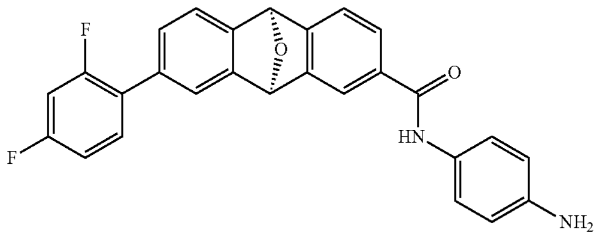 [SMILES: Nc1ccc(NC(=O)c2ccc3c(c2)[C@@H]2O[C@H]3c3ccc(-c4ccc(F)cc4F)cc32)cc1] | Single enantiomer | 4 | (1R,8S)-N-(4-aminophenyl)-12-(2,4-difluoro-phenyl)-15-oxatetracyclo[6.6.1.0$^2$,$^7$.0$^9$,$^{14}$]-pentadeca-2,4,6,9,11,13-hexaene-4-carboxamide |
| 289 | 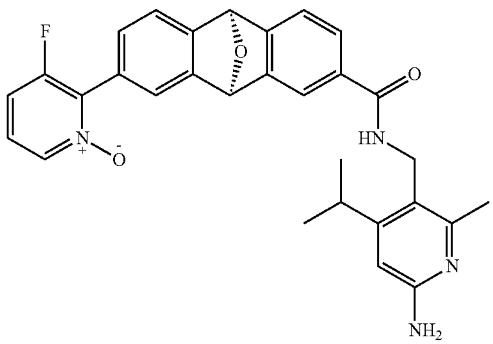 | Single enantiomer | 6.91 | 2-[(1R,8S)-12-({[6-amino-2-methyl-4-(propan-2-yl)pyridin-3-yl]methyl}carbamoyl)-15-oxatetracyclo[6.6.1.0$^2$,$^7$.0$^9$,$^{14}$]pentadeca-2,4,6,9,11,13-hexaen-4-yl]-3-fluoropyridin-1-ium-1-olate |
| 290 | 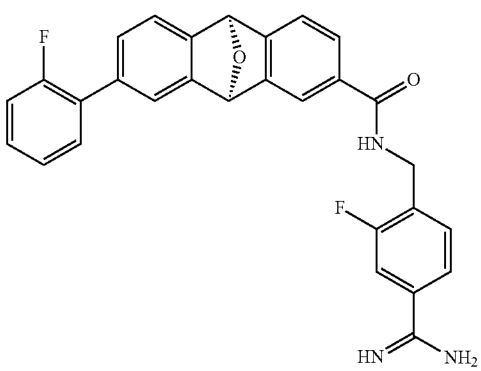 [SMILES: N=C(N)c1ccc(CNC(=O)c2ccc3c(c2)[C@@H]2O[C@H]3c3ccc(-c4ccccc4F)cc32)c(F)c1] | Single enantiomer | 9 | (1R,8S)-N-[(4-carbamimidoyl-2-fluorophenyl)-methyl]-12-(2-fluorophenyl)-15-oxatetracyclo[6.6.1.0$^2$,$^7$.0$^9$,$^{14}$]pentadeca-2,4,6,9,11,13-hexaene-4-carboxamide |
| 291 | 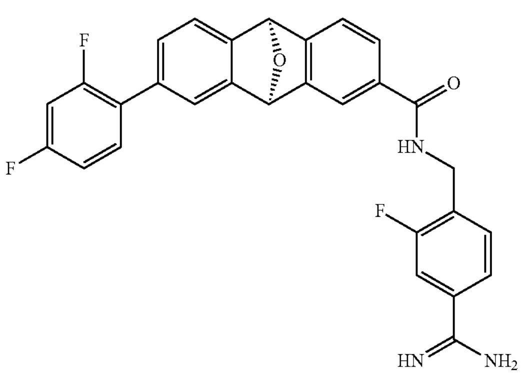 [SMILES: N=C(N)c1ccc(CNC(=O)c2ccc3c(c2)[C@@H]2O[C@H]3c3ccc(-c4ccc(F)cc4F)cc32)c(F)c1] | Single enantiomer | 9 | (1R,8S)-N-[(4-carbamimidoyl-2-fluorophenyl)-methyl]-12-(2,4-difluorophenyl)-15-oxatetracyclo[6.6.1.0$^2$,$^7$.0$^9$,$^{14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 292 | 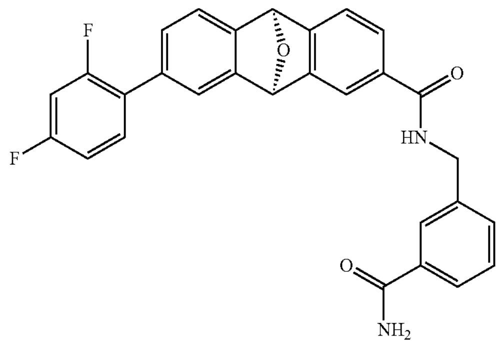 [SMILES: NC(=O)c1cccc(CNC(=O)c2ccc3c(c2)[C@@H]2O[C@H]3c3ccc(-c4ccc(F)cc4F)cc32)c1] | Single enantiomer | 4 | (1R,8S)-N-[(3-carbamoylphenyl)methyl]-12-(2,4-difluorophenyl)-15-oxatetracyclo[6.6.1.0$^{2,7}$.0$^{9,14}$]-pentadeca-2,4,6,9,11,13-hexaene-4-carboxamide |
| 293 | 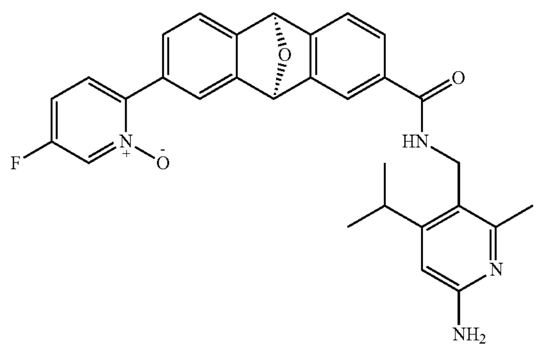 | Single enantiomer | | 2-[(1R,8S)-12-({[6-amino-2-methyl-4-(propan-2-yl)pyridin-3-yl]methyl}carbamoyl)-15-oxatetracyclo[6.6.1.0$^{2,7}$.0$^{9,14}$]pentadeca-2,4,6,9,11,13-hexaen-4-yl]-5-fluoropyridin-1-ium-1-olate |
| 294 | 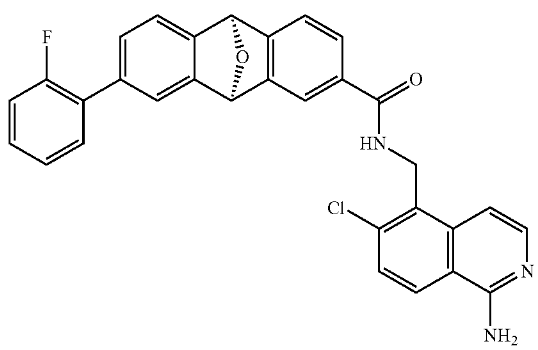 | Single enantiomer | 7.68 | (1R,8S)-N-[(1-amino-6-chloroisoquinolin-5-yl)methyl]-12-(2-fluorophenyl)-15-oxatetracyclo[6.6.1.0$^{2,7}$.0$^{9,14}$]pentadeca-2,4,6,9,11,13-hexaene-4-carboxamide |
| 295 | 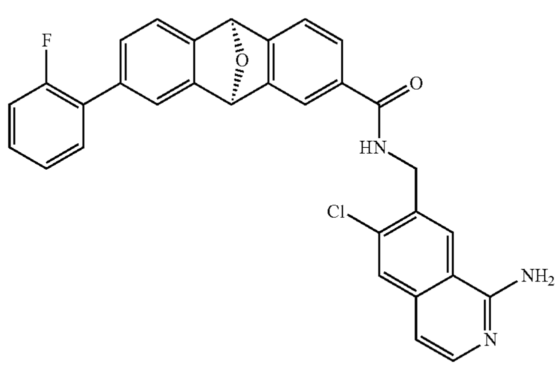 | Single enantiomer | 5 | (1R,8S)-N-[(1-amino-6-chloroisoquinolin-7-yl)methyl]-12-(2-fluorophenyl)-15-oxatetracyclo[6.6.1.0$^{2,7}$.0$^{9,14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 296 | 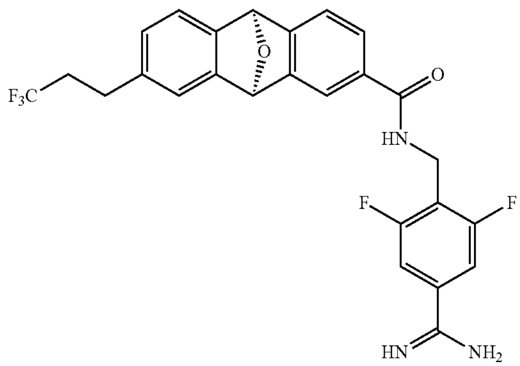 [SMILES: N=C(N)c1cc(F)c(CNC(=O)c2ccc3c(c2)[C@@H]2O[C@H]3c3ccc(CCC(F)(F)F)cc32)c(F)c1] | Single enantiomer | 9 | (1R,8S)-N-[(4-carbamimidoyl-2,6-difluorophenyl)methyl]-12-(3,3,3-trifluoropropyl)-15-oxatetracyclo[6.6.1.0$^2$,$^7$.0$^9$,$^{14}$]pentadeca-2,4,6,9,11,13-hexaene-4-carboxamide |
| 297 | 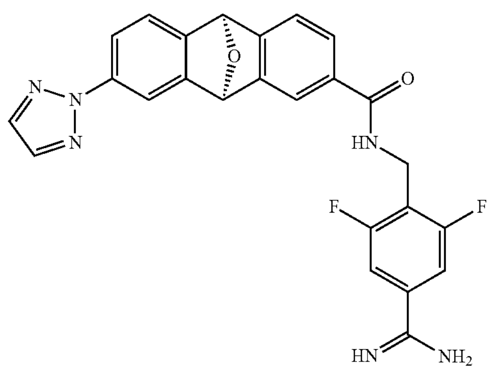 [SMILES: N=C(N)c1cc(F)c(CNC(=O)c2ccc3c(c2)[C@@H]2O[C@H]3c3ccc(-n4nccn4)cc32)c(F)c1] | Single enantiomer | 7.52 | (1S,8R)-N-[(4-carbamimidoyl-2,6-difluoro-phenyl)methyl]-12-(2H-1,2,3-triazol-2-yl)-15-oxatetracyclo[6.6.1.0$^2$,$^7$.0$^9$,$^{14}$]pentadeca-2,4,6,9,11,13-hexaene-4-carboxamide |
| 298 | 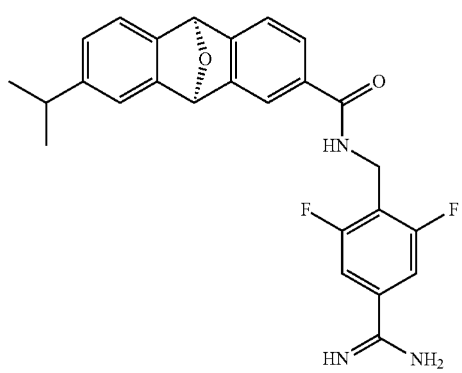 [SMILES: CC(C)c1ccc2c(c1)[C@H]1O[C@@H]2c2ccc(C(=O)NCc3c(F)cc(C(=N)N)cc3F)cc21] | Single enantiomer | 8.7 | (1R,8S)-N-[(4-carbamimidoyl-2,6-difluoro-phenyl)methyl]-12-(propan-2-yl)-15-oxatetracyclo[6.6.1.0$^2$,$^7$.0$^9$,$^{14}$]pentadeca-2,4,6,9,11,13-hexaene-4-carboxamide |
| 299 | 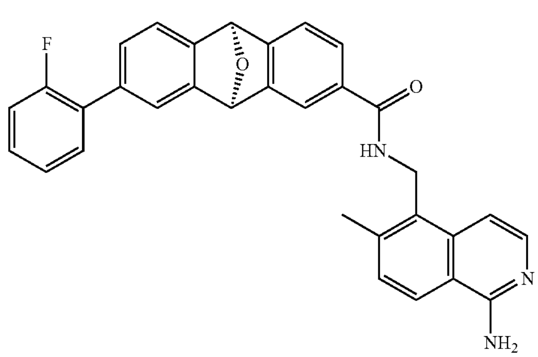 [SMILES: Cc1ccc2c(N)nccc2c1CNC(=O)c1ccc2c(c1)[C@@H]1O[C@H]2c2ccc(-c3ccccc3F)cc21] | Single enantiomer | 7.51 | (1R,8S)-N-[(1-amino-6-methylisoquinolin-5-yl)methyl]-12-(2-fluorophenyl)-5-oxatetracyclo[6.6.1.0$^2$,$^7$.0$^9$,$^{14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 300 | 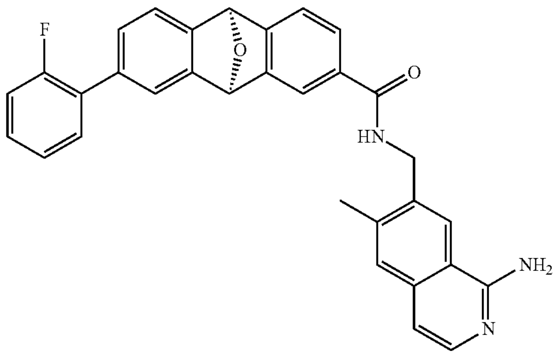 [SMILES: Cc1cc2ccnc(N)c2cc1CNC(=O)c1ccc2c(c1)[C@@H]1O[C@H]2c2ccc(-c3ccccc3F)cc21] | Single enantiomer | 5.5 | (1R,8S)-N-[(1-amino-6-methylisoquinolin-7-yl)methyl]-12-(2-fluorophenyl)-15-oxatetracyclo[6.6.1.0$^2$,$^7$.0$^9$,$^{14}$]pentadeca-2,4,6,9,11,13-hexaene-4-carboxamide |
| 301 | 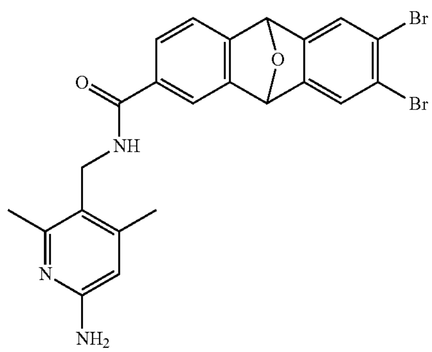 [SMILES: Cc1cc(N)nc(C)c1CNC(=O)c1ccc2c(c1)C1OC2c2cc(Br)c(Br)cc21] | Racemic mixture | 6.41 | N-[(6-amino-2,4-dimethylpyridin-3-yl)methyl]-11,12-dibromo-15-oxatetracyclo[6.6.1.0$^2$,$^7$.0$^9$,$^{14}$]-pentadeca-2,4,6,9,11,13-hexaene-4-carboxamide |
| 302 | 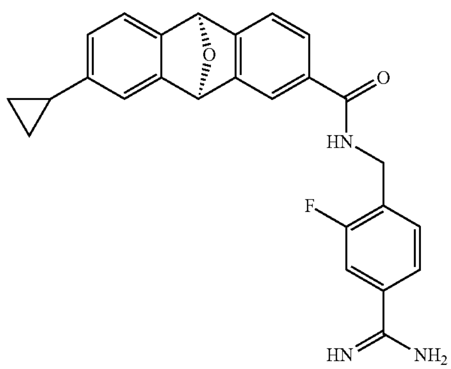 | Single enantiomer | 9 | (1R,8S)-N-[(4-carbamimidoyl-2-fluorophenyl)-methyl]-12-cyclopropyl-15-oxatetracyclo-[6.6.1.0$^2$,$^7$.0$^9$,$^{14}$]pentadeca-2,4,6,9,11,13-hexaene-4-carboxamide |
| 303 | 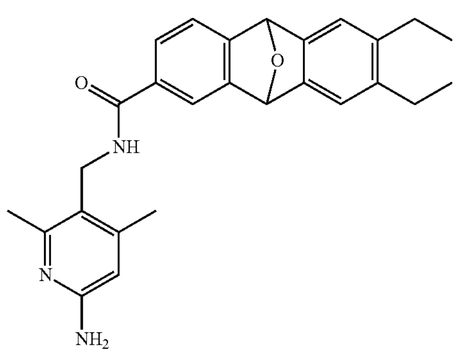 [SMILES: CCc1cc2c(cc1CC)C1OC2c2ccc(C(=O)NCc3c(C)cc(N)nc3C)cc21] | Racemic mixture | 6.68 | (±)-N-[(6-amino-2,4-dimethylpyridin-3-yl)methyl]-11,12-diethyl-15-oxatetracyclo[6.6.1.0$^2$,$^7$.0$^9$,$^{14}$]pentadeca-2,4,6,9(14),10,12-hexaene-4-carboxamide |

| Cpd. No | Structure | Compound Type | KLKB1 pIC$_{50}$ | IUPAC Name |
|---|---|---|---|---|
| 304 | 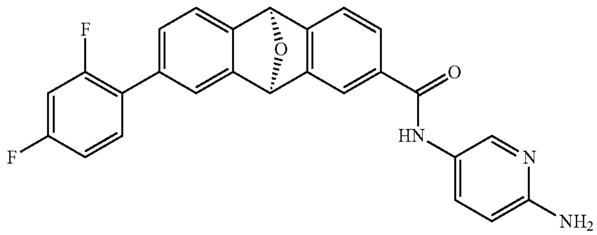 | Single enantiomer | 5 | (1R,8S)-N-(6-aminopyridin-3-yl)-12-(2,4-difluorophenyl)-15-oxatetracyclo[6.6.1.0$^2$,$^7$.0$^9$,$^{14}$]-pentadeca-2,4,6,9,11,13-hexaene-4-carboxamide |
| 305 | 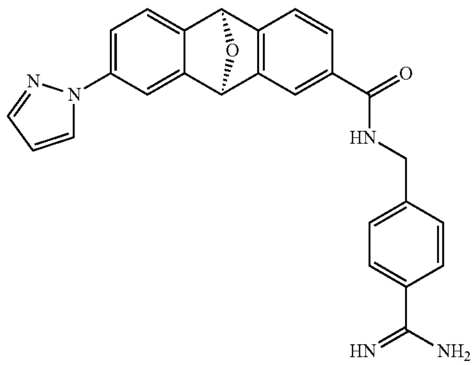 [SMILES: N=C(N)c1ccc(CNC(=O)c2ccc3c(c2)[C@@H]2O[C@H]3c3ccc(-n4cccn4)cc32)cc1] | Single enantiomer | 8.05 | (1S,8R)-N-[(4-carbamimidoylphenyl)methyl]-12-(1H-pyrazol-1-yl)-15-oxatetracyclo-[6.6.1.0$^2$,$^7$.0$^9$,$^{14}$]pentadeca-2,4,6,9,11,13-hexaene-4-carboxamide |
| 306 | 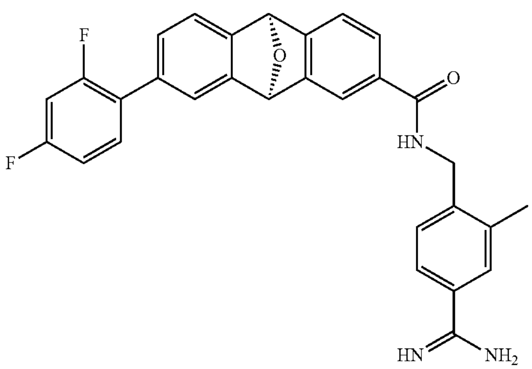 [SMILES: Cc1cc(C(=N)N)ccc1CNC(=O)c1ccc2c(c1)[C@@H]1O[C@H]2c2ccc(-c3ccc(F)cc3F)cc21] | Single enantiomer | 9 | (1R,8S)-N-[(4-carbamimidoyl-2-methylphenyl)-methyl]-12-(2,4-difluorophenyl)-15-oxatetracyclo[6.6.1.0$^2$,$^7$.0$^9$,$^{14}$]pentadeca-2,4,6,9,11,13-hexaene-4-carboxamide |
| 307 | 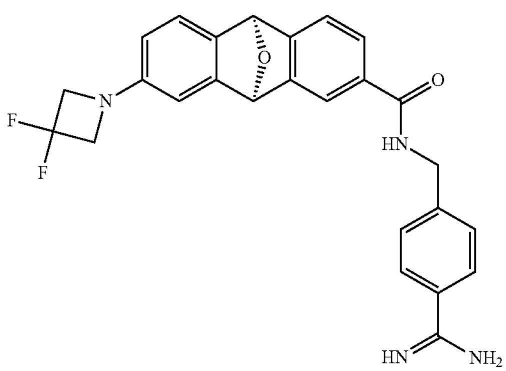 [SMILES: N=C(N)c1ccc(CNC(=O)c2ccc3c(c2)[C@@H]2O[C@H]3c3ccc(N4CC(F)(F)C4)cc32)cc1] | Single enantiomer | 9 | (1S,8R)-N-[(4-carbamimidoyl-phenyl)methyl]-12-(3,3-difluoroazetidin-l-yl)-15-oxatetracyclo-[6.6.1.0$^2$,$^7$.0$^9$,$^{14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 308 | 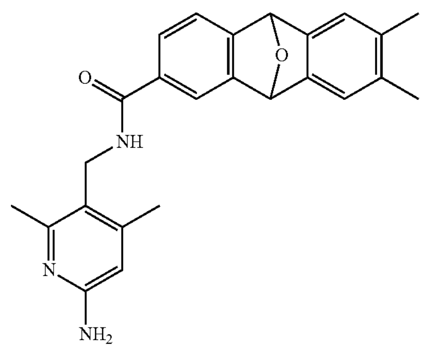 | Racemic mixture | 6.65 | (±)-N-[(6-amino-2,4-dimethylpyridin-3-yl)methyl]-11,12-dimethyl-15-oxatetracyclo[6.6.1.0$^2$,$^7$.0$^9$,$^{14}$]pentadeca-2,4,6,9(14),10,12-hexaene-4-carboxamide |
| 309 | 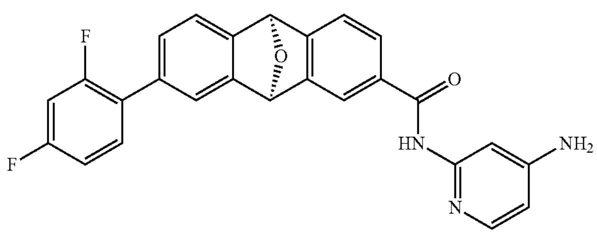 [SMILES: Nc1ccnc(NC(=O)c2ccc3c(c2)[C@@H]2O[C@H]3c3ccc(-c4ccc(F)cc4F)cc32)c1] | Single enantiomer | 4 | (1R,8S)-N-(4-aminopyridin-2-yl)-12-(2,4-difluorophenyl)-15-oxatetracyclo[6.6.1.0$^2$,$^7$.0$^9$,$^{14}$]-pentadeca-2,4,6,9,11,13-hexaene-4-carboxamide |
| 310 | | Racemic mixture | 7.7 | (±)-N-[(6-amino-2,4-dimethylpyridin-3-yl)methyl]-12-(2,4-difluorophenyl)-11-methyl-15-oxatetracyclo[6.6.1.0$^2$,$^7$.0$^9$,$^{14}$]pentadeca-2,4,6,9(14),10,12-hexaene-4-carboxamide and (±)-N-[(6-amino-2,4-dimethylpyridin-3-yl)methyl]-11-(2,4-difluorophenyl)-12-methyl-15-oxatetracyclo[6.6.1.0$^2$,$^7$.0$^9$,$^{14}$]pentadeca-2,4,6,9(14),10,12-hexaene-4-carboxamide |

TABLE 1-continued

| Cpd. No | Structure | Compound Type | KLKB1 pIC$_{50}$ | IUPAC Name |
|---|---|---|---|---|
| 311 | 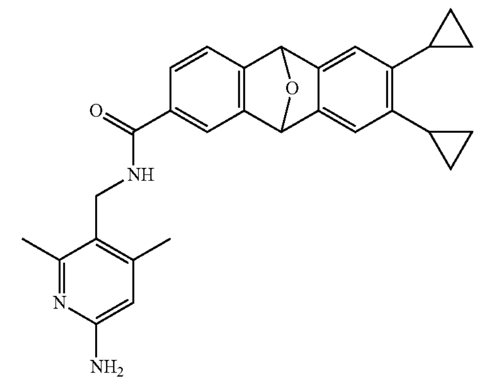 [SMILES: Cc1cc(N)nc(C)c1CNC(=O)c1ccc2c(c1)C1OC2c2cc(C3CC3)c(C3CC3)cc21] | Racemic mixture | 7.49 | (±)-N-[(6-amino-2,4-dimethylpyridin-3-yl)-methyl]-11,12-dicyclopropyl-15-oxatetracyclo[6.6.1.0$^2$,$^7$.0$^9$,$^{14}$]pentadeca-2,4,6,9,11,13-hexaene-4-carboxamide |
| 312 | 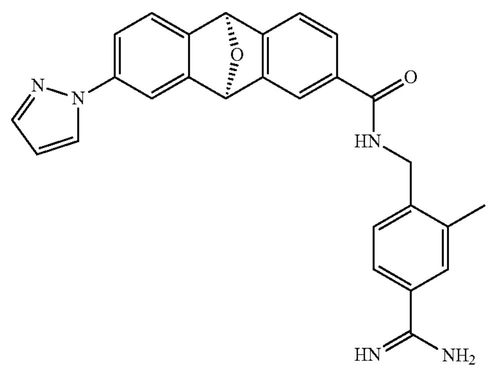 [SMILES: Cc1cc(C(=N)N)ccc1CNC(=O)c1ccc2c(c1)[C@@H]1O[C@H]2c2ccc(-n3cccn3)cc21] | Single enantiomer | 9 | (1S,8R)-N-[(4-carbamimidoyl-2-methylphenyl)-methyl]-12-(1H-pyrazol-1-yl)-15-oxatetracyclo[6.6.1.0$^2$,$^7$.0$^9$,$^{14}$]pentadeca-2,4,6,9,11,13-hexaene-4-carboxamide |
| 313 | 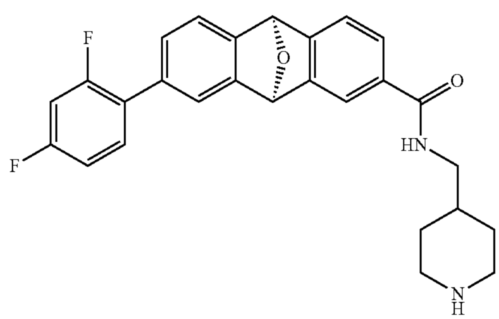 [SMILES: O=C(NCC1CCNCC1)c1ccc2c(c1)[C@@H]1O[C@H]2c2ccc(-c3ccc(F)cc3F)cc21] | Single enantiomer | 4.32 | (1R,8S)-12-(2,4-difluorophenyl)-N-[(piperidin-4-yl)methyl]-15-oxatetracyclo[6.6.1.0$^2$,$^7$.0$^9$,$^{14}$]-pentadeca-2,4,6,9,11,13-hexaene-4-carboxamide |
| 314 | 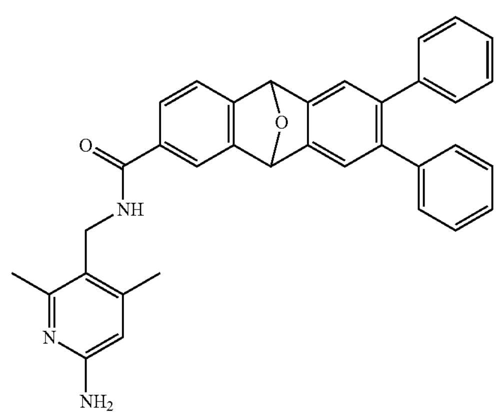 [SMILES: Cc1cc(N)nc(C)c1CNC(=O)c1ccc2c(c1)C1OC2c2cc(-c3ccccc3)c(-c3ccccc3)cc21] | Racemic mixture | 6.06 | (±)-N-[(6-amino-2,4-dimethylpyridin-3-yl)-methyl]-11,12-diphenyl-15-oxatetracyclo-[6.6.1.0$^2$,$^7$.0$^9$,$^{14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 315 | 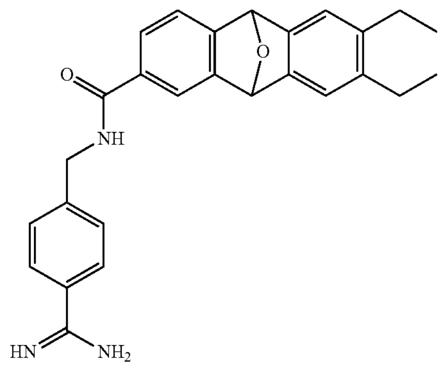 [SMILES: CCc1cc2c(cc1CC)C1OC2c2ccc(C(=O)NCc3ccc(C(=N)N)cc3)cc21] | Racemic mixture | 8.74 | (±)-N-[(4-carbamimidoylphenyl)methyl]-11,12-diethyl-15-oxatetracyclo[6.6.1.0$^{2,7}$.0$^{9,14}$]-pentadeca-2,4,6,9(14),10,12-hexaene-4-carboxamide |
| 316 | 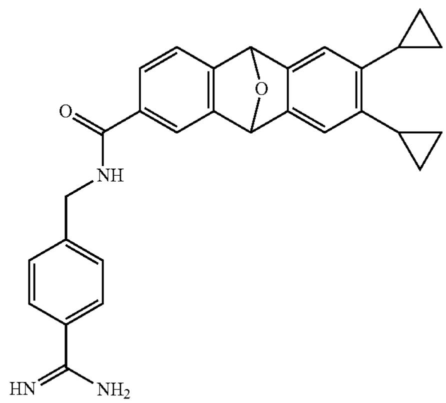 [SMILES: N=C(N)c1ccc(CNC(=O)c2ccc3c(c2)C2OC3c3cc(C4CC4)c(C4CC4)cc32)cc1] | Racemic mixture | 8.31 | (±)-N-[(4-carbamimidoylphenyl)methyl]-11,12-dicyclopropyl-15-oxatetracyclo[6.6.1.0$^{2,7}$.0$^{9,14}$]-pentadeca-2,4,6,9,11,13-hexaene-4-carboxamide |
| 317 | 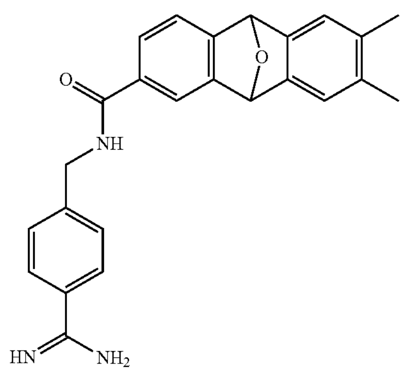 [SMILES: Cc1cc2c(cc1C)C1OC2c2ccc(C(=O)NCc3ccc(C(=N)N)cc3)cc21] | Racemic mixture | 7.54 | (±)-N-[(4-carbamimidoylphenyl)methyl]-11,12-dimethyl-15-oxatetracyclo[6.6.1.0$^{2,7}$.0$^{9,14}$]-pentadeca-2,4,6,9(14),10,12-hexaene-4-carboxamide |
| 318 | 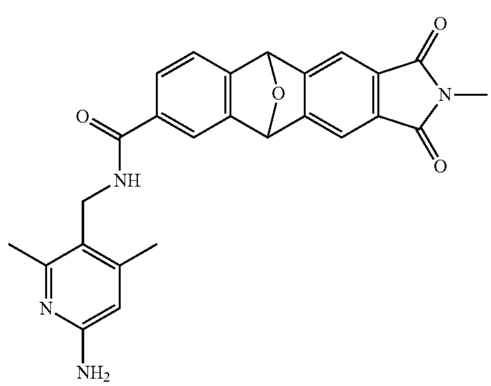 | Racemic mixture | 7.76 | (±)-N-[(6-amino-2,4-dimethylpyridin-3-yl)methyl]-6-methyl-5,7-dioxo-18-oxa-6-azapenta-cyclo[9.6.1.0$^{2,10}$.0$^{4,8}$.0$^{12,17}$]octadeca-2(10),3,8,12,14,16-hexaene-14-carboxamide |

TABLE 1-continued

| Cpd. No | Structure | Compound Type | KLKB1 pIC$_{50}$ | IUPAC Name |
|---|---|---|---|---|
| 319 | 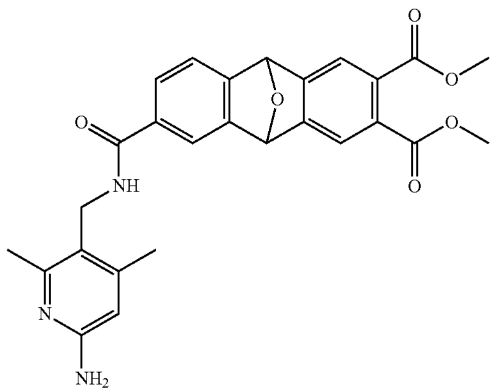 | Racemic mixture | 5.61 | (±)-4,5-dimethyl 11-{[(6-amino-2,4-dimethyl-pyridin-3-yl)methyl]carbamoyl}-15-oxatetracyclo[6.6.1.0$^{2,7}$.0$^{9,14}$] pentadeca-2(7),3,5,9,11,13-hexaene-4,5-dicarboxylate |
| 320 | 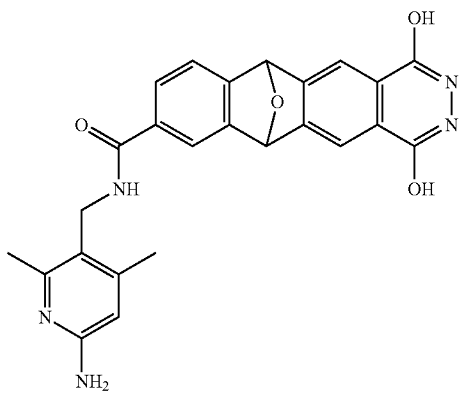 [SMILES: Cc1cc(N)nc(C)c1CNC(=O)c1ccc2c(c1)C1OC2c2cc3c(O)nnc(O)c3cc21] | Racemic mixture | 4.99 | (±)-N-[(6-amino-2,4-dimethylpyridin-3-yl)methyl]-5,8-dihydroxy-19-oxa-6,7-diazapenta-cyclo[10.6.1.0$^{2,11}$.0$^{4,9}$.0$^{13,18}$] nonadeca-2(11),3,5,7,9,13,15,17-octaene-15-carboxamide |
| 321 | | Racemic mixture | 8.09 | (±)-N-[(6-amino-2,4-dimethylpyridin-3-yl)methyl]-12-(2,4-difluorophenyl)-11-ethyl-15-oxatetracyclo[6.6.1.0$^{2,7}$.0$^{9,14}$] pentadeca-2,4,6,9(14),10,12-hexaene-4-carboxamide and (±)-N-[(6-amino-2,4-dimethylpyridin-3-yl)methyl]-11-(2,4-difluorophenyl)-12-ethyl-15-oxatetracyclo[6.6.1.0$^{2,7}$.0$^{9,14}$] pentadeca-2,4,6,9(14),10,12-hexaene-4-carboxamide |

TABLE 1-continued

| Cpd. No | Structure | Compound Type | KLKB1 pIC$_{50}$ | IUPAC Name |
|---|---|---|---|---|
| 322 | 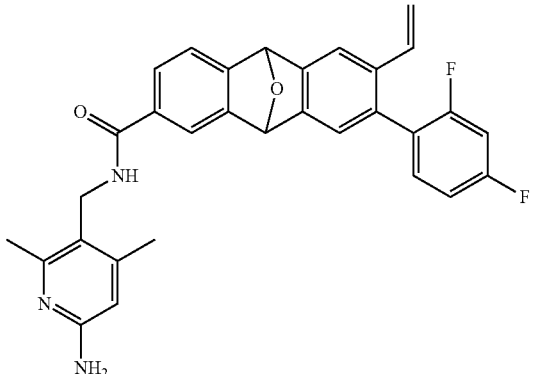 | Racemic mixture | 8.57 | (±)-N-[(6-amino-2,4-dimethylpyridin-3-yl)methyl]-12-(2,4-difluorophenyl)-11-ethenyl-15-oxatetracyclo[6.6.1.0$^2$,$^7$.0$^9$,$^{14}$]pentadeca-2,4,6,9,11,13-hexaene-4-carboxamide and (±)-N-[(6-amino-2,4-dimethylpyridin-3-yl)methyl]-11-(2,4-difluorophenyl)-12-ethenyl-15-oxatetracyclo[6.6.1.0$^2$,$^7$.0$^9$,$^{14}$]pentadeca-2,4,6,9,11,13-hexaene-4-carboxamide |
| 323 | 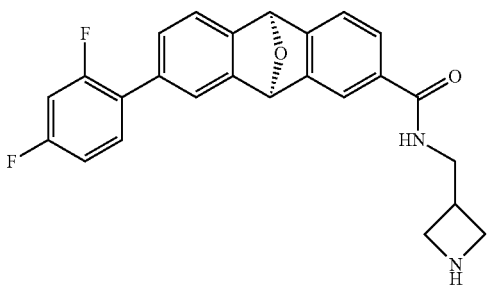 [SMILES: O=C(NCC1CNC1)c1ccc2c(c1)[C@@H]1O[C@H]2c2ccc(-c3ccc(F)cc3F)cc21] | Single enantiomer | 4 | (1R,8S)-N-[(azetidin-3-yl)methyl]-12-(2,4-difluorophenyl)-15-oxatetracyclo[6.6.1.0$^2$,$^7$.0$^9$,$^{14}$]-pentadeca-2,4,6,9,11,13-hexaene-4-carboxamide |
| 324 | 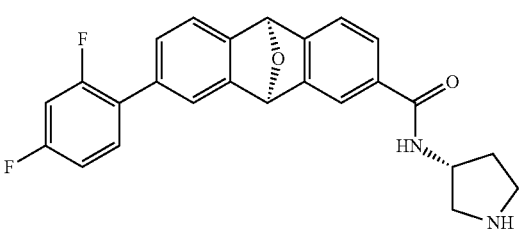 [SMILES: O=C(N[C@@H]1CCNC1)c1ccc2c(c1)[C@@H]1O[C@H]2c2ccc(-c3ccc(F)cc3F)cc21] | Single enantiomer | 4 | (1R,8S)-12-(2,4-difluorophenyl)-N-[(3R)-pyrrolidin-3-yl]-15-oxatetracyclo[6.6.1.0$^2$,$^7$.0$^9$,$^{14}$]-pentadeca-2,4,6,9,11,13-hexaene-4-carboxamide |
| 325 | 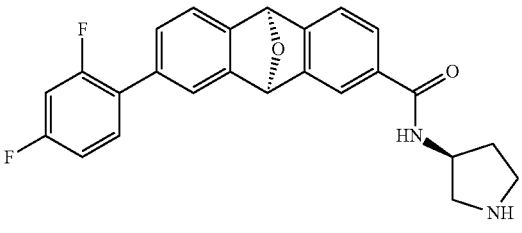 [SMILES: O=C(N[C@H]1CCNC1)c1ccc2c(c1)[C@@H]1O[C@H]2c2ccc(-c3ccc(F)cc3F)cc21] | Single enantiomer | 4.37 | (1R,8S)-12-(2,4-difluorophenyl)-N-[(3S)-pyrrolidin-3-yl]-15-oxatetracyclo[6.6.1.0$^2$,$^7$.0$^9$,$^{14}$]-pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 326 | 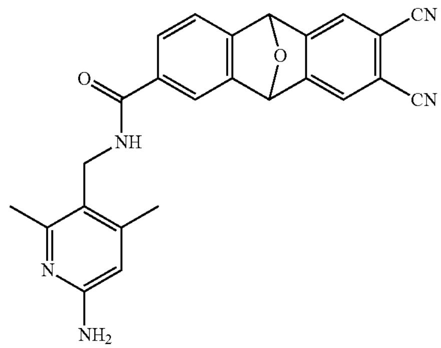 [SMILES: Cc1cc(N)nc(C)c1CNC(=O)c1ccc2c(c1)C1OC2c2cc(C#N)c(C#N)cc21] | Racemic mixture | 6.07 | (±)-N-[(6-amino-2,4-dimethylpyridin-3-yl)methyl]-11,12-dicyano-15-oxatetracyclo-[6.6.1.0$^{2,7}$.0$^{9,14}$]pentadeca-2,4,6,9,11,13-hexaene-4-carboxamide |
| 327 | 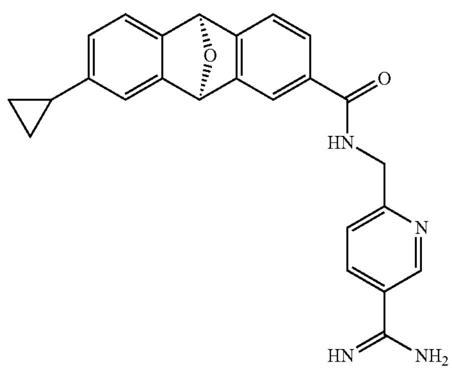 | Single enantiomer | 6.37 | (1R,8S)-N-[(5-carbamimidoyl-pyridin-2-yl)methyl]-12-cyclopropyl-15-oxatetracyclo-[6.6.1.0$^{2,7}$.0$^{9,14}$]pentadeca-2,4,6,9,11,13-hexaene-4-carboxamide |
| 328 | 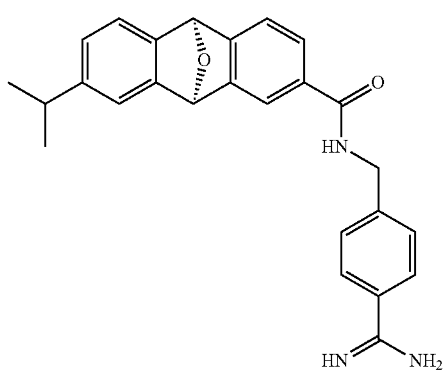 [SMILES: CC(C)c1ccc2c(c1)[C@H]1O[C@@H]2c2ccc(C(=O)NCc3ccc(C(=N)N)cc3)cc21] | Single enantiomer | 8.15 | (1R,8S)-N-[(4-carbamimidoyl-phenyl)methyl]-12-(propan-2-yl)-15-oxatetracyclo[6.6.1.0$^{2,7}$.0$^{9,14}$]-pentadeca-2,4,6,9,11,13-hexaene-4-carboxamide |
| 329 | 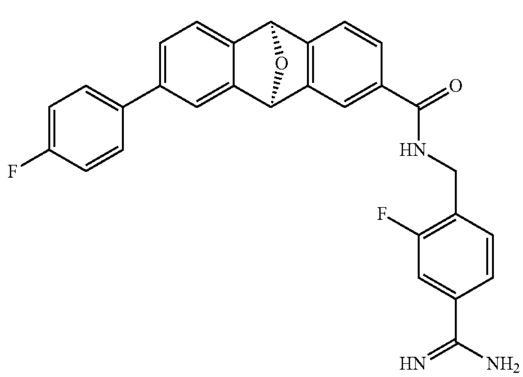 [SMILES: N=C(N)c1ccc(CNC(=O)c2ccc3c(c2)[C@@H]2O[C@H]3c3ccc(-c4ccc(F)cc4)cc32)c(F)c1] | Single enantiomer | 9 | (1R,8S)-N-[(4-carbamimidoyl-2-fluorophenyl)-methyl]-12-(4-fluorophenyl)-15-oxatetracyclo[6.6.1.0$^{2,7}$.0$^{9,14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 330 | 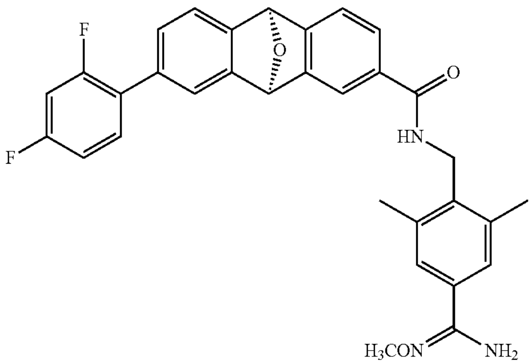 | Single enantiomer | | (1R,8S)-12-(2,4-difluorophenyl)-N-{[4-(N'-methoxycarbamimidoyl)-2,6-dimethylphenyl]-methyl}-15-oxatetracyclo[6.6.1.0$^{2,7}$.0$^{9,14}$]-pentadeca-2,4,6,9,11,13-hexaene-4-carboxamide |
| 331 | 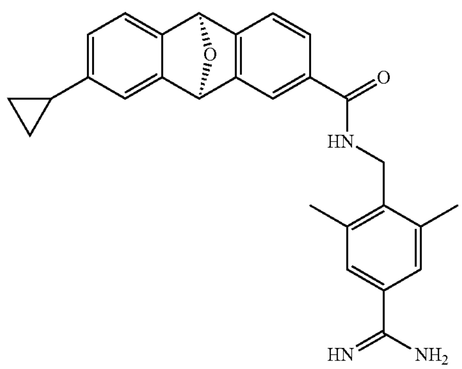 [SMILES: Cc1cc(C(=N)N)cc(C)c1CNC(=O)c1ccc2c(c1)[C@@H]1O[C@H]2c2ccc(C3CC3)cc21] | Single enantiomer | 9 | (1R,8S)-N-[(4-carbamimidoyl-2,6-dimethyl-phenyl)methyl]-12-cyclopropyl-15-oxatetracyclo[6.6.1.0$^{2,7}$.0$^{9,14}$]pentadeca-2,4,6,9,11,13-hexaene-4-carboxamide |
| 332 | 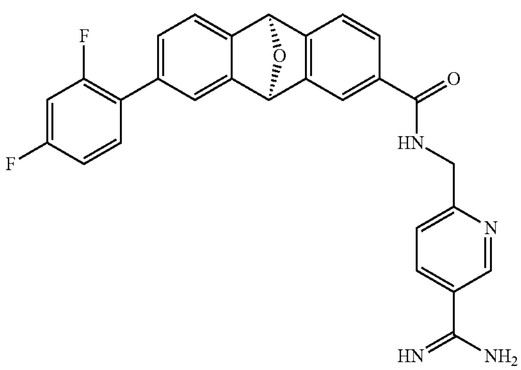 | Single enantiomer | 7.2 | (1R,8S)-N-[(5-carbamimidoyl-pyridin-2-yl)-methyl]-12-(2,4-difluorophenyl)-15-oxatetracyclo[6.6.1.0$^{2,7}$.0$^{9,14}$]pentadeca-2,4,6,9,11,13-hexaene-4-carboxamide |
| 333 | 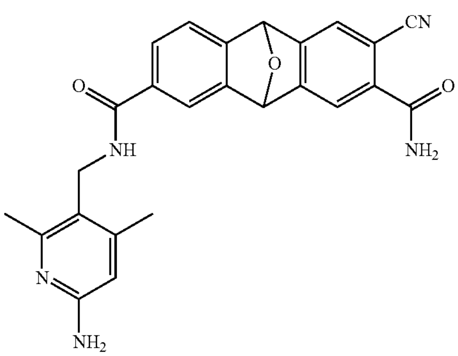 | Racemic mixture | 5.64 | (±)-N4-[(6-amino-2,4-dimethylpyridin-3-yl)methyl]-11-cyano-15-oxatetracyclo-[6.6.1.0$^{2,7}$.0$^{9,14}$]pentadeca-2,4,6,9,11,13-hexaene-4,12-dicarboxamide and (±)-N4-[(6-amino-2,4-dimethylpyridin-3-yl)methyl]-12-cyano-15-oxatetracyclo[6.6.1.0$^{2,7}$.0$^{9,14}$]pentadeca-2,4,6,9,11,13-hexaene-4,11-dicarboxamide |

TABLE 1-continued

| Cpd. No | Structure | Compound Type | KLKB1 pIC$_{50}$ | IUPAC Name |
|---|---|---|---|---|
| | 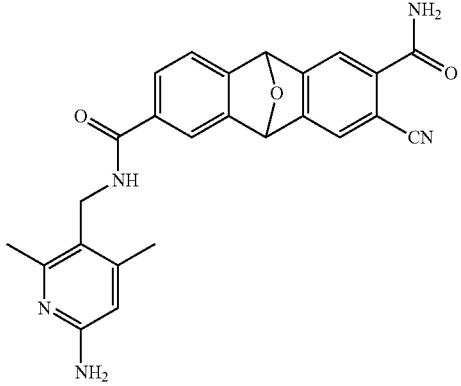 [SMILES: Cc1cc(N)nc(C)c1CNC(=O)c1ccc2c(c1)C1OC2c2cc(C(N)=O)c(C#N)cc21] | | | |
| 334 | 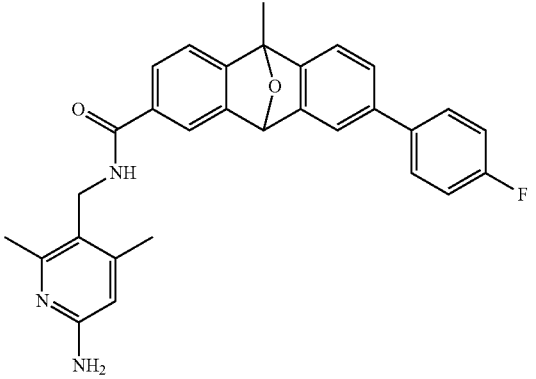 | Racemic mixture | 5.6 | (±)-N-[(6-amino-2,4-dimethylpyridin-3-yl)methyl]-12-(4-fluorophenyl)-8-methyl-15-oxatetracyclo[6.6.1.0$^2$,$^7$.0$^9$,$^{14}$]pentadeca-2,4,6,9,11,13-hexaene-4-carboxamide (±)-N-[(6-amino-2,4-dimethylpyridin-3-yl)methyl]-11-(4-fluorophenyl)-8-methyl-15-oxatetracyclo[6.6.1.0$^2$,$^7$.0$^9$,$^{14}$]pentadeca-2,4,6,9,11,13-hexaene-4-carboxamide |
| | 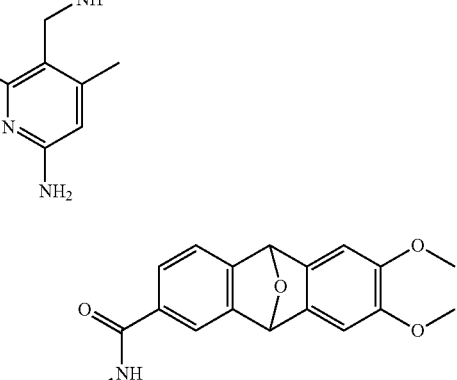 | | | |
| 335 | 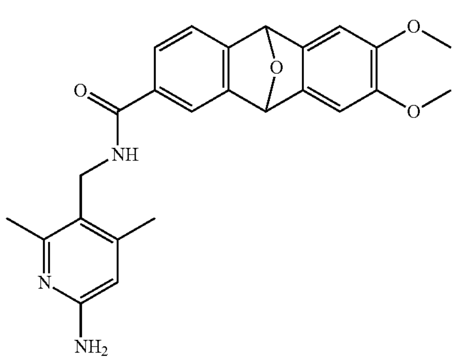 | Racemic mixture | 5.79 | (±)-N-[(6-amino-2,4-dimethylpyridin-3-yl)methyl]-11,12-dimethoxy-15-oxatetracyclo[6.6.1.0$^2$,$^7$.0$^9$,$^{14}$]pentadeca-2,4,6,9(14),10,12-hexaene-4-carboxamide |

TABLE 1-continued

| Cpd. No | Structure | Compound Type | KLKB1 pIC$_{50}$ | IUPAC Name |
|---|---|---|---|---|
| 336 | 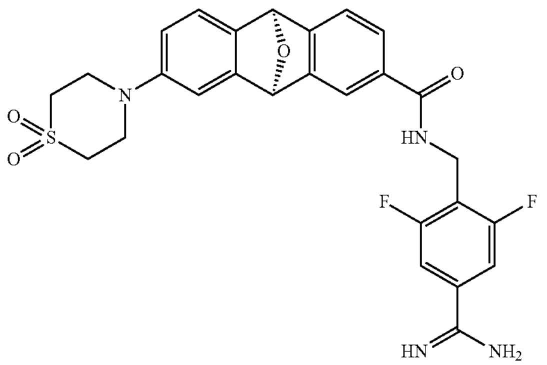 [SMILES: N=C(N)c1cc(F)c(CNC(=O)c2ccc3c(c2)[C@@H]2O[C@H]3c3ccc(N4CCS(=O)(=O)CC4)cc32)c(F)c1] | Single enantiomer | 8.3 | (1S,8R)-N-[(4-carbamimidoyl-2,6-difluoro-phenyl)methyl]-12-(1,1-dioxo-1λ$^6$-thiomorpholin-4-yl)-15-oxatetracyclo-[6.6.1.0$^2$,$^7$.0$^9$,$^{14}$]pentadeca-2,4,6,9,11,13-hexaene-4-carboxamide |
| 337 | 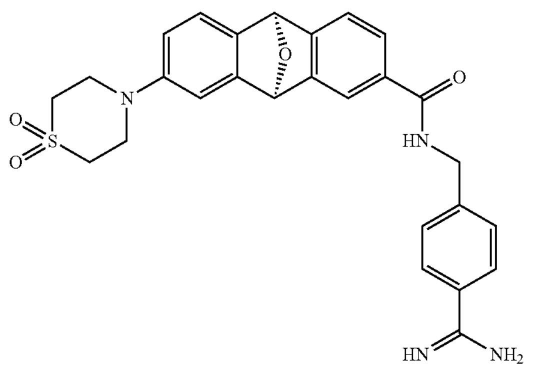 [SMILES: N=C(N)c1ccc(CNC(=O)c2ccc3c(c2)[C@@H]2O[C@H]3c3ccc(N4CCS(=O)(=O)CC4)cc32)cc1] | Single enantiomer | 7.57 | (1S,8R)-N-[(4-carbamimidoyl-phenyl)methyl]-12-(1,1-dioxo-1λ$^6$-thiomorpholin-4-yl)-15-oxatetracyclo[6.6.1.0$^2$,$^7$.0$^9$,$^{14}$]pentadeca-2,4,6,9,11,13-hexaene-4-carboxamide |
| 338 | 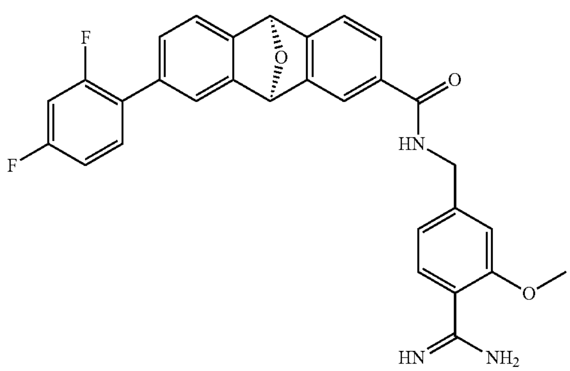 [SMILES: COc1cc(CNC(=O)c2ccc3c(c2)[C@@H]2O[C@H]3c3ccc(-c4ccc(F)cc4F)cc32)ccc1C(=N)N] | Single enantiomer | 8.23 | (1R,8S)-N-[(4-carbamimidoyl-3-methoxyphenyl)-methyl]-12-(2,4-difluorophenyl)-15-oxatetracyclo[6.6.1.0$^2$,$^7$.0$^9$,$^{14}$]pentadeca-2,4,6,9,11,13-hexaene-4-carboxamide |
| 339 | 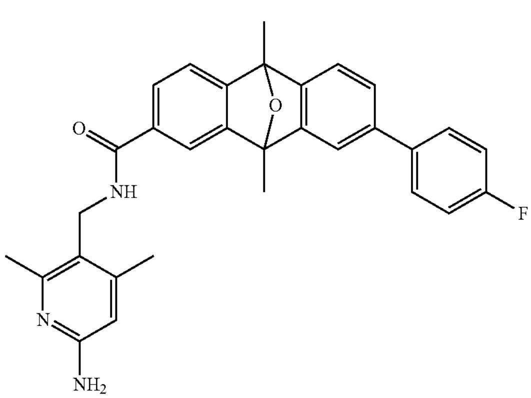 | Racemic mixture | 4 | (±)-N-[(6-amino-2,4-dimethylpyridin-3-yl)methyl]-12-(4-fluorophenyl)-1,8-dimethyl-15-oxatetracyclo[6.6.1.0$^2$,$^7$.0$^9$,$^{14}$]pentadeca-2,4,6,9,11,13-hexaene-4-carboxamide and (±)-N-[(6-amino-2,4-dimethylpyridin-3-yl)methyl]-11-(4-fluorophenyl)-1,8-dimethyl-15-oxatetracyclo[6.6.1.0$^2$,$^7$.0$^9$,$^{14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 340 | | Racemic mixture + | 6.64 | (±)-N-[(6-amino-2,4-dimethylpyridin-3-yl)methyl]-12-(4-fluorophenyl)-10-methyl-15-oxatetracyclo[6.6.1.0$^2$,$^7$.0$^9$,$^{14}$]pentadeca-2,4,6,9(14),10,12-hexaene-4-carboxamide and (±)-N-[(6-amino-2,4-dimethylpyridin-3-yl)methyl]-11-(4-fluorophenyl)-13-methyl-15-oxatetracyclo[6.6.1.0$^2$,$^7$.0$^9$,$^{14}$]pentadeca-2,4,6,9(14),10,12-hexaene-4-carboxamide |

TABLE 1-continued

| Cpd. No | Structure | Compound Type | KLKB1 pIC$_{50}$ | IUPAC Name |
|---|---|---|---|---|
| 341 | | Racemic mixture | 8.15 | (±)-N-[(4-carbamimidoyl-phenyl)methyl]-12-(4-fluorophenyl)-10-methyl-15-oxatetracyclo-[6.6.1.0$^{2,7}$.0$^{9,14}$]pentadeca-2,4,6,9(14),10,12-hexaene-4-carboxamide and (±)-N-[(4-carbamimidoyl-phenyl)methyl]-11-(4-fluorophenyl)-13-methyl-15-oxatetracyclo-[6.6.1.0$^{2,7}$.0$^{9,14}$]pentadeca-2,4,6,9(14),10,12-hexaene-4-carboxamide |
| 342 | 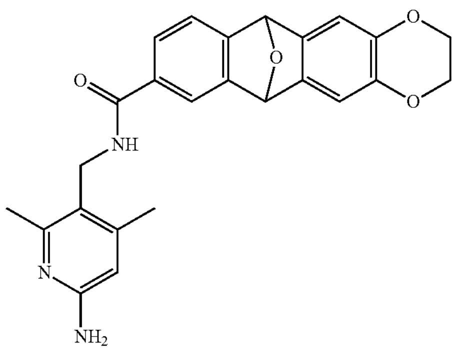 [SMILES: Cc1cc(N)nc(C)c1CNC(=O)c1ccc2c(c1)C1OC2c2cc3c(cc21)OCCO3] | Racemic mixture | 6.26 | (±)-N-[(6-amino-2,4-dimethylpyridin-3-yl)methyl]-5,8,19-trioxapenta-cyclo-[10.6.1.0$^{2,11}$.0$^{4,9}$.0$^{13,18}$]nonadeca-2,4(9),10,13,15,17-hexaene-15-carboxamide |
| 343 | 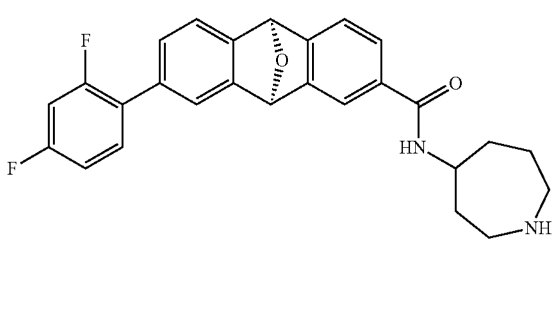 [SMILES: O=C(NC1CCCNCC1)c1ccc2c(c1)[C@@H]1O[C@H]2c2ccc(-c3ccc(F)cc3F)cc21] | Single enantiomer | 4 | (1R,8S)-N-(azepan-4-yl)-12-(2,4-difluorophenyl)-15-oxatetracyclo[6.6.1.0$^{2,7}$.0$^{9,14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 344 | 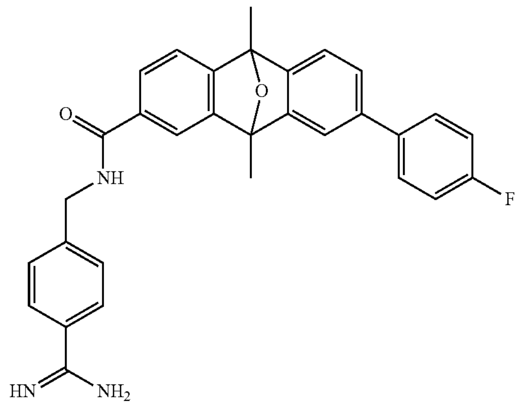 [SMILES: CC12OC(C)(c3cc(C(=O)NCc4ccc(C(=N)N)cc4)ccc31)c1cc(-c3ccc(F)cc3)ccc12] | Racemic mixture | 6.37 | N-[(4-carbamimidoylphenyl)methyl]-12-(4-fluorophenyl)-1,8-dimethyl-15-oxatetracyclo-[6.6.1.0$^{2,7}$.0$^{9,14}$]pentadeca-2,4,6,9,11,13-hexaene-4-carboxamide |
| 345 | 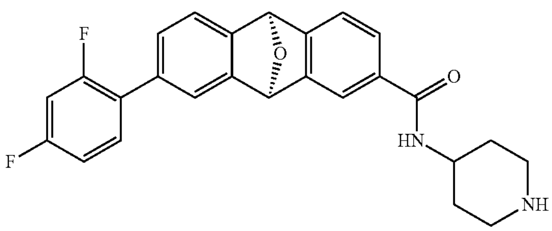 [SMILES: O=C(NC1CCNCC1)c1ccc2c(c1)[C@@H]1O[C@H]2c2ccc(-c3ccc(F)cc3F)cc21] | Single enantiomer | 4.47 | (1R,8S)-12-(2,4-difluorophenyl)-N-(piperidin-4-yl)-15-oxatetracyclo[6.6.1.0$^{2,7}$.0$^{9,14}$]pentadeca-2,4,6,9,11,13-hexaene-4-carboxamide |
| 346 | | Racemic mixture | 7.26 | (±)-N-[(4-carbamimidoylphenyl)methyl]-12-(4-fluorophenyl)-8-methyl-15-oxatetracyclo-[6.6.1.0$^{2,7}$.0$^{9,14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 347 | 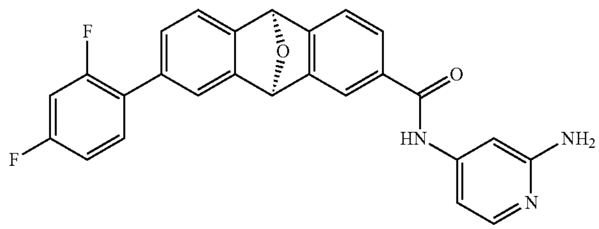 [SMILES: Nc1cc(NC(=O)c2ccc3c(c2)[C@@H]2O[C@H]3c3ccc(-c4ccc(F)cc4F)cc32)ccn1] | Single enantiomer | 4 | (1R,8S)-N-(2-aminopyridin-4-yl)-12-(2,4-difluorophenyl)-15-oxatetracyclo[6.6.1.0$^{2,7}$.0$^{9,14}$]-pentadeca-2,4,6,9,11,13-hexaene-4-carboxamide |
| 348 | 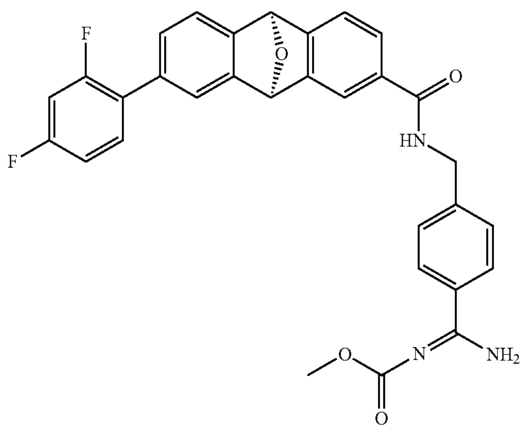 [SMILES: COC(=O)N=C(N)c1ccc(CNC(=O)c2ccc3c(c2)[C@@H]2O[C@H]3c3ccc(-c4ccc(F)cc4F)cc32)cc1] | Single enantiomer | | methyl N-[1-amino[4-({[(1R,8S)-12-(2,4-difluorophenyl)-15-oxatetracyclo[6.6.1.0$^{2,7}$.0$^{9,14}$]-pentadeca-2,4,6,9,11,13-hexaen-4-yl]formamido}-methyl)phenyl]methylidene]carbamate |
| 349 | 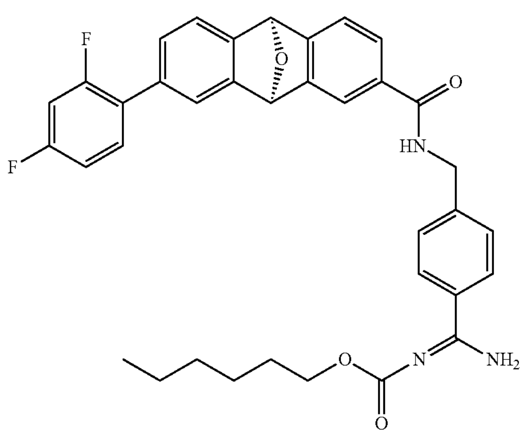 [SMILES: CCCCCCOC(=O)N=C(N)c1ccc(CNC(=O)c2ccc3c(c2)[C@@H]2O[C@H]3c3ccc(-c4ccc(F)cc4F)cc32)cc1] | Single enantiomer | | hexyl N-[1-amino[4-({[(1R,8S)-12-(2,4-difluorophenyl)-15-oxatetracyclo[6.6.1.0$^{2,7}$.0$^{9,14}$]-pentadeca-2,4,6,9,11,13-hexaen-4-yl]formamido}-methyl)phenyl]methylidene]carbamate |
| 350 | 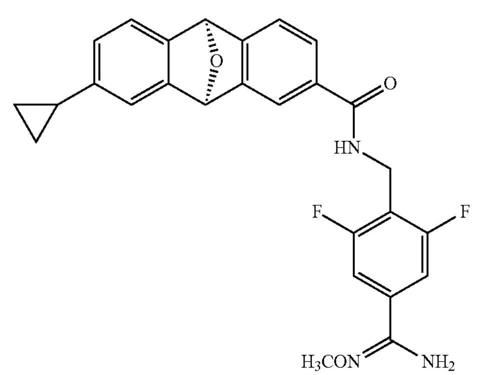 | Single enantiomer | | (1R,8S)-12-cyclopropyl-N-({2,6-difluoro-4-[N'-methoxycarbamimidoyl]phenyl}methyl)-15-oxatetracyclo[6.6.1.0$^{2,7}$.0$^{9,14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 351 | 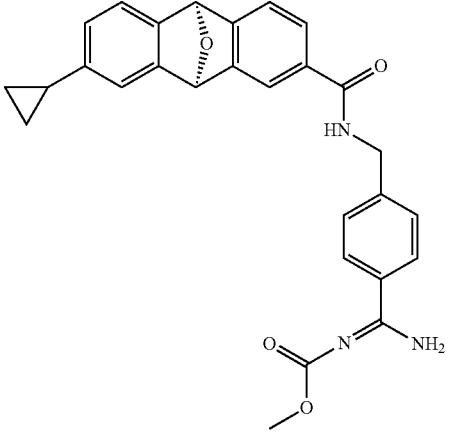 [SMILES: COC(=O)N=C(N)c1ccc(CNC(=O)c2ccc3c(c2)[C@@H]2O[C@H]3c3ccc(C4CC4)cc32)cc1] | Single enantiomer | | methyl N-[(1)-amino[4-({[(1R,8S)-12-cyclopropyl-15-oxatetracyclo[6.6.1.0$^{2,7}$.0$^{9,14}$]-pentadeca-2,4,6,9,11,13-hexaen-4-yl]formamido}methyl)phenyl]methylidene]carbamate |
| 352 | 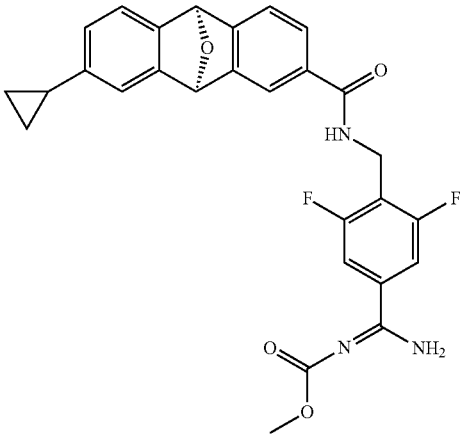 [SMILES: COC(=O)N=C(N)c1cc(F)c(CNC(=O)c2ccc3c(c2)[C@@H]2O[C@H]3c3ccc(C4CC4)cc32)c(F)c1] | Single enantiomer | | methyl N-[1-amino[4-({[(1R,8S)-12-cyclopropyl-15-oxatetracyclo[6.6.1.0$^{2,7}$.0$^{9,14}$]-pentadeca-2,4,6,9,11,13-hexaen-4-yl]formamido}-methyl)-3,5-difluorophenyl]methylidene]-carbamate |
| 353 | 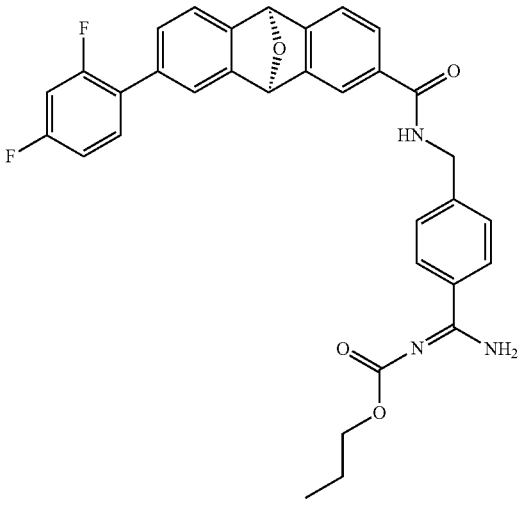 [SMILES: CCCOC(=O)N=C(N)c1ccc(CNC(=O)c2ccc3c(c2)[C@@H]2O[C@H]3c3ccc(-c4ccc(F)cc4F)cc32)cc1] | Single enantiomer | | propyl N-[1-amino[4-({[(1R,8S)-12-(2,4-difluorophenyl)-15-oxatetracyclo[6.6.1.0$^{2,7}$.0$^{9,14}$]-pentadeca-2,4,6,9,11,13-hexaen-4-yl]formamido}-methyl)phenyl]methylidene]carbamate |

TABLE 1-continued

| Cpd. No | Structure | Compound Type | KLKB1 pIC$_{50}$ | IUPAC Name |
|---|---|---|---|---|
| 354 | 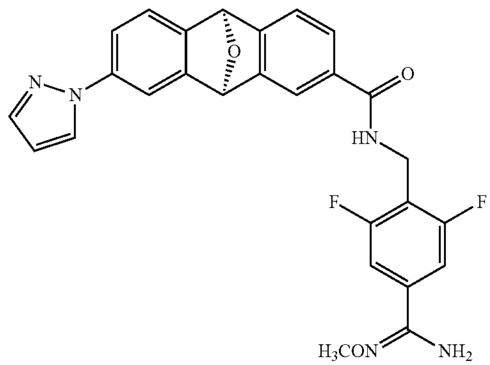 | Single enantiomer | | (1S,8R)-N-({2,6-difluoro-4-[N'-methoxycarbamimidoyl]phenyl}methyl)-12-(1H-pyrazol-1-yl)-15-oxatetracyclo[6.6.1.0$^{2,7}$.0$^{9,14}$]-pentadeca-2,4,6,9,11,13-hexaene-4-carboxamide |
| 355 | 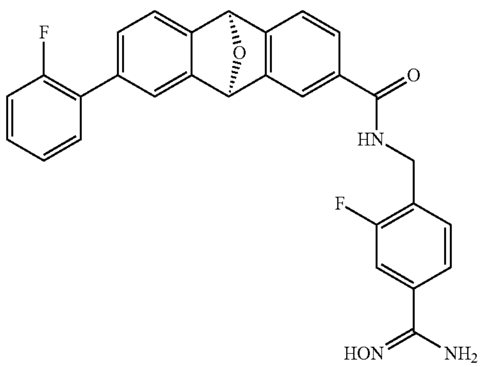 | Single enantiomer | | (1R,8S)-N-{[2-fluoro-4-(N'-hydroxy-carbamimidoyl)phenyl]methyl}-12-(2-fluorophenyl)-15-oxatetracyclo[6.6.1.0$^{2,7}$.0$^{9,14}$]-pentadeca-2,4,6,9,11,13-hexaene-4-carboxamide |
| 356 | 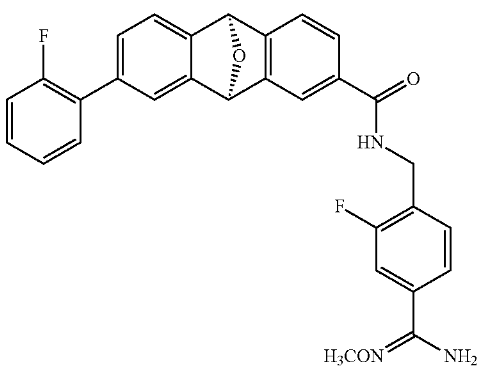 | Single enantiomer | | (1R,8S)-N-{[2-fluoro-4-(N'-methoxy-carbamimidoyl)phenyl]methyl}-12-(2-fluorophenyl)-15-oxatetracyclo[6.6.1.0$^{2,7}$.0$^{9,14}$]-pentadeca-2,4,6,9,11,13-hexaene-4-carboxamide |
| 357 | 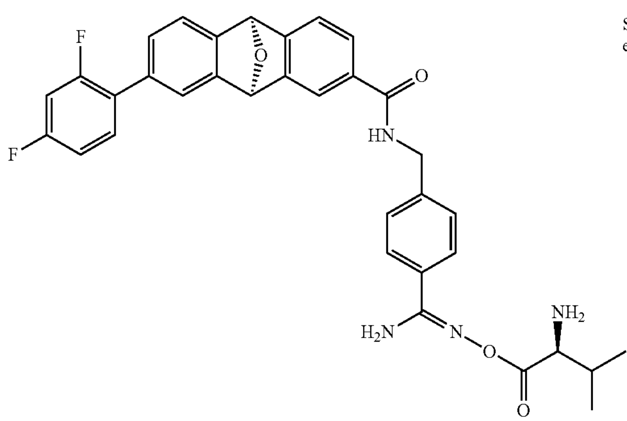 [SMILES: CC(C)[C@H](N)C(=O)ON=C(N)c1ccc(CNC(=O)c2ccc3c(c2)[C@@H]2O[C@H]3c3ccc(-c4ccc(F)cc4F)cc32)cc1] | Single enantiomer | | {amino[4-({[(1R,8S)-12-(2,4-difluorophenyl)-15-oxatetracyclo[6.6.1.0$^{2,7}$.0$^{9,14}$]pentadeca-2,4,6,9,11,13-hexaen-4-yl]formamido}methyl)-phenyl]methylidene}amino (2S)-2-amino-3-methylbutanoate |

TABLE 1-continued

| Cpd. No | Structure | Compound Type | KLKB1 pIC$_{50}$ | IUPAC Name |
|---|---|---|---|---|
| 358 | 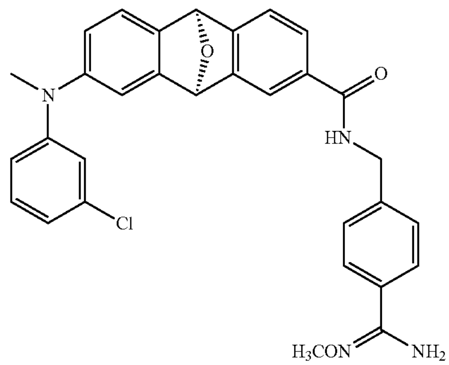 | Single enantiomer | | (1S,8R)-12-[(3-chlorophenyl)(methyl)amino]-N-({4-[N'-methoxycarbamimidoyl]phenyl}-methyl)-15-oxatetracyclo[6.6.1.0$^{2,7}$.0$^{9,14}$]-pentadeca-2,4,6,9,11,13-hexaene-4-carboxamide |
| 359 | 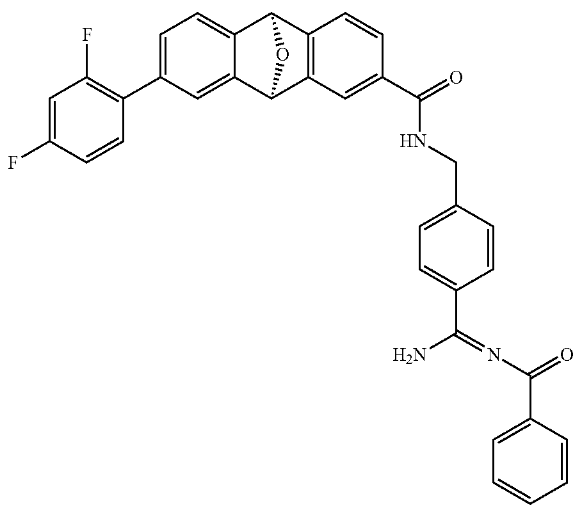 [SMILES: NC(=NC(=O)c1ccccc1)c1ccc(CNC(=O)c2ccc3c(c2)[C@@H]2O[C@H]3c3ccc(-c4ccc(F)cc4F)cc32)cc1] | Single enantiomer | | (1R,8S)-N-({4-[(1)-amino({[benzoyl]-imino})methyl]phenyl}methyl)-12-(2,4-difluorophenyl)-15-oxatetracyclo-[6.6.1.0$^{2,7}$.0$^{9,14}$]pentadeca-2,4,6,9,11,13-hexaene-4-carboxamide |
| 360 | 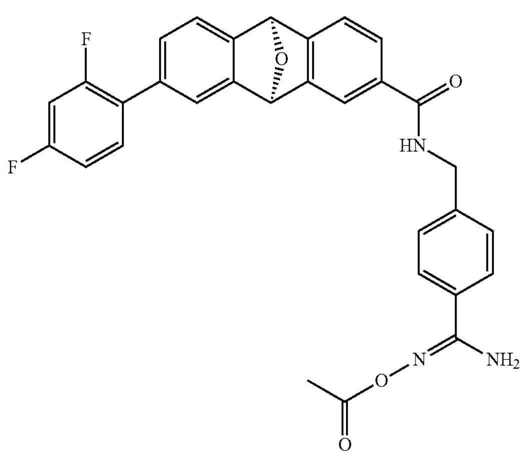 [SMILES: CC(=O)ON=C(N)c1ccc(CNC(=O)c2ccc3c(c2)[C@@H]2O[C@H]3c3ccc(-c4ccc(F)cc4F)cc32)cc1] | Single enantiomer | | {amino[4-({[(1R,8S)-12-(2,4-difluorophenyl)-15-oxatetracyclo[6.6.1.0$^{2,7}$.0$^{9,14}$]pentadeca-2,4,6,9,11,13-hexaen-4-yl]formamido}methyl)phenyl]methylidene}amino acetate |

TABLE 1-continued

| Cpd. No | Structure | Compound Type | KLKB1 pIC$_{50}$ | IUPAC Name |
| --- | --- | --- | --- | --- |
| 361 | 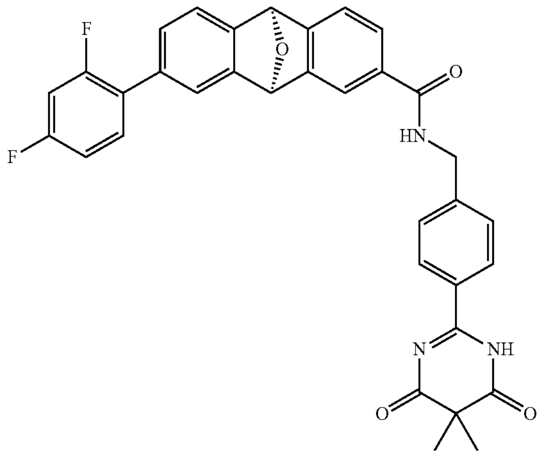 [SMILES: CC1(C)C(=O)N=C(c2ccc(CNC(=O)c3ccc4c(c3)[C@@H]3O[C@H]4c4ccc(-c5ccc(F)cc5F)cc43)cc2)NC1=O] | Single enantiomer | | (1R,8S)-12-(2,4-difluorophenyl)-N-{[4-(5,5-dimethyl-4,6-dioxo-1,4,5,6-tetrahydro-pyrimidin-2-yl)phenyl]methyl}-15-oxatetracyclo-[6.6.1.0$^{2,7}$.0$^{9,14}$]pentadeca-2,4,6,9,11,13-hexaene-4-carboxamide |
| 362 | 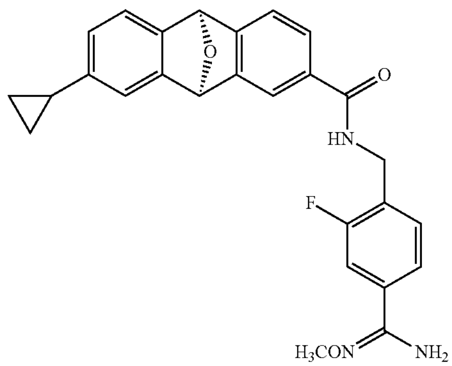 | Single enantiomer | | (1R,8S)-12-cyclopropyl-N-{[2-fluoro-4-(N'-methoxycarbamimidoyl)phenyl]methyl}-15-oxatetracyclo[6.6.1.0$^{2,7}$.0$^{9,14}$]pentadeca-2,4,6,9,11,13-hexaene-4-carboxamide |
| 363 | 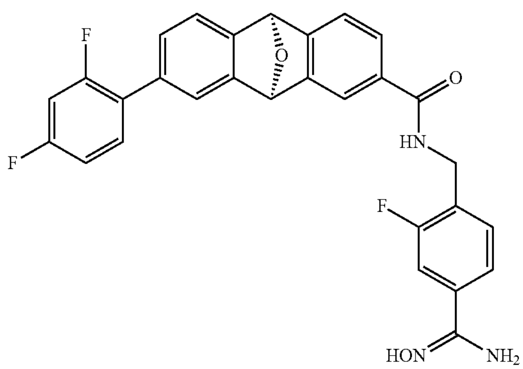 | Single enantiomer | | (1R,8S)-12-(2,4-difluorophenyl)-N-{[2-fluoro-4-(N'-hydroxycarbamimidoyl)phenyl]methyl}-15-oxatetracyclo[6.6.1.0$^{2,7}$.0$^{9,14}$]pentadeca-2,4,6,9,11,13-hexaene-4-carboxamide |
| 364 | 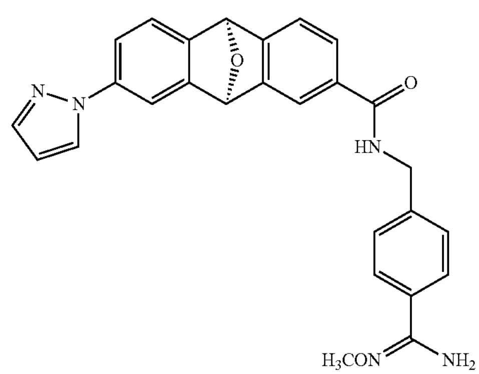 | Single enantiomer | | (1S,8R)-N-({4-[N'-methoxy-carbamimidoyl]-phenyl}methyl)-12-(1H-pyrazol-1-yl)-15-oxatetracyclo[6.6.1.0$^{2,7}$.0$^{9,14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 365 | 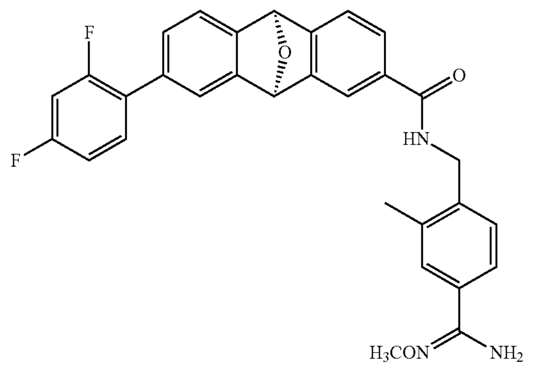 | Single enantiomer | | (1R,8S)-12-(2,4-difluorophenyl)-N-{[4-(N'-methoxycarbamimidoyl)-2-methylphenyl]methyl}-15-oxatetracyclo[6.6.1.0$^2$,$^7$.0$^9$,$^{14}$]pentadeca-2,4,6,9,11,13-hexaene-4-carboxamide |
| 366 | 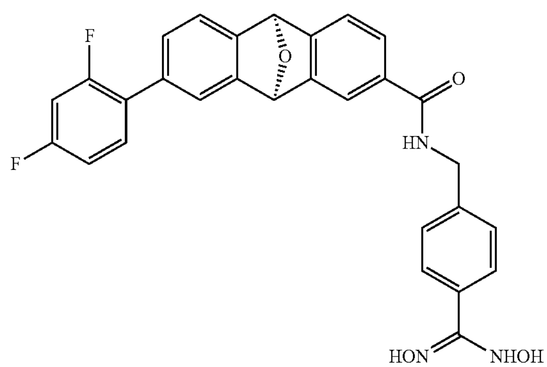 | Single enantiomer | | (1R,8S)-12-(2,4-difluorophenyl)-N-{[4-(N,N'-dihydroxycarbamimidoyl)phenyl]methyl}-15-oxatetracyclo[6.6.1.0$^2$,$^7$.0$^9$,$^{14}$]pentadeca-2,4,6,9,11,13-hexaene-4-carboxamide |
| 367 | 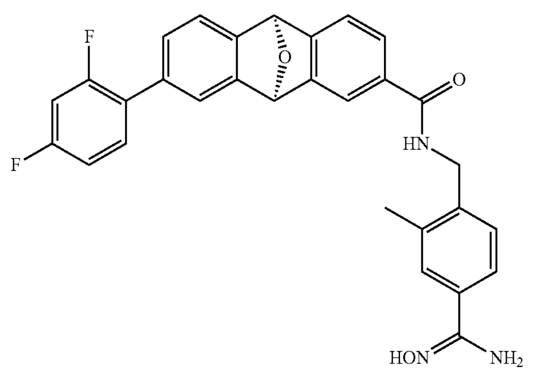 | Single enantiomer | | (1R,8S)-12-(2,4-difluorophenyl)-N-{[4-(N'-hydroxy-carbamimidoyl)-2-methyl-phenyl]methyl}-15-oxatetracyclo[6.6.1.0$^2$,$^7$.0$^9$,$^{14}$]pentadeca-2,4,6,9,11,13-hexaene-4-carboxamide |
| 368 | 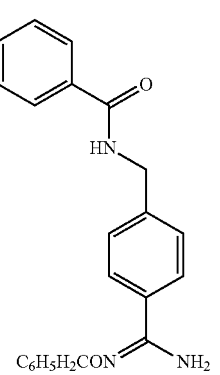 | Single enantiomer | | (1R,8S)-N-({4-[N'-(benzyloxy)carbamimidoyl]-phenyl}methyl)-12-(2,4-difluorophenyl)-15-oxatetracyclo[6.6.1.0$^2$,$^7$.0$^9$,$^{14}$]pentadeca-2,4,6,9,11,13-hexaene-4-carboxamide |

| Cpd. No | Structure | Compound Type | KLKB1 pIC$_{50}$ | IUPAC Name |
|---|---|---|---|---|
| 369 | 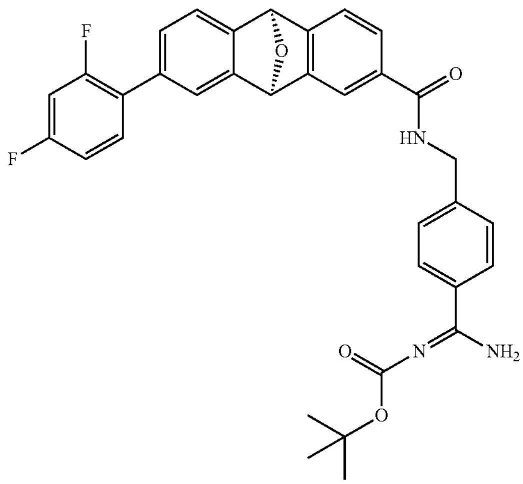 [SMILES: CC(C)(C)OC(=O)N=C(N)c1ccc(CNC(=O)c2ccc3c(c2)[C@@H]2O[C@H]3c3ccc(-c4ccc(F)cc4F)cc32)cc1] | Single enantiomer | | tert-butyl N-[1-amino[4-({[(1R,8S)-12-(2,4-difluorophenyl)-15-oxatetracyclo-[6.6.1.0$^{2,7}$.0$^{9,14}$]pentadeca-2,4,6,9,11,13-hexaen-4-yl]formamido}methyl)phenyl]methylidene]carbamate |
| 370 | 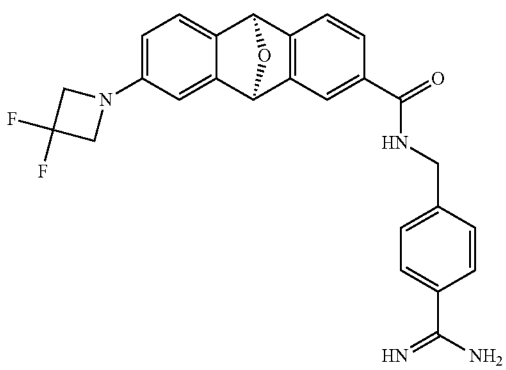 [SMILES: N=C(N)c1ccc(CNC(=O)c2ccc3c(c2)[C@@H]2O[C@H]3c3ccc(N4CC(F)(F)C4)cc32)cc1] | Single enantiomer | | (1S,8R)-N-[(4-carbamimidoyl-phenyl)methyl]-12-(3,3-difluoroazetidin-1-yl)-15-oxatetracyclo-[6.6.1.0$^{2,7}$.0$^{9,14}$]pentadeca-2,4,6,9,11,13-hexaene-4-carboxamide |
| 371 | 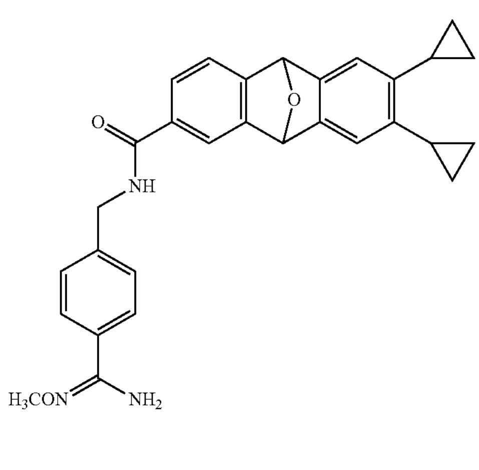 | Racemic mixture | | (±)-11,12-dicyclopropyl-N-({4-[N'-methoxy-carbamimidoyl]phenyl}methyl)-15-oxatetracyclo-[6.6.1.0$^{2,7}$.0$^{9,14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 372 | 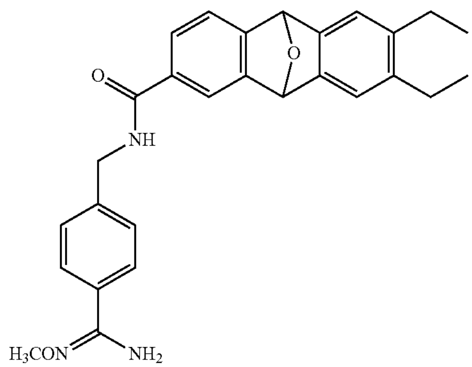 | Racemic mixture | | (±)-11,12-diethyl-N-({4-[N'-methoxy-carbamimidoyl]phenyl}methyl)-15-oxatetracyclo[6.6.1.0$^{2,7}$.0$^{9,14}$]pentadeca-2,4,6,9(14),10,12-hexaene-4-carboxamide |
| 373 | 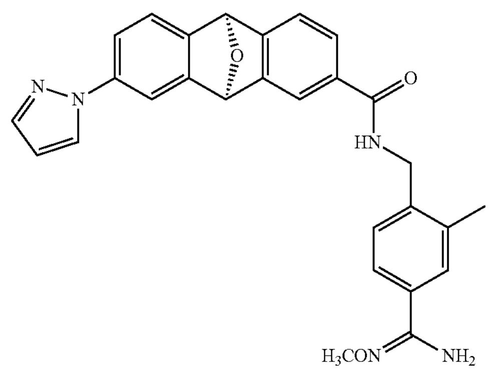 | Single enantiomer | | (1S,8R)-N-({4-[N'-methoxy-carbamimidoyl]-2-methylphenyl}methyl)-12-(1H-pyrazol-1-yl)-15-oxatetracyclo[6.6.1.0$^{2,7}$.0$^{9,14}$]pentadeca-2,4,6,9,11,13-hexaene-4-carboxamide |
| 374 | 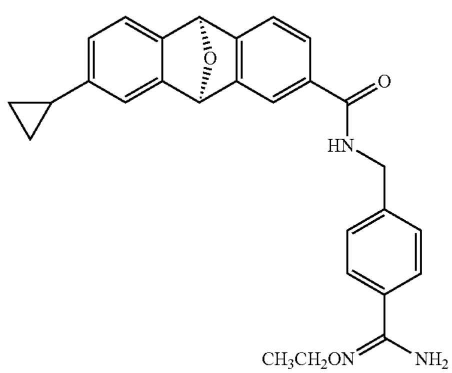 | Single enantiomer | | (1R,8S)-12-cyclopropyl-N-{[4-(N-ethoxy-carbamimidoyl)phenyl]methyl}-15-oxatetracyclo[6.6.1.0$^{2,7}$.0$^{9,14}$]pentadeca-2,4,6,9,11,13-hexaene-4-carboxamide |
| 375 | 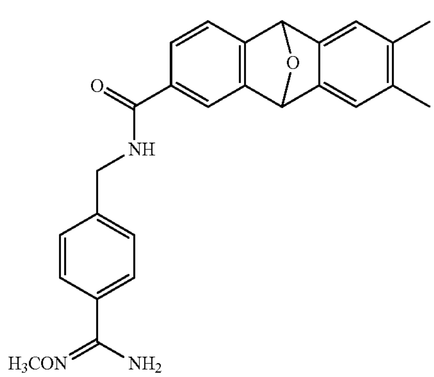 | Racemic mixture | | (±)-N-({4-[N'-methoxy-carbamimidoyl]-phenyl}methyl)-11,12-dimethyl-15-oxatetracyclo[6.6.1.0$^{2,7}$.0$^{9,14}$]pentadeca-2,4,6,9,11,13-hexaene-4-carboxamide |

| Cpd. No | Structure | Compound Type | KLKB1 pIC$_{50}$ | IUPAC Name |
|---|---|---|---|---|
| 376 | 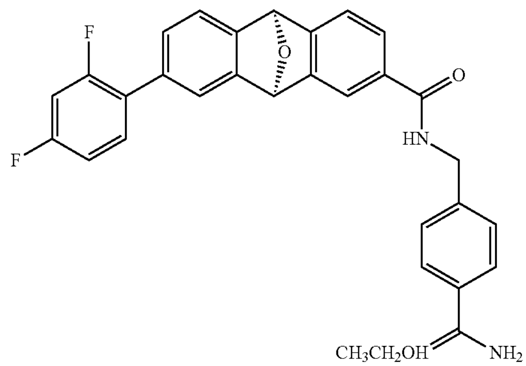 | Single enantiomer | | (1R,8S)-12-(2,4-difluorophenyl)-N-{[4-(N'-ethoxy-carbamimidoyl)phenyl]methyl}-15-oxatetracyclo[6.6.1.0$^2$,$^7$.0$^9$,$^{14}$]pentadeca-2,4,6,9,11,13-hexaene-4-carboxamide |
| 377 | 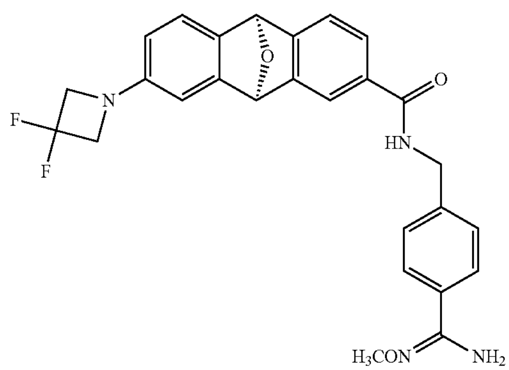 | Single enantiomer | | (1S,8R)-12-(3,3-difluoroazetidin-1-yl)-N-({4-[N'-methoxycarbamimidoyl]phenyl}methyl)-15-oxatetracyclo[6.6.1.0$^2$,$^7$.0$^9$,$^{14}$]pentadeca-2,4,6,9,11,13-hexaene-4-carboxamide |
| 378 | 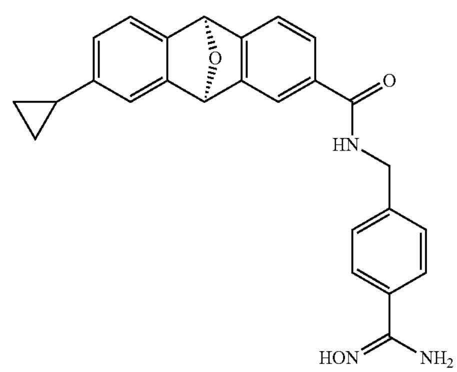 | Single enantiomer | | (1R,8S)-12-cyclopropyl-N-{[4-(N'-hydroxy-carbamimidoyl)phenyl]methyl}-15-oxatetracyclo[6.6.1.0$^2$,$^7$.0$^9$,$^{14}$]pentadeca-2,4,6,9,11,13-hexaene-4-carboxamide |
| 379 | 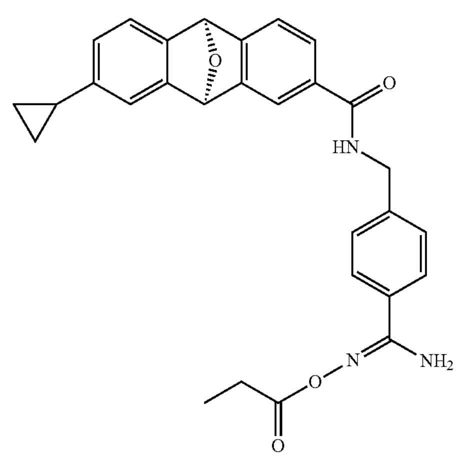 [SMILES: CCC(=O)ON=C(N)c1ccc(CNC(=O)c2ccc3c(c2)[C@@H]2O[C@H]3c3ccc(C4CC4)cc32)cc1] | Single enantiomer | | {amino[4-({[(1R,8S)-12-cyclopropyl-15-oxatetracyclo[6.6.1.0$^2$,$^7$.0$^9$,$^{14}$]pentadeca-2,4,6,9,11,13-hexaen-4-yl]formamido}methyl)phenyl]methylidene}amino propanoate |

TABLE 1-continued

| Cpd. No | Structure | Compound Type | KLKB1 pIC$_{50}$ | IUPAC Name |
|---|---|---|---|---|
| 380 | 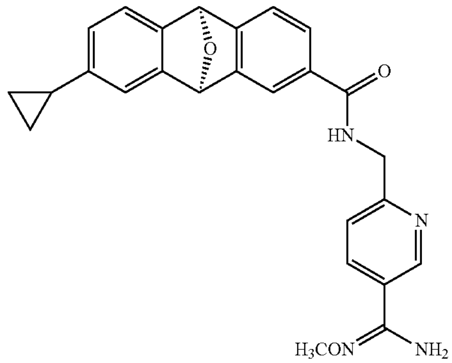 | Single enantiomer | | (1R,8S)-12-cyclopropyl-N-{[5-(N'-methoxy-carbamimidoyl)pyridin-2-yl]methyl}-15-oxatetracyclo[6.6.1.0$^{2,7}$.0$^{9,14}$]pentadeca-2,4,6,9,11,13-hexaene-4-carboxamide |
| 381 | 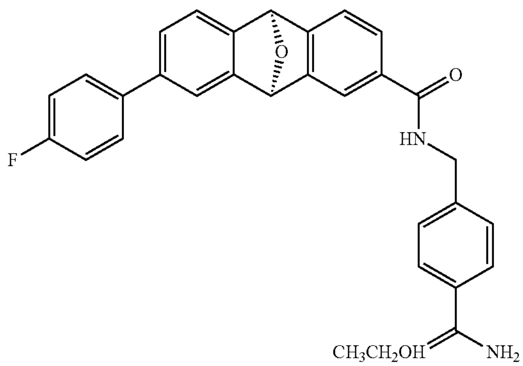 | Single enantiomer | | (1R,8S)-N-({4-[N'-ethoxy-carbamimidoyl]-phenyl}methyl)-12-(4-fluorophenyl)-15-oxatetracyclo[6.6.1.0$^{2,7}$.0$^{9,14}$]pentadeca-2,4,6,9,11,13-hexaene-4-carboxamide |
| 382 | 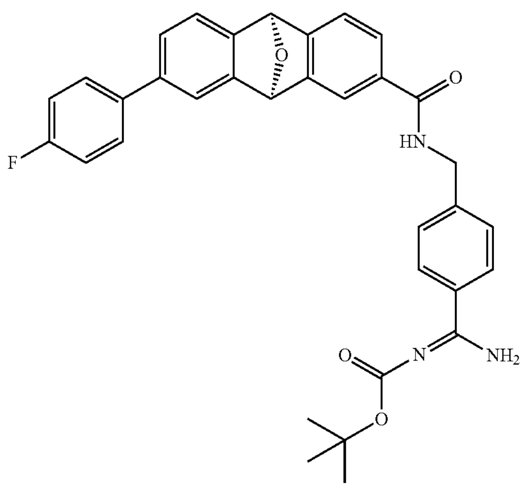 [SMILES: CC(C)(C)OC(=O)N=C(N)c1ccc(CNC(=O)c2ccc3c(c2)[C@@H]2O[C@H]3c3ccc(-c4ccc(F)cc4)cc32)cc1] | Single enantiomer | | tert-butyl N-[1-amino[4-({[(1R,8S)-12-(4-fluorophenyl)-15-oxatetracyclo[6.6.1.0$^{2,7}$.0$^{9,14}$]-pentadeca-2,4,6,9,11,13-hexaen-4-yl]formamido}-methyl)phenyl]methylidene]carbamate |
| 383 | 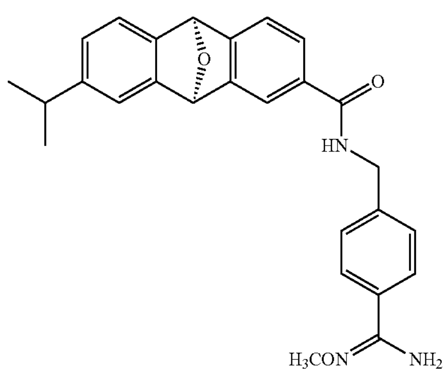 | Single enantiomer | | (1R,8S)-N-({4-[N'-methoxycarbamimidoyl]-phenyl}methyl)-12-(propan-2-yl)-15-oxatetracyclo[6.6.1.0$^{2,7}$.0$^{9,14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 384 | 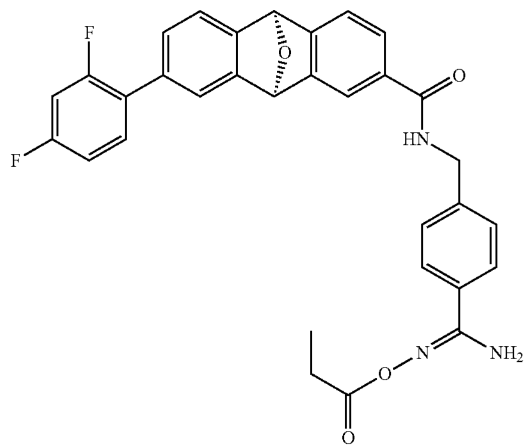 [SMILES: CCC(=O)ON=C(N)c1ccc(CNC(=O)c2ccc3c(c2)[C@@H]2O[C@H]3c3ccc(-c4ccc(F)cc4F)cc32)cc1] | Single enantiomer | | {amino[4-({[(1R,8S)-12-(2,4-difluorophenyl)-15-oxatetracyclo[6.6.1.0$^2$,$^7$.0$^9$,$^{14}$]pentadeca-2,4,6,9,11,13-hexaen-4-yl]formamido}methyl)phenyl]methylidene}amino propanoate |
| 385 | 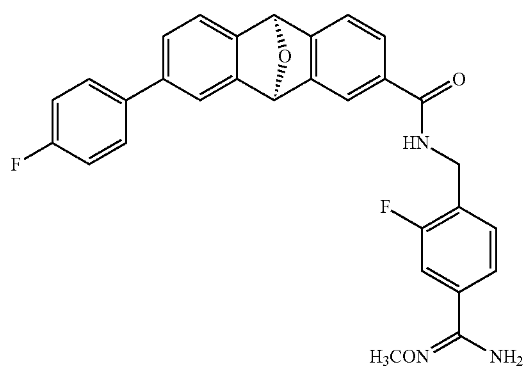 | Single enantiomer | | (1R,8S)-N-{[2-fluoro-4-(N'-methoxy-carbamimidoyl)phenyl]methyl}-12-(4-fluorophenyl)-15-oxatetracyclo[6.6.1.0$^2$,$^7$.0$^9$,$^{14}$]-pentadeca-2,4,6,9,11,13-hexaene-4-carboxamide |
| 386 | 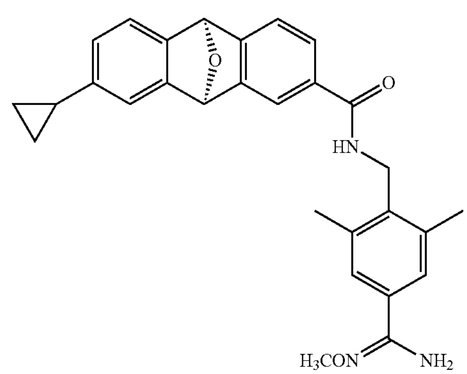 | Single enantiomer | | (1R,8S)-12-cyclopropyl-N-{[4-(N'-methoxy-carbamimidoyl)-2,6-dimethylphenyl]methyl}-15-oxatetracyclo[6.6.1.0$^2$,$^7$.0$^9$,$^{14}$]pentadeca-2,4,6,9,11,13-hexaene-4-carboxamide |
| 387 | 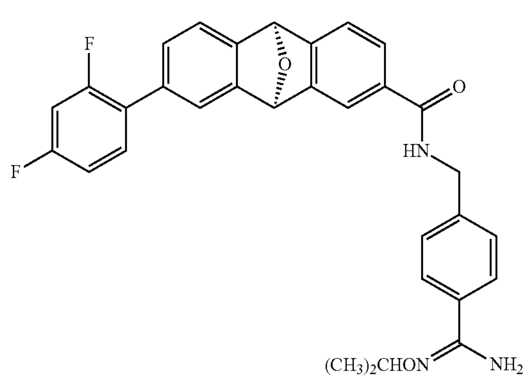 | Single enantiomer | | (1R,8S)-12-(2,4-difluorophenyl)-N-({4-[N'-(propan-2-yloxy)carbamimidoyl]phenyl}methyl)-15-oxatetracyclo[6.6.1.0$^2$,$^7$.0$^9$,$^{14}$]pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 388 | 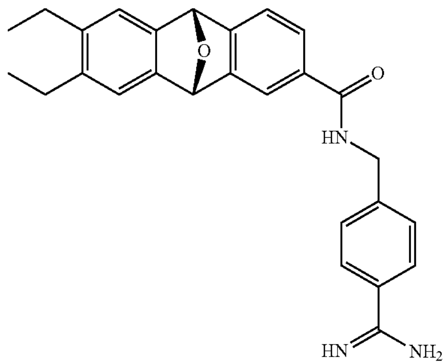 [SMILES: CCc1cc2c(cc1CC)[C@H]1O[C@@H]2c2cc(C(=O)NCc3ccc(C(=N)N)cc3)ccc21] | Single enantiomer | | (1R,8S)-N-[(4-carbamimidoyl-phenyl)methyl]-11,12-diethyl-15-oxatetracyclo[6.6.1.0$^{2,7}$.0$^{9,14}$]-pentadeca-2,4,6,9(14),10,12-hexaene-4-carboxamide |
| 389 | 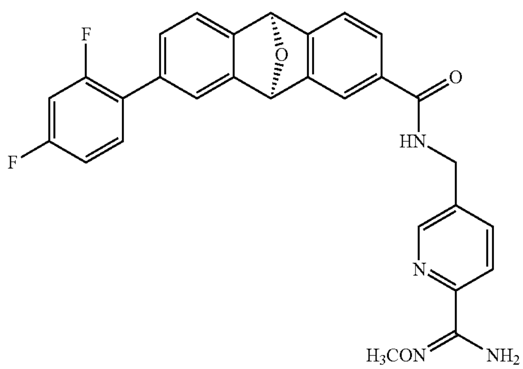 | Single enantiomer | | (1R,8S)-12-(2,4-difluorophenyl)-N-{[6-(N'-methoxycarbamimidoyl)pyridin-3-yl]methyl}-15-oxatetracyclo[6.6.1.0$^{2,7}$.0$^{9,14}$]pentadeca-2,4,6,9,11,13-hexaene-4-carboxamide |
| 390 | 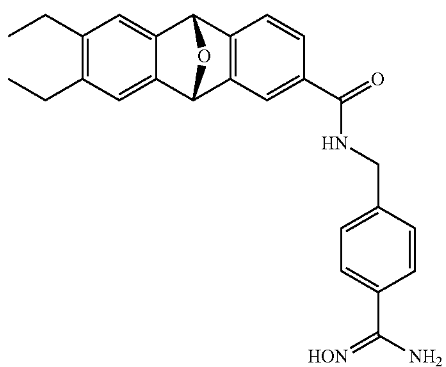 | Single enantiomer | | (1R,8S)-11,12-diethyl-N-({4-[N'-hydroxycarbamimidoyl]phenyl}methyl)-15-oxatetracyclo[6.6.1.0$^{2,7}$.0$^{9,14}$]pentadeca-2,4,6,9(14),10,12-hexaene-4-carboxamide |
| 391 | 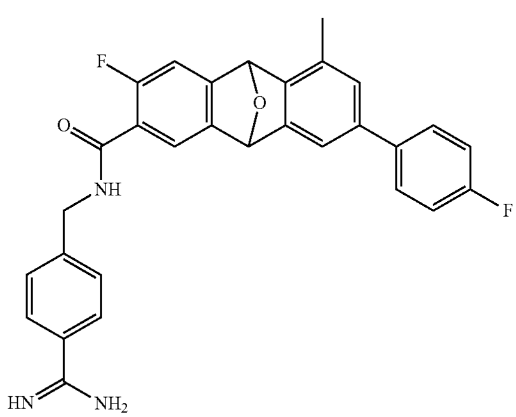 | Racemic mixture | | (±)-N-[(4-carbamimidoyl-phenyl)methyl]-5-fluoro-12-(4-fluorophenyl)-10-methyl-15-oxatetracyclo[6.6.1.0$^{2,7}$.0$^{9,14}$]pentadeca-2,4,6,9(14),10,12-hexaene-4-carboxamide and (±)-N-[(4-carbamimidoylphenyl)methyl]-5-fluoro-11-(4-fluorophenyl)-13-methyl-15-oxatetracyclo[6.6.1.0$^{2,7}$.0$^{9,14}$]pentadeca-2,4,6,9(14),10,12-hexaene-4-carboxamide |

| Cpd. No | Structure | Compound Type | KLKB1 pIC$_{50}$ | IUPAC Name |
|---|---|---|---|---|
| | | | | |
| 392 | 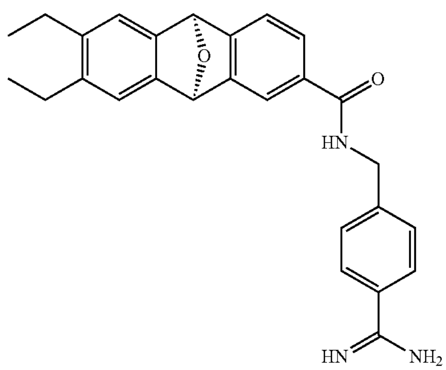 [SMILES: CCc1cc2c(cc1CC)[C@H]1O[C@@H]2c2ccc(C(=O)NCc3ccc(C(=N)N)cc3)cc21] | Single enantiomer | 9 | (1S,8R)-N-[(4-carbamimidoyl-phenyl)methyl]-11,12-diethyl-15-oxatetracyclo[6.6.1.0$^{2,7}$.0$^{9,14}$]-pentadeca-2,4,6,9(14),10,12-hexaene-4-carboxamide |
| 393 | 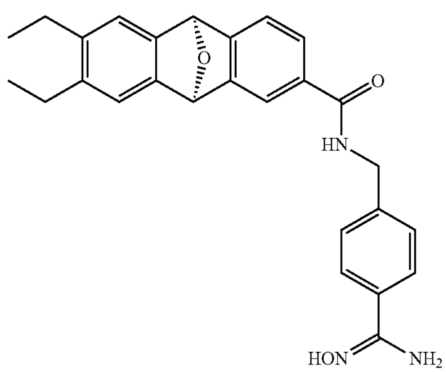 | Single enantiomer | | (1S,8R)-11,12-diethyl-N-({4-[N'-hydroxy-carbamimidoyl]phenyl}methyl)-15-oxatetracyclo[6.6.1.0$^{2,7}$.0$^{9,14}$]pentadeca-2,4,6,9(14),10,12-hexaene-4-carboxamide |
| 394 | 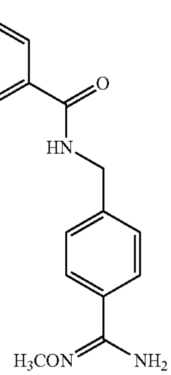 | Single enantiomer | | (1R,8S)-11,12-diethyl-N-({4-[N'-methoxy-carbamimidoyl]phenyl}methyl)-15-oxatetracyclo[6.6.1.0$^{2,7}$.0$^{9,14}$]pentadeca-2,4,6,9(14),10,12-hexaene-4-carboxamide |

TABLE 1-continued

| Cpd. No | Structure | Compound Type | KLKB1 pIC$_{50}$ | IUPAC Name |
|---|---|---|---|---|
| 395 | 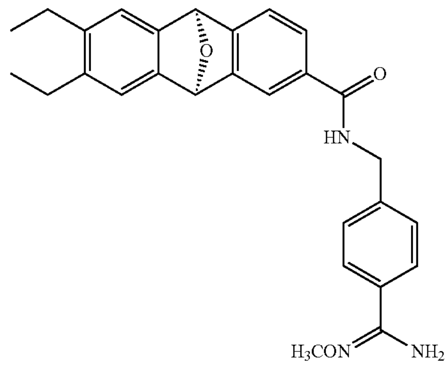 | Single enantiomer | | (1S,8R)-11,12-diethyl-N-({4-[N'-methoxy-carbamimidoyl]phenyl}methyl)-15-oxatetracyclo[6.6.1.0$^{2,7}$.0$^9$,1$^4$]pentadeca-2,4,6,9(14),10,12-hexaene-4-carboxamide |
| 396 | 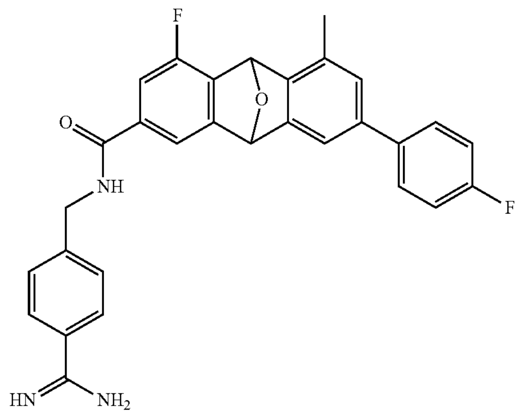 [SMILES: Cc1cc(-c2ccc(F)cc2)cc2c1C1OC2c2cc(C(=O)NCc3ccc(C(=N)N)cc3)cc(F)c21] | Racemic mixture | 8.3 | (±)-N-[(4-carbamimidoyl-phenyl)methyl]-6-fluoro-12-(4-fluorophenyl)-10-methyl-15-oxatetracyclo[6.6.1.0$^{2,7}$.0$^9$,1$^4$]pentadeca-2(7),3,5,9(14),10,12-hexaene-4-carboxamide |
| 397 | 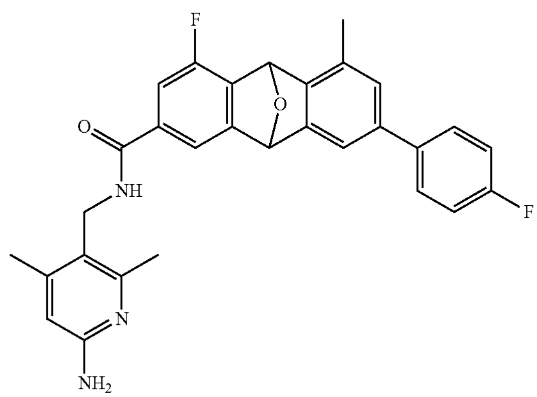 [SMILES: Cc1cc(N)nc(C)c1CNC(=O)c1cc(F)c2c(c1)C1OC2c2c(C)cc(-c3ccc(F)cc3)cc21] | Racemic mixture | 7.7 | (±)-N-[(6-amino-2,4-dimethylpyridin-3-yl)methyl]-6-fluoro-12-(4-fluorophenyl)-10-methyl-15-oxatetracyclo[6.6.1.0$^{2,7}$.0$^9$,1$^4$]-pentadeca-2(7),3,5,9(14),10,12-hexaene-4-carboxamide |
| 398 | 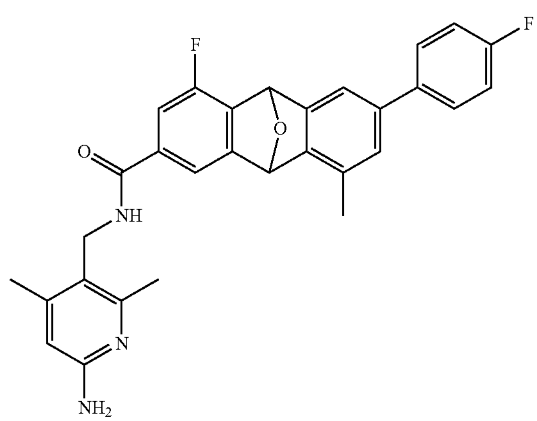 [SMILES: Cc1cc(N)nc(C)c1CNC(=O)c1cc(F)c2c(c1)C1OC2c2cc(-c3ccc(F)cc3)cc(C)c21] | Racemic mixture | 6.4 | N-[(6-amino-2,4-dimethylpyridin-3-yl)methyl]-6-fluoro-11-(4-fluorophenyl)-13-methyl-15-oxatetracyclo[6.6.1.0$^{2,7}$.0$^9$,1$^4$]pentadeca-2,4,6,9(14),10,12-hexaene-4-carboxamide |

TABLE 1-continued

| Cpd. No | Structure | Compound Type | KLKB1 pIC$_{50}$ | IUPAC Name |
|---|---|---|---|---|
| 399 | 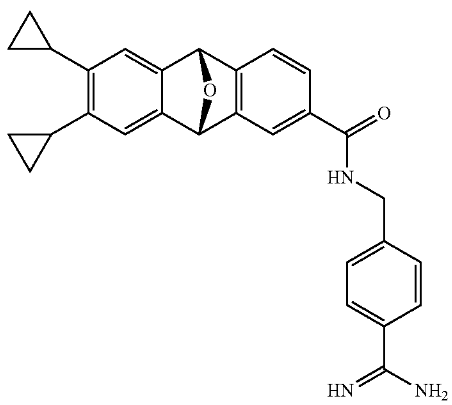 [SMILES: N=C(N)c1ccc(CNC(=O)c2ccc3c(c2)[C@H]2O[C@@H]3c3cc(C4CC4)c(C4CC4)cc32)cc1] | Single enantiomer | 7 | (1R,8S)-N-[(4-carbamimidoyl-phenyl)methyl]-11,12-dicyclopropyl-15-oxatetracyclo-[6.6.1.0$^2$,$^7$.0$^9$,$^{14}$] pentadeca-2,4,6,9,11,13-hexaene-4-carboxamide |
| 400 | 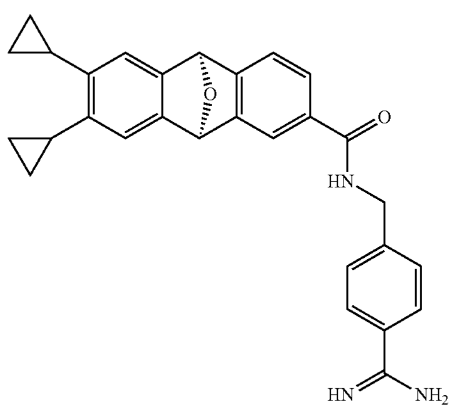 | Single enantiomer | 9 | (1S,8R)-N-[(4-carbamimidoyl-phenyl)methyl]-11,12-dicyclopropyl-15-oxatetracyclo-[6.6.1.0$^2$,$^7$.0$^9$,$^{14}$] pentadeca-2,4,6,9,11,13-hexaene-4-carboxamide |
| 401 | 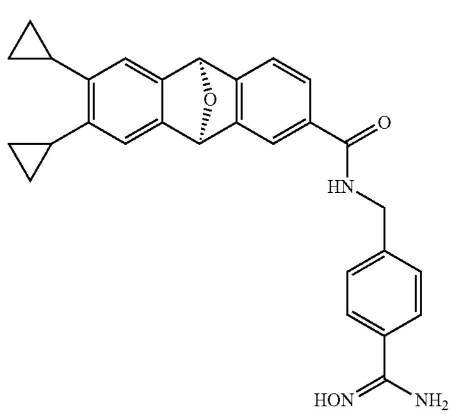 | Single enantiomer | | (1S,8R)-11,12-dicyclopropyl-N-({4-[N'-hydroxycarbamimidoyl]phenyl}methyl)-15-oxatetracyclo[6.6.1.0$^2$,$^7$.0$^9$,$^{14}$] pentadeca-2,4,6,9,11,13-hexaene-4-carboxamide |

TABLE 1-continued

| Cpd. No | Structure | Compound Type | KLKB1 pIC$_{50}$ | IUPAC Name |
|---|---|---|---|---|
| 402 | 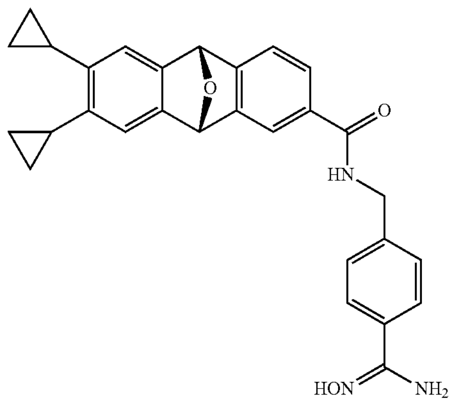 | Single enantiomer | | (1R,8S)-11,12-dicyclopropyl-N-({4-[N'-hydroxy-carbamimidoyl]phenyl}methyl)-15-oxatetracyclo[6.6.1.0$^2$,$^7$.0$^9$,1$^4$]pentadeca-2,4,6,9,11,13-hexaene-4-carboxamide |
| 403 | 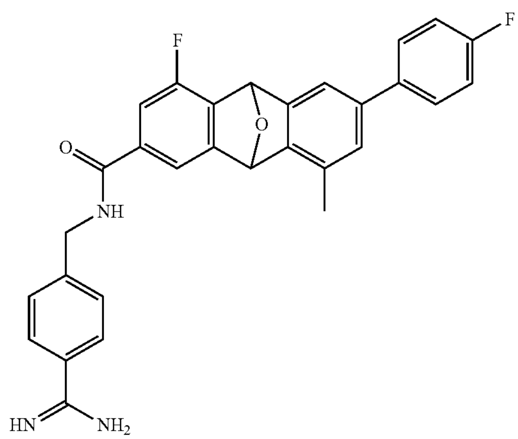 [SMILES: Cc1cc(-c2ccc(F)cc2)cc2c1C1OC2c2c(F)cc(C(=O)NCc3ccc(C(=N)N)cc3)cc21] | Racemic mixture | | (±)-N-[(4-carbamimidoylphenyl)methyl]-6-fluoro-11-(4-fluorophenyl)-13-methyl-15-oxatetracyclo[6.6.1.0$^2$,$^7$.0$^9$,1$^4$]pentadeca-2,4,6,9(14),10,12-hexaene-4-carboxamide |
| 404 | 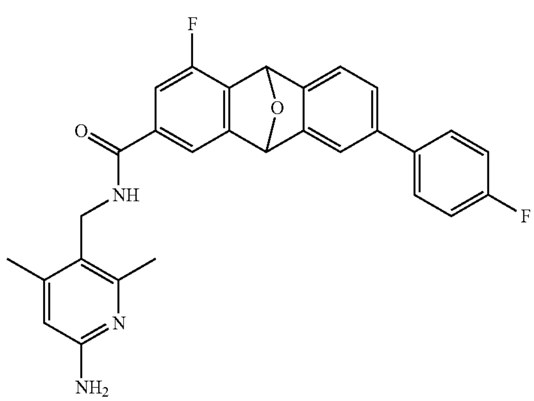 [SMILES: Cc1cc(N)nc(C)c1CNC(=O)c1cc(F)c2c(c1)C1OC2c2ccc(-c3ccc(F)cc3)cc21] | Racemic mixture | | (±)-N-[(6-amino-2,4-dimethylpyridin-3-yl)methyl]-6-fluoro-12-(4-fluorophenyl)-15-oxatetracyclo[6.6.1.0$^2$,$^7$.0$^9$,1$^4$]pentadeca-2(7),3,5,9,11,13-hexaene-4-carboxamide |

TABLE 1-continued

| Cpd. No | Structure | Compound Type | KLKB1 pIC$_{50}$ | IUPAC Name |
|---|---|---|---|---|
| 405 | 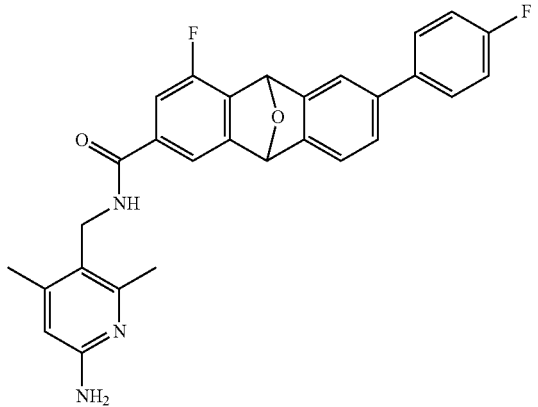 [SMILES: Cc1cc(N)nc(C)c1CNC(=O)c1cc(F)c2c(c1)C1OC2c2cc(-c3ccc(F)cc3)ccc21] | Racemic mixture | | (±)-N-[(6-amino-2,4-dimethylpyridin-3-yl)-methyl]-6-fluoro-11-(4-fluorophenyl)-15-oxatetracyclo[6.6.1.0$^{2,7}$.0$^{9,14}$]pentadeca-2(7),3,5,9,11,13-hexaene-4-carboxamide |
| 406 | 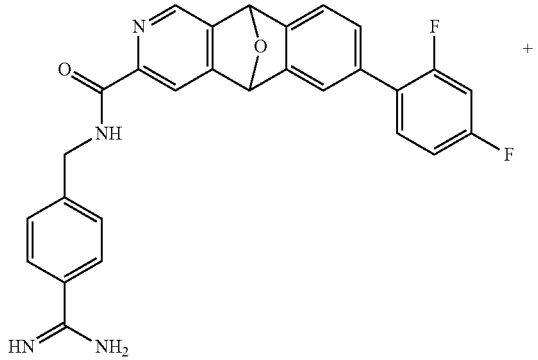 [SMILES: N=C(N)c1ccc(CNC(=O)c2cc3c(cn2)C2OC3c3cc(-c4ccc(F)cc4F)ccc32)cc1] 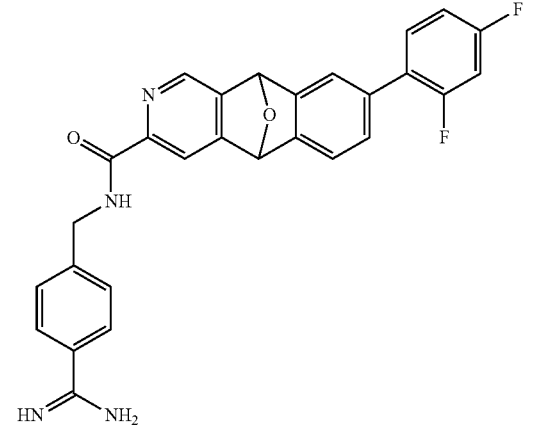 [SMILES: N=C(N)c1ccc(CNC(=O)c2cc3c(cn2)C2OC3c3ccc(-c4ccc(F)cc4F)cc32)cc1] | Racemic mixture | + | (±)-N-[(4-carbamimidoyl-phenyl)methyl]-11-(2,4-difluorophenyl)-15-oxa-4-azatetracyclo-[6.6.1.0$^{2,7}$.0$^{9,14}$]pentadeca-2(7),3,5,9,11,13-hexaene-5-carboxamide and (±)-N-[(4-carbamimidoyl-phenyl)methyl]-12-(2,4-difluorophenyl)-15-oxa-4-azatetracyclo-[6.6.1.0$^{2,7}$.0$^{9,14}$]pentadeca-2(7),3,5,9,11,13-hexaene-5-carboxamide |

TABLE 1-continued

| Cpd. No | Structure | Compound Type | KLKB1 pIC$_{50}$ | IUPAC Name |
|---|---|---|---|---|
| 407 | 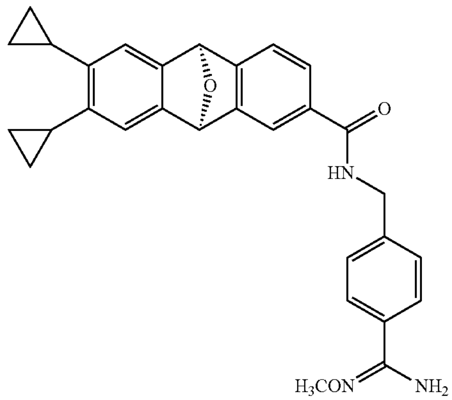 | Single enantiomer | | (1S,8R)-11,12-dicyclopropyl-N-({4-[N'-methoxy-carbamimidoyl]phenyl}methyl)-15-oxatetracyclo[6.6.1.0$^2$,$^7$.0$^9$,$^{14}$]pentadeca-2,4,6,9,11,13-hexaene-4-carboxamide |
| 408 | | Racemic mixture | + | (±)-N-[(6-amino-2,4-dimethylpyridin-3-yl)methyl]-5-fluoro-12-(4-fluorophenyl)-15-oxatetracyclo[6.6.1.0$^2$,$^7$.0$^9$,$^{14}$]pentadeca-2(7),3,5,9,11,13-hexaene-4-carboxamide and (±)-N-[(6-amino-2,4-dimethylpyridin-3-yl)methyl]-5-fluoro-11-(4-fluorophenyl)-15-oxatetracyclo[6.6.1.0$^2$,$^7$.0$^9$,$^{14}$]pentadeca-2(7),3,5,9,11,13-hexaene-4-carboxamide |
| 409 | 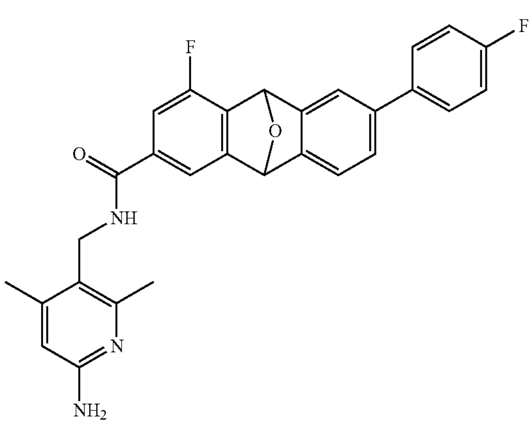 [SMILES: Cc1cc(N)nc(C)c1CNC(=O)c1cc(F)c2c(c1)C1OC2c2cc(-c3ccc(F)cc3)ccc21] | Racemic mixture | | (±)-N-[(6-amino-2,4-dimethylpyridin-3-yl)-methyl]-6-fluoro-11-(4-fluorophenyl)-15-oxatetracyclo[6.6.1.0$^2$,$^7$.0$^9$,$^{14}$]pentadeca-2(7),3,5,9,11,13-hexaene-4-carboxamide |

TABLE 1-continued

| Cpd. No | Structure | Compound Type | KLKB1 pIC$_{50}$ | IUPAC Name |
|---|---|---|---|---|
| 410 | 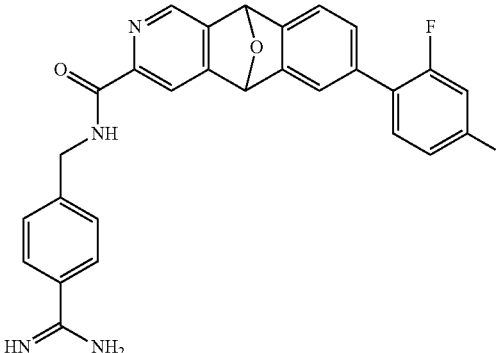 | Racemic mixture | + | (±)-N-[(4-carbamimidoyl-phenyl)methyl]-11-(2,4-difluorophenyl)-15-oxa-4-azatetracyclo-[6.6.1.0$^{2,7}$.0$^{9,14}$]pentadeca-2(7),3,5,9,11,13-hexaene-5-carboxamide and (±)-N-[(4-carbamimidoyl-phenyl)methyl]-12-(2,4-difluorophenyl)-15-oxa-4-azatetracyclo-[6.6.1.0$^{2,7}$.0$^{9,14}$]pentadeca-2(7),3,5,9,11,13-hexaene-5-carboxamide |
| | 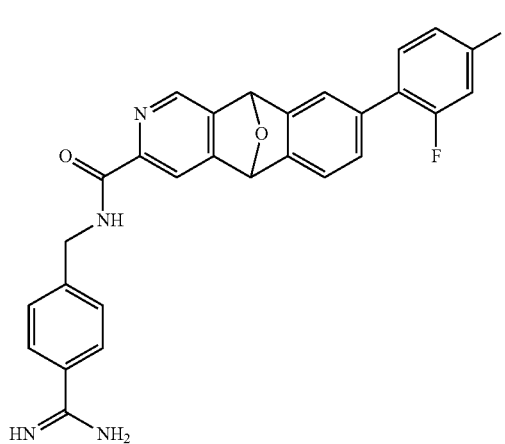 | | | |

In one embodiment, the compound of Formula (I) is selected from:

(1R,8S)—N-[(6-amino-2,4-dimethylpyridin-3-yl)methyl]-12-(2,4-difluorophenyl)-15-oxatetracyclo[6.6.1.0$^{2,7}$.0$^{9,14}$]pentadeca-2,4,6,9,11,13-hexaene-4-carboxamide, (±)-N-[(6-amino-4-cyclopropyl-2-methylpyridin-3-yl)methyl]-12-(2,4-difluorophenyl)-15-oxatetracyclo[6.6.1.0$^{2,7}$.0$^{9,14}$]pentadeca-2,4,6,9,11,13-hexaene-4-carboxamide, (1R,8S)—N-[(6-amino-2,4-dimethylpyridin-3-yl)methyl]-12-[(4-methyl-1H-pyrazol-1-yl)methyl]-15-oxatetracyclo[6.6.1.0$^{2,7}$.0$^{9,14}$]pentadeca-2,4,6,9,11,13-hexaene-4-carboxamide, (1R,8S)—N-[(6-amino-4-ethyl-2-methylpyridin-3-yl)methyl]-12-(2,4-difluorophenyl)-15-oxatetracyclo[6.6.1.0$^{2,7}$.0$^{9,14}$]pentadeca-2,4,6,9,11,13-hexaene-4-carboxamide, (1R,8S)—N-[(4-carbamimidoylphenyl)methyl]-12-(2-fluorophenyl)-15-oxatetracyclo[6.6.1.0$^{2,7}$.0$^{9,14}$]pentadeca-2,4,6,9,11,13-hexaene-4-carboxamide, (1R,8S)—N-[(4-carbamimidoyl-2,6-dimethylphenyl)methyl]-12-(2,4-difluorophenyl)-15-oxatetracyclo[6.6.1.0$^{2,7}$.0$^{9,14}$]pentadeca-2,4,6,9,11,13-hexaene-4-carboxamide, (1R,8S)—N-[(4-carbamimidoylphenyl)methyl]-12-(4-fluorophenyl)-15-oxatetracyclo[6.6.1.0$^{2,7}$.0$^{9,14}$]pentadeca-2,4,6,9,11,13-hexaene-4-carboxamide, (1R,8S)—N-[(4-carbamimidoylphenyl)methyl]-12-(2,4-difluorophenyl)-15-oxatetracyclo[6.6.1.0$^{2,7}$.0$^{9,14}$]pentadeca-2,4,6,9,11,13-hexaene-4-carboxamide (1R,8S)-12-(2,4-difluorophenyl)-N-{[4-(N'-hydroxycarbamimidoyl)phenyl]methyl}-15-oxatetracyclo[6.6.1.0$^{2,7}$.0$^{9,14}$]pentadeca-2,4,6,9,11,13-hexaene-4-carboxamide, (1R,8S)-12-(2-fluorophenyl)-N-{[4-(N'-hydroxycarbamimidoyl)phenyl]methyl}-15-oxatetracyclo[6.6.1.0$^{2,7}$.0$^{9,14}$]pentadeca-2,4,6,9,11,13-hexaene-4-carboxamide, (1R,8S)—N-{[6-amino-2-methyl-4-(propan-2-yl)pyridin-3-yl]methyl}-12-(2,4-difluorophenyl)-15-oxatetracyclo[6.6.1.0$^{2,7}$.0$^{9,14}$]pentadeca-2,4,6,9,11,13-hexaene-4-carboxamide, (1R,8S)—N-[(4-carbamimidoyl-3-fluorophenyl)methyl]-12-(2,4-difluorophenyl)-15-oxatetracyclo[6.6.1.0$^{2,7}$.0$^{9,14}$]pentadeca-2,4,6,9,11,13-hexaene-4-carboxamide, (1S,8R)—N-[(4-carbamimidoylphenyl)methyl]-12-(5-chlorothiophen-2-yl)-15-oxatetracyclo[6.6.1.0$^{2,7}$.0$^{9,14}$]pentadeca-2,4,6,9,11,13-hexaene-4-carboxamide, (1R,8S)-12-(2,4-difluorophenyl)-N-{[4-(N'-methoxycarbamimidoyl)phenyl]methyl}-15-oxatetracyclo[6.6.1.0$^{2,7}$.0$^{9,14}$]pentadeca-2,4,6,9,11,13-hexaene-4-carboxamide, (1R,8S)—N-[(4-carbamimidoylphenyl)methyl]-12-ethyl-15-oxatetracyclo-[6.6.1.0$^{2,7}$.0$^{9,14}$]pentadeca-2,4,6,9,11,13-hexaene-4-carboxamide, (1R,8S)—N-{[4-(N'-methoxycarbamimidoyl)phenyl]methyl}-12-(2-fluorophenyl)-15-oxatetracyclo[6.6.1.0$^{2,7}$.0$^{9,14}$]pentadeca-2,4,6,9,11,13-hexaene-4-carboxamide, (1R,8S)-12-(4-fluorophenyl)-N-{[4-(N'-methoxycarbamimidoyl)phenyl]methyl}-15-oxatetracyclo[6.6.1.0$^{2,7}$.0$^{9,14}$]pentadeca-2,4,6,9,11,13-hexaene-4-carboxamide, (1S,8R)-12-(5-chlorothiophen-2-yl)-N-({4-[N'-methoxycarbamimidoyl]-phenyl}methyl)-15-oxatetracyclo[6.6.1.0$^{2,7}$.0$^{9,14}$]pentadeca-2,4,6,9,11,13-hexaene-4-carboxamide, (1R,8S)—N-({2,6-difluoro-4-[N'-methoxycarbamimidoyl]phenyl}methyl)-12-(2,4-difluorophenyl)-15-oxatetracyclo[6.6.1.0$^{2,7}$.0$^{9,14}$]pentadeca-2,4,6,9,11,13-hexaene-4-carboxamide, (1R,8S)—N-[(4-carbamimidoyl-2,6-difluorophenyl)
methyl]-12-(2,4-difluorophenyl)-15-oxatetracyclo
[6.6.1.0$^{2,7}$.0$^{9,14}$]pentadeca-2,4,6,9,11,13-hexaene-4-carboxamide,
(1R,8S)—N-[(4-carbamimidoylphenyl)methyl]-12-cyclopropyl-15-oxatetracyclo[6.6.1.0$^{2,7}$.0$^{9,14}$]pentadeca-2,4,6,9,11,13-hexaene-4-carboxamide,
(1R,8S)—N-({2,6-difluoro-4-[N'-hydroxycarbamimidoyl]phenyl}methyl)-12-(2,4-difluorophenyl)-15-oxatetracyclo[6.6.1.0$^{2,7}$.0$^{9,14}$]pentadeca-2,4,6,9,11,13-hexaene-4-carboxamide,
ethyl N-[(1Z)-amino[4-({[(1R,8S)-12-(2,4-difluorophenyl)-15-oxatetracyclo-[6.6.1.0$^{2,7}$.0$^{9,14}$]pentadeca-2,4,6,9,11,13-hexaen-4-yl]formamido}methyl)-3,5-difluorophenyl]methylidene]carbamate,
(1S,8R)-12-(5-chlorothiophen-2-yl)-N-{[4-(N'-hydroxycarbamimidoyl)phenyl]methyl}-15-oxatetracyclo[6.6.1.0$^{2,7}$.0$^{9,14}$]pentadeca-2,4,6,9,11,13-hexaene-4-carboxamide,
(1R,8S)—N-[(4-carbamimidoyl-2,6-difluorophenyl)methyl]-12-cyclopropyl-15-oxatetracyclo[6.6.1.0$^{2,7}$.0$^{9,14}$]pentadeca-2,4,6,9,11,13-hexaene-4-carboxamide,
(1R,8S)—N-[(4-carbamimidoyl-2-fluorophenyl)methyl]-12-(2-fluorophenyl)-15-oxatetracyclo[6.6.1.0$^{2,7}$.0$^{9,14}$]pentadeca-2,4,6,9,11,13-hexaene-4-carboxamide,
(1R,8S)—N-[(4-carbamimidoyl-2-fluorophenyl)methyl]-12-(2,4-difluorophenyl)-15-oxatetracyclo[6.6.1.0$^{2,7}$.0$^{9,14}$]pentadeca-2,4,6,9,11,13-hexaene-4-carboxamide,
(1R,8S)—N-[(4-carbamimidoyl-2,6-difluorophenyl)methyl]-12-(propan-2-yl)-15-oxatetracyclo[6.6.1.0$^{2,7}$.0$^{9,14}$]pentadeca-2,4,6,9,11,13-hexaene-4-carboxamide,
(±)-N-[(4-carbamimidoylphenyl)methyl]-11,12-dicyclopropyl-15-oxatetracyclo-[6.6.1.0$^{2,7}$.0$^{9,14}$]pentadeca-2,4,6,9,11,13-hexaene-4-carboxamide,
(1R,8S)—N-[(4-carbamimidoyl-2-fluorophenyl)methyl]-12-(4-fluorophenyl)-15-oxatetracyclo[6.6.1.0$^{2,7}$.0$^{9,14}$]pentadeca-2,4,6,9,11,13-hexaene-4-carboxamide,
(1R,8S)-12-(2,4-difluorophenyl)-N-{[4-(N'-methoxycarbamimidoyl)-2,6-dimethylphenyl]methyl}-15-oxatetracyclo[6.6.1.0$^{2,7}$.0$^{9,14}$]pentadeca-2,4,6,9,11,13-hexaene-4-carboxamide,
(1R,8S)-12-cyclopropyl-N-({2,6-difluoro-4-[N'-methoxycarbamimidoyl]-phenyl}methyl)-15-oxatetracyclo[6.6.1.0$^{2,7}$.0$^{9,14}$]pentadeca-2,4,6,9,11,13-hexaene-4-carboxamide,
methyl N-[1-amino[4-({[(1R,8S)-12-cyclopropyl-15-oxatetracycl[6.6.1.0$^{2,7}$.0$^{9,14}$]pentadeca-2,4,6,9,11,13-hexaen-4-yl]formamido}methyl)phenyl]methylidene]carbamate,
methyl N-[1-amino[4-({[(1R,8S)-12-cyclopropyl-15-oxatetracycl[6.6.1.0$^{2,7}$.0$^{9,14}$]pentadeca-2,4,6,9,11,13-hexaen-4-yl]formamido}methyl)-3,5-difluorophenyl]-methylidene]carbamate,
(1S,8R)—N-({2,6-difluoro-4-[N'-methoxycarbamimidoyl]phenyl}methyl)-12-(1H-pyrazol-1-yl)-15-oxatetracyclo[6.6.1.0$^{2,7}$.0$^{9,14}$]pentadeca-2,4,6,9,11,13-hexaene-4-carboxamide,
(1S,8R)—N-[(4-carbamimidoylphenyl)methyl]-11,12-diethyl-15-oxatetracyclo-[6.6.1.0$^{2,7}$.0$^{9,14}$]-pentadeca-2,4,6,9(14),10,12-hexaene-4-carboxamide,
(1S,8R)-11,12-diethyl-N-({4-[N'-hydroxycarbamimidoyl]phenyl}methyl)-15-oxatetracyclo[6.6.1.0$^{2,7}$.0$^{9,14}$]pentadeca-2,4,6,9(14),10,12-hexaene-4-carboxamide,
(1S,8R)-11,12-diethyl-N-({4-[N'-methoxycarbamimidoyl]phenyl}methyl)-15-oxatetracyclo[6.6.1.0$^{2,7}$.0$^{9,14}$]pentadeca-2,4,6,9(14),10,12-hexaene-4-carboxamide,
(1S,8R)—N-[(4-carbamimidoylphenyl)methyl]-11,12-dicyclopropyl-15-oxatetracyclo-[6.6.1.0$^{2,7}$.0$^{9,14}$]pentadeca-2,4,6,9,11,13-hexaene-4-carboxamide,
(1S,8R)-11,12-dicyclopropyl-N-({4-[N'-hydroxycarbamimidoyl]phenyl}methyl)-15-oxatetracyclo[6.6.1.0$^{2,7}$.0$^{9,14}$]pentadeca-2,4,6,9,11,13-hexaene-4-carboxamide, or
(1S,8R)-11,12-dicyclopropyl-N-({4-[N'-methoxycarbamimidoyl]phenyl}methyl)-15-oxatetracyclo[6.6.1.0$^{2,7}$.0$^{9,14}$]pentadeca-2,4,6,9,11,13-hexaene-4-carboxamide, or
an (E) or (Z) isomer thereof,
or a pharmaceutically acceptable salt of any of the foregoing compounds.

In another embodiment the compound selected from:
(1R,8S)—N-[(4-carbamimidoylphenyl)methyl]-12-(2-fluorophenyl)-15-oxatetracyclo-[6.6.1.0$^{2,7}$.0$^{9,14}$]pentadeca-2,4,6,9,11,13-hexaene-4-carboxamide;
(1R,8S)—N-[(4-carbamimidoylphenyl)methyl]-12-(4-fluorophenyl)-15-oxatetracyclo-[6.6.1.0$^{2,7}$.0$^{9,14}$]pentadeca-2,4,6,9,11,13-hexaene-4-carboxamide;
(1R,8S)—N-[(4-carbamimidoylphenyl)methyl]-12-(2,4-difluorophenyl)-15-oxatetracyclo-[6.6.1.0$^{2,7}$.0$^{9,14}$]pentadeca-2,4,6,9,11,13-hexaene-4-carboxamide;
(1R,8S)-12-(2,4-difluorophenyl)-N-{[4-(N'-hydroxycarbamimidoyl)phenyl]methyl}-15-oxatetracyclo[6.6.1.0$^{2,7}$.0$^{9,14}$]pentadeca-2,4,6,9,11,13-hexaene-4-carboxamide;
(1R,8S)-12-(2-fluorophenyl)-N-{[4-(N'-hydroxycarbamimidoyl)phenyl]methyl}-15-oxatetracyclo[6.6.1.0$^{2,7}$.0$^{9,14}$]pentadeca-2,4,6,9,11,13-hexaene-4-carboxamide;
(1R,8S)-12-(2,4-difluorophenyl)-N-{[4-(N'-methoxycarbamimidoyl)phenyl]methyl}-15-oxatetracyclo[6.6.1.0$^{2,7}$.0$^{9,14}$]pentadeca-2,4,6,9,11,13-hexaene-4-carboxamide;
(1R,8S)-12-(2-fluorophenyl)-N-{[4-(N'-methoxycarbamimidoyl)phenyl]methyl}-15-oxatetracyclo[6.6.1.0$^{2,7}$.0$^{9,14}$]pentadeca-2,4,6,9,11,13-hexaene-4-carboxamide;
(1R,8S)-12-(4-fluorophenyl)-N-{[4-(N'-methoxycarbamimidoyl)phenyl]methyl}-15-oxatetracyclo[6.6.1.0$^{2,7}$.0$^{9,14}$]pentadeca-2,4,6,9,11,13-hexaene-4-carboxamide;
(1R,8S)—N-[(4-carbamimidoyl-2-fluorophenyl)methyl]-12-(2-fluorophenyl)-15-oxatetra-cyclo[6.6.1.0$^{2,7}$.0$^{9,14}$]pentadeca-2,4,6,9,11,13-hexaene-4-carboxamide;
(1R,8S)—N-[(4-carbamimidoyl-2-fluorophenyl)methyl]-12-(4-fluorophenyl)-15-oxatetra-cyclo[6.6.1.0$^{2,7}$.0$^{9,14}$]pentadeca-2,4,6,9,11,13-hexaene-4-carboxamide;
(1R,8S)—N-{[2-fluoro-4-(N'-hydroxycarbamimidoyl)phenyl]methyl}-12-(2-fluoro-phenyl)-15-oxatetracyclo[6.6.1.0$^{2,7}$.0$^{9,14}$]pentadeca-2,4,6,9,11,13-hexaene-4-carboxamide;
(1R,8S)—N-{[2-fluoro-4-(N'-methoxycarbamimidoyl)phenyl]methyl}-12-(2-fluoro-phenyl)-15-oxatetracyclo[6.6.1.0$^{2,7}$.0$^{9,14}$]pentadeca-2,4,6,9,11,13-hexaene-4-carboxamide;
(1R,8S)-12-(2,4-difluorophenyl)-N-{[4-(N'-ethoxycarbamimidoyl)phenyl]methyl}-15-oxatetracyclo[6.6.1.0$^{2,7}$.0$^{9,14}$]pentadeca-2,4,6,9,11,13-hexaene-4-carboxamide;
(1R,8S)—N-({4-[N'-ethoxycarbamimidoyl]phenyl}methyl)-12-(4-fluorophenyl)-15-oxatetracyclo[6.6.1.0$^{2,7}$.0$^{9,14}$]pentadeca-2,4,6,9,11,13-hexaene-4-carboxamide;
tert-butyl N-[1-amino[4-({[(1R,8S)-12-(4-fluorophenyl)-15-oxatetracyclo-[6.6.1.0$^{2,7}$.0$^{9,14}$]-pentadeca-2,4,6,9,11,13-hexaen-4-yl]formamido}methyl)phenyl]-methylidene]carbamate; or
(1R,8S)—N-{[2-fluoro-4-(N'-methoxycarbamimidoyl)phenyl]methyl}-12-(4-fluoro-phenyl)-15-oxatetracyclo[6.6.1.0$^{2,7}$.0$^{9,14}$]pentadeca-2,4,6,9,11,13-hexaene-4-carboxamide;
or an E or Z isomer thereof;
or a pharmaceutically acceptable salt of any of the foregoing compounds.

In yet another embodiment the compound is selected from:
(1S,8R)-11,12-dicyclopropyl-N-({4-[N'-methoxycarbamimidoyl]phenyl}methyl)-15-oxatetra-cyclo[6.6.1.0$^{2,7}$.0$^{9,14}$]pentadeca-2,4,6,9,11,13-hexaene-4-carboxamide;

(1S,8R)-11,12-dicyclopropyl-N-({4-[N'-hydroxycarbamim-idoyl]phenyl}methyl)-15-oxatetra-cyclo[6.6.1.0$^{2,7}$.0$^{9,14}$]pentadeca-2,4,6,9,11,13-hexaene-4-carboxamide;

(1S,8R)—N-[(4-carbamimidoylphenyl)methyl]-11,12-dicyclopropyl-15-oxatetracyclo-[6.6.1.0$^{2,7}$.0$^{9,14}$]pentadeca-2,4,6,9,11,13-hexaene-4-carboxamide;

(1R,8S)-12-cyclopropyl-N-{[4-(N'-hydroxycarbamimidoyl)phenyl]methyl}-15-oxatetra-cyclo[6.6.1.0$^{2,7}$.0$^{9,14}$]pentadeca-2,4,6,9,11,13-hexaene-4-carboxamide;

(1R,8S)-12-cyclopropyl-N-{[4-(N-ethoxycarbamimidoyl)phenyl]methyl}-15-oxatetra-cyclo[6.6.1.0$^{2,7}$.0$^{9,14}$]pentadeca-2,4,6,9,11,13-hexaene-4-carboxamide;

methyl N-[1-amino[4-({[(1R,8S)-12-cyclopropyl-15-oxa-tetracyclo-[6.6.1.0$^{2,7}$.0$^{9,14}$]-pentadeca-2,4,6,9,11,13-hexaen-4-yl]formamido}methyl)-phenyl]methylidene]carbamate;

(1R,8S)-12-cyclopropyl-N-({4-[N'-methoxycarbamim-idoyl]phenyl}methyl)-15-oxatetracyclo[6.6.1.0$^{2,7}$.0$^{9,14}$]pentadeca-2,4,6,9,11,13-hexaene-4-carboxamide; or (1R,8S)—N-[(4-carbamimidoylphenyl)methyl]-12-cyclopropyl-15-oxatetracyclo-[6.6.1.0$^{2,7}$.0$^{9,14}$]pentadeca-2,4,6,9,11,13-hexaene-4-carboxamide; or an E or Z isomer thereof;

or a pharmaceutically acceptable salt of any of the foregoing compounds.

In yet another embodiment the compound is selected from:

(1S,8R)-11,12-diethyl-N-({4-[N'-methoxycarbamimidoyl]phenyl}methyl)-15-oxatetra-cyclo[6.6.1.0$^{2,7}$.0$^{9,14}$]pentadeca-2,4,6,9(14), 10, 12-hexaene-4-carboxamide;

(1S,8R)-11,12-diethyl-N-({4-[N'-hydroxycarbamimidoyl]phenyl}methyl)-15-oxatetra-cyclo[6.6.1.0$^{2,7}$.0$^{9,14}$]pentadeca-2,4,6,9(14),10,12-hexaene-4-carboxamide; or (1S,8R)—N-[(4-carbamimidoylphenyl)methyl]-11,12-diethyl-15-oxatetracyclo-[6.6.1.0$^{2,7}$.0$^{9,14}$]pentadeca-2,4,6,9(14),10,12-hexaene-4-carboxamide;

or an E or Z isomer thereof;

In one embodiment, the compound provided or utilized herein excludes:

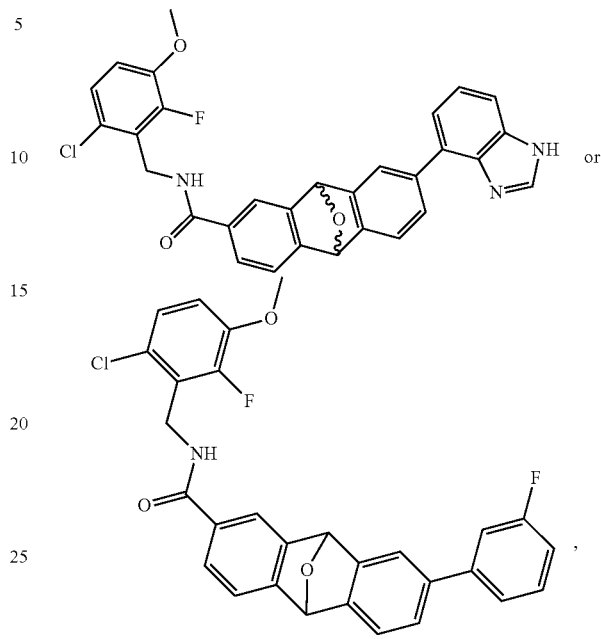

or a pharmaceutically acceptable salt therein.

The compounds provided herein include a pure enantiomer, a substantially pure enantiomer (containing e.g., 6-99%, or 80-99% of an enantiomer), or a mixture of enantiomers and diasteroisomers such as regioisomers. For example and without limitation, the following scheme illustrates how a mixture of 4 compounds is a mixture of 2 regio- and 2 stereoisomers; a racemate is a mixture of 2 enantiomers.

General Synthetic Scheme

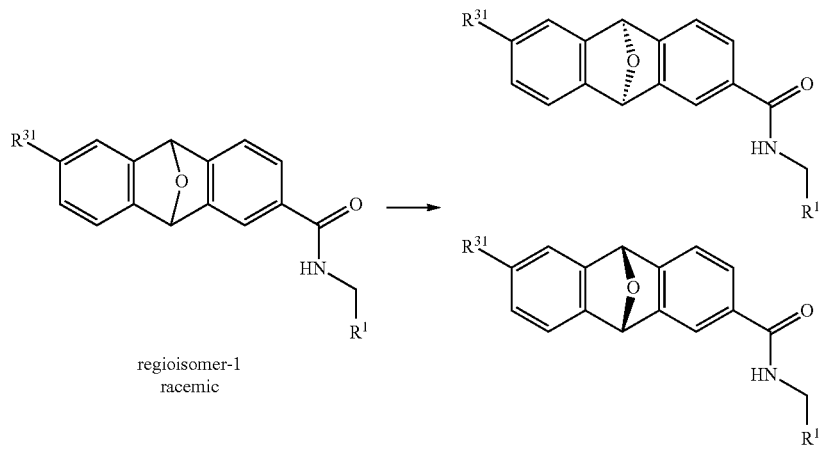

regioisomer-1
racemic

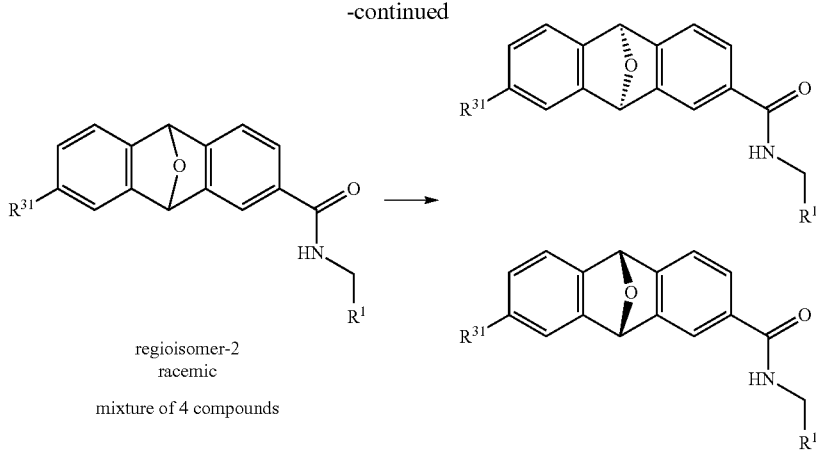

regioisomer-2
racemic mixture of 4 compounds

Compounds of this disclosure can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this disclosure can be synthesized, and various modifications to these schemes can be made and will be suggested to one skilled in the art reading this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., such as from about 0° C. to about 125° C. and further such as at about room (or ambient) temperature, e.g., about 20° C. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

Compounds of Formula (I) where A is a bond and B is O, $NCOR^b$, $NCONHR^c$, or $CR^8R^9$, or A is $NR^a$ and B is a bond, $R^3$ and $R^4$ together with the carbon they are attached to form C=O; $R^2$ and $R^7$ together with the atoms to which they are attached form ring D where ring D is aryl or heteroaryl, and ring C, $R^5$, $R^6$, Z, $X^1$, $R^1$, $R^a$, $R^b$, $R^c$, $R^8$, $R^9$, $R^{30}$ and $R^{31}$ are as defined in the Summary, can be prepared by the following procedure described in Scheme 1 below.

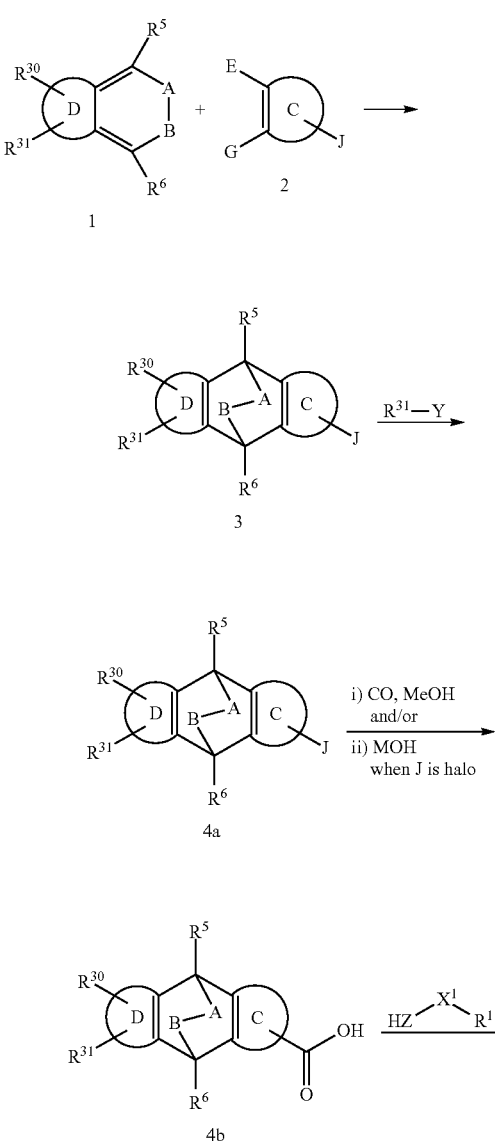

Scheme 1

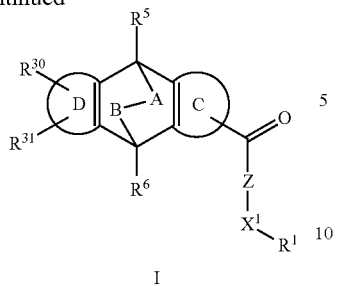

I

Reaction of a compound of formula 1, where $R^{31}$ is H or halo, with a compound of formula 2 where C is aryl, heteroaryl, cycloalkenyl, or heterocyclyl, one of E and G is halo or TMS, and the other of E and G is halo, $I^+(^-OSO_2CF_3)Ph$ or $—OSO_2-Q^1$ (where $Q^1$ is tolyl, 4-chlorophenyl or $CF_3$), and J is halo or $C(=O)OMe$, in the presence of either $TBAF$, nBuLi, or iPrMgCl in a suitable halogenated or ether organic solvent such as dichloromethane (DCM), tetrahydrofuran (THF) or diethyl ether ($Et_2O$) provides a tricyclic, bridged compound of formula 3. Compounds of formula 2 such as 1,2,4-trichlorobenzene, 4-bromo-1,2-dichlorobenzene, 2,4-dichloro-1-fluorobenzene, methyl 4-(((trifluoromethyl)sulfonyl)-oxy)-3-(trimethylsilyl)benzoate, 5-bromo-6-chloro-3-pyridinecarboxylic acid methyl ester and methyl 2-oxo-2H-pyran-5-carboxylate are commercially available. Compounds of formula 1 such as 5-bromoisobenzofuran and tert-butyl-(isobenzofuran-5-yl-methoxy)dimethylsilane are commercially available or can be prepared from commercially available compounds according to procedures known to those skilled in the art. Some such procedures are shown in methods (a) and (b) below.

formula 6 where A is a bond and B is O, $NCOR^b$, $NCONHR^c$, or $CR^8R^9$ or A is $NR^a$ and B is a bond, and $R^5$, $R^6$, $R^a$, $R^b$, $R^c$, $R^{30}$ and $R^{31}$ are as defined above in the presence of a base such as nBuLi in solvents such as THF or toluene (PhMe) at temperatures ranging from −30 to 0° C. provides a compound of formula 7. Compounds of formula 5 such as 2,3,5-trichloro-pyridine, 3,4-dichloro-toluene, 4-bromo-3-iodoanisole, 1-bromo-2-iodo-4,5-(methylenedioxy)benzene, 1-bromo-2-fluoro-4-nitrobenzene, 6-fluoro-7-chloro-isoquinoline and compounds of formula 6 such as furan, pyrrole, N-methylpyrrole, 2-methylfuran, 2,5-dimethylfuran are commercially available or they can be prepared by procedures known to those who are skilled in the art. Reaction of a compound of formula 7 with compound 8 in solvents such as DCM, $Et_2O$, or THF at refluxing temperatures provides a compound of formula 1. Typically, compounds of formula 1 are not isolated but are kept as a solution in the solvent in which they were prepared and are used, as soon as they are prepared, directly in the first step described in Scheme 1.

Compounds of formula 1 where $R^5$ and $R^6$ are both hydrogen, A is a bond, B is oxygen, and ring D, $R^{30}$ and $R^{31}$ are as defined above, can be prepared as shown in Method (b) below.

Method (b)

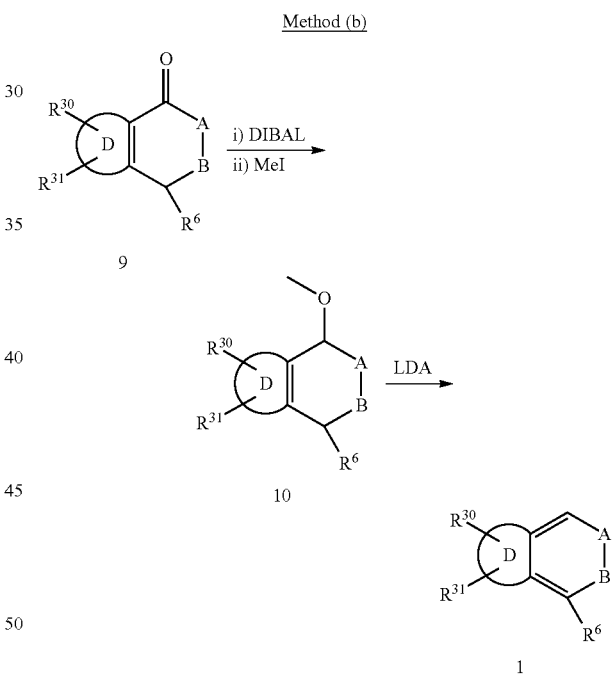

Method (a)

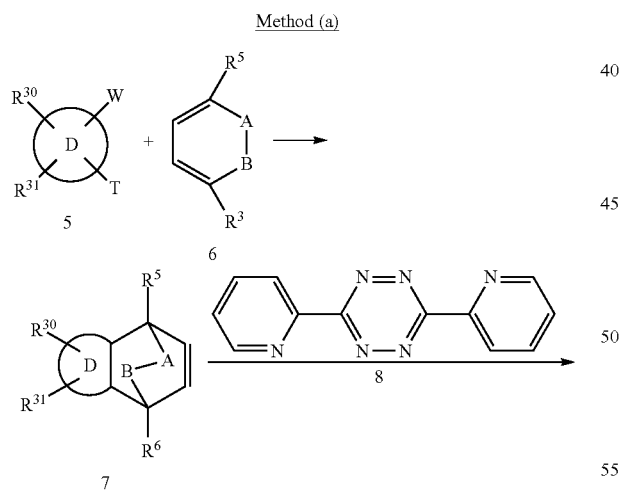

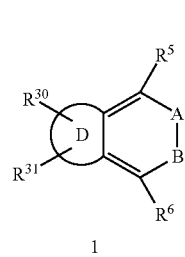

1

Reaction of compound 5 where D is aryl or heteroaryl, W and T are independently H or halo, with a compound of Reduction of the keto group in compound 9 with a suitable reducing agent such as diisobutyl aluminum hydride in solvents such as DCM or PhMe, followed by treatment with methyl iodide provides a compound of formula 10. Compounds of formula 9 such as 5,7-dimethoxyphthalide, 5-bromo-4-methylisobenzofuran-1 (3H)-one, 4,7-dimethylphthalide, and 5-(tert-butyl)-7-methylisobenzofuran-(3H)-one are available from commercial sources or can be prepared by procedures known to those who are skilled in the art. Treatment of compound 10 with a strong organic base such as LDA in an aprotic organic solvent such as tetrahydrofuan provides a compound of formula 1.

Compounds of formula 4a where $R^{31}$ is other than hydrogen or halo can be synthesized by methods well-known in the art. For example compounds of formula 3 where either or both of $R^{30}$ and $R^{31}$ are halo can be reacted with compounds of formula $R^{31}$—Y where Y is $B(OH)_2$, and $R^{31}$ is $C_1$-$C_6$alkyl, $C_1$-$C_6$haloalkyl, $C_1$-$C_6$haloalkoxy, hydroxy$C_1$-$C_6$alkyl, $C_1$-$C_6$alkoxy$C_1$-$C_6$alkyl, $C_3$-$C_6$cycloalkyl, mono or bicyclic aryl, mono or bicyclic heteroaryl, mono or bicyclic heterocyclyl, fused heterocyclyl, mono or bicyclic aryl$C_1$-$C_6$alkyl, mono or bicyclic heteroaryl$C_1$-$C_6$alkyl mono or bicyclic heterocyclyl$C_1$-$C_6$alkyl (wherein the alkylene chain in aryl$C_1$-$C_6$alkyl, heteroaryl$C_1$-$C_6$alkyl or heterocyclyl$C_1$-$C_6$alkyl is optionally substituted with deuterium), spiro heterocycloamino, bridged heterocycloamino (as in 2,4,6-trifluoroboronic acid, 3,5-bis(trifluoromnethyl)-phenylboronic acid, (2,6-dichloropyridin-3-yl)boronic acid, or 2-methoxy-3-quinolin-3-ylboronic acid), under common literature coupling conditions such as treatment with a Pd catalyst such as [1,1'-bis(diphenylphosphino)-ferrocene]-dichloro-palladium(II) in the presence of a based such as cesium carbonate in a mixed solvent system such as methanol in 1,4-dioxane at 80° C., to provide compounds of formula 4a.

In addition, compounds of formula 3 where either or both of $R^{30}$ and $R^{31}$ are halo can be reacted with compounds of formula $R^{31}$—Y where Y is OH, SH, or $NH_2$ and $R^{31}$ is as defined above (as in 4-tert-butylphenol, 5-methyl-2-(1-methylethyl)phenol, 3-chlorobenzenethiol or 2,4-dimethylthiophenol, o-toluidine, 3-chloro-4-fluorophenylamine or 1-methyl-2-aminopyrrole), under common literature coupling conditions such as treatment with copper(I) bromide in the presence of 2,5-pentanedione and potassium carbonate in a solvent such as DMF at temperatures ranging from 80 to 130° C. or treatment with sodium tert-butoxide and palladium (II) acetate in the presence of a suitable ligand such as (R)-1-[(SP)-2-(dicyclohexylphosphino)-ferrocenyl]-ethyldi-tert-butylphosphine (Di-tert-butyl-Josiphos), in a solvent such as dimethoxy ethane (DME) at 100° C. or treatment with cesium carbonate and tris(dibenzylideneacetone)-dipalladium(0) ($Pd_2(dba)_3$) in the presence of a suitable ligand such as 4,5-bis(diphenyl-phosphino)-9,9-dimethylxanthene (Xantphos), in a solvent such as PhMe at 100° C. to provide compounds of formula 4a.

Furthermore, compounds of formula 3 where either or both of $R^{30}$ and $R^{31}$ are halo can be reacted with compounds of formula $R^{31}$—Y where Y is H and $R^{31}$ is mono or bicyclic heteroaryl, mono or bicyclic heterocyclyl, fused heterocyclyl, spiro heterocycloamino, bridged heterocycloamino, —$NR^{32}R^{33}$ or —$NR^{43}C(=O)R^{44}$; where $R^{32}$, $R^{33}$, $R^{43}$, and $R^{44}$ are independently, $C_1$-$C_6$alkyl, or $R^{32}$ and $R^{33}$ or $R^{41}$ and $R^{42}$ together with the nitrogen atom they are bonded to form heterocycloamino (as piperidin-2-one, (2S)-2-(methoxymethyl)-1-pyrrolidine, 1,2,3,4-tetrahvdroisoquinoline, 3-methyl-1H-pyrazole or 1H-pyrazolo[3,4-b]pyridine), under common literature coupling conditions such as treatment with copper (I) iodide and potassium carbonate in the presence of $N^1,N^2$-dimethylethane-1,2-diamine, in a solvent such as PhMe at 95° C., or treatment with cesium carbonate and $Pd_2(dba)_3$, in the presence of a suitable ligand such as 2-dicyclohexylphosphino-2',4',6'-triisopropylbiphenyl (XPhos), in a solvent such as DMF at 120° C. to provide compounds of formula 4a.

Compounds of formula 4b are prepared from compounds of formula 4a by methods well known in the art. For example, when J is C(=O)OMe, hydrolysis with a metal hydroxide (M-OH in scheme 1 where M is Li, K, or Na) in a mixed solvent system such as THF and methanol (MeOH) or THF and water at temperatures ranging from 20 to 60° C. generates carboxylic acids of formula 4b. When J is a halogen, carbonylation of 4a under well-known methods such as treatment with catalytic amounts of palladium (II) acetate and Xantphos (vide supra) in the presence of triethylamine ($Et_3N$) in a mixed solvent system such as methanol in 1,4-dioxane at 80° C., under an atmosphere of carbon monoxide (CO) provides a methyl carboxylate intermediate which can then be hydrolyzed under conditions described above, to provide carboxylic acids of formula 4b.

Coupling of an acid of formula 4b and a compound of formula HZ—$X^1$—$R^1$ then provides a compound of Formula (I). The reaction conditions depend on the nature of $R^3$, $R^4$, Z, $X^1$ groups. For example, compounds of Formula (I) where $R^3$ and $R^4$ together with the carbon they are attached to form C=O and Z is $NR^{13}$ can be prepared by reacting a compound of formula 4b where $R^3$ and $R^4$ together with the carbon they are attached to form C=O with a compound of formula $R^{13}NH$—$X^1$—$R^1$ in the presence of a coupling agent such as 1-[bis(dimethylamino)-methylene]-1H-1,2,3-triazolo[4,5-b]pyridinium 3-oxid hexafluorophosphate (HATU) and hydroxybenzotriazol (HOBt), or 1-ethyl-3-(3-dimethylaminopropyl)carbodiimide (EDCI) and HOBt, or benzotriazol-1-yl-oxytripyrrolidinophosphonium hexafluorophosphate (PyBOP) in an appropriate solvent such as dimethylformamide (DMF) at ambient temperature to provide a compounds of Formula (I).

It will be readily apparent to a person skilled in the art that compounds of Formula (I)

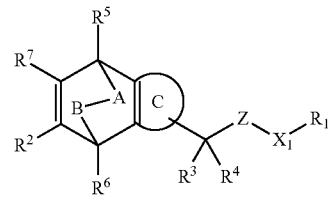

can be prepared as described above by replacing compound of formula 1 with a compound of formula 11

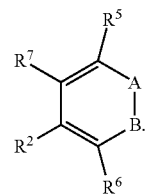

Compounds of formula 11 such as 3-phenylfuran, 3,4-dimethoxyfuran, 3-bromo-1-(triisopropylsilyl)pyrrole, 1-[1-(benzenesulfonyl)-1H-pyrrol-3-yl]ethanone are available from commercial sources or can be prepared by methods known to those who are skilled in the art. Other compounds can be prepared following methods known in the art, or by adapting methods known in the art or provided herein.

Pharmaceutical Compositions

In further aspects of the application, provided is a pharmaceutical composition comprising a compound of Formula (I), (A1) or (B1) (and embodiments thereof disclosed herein) as provided herein or a pharmaceutically acceptable salt thereof, and at least one pharmaceutically acceptable excipient.

The compositions disclosed herein may be used in conjunction with any of the vehicles and excipients commonly employed in pharmaceutical preparations, e.g., talc, gum arabic, lactose, starch, magnesium stearate, cocoa butter, aqueous or non-aqueous solvents, oils, paraffin derivatives, glycols, etc. Coloring and flavoring agents may also be added to preparations, particularly to those for oral administration. Solutions can be prepared using water or physiologically compatible organic solvents such as ethanol, 1,2-propylene glycol, polyglycols, dimethylsulfoxide, fatty alcohols, triglycerides, partial esters of glycerin and the like.

Solid pharmaceutical excipients include starch, cellulose, hydroxypropyl cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc.

The concentration of the excipient is one that can readily be determined to be effective by those skilled in the art, and can vary depending on the particular excipient used. The total concentration of the excipients in the solution can be from about 0.001% to about 90% or from about 0.001% to about 10%.

The concentration of compounds provided herein and/or utilized herein can be from about 1 to about 99% by weight in the pharmaceutical compositions provided herein. In certain embodiments, the concentration of compounds provided herein and/or utilized herein in the pharmaceutical composition is about 5% by weight, or alternatively, about 10%, or about 20%, or about 1%, or about 2%, or about 3%, or about 4%, or about 6%, or about 7%, or about 8%, or about 9%, or about 11%, or about 12%, or about 14%, or about 16%, or about 18%, or about 22%, or about 25%, or about 26%, or about 28%, or about 30%, or about 32%, or about 34%, or about 36%, or about 38%, or about 40%, or about 42%, or about 44%, or about 46%, or about 48%, or about 50%, or about 52%, or about 54%, or about 56%, or about 58%, or about 60%, or about 64%, or about 68%, or about 72%, or about 76%, or about 80% by weight. About as used herein means±10% of specific value provided above.

Compounds and pharmaceutical compositions disclosed herein may be used alone or in combination with other compounds. When administered with another agent, the co-administration can be in any manner in which the pharmacological effects of both are manifest in the patient at the same time. Thus, co-administration does not require that a single pharmaceutical composition, the same dosage form, or even the same route of administration be used for administration of a compound disclosed herein and the other agent or that the two agents be administered at precisely the same time. However, co-administration will be accomplished most conveniently by the same dosage form and the same route of administration, at substantially the same time. Obviously, such administration most advantageously proceeds by delivering both active ingredients simultaneously in a novel pharmaceutical. In some embodiments, a compound provided herein can be used as an adjunct to conventional drug therapy of the conditions described herein.

Pharmaceutical compositions can be formulated for different routes of administration, including oral delivery and other routes such as intravenous, intraarterial, pulmonary, rectal, nasal, vaginal, lingual, intramuscular, intraperitoneal, intracutaneous, transdermal, intracranial, and subcutaneous routes. Other dosage forms include tablets, capsules, pills, powders, aerosols, suppositories, parenterals, and oral liquids, including suspensions, solutions and emulsions. All dosage forms may be prepared using methods that are standard in the art (see e.g., Remington's Pharmaceutical Sciences, $22^{th}$ ed., 2012, ISBN 978 0 85711 062 6).

Utility

In another aspect, this application provides a method for inhibiting plasma kallikrein activity in a subject, the method comprising administering to the subject an effective amount of a compound or a pharmaceutical composition provided herein.

Kallikrein inhibitors are contemplated to have clinical utility in disease states such as hereditary angioedema (HAE), diabetic retinopathy, macular edema and other inflammatory disorders. The contact pathway of blood coagulation, leading to kallikrein production, is activated during acute episodes of swelling of face, extremities, larynx and gastrointestinal tract in HAE patients. Blisters formed during attacks contain high levels of kallikrein which mediates a potent inflammatory response via bradykinin formation. HAE patients are genetically deficient in the physiologic inhibitor of plasma kallikrein (C1 inhibitor) or have a dysfunctional C1 inhibitor or F12 gene mutations and cannot suppress the enzyme's catalytic activity. An oral kallikrein inhibitor is contemplated to provide benefit during both acute attacks and in prophylactic suppression of bradykinin production in HAE patients. Angioedema induced by treatment with angiotensin-converting-enzyme (ACE) inhibitors accounts for one third of angioedema cases in the emergency room. The largest groups of patients with drug induced angioedema are those treated with ACE inhibitors; kallikrein inhibitors are contemplated to be useful for treating this patient population.

Plasma kallikrein are contemplated to have implications in disorders such as (HAE) (see Nzeako et al., Arch Intern Med., 161, 2417-2429, 2001), retinopathy or diabetic retinopathy (see A. C. Clermont et al, Abstract 5035-0883, ARVO 2010, Fort Lauderdale, Fla.), proliferative and non-proliferative retinopathy, diabetic macular edema (DME), clinically significant macular edema (CSME), cystoid macular edema (CME), CME following cataract extraction, CME induced by cryotherapy, CME induced by uveitis, CME following vascular occlusion (e.g. central retina vein occlusion, branch retinal vein occlusion, or hemiretinal vein occlusion), retinal edema, complications related to cataract surgery in diabetic retinopathy, hypertensive retinopathy (see J. A. Phipps et al, Hypertension, 53, 175-181, 2009), retinal trauma, dry and wet aged-related macular degeneration (AMD), ischemic reperfusion injuries (see C. Storoni et. al., JPET, 318, 849-954, 2006), e.g. in all kind of contexts associated with tissue and/or organ transplantation, surgically-induced brain injury, focal cerebral ischemia, global cerebral ischemia, glioma-associated edema, spinal cord injury, pain, ischemia, focal brain ischemia, neurological and cognitive deficits, deep vein thrombosis, stroke, myocardial infarction, acquired angioedema drug-related (ACE-inhibitors), high altitude cerebral edema, cytotoxic cerebral edema, osmotic cerebral edema, obstructive hydrocephalus, radiation induced edema, lymph edema, traumatic brain injury, hemorrhagic stroke (e.g., cerebral stroke or subarachnoid stroke), intracerebral hemorrhage, cerebral trauma associate with injury or surgery, brain aneurysm, arteriovenous malformation, reduction of blood losses during surgical procedures (e.g. cardiothoracic surgery, such as cardiopulmonary bypass or coronary artery bypass grafting)

or insertion of left ventricular assist device (LVAD), blood coagulation disorders such as thrombosis, itch, disorders with an inflammation component (such as multiple sclerosis), epilepsy, encephalitis, Alzheimer's disease, excessive daytime sleepiness, essential hypertension, increased blood pressure associated with diabetes or hyperlipidemia, renal insufficiency, chronic kidney disease, heart failure, microalbuminuria, albuminuria, proteinuria, disorders associated with increased vascular permeability (e.g. increased retinal vascular permeability, increased leg, feet, ankle vascular permeability), coagulation from post fibrinolytic treatments, angina, angioedema, sepsis, arthritis (e.g. rheumatoid arthritis, osteoarthritis, infection arthritis), lupus, gout, psoriasis, inflammatory bowel, diabetes, diabetic complications, infectious diseases, Parkinson's disease, amyotrophic lateral sclerosis, Creutzfeld-Jacob disease, stroke, epilepsy and trauma (e.g. brain trauma).

In some embodiments, plasma kallikrein inhibitors are contemplated to be useful in the treatment of a wide range of disorders implicating plasma kallikrein, in particular retinopathy or edema-associated diseases, such as hereditary angioedema, diabetes macular edema, macular edema and brain edema.

In some embodiments, plasma kallikrein inhibitors are considered to be useful in the treatment of retinopathy, e.g. retinopathy associated with diabetes and/or hypertension.

Kallikrein inhibitors are contemplated to be suitable for use in amelioration of hyperglycemia induced retinopathy and related inflammatory disorders.

Plasma kallikrein inhibitors are contemplated to be especially useful in the treatment of hereditary angioedema. In other embodiments, plasma kallikrein inhibitors are contemplated to be especially useful in the treatment of edema formation in diseases, e.g. edema formation related to ischemic reperfusion injuries. In other embodiments, plasma kallikrein inhibitors are contemplated to be especially useful in the treatment of macular edema, e.g. macular edema associated with diabetes and/or hypertension.

In other embodiments, plasma kallikrein inhibitors are contemplated to be especially useful in the prevention and treatment of thrombosis. In other embodiments, plasma kallikrein inhibitors are contemplated to be especially useful in the treatment of intracerebral hemorrhage induced by hyperglycemia in diabetic patients. In other embodiments, plasma kallikrein inhibitors are contemplated to be especially useful in the treatment of retinal vascular permeability induced by angiotensin in hypertensive patients.

The compounds disclosed herein are also useful in the treatment of impaired visual acuity, diabetes, pancreatitis, cerebral hemorrhage, nephropathy, cardiomyopathy, neuropathy, inflammatory bowel disease, arthritis, inflammation, septic shock, cancer, or ARDS.

In some embodiments of the method for treatment, upon administration to the patient, a therapeutically effective amount of a compound provided herein, reduces protease activity, such as kallikrein activity, for up to 12, 24, 26 or 48 hours after administration.

Routes of administration refer to the method for administering a compound of Formula (I) or a composition thereof to a mammal. Administration can be achieved by a variety of methods. These include but are not limited to oral, subcutaneous, intravenous, transdermal, or sublingual, administration or by intraperitoneal injection.

In certain aspects, the methods described herein relate to administering the compound provided herein in vitro. In other aspects the administration is in vivo. In yet other aspects, the in vivo administration is to a mammalian patient. Mammals include but are not limited to humans and common laboratory research animals such as, for example, mice, rats, dogs, pigs, cats, and rabbits.

EXAMPLES

Synthetic Procedures

Reference 1

Synthesis of 5-bromoisobenzofuran (INT-1)

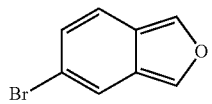

Step 1:
To a stirred solution of 5-bromo-2-benzofuran-1(3H)-one (12.60 g; 59.15 mmol; 1 eq.) in dichloromethane (591 mL) cooled to −78° C. was added DIBAL (59.15 ml; 1 mol/l; 59.15 mmol; 1 eq.) (1 M solution in toluene) dropwise and the mixture was stirred at −78° C. After 60 minutes, approximately 10% more DIBAL solution was added (6 mL) and the reaction left for additional 30 minutes. Before proceeding with the work up, celite was added to the reaction mix, followed up with addition of water (2.64 mL), then 15% NaOH (2.64 mL) and water (6.6 mL). The reaction mix was removed from bath and left to reach RT, then stirred at RT for 40 min before filtering it over celite. The filtered solution was dried over $Na_2SO_4$, filtered and concentrated to dryness to give 5-bromo-1,3-dihydro-2-benzofuran-1-ol as a white solid. Partial Yield: ~10.0 g. The celite cake was transferred to a round bottom flask and stirred with DCM for 30 minutes, filtered and dried over $Na_2SO_4$; filtered again and concentrated to give additional 1.3 g of product and a total of 11.3 g were obtained (~89% yield).

Step 2:
Sodium hydride (2.41 g; 60.16 mmol; 1.25 eq.) was suspended in THF (600 mL) and the mixture was cooled to 0° C. in an ice bath. A solution of 5-bromo-1,3-dihydro-2-benzofuran-1-ol (10.35 g; 48.13 mmol; 1 eq.) in THF (200 mL) was added slowly to the suspension and the resulting mixture was stirred for 30 minutes. Iodomethane (14.98 mL; 240.65 mmol; 5 eq.) was added over a 5 minute period and the mixture was allowed to warm to RT. After stirring overnight, the reaction mixture was quenched with ice water and extracted with diethyl ether. The aqueous layer was back extracted once and the combined organics were washed with brine, then dried over $MgSO_4$, filtered and concentrated. The crude material was purified on a silica gel column using 0-10% EtOAc in heptane to give the desired product as clear oil which solidified under high vacuum to give 5-bromo-1-methoxy-1,3-dihydro-2-benzofuran 9.0 g (78%).

Step 3:
To a solution of 5-bromo-1-methoxy-1,3-dihydro-2-benzofuran (12.15 g; 53.04 mmol; 1 eq.) in diethyl ether (200 mL) cooled to 0° C. was added commercial 2M LDA solution in THF/heptane/ethylbenzene (79.56 mL; 2 mol/l; 159.12 mmol; 3 eq.) dropwise. The reaction mix turned progressively dark brown and the dark cloudy mixture was stirred at 0° C. After 15-20 minutes, the reaction mix was diluted with diethyl ether and quenched with saturated solution of $NH_4Cl$. The organic layer was isolated and the aqueous layer was back extracted with ether. The combined organics were dried over Na₂SO₄, filtered and concentrated to give 5-bromoisobenzofuran (100%) which was used directly for the next reaction.

Alternate Synthesis:

Step 1:

Into a 5-L 3-necked round-bottom flask purged and maintained with an inert atmosphere of nitrogen, was placed a solution of 1,4-dibromo-2-fluorobenzene (600.0 g, 2.38 mol, 1.00 equiv) and furan (485.7 g, 7.14 mol, 3.00 equiv) in toluene (1.8 L) with stirring at ~30° C., followed by the drop-wise addition of n-BuLi (2.5 mol/L; 952 mL, 2.38 mol, 1.00 equiv) over a period of 10 min at −30° C. The resulting solution was stirred for an additional 30 min at room temperature then it was quenched with water. The resulting mixture was extracted with ethyl acetate and washed with H₂O. The organic layers were combined and dried over anhydrous sodium sulfate and concentrated under vacuum. The residue was purified by a silica gel column eluting with ethyl acetate/petroleum ether (1:10) o deliver 336.0 g (1.51 mol, 63.3%) of (±) 4-bromo-11-oxatricyclo[6.2.1.0$^{2,7}$]-undeca-2,4,6,9-tetraene as a yellow solid.

Step 2:

Into a 3-L 3-necked round-bottom flask purged and maintained with an inert atmosphere of nitrogen, was placed a solution of (±) 4-bromo-11-oxatricyclo[6.2.1.0$^{2,7}$]undeca-2,4,6,9-tetraene (100.0 g, 448.3 mmol, 1.00 equiv) in dichloromethane (500 mL), followed by the addition of a solution of bis(pyridin-2-yl)-1,2,4,5-tetrazine (116.5 g, 493.2 mmol, 1.10 equiv) in dichloromethane (500 mL) dropwise with stirring at 0° C. over 5 min. The resulting solution was heated to reflux for 1 h then cooled to 0° C. and used directly in the synthesis of INT-3 below.

Reference 2

Synthesis of (5-(methoxycarbonyl)-2-(trimethylsilyl)phenyl)(phenyl)-iodonium triflate Salt (INT-2)

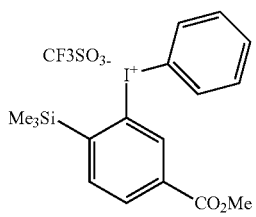 [SMILES: COC(=O)c1ccc([Si](C)(C)C)c([I+]c2ccccc2)c1]

Step 1:

In a screw-cap thick-wall reaction vessel, methyl 2-oxo-2H-pyran-5-carboxylate (4.00 g; 25.95 mmol; 1 eq.) and trimethyl[(trimethylsilyl)ethynyl]silane (13.27 g; 77.86 mmol; 3 eq.) were combined. The vessel was sealed and stirred in a metal sand bath at 200° C. After 24 h, the vessel was cooled, and the contents was adsorbed on to silica gel and purified by silica gel chromatography (ethyl acetate/hexanes gradient) to give methyl 3,4-bis(trimethylsilyl)benzoate (7.14 g) as a colorless oily residue.

Step 2:

In a round-bottom flask, (diacetoxyiodo)benzene (8.20 g; 25.45 mmol; 1 eq.) was dissolved in DCM (100 mL) and cooled in an ice bath. Trifluoromethanesulfonic acid (4.50 mL; 50.91 mmol; 2 eq.) was added slowly and the reaction was stirred for 30 m at 25° C. The reaction was then re-cooled in an ice bath and methyl 3,4-bis(trimethylsilyl) benzoate (7.14 g; 25.45 mmol; 1 eq.) dissolved in DCM (15 mL) was added. The reaction was stirred to 25° C. over 16 h. The solvent was evaporated and the residue was triturated and sonicated with diethyl ether (300 mL) to give (5-(methoxycarbonyl)-2-(trimethylsilyl)phenyl)(phenyl)iodonium trifluoromethanesulfonate (14.26 g) as a white solid.

Reference 3

Synthesis of (±) methyl 12-bromo-15-oxatetracyclo[6.6.1.0$^{2,7}$.0$^{9,14}$]pentadeca-2,4,6,9,11,13-hexaene-4-carboxylate and (±) methyl 11-bromo-15-oxatetracyclo[6.6.1.0$^{2,7}$.0$^{9,14}$]pentadeca-2,4,6,9,11,13-hexaene-4-carboxylate (INT-3)

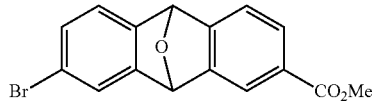

and

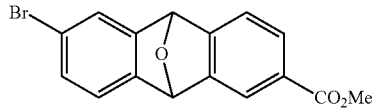

To a stirred solution of [5-(methoxycarbonyl)-2-(trimethylsilyl)phenyl]-(phenyl)iodanium trifluoromethanesulfonate (INT-2; 11.00 g; 19.63 mmol; 1 eq.) in dichloromethane (196 mL) at 0° C. was added a solution in ether of 5-bromo-2-benzofuran (INT-1, 10.44 g; 53 mmol; 2.7 eq.) over a 10 minute period. To this dark mixture was added tetrabutylammonium fluoride (25.52 mL; 1.00 mol/l; 25.52 mmol; 1.3 eq.) and the mixture was stirred at 0° C. LC/MS after 20 min showed formation of a single product (mass is consistent with desired product, Rt 1.03 min, MS+ 330/332. The mixture was diluted with water and extracted with DCM; the combined organics were dried over MgSO₄, filtered and concentrated to afford a dark oil. The crude material was purified by column chromatography eluting with 0-15% EtOAc in hexanes to provide a mixture of the title compounds. Regioisomers could not be isolated. Yield: 5.45 g (83%).

Reference 4

Separation of (±) methyl 12-bromo-15-oxatetracyclo[6.6.1.0$^{2,7}$.0$^{9,14}$]pentadeca-2,4,6,9,11,13-hexaene-4-carboxylate (INT-3a) and (±) methyl 11-bromo-15-oxatetracyclo[6.6.1.0$^{2,7}$.0$^{9,14}$]pentadeca-2,4,6,9,11,13-hexaene-4-carboxylate (INT-3b)

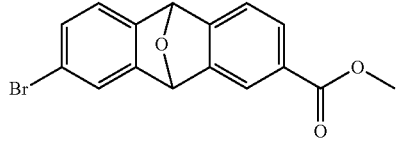

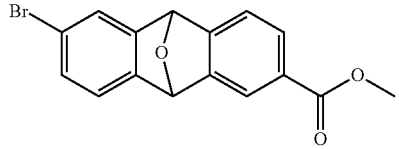

Step 1:

Sodium hydroxide (22.65 mL; 2.00 mol/L; 45.3 mmol; 15 eq.) was added to a solution of (±) methyl 12-bromo-15-oxatetracyclo[6.6.1.0$^{2,7}$.0$^{9,14}$]pentadeca-2,4,6,9,11,13-hexaene-4-carboxylate and (±) methyl 11-bromo-15-oxatetracyclo[6.6.1.0$^{2,7}$.0$^{9,14}$]pentadeca-2,4,6,9,11,13-hexaene-4-carboxylate (1000 mg; 3.02 mmol; 1 eq.) in acetonitrile (15.1 mL) and methanol (15.1 mL). The mixture was heated at 60° C. for 20 minutes and then cooled to RT. Organic solvents were removed under reduced pressure and the aqueous layer was washed with ethyl ether.

The aqueous layer was concentrated under reduced pressure to remove volatile organics. The remaining aqueous layer was cooled and kept at room temperature. White precipitates were collected by vacuum filtration and washed with small amount of cold water. After drying, (±) sodium 12-bromo-15-oxatetracyclo[6.6.1.0$^{2,7}$.0$^{9,14}$]pentadeca-2,4,6,9,11,13-hexaene-4-carboxylate (INT-5a) was obtained (0.4 g). The recrystallization process can be repeated until desired regioisomerical purity (e.g. 98%) was reached as analyzed by LC/MS. The filtrate contains (±) sodium 11-bromo-15-oxatetracyclo[6.6.1.0$^{2,7}$.0$^{9,14}$]pentadeca-2,4,6,9,11,13-hexaene-4-carboxylate (INT-5b).

Step 2:

To a mixture (±) sodium 12-bromo-15-oxatetracyclo[6.6.1.0$^{2,7}$.0$^{9,14}$]pentadeca-2,4,6,9,11,13-hexaene-4-carboxylate (INT-5a); 500 mg; 1.47 mmol; 1 eq.) and potassium carbonate (407 mg; 2.95 mmol; 2 eq.) in N,N-dimethylformamide (4.9 mL) was added iodomethane (0.18 mL; 2.95 mmol; 2 eq.). The mixture was heated to 50° C. for 1 h and cooled to RT. The reaction mixture was the diluted with water and extracted with ethyl ether. The combined organics were dried with MgSO$_4$, filtered, and concentrated to afford (±) methyl 12-bromo-15-oxatetracyclo[6.6.1.0$^{2,7}$.0$^{9,14}$]pentadeca-2,4,6,9,11,13-hexaene-4-carboxylate (INT-3a) as a white solid (488 mg; 99%). This methyl ester can be used directly for subsequent reactions without further purification. MS (M+H)$^+$ found for C$_{16}$H$_{11}$BrO$_3$: 331.2, 332. LC/MS conditions, Column: Phenomenex Kinetex F5, 150×4.6 mm; Solvent A: 0.1% TFA in Water; Solvent B: Acetonitrile; Flow Rate: 0.75 ml/min; 17 run time; 5-40% gradient solvent B.

Reference 5

Isolation of methyl (1S,8R)-12-bromo-15-oxatetracyclo[6.6.1.0$^{2,7}$.0$^{9,14}$]pentadeca-2,4,6,9,11,13-hexaene-4-carboxylate (INT-3a1), methyl (1R,8S)-12-bromo-15-oxatetracyclo[6.6.1.0$^{2,7}$.0$^{9,14}$]pentadeca-2,4,6,9,11,13-hexaene-4-carboxylate (INT-3a2), methyl (1R,8R)-11-bromo-15-oxatetracyclo[6.6.1.0$^{2,7}$.0$^{9,14}$]pentadeca-2,4,6,9,11,13-hexaene-4-carboxylate (INT-3b1) and methyl (1S,8S)-11-bromo-15-oxatetracyclo[6.6.1.0$^{2,7}$.0$^{9,14}$]pentadeca-2,4,6,9,11,13-hexaene-4-carboxylate (INT-3b2) and corresponding acids and salts thereof

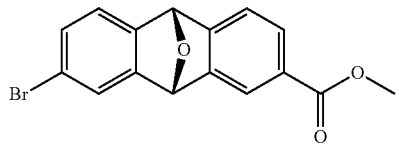

INT-3a1

-continued

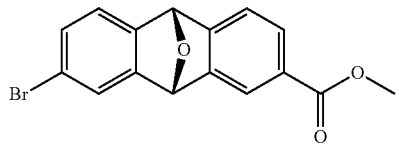

INT-3a2

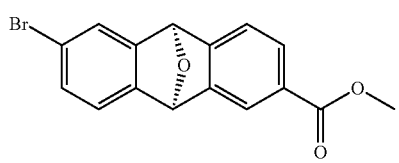

INT-3b1

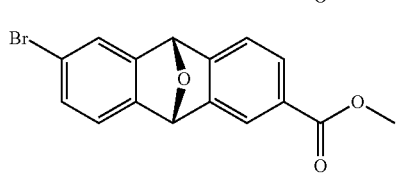

INT-3b2

By Chiral Separation:

The racemic mixture of INT-3a (i.e., (±) methyl 12-bromo-15-oxatetracyclo[6.6.1.0$^{2,7}$.0$^{9,14}$]pentadeca-2,4,6,9,11,13-hexaene-4-carboxylate) or INT-3b (i.e., (±) methyl 11-bromo-15-oxatetracyclo[6.6.1.0$^{2,7}$.0$^{9,14}$]pentadeca-2,4,6,9,11,13-hexaene-4-carboxylate) can be separated into their enantiomerically pure components (INT-3a1 and INT-3a2 and INT-3b1 and INT-3b2 respectively) by chiral HPLC or SFC using commercial chiral columns such as DAICEL CHIRALCEL OJ-3, 50×4.6 mm, 3.0 μm under normal phase conditions (e.g., using hexane/EtOH or iPrOH) or Lux Amylose-2 column 5 uM 4.6×100 column under reverse phase conditions (e.g., water/acetonitrile, with 0.1% TFA or HCOOH). Similar conditions can be used for the separation of the corresponding carboxylic acids ((±) 12-bromo-15-oxatetracyclo[6.6.1.0$^{2,7}$.0$^{9,14}$]pentadeca-2,4,6,9,11,13-hexaene-4-carboxylic acid designated INT-4a1 and INT-4a2 and (±)11-bromo-15-oxatetracyclo[6.6.1.0$^{2,7}$.0$^{9,14}$]-pentadeca-2,4,6,9,11,13-hexaene-4-carboxylic acid designated INT-4b1 and INT-4b2 respectively).

By enzymatic resolution: lipase or esterase can also be used to selectively hydrolyze one of the enantiomers of the racemic mixture of esters INT-3a or INT-3b or selectively esterify of one of the enantiomers of the racemic mixture of acids INT-4a or INT-4b.

Applying the conditions described above, INT-3a (200 mg) gave 75 mg of methyl (1S,8R)-12-bromo-15-oxatetracyclo[6.6.1.0$^{2,7}$.0$^{9,14}$]pentadeca-2,4,6,9,11,13-hexaene-4-carboxylate (INT-3a1) and 74 mg of methyl (1R,8S)-12-bromo-15-oxatetracyclo[6.6.1.0$^{2,7}$.0$^{9,14}$]-pentadeca-2,4,6,9,11,13-hexaene-4-carboxylate (INT-3a2) after chiral HPLC separation.

methyl (1S,8R)-12-bromo-15-oxatetracyclo[6.6.1.0$^{2,7}$.0$^{9,14}$]pentadeca-2,4,6,9,11,13-hexaene-4-carboxylate (INT-3a1): $^1$H NMR (300 MHz, CDCl$_3$) δ 7.98 (s, 1H), 7.82 (dd, J=7.5, 1.5 Hz, 1H), 7.50 (s, 1H), 7.39 (d, J=7.5 Hz, 1H), 7.28 (s, 1H), 7.21 (m, 2H), 6.09 (d, J=1.5 Hz, 2H), 3.90 (s, 3H). MS (M+H)$^+$ found for C$_{16}$H$_{11}$BrO$_3$: 331.2, found 331.

methyl (1R,8S)-12-bromo-15-oxatetracyclo[6.6.1.0$^{2,7}$.0$^{9,14}$]pentadeca-2,4,6,9,11,13-hexaene-4-carboxylate (INT-3a2): $^1$H NMR (300 MHz, CDCl$_3$) δ 7.98 (s, 1H), 7.83 (dd, J=7.5, 1.2 Hz, 1H), 7.50 (s, 1H), 7.40 (d, J=7.5 Hz, 1H), 7.28 (s, 1H), 7.21 (m, 2H), 6.09 (s, 2H), 3.90 (s, 3H). MS (M+H)$^+$ found for C$_{16}$H$_{11}$BrO$_3$: 331.2, found 331.

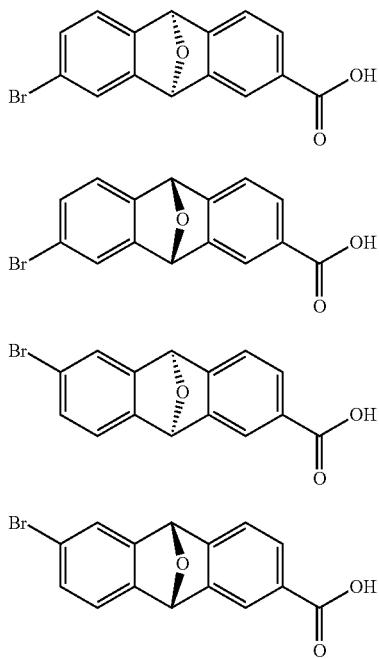

INT-4a1

INT-4a2

INT-4b1

INT-4b2

By recrystallization: Another methodology to separate pure enantiomers from the racemic mixture of acids INT-4a (or INT-4b) involves the recrystallization of the salts of the racemic acid with a chiral amine such as (S)-1-phenylethan-1-amine or (R)-1-phenylethan-1-amine.

Step 1:

A mixture of (±) 12-bromo-15-oxatetracyclo[6.6.1.0$^{2,7}$.0$^{9,14}$]pentadeca-2,4,6,9,11,13-hexaene-4-carboxylic acid (INT-4a; 35.6 g, 112 mmol; 95% d.e) and (R)-1-phenylethanamine (13.6 g, 112 mmol) were dissolved in acetonitrile (2,265 mL) at 60° C. To this solution was added H$_2$O (113.3 mL) until it became cloudy, then a few drops of acetonitrile were added to form a clear solution at 60° C. The mixture was then cooled slowly to room temperature overnight. The precipitate thus formed was collected by filtration and dried under vacuum to afford 13.9 g of (1R)-1-phenylethan-1-aminium (1S,8R)-12-bromo-15-oxatetracyclo-[6.6.1.0$^{2,7}$.0$^{9,14}$]pentadeca-2,4,6,9,11,13-hexaene-4-carboxylate as an off-white solid (with approximately 90% e.e.). The collected solids were treated with a small amount of water (~120% by weight of solids) and stirred for 1 hr. The slurry was then filtered and the solids were dried to obtain 9.3 g of enantio-enriched (1R)-1-phenylethan-1-aminium (1S,8R)-12-bromo-15-oxatetracyclo[6.6.1.0$^{2,7}$.0$^{9,14}$]pentadeca-2,4,6,9,11,13-hexaene-4-carboxylate (95% e.e.). The mother liquor was recycled for reuse.

Step 2:

Into a 500-mL round-bottom flask, was placed a solution of (1R)-1-phenylethan-1-aminium (1S,8R)-12-bromo-15-oxatetracyclo[6.6.1.0$^{2,7}$.0$^{9,14}$]pentadeca-2,4,6,9,11,13-hexaene-4-carboxylate (15.3 g, 34.91 mmol, 1.00 equiv) in water (250 mL). The resulting solution was acidified by 1 M aqueous HCl to pH 4 with stirring. The resulting mixture was extracted with ethyl acetate and the combined organic layers were dried over anhydrous sodium sulfate and concentrated under vacuum to afford 9.3 g (84%) of (1S,8R)-12-bromo-15-oxatetracyclo-[6.6.1.0$^{2,7}$.0$^{9,14}$]pentadeca-2,4,6,9,11,13-hexaene-4-carboxylic acid as a white solid.

Reference 6

Synthesis of tert-butyl (isobenzofuran-5-ylmethoxy)dimethylsilane (INT-5)

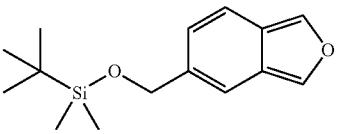 [SMILES: CC(C)(C)[Si](C)(C)OCc1ccc2cocc2c1]

Step 1:

5-(Hydroxymethyl)isobenzofuran-1(3H)-one was synthesized from 1-oxo-1,3-dihydroisobenzofuran-5-carboxylic acid (97%, PharmaBlock R&D Co. Ltd) according to the procedure described by Spicer, J. A. et al. in *Bioorg. Med. Chem.*, 2012, 20(3), 1319-1336.

Step 2:

A mixture of 5-(hydroxymethyl)isobenzofuran-1(3H)-one (400 mg; 2.44 mmol; 1 eq.), tert-butyl(chloro)dimethylsilane (477 mg; 3.17 mmol; 1.3 eq.) and 1H-imidazole (216 mg; 3.17 mmol; 1.3 eq.) in N,N-dimethylformamide (9 mL) was stirred at ambient temperature for 16 h. The mixture was then diluted with 1:1 toluene/EtOAc (50 mL) and washed with water. The organic phase was dried over MgSO$_4$, filtered and concentrated. The crude material was purified by column chromatography on a 12 g ISCO Gold column eluting with 30% EtOAc in hexanes to provide 5-(((tert-butyldimethylsilyl)oxy)methyl)isobenzofuran-1(3H)-one as a white solid (500 mg; 73.7%).

Step 3:

To a stirred solution of 5-(((tert-butyldimethylsilyl)oxy)methyl)isobenzofuran-1(3H)-one (910 mg; 3.27 mmol; 1 eq.) in DCM (32.7 mL) cooled to −78° C. was added diisobutylaluminium hydride (1 M solution in DCM; 3.9 mL; 3.9 mmol; 1.2 eq.) drop-wise. The mixture was stirred at −78° C. and after 20 min it was quenched with 10% NaOH (10 mL), allowed to reach ambient temperature and then diluted with water. The organic layer was separated and the aqueous layer was extracted with DCM. The combined organics were dried over MgSO$_4$, filtered and concentrated to give (S)-5-(((tert-butyldimethylsilyl)oxy)methyl)-1,3-dihydroisobenzofuran-1-ol and (R)-5-(((tert-butyldimethylsilyl)oxy)methyl)-1,3-dihydroisobenzofuran-1-ol. $^1$H NMR of the crude material confirmed formation of the title compound in equilibrium with the corresponding open form aldehyde. This material was taken on without further purification.

Step 4:

(To a stirred solution of (S)-5-(((tert-butyldimethylsilyl)oxy)methyl)-1,3-dihydroisobenzo-furan-1-ol and (R)-5-(((tert-butyldimethylsilyl)oxy)methyl)-1,3-dihydroisobenzofuran-1-ol (916 mg; 3.27 mmol; 1 eq.) in THF (32.7 mL) cooled to 0° C. was added sodium hydride (157 mg; 6.53 mmol; 2 eq.) in one portion and the mixture was stirred at 0° C. for 15 min. Iodomethane (1 mL; 16.3 mmol; 5 eq.) was then added drop-wise and the mixture was allowed to warm to ambient temperature. The progress of the reaction was monitored by TLC (20% EtOAc in hexanes) and upon completion (~36 h) the mixture was quenched and diluted with water and extracted with EtOAc. The combined organics were washed with brine, then dried over MgSO$_4$, filtered and concentrated. The crude material was purified by column chromatography on a 24 g ISCO Gold column eluting with 10% EtOAc in hexanes to provide (S)-tert-butyl((1-methoxy-1,3-dihydroisobenzofuran-5-yl)methoxy)dimethylsilane and (R)-tert-butyl((1-methoxy-1,3-dihydroisobenzofuran-5-yl)methoxy)dimethylsilane as a clear oil (759 mg; 78.9% for the two steps).

Step 5:

To a solution of (S)-tert-butyl ((1-methoxy-1,3-dihydroisobenzofuran-5-yl)methoxy)-dimethylsilane and (R)-tert-butyl ((1-methoxy-1,3-dihydroisobenzofuran-5-yl)methoxy)-dimethylsilane (170 mg; 0.58 mmol; 1 eq.) in Et$_2$O (1.92 mL) cooled to 0° C. was added freshly prepared LDA (1M solution in THF, 1.8 mL~3 eq.) drop-wise. The dark cloudy mixture was stirred at 0° C. $^1$H NMR of a small aliquot of the reacting mixture after 15 minutes confirmed formation of the desired product. The reacting mixture was then diluted with Et$_2$O, washed with NH$_4$Cl and water, dried over MgSO$_4$ and filtered. This crude product solution was concentrated to ~1 mL, kept at 0° C. and used in the next step without further purification.

Reference 7

Synthesis of tert-butyl (5-(aminomethyl)-4,6-dimethylpyridin-2-yl)carbamate

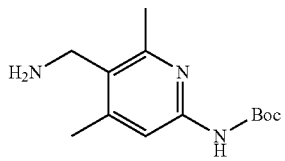 [SMILES: Cc1cc(NC(=O)OC(C)(C)C)nc(C)c1CN]

Step 1:

Into a 500-mL three neck round-bottom flask, was placed polyphosphoric acid (PPA) (300 g). This was followed by the addition of (2E)-3-aminobut-2-enenitrile (30 g, 365.39 mmol, 1 eq.) at 100° C. The resulting solution was stirred for 3 h at 165° C. The reaction mixture was cooled to 90° C. and then quenched by the addition of water/ice. The pH value of the solution was adjusted to 9 with sodium hydroxide (10%). The resulting solution was extracted with ethyl acetate and the organic layers combined and dried over anhydrous sodium sulfate and concentrated under vacuum to give 12.4 g (23%) of 6-amino-2,4-dimethylpyridine-3-carbonitrile as a yellow solid.

Step 2:

Into a 500-mL round-bottom flask, was placed 6-amino-2,4-dimethylpyridine-3-carbonitrile (12.4 g, 84.25 mmol, 1 eq.), 4-dimethylaminopyridine (1.03 g, 8.43 mmol, 0.1 eq.), and tetrahydrofuran (100 mL). This was followed by the addition of a solution of Boc$_2$O (55 g, 252 mmol, 3 eq.) in tetrahydrofuran (100 mL) dropwise with stirring. The resulting solution was stirred overnight at room temperature. The resulting solution was diluted with H$_2$O and extracted with ethyl acetate and the organic layers combined. The resulting mixture was washed with brine. The combined organics were dried over anhydrous sodium sulfate and concentrated under vacuum. The residue was applied onto a silica gel column with ethyl acetate/petroleum ether (1:10) as eluent. This resulted in 13.2 g (45%) of tert-butyl N-[(tert-butoxy)carbonyl]-N-(5-cyano-4,6-dimethylpyridin-2-yl)carbamate as a light yellow solid.

Step 3:

Into a 250-mL round-bottom flask, was placed tert-butyl N-[(tert-butoxy)carbonyl]-N-(5-cyano-4,6-dimethylpyridin-2-yl)carbamate (7.1 g, 20.44 mmol, 1 eq.), methanol (70 mL), dichloromethane (20 mL). This was followed by the addition of H$_2$O$_2$ (2.69 mL, 1.5 eq.) dropwise with stirring. To this was added a solution of sodium hydroxide (1.228 g, 30.7 mmol, 1.5 eq.) in water (10 mL) dropwise with stirring. The resulting solution was stirred for 2 h at 0° C. in a water/ice bath. The reaction was then quenched by the addition of 10% Na$_2$CO$_3$ (100 mL). The resulting solution was extracted with ethyl acetate and the organic layers combined and dried over anhydrous sodium sulfate and concentrated under vacuum. The residue was applied onto a silica gel column with ethyl acetate/petroleum ether (1:3) as eluent. This resulted in 3.8 g (75%) of tert-butyl N-(5-cyano-4,6-dimethylpyridin-2-yl)carbamate as a white solid.

Step 4:

Into a 100-mL round-bottom flask, was placed tert-butyl N-(5-cyano-4,6-dimethylpyridin-2-yl)carbamate (3.8 g, 15.37 mmol, 1 eq.), NH$_3$/MeOH (10 mL), methanol (20 mL), and Raney-Ni (3.8 g). To the above, hydrogen was introduced. The resulting solution was stirred overnight at room temperature under 1 atm of hydrogen. The solids were filtered. The resulting mixture was concentrated under vacuum. This resulted in 3.2 g (83%) of tert-butyl N-[5-(aminomethyl)-4,6-dimethylpyridin-2-yl]carbamate as a white solid.

Reference 8

Synthesis of 5-(aminomethyl)-4,6-dimethylpyridin-2-amine (INT 6a)

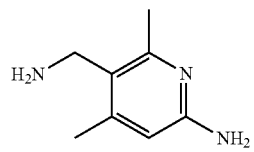

Step 1:

Into a 100-mL round-bottom flask was placed a solution of tert-butyl N-[5-(aminomethyl)-4,6-dimethylpyridin-2-yl]carbamate (2.51 g, 10 mmol, 1 eq.) in dichloromethane (52 mL) and then added TFA (2.7 mL) dropwise with stirring. The resulting solution was stirred overnight at room temperature. The resulting mixture was concentrated under vacuum. The crude product was purified by Combi-Flash with the following conditions: column C18, 20-45 um, 100 A, 120 g. Mobile phase: solvent A: water contains 0.05% TFA, solvent B: CH$_3$CN. Gradient: 5-28%. Run time: 12 min. Flow rate: 80 mL/min. This resulted in 1.40 g (53%) of 5-(amino-methyl)-4,6-dimethylpyridin-2-amine in form of its corresponding trifluoroacetic acid salt as a light green solid.

Alternative Route:

Step 1:

Into a 5000-mL round-bottom flask, was placed a mixture of tert-butyl N-[(tert-butoxy)carbonyl]-N-(5-cyano-4,6-dimethylpyridin-2-yl)carbamate (210 g, 0.605 mol, 1.00 equiv), methanol (3000 mL), ammonia (300 mL) and Raney-Ni (60 g). The solution was purged with hydrogen 3 times and stirred under an atmosphere of hydrogen overnight at room temperature. The solids were separated by filtration and the filtrate was concentrated under vacuum to afford 180 g (84.8%) of tert-butyl N-[5-(aminomethyl)-4,6-dimethylpyridin-2-yl]-N-[(tert-butoxy)carbonyl]carbamate (INT-6b).

Step 2:

Into a 5000-mL 3-necked round-bottom flask, was placed a solution of tert-butyl N-[5-(aminomethyl)-4,6-dimethylpyridin-2-yl]carbamate (130.0 g, 517.26 mmol, 1.00 equiv) in dioxane (3000 mL) and the solution was sparged with hydrogen chloride (gas) with stirring until the solution was saturated. The resulting mixture was stirred for 16 h at room temperature then it was concentrated under vacuum. The residue was washed with of ether and dried to afford 90.0 g (69%) of 5-(aminomethyl)-4,6-dimethylpyridin-2-amine (also may be called 5-(azaniumyl-methyl)-4,6-dimethylpyridin-2-aminium) dichloride (INT-6a) as a white solid. LCMS (ES) [M+1]$^+$ m/z 152.0.

Reference 9

Synthesis of 4-(aminomethyl)-N'-methoxybenzimidamide dihydrochloride (INT-7)

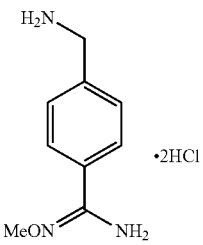

Step 1:

Into a 20-L 4-necked round-bottom flask, was placed a mixture of tert-butyl N-[(tert-butoxy)carbonyl]carbamate (1113 g, 5.12 mol, 1.00 equiv), THF (10 L), 4-(bromomethyl)-benzonitrile (1000 g, 5.10 mol, 1.00 equiv), Cs$_2$CO$_3$ (1672 g, 5.13 mol, 1.00 equiv) and LiI (34.0 g, 255 mmol, 0.05 equiv). The resulting mixture was stirred for 12 h at 70° C., then it was cooled to room temperature and filtered. The filtrate was diluted with EtOAc (10 L), washed with brine, dried over anhydrous Na$_2$SO$_4$ and concentrated to dryness. The crude product was washed with ethyl acetate/petroleum (1/2) and the solids were collected by filtration to afford 820 g (48%) of tert-butyl N-[(tert-butoxy)carbonyl]-N-[(4-cyanophenyl)-methyl]carbamate as a white solid.

Step 2:

Into a 10-L 4-necked round-bottom flask purged and maintained with an inert atmosphere of nitrogen, was placed a mixture of tert-butyl N-[(tert-butoxy)carbonyl]-N-[(4-cyanophenyl)methyl]carbamate (600 g, 1.81 mol, 1.00 equiv) in ethanol (4.2 L) and the temperature was gradually raised to 55° C. After almost complete dissolution, trimethylamine (TEA; 876 mL, 3.50 equiv) was added, then a solution of O-methylhydroxylamine hydrochloride (435 g, 5.21 mol. 2.00 equiv) in water (1.02 L) was added dropwise with stirring over 50 min. Mercaptoacetic acid (126 mL, 5.21 mol, 1.00 equiv) was then added and the resulting solution was stirred for 21 h at 90° C. The mixture was then concentrated under vacuum, diluted with H$_2$O and extracted with n-BuOAc. The organic phase was further washed with saturated aq. K$_2$CO$_3$, dried over anhydrous sodium sulfate and concentrated under vacuum by half. This was followed by addition of 800 mL of ethanol. The mixture containing tert-butyl N-[(tert-butoxy)carbonyl]-N-([4-[N-methoxycarbamimidoyl]phenyl]-methyl)carbamate was directly used in the next step.

Step 3:

Into a 10-L 3-necked round-bottom flask purged and maintained with an inert atmosphere of nitrogen at room temperature, was placed a mixture of tert-butyl N-[(tert-butoxy)carbonyl]-N-([4-[N-methoxycarbamimidoyl]phenyl]methyl)carbamate (600 g, 1.58 mol, 1.00 equiv), n-BuOAc (3.0 L) and ethanol (500 mL) followed by concentrated hydrogen chloride aqueous solution (527 mL, 6.32 mol, 4.00 equiv) slowly. The resulting mixture was stirred for 4 h at 35° C., then it was cooled to 0° C. and aged for 1 h. The solids thus formed were collected by filtration. The filter cake was washed with n-BuOAc/ethanol (24/7) and dried under vacuum to afford 336 g (84%) of the title compound (INT-7) as a brown solid. LC-MS (ES) [M−2HCl+1]$^+$ m/z: 180.1

Reference 10

Synthesis of 4-(aminomethyl)-N'-hydroxybenzimidamide hydrochloride chloride (INT-8)

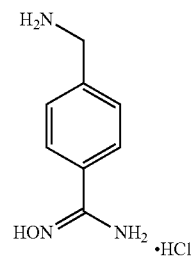

Step 1:

Into a 1-L round-bottom flask, was placed a mixture of tert-butyl N-[(tert-butoxy)carbonyl]-N-[(4-cyanophenyl)methyl]carbamate (40.0 g, 120.34 mmol, 1.00 equiv), methanol (500 mL), potassium carbonate (33.1 g, 239.49 mmol, 2.00 equiv) and NH$_2$OH.HCl (16.7 g, 240.28 mmol, 2.00 equiv). The resulting solution was stirred for 3 h at 70° C. and concentrated under vacuum. The residue was diluted with 600 mL of EtOAc, washed with 3×200 mL of brine, dried over anhydrous sodium sulfate and concentrated under vacuum to afford 27.0 g (61%) of tert-butyl N-[(tert-butoxy) carbonyl]-N-([4-[N-hydroxycarbamimidoyl]-phenyl] methyl)carbamate as a white solid.

Step 2:

Into a 500-mL round-bottom flask, was placed a mixture of tert-butyl N-[(tert-butoxy)carbonyl]-N-[[4-(N-hydroxycarbamimidoyl)phenyl]methyl]carbamate (27.0 g, 73.97 mmol, 1.00 equiv) in dichloromethane (300 mL), followed by dioxane (150 mL) which was freshly saturated with hydrochloride (gas). The resulting solution was stirred for 16 h at room temperature. The solids were collected by filtration and dried to afford 11.088 g (64%) of the title compound (INT-8) as a white solid. LCMS (ES) [M+1]$^+$ m/z: 166.0.

Reference 11

Synthesis of 4-(aminomethyl)-3,5-difluoro-N'-hydroxybenzimidamide dichloride (INT-9)

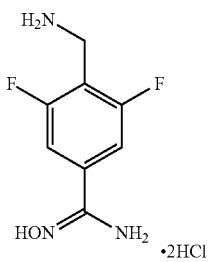

Step 1:

Into a 1-L round-bottom flask, was placed a solution of 4-bromo-2,6-difluorobenzaldehyde (43.0 g, 195.45 mmol, 1.00 equiv) in methanol (500 mL) with stirring at 0° C. Sodium borohydride (NaBH$_4$; 7.4 g, 195.45 mmol, 1.00 equiv) was then added in portions and the resulting mixture was stirred for 10 min at 0° C. and then concentrated under vacuum. The residue was diluted with EtOAc, washed with brine, dried over anhydrous sodium sulfate and concentrated under vacuum to afford 43.0 g of (4-bromo-2,6-difluorophenyl)methanol as a white solid.

Step 2:

Into a 1-L round-bottom flask, was placed a solution of (4-bromo-2,6-difluorophenyl)methanol (43.0 g, 193.69 mmol, 1.00 equiv) in dichloromethane (600 mL) with stirring at 0° C. Thionyl chloride (46.1 g, 387.38 mmol, 2.00 equiv) was then added dropwise and the resulting mixture was stirred for 16 h at room temperature, then it was concentrated under vacuum to afford 46 g of 5-bromo-2-(chloromethyl)-1,3-difluorobenzene as yellow oil. Step 3:
Into a 1-L round-bottom flask, was placed a solution of ammonia (300 mL) and dioxane (300 mL) and 5-bromo-2-(chloromethyl)-1,3-difluorobenzene (46.0 g, 190.08 mmol, 1.00 equiv) in dioxane (50 mL) was added dropwise with stirring over 1 h. The resulting mixture was stirred for 16 h at room temperature then it was concentrated under vacuum to afford 47.0 g of (4-bromo-2,6-difluorophenyl)methanamine as a white crude solid.

Step 4:

Into a 1-L round-bottom flask, was placed a solution of (4-bromo-2,6-difluorophenyl)methanamine (47.0 g, 212.67 mmol, 1.00 equiv), dichloromethane (600 mL), methanol (60 mL), Boc$_2$O (139.1 g, 638.01 mmol, 3.00 equiv) and 4-dimethylaminopyridine (2.6 g, 21.27 mmol, 0.10 equiv). The resulting mixture was stirred for 1 h at room temperature then it was concentrated under vacuum. The residue was purified by silica gel column chromatography eluting with ethyl acetate/petroleum ether (1/4) to afford 24.0 g (35%) of tert-butyl N-[(4-bromo-2,6-difluorophenyl)methyl]carbamate as white solid.

Step 5:

Into a 500-mL round-bottom flask, was placed a mixture of tert-butyl N-[(4-bromo-2,6-difluorophenyl)methyl]carbamate (24.0 g, 74.77 mmol, 1.00 equiv), N,N-dimethylformamide (300 mL), water (3 mL), Zn(CN)$_2$ (10.50 g, 89.72 mmol, 1.20 equiv), tris(dibenzylideneacetone)dipalladium, chloroform complex (Pd$_2$(dba)$_3$.CHCl$_3$; 3.87 g, 3.74 mmol, 0.05 equiv) and 1,1'-bis(diphenylphosphino)ferrocene (dppf, 4.97 g, 8.97 mmol, 0.12 equiv). The resulting mixture was stirred for 1 h at 120° C. under N$_2$. After concentration, the residue was diluted with EtOAc, washed with brine, dried over anhydrous sodium sulfate and concentrated under vacuum. The residue was purified by silica gel column chromatography eluting with ethyl acetate/petroleum ether (1/4) to afford 20.0 g (100%) of tert-butyl N-[(4-cyano-2,6-difluorophenyl)methyl]carbamate as white solid.

Step 6:

Into a 250-mL round-bottom flask, was placed a mixture of tert-utyl N-[(4-cyano-2,6-difluorophenyl)methyl]carbamate (11.0 g, 41.04 mmol, 1.00 equiv), methanol (150 mL), potassium carbonate (8.50 g, 61.56 mmol, 1.50 equiv) and NH$_2$OH.HCl (5.71 g, 82.08 mmol, 2.00 equiv). The resulting mixture was stirred for 1 h at 60° C. and concentrated under vacuum. The residue was diluted with EtOAc, washed with brine, dried over anhydrous sodium sulfate and concentrated under vacuum. The residue was purified by silica gel column chromatography eluting with ethyl acetate/petroleum ether (1/1) to afford 10.2 g (83%) of tert-butyl N-([2,6-difluoro-4-[N-hydroxycarbamimidoyl]phenyl]methyl)carbamate as a yellow solid.

Step 7:

Into a 250-mL round-bottom flask, was placed a mixture of tert-butyl N-([2,6-difluoro-4-[N-hydroxycarbamimidoyl]phenyl]methyl)carbamate (4.50 g, 14.95 mmol, 1.00 equiv) in dichloromethane (30 mL), followed by dioxane (100 mL) which was freshly saturated with hydrochloride (gas). The resulting mixture was stirred for 2 h at room temperature. The solids were collected by filtration to afford 2.65 g (65%) of the title compound (INT-9) as a white solid. LC-MS (ESI) m/z: calculated for C$_8$H$_{11}$C$_{12}$F$_2$N$_3$O: 273.02. found: 202 [M-2HCl+H]$^+$. Rt: 0.96 min.

Reference 12

Synthesis of 4-(aminomethyl)-3,5-difluorobenzimidamide dihydrochloride (INT-10)

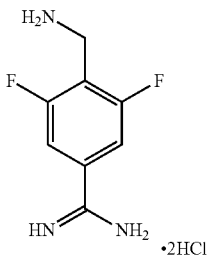 [SMILES: N=C(N)c1cc(F)c(CN)c(F)c1]

Step 1:

Into a 250-mL round-bottom flask, was placed a mixture of tert-butyl N-([2,6-difluoro-4-[N-hydroxycarbamimidoyl]phenyl]methyl)carbamate (5.70 g, 18.94 mmol, 1.00 equiv), AcOH (80 mL), HCOONH$_4$ (6.00 g, 94.7 mmol, 5.00 equiv) and 5% Pd on C (2.00 g). The resulting mixture was stirred for 1 h at 120° C. The solids were collected by filtration and the filtrate was concentrated under vacuum. The residue was dissolved in H$_2$O and the pH of the solution was adjusted to 9 with sodium hydroxide aqueous solution. To this mixture was added methanol (100 mL), Boc$_2$O (8.26 g, 37.88 mmol, 2.00 equiv) and 4-dimethylamino-pyridine (231 mg, 1.89 mmol, 0.10 equiv) and the resulting mixture was stirred for 1 h at room temperature then it was concentrated under vacuum. The residue was diluted with ethyl acetate, washed with brine, dried over anhydrous sodium sulfate and concentrated under vacuum. The residue was suspended in 10 mL of EtOAc and stirred for 10 min. The solid was collected by filtration and dried to afford 2.50 g (46%) of tert-butyl N-[(4-carbamimidoyl-2,6-difluorophenyl) methyl]carbamate as white solid.

Step 2:

Into a 50-mL round-bottom flask, was placed a solution of tert-butyl N-[(4-carbamimidoyl-2,6-difluorophenyl)methyl] carbamate (2.50 g, 8.77 mmol, 1.00 equiv) in dichloromethane (20 mL), followed by dioxane (10 mL) which was freshly saturated with hydrochloride (gas) and the resulting mixture was stirred for 0.5 h at room temperature. The solids were collected by filtration and dried to afford 1.36 g (60%) of the title compound (INT-10) as an off-white solid. LC-MS (ESI) m/z: calculated for $C_8H_{11}C_{12}F_2N_3$: 257.03. found: 186 [M-2HCl+H]$^+$. Rt: 0.58 min.

Reference 13

Synthesis of 4-(aminomethyl)-3,5-difluoro-N'-methoxybenzimidamide hydrochloride (INT-11)

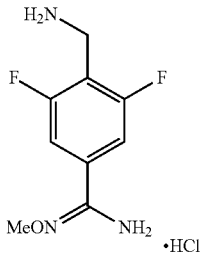

Step 1:

Into a 250-mL round-bottom flask, was placed a mixture of tert-butyl N-[(4-cyano-2,6-difluorophenyl)methyl]carbamate (7.70 g, 28.70 mmol, 1.00 equiv), methoxylamine hydrochloride (4.7 g, 57.32 mmol, 2.00 equiv), 2-sulfanylacetic acid (2.64 g, 28.66 mmol, 1.00 equiv), TEA (5.8 g, 57.32 mmol, 2.00 equiv) in ethanol (120 mL). The resulting mixture was stirred for 16 hours at 90° C. then it was concentrated. The residue was purified by column flash chromatography eluting with ethyl acetate/petroleum ether (1/10) to afford 5.80 g (64%) of tert-butyl N-([2,6-difluoro-4-[N'-methoxycarbamimidoyl]phenyl]methyl)carbamate as a light yellow solid.

Step 2:

Into an 100-mL round-bottom flask, was placed tert-butyl N-([2,6-difluoro-4-[N'-ethoxycarbamimidoyl]phenyl] methyl)carbamate (4.00 g, 12.69 mmol, 1.00 equiv) with stirring followed by a solution of 4 N HCl in dioxane (50 mL). The resulting mixture was stirred for 1 hour at room temperature. The solids were collected by filtration and dried to afford 2.1607 g (79%) of the title compound as a white solid. LC-MS (ESI) m/z: calculated for $C_9H_{11}F_2N_3O$: 215.09. found: 216[M+H]$^+$. Rt: 1.339 min.

Example 1

Synthesis of (±)-N-[(6-amino-2,4-dimethylpyridin-3-yl)methyl]-12-[(1H-pyrazol-1-yl)methyl]-15-oxa-tetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-[(1H-pyrazol-1-yl) methyl]-15-oxatetracyclo-[6.6.1.0$^{2,7}$.0$^{9,14}$]pentadeca-2,4,6,9,11, 13-hexaene-4-carboxamide

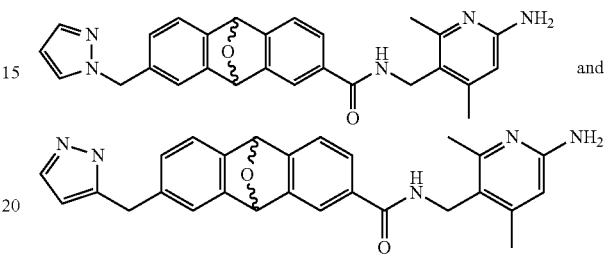

Step 1:

To a stirred solution of (5-(methoxycarbonyl)-2-(trimethylsilyl)phenyl)(phenyl)iodonium trifluoromethanesulfonate (INT-2), 100 mg; 0.18 mmol; 1 eq.) in DCM (1.8 mL) at 0° C. was added tert-butyl (isobenzofuran-5-ylmethoxy)dimethylsilane (INT-5, 151 mg; 0.58 mmol; 3.22 eq.) as a solution in Et$_2$O prepared as described above. To this orange mixture was added tetrabutylammonium fluoride (1M solution in THF; 0.23 mL; 0.23 mmol; 1.3 eq.) and the mixture was stirred at 0° C. for 30 min. The mixture was then diluted with water and extracted with DCM; the combined organics were dried over MgSO$_4$, filtered and concentrated to afford a dark oil. The crude material was purified by column chromatography on a 12 g ISCO Gold column eluting with 10% EtOAc in hexanes to provide methyl (9S,10R)-7-(((tert-butyldimethylsilyl)oxy)-methyl)-9,10-dihydro-9,10-epoxyanthracene-2-carboxylate, methyl (9R,10S)-7-(((tert-butyldimethylsilyl)oxy)methyl)-9,10-dihydro-9,10-epoxyanthracene-2-carboxylate, methyl (9S,10S)-6-(((tert-butyldimethylsilyl)oxy)methyl)-9,10-dihydro-9,10-epoxyanthracene-2-carboxylate and methyl (9R,10R)-6-((((tert-butyldimethylsilyl)oxy)-methyl)-9,10-dihydro-9,10-epoxyanthracene-2-carboxylate (59 mg; 83%).

Step 2:

To a stirred solution of methyl (9S,10R)-7-(((tert-butyldimethylsilyl)oxy)methyl)-9,10-dihydro-9,10-epoxyanthracene-2-carboxylate, methyl (9R,10S)-7-(((tert-butyldimethylsilyl)oxy)methyl)-9,10-dihydro-9,10-epoxyanthracene-2-carboxylate, methyl (9S,10S)-6-(((tert-butyldimethylsilyl)oxy)methyl)-9,10-dihydro-9,10-epoxyanthracene-2-carboxylate and methyl (9R,10R)-6-((((tert-butyldimethylsilyl)oxy)-methyl)-9,10-dihydro-9,10-epoxyanthracene-2-carboxylate (55 mg; 0.14 mmol; 1 eq.) in THF (1.4 mL) at ambient temperature was added tetrabutylammonium fluoride (1M in THF; 0.18 mL; 0.18 mmol; 1.3 eq.) and the mixture was stirred at ambient temperature for 30 min. The mixture was then quenched with sat. NH$_4$Cl and diluted with water, then extracted with EtOAc; the combined organics were dried over MgSO$_4$, filtered and concentrated. The crude material was purified by column chromatography on a 4 g ISCO Gold column eluting with 30% EtOAc in hexanes to provide methyl (9S,10R)-7-(hydroxymethyl)-9,10-dihydro-9,10-epoxyanthracene-2-carboxylate, methyl (9R,10S)-7-(hydroxymethyl)-9,10-dihydro-9,10-epoxyanthracene-2-carboxylate, methyl (9S, 10S)-6-(hydroxymethyl)-9,10-dihydro-9,10-epoxyanthracene-2-carboxylate, and methyl (9R,10R)-6-(hydroxymethyl)-9,10-dihydro-9,10-epoxyanthracene-2-carboxylate (36 mg; 92%).

Step 3:

To a stirred solution of methyl (9S,10R)-7-(hydroxymethyl)-9,10-dihydro-9,10-epoxyanthracene-2-carboxylate, methyl (9R,10S)-7-(hydroxymethyl)-9,10-dihydro-9,10-epoxyanthracene-2-carboxylate, methyl (9S,10S)-6-(hydroxymethyl)-9,10-dihydro-9,10-epoxyanthracene-2-carboxylate and methyl (9R,10R)-6-(hydroxymethyl)-9,10-dihydro-9,10-epoxyanthracene-2-carboxylate (35 mg; 0.12 mmol; 1 eq.) in DCM (0.62 mL) cooled to 0° C. was added Hunig's base (0.03 mL; 0.15 mmol; 1.2 eq.) followed by methanesulfonyl chloride (0.01 mL; 0.14 mmol; 1.1 eq.) and the mixture was stirred at 0° C. After 1 h the mixture was diluted with DCM, washed with sat. NH$_4$Cl and brine, dried over Na$_2$SO$_4$, filtered and concentrated.

To a mixture of methyl (9S,10R)-7-(methylsulfonyloxymethyl)-9,10-dihydro-9,10-epoxyanthracene-2-carboxylate, methyl (9R,10S)-7-(methylsulfonyloxymethyl)-9,10-dihydro-9,10-epoxyanthracene-2-carboxylate, methyl (9S,10S)-6-(methylsulfonyloxymethyl)-9,10-dihydro-9,10-epoxyanthracene-2-carboxylate and methyl (9R,10R)-6-(methylsulfonyloxy-methyl)-9,10-dihydro-9,10-epoxyanthracene-2-carboxylate, 1H-pyrazole (10.1 mg; 0.15 mmol; 1.2 eq.) and cesium carbonate (60.6 mg; 0.19 mmol; 1.5 eq.) in N,N-dimethylformamide (1.24 mL) was stirred at ambient temperature overnight. The mixture was then diluted with 20 mL 1:1 EtOAc/PhMe washed once with water (20 mL), dried over MgSO$_4$, filtered and concentrated. The residue was purified by column chromatography on a 12 G ISCO Gold column eluting with 20% and 40% EtOAc in hexanes. This material was resubjected to the reaction conditions adding 1 eq. of NaI. After 12 h, the reaction mixture was worked up and the crude material was purified as described above to afford methyl (9S,10R)-7-((1H-pyrazol-1-yl)methyl)-9,10-dihydro-9,10-epoxyanthracene-2-carboxylate, methyl (9R,10S)-7-((1H-pyrazol-1-yl)methyl)-9,10-dihydro-9,10-epoxyanthracene-2-carboxylate, methyl (9S,10S)-6-((1H-pyrazol-1-yl)methyl)-9,10-dihydro-9,10-epoxyanthracene-2-carboxylate and methyl (9R,10R)-6-((1H-pyrazol-1-yl)methyl)-9,10-dihydro-9,10-epoxyanthracene-2-carboxylate (19 mg; 50%).

Step 4:

To a stirred solution of methyl (9S,10R)-7-((1H-pyrazol-1-yl)methyl)-9,10-dihydro-9,10-epoxyanthracene-2-carboxylate and methyl (9R,10S)-7-((1H-pyrazol-1-yl)methyl)-9,10-dihydro-9,10-epoxyanthracene-2-carboxylate and methyl (9S,10S)-6-((1H-pyrazol-1-yl)methyl)-9,10-dihydro-9,10-epoxyanthracene-2-carboxylate and methyl (9R, 10R)-6-((1H-pyrazol-1-yl)methyl)-9,10-dihydro-9,10-epoxyanthracene-2-carboxylate (19 mg; 0.06 mmol; 1 eq.) in THF (0.6 mL) and methanol (0.3 mL) was added 1N lithium hydroxide (0.3 mL; 0.3 mmol; 5 eq.) and the mixture was stirred at ambient temperature for 2.5 h. The mixture was then quenched with 1N HCl (0.6 mL), extracted with EtOAc, dried over MgSO$_4$, filtered and concentrated. The crude material was dried under high vacuum for 30 min to give (9S,10R)-7-((1H-pyrazol-1-yl)methyl)-9,10-dihydro-9, 10-epoxyanthracene-2-carboxylic acid, (9R,10S)-7-((1H-pyrazol-1-yl)methyl)-9,10-dihydro-9,10-epoxyanthracene-2-carboxylic acid, (9S,10S)-6-((1H-pyrazol-1-yl)methyl)-9, 10-dihydro-9,10-epoxyanthracene-2-carboxylic acid, and (9R,10R)-6-((1H-pyrazol-1-yl)methyl)-9,10-dihydro-9,10-epoxyanthracene-2-carboxylic acid which was then taken on to the next step without further purification.

Step 5:

To a stirred solution of (9S,10R)-7-((1H-pyrazol-1-yl) methyl)-9,10-dihydro-9,10-epoxyanthracene-2-carboxylic acid, (9R,10S)-7-((1H-pyrazol-1-yl)methyl)-9,10-dihydro-9,10-epoxyanthracene-2-carboxylic acid and (9S,10S)-6-((1H-pyrazol-1-yl)methyl)-9,10-dihydro-9,10-epoxyanthracene-2-carboxylic acid, (9R,10R)-6-((1H-pyrazol-1-yl) methyl)-9,10-dihydro-9,10-epoxyanthracene-2-carboxylic acid (18 mg; 0.06 mmol; 1 eq.) and 5-(aminomethyl)-4,6-dimethylpyridin-2-amine (INT6a, 9.4 mg; 0.06 mmol; 1.1 eq.) (previously azeotroped together with 1 mL PhMe for 30 min) in N,N-dimethylformamide (0.6 mL) at ambient temperature was added Hunig's base (0.03 mL; 0.17 mmol; 3 eq.) followed by HATU (21.5 mg; 0.06 mmol; 1 eq.). The orange mixture was stirred for 20 min. then it was diluted with 1 mL water (clear solution turned cloudy) and directly purified via R-Phase preparative HPLC (13 min. method at 28 mL/min eluting with a gradient of 95-0% water (containing 0.1% formic acid) in acetonitrile) affording the title compounds as a white powder (7.9 mg; 31% for the two steps). MS ES+ m/z=452.11 (M+H)$^+$.

Example 2

Synthesis of (±)-N-[(6-amino-2,4-dimethylpyridin-3-yl)methyl]-12-[(1H-pyrazol-1-yl)methyl]-15-oxa-tetracyclo[6.6.1.0$^{2,7}$.0$^{9,14}$]pentadeca-2,4,6,9,11,13-hexaene-4-carboxamide

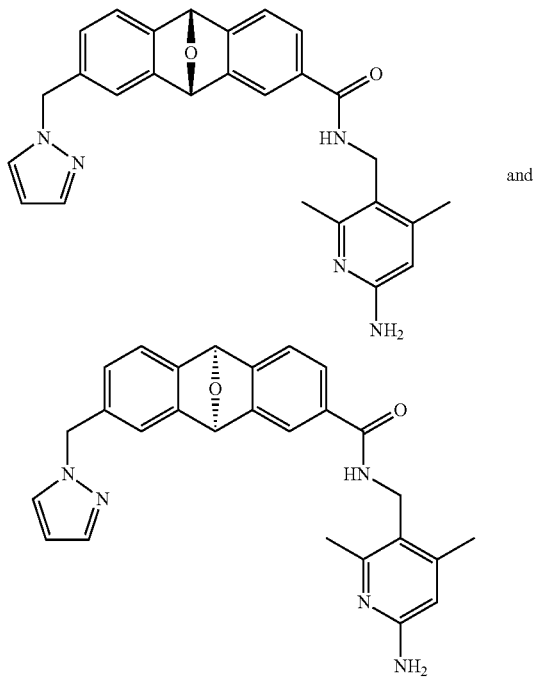

and (±)-N-[(6-Amino-2,4-dimethylpyidin-3-yl)methyl]-12-[(1H-pyrazol-1-yl))methyl]-15-oxatetracyclo[6.6.1.0$^{2,7}$. 0$^{9,14}$]pentadeca-2,4,6,9,11,13-hexaene-4-carboxamide and (±)-N-[(6-amino-2,4-dimethylpyidin-3-yl)methyl]-11-[(1H-pyrazol-1-yl)methyl]-15-oxatetracyclo-[6.6.1.0$^{2,7}$. 0$^{9,14}$]pentadeca-2,4,6,9,11,13-hexaene-4-carboxamide (Example 1; 25 mg) was purified via R-Phase preparative HPLC (Rt=24.0 min, see conditions below) affording title compounds as the less polar eluting component (10.4 mg).

LC/MS Conditions:

column used: Waters, XSelect CSH Prep C18, 250×19 mm Solvent A: 0.1% Formic Acid in Water; Solvent B: Acetonitrile; 30 min run, Flow Rate: 29 ml/min

| Time (min) | A % | B % |
|---|---|---|
| 0 | 100 | 0 |
| 1.0 | 100 | 0 |
| 4.0 | 91 | 9 |
| 26.0 | 77 | 23 |
| 27.0 | 50 | 50 |
| 28.5 | 50 | 50 |
| 29.0 | 100 | 0 |

Example 3

Synthesis of (±)N-[(6-amino-2,4-dimethylpyridin-3-yl)methyl]-11-(1H-pyrazol-1-ylmethyl)-15-oxatetracyclo[6.6.1.0$^{2,7}$.0$^{9,14}$]pentadeca-2,4,6,9,11,13-hexaene-4-carboxamide

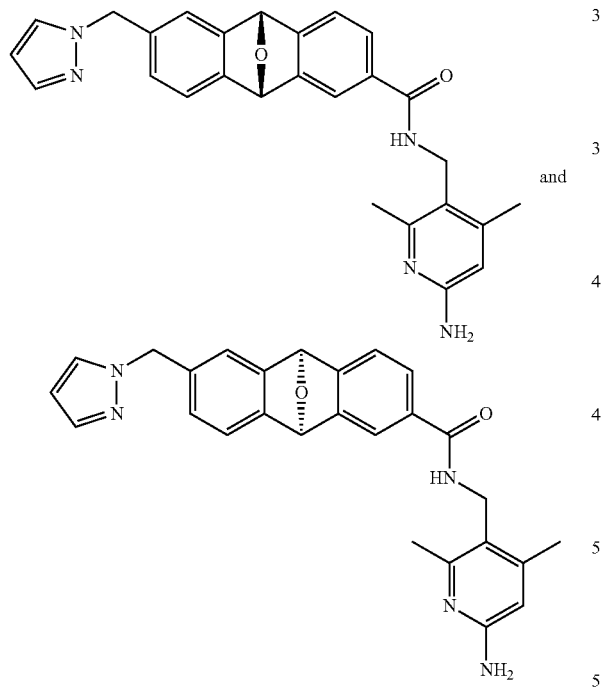

((±)-N-[(6-Amino-2,4-dimethylpyridin-3-yl)methyl]-12-[(1H-pyrazol-1-yl)methyl]-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-[(1H-pyrazol-1-yl)methyl]-15-oxatetracyclo-[6.6.1.0$^{2,7}$.0$^{9,14}$]pentadeca-2,4,6,9,11,13-hexaene-4-carboxamide (Example 1; 25 mg) was purified via R-Phase preparative HPLC (Rt=23.5 min, see conditions for Example 2) affording the title compounds as the more polar eluting component (11.5 mg).

Example 4

Synthesis of (±)-N-[(6-amino-2,4-dimethylpyridin-3-yl)methyl]-12-[(4-methyl-1H-pyrazol-1-yl)methyl]-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-[(4-methyl-1H-pyrazol-1-yl)methyl]-15-oxatetracyclo[6.6.1.0$^{2,7}$.0$^{9,14}$]pentadeca-2,4,6,9,11,13-hexaene-4-carboxamide

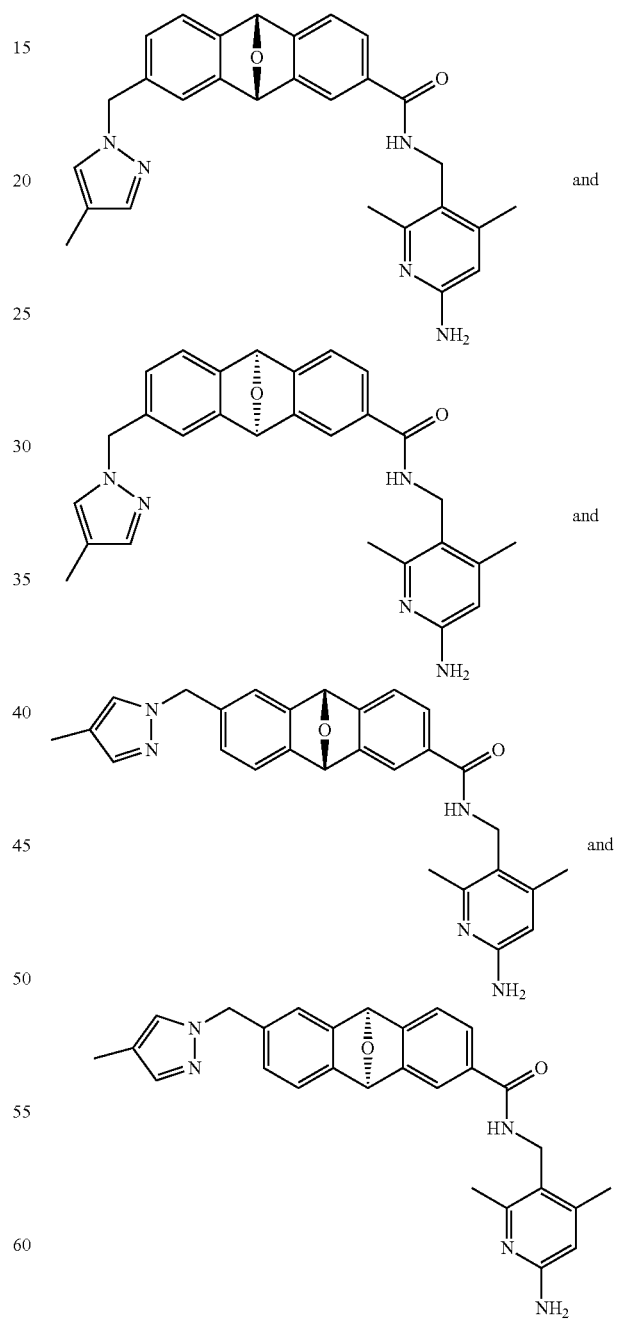

Step 1:

A stirred suspension of a mixture of INT-3 (100 mg; 0.30 mmol; 1 eq.), methylboronic acid (36.2 mg; 0.6 mmol; 2 eq.), cesium carbonate (246 mg; 0.75 mmol; 2.5 eq.) and 1,1'-bis(diphenylphosphino)ferrocene]-dichloropalladium (II) (22 mg; 0.03 mmol; 0.1 eq.) in 1,4-dioxane (12.1 mL) and methanol (3.4 mL) was heated to 80° C. After 1 h, the reacting mixture was cooled to ambient temperature, filtered with additional MeOH and concentrated. The brown residue was purified by column chromatography on a 24 g ISCO Gold column eluting with 10% EtOAc in heptane to provide a mixture of (±) methyl 12-methyl-15-oxatetracyclo [6.6.1.0$^{2,7}$.0$^{9,14}$]pentadeca-2,4,6,9,11,13-hexaene-4-carboxylate and (±) methyl 11-methyl-15-oxatetracyclo [6.6.1.0$^{2,7}$.0$^{9,14}$]pentadeca-2,4,6,9,11,13-hexaene-4-carboxylate (68 mg; 85%).

Step 2:

To a mixture of (±) methyl 12-methyl-15-oxatetracyclo [6.6.1.0$^{2,7}$.0$^{9,14}$]-pentadeca-2,4,6,9,11,13-hexaene-4-carboxylate and (±) methyl 11-methyl-15-oxatetracyclo-[6.6.1.0$^{2,7}$.0$^{9,14}$]pentadeca-2,4,6,9,11,13-hexaene-4-carboxylate (68 mg; 0.26 mmol; 1 eq.), and N-bromosuccinimide (47.7 mg; 0.27 mmol; 1.05 eq.) in carbon tetrachloride (2.6 mL) was added AIBN (2.1 mg; 0.01 mmol; 0.05 eq.). The resulting mixture was heated to 75° C. for 2 h. The reacting mixture was then cooled to ambient temperature, diluted with DCM, washed with sat. NaHCO$_3$, dried over MgSO$_4$, filtered and concentrated. The crude material was purified by column chromatography on a 12 g ISCO Gold column eluting with 10% EtOAc in heptane to provide a mixture of (±) methyl 12-(bromomethyl)-15-oxatetracyclo[6.6.1.0$^{2,7}$.0$^{9,14}$]pentadeca-2,4,6,9,11,13-hexaene-4-carboxylate and (±) methyl 11-(bromomethyl)-15-oxatetracyclo-[6.6.1.0$^{2,7}$.0$^{9,14}$]pentadeca-2,4,6,9,11,13-hexaene-4-carboxylate (67 mg; 76%).

Step 3:

To a stirred solution of a mixture of (±) methyl 12-(bromomethyl)-15-oxatetracyclo[6.6.1.0$^{2,7}$.0$^{9,14}$]pentadeca-2,4,6,9,11,13-hexaene-4-carboxylate and (±) methyl 11-(bromomethyl)-15-oxatetracyclo-[6.6.1.0$^{2,7}$.0$^{9,14}$] pentadeca-2,4,6,9,11,13-hexaene-4-carboxylate (67.00 mg; 0.19 mmol; 1.00 eq.) and 4-methyl-1H-pyrazole (0.03 mL; 0.39 mmol; 2 eq.) in N,N-dimethylformamide (1.9 mL) was added cesium carbonate (126.5 mg; 0.39 mmol; 2 eq.). The mixture was stirred at ambient temperature overnight then it was diluted with EtOAc, washed with water, dried over MgSO$_4$, filtered and concentrated. The crude material was purified by column chromatography on a 4 g ISCO Gold column eluting with 10 and 40% EtOAc in heptane to provide a mixture of (±) methyl 12-[(4-methyl-1H-pyrazol-1-yl)methyl]-15-oxatetracyclo-[6.6.1.0$^{2,7}$.0$^{9,14}$]pentadeca-2,4,6,9,11,13-hexaene-4-carboxylate and (±) methyl 11-[(4-methyl-1H-pyrazol-1-yl)methyl]-15-oxatetracyclo-[6.6.1.0$^{2,7}$.0$^{9,14}$]pentadeca-2,4,6,9,11,13-hexaene-4-carboxylate (52 mg; 77%).

Step 4:

(±) Methyl 12-[(4-methyl-1H-pyrazol-1-yl)methyl]-15-oxatetracyclo-[6.6.1.0$^{2,7}$.0$^{9,14}$]pentadeca-2,4,6,9,11,13-hexaene-4-carboxylate and (±) methyl 11-[(4-methyl-1H-pyrazol-1-yl)methyl]-15-oxatetracyclo-[6.6.1.0$^{2,7}$.0$^{9,14}$] pentadeca-2,4,6,9,11,13-hexaene-4-carboxylate was converted to (±) 12-[(4-methyl-1H-pyrazol-1-yl)methyl]-15-oxatetracyclo-[6.6.1.0$^{2,7}$.0$^{9,14}$]pentadeca-2,4,6,9,11,13-hexaene-4-carboxylic acid and (±) 11-[(4-methyl-1H-pyrazol-1-yl)methyl]-15-oxatetracyclo-[6.6.1.0$^{2,7}$.0$^{9,14}$] pentadeca-2,4,6,9,11,13-hexaene-4-carboxylic acid according to the procedure described for Example 1, Step 4 and the crude material was converted to the title compounds following the procedure described for Example 1, Step 5. The reaction mixture was diluted with 0.8 mL water and directly purified via R-Phase prep HPLC (13 min. method at 28 mL/min eluting with a gradient of 95-0% water (containing 0.1% formic acid) in acetonitrile) affording the title compounds as a white powder (10 mg; 29%). MS ES+m/z=466.05 (M+H)$^+$.

Example 5

Synthesis of (±)N-[(6-amino-2,4-dimethylpyridin-3-yl)methyl]-12-(2-fluorophenyl)-15-oxatetracyclo [6.6.1.0$^{2,7}$.0$^{9,14}$]pentadeca-2,4,6,9,11,13-hexaene-4-carboxamide

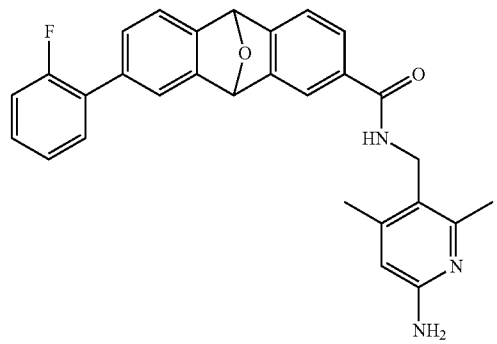 [SMILES: Cc1cc(N)nc(C)c1CNC(=O)c1ccc2c(c1)C1OC2c2ccc(-c3ccccc3F)cc21]

Step 1:

To a solution of methyl 7-bromo-9,10-dihydro-9,10-epoxyanthracene-2-carboxylate (50 mg; 0.15 mmol; 1 eq.) and (2-fluorophenyl)boronic acid (25 mg; 0.18 mmol) in p-dioxane (1.2 mL) was added 1,1'-bis(diphenylphosphino)-ferrocene]dichloropalladium (II) (11.05 mg; 0.015 mmol) and sodium carbonate (32 mg; 0.3 mmol) in water (0.4 mL). After heating at 90° C. for 1 h, the mixture was cooled and diluted with EtOAc, organic layer was washed with water, brine, dried and concentrated to give crude product, which was purified by column chromatography (Hexanes/EtOAc=3:1) to give methyl 7-(2-fluorophenyl)-9,10-dihydro-9,10-epoxyanthracene-2-carboxylate (45 mg).

Step 2:

To a solution of methyl 7-(2-fluorophenyl)-9,10-dihydro-9,10-epoxyanthracene-2-carboxylate (45 mg, 0.13 mmol) in THF (1 mL) and MeOH (0.5 mL) was added a solution of LiOH (7 mg, 0.3 mmol) in water (0.5 mL), after stirred at ambient temperature for 2 h, the mixture was added 1N HCl to pH=3, and the acidified mixture was concentrated to dryness to give 7-(2-fluorophenyl)-9,10-dihydro-9,10-epoxyanthracene-2-carboxylic acid, which was used for next step without further purification.

Step 3:

To a solution of above crude 7-(2-fluorophenyl)-9,10-dihydro-9,10-epoxyanthracene-2-carboxylic acid and 5-(aminomethyl)-4,6-dimethylpyridin-2-amine (34 mg; 0.23 mmol) in DMF (1 mL) was added diisopropylethylamine (0.1 mL, 0.6 mmol) and HATU-1-[bis(dimethylamino)methylene]-1H-1,2,3-triazolo[4,5-b]pyridinium 3-oxid hexafluorophosphate (63 mg; 0.17 mmol), after stirred for 30 min at ambient temperature, it was diluted with water and was purified by column to give the title compounds (42 mg). MS: (M+H)$^+$ found for C$_{29}$H$_{24}$FN$_3$O$_2$: 466.5.

Example 6

Synthesis of (±)N-[(6-amino-2,4-dimethylpyridin-3-yl)methyl]-12-(2,4-difluorophenyl)-15-oxatetracyclo[6.6.1.0$^{2,7}$.0$^{9,14}$]pentadeca-2,4,6,9,11,13-hexaene-4-carboxamide

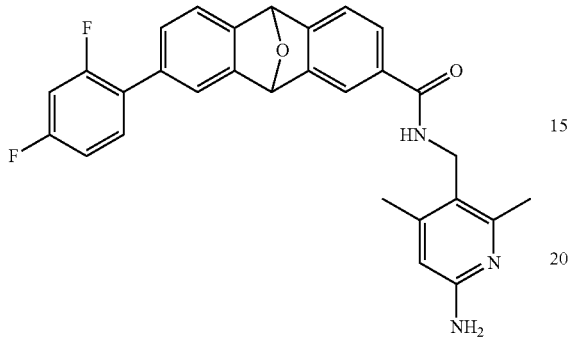

Step 1:

To a solution of methyl 6- and 7-bromo-9,10-dihydro-9,10-epoxyanthracene-2-carboxylate (INT-3, 50 mg; 0.15 mmol; 1 eq., regioisomer mixtures) and 2,4-difluorophenylboronic acid (29 mg; 0.18 mol; 1.2 eq.) in dioxane (1.2 mL) was added 1,1'-bis(diphenylphosphino)ferrocene]dichloropalladium(II) (11 mg; 0.015 mol; 0.1 eq.) and sodium carbonate (32 mg; 0.3 mol; 2 eq.) in water (0.4 mL). After heating at 90° C. for 1 hr, the reaction mixture was diluted with EtOAc and brine, aqueous layer was separated and extracted with EtOAc, and organic layers were combined, dried and concentrated to give crude product, which was purified by column (Hexanes/EtOAc=4:1) to give methyl 6- and 7-(2,4-difluorophenyl)-9,10-dihydro-9,10-epoxyanthracene-2-carboxylate (36 mg).

Step 2:

A mixture of methyl 6- and 7-(2,4-difluorophenyl)-9,10-dihydro-9,10-epoxyanthracene-2-carboxylate was dissolved in THF (1 mL) and MeOH (0.5 mL) and lithium hydroxide (7 mg; 0.3 mmol; 2 eq.) in water (0.5 mL) was added. After stirring at room temperature for 2 h, the reaction mixture was acidified with 1N HCl and lyophilized to give a mixture of 6- and 7-(2,4-difluorophenyl)-9,10-dihydro-9,10-epoxyanthracene-2-carboxylic acid as crude product. The regioisomers were separated by HPLC.

Step 3:

To crude 7-(2,4-difluorophenyl)-9,10-dihydro-9,10-epoxyanthracene-2-carboxylic acid in DMF (1.5 mL) was added 5-(aminomethyl)-4,6-dimethylpyridin-2-amine (46 mg; 0.3 mmol; 2 eq.) and Hunig's base (0.11 mL; 0.6 mmol; 4 eq.) followed by HATU (63 mg; 0.17 mmol; 1.1 eq.). After stirring for 20 min at room temperature the mixture was diluted with water and CH$_3$CN and was purified by preparatory HPLC to give the title compound (29 mg). MS: (M+H)$^+$ found for C$_{29}$H$_{23}$F$_2$N$_3$O$_2$: 484.2

Example 7

Synthesis of (1R,8S)—N-[(6-amino-2,4-dimethylpyridin-3-yl)methyl]-12-(2,4-difluorophenyl)-15-oxatetracyclo[6.6.1.0$^{2,7}$.0$^{9,14}$]pentadeca-2,4,6,9,11,13-hexaene-4-carboxamide

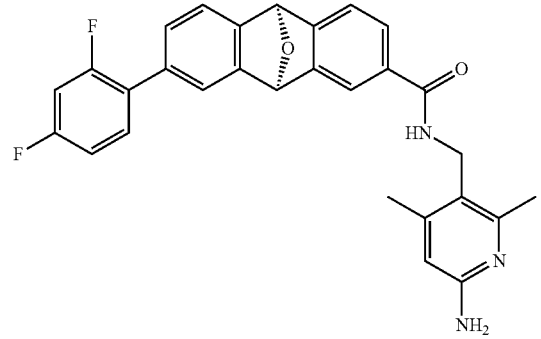 [SMILES: Cc1cc(N)nc(C)c1CNC(=O)c1ccc2c(c1)[C@@H]1O[C@H]2c2ccc(-c3ccc(F)cc3F)cc21]

Step 1:

To a solution of (1S,8R)-12-bromo-15-oxatetracyclo[6.6.1.0$^{2,7}$.0$^{9,14}$]-pentadeca-2,4,6,9,11,13-hexaene-4-carboxylate INT-3a1(75 mg; 0.23 mmol; 1 eq.) in dioxane (1.5 mL) was added 2,4-difluoropheny-lboronic acid (43 mg; 0.27 mmol; 1.2 eq.) and 1,1'-bis(diphenylphosphino)-ferrocene]-dichloropalladichloropalladium(II) (17 mg; 0.02 mmol; 0.1 eq.) followed by sodium carbonate (48 mg; 0.45 mmol; 2 eq.) in water (0.5 mL). After stirring for 1.5 hr at approx. 90° C., the reaction mixture was cooled and diluted with EtOAc and brine, aqueous layer was separated and extracted with EtOAc, and organic layers were combined, dried and concentrated to give crude product, which was purified by column (Hexanes/EtOAc=4:1) to give methyl (1R,8S)-12-(2,4-difluorophenyl)-15-oxatetracyclo[6.6.1.0$^{2,7}$.0$^{9,14}$]pentadeca-2,4,6,9,11,13-hexaene-4-carboxylate (57 mg, 69%).

Step 2:

To a solution of methyl (1R,8S)-12-(2,4-difluorophenyl)-15-oxatetracyclo-[6.6.1.0$^{2,7}$.0$^{9,14}$]pentadeca-2,4,6,9,11,13-hexaene-4-carboxylate (55 mg; 0.15 mmol; 1 eq.) in THF (1 mL) and MeOH (0.5 mL) was added lithium hydroxide (7 mg; 0.3 mmol; 2 eq.) in water (0.5 mL). After stirring for 3 h, the reaction mixture was acidified by 1N HCl to pH=3 and the mixture were lyophilized to give (1R,8S)-12-(2,4-difluorophenyl)-15-oxatetracyclo-[6.6.1.0$^{2,7}$.0$^{9,14}$]pentadeca-2,4,6,9,11,13-hexaene-4-carboxylic acid as crude product.

Step 3:

To (1R,8S)-12-(2,4-difluorophenyl)-15-oxatetracyclo-[6.6.1.0$^{2,7}$.0$^{9,14}$]pentadeca-2,4,6,9,11,13-hexaene-4-carboxylic acid in DMF (1.5 mL) was added 5-(aminomethyl)-4,6-dimethylpyridin-2-amine (46 mg; 0.3 mmol; 2 eq.) and Hunig's base (0.11 mL; 0.6 mmol; 4 eq.) followed by HATU (63 mg; 0.17 mmol; 1.1 eq.). After stirring for 20 min at room temperature the mixture was purified by preparatory HPLC to give the title compound (73 mg, 100%). MS: (M+H)$^+$ found for C$_{29}$H$_{23}$F$_2$N$_3$O$_2$: 484.2

Example 8

Synthesis of (±)N-[(6-amino-2,4-dimethylpyridin-3-yl)methyl]-12-(1,3-benzoxazol-4-yl)-15-oxatetracyclo[6.6.1.0$^{2,7}$.0$^{9,14}$]pentadeca-2,4,6,9,11,13-hexaene-4-carboxamide and (±)N-[(6-amino-2,4-dimethylpyridin-3-yl)methyl]-11-(1,3-benzoxazol-4-yl)-15-oxatetracyclo[6.6.1.0$^{2,7}$.0$^{9,14}$]pentadeca-2,4,6,9,11,13-hexaene-4-carboxamide

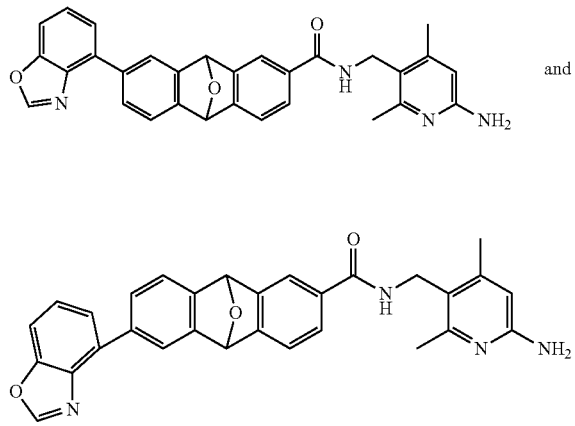

Step 1:

Yttrium tris(trifluoromethanesulfonate) (35.64 mg; 0.07 mmol; 0.05 eq.) and (diethoxymethoxy)ethane (2.2 mL; 13.3 mmol; 10 eq.) were combined. To this mixture was added a solution of 2-amino-3-bromophenol (0.25 g; 1.33 mmol; 1 eq.) in pyridine (215 µL; 2.66 mmol; 2 eq.) and DMSO (1 mL). The reaction mixture was stirred in a heat block at 70° C. for 4 h. After cooling the reaction mixture was taken up in ethyl acetate and water. The phases were separated, the aqueous phase was extracted with ethyl acetate, the combined organic phases were washed with water and brine, and then dried over sodium sulfate. After evaporation of solvent, the residue was purified by silica gel chromatography (ethyl acetate/hexanes gradient) to give 4-bromobenzo[d]-oxazole (0.19 g) as an off-white crystalline solid.

Step 2:

4-Bromo-1,3-benzoxazole (320 mg; 1.62 mmol; 1 eq.) (g-cxy-000589) was dissolved in 1,4-dioxane (5 mL) and the solution was purged with argon gas. 4,4,4',4',5,5,5',5'-Octamethyl-2,2'-bi(1,3,2-dioxaborolane) (1026 mg; 4.04 mmol; 2.5 eq.), tricyclohexylphosphane (32 mg; 0.11 mmol; 0.07 eq.), potassium acetate (476 mg; 4.85 mmol; 3 eq.) and tris(dibenzylideneacetone)dipalladium(0) (74 mg; 0.08 mmol; 0.05 eq.) were added and the reaction mixture was sealed and stirred in a heat block at 90° C. After 2 h, the reaction mixture was cooled and taken up in ethyl acetate and ammonium chloride solution. The phases were separated, the aqueous phase was extracted with more ethyl acetate and the combined organic phases were dried over sodium sulfate. After evaporation of solvent the residue was purified by silica gel chromatography (methanol/DCM gradient) to give 4-(4,4,5,5-tetramethyl-1,3,2-dioxaborolan-2-yl)benzo[d]oxazole (0.29 g) as an oil.

Step 3:

4-(Tetramethyl-1,3,2-dioxaborolan-2-yl)-1,3-benzoxazole (110 mg; 0.42 mmol; 1.1 eq.) and a mixture of methyl 6-bromo-9,10-dihydro-9,10-epoxyanthracene-2-carboxylate/methyl 7-bromo-9,10-dihydro-9,10-epoxyanthracene-2-carboxylate (127 mg; 0.38 mmol; 1 eq.) were dissolved in 1,4-dioxane (2.5 mL) and sodium carbonate solution (0.44 mL; 2.60 mol/l; 1.15 mmol; 3 eq.) The solution was purged with argon gas. 1,1'-bis(diphenyl-phosphino)ferrocene]dichloropalladium(II) (28 mg; 0.04 mmol; 0.1 eq.) was added, the reaction was sealed and stirred in a heat block at 90° C. for 1.5 h. The cooled mixture was taken up in ethyl acetate and sodium bicarbonate solution. The phases were separated, the aqueous phase was extracted with more ethyl acetate and the combined organic phases were washed with brine. After drying over sodium sulfate and evaporation of solvent the residue was purified by silica gel chromatography (ethyl acetate/hexanes gradient) to give a mixture of methyl 6-(benzo[d]oxazol-4-yl)-9,10-dihydro-9,10-epoxyanthracene-2-carboxylate/methyl 7-(benzo[d]oxazol-4-yl)-9,10-dihydro-9,10-epoxyanthracene-2-carboxylate (0.1 g) as a colorless film.

Step 4:

A mixture of methyl 6-(benzo[d]oxazol-4-yl)-9,10-dihydro-9,10-epoxyanthracene-2-carboxylate and methyl 7-(benzo[d]oxazol-4-yl)-9,10-dihydro-9,10-epoxyanthracene-2-carboxylate (mixture of stereoisomers, 100 mg; 0.27 mmol; 1 eq.) was dissolved in THF (2.7 mL) and methanol (0.9 mL) and cooled in an ice bath. Lithium hydroxide (32 mg; 1.35 mmol; 5 eq.) dissolved in water (1.3 mL) was added dropwise and the reaction was then stirred at 25° C. After 2.5 h, water, ethyl acetate and 1 M HCl to adjust the pH to 4 were added. The mixture was partitioned into ammonium chloride solution and ethyl acetate, and the phases were separated and the aqueous phase was extracted with more ethyl acetate. The combined organic phases were washed with brine and dried over sodium sulfate. Evaporation of solvent gave a mixture of 6-(benzo[d]oxazol-4-yl)-9,10-dihydro-9,10-epoxyanthracene-2-carboxylic acid and 7-(benzo[d]oxazol-4-yl)-9,10-dihydro-9,10-epoxyanthracene-2-carboxylic acid which was used directly in the next step.

Step 5:

A mixture of 6-(benzo[d]oxazol-4-yl)-9,10-dihydro-9,10-epoxyanthracene-2-carboxylic acid and 7-(benzo[d]oxazol-4-yl)-9,10-dihydro-9,10-epoxyanthracene-2-carboxylic acid (mixture of stereoisomers, 96 mg; 0.27 mmol; 1 eq.) was dissolved in DMF (6 mL). Hunig's base-ethylbis(propan-2-yl)amine (376 µL; 2.16 mmol; 8 eq.), 5-(azaniumylmethyl)-4,6-dimethylpyridin-2-aminium ditrifluoroacetate (180 mg; 0.3 mmol; 1.1 eq.), then HATU-hexafluoro-5-phosphanuide 1-[(dimethylamino)(dimethyliminiumyl)methyl]-1H-[1,2,3]triazolo[4,5-b]pyridin-3-ium-3-olate (205 mg; 0.54 mmol; 2 eq.) were added and the reaction mixture was stirred at 25° C. After 16 h, the reaction mixture was warmed to 50° C. in a heat block for 2.5 h then cooled and taken up in water, sodium bicarbonate solution and ethyl acetate. The phases were separated and the aqueous phase was extracted with more ethyl acetate. The combined organic phases were washed with brine, dried over sodium sulfate and evaporated to a residue which was purified by reverse phase chromatography (acetonitrile gradient with 0.1% aqueous formic acid, Waters XSelect CSH column) to give a mixture of the title compounds (14 mg) as a white solid. MS (M+H)$^+$ found for $C_{30}H_{24}N_4O_3$: 489.4.

Example 9

Synthesis of (±)N-[(6-amino-2,4-dimethylpyridin-3-yl)methyl]-12-(2-cyano-4-methylphenyl)-15-oxatetracyclo[6.6.1.0$^{2,7}$.0$^{9,14}$]pentadeca-2,4,6,9,11,13-hexaene-4-carboxamide

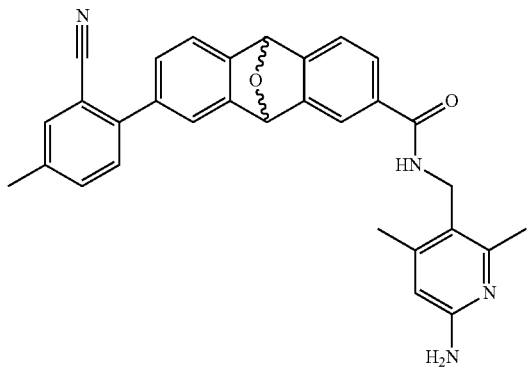

Step 1:

(5-Methyl-2-(tetramethyl-1,3,2-dioxaborolan-2-yl)benzonitrile (59 mg; 0.24 mmol; 1 eq.), methyl (±) 7-bromo-9,10-dihydro-9,10-epoxyanthracene-2-carboxylate (INT-3a, 80 mg; 0.24 mmol; 1 eq.) and potassium carbonate (67 mg; 0.48 mmol; 2 eq.) were dissolved THF (1.2 mL) and water (0.6 mL). The solution was purged with Ar gas and [1,1'-bis(di-t-butyl-phosphino)ferrocene]palladium (II) dichloride (7.9 mg; 0.01 mmol; 0.05 eq.) was added and the reaction was sealed and stirred in a heat block at 60° C. for 7 h. The cooled mixture was partitioned into ethyl acetate and sodium bicarbonate solution, and the phases were separated. The aqueous phase was extracted with more ethyl acetate, the combined organics were washed brine, and dried over sodium sulfate. After evaporation the residue was purified by silica gel chromatography (ethyl acetate/hexanes gradient) to give methyl (±)7-(2-cyano-4-methylphenyl)-9,10-dihydro-9,10-epoxyanthracene-2-carboxylate (77 mg) as a colorless film.

Step 2:

Methyl (±)7-(2-cyano-4-methylphenyl)-9,10-dihydro-9,10-epoxyanthracene-2-carboxylate (77 mg; 0.21 mmol; 1 eq.) was dissolved in THF (2 mL) and methanol (0.7 mL). Lithium hydroxide (anhydrous) (25.1 mg; 1.05 mmol; 5 eq.) in water (1 mL) was added dropwise and the mixture was stirred at 25° C. for 4 h. Dilute aqueous HCl and water were added to adjust the pH to <4. Ethyl acetate and aqueous ammonium chloride solution were added, the phases were separated, and the aqueous phase was extracted with more ethyl acetate. The combined organic phases were washed with brine and dried over sodium sulfate. The solution was evaporated to 0.06 g of (±)7-(2-cyano-4-methylphenyl)-9,10-dihydro-9,10-epoxyanthracene-2-carboxylic acid as a white solid, which was used directly in the next step.

Step 3:

(±) 7-(2-Cyano-4-methylphenyl)-9,10-dihydro-9,10-epoxyanthracene-2-carboxylic acid (74 mg; 0.21 mmol; 1 eq.) was dissolved in DMF (2 mL). Hunig's base-ethylbis(propan-2-yl)amine (292 µL; 1.68 mmol; 8 eq.), 5-(azaniumylmethyl)-4,6-dimethylpyridin-2-aminium ditrifluoroacetate (amine-la, 159 mg; 0.31 mmol; 1.5 eq.), then 1-[bis(dimethylamino)-methylene]-1H-1,2,3-triazolo[4,5-b]pyridinium 3-oxid hexafluorophosphate (159 mg; 0.42 mmol; 2 eq.) were added and the reaction was stirred at 25° C. for 14 h. The reaction mixture was then partitioned into sodium bicarbonate solution and ethyl acetate. The phases were separated and the aqueous phase was extracted with more ethyl acetate. The combined organic phases were washed with brine and dried over sodium sulfate. After evaporation the residue was purified by reverse phase chromatography (acetonitrile gradient with 0.1% aqueous formic acid, Waters XSelect CSH column) to give the title compound (50 mg) as a white solid. MS: (M+H)$^+$ found for $C_{31}H_{26}N_4O_2$: 487.4.

Example 10

Synthesis of (±)N-[(6-amino-2,4-dimethylpyridin-3-yl)methyl]-12-[(pyrrolidin-1-yl)methyl]-15-oxatetracyclo[6.6.1.0$^{2,7}$.0$^{9,14}$]pentadeca-2,4,6,9,11,13-hexaene-4-carboxamide and (±)N-[(6-amino-2,4-dimethylpyridin-3-yl)methyl]-11-[(pyrrolidin-1-yl)methyl]-15-oxatetracyclo[6.6.1.0$^{2,7}$.0$^{9,14}$]pentadeca-2,4,6,9,11,13-hexaene-4-carboxamide

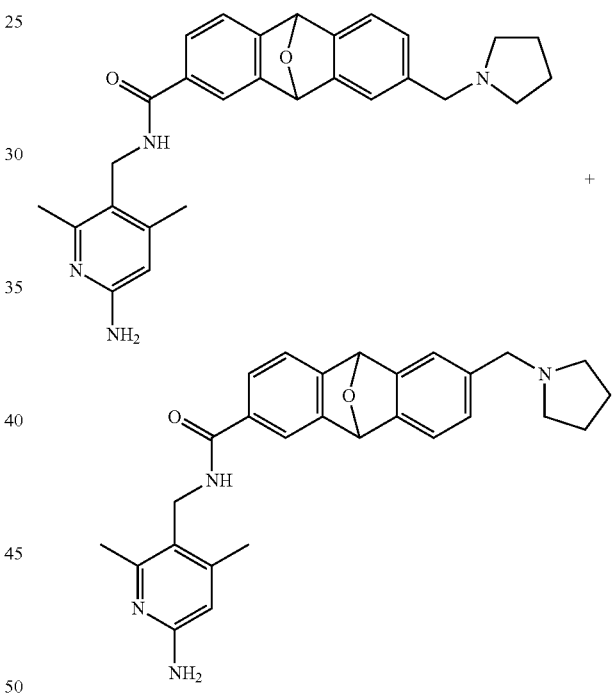

Step 1:

A stirred suspension of (±) methyl 12-bromo-15-oxatetracyclo-[6.6.1.0$^{2,7}$.0$^{9,14}$]-pentadeca-2,4,6,9,11,13-hexaene-4-carboxylate and (±) methyl 11-bromo-15-oxatetracyclo-[6.6.1.0$^{2,7}$.0$^{9,14}$]pentadeca-2,4,6,9,11,13-hexaene-4-carboxylate (INT-3; 100.00 mg; 0.30 mmol; 1.00 eq.), methylboronic acid (36.2 mg; 0.60 mmol; 2.00 eq.), cesium carbonate (246.0 mg; 0.75 mmol; 2.50 eq.) and 1,1'-bis(diphenylphosphino)-ferrocene]-dichloropalladium(II) (Pd(dppf)Cl$_2$; 22.1 mg; 0.03 mmol; 0.10 eq.) in 1,4-dioxane (12.1 ml) and methanol (3.4 ml) was heated to 80° C. LC/MS analysis after 1 h showed complete conversion to a mixture of the desired product (major) and the de-brominated starting material (minor). The reacting mixture was cooled to RT, filtered with additional MeOH and concentrated. The brown residue was purified by column chromatography (24 G ISCO Gold) eluting with 10% EtOAc in heptane to provide a mixture of (±) methyl 12-methyl-15-oxatetracyclo[6.6.1.0$^{2,7}$.0$^{9,14}$]pentadeca-2,4,6,9,11,13-hexaene-4-carboxylate, (±) methyl 11-methyl-15-oxatetracyclo[6.6.1.0$^{2,7}$.0$^{9,14}$]pentadeca-2,4,6,9,11,13-hexaene-4-carboxylate and (±) methyl 15-oxatetracyclo[6.6.1.0$^{2,7}$.0$^{9,14}$]pentadeca-2,4,6,9,11,13-hexaene-4-carboxylate (68 mg; 85%).

Step 2:

To a mixture of (±) methyl 12-methyl-15-oxatetracyclo[6.6.1.0$^{2,7}$.0$^{9,14}$]-pentadeca-2,4,6,9,11,13-hexaene-4-carboxylate, (±) methyl 11-methyl-15-oxatetracyclo-[6.6.1.0$^{2,7}$.0$^{9,14}$]-pentadeca-2,4,6,9,11,13-hexaene-4-carboxylate and (±) methyl 15-oxatetracyclo[6.6.1.0$^{2,7}$.0$^{9,14}$]-pentadeca-2,4,6,9,11,13-hexaene-4-carboxylate (50.0 mg; 0.19 mmol; 1.00 eq.), and N-bromosuccinimide (NBS; 33.4 mg; 0.19 mmol; 1.00 eq.) in carbon tetrachloride (1.9 ml) was added 2,2'-azobis(2-methylpropionitrile) (AIBN; 1.5 mg; 0.01 mmol; 0.05 eq.). The resulting mixture was heated to 75° C. and after 3 h more N-bromosuccinimide (0.5 eq.) was added and the temperature was increased to 82° C. LC/MS after 4 h showed complete conversion of the starting material. The reaction mixture was cooled to RT, diluted with DCM, washed with sat. NaHCO$_3$, dried over MgSO$_4$, filtered and concentrated. The residue was purified by column chromatography (12 G ISCO Gold) eluting with 10% EtOAc in heptane to provide an inseparable mixture of (±) methyl 12-(bromomethyl)-15-oxatetracyclo-[6.6.1.0$^{2,7}$.0$^{9,14}$]-pentadeca-2,4,6,9,11,13-hexaene-4-carboxylate and (±) methyl 11-(bromomethyl)-15-oxatetracyclo[6.6.1.0$^{2,7}$.0$^{9,14}$]pentadeca-2,4,6,9,11,13-hexaene-4-carboxylate (1:1; minor component) and (±) methyl 12-(dibromomethyl)-15-oxatetracyclo[6.6.1.0$^{2,7}$.0$^{9,14}$]-pentadeca-2,4,6,9,11,13-hexaene-4-carboxylate and (±) methyl 11-(dibromomethyl)-15-oxatetracyclo[6.6.1.0$^{2,7}$.0$^{9,14}$]pentadeca-2,4,6,9,11,13-hexaene-4-carboxylate (1:1; major component); (60 mg).

Step 3:

To a stirred solution of (±) methyl 12-(bromomethyl)-15-oxatetracyclo-[6.6.1.0$^{2,7}$.0$^{9,14}$]pentadeca-2,4,6,9,11,13-hexaene-4-carboxylate, (±) methyl 11-(bromomethyl)-15-oxatetracyclo[6.6.1.0$^{2,7}$.0$^{9,14}$]pentadeca-2,4,6,9,11,13-hexaene-4-carboxylate, (±) methyl 12-(dibromomethyl)-15-oxatetracyclo[6.6.1.0$^{2,7}$.0$^{9,14}$]pentadeca-2,4,6,9,11,13-hexaene-4-carboxylate and (±) methyl 11-(dibromomethyl)-15-oxatetracyclo[6.6.1.0$^{2,7}$.0$^{9,14}$]pentadeca-2,4,6,9,11,13-hexaene-4-carboxylate (60.0 mg; 0.17 mmol; 1.00 eq.) and, 1H-pyrazole (23.7 mg; 0.35 mmol; 2.00 eq.) in N,N-dimethylformamide (1.7 ml) was added cesium carbonate (113.3 mg; 0.35 mmol; 2.00 eq.). The mixture was stirred at RT for 10 min then it was diluted with EtOAc, washed with water, dried over MgSO$_4$, filtered and concentrated. The residue was purified by column chromatography (4 G ISCO Gold) eluting with a gradient of 0-10% (7 min) and 10-40% (8 min) EtOAc in heptane to provide a mixture of (±) methyl 12-(dibromomethyl)-15-oxatetracyclo[6.6.1.0$^{2,7}$.0$^{9,14}$]-pentadeca-2,4,6,9,11,13-hexaene-4-carboxylate and (±) methyl 11-(dibromomethyl)-15-oxatetracyclo[6.6.1.0$^{2,7}$.0$^{9,14}$]pentadeca-2,4,6,9,11,13-hexaene-4-carboxylate (30 mg).

Step 4:

A solution of (±) methyl 12-(dibromomethyl)-15-oxatetracyclo-[6.6.1.0$^{2,7}$.0$^{9,14}$]-pentadeca-2,4,6,9,11,13-hexaene-4-carboxylate and (±) methyl 11-(dibromomethyl)-15-oxatetracyclo[6.6.1.0$^{2,7}$.0$^{9,14}$]pentadeca-2,4,6,9,11,13-hexaene-4-carboxylate (47.0 mg; 0.11 mmol; 1.00 eq.) in tetrahydrofuran (0.3 ml) was cooled to 0° C. and Hunig's base-ethylbis(propan-2-yl)amine (DIEA; 0.02 ml; 0.12 mmol; 1.05 eq.) was added drop-wise, followed by diethoxyphosphinous acid (0.01 ml; 0.12 mmol; 1.05 eq.). The mixture was stirred at room temperature. On observing no reaction after overnight stirring the mixture was quenched with 0.2 mL of water and it was extracted with EtOAc. The organic layer was washed with sat. aq. NH$_4$Cl and brine then dried over MgSO$_4$, filtered and concentrated. The residue was treated with NaI in DMF and heated to 80° C. LC/MS analysis after 1 h showed complete conversion of the starting material. The black mixture was cooled to RT, diluted with brine, extracted with EtOAc, dried over MgSO$_4$, filtered and concentrated. The residue was purified by column chromatography (4 G ISCO Gold) eluting with 10% EtOAc in heptane to provide a mixture of (±) methyl 12-formyl-15-oxatetracyclo[6.6.1.0$^{2,7}$.0$^{9,14}$]pentadeca-2,4,6,9,11,13-hexaene-4-carboxylate and (±) methyl 11-formyl-15-oxatetracyclo[6.6.1.0$^{2,7}$.0$^{9,14}$]pentadeca-2,4,6,9,11,13-hexaene-4-carboxylate (20.0 mg; 64%).

Step 5:

A solution of (±) methyl 12-formyl-15-oxatetracyclo[6.6.1.0$^{2,7}$.0$^{9,14}$]-pentadeca-2,4,6,9,11,13-hexaene-4-carboxylate and (±) methyl 11-formyl-15-oxatetracyclo[6.6.1.0$^{2,7}$.0$^{9,14}$]-pentadeca-2,4,6,9,11,13-hexaene-4-carboxylate (20.0 mg; 0.07 mmol; 1.00 eq.) in tetrahydrofuran (0.7 ml) at RT was added pyrrolidine (0.01 ml; 0.09 mmol; 1.20 eq.). After 10 min, sodium cyanoborohydride (1.4 mg; 0.02 mmol; 0.30 eq.) was added and the mixture was stirred at RT. On observing no reaction after overnight stirring, acetic acid (few drops) was added and LC/MS analysis after a few minutes showed complete conversion of the starting material. The mixture was quenched with sat. NaHCO$_3$, diluted with water and extracted with EtOAc. The combined organics were dried over MgSO$_4$, filtered and concentrated. The residue was purified by column chromatography (4 G ISCO Gold) eluting with 100% EtOAC to provide (±) methyl 12-(pyrrolidin-1-ylmethyl)-15-oxatetracyclo[6.6.1.0$^{2,7}$.0$^{9,14}$]pentadeca-2,4,6,9,11,13-hexaene-4-carboxylate and (±) methyl 11-(pyrrolidin-1-ylmethyl)-15-oxatetracyclo-[6.6.1.0$^{2,7}$.0$^{9,14}$]pentadeca-2,4,6,9,11,13-hexaene-4-carboxylate (12.8 mg; 54%).

Step 6:

To a stirred solution of (±) methyl 12-(pyrrolidin-1-ylmethyl)-15-oxatetracyclo-[6.6.1.0$^{2,7}$.0$^{9,14}$]pentadeca-2,4,6,9,11,13-hexaene-4-carboxylate and (±) methyl 11-(pyrrolidin-1-ylmethyl)-15-oxatetracyclo[6.6.1.0$^{2,7}$.0$^{9,14}$]pentadeca-2,4,6,9,11,13-hexaene-4-carboxylate (12.0 mg; 0.04 mmol; 1.00 eq.) in 0.4 mL THF and 0.2 mL of MeOH at RT was added 0.2 mL of 1M LiOH. The mixture was stirred at RT for 2.5 h then it was quenched with 0.4 mL 1N HCl, extracted with EtOAc, dried over MgSO$_4$, filtered and concentrated to give the corresponding acid compounds.

Step 7:

To a mixture of 12-(pyrrolidin-1-ylmethyl)-15-oxatetracyclo[6.6.1.0$^{2,7}$.0$^{9,14}$]-pentadeca-2,4,6,9,11,13-hexaene-4-carboxylic acid and (±) methyl 11-(pyrrolidin-1-ylmethyl)-15-oxatetracyclo[6.6.1.0$^{2,7}$.0$^{9,14}$]pentadeca-2,4,6,9,11,13-hexaene-4-carboxylic acid and 5-(aminomethyl)-4,6-dimethylpyridin-2-amine (5.9 mg; 0.04 mmol; 1.10 eq.) (previously azeotroped with 0.8 mL PhMe for 1.5 h) in N,N-dimethylformamide (0.4 ml) at RT was added Hunig's base (0.02 ml; 0.11 mmol; 3.00 eq.) followed by (1-[bis(dimethylamino)methylene]-1H-1,2,3-triazolo[4,5-b]pyridinium 3-oxid hexafluorophosphate) (HATU; 13.6 mg; 0.04 mmol; 1.00 eq.). After 15 minutes, the reacting mixture was diluted with 0.4 mL water (clear solution turned cloudy) and directly purified via R-Phase prep. HPLC (gradient 0% to 75% MeCN with 0.1% formic acid in water with 0.1% formic acid) to obtain the title compounds. MS: (M+H)+ found for $C_{28}H_{30}N_4O_2$: 455.1. (4.0 mg).

Example 11

Synthesis of (1R,8S)—N-[(6-amino-2,4-dimethyl-pyridin-3-yl)methyl]-12-[(4-fluoro-1H-pyrazol-1-yl)methyl]-15-oxatetracyclo[6.6.1.0$^{2,7}$.0$^{9,14}$]pentadeca-2,4,6,9,11,13-hexaene-4-carboxamide

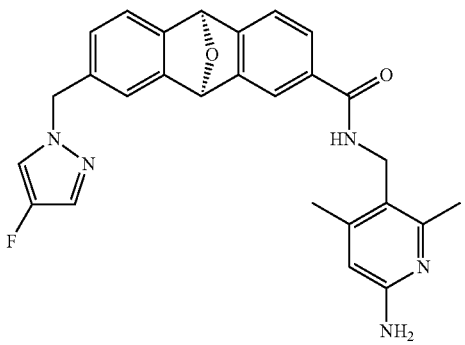 [SMILES: Cc1cc(N)nc(C)c1CNC(=O)c1ccc2c(c1)[C@@H]1O[C@H]2c2ccc(Cn3cc(F)cn3)cc21]

Step 1:
A stirred suspension of methyl (1S,8R)-12-bromo-15-oxatetracyclo-[6.6.1.0$^{2,7}$.0$^{9,14}$]pentadeca-2,4,6,9,11,13-hexaene-4-carboxylate (INT-3a1; 480.00 mg; 1.45 mmol; 1.00 eq.), methylboronic acid (173.53 mg; 2.90 mmol; 2.00 eq.), cesium carbonate (1180.65 mg; 3.62 mmol; 2.50 eq.) and 1,1'-bis(diphenylphosphino)ferrocene]dichloro palladium(II) (106.06 mg; 0.14 mmol; 0.10 eq.) in 1,4-dioxane (57.98 ml) and methanol (16.10 ml) was heated to 80° C. After 1 h the reacting mixture was cooled to RT, filtered with additional MeOH and concentrated. The brown residue was purified by column chromatography (40 G ISCO Gold) eluting with 10% EtOAc in heptane to provide the desired methyl (1R,8S)-12-methyl-15-oxatetracyclo[6.6.1.0$^{2,7}$.0$^{9,14}$]pentadeca-2,4,6,9,11,13-hexaene-4-carboxylate contaminated with inseparable methyl (1R,8S) 15-oxatetracyclo-[6.6.1.0$^{2,7}$.0$^{9,14}$]pentadeca-2,4,6,9,11,13-hexaene-4-carboxylate (320 mg).

Step 2:
To a stirred suspension of methyl (1R,8S)-12-methyl-15-oxatetracyclo-[6.6.1.0$^{2,7}$.0$^{9,14}$]pentadeca-2,4,6,9,11,13-hexaene-4-carboxylate and methyl (1R,8S) 15-oxatetracyclo[6.6.1.0$^{2,7}$.0$^{9,14}$]pentadeca-2,4,6,9,11,13-hexaene-4-carboxylate (320.00 mg; 1.20 mmol; 1.00 eq.), and N-bromosuccinimide (224.58 mg; 1.26 mmol; 1.05 eq.) in carbon tetrachloride (12.02 ml) was added AIBN (9.87 mg; 0.06 mmol; 0.05 eq.). The resulting mixture was heated to 75° C. After 3 h the reacting mixture was cooled to RT diluted with DCM, washed with sat. NaHCO$_3$, dried over MgSO$_4$, filtered and concentrated. The crude material was purified by column chromatography (12 G ISCO Gold) eluting with 10% EtOAc in heptane to provide methyl (1S,8R)-12-(bromomethyl)-15-oxatetracyclo-[6.6.1.0$^{2,7}$.0$^{9,14}$]pentadeca-2,4,6,9,11,13-hexaene-4-carboxylate contaminated by inseparable methyl (1S,8R)-12-(dibromomethyl)-15-oxatetracyclo[6.6.1.0$^{2,7}$.0$^{9,14}$]pentadeca-2,4,6,9,11,13-hexaene-4-carboxylate (273 mg).

Step 3:
To a stirred solution of methyl (1S,8R)-12-(bromomethyl)-15-oxatetracyclo-[6.6.1.0$^{2,7}$.0$^{9,14}$]pentadeca-2,4,6,9,11,13-hexaene-4-carboxylate and methyl (1S,8R)-12-(dibromomethyl)-15-oxatetracyclo[6.6.1.0$^{2,7}$.0$^{9,14}$]pentadeca-2,4,6,9,11,13-hexaene-4-carboxylate (50.00 mg; 0.14 mmol; 1.00 eq.) and 4-fluoro-1H-pyrazole (24.93 mg; 0.29 mmol; 2.00 eq.) in N,N-dimethylformamide (1.45 ml) was added cesium carbonate (94.39 mg; 0.29 mmol; 2.00 eq.). The mixture was stirred at RT overnight then it was diluted with EtOAc, washed with water, dried over MgSO$_4$, filtered and concentrated. The crude material was purified by column chromatography (12 G ISCO Gold) eluting with a gradient of 0-10% (7 minutes) then 10-40% (8 minutes) EtOAc in heptane to provide methyl (1R,8S)-12-[(4-fluoro-1H-pyrazol-1-yl)methyl]-15-oxatetracyclo[6.6.1.0$^{2,7}$.0$^{9,14}$]pentadeca-2,4,6,9,11,13-hexaene-4-carboxylate (34.9 mg).

Step 4:
To a stirred solution of methyl (1R,8S)-12-[(4-fluoro-1H-pyrazol-1-yl)methyl]-15-oxatetracyclo[6.6.1.0$^{2,7}$.0$^{9,14}$]pentadeca-2,4,6,9,11,13-hexaene-4-carboxylate (35.00 mg; 0.10 mmol; 1.00 eq.) in 0.8 mL THF and 0.4 mL of MeOH at RT was added 0.4 mL of 1M LiOH. The mixture was stirred at RT for 2 h then it was quenched with 0.8 mL 1N HCl, extracted with EtOAc, dried over MgSO$_4$, filtered and concentrated.

Step 5:
To a mixture of (1R,8S)-12-[(4-fluoro-1H-pyrazol-1-yl)methyl]-15-oxatetracyclo-[6.6.1.0$^{2,7}$.0$^{9,14}$]pentadeca-2,4,6,9,11,13-hexaene-4-carboxylic acid and 5-(aminomethyl)-4,6-dimethylpyridin-2-amine (30.21 mg; 0.20 mmol; 2.00 eq.) (previously azeotroped with 0.8 mL PhMe) in N,N-dimethylformamide (1.00 ml) at RT was added Hunig's base (0.14 ml; 0.80 mmol; 8.00 eq.) followed by HATU (37.99 mg; 0.10 mmol; 1.00 eq). After 1 h the reacting mixture was diluted with 1 mL water (clear solution turned cloudy) and directly purified via R-Phase prep HPLC (gradient 0% to 75% MeCN with 0.1% formic acid in water with 0.1% formic acid). The fractions containing the product were collected, combined and lyophilized to afford the title compound. MS: (M+H)+ found for $C_{27}H_{24}FN_5O_2$: 470.1. (34.2 mg).

Example 12

Synthesis of (1R,8S)—N-[(6-amino-2,4-dimethyl-pyridin-3-yl)methyl]-12-[(4-methyl-1H-pyrazol-1-yl)methyl]-15-oxatetracyclo[6.6.1.0$^{2,7}$.0$^{9,14}$]pentadeca-2,4,6,9,11,13-hexaene-4-carboxamide

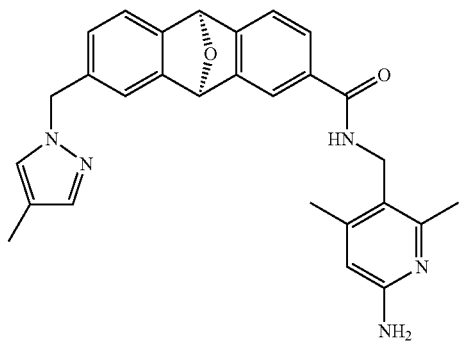

Step 1:
To a stirred solution of methyl (1S,8R)-12-(bromomethyl)-15-oxatetracyclo-[6.6.1.0$^{2,7}$.0$^{9,14}$]pentadeca-2,4,6,9,11,13-hexaene-4-carboxylate and methyl (1S,8R)-12-(dibromomethyl)-15-oxatetracyclo[6.6.1.0$^{2,7}$.0$^{9,14}$]pentadeca- 2,4,6,9,11,13-hexaene-4-carboxylate (Example 11, Steps 1-2; 182.00 mg; 0.53 mmol; 1.00 eq.) and 4-methyl-1H-pyrazole (0.08 ml; 1.05 mmol; 2.00 eq.) in N,N-dimethylformamide (5.27 ml) was added cesium carbonate (343.58 mg; 1.05 mmol; 2.00 eq.). The mixture was stirred at RT then it was diluted with EtOAc, washed with water, dried over $MgSO_4$, filtered and concentrated. The crude material was purified by column chromatography (4 G ISCO Gold) eluting with a gradient of 0-10% (7 minutes) then 10-40% (8 minutes) EtOAc in heptane to provide methyl (1R,8S)-12-[(4-methyl-1H-pyrazol-1-yl)methyl]-15-oxatetracyclo[$6.6.1.0^{2,7}.0^{9,14}$]pentadeca-2,4,6,9,11,13-hexaene-4-carboxylate (153 mg).

Step 2:
To a stirred solution of methyl (1R,8S)-12-[(4-methyl-1H-pyrazol-1-yl)methyl]-15-oxatetracyclo[$6.6.1.0^{2,7}.0^{9,14}$]pentadeca-2,4,6,9,11,13-hexaene-4-carboxylate (153.00 mg; 0.44 mmol; 1.00 eq.) in 3.2 mL THF and 1.6 mL of MeOH at RT was added 1.6 mL of 1M LiOH. The mixture was stirred at RT for 2 h then it was quenched with 3.2 mL 1N HCl, extracted with EtOAc, dried over MgSO4, filtered and concentrated.

Step 3:
To a mixture of (1R,8S)-12-[(4-methyl-1H-pyrazol-1-yl)methyl]-15-oxatetracyclo[$6.6.1.0^{2,7}.0^{9,14}$]pentadeca-2,4,6,9,11,13-hexaene-4-carboxylic acid (153.00 mg; 0.44 mmol; 1.00 eq.) and 5-(aminomethyl)-4,6-dimethylpyridin-2-amine (133.58 mg; 0.88 mmol; 2.00 eq.) (previously azeotroped with 2 mL PhMe) in N,N-dimethylformamide (4.42 ml) at RT was added Hunig's base (0.62 ml; 3.53 mmol; 8.00 eq.) followed by HATU (167.95 mg; 0.44 mmol; 1.00 eq.). After 1 h the reacting mixture was diluted with 4.5 mL water (clear solution turned cloudy) and directly purified via R-Phase prep HPLC (gradient 0% to 75% MeCN with 0.1% formic acid in water with 0.1% formic acid; 4 injections 2.1 mL each). The fractions containing the product from the four runs were collected, combined and lyophilized to afford (1R,8S)—N-[(6-amino-2,4-dimethylpyridin-3-yl)methyl]-12-[(4-methyl-1H-pyrazol-1-yl)methyl]-15-oxatetracyclo[$6.6.1.0^{2,7}.0^{9,14}$]pentadeca-2,4,6,9,11,13-hexaene-4-carboxamide. MS: $(M+H)^+$ found for $C_{28}H_{27}N_5O_2$: 466.2. (77.2 mg).

Example 13

Synthesis of (1R,8R)—N-[(6-amino-2,4-dimethylpyridin-3-yl)methyl]-11-(3-fluorophenoxy)-15-oxatetracyclo[$6.6.1.0^{2,7}.0^{9,14}$]pentadeca-2,4,6,9,11,13-hexaene-4-carboxamide Step 1:
A mixture of methyl (1R,8R)-11-bromo-15-oxatetracyclo[$6.6.1.0^{2,7}.0^{9,14}$]-pentadeca-2,4,6,9,11,13-hexaene-4-carboxylate (INT-3b1; 59.00 mg; 0.18 mmol; 1.00 eq.), 3-fluorophenol (0.02 ml; 0.23 mmol; 1.30 eq.), copper(I) bromide (3.83 mg; 0.03 mmol; 0.15 eq.), 2,4-pentanedione (3.66 µL; 0.04 mmol; 0.20 eq.) and potassium carbonate (31.96 mg; 0.23 mmol; 1.30 eq.) in N,N-dimethylformamide (0.59 ml) at RT (the mixture started turning dark and cloudy but no reaction was detected by LC/MS) was evacuated and back-filled with Argon (from a balloon) and the mixture was heated to 120° C. under Argon. After 4 h the mixture was allowed to reach RT, and directly injected onto a 12 G ISCO Gold column and purified eluting with 10% EtOAc in heptane. The semi pure methyl (1R,8R)-11-(3-fluorophenoxy)-15-oxatetracyclo[$6.6.1.0^{2,7}.0^{9,14}$]pentadeca-2,4,6,9,11,13-hexaene-4-carboxylate thus obtained was taken on without further purification (54.9 mg).

Step 2:
To a stirred solution of methyl (1R,8R)-11-(3-fluorophenoxy)-15-oxatetracyclo-[$6.6.1.0^{2,7}.0^{9,14}$]pentadeca-2,4,6,9,11,13-hexaene-4-carboxylate (50.00 mg; 0.14 mmol; 1.00 eq.) in 1.0 mL THF and 0.5 mL of MeOH at RT was added 0.5 mL of 1M LiOH. The mixture was stirred at RT for 2 h then it was quenched with 1.0 mL 1N HCl, extracted with EtOAc, dried over MgSO4, filtered and concentrated.

Step 3:
To a mixture of (1R,8R)-1-(3-fluorophenoxy)-15-oxatetracyclo-[$6.6.1.0^{2,7}.0^{9,14}$]-pentadeca-2,4,6,9,11,13-hexaene-4-carboxylic acid and 5-(aminomethyl)-4,6-dimethylpyridin-2-amine (41.73 mg; 0.28 mmol; 2.00 eq.) (previously azeotroped with 1 mL PhMe for 1 h) in N,N-dimethylformamide (1.38 ml) at RT was added Hunig's base (0.19 ml; 1.10 mmol; 8.00 eq.) followed by HATU (52.47 mg; 0.14 mmol; 1.00 eq.). After 1 h the reacting mixture was diluted with 1.5 mL water (clear solution turned cloudy) and 0.5 mL MeOH and directly purified via R-Phase prep HPLC (gradient 0% to 75% MeCN with 0.1% formic acid in water with 0.1% formic acid; 2 injections 1.4 mL each). The fractions containing the product from the two runs were collected, combined and lyophilized to afford (1R,8R)—N-[(6-amino-2,4-dimethylpyridin-3-yl)methyl]-11-(3-fluorophenoxy)-15-oxatetracyclo[$6.6.1.0^{2,7}.0^{9,14}$]pentadeca-2,4,6,9,11,13-hexaene-4-carboxamide. MS: $(M+H)^+$ found for $C_{29}H_{24}FN_3O_3$: 482.1. (26.3 mg).

Example 14

Synthesis of (1R,8S)—N-[(4-carbamimidoylphenyl)methyl]-12-cyclopropyl-15-oxatetracyclo-[$6.6.1.0^{2,7}.0^{9,14}$]pentadeca-2,4,6,9,11,13-hexaene-4-carboxamide

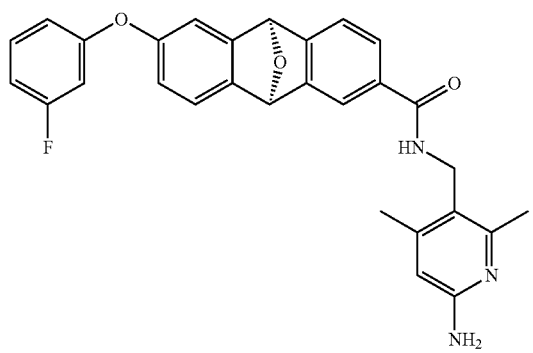 [SMILES: Cc1cc(N)nc(C)c1CNC(=O)c1ccc2c(c1)[C@@H]1O[C@H]2c2cc(Oc3cccc(F)c3)ccc21]

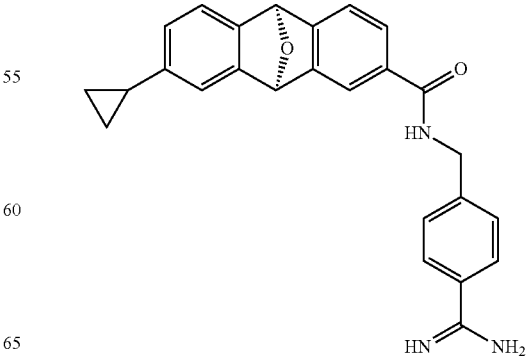

Step 1:

A stirred suspension of (1S,8R)-12-bromo-15-oxatetracyclo[6.6.1.0$^{2,7}$.0$^{9,14}$]-pentadeca-2,4,6,9,11,13-hexaene-4-carboxylic acid (INT-4a1; 100.00 mg; 0.32 mmol; 1.00 eq.), cyclopropylboronic acid (54.17 mg; 0.63 mmol; 2.00 eq.), cesium carbonate (256.85 mg; 0.79 mmol; 2.50 eq.) and 1,1'-bis(diphenylphosphino)ferrocene]dichloropalladium (II) (23.07 mg; 0.03 mmol; 0.10 eq.) in 1,4-dioxane (1.58 ml) and methanol (0.53 ml) was heated to 80° C. After 2 h the reacting mixture was cooled to RT, diluted with EtOAc and water and acidified with 1N HCl. The organic phase was separated dried over MgSO$_4$, filtered and concentrated. The oily orange residue was taken up in Et$_2$O and filtered. The clear yellow filtrate was concentrated to provide a yellowish solid. This material was taken on without further purification (34 mg).

Step 2:

To a mixture of (1R,8S)-12-cyclopropyl-15-oxatetracyclo[6.6.1.0$^{2,7}$.0$^{9,14}$]-pentadeca-2,4,6,9,11,13-hexaene-4-carboxylic acid (34.00 mg; 0.12 mmol; 1.00 eq.) in N,N-dimethylformamide (1.22 ml) at RT was added Hunig's base (0.04 ml; 0.24 mmol; 2.00 eq.) followed by 1H-1,2,3-benzotriazol-1-ol hydrate (HOBt; 28.06 mg; 0.18 mmol; 1.50 eq.) and N-[3-(dimethylamino)propyl]-N'-ethylcarbodiimide hydrochloride (EDC; 46.84 mg; 0.24 mmol; 2.00 eq.). After stirring for 5 min 4-(aminomethyl)benzene-1-carboximidamide (27.34 mg; 0.18 mmol; 1.50 eq.) was added and the resulting mixture was stirred at RT. After 3.5 h the mixture was diluted with 1.3 mL water and directly purified by R-Phase prep HPLC (gradient 0% to 75% MeCN with 0.1% formic acid in water with 0.1% formic acid; 2 injections 1.2 mL each). The fractions containing the product from the two runs were collected, combined and lyophilized to afford the title compound. MS: (M+H)$^+$ found for C$_{26}$H$_{23}$N$_3$O$_2$: 410.1. (19.7 mg).

Example 15

Synthesis of (1R,8S)—N-[(4-carbamimidoyl-2,6-difluorophenyl)methyl]-12-(prop-1-en-2-yl)-15-oxatetracyclo[6.6.1.0$^{2,7}$.0$^{9,14}$]pentadeca-2,4,6,9,11,13-hexaene-4-carboxamide

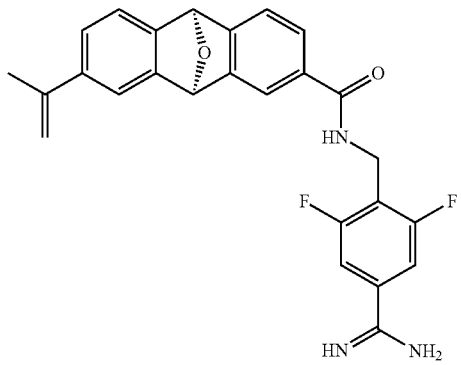 [SMILES: C=C(C)c1ccc2c(c1)[C@H]1O[C@@H]2c2ccc(C(=O)NCc3c(F)cc(C(=N)N)cc3F)cc21]

Step 1:

A stirred solution of sodium (1S,8R)-12-bromo-15-oxatetracyclo-[6.6.1.0$^{2,7}$.0$^{9,14}$]-pentadeca-2,4,6,9,11,13-hexaene-4-carboxylate (INT-5a1; 150.00 mg; 0.44 mmol; 1.00 eq.), potassium trifluoro(prop-1-en-2-yl)boranuide (104.73 mg; 0.71 mmol; 1.60 eq.), triethylamine (0.14 ml; 0.97 mmol; 2.20 eq.) and 1,1'-bis(diphenylphosphino)ferrocene]-dichloropalladium(II) (6.47 mg; 0.01 mmol; 0.02 eq.) in 1-butanol (7.37 ml) was heated to 80° C. under nitrogen. After 5.5 h the reacting mixture was cooled to RT, filtered, diluted with water, acidified with 1N HCl and extracted with EtOAc. The organic phase was dried over MgSO$_4$, filtered and concentrated to give an orange oil which turned into a solid under high vacuum. This material was taken up in Et$_2$O and filtered; the clear yellow filtrate was concentrated to provide a yellowish solid which was dried under high vacuum. This material was taken on without further purification (59 mg).

Step 2:

To a mixture of (1R,8S)-12-(prop-1-en-2-yl)-15-oxatetracyclo-[6.6.1.0$^{2,7}$.0$^{9,14}$]-pentadeca-2,4,6,9,11,13-hexaene-4-carboxylic acid (9.00 mg; 0.03 mmol; 1.00 eq.) and 4-(aminomethyl)-3,5-difluorobenzimidamide dichloride (INT-10; 16.69 mg; 0.06 mmol; 2.00 eq.) in N,N-dimethylformamide (0.32 ml) at RT was added Hunig's base (0.05 ml; 0.26 mmol; 8.00 eq.) followed by HATU (12.30 mg; 0.03 mmol; 1.00 eq.). After 30 min the reacting mixture was diluted with 0.4 mL water and 0.3 mL MeCN and directly purified by R-Phase prep HPLC (gradient 0% to 75% MeCN with 0.1% formic acid in water with 0.1% formic acid). The fractions containing the product were collected, combined and lyophilized to afford the title compound. MS: (M+H)$^+$ found for C$_{26}$H$_{21}$F$_2$N$_3$O$_2$: 446.1. (6.3 mg).

Example 16

Synthesis of (1R,8S)—N-[(4-carbamimidoyl-2,6-difluorophenyl)methyl]-12-(3,3,3-trifluoropropyl)-15-oxatetracyclo[6.6.1.0$^{2,7}$.0$^{9,14}$]pentadeca-2,4,6,9,11,13-hexaene-4-carboxamide

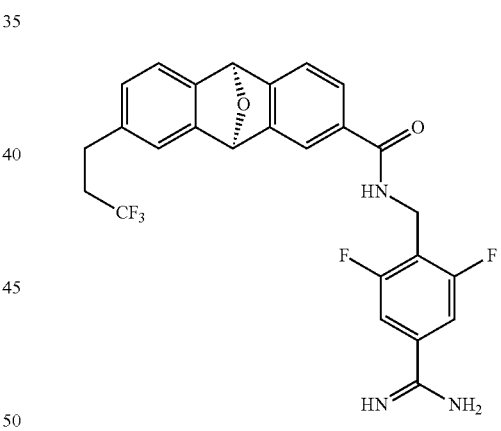

Step 1:

A stirred solution of (1S,8R)-12-bromo-15-oxatetracyclo[6.6.1.0$^{2,7}$.0$^{9,14}$-pentadeca-2,4,6,9,11,13-hexaene-4-carboxylic acid (INT-4a1; 76.00 mg; 0.24 mmol; 1.00 eq.), potassium trifluoro(3,3,3-trifluoropropyl)boranuide (97.76 mg; 0.48 mmol; 2.00 eq.), cesium carbonate (351.37 mg; 1.08 mmol; 4.50 eq.) and 1,1'-bis(diphenylphosphino)ferrocene]-dichloropalladium(II) (2.63 mg; 0.00 mmol; 0.02 eq.) in toluene (3.69 ml) and water (1.20 ml) was heated to 90° C. under nitrogen for 3 h. The mixture was then stirred at RT overnight then again at 90° C. for 7 h. The mixture was then diluted with EtOAc and water and acidified with 1N HCl, extracted with EtOAc then dried over MgSO$_4$, filtered and concentrated. The residue was taken up in Et$_2$O, filtered and concentrated. The resulting yellow crude solid was taken on without further purification (40 mg).

Step 2:

To a mixture of the crude material from step 1 (40.00 mg; 0.12 mmol; 1.00 eq.) in N,N-dimethylformamide (1.20 ml) at RT was added Hunig's base (0.04 ml; 0.24 mmol; 2.00 eq.) followed by 1H-1,2,3-benzotriazol-1-ol hydrate (27.49 mg; 0.18 mmol; 1.50 eq.) and N-[3-(dimethylamino)propyl]-N'-ethylcarbodiimide hydrochloride (45.88 mg; 0.24 mmol; 2.00 eq.) After stirring for 5 min, 4-(aminomethyl)-3,5-difluorobenzimidamide dichloride (INT-10; 46.32 mg; 0.18 mmol; 1.50 eq.) was added and the resulting mixture was stirred at RT. After 4 h the mixture was directly purified by R-Phase prep HPLC (gradient 0% to 75% MeCN with 0.1% formic acid in water with 0.1% formic acid; 2 injections 0.8 mL each). The fractions containing the product from the two runs were collected, combined and lyophilized to afford (1R,8S)—N-[(4-carbamimidoyl-2,6-difluorophenyl)methyl]-12-(3,3,3-trifluoropropyl)-15-oxatetracyclo-[6.6.1.0$^{2,7}$.0$^{9,14}$]pentadeca-2,4,6,9,11,13-hexaene-4-carboxamide. MS: (M+H)$^+$ found for $C_{26}H_{20}F_5N_3O_2$: 502.1. (10.2 mg).

Example 17

Synthesis of (1R,8S)—N-[(4-carbamimidoyl-2,6-difluorophenyl)methyl]-12-(propan-2-yl)-15-oxatetracyclo[6.6.1.0$^{2,7}$.0$^{9,14}$]pentadeca-2,4,6,9,11,13-hexaene-4-carboxamide

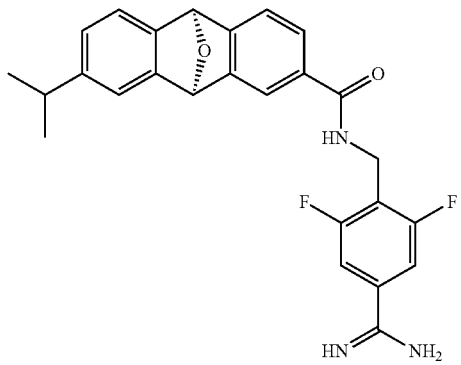 [SMILES: CC(C)c1ccc2c(c1)[C@H]1O[C@@H]2c2ccc(C(=O)NCc3c(F)cc(C(=N)N)cc3F)cc21]

Step 1:

To a solution of (1R,8S)-12-(prop-1-en-2-yl)-15-oxatetracyclo-[6.6.1.0$^{2,7}$.0$^{9,14}$]-pentadeca-2,4,6,9,11,13-hexaene-4-carboxylic acid (54.00 mg; 0.19 mmol; 1.00 eq.) in methanol (3.88 ml) was added platinum (IV) oxide (4.41 mg; 0.02 mmol; 0.10 eq.). The reaction mixture was stirred under an atmosphere of hydrogen (from a balloon after 3 cycles of evacuation/backfilling) at room temperature. After 3 h the reaction mixture was filtered through a syringe filter with additional MeOH and concentrated. This material was taken on to the next step without further purification (54 mg).

Step 2:

To a mixture of the crude material from step 1 (54.00 mg; 0.19 mmol; 1.00 eq.) in N,N-dimethylformamide (1.93 ml) at RT was added Hunig's base (0.07 ml; 0.39 mmol; 2.00 eq.) followed by 1H-1,2,3-benzotriazol-1-ol hydrate (44.25 mg; 0.29 mmol; 1.50 eq.) and N-[3-(dimethylamino)propyl]-N'-ethylcarbodiimide hydrochloride (73.86 mg; 0.39 mmol; 2.00 eq.). After stirring for 5 min 4-(aminomethyl)-3,5-difluorobenzimidamide dichloride (INT-10; 74.58 mg; 0.29 mmol; 1.50 eq.) was added and the resulting mixture was stirred at RT. After 2.5 h the mixture was directly purified by R-Phase prep HPLC (gradient 0% to 75% MeCN with 0.1% formic acid in water with 0.1% formic acid; 3 injections 0.7 mL each). The fractions containing the product from the two runs were collected, combined and lyophilized to afford the title compound. MS: (M+H)$^+$ found for $C_{26}H_{23}F_2N_3O_2$: 448.1. (23 mg).

Example 18

Synthesis of (1S,8R)—N-[(4-carbamimidoylphenyl)methyl]-12-(3,3-difluoroazetidin-1-yl)-15-oxatetracyclo[6.6.1.0$^{2,7}$.0$^{9,14}$]pentadeca-2,4,6,9,11,13-hexaene-4-carboxamide

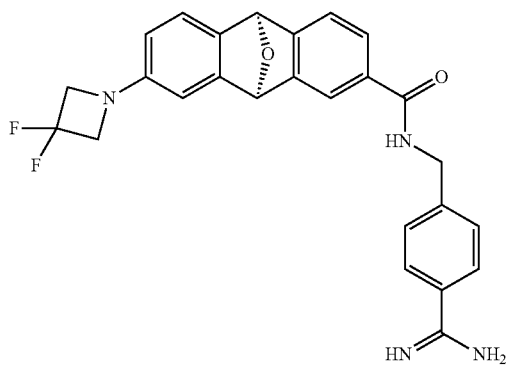 [SMILES: N=C(N)c1ccc(CNC(=O)c2ccc3c(c2)[C@@H]2O[C@H]3c3ccc(N4CC(F)(F)C4)cc32)cc1]

Step 1:

A mixture of sodium (1S,8R)-12-bromo-15-oxatetracyclo[6.6.1.0$^{2,7}$.0$^{9,14}$]-pentadeca-2,4,6,9,11,13-hexaene-4-carboxylate (INT-5a1; 95.00 mg; 0.28 mmol; 1.00 eq.), 3,3-difluoroazetidin-1-ium chloride (54.43 mg; 0.42 mmol; 1.50 eq.), Pd$_2$(dba)$_3$ (12.83 mg; 0.01 mmol; 0.05 eq.), 2-dicyclohexylphosphino-2',4',6'-triisopropylbiphenyl (XPhos; 13.35 mg; 0.03 mmol; 0.10 eq.), and cesium carbonate (365.10 mg; 1.12 mmol; 4.00 eq.) in N,N-dimethylformamide (1.00 ml) was heated to 120° C. under an atmosphere of Argon. After 1 h the mixture was diluted with water and extracted with ethyl acetate. The organic phase contained only an insignificant amount of desired product. The aqueous phase was acidified with 1N HCl and extracted with EtOAc. The combined organics were dried over MgSO$_4$, filtered and concentrated. The oily residue was taken up in Et$_2$O, filtered and concentrated to afford an orange solid. This material was taken up again in Et$_2$O and the insoluble light yellow material was separated, air dried and taken on to the next step without further purification (40 mg).

Step 2:

To a mixture of crude (1S,8R)-12-(3,3-difluoroazetidin-1-yl)-15-oxatetracyclo[6.6.1.0$^{2,7}$.0$^{9,14}$]pentadeca-2,4,6,9,11,13-hexaene-4-carboxylic acid (40.00 mg; 0.12 mmol; 1.00 eq.) in N,N-dimethylformamide (1.21 ml) at RT was added Hunig's base (0.06 ml; 0.36 mmol; 3.00 eq.) followed by 1H-1,2,3-benzotriazol-1-ol hydrate (27.90 mg; 0.18 mmol; 1.50 eq.) and N-[3-(dimethylamino)propyl]-N'-ethylcarbodiimide hydrochloride (46.57 mg; 0.24 mmol; 2.00 eq.). After 5 min, 4-(aminomethyl)benzimidamide dichloride (40.47 mg; 0.18 mmol; 1.50 eq.) was added and the resulting mixture was stirred at RT. After 3.5 h the mixture was filtered through a syringe filter and directly purified by R-Phase prep HPLC (gradient 0% to 75% MeCN with 0.1% formic acid in water with 0.1% formic acid; 2 injections 0.7 mL each). The fractions containing the product from the two runs were collected, combined and lyophilized to afford the title compound. MS: (M+H)$^+$ found for $C_{26}H_{22}F_2N_4O_2$: 461.1. (34.1 mg; 26% over the two steps).

Example 19

Synthesis of (1S,8R)-12-(3,3-difluoroazetidin-1-yl)-N-({4-N'-methoxycarbamimidoyl]phenyl}-methyl)-15-oxatetracyclo[6.6.1.0$^{2,7}$.0$^{9,14}$]pentadeca-2,4,6,9,11,13-hexaene-4-carboxamide

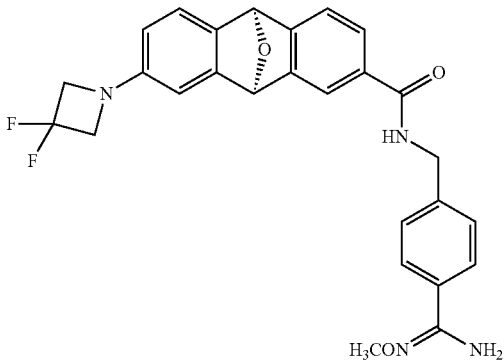

To a mixture of (1S,8R)-12-(3,3-difluoroazetidin-1-yl)-15-oxatetracyclo-[6.6.1.0$^{2,7}$.0$^{9,14}$]-pentadeca-2,4,6,9,11,13-hexaene-4-carboxylic acid (20.00 mg; 0.06 mmol; 1.00 eq.) in N,N-dimethylformamide (0.61 ml) at RT was added Hunig's base (0.03 ml; 0.18 mmol; 3.00 eq.) followed by 1H-1,2,3-benzotriazol-1-ol hydrate (13.95 mg; 0.09 mmol; 1.50 eq.) and N-[3-(dimethylamino)propyl]-N'-ethylcarbodiimide hydrochloride (23.29 mg; 0.12 mmol; 2.00 eq.). After 5 min, 4-(aminomethyl)-N'-methoxybenzimidamide dihydrochloride (INT-7; 19.65 mg; 0.09 mmol; 1.50 eq.) was added an the resulting mixture was stirred at RT. After 6 h the mixture was directly purified by R-Phase prep HPLC (gradient 0% to 75% MeCN with 0.1% formic acid in water with 0.1% formic acid). The fractions containing the product were collected, combined and lyophilized to afford the title compound. MS: (M+H)$^+$ found for $C_{27}H_{24}F_2N_4O_3$: 491.1. (18.1 mg; 61%).

Example 20

Synthesis of (1R,8S)—N-({4-[N'-methoxycarbamimidoyl]phenyl}methyl)-12-(propan-2-yl)-15-oxatetracyclo[6.6.1.0$^{2,7}$.0$^{9,14}$]pentadeca-2,4,6,9,11,13-hexaene-4-carboxamide

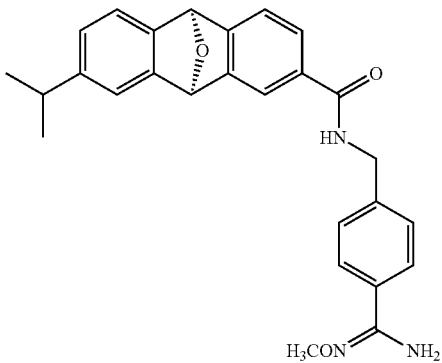

To a mixture of (1R,8S)-12-(propan-2-yl)-15-oxatetracyclo[6.6.1.0$^{2,7}$.0$^{9,14}$]pentadeca-2,4,6,9,11,13-hexaene-4-carboxylic acid (40.00 mg; 0.14 mmol; 1.00 eq.) in N,N-dimethylformamide (1.43 ml) at RT was added Hunig's base (0.07 ml; 0.43 mmol; 3.00 eq.) followed by 1H-1,2,3-benzotriazol-1-ol hydrate (32.78 mg; 0.21 mmol; 1.50 eq.) and N-[3-(dimethylamino)-propyl]-N'-ethylcarbodiimide hydrochloride (54.71 mg; 0.29 mmol; 2.00 eq.). After stirring for 5 min 4-(aminomethyl)-N'-methoxybenzimidamide dihydrochloride (INT-7; 46.16 mg; 0.21 mmol; 1.50 eq.) was added and the resulting mixture was stirred at RT. After 2 h the mixture was directly purified by R-Phase prep HPLC (gradient 0% to 75% MeCN with 0.1% formic acid in water with 0.1% formic acid). The fractions containing the product were collected, combined and lyophilized to afford the title compound. MS: (M+H)$^+$ found for $C_{27}H_{27}N_3O_3$: 442.1. (25 mg; 40%).

Example 21

Synthesis of (1S,8R)—N-[(4-carbamimidoylphenyl)methyl]-12-(pyrrolidin-1-yl)-15-oxatetra-cyclo[6.6.1.0$^{2,7}$.0$^{9,14}$]pentadeca-2,4,6,9,11,13-hexaene-4-carboxamide

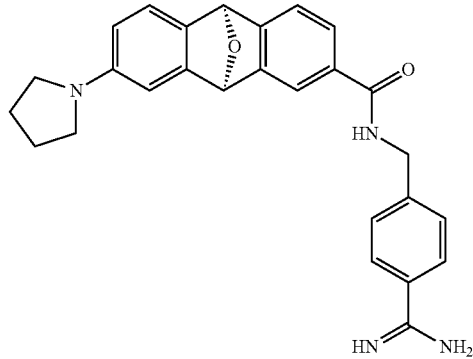 [SMILES: N=C(N)c1ccc(CNC(=O)c2ccc3c(c2)[C@@H]2O[C@H]3c3ccc(N4CCCC4)cc32)cc1]

Step 1:
Combined methyl (1S,8R)-12-bromo-15-oxatetracyclo-[6.6.1.0$^{2,7}$.0$^{9,14}$]-pentadeca-2,4,6,9,11,13-hexaene-4-carboxylate (INT-3a1; 280 mgs, 0.9 mmol), pyrrolidine (90 mgs, 1.3 mmol), Pd$_2$(dba)$_3$ (38 mgs, 0.04 mmol), XPhos (40 mgs, 0.08), and cesium carbonate (826 mgs, 2.5 mmol) in DMF (2 mL) in a microwave vial. The reaction mixture was heated in a microwave at 120° C. for 1 hour. The reaction mixture was filtered thru a short plug of Celite. The resulting solution was diluted with water and extracted with ethyl acetate. The combined organics was dried over magnesium sulfate, filtered and evaporated to provide crude methyl (1S,8R)-12-(pyrrolidin-1-yl)-15-oxatetracyclo[6.6.1.0$^{2,7}$.0$^{9,14}$]-pentadeca-2,4,6,9,11,13-hexaene-4-carboxylate (270 mgs).

Step 2:
To a solution of methyl (1S,8R)-12-(pyrrolidin-1-yl)-15-oxatetracyclo-[6.6.1.0$^{2,7}$.0$^{9,14}$]-pentadeca-2,4,6,9,11,13-hexaene-4-carboxylate (270 mgs, 0.8 mmol) in methanol (10 mL) was added 2M NaOH (1.7 mL). The reaction was heated to 60° C. for 1 hour. The reaction was cooled to room temperature, concentrated and purified by prep HPLC (gradient 0% to 75% MeCN with 0.1% formic acid in water with 0.1% formic acid) to afford (1S,8R)-12-(pyrrolidin-1-yl)-15- oxatetracyclo[6.6.1.0²,⁷.0⁹,¹⁴]pentadeca-2,4,6,9,11,13-hexaene-4-carboxylic acid (100 mgs).

Step 3:

To a solution of (1S,8R)-12-(pyrrolidin-1-yl)-15-oxatetracyclo-[6.6.1.0²,⁷.0⁹,¹⁴]-pentadeca-2,4,6,9,11,13-hexaene-4-carboxylic acid (100 mgs, 0.3 mmol) in Hunig's base (0.17 mL, 1.0 mmol) and DMF (2 mL) was added HATU (124 mgs, 0.3 mmol). 4-(aminomethyl)benzene-1-carboximidamide dihydrochloride (72 mgs, 0.3 mmol) was added to the reaction mixture and stirred for 15 minutes. The residue was purified by prep HPLC (gradient 0% to 75% MeCN with 0.1% formic acid in water with 0.1% formic acid) to afford the title compound (7 mgs). MS: (M+H)⁺ found for $C_{27}H_{26}N_4O_2$: 439.1.

Example 22

Synthesis (1R,8S)—N-[(6-carbamimidoylpyridin-3-yl)methyl]-12-(2,4-difluorophenyl)-15-oxatetracyclo[6.6.1.0²,⁷.0⁹,¹⁴]pentadeca-2,4,6,9,11,13-hexaene-4-carboxamide

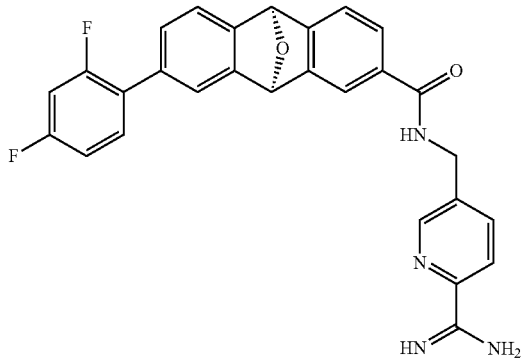 [SMILES: N=C(N)c1ccc(CNC(=O)c2ccc3c(c2)[C@@H]2O[C@H]3c3ccc(-c4ccc(F)cc4F)cc32)cn1]

Step 1:

Combined 5-(bromomethyl)pyridine-2-carbonitrile (200 mgs) and 7 N ammonia in methanol (2 mL) in a capped reaction vial. The reaction mixture was heated at 65° C. for 2 hours. The reaction was cooled cool to rt and the solvents were evaporated. The residue was purified using prep HPLC (100% water) to afford 5-(aminomethyl)pyridine-2-carboximidamide (31 mgs).

Step 2:

To a solution of (1R,8S)-12-(2,4-difluorophenyl)-15-oxatetracyclo-[6.6.1.0²,⁷.0⁹,¹⁴]pentadeca-2,4,6,9,11,13-hexaene-4-carboxylic acid (Example 7, Steps 1-2; 47 mgs, 0.1 mmol) and Hunig's base (0.07 mL, 0.4 mmol) in DMA (2 mL) was added HATU (50 mgs, 0.1 mmol). 5-(Aminomethyl)pyridine-2-carboximidamide (20 mg, 0.1 mmol) was added to the reaction mixture and stirred for 15 minutes. The mixture was purified by prep HPLC (gradient 0% to 75% MeCN with 0.1% formic acid in water with 0.1% formic acid) to afford the title compound (3 mgs). MS: (M+H)⁺ found for $C_{28}H_{20}F_2N_4O_2$: 483.1.

Example 23

Synthesis (1R,8S)-12-cyclopropyl-N-({4-[N'-methoxycarbamimidoyl]phenyl}methyl)-15-oxatetracyclo[6.6.1.0²,⁷.0⁹,¹⁴]pentadeca-2,4,6,9,11,13-hexaene-4-carboxamide

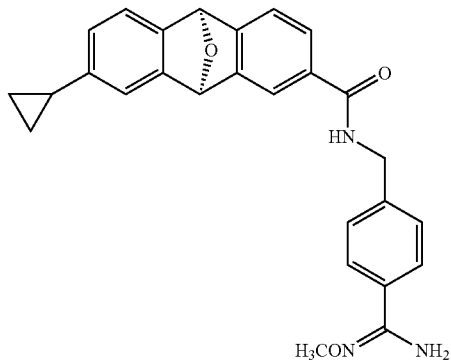

Step 1:

To a solution of (1S,8R)-12-bromo-15-oxatetracyclo[6.6.1.0²,⁷.0⁹,¹⁴]-pentadeca-2,4,6,9,11,13-hexaene-4-carboxylic acid (INT-4a1; 230 mgs, 0.7 mmol) and Hunig's base (0.63 mL, 3.6 mmol) in dimethylacetamide (DMA; 3 mL), was added HATU (275 mgs, 0.7 mmol). 4-(Aminomethyl)-N'-methoxybenzene-1-carboximidamide dihydrochloride (INT-7; 181 mgs, 0.7 mmol) was added to the reaction. The reaction was stirred for 15 minutes. The reaction mixture was purified by prep HPLC (gradient 0% to 75% MeCN with 0.1% formic acid in water with 0.1% formic acid) to afford (1S,8R)-12-bromo-N-({4-[N'-methoxycarbamimidoyl]phenyl}-methyl)-15-oxatetracyclo[6.6.1.0²,⁷.0⁹,¹⁴]pentadeca-2,4,6,9,11,13-hexaene-4-carboxamide (200 mgs).

Step 2:

A solution of (1S,8R)-12-bromo-N-({4-[N'-methoxycarbamimidoyl]-phenyl}-methyl)-15-oxatetracyclo[6.6.1.0²,⁷.0⁹,¹⁴]pentadeca-2,4,6,9,11,13-hexaene-4-carboxamide (200 mgs, 0.4 mmol), cyclopropylboronic acid (90 mgs, 1.1 mmol), Pd(dppf)₂Cl₂ (17 mgs, 0.02 mmol), and 2M potassium carbonate (0.63 mL) in DMF (3 mL) was sealed in a microwave vial. The reaction mixture was heated to 100° C. for 30 minutes. The reaction mixture was filtered, concentrated and purified by prep HPLC (gradient 0% to 75% MeCN with 0.1% formic acid in water with 0.1% formic acid) to afford the title compound (41 mgs). MS: (M+H)⁺ found for $C_{27}H_{25}N_3O_3$: 440.1

Example 24

Synthesis of (1R,8S)—N-[(4-carbamimidoyl-2,6-difluorophenyl)methyl]-12-cyclopropyl-15-oxatetracyclo[6.6.1.0$^{2,7}$.0$^{9,14}$]pentadeca-2,4,6,9,11,13-hexaene-4-carboxamide

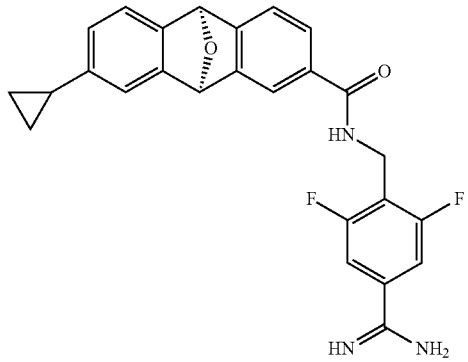 [SMILES: N=C(N)c1cc(F)c(CNC(=O)c2ccc3c(c2)[C@@H]2O[C@H]3c3ccc(C4CC4)cc32)c(F)c1]

To a solution of (1R,8S)-12-cyclopropyl-15-oxatetracyclo[6.6.1.0$^{2,7}$.0$^{9,14}$]pentadeca-2,4,6,9,11,13-hexaene-4-carboxylic acid (Example 14, Step 1; 40 mgs, 0.1 mmol) and Hunig's base (0.13 mL, 0.7 mmol) in N-methyl-2-pyrrolidone (NMP; 2 mL) was added HATU (55 mgs, 0.1 mmol). To the resulting reaction mixture, 4-(aminomethyl)-3,5-difluorobenzimidamide dihydrochloride (INT-10; 37 mgs, 0.1 mmol) was added. The reaction was stirred for 15 minutes and the purified by prep HPLC (gradient 0% to 75% MeCN with 0.1% formic acid in water with 0.1% formic acid) to afford the title compound. (23 mgs). MS: (M+H)$^+$ found for C$_{26}$H$_{21}$F$_2$N$_3$O$_2$: 446.2 (M+1).

Example 25

Synthesis of (1R,8S)-12-cyclopropyl-N-{[2,6-difluoro-4-(N-methoxycarbamimidoyl)phenyl]methyl})-15-oxatetracyclo[6.6.1.0$^{2,7}$.0$^{9,14}$]pentadeca-2,4,6,9,11,13-hexaene-4-carboxamide

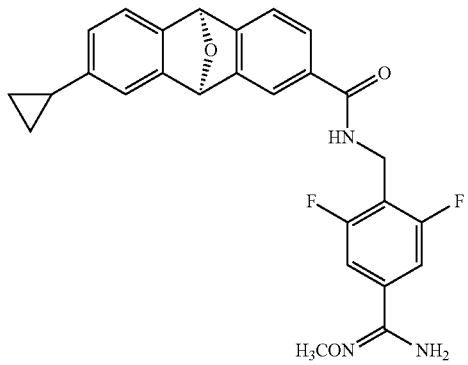

The title compound was prepared as described in Example 24, but using 4-(amino-methyl)-3,5-difluoro-N'-methoxybenzimidamide (INT-11) instead of 4-(aminomethyl)-3,5-difluorobenzene-1-carboximidamide dihydrochloride. MS: (M+H)$^+$ found for C$_{27}$H$_{23}$F$_2$N$_3$O$_3$: 476.1.

Example 26

Synthesis of {amino[4-({[(1R,8S)-12-(2,4-difluorophenyl)-15-oxatetracyclo[6.6.1.0$^{2,7}$.0$^{9,14}$]-pentadeca-2,4,6,9,11,13-hexaen-4-yl]formamido}methyl)phenyl]methylidene}amino (2S)-2-amino-3-methylbutanoate

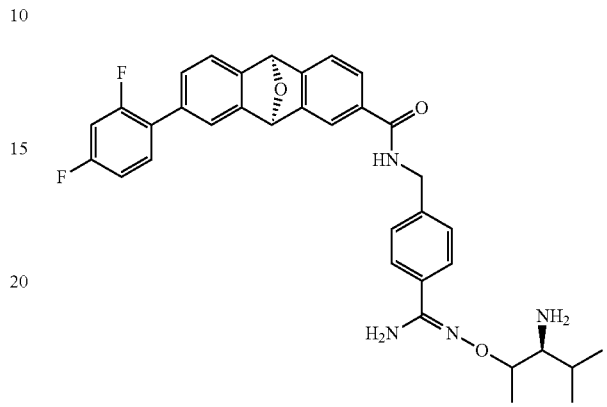

To a solution of (1R,8S)-12-(2,4-difluorophenyl)-N-({4-[N'-hydroxycarbamimidoyl]-phenyl}methyl)-15-oxatetracyclo[6.6.1.0$^{2,7}$.0$^{9,14}$]pentadeca-2,4,6,9,11,13-hexaene-4-carboxamide (Example 7; 140 mgs, 0.3 mmol) and Hunig's base (0.1 mL, 0.6 mmol) in NMP (5 mL) was added 2,5-dioxopyrrolidin-1-yl (2S)-2-{[(tert-butoxy)carbonyl]-amino}-3-methylbutanoate (88 mgs, 0.3 mmol). The reaction was stirred for 4 hours. Purified by prep HPLC (gradient 0% to 75% MeCN with 0.1% formic acid in water with 0.1% formic acid) to afford the title compound (35 mgs). MS: (M+H)$^+$ found for C$_{34}$H$_{30}$F$_2$N$_4$O$_4$: 597.1.

Example 27

Synthesis of (1R,8S)-12-(2,4-difluorophenyl)-N-{[6-(N'-methoxycarbamimidoyl)-pyridin-3-yl]methyl}-15-oxatetracyclo[6.6.1.0$^{2,7}$.0$^{9,14}$]pentadeca-2,4,6,9,11,13-hexaene-4-carboxamide

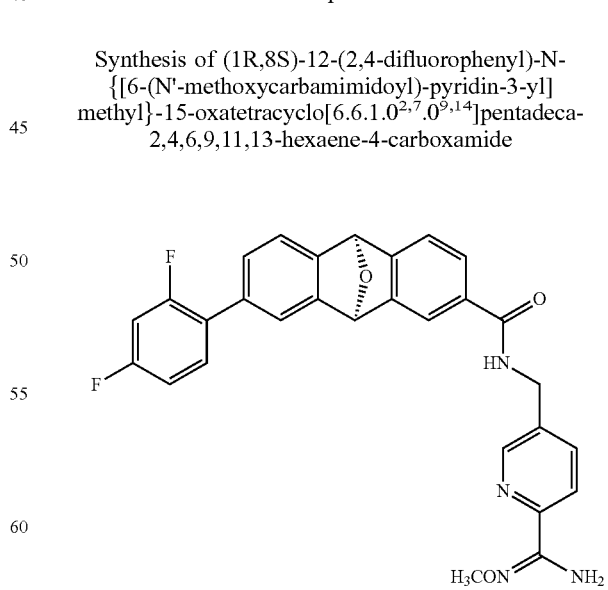

Step 1:

To a solution of tert-butyl N-[(6-cyanopyridin-3-yl)methyl]carbamate (130 mgs, 0.6 mmol), thioglycolic acid (0.08 mL, 1.1 mmol), and Hunig's base (0.39 mL, 2.2 mmol) was added O-methylhydroxylamine hydrochloride (140 mgs, 1.7 mmol) in 2-propanol (2 mL) into a capped reaction vial. The reaction mixture was heated at 80° C. overnight. The reaction was cooled to room temperature, diluted reaction with water and extracted with ethyl acetate. The combined organics, dried with $MgSO_4$, filtered, concentrated and purified by Combiflash silica gel column using 5% MeOH in DCM to afford tert-butyl N-{[6-(N-methoxycarbamimidoyl)-pyridin-3-yl]methyl}carbamate (109 mgs). The resulting product was treated with 4M HCl in dioxanes (3 mL). After stirred for 2 hours the reaction mixture was concentrated to afford 5-(aminomethyl)-N-methoxypyridine-2-carboximidamide dihydrochloride (107 mgs).

Step 2:

To a solution of (1R,8S)-12-(2,4-difluorophenyl)-15-oxatetracyclo-[6.6.1.0$^{2,7}$.0$^{9,14}$]pentadeca-2,4,6,9,11,13-hexaene-4-carboxylic acid (Example 7, Step 1-2; 150 mgs, 0.4 mmol) and Hunig's base (0.3 mL, 1.7 mmol) in NMP (3 mL) was added HATU (163 mgs, 0.4 mmol). 5-(Aminomethyl)-N-methoxypyridine-2-carboximidamide dihydrochloride (107 mgs, 0.4 mmol) was added to the reaction mixture. The reaction mixture was stirred for 15 minutes and purified by prep HPLC (gradient 0% to 75% MeCN with 0.1% formic acid in water with 0.1% formic acid) to afford the title compound (119 mgs). MS: (M+H)$^+$ found for $C_{29}H_{22}F_2N_4O_3$: 513.3.

Example 28

Synthesis of (1R,8S)-12-(2,4-difluorophenyl)-N-{[4-(N'-methoxycarbamimidoyl)phenyl]methyl}-15-oxatetracyclo[6.6.1.0$^{2,7}$.0$^{9,14}$]pentadeca-2,4,6,9,11,13-hexaene-4-carboxamide

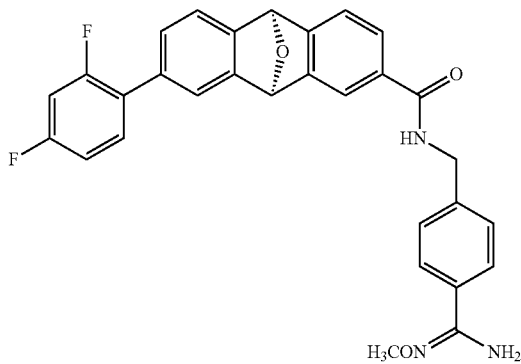

The title compound was prepared as in Example 45, step 8, but substituting 4-(aminomethyl)-3,5-dimethylbenzene-1-carboximidamide with {4-(aminomethyl)-N'-methoxybenzimidamide dihydrochloride (INT-7). MS (ESI, pos. ion) m/z: 512.2 (M+1).

Example 29

Synthesis of (±)-N-[(6-amino-2,4-dimethylpyridin-3-yl)methyl]-12-(phenylsulfanyl)-15-oxatetracyclo [6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(phenylsulfanyl)-15-oxatetracyclo-[6.6.1.0$^{2,7}$.0$^{9,14}$]pentadeca-2,4,6,9,11,13-hexaene-4-carboxamide

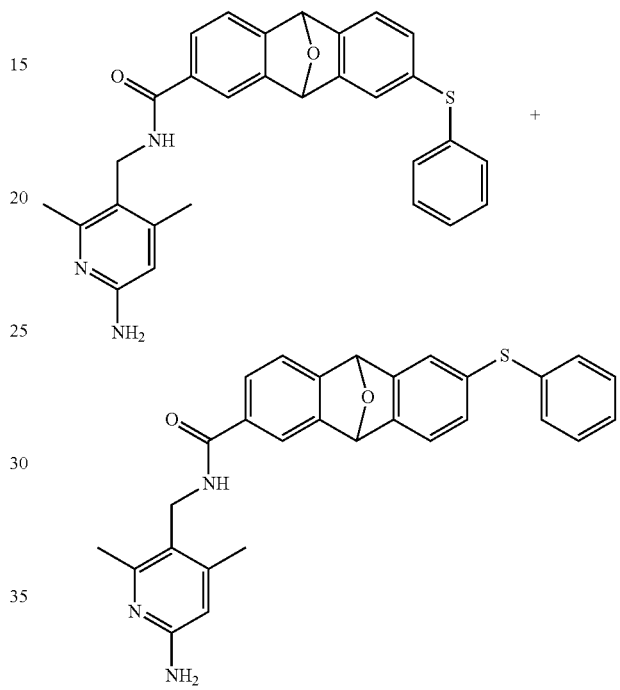

Step 1:

A solution of diacetoxypalladium (2.03 mg; 0.01 mmol; 0.05 eq.) and (R)-1-[(SP)-2-(dicyclohexylphosphino)ferrocenyl]ethyldi-tert-butylphosphine (5.02 mg; 0.01 mmol; 0.05 eq.) in dimethoxyethane (DME; 0.5 mL) was stirred for 15 min and the mixture was then added (±)-methyl 12-bromo-15-oxatetracyclo[6.6.1.0$^{2,7}$.0$^{9,14}$]pentadeca-2,4,6,9,11,13-hexaene-4-carboxylate and (±)-methyl 11-bromo-15-oxatetracyclo-[6.6.1.0$^{2,7}$.0$^{9,14}$]pentadeca-2,4,6,9,11,13-hexaene-4-carboxylate (INT-3; 60.00 mg; 0.18 mmol; 1.00 eq.), phenyl hydrosulfide (21.96 mg; 0.20 mmol; 1.10 eq.), and (tert-butoxy)sodium (19.15 mg; 0.20 mmol; 1.10 eq.). The reaction mixture was heated at 100° C. for 3 h. The reaction mixture was cooled and diluted with EtOAc and dilute HCl solution. The organic layer was separated and the aqueous layer was further extracted with EtOAc. The organic layers were combined, dried and concentrated to give crude product, which was purified by column chromatography (Hexanes/EtOAc (0.3% AcOH)=3:1) to give inseparable mixture of (±)-12-(phenylsulfanyl)-15-oxatetracyclo[6.6.1.0$^{2,7}$.0$^{9,14}$]pentadeca-2,4,6,9,11,13-hexaene-4-carboxylic acid and (±)-11-(phenylsulfanyl)-15-oxatetracyclo[6.6.1.0$^{2,7}$.0$^{9,14}$]pentadeca-2,4,6,9,11,13-hexaene-4-carboxylic acid (40 mg).

Step 2:

To a suspension of a mixture of (±)-12-(phenylsulfanyl)-15-oxatetracyclo-[6.6.1.0$^{2,7}$.0$^{9,14}$]pentadeca-2,4,6,9,11,13- hexaene-4-carboxylic acid and (±)-11-(phenylsulfanyl)-15-oxatetracyclo[6.6.1.0$^{2,7}$.0$^{9,14}$]pentadeca-2,4,6,9,11,13-hexaene-4-carboxylic acid (40.00 mg; 0.12 mmol; 1.00 eq.) and 5-(aminomethyl)-4,6-dimethylpyridin-2-amine (34.92 mg; 0.23 mmol; 2.00 eq.) in DMF (1 mL) was added Hunig's base (0.06 ml; 0.35 mmol; 3.00 eq.) and HATU (48.30 mg; 0.13 mmol; 1.10 eq.). After stirring for 15 min, the reaction mixture was diluted with water and AcCN and purified by preparative HPLC to give the title compounds. MS: (M+H)$^+$ found for $C_{29}H_{25}N_3O_2S$: 480.1.

Example 30

Synthesis of (1R,8 S)—N-[(4-carbamimidoyl-3-fluorophenyl)methyl]-12-(2,4-difluorophenyl)-15-oxatetracyclo[6.6.1.0$^{2,7}$.0$^{9,14}$]pentadeca-2,4,6,9,11,13-hexaene-4-carboxamide

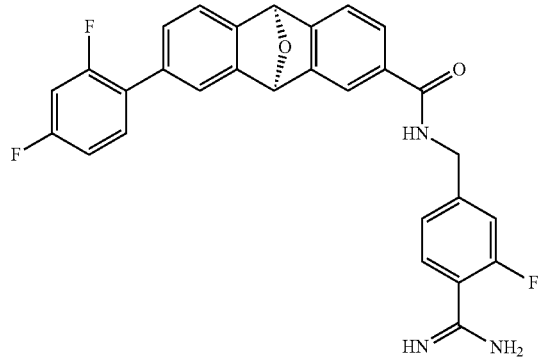 [SMILES: N=C(N)c1ccc(CNC(=O)c2ccc3c(c2)[C@@H]2O[C@H]3c3ccc(-c4ccc(F)cc4F)cc32)cc1F]

Step 1:
To a solution of tert-butyl N-[(4-cyano-3-fluorophenyl)methyl]carbamate (0.50 g; 2.00 mmol; 1.00 eq.) in MeOH (10 mL) was added hydroxylamine (0.20 g; 5.99 mmol; 3.00 eq.) and sodium carbonate (0.64 g; 5.99 mmol; 3.00 eq.). The mixture was heated at 80° C. for 4 h, then cooled and diluted with EtOAc and water. The organic layer was separated, dried and concentrated to give tert-butyl N-({3-fluoro-4-[N'-hydroxy-carbamimidoyl]phenyl}methyl)-carbamate (0.60 g).

Step 2:
To a solution of tert-butyl N-({3-fluoro-4-[N'-hydroxy-carbamimidoyl]-phenyl}methyl)carbamate (500.00 mg; 1.76 mmol; 1.00 eq.) in AcOH (40 mL) was added acetic anhydride (0.18 ml; 1.85 mmol; 1.05 eq.) followed by Pd/C (180.00 mg; 1.69 mmol; 0.96 eq.) and the reaction mixture was put on Parr shaker and charged with H$_2$ (68 psi). After 4 h, the reaction mixture t was filtered and the filtrate was concentrated to give tert-butyl N-[(4-carbamimidoyl-3-fluorophenyl)methyl]carbamate, which was added with 4N HCl (4 mL) at room temperature and was stirred further for 1 h, after which the mixture was concentrated to give 4-(aminomethyl)-2-fluorobenzimidamide as HCl salt (410 mg).

Step 3:
To a solution of (1R,8S)-12-(2,4-difluorophenyl)-15-oxatetracyclo-[6.6.1.0$^{2,7}$.0$^{9,14}$]pentadeca-2,4,6,9(14),10,12-hexaene-4-carboxylic acid (Example 7, Step 1-2; 60.00 mg; 0.17 mmol; 1.00 eq.) and 4-(aminomethyl)-2-fluorobenzimidamide HCl salt (44.86 mg; 0.19 mmol; 1.10 eq.) in DMF (1 mL) at rt was added diisopropylethylamine (0.15 ml; 0.86 mmol; 5.00 eq.) followed by HATU (71.64 mg; 0.19 mmol; 1.10 eq.). Ater stirring the reaction mixture at ambient temperature for 30 min, the reaction mixture was then diluted with water and AcCN and was purified by preparatory HPLC to give the title compound (25 mg). MS: (M+H)$^+$ found for $C_{29}H_{20}F_3N_3O_2$: 500.1.

Example 31

Synthesis of (1R,8S)—N-[(6-amino-2,4-dimethylpyridin-3-yl)methyl]-12-benzyl-15-oxatetracyclo[6.6.1.0$^{2,7}$.0$^{9,14}$]pentadeca-2,4,6,9,11,13-hexaene-4-carboxamide

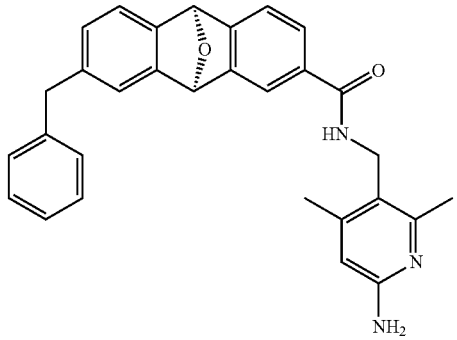 [SMILES: Cc1cc(N)nc(C)c1CNC(=O)c1ccc2c(c1)[C@@H]1O[C@H]2c2ccc(Cc3ccccc3)cc21]

Step 1:
To a solution of methyl (1S,8R)-12-bromo-15-oxatetracyclo[6.6.1.0$^{2,7}$.0$^{9,14}$]-pentadeca-2,4,6,9,11,13-hexaene-4-carboxylate (INT-3a1; 75.00 mg; 0.23 mmol; 1.00 eq.) in THF (1 mL) was added 1,1'-bis(diphenylphosphino)ferrocene]-dichloropalladium(II) (16.57 mg; 0.02 mmol; 0.10 eq.) followed by benzyl(bromo)zinc (1.36 ml; 0.50 mol/l; 0.68 mmol; 3.00 eq.). The mixture was flushed with N$_2$, sealed and heated at 60° C. for 15 h. The reaction mixture was diluted with EtOAc and water and the organic layer was separated. The aqueous layer was further extracted with EtOAc, the organic layers were combined, dried over MgSO4 and concentrated to give crude product, which was purified by column chromatography (Hexanes/EtOAc=65:35) to give methyl (1R,8S)-12-benzyl-15-oxatetracyclo[6.6.1.0$^{2,7}$.0$^{9,14}$]pentadeca-2,4,6,9,11,13-hexaene-4-carboxylate (68 mg).

Step 2:
To a solution of methyl (1R,8S)-12-benzyl-15-oxatetracyclo[6.6.1.0$^{2,7}$.0$^{9,14}$]-pentadeca-2,4,6,9,11,13-hexaene-4-carboxylate (66.00 mg; 0.19 mmol; 1.00 eq.) in THF (1 mL) was added MeOH (0.5 mL) and water (0.5 mL). Lithium hydroxide (23.08 mg; 0.96 mmol; 5.00 eq.) was added and after stirring for 4 hr at room temperature, the reaction mixture was diluted with 1N HCl and lyophilized to give crude acid, which was dissolved in DMF (1 mL). 5-(Aminomethyl)-4,6-dimethylpyridin-2-amine (58.30 mg; 0.39 mmol; 2.00 eq.) was added, followed by Hunig's base (0.10 ml; 0.58 mmol; 3.00 eq.) and HATU (80.62 mg; 0.21 mmol; 1.10 eq.) and the reaction mixture was stirred further until the reaction was complete. The mixture as diluted with water and AcCN and purified by preparatory HPLC to give the title compound. MS: (M+H)$^+$ found for $C_{30}H_{27}N_3O_2$: 462.1.

Example 32

Synthesis of (1R,8S)—N-[(4-carbamimidoyl-2,6-difluorophenyl)methyl]-12-(2,4-difluorophenyl)-15-oxatetracyclo[6.6.1.0$^{2,7}$.0$^{9,14}$]pentadeca-2,4,6,9,11,13-hexaene-4-carboxamide

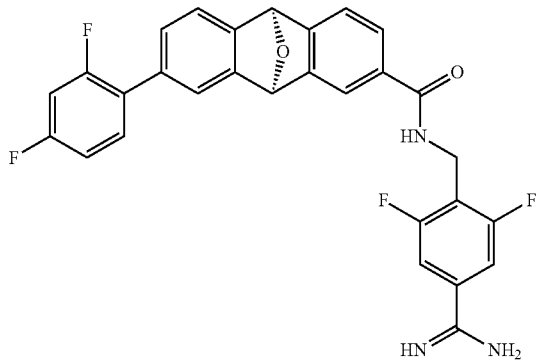 [SMILES: N=C(N)c1cc(F)c(CNC(=O)c2ccc3c(c2)[C@@H]2O[C@H]3c3ccc(-c4ccc(F)cc4F)cc32)c(F)c1]

To a solution of (1R,8S)-12-(2,4-difluorophenyl)-15-oxatetracyclo[6.6.1.0$^{2,7}$.0$^{9,14}$]-pentadeca-2,4,6,9,11,13-hexaene-4-carboxylic acid (Example 7, Steps 1-2; 50.00 mg; 0.14 mmol; 1.00 eq.) in DMF (1 mL) was added 4-(aminomethyl)-3,5-difluorobenzene-1-carboximidamide dihydrochloride (INT-10; 29.07 mg; 0.16 mmol; 1.10 eq.) and diisopropylethylamine (0.12 ml; 0.71 mmol; 5.00 eq.) followed by HATU (56.98 mg; 0.15 mmol; 1.05 eq.). After stirring for 15 min, the reaction mixture was diluted with water and MeCN and purified by preparatory HPLC to the title compound (42 mg). MS: (M+H)$^+$ found for C$_{29}$H$_{19}$F$_4$N$_3$O$_2$: 518.1.

Example 33

Synthesis of (1S,8R)—N-({2,6-difluoro-4-[N'-methoxycarbamimidoyl]phenyl}-methyl)-12-(1,3-thiazol-2-yl)-15-oxatetracyclo[6.6.1.0$^{2,7}$.0$^{9,14}$]pentadeca-2,4,6,9,11,13-hexaene-4-carboxamide

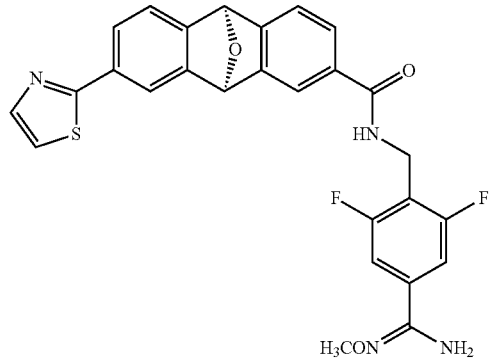

Step 1:

To a solution of methyl (1S,8R)-12-bromo-15-oxatetracyclo[6.6.1.0$^{2,7}$.0$^{9,14}$]-pentadeca-2,4,6,9,11,13-hexaene-4-carboxylate (INT-3a1; 120.00 mg; 0.36 mmol; 1.00 eq.) and 2-(tributylstannyl)-1,3-thiazole (271.17 mg; 0.72 mmol; 2.00 eq.) in DMF (1.2 mL) was added bis(triphenylphosphine)dichloropalladium (25.43 mg; 0.04 mmol; 0.10 eq.). After heating at 95 degree for 2 h, the reaction mixture was cooled down and purified by column chromatography (Hexanes/EtOAc=65:35) to give methyl (1S,8R)-12-(1,3-thiazol-2-yl)-15-oxatetracyclo-[6.6.1.0$^{2,7}$.0$^{9,14}$]pentadeca-2,4,6,9,11,13-hexaene-4-carboxylate. The product was dissolved in THF (2 mL) and MeOH (1 mL) and water (1 mL) were added, followed by lithium hydroxyde (17.36 mg; 0.72 mmol; 2.00 eq.). After stirring at room temperature for 2 h, the mixture was acidified by 1N HCl and then lyophilized to give (1S,8R)-12-(1,3-thiazol-2-yl)-15-oxatetracyclo[6.6.1.0$^{2,7}$.0$^{9,14}$]pentadeca-2,4,6,9,11,13-hexaene-4-carboxylic acid (45 mg).

Step 2:

To a solution of (1S,8R)-12-(1,3-thiazol-2-yl)-15-oxatetracyclo[6.6.1.0$^{2,7}$.0$^{9,14}$]-pentadeca-2,4,6,9,11,13-hexaene-4-carboxylic acid (45.00 mg; 0.14 mmol; 1.00 eq.) and 4-(aminomethyl)-3,5-difluoro-N'-methoxybenzene-1-carboximidamide (INT-11; 60.27 mg; 0.28 mmol; 2.00 eq.) in DMF (1.5 mL) was added diisopropylethylamine (0.10 ml; 0.56 mmol; 4.00 eq.) followed by HATU (58.57 mg; 0.15 mmol; 1.10 eq.). After stirring at room temperature for 30 min, the reaction mixture was diluted with water and MeCN and was purified by preparatory HPLC to the title compound (30 mg). MS: (M+H)$^+$ found for C$_{27}$H$_{20}$F$_2$N$_4$O$_3$S: 519.0.

Example 34

Synthesis of (1S,8R)—N-[(4-carbamimidoyl-2,6-difluorophenyl)methyl]-12-(1,3-thiazol-2-yl)-15-oxatetracyclo[6.6.1.0$^{2,7}$.0$^{9,14}$]pentadeca-2,4,6,9,11,13-hexaene-4-carboxamide

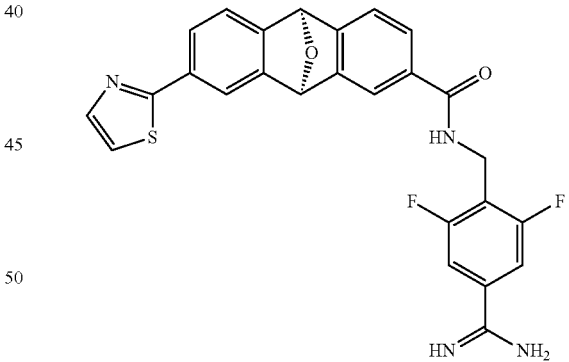

To a solution of (1S,8R)-12-(1,3-thiazol-2-yl)-15-oxatetracyclo[6.6.1.0$^{2,7}$.0$^{9,14}$]-pentadeca-2,4,6,9,11,13-hexaene-4-carboxylic acid (Example 33, Step 1; 45.00 mg; 0.14 mmol; 1.00 eq.) and 4-(aminomethyl)-3,5-difluorobenzene-1-carboximidamide (INT-10; 51.86 mg; 0.28 mmol; 2.00 eq.) in DMF (1.5 mL) was added diisopropylethylamine (0.10 ml; 0.56 mmol; 4.00 eq.) followed by HATU (58.57 mg; 0.15 mmol; 1.10 eq.). After stirring for 30 min, the reaction mixture was diluted with water and MeCN and purified by preparatory HPLC to give the title compound (26 mg). (M+H)$^+$ found for C$_{26}$H$_{18}$F$_2$N$_4$O$_2$S: 489.1.

Example 35

Synthesis of (1S,8R)—N-[(4-carbamimidoyl-2,6-difluorophenyl)methyl]-12-(1H-pyrazol-1-yl)-15-oxatetracyclo[6.6.1.0$^{2,7}$.0$^{9,14}$]pentadeca-2,4,6,9,11,13-hexaene-4-carboxamide

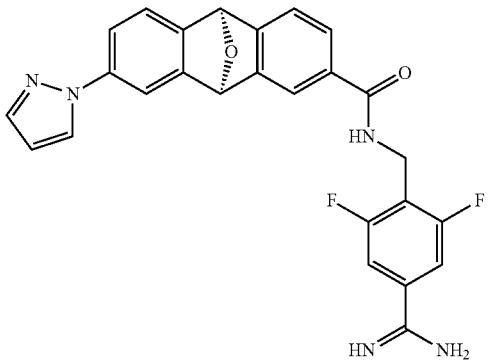

Step 1:

To a solution of (1S,8R)-12-bromo-15-oxatetracyclo[6.6.1.0$^{2,7}$.0$^{9,14}$]-pentadeca-2,4,6,9,11,13-hexaene-4-carboxylic acid (INT-4a1; 100.00 mg; 0.32 mmol; 1.00 eq.) in DMF (1 mL) was added 1H-pyrazole (42.93 mg; 0.63 mmol; 2.00 eq.) followed by potassium phosphate (tribasic) (133.87 mg; 0.63 mmol; 2.00 eq.), copper iodide (12.01 mg; 0.06 mmol; 0.20 eq.) and (1S,2S)—N~1~,N~2~-dimethyl-1,2-cyclohexanediamine (17.94 mg; 0.13 mmol; 0.40 eq.). The reaction mixture was degassed for 2 min, sealed and heated at 110 degree for 15 h. The reaction mixture was diluted with water and EtOAc, the aqueous layer was acidified to pH=3 and then extracted with EtOAc. The organic layers were combined, dried over MgSO$_4$ and was concentrated to give desired crude product, which was tritrirated to give (1S,8R)-12-(1H-pyrazol-1-yl)-15-oxatetracyclo[6.6.1.0$^{2,7}$.0$^{9,14}$]pentadeca-2,4,6,9,11,13-hexaene-4-carboxylic acid (50 mg).

Step 2:

To a solution of (1S,8R)-12-(1H-pyrazol-1-yl)-15-oxatetracyclo-[6.6.1.0$^{2,7}$.0$^{9,14}$]-pentadeca-2,4,6,9,11,13-hexaene-4-carboxylic acid (10.00 mg; 0.03 mmol; 1.00 eq.) and 4-(aminomethyl)-3,5-difluorobenzene-1-carboximidamide dihydrochloride (INT-10; 12.17 mg; 0.07 mmol; 2.00 eq.) in DMF (1.5 mL) was added Hunig's base (0.02 ml; 0.13 mmol; 4.00 eq.) followed by HATU (13.74 mg; 0.04 mmol; 1.10 eq.). After stirred for 30 min, it was diluted with water and MeCN and was purified by preparatory HPLC to give the title compound (11 mg). MS: (M+H)$^+$ found for C$_{26}$H$_{19}$F$_2$N$_5$O$_2$: 472.2.

Example 36

Synthesis of (1S,8R)—N-[(4-carbamimidoyl-2-methylphenyl)methyl]-12-(1H-pyrazol-1-yl)-15-oxatetracyclo[6.6.1.0$^{2,7}$.0$^{9,14}$]pentadeca-2,4,6,9,11,13-hexaene-4-carboxamide

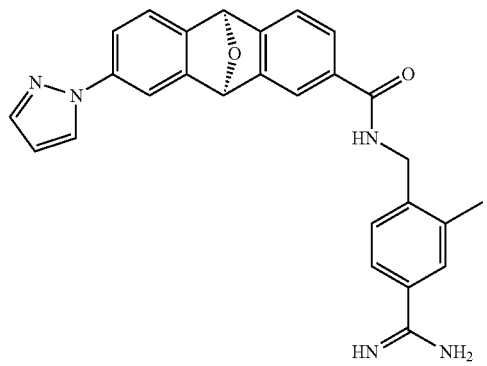 [SMILES: Cc1cc(C(=N)N)ccc1CNC(=O)c1ccc2c(c1)[C@@H]1O[C@H]2c2ccc(-n3cccn3)cc21]

To a solution of (1S,8R)-12-(1H-pyrazol-1-yl)-15-oxatetracyclo[6.6.1.0$^{2,7}$.0$^{9,14}$]-pentadeca-2,4,6,9,11,13-hexaene-4-carboxylic acid (Example 35, Step 1; 9.00 mg; 0.03 mmol; 1.00 eq.) in DMF (0.6 mL) was added 1H-1,2,3-benzotriazol-1-ol hydrate (9.06 mg; 0.06 mmol; 2.00 eq.) and Hunig's base (0.02 ml; 0.12 mmol; 4.00 eq.) followed by 3-{[(ethylimino)methylene]-amino}-N,N,N-trimethyl-1-propanaminium iodide (17.58 mg; 0.06 mmol; 2.00 eq.), then it was added 4-(aminomethyl)-3-methylbenzene-1-carboximidamide (Example 48, Steps 1-5; 9.65 mg; 0.06 mmol; 2.00 eq.) and stirred overnight. The reaction mixture was diluted with water and MeCN and was purified by preparatory HPLC to give the title compound (4.5 mg). MS: (M+H)$^+$ found for C$_{27}$H$_{23}$N$_5$O$_2$: 450.1.

Example 37

Synthesis of (1S,8R)—N-({2,6-difluoro-4-[N'-methoxycarbamimidoyl]-phenyl}methyl)-12-(1H-pyrazol-1-yl)-15-oxatetracyclo[6.6.1.0$^{2,7}$.0$^{9,14}$]pentadeca-2,4,6,9,11,13-hexaene-4-carboxamide

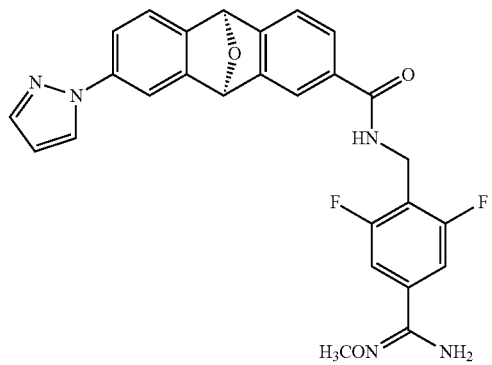

To a solution of (1S,8R)-12-(1H-pyrazol-1-yl)-15-oxatetracyclo[6.6.1.0$^{2,7}$.0$^{9,14}$]-pentadeca-2,4,6,9,11,13-hexaene-4-carboxylic acid (Example 35, Step 1; 40.00 mg; 0.13 mmol; 1.00 eq.) and 4-(aminomethyl)-3,5-difluoro-N'- methoxybenzene-1-carboximidamide (INT-11; 56.58 mg; 0.26 mmol; 2.00 eq.) in DMF (1.5 mL) was added diisopropylethylamine (0.09 ml; 0.53 mmol; 4.00 eq.), followed by HATU (54.98 mg; 0.14 mmol; 1.10 eq.). After stirring for 30 min, the reaction mixture was diluted with water and MeCN and was purified by preparatory HPLC to give the title compound (38 mg). MS: (M+H)$^+$ found for $C_{27}H_{21}F_2N_5O_3$: 502.1.

Example 38

Synthesis of (1S,8R)—N-({4-[N'-methoxycarbamimidoyl]phenyl}methyl)-12-(1H-pyrazol-1-yl)-15-oxatetracyclo[6.6.1.0$^{2,7}$.0$^{9,14}$]pentadeca-2,4,6,9,11,13-hexaene-4-carboxamide

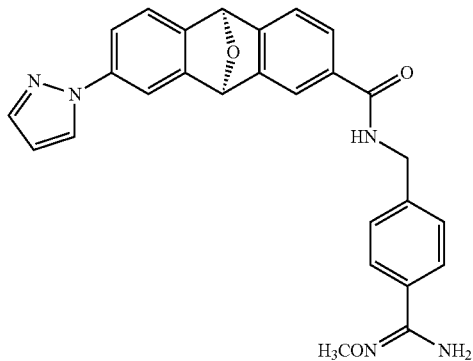

To a solution of (1S,8R)-12-(1H-pyrazol-1-yl)-15-oxatetracyclo[6.6.1.0$^{2,7}$.0$^{9,14}$]pentadeca-2,4,6,9,11,13-hexaene-4-carboxylic acid (Example 35, Step 1; 39.00 mg; 0.13 mmol; 1.00 eq.) and 4-(aminomethyl)-N'-methoxybenzimidamide dihydrochloride (INT-7; 45.94 mg; 0.26 mmol; 2.00 eq.) in DMF (1 mL) was added diisopropylethylamine (0.09 ml; 0.51 mmol; 4.00 eq.), followed by HATU (53.60 mg; 0.14 mmol; 1.10 eq.). After stirring for 10 min, the reaction mixture was diluted with water and was purified by preparatory HPLC to give the title compound (31 mg). MS: (M+H)$^+$ found for $C_{27}H_{23}N_5O_3$: 466.1.

Example 39

Synthesis of (1S,8R)—N-({4-[N'-methoxycarbamimidoyl]-2-methylphenyl}methyl)-12-(1H-pyrazol-1-yl)-15-oxatetracyclo[6.6.1.0$^{2,7}$.0$^{9,14}$]pentadeca-2,4,6,9,11,13-hexaene-4-carboxamide

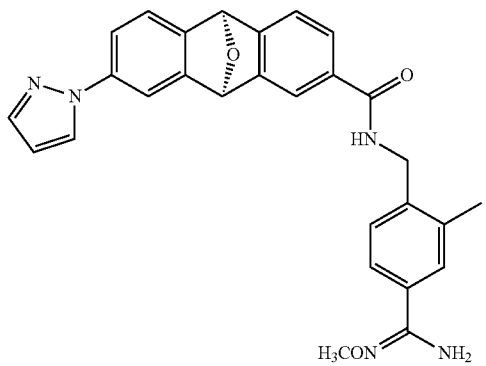

To a solution of (1S,8R)-12-(1H-pyrazol-1-yl)-15-oxatetracyclo[6.6.1.0$^{2,7}$.0$^{9,14}$]-pentadeca-2,4,6,9,11,13-hexaene-4-carboxylic acid (Example 35, Step 1; 38.00 mg; 0.12 mmol; 1.00 eq.) in DMF (1 mL) was added 4-(aminomethyl)-N'-methoxy-3-methylbenzene-1-carboximidamide (Example 49, Steps 1-2; 48.26 mg; 0.25 mmol; 2.00 eq.) and diisopropylethylamine (0.09 ml; 0.50 mmol; 4.00 eq.), followed by HATU (52.23 mg; 0.14 mmol; 1.10 eq.). After stirring overnight, the reaction mixture was diluted with water and MeCN and was purified by preparatory HPLC to give the title compound (42 mg). MS: (M+H)$^+$ found for $C_{28}H_{25}N_5O_3$: 480.1.

Example 40

Synthesis of (±)-N-[(6-amino-2,4-dimethylpyridin-3-yl)methyl]-11-methyl-10-phenyl-11-azatricyclo[6.2.1.0$^{2,7}$]undeca-2,4,6,9-tetraene-4-carboxamide and (±)-N-[(6-amino-2,4-dimethylpyridin-3-yl)methyl]-11-methyl-9-phenyl-11-azatricyclo[6.2.1.0$^{2,7}$]undeca-2,4,6,9-tetraene-4-carboxamide

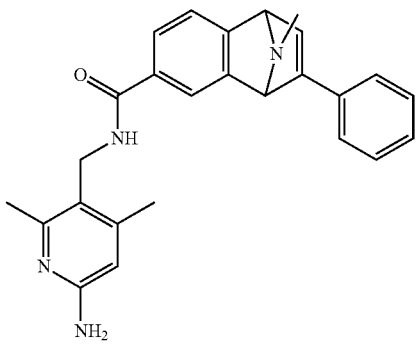

and

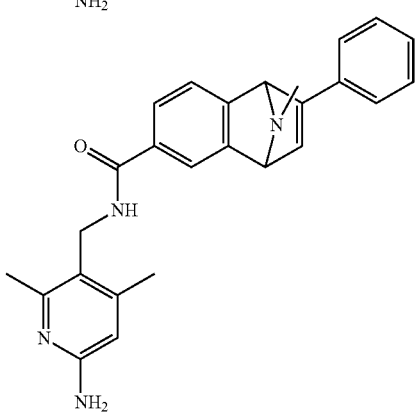

Step 1:
3-Bromo-1-(triisopropylsilyl)-1H-pyrrole (0.15 g, 0.50 mmol) was dissolved in toluene (2.6 ml) and methanol (0.9 ml), and purged with Ar gas. Phenylboronic acid (63.5 mg, 0.52 mmol), 1,1'-bis(diphenylphosphino)ferrocene]dichloropalladium(II) (18.15 mg, 0.02 mmol) and then sodium carbonate (0.56 ml, 2.65 M aq. solution, 1.49 mmol) were added. The reaction vessel was sealed and stirred in a heat block at 80° C. for 2.75 h, then to 25° C. over 16 h. More bis(diphenylphosphino)ferrocene]dichloropalladium(II) (9 mg, 0.01 mmol) was added and the reaction was heated at 80° C. for 7 h, then cooled and taken up in DCM and water. The phases were separated, the aqueous phase was extracted once with DCM, and the combined organics were washed with saturated sodium chloride solution. After drying over sodium sulfate, filtration and evaporation, the resulting residue was purified by silica gel chromatography (ethyl acetate/hexanes gradient) to give 3-phenyl-1-[tris(propan-2-yl)silyl]-1H-pyrrole as a colored oil (100 mg).

Step 2:

3-Phenyl-1-[tris(propan-2-yl)silyl]-1H-pyrrole (100 mg, 0.18 mmol, 55% pure) was dissolved in THF (1 ml). Tetrabutylammonium fluoride (0.55 ml, 1 M THF solution, 0.55 mmol) was then added and the reaction was stirred for 1 h. The solution was evaporated carefully and the residue was dissolved in diethyl ether and water. The phases were separated and the aqueous phase was extracted once with more ether. The combined organics were washed with water and then saturated sodium chloride solution, dried over sodium sulfate, filtered and evaporated. The resulting residue was purified by silica gel chromatography (ethyl acetate/hexanes gradient) to give crude 3-phenyl-1H-pyrrole (100 mg).

Step 3:

3-Phenyl-1H-pyrrole (100 mg, 0.14 mmol, 20% pure) was dissolved in DMSO (1 ml) and cyclohexane (1 ml). 18-Crown-6 (4.4 mg, 0.02 mmol) and potassium tert-butoxide (19.6 mg, 0.17 mmol) were added and then iodomethane (26 ul, 0.42 mmol) was added in portions over 10 m. After 1.5 h, water and diethyl ether were added and the phases were separated. The aqueous phase was extracted once more with ether, the combined organics were washed with saturated sodium chloride solution and dried over sodium sulfate. Filtration and evaporated gave a residue which was purified by silica gel chromatography (ethyl acetate/hexanes gradient) to give 1-methyl-3-phenyl-1H-pyrrole (45 mg).

Step 4: [5-(Methoxycarbonyl)-2-(trimethylsilyl)phenyl](phenyl)iodanium trifluoromethanesulfonate (50 mg, 0.09 mmol) was added to a solution of 1-methyl-3-phenyl-1H-pyrrole (21 mg, 0.13 mmol) in DCM (1 ml) at 0° C. Tetrabutylammonium fluoride (0.12 ml 1 M THF solution, 0.12 mmol) was then added slowly at 0° C. After 30 m, water and more DCM were added, and the phases were separated. The aqueous phase was extracted twice more with DCM. The combined organic phases were washed with saturated sodium chloride solution, dried over sodium sulfate, filtered and evaporated to a residue. The residue was purified by silica gel chromatography (ethyl acetate/dichloromethane gradient) to give a mixture of (±)-methyl 11-methyl-10-phenyl-11-azatricyclo[6.2.1.0$^{2,7}$]undeca-2,4,6,9-tetraene-4-carboxylate and (±)-methyl 11-methyl-9-phenyl-11-azatricyclo[6.2.1.0$^{2,7}$]undeca-2,4,6,9-tetraene-4-carboxylate (35 mg).

Step 5:

A mixture of (±)-methyl 11-methyl-10-phenyl-11-azatricyclo[6.2.1.0$^{2,7}$]undeca-2,4,6,9-tetraene-4-carboxylate and (±)-methyl 11-methyl-9-phenyl-11-azatricyclo[6.2.1.0$^{2,7}$]-undeca-2,4,6,9-tetraene-4-carboxylate (35 mg, 0.12 mmol) was dissolved in THF (3 ml) and methanol (0.8 ml). The solution was cooled in an ice bath and lithium hydroxide (11.5 mg, 0.48 mmol) in water (2 ml) was added. The reaction was stirred at 25° C. for 17 h. More lithium hydroxide (6 mg, 0.24 mmol) in water (1 ml) was added and the reaction was stirred for 3 h more, then warmed to 50° C. After 3.5 h the reaction was cooled, saturated sodium chloride solution and ethyl acetate were added, and the pH was adjusted to 5-6 using aqueous HCl. The phases were separated, the aqueous phase was extracted five times more with warm ethyl acetate and the combined organics were dried over sodium sulfate. Filtration and evaporation gave a crude mixture of (±)-11-methyl-10-phenyl-11-azatricyclo[6.2.1.0$^{2,7}$]undeca-2,4,6,9-tetraene-4-carboxylic acid and (±)-11-methyl-9-phenyl-11-azatricyclo[6.2.1.0$^{2,7}$]undeca-2,4,6,9-tetraene-4-carboxylic acid (74 mg).

Step 6:

A mixture of (±)-11-methyl-10-phenyl-11-azatricyclo[6.2.1.0$^{2,7}$]undeca-2,4,6,9-tetraene-4-carboxylic acid and (±)-11-methyl-9-phenyl-11-azatricyclo-[6.2.1.0$^{2,7}$]undeca-2,4,6,9-tetraene-4-carboxylic acid (33 mg, 0.012 mmol) was dissolved in DMF (1.2 ml). Ethyl bis(propan-2-yl)amine (83 ul, 0.48 mmol), 5-(aminomethyl)-4,6-dimethylpyridin-2-amine (27 mg, 0.18 mmol), and then hexafluoro-$\lambda^5$-phosphanuide 1-[bis(dimethylamino)methyl-iumyl]-1H-[1,2,3]triazolo[4,5-b]pyridin-3-ium-3-olate (90 mg, 0.24 mmol) were added. After 16 h, aqueous sodium bicarbonate solution and ethyl acetate were added. The phases were separated and the aqueous phase was extracted with ethyl acetate twice more. The combined organic phases were washed with saturated sodium chloride solution and dried over sodium sulfate. After filtration and evaporation, the residue was purified by reverse phase chromatography (acetonitrile gradient with 0.1% aqueous formic acid, Waters XSelect CSH C18 column) to give the title compounds as a white solid (5.8 mg, 11%). MS: (M+H)$^+$ found for $C_{26}H_2N_4O$: 411.2.

Example 41

Synthesis of (±)-N-[(6-amino-2,4-dimethylpyridin-3-yl)methyl]-12-(4-benzoylpiperazin-1-yl)-15-oxa-tetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(4-benzoylpiperazin-1-yl)-15-oxatetracyclo[6.6.1.0$^{2,7}$.0$^{9,14}$]pentadeca-2,4,6,9,11,13-hexaene-4-carboxamide

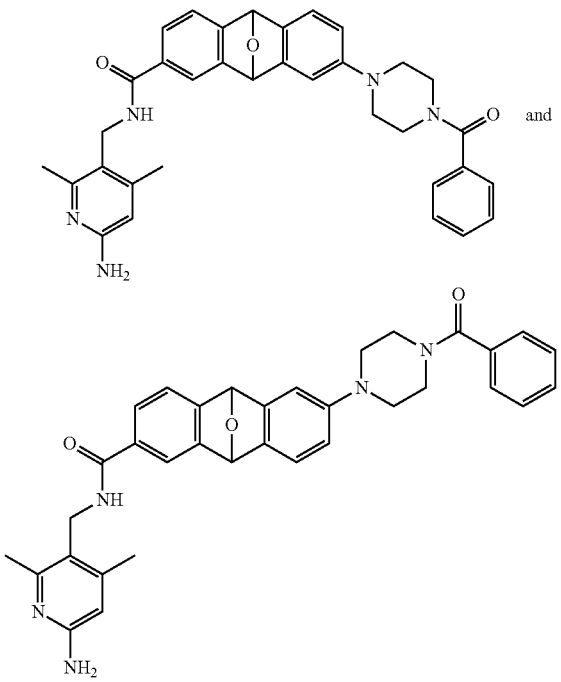

Step 1:

Tert-butyl 1-piperazinecarboxylate (1 g, 5.37 mmol) was dissolved in DCM (18 ml). Triethylamine (1.5 ml, 10.74 mmol) was added and the solution was cooled in an ice bath. Benzoyl chloride (0.65 ml, 5.64 mmol) (diluted with DCM (0.3 ml)) was added dropwise and the reaction was stirred to 25° C. After 3 h, water and DCM were added, the phases were separated and the aqueous phase was extracted twice more with DCM. The combined organics were washed with brine, dried over sodium sulfate, filtered and evaporated to a white solid. Purification of this solid by silica gel chromatography (ethyl acetate/heptanes gradient) gave tert-butyl 4-benzoylpiperazine-1-carboxylate as a white solid (1.53 g, 98%).

Step 2:

Tert-butyl 4-benzoylpiperazine-1-carboxylate (1 g; 3.44 mmol) was dissolved in DCM (8 ml) and cooled in an ice bath. Trifluoroacetic acid (5.3 ml, 69 mmol) was added slowly. The reaction was stirred at 25° C. for 2.5 h and then evaporated. The residue was taken up in ethyl acetate and saturated sodium bicarbonate solution, the phases were separated and the aqueous phase was extracted five times with ethyl acetate. The combined organics were dried over sodium sulfate, filtered and evaporated to a glassy residue of 1-benzoylpiperazine (0.83 g).

Step 3:

{1-[2-(diphenylphosphanyl)naphthalen-1-yl]naphthalen-2-yl}-diphenylphosphane (28 mg, 0.05 mmol) and palladium acetate (10.2 mg, 0.05 mmol) were combined in toluene (1.5 ml), purged with Ar gas and stirred at 25° C. for 1 h. A mixture of methyl 12-bromo-15-oxatetracyclo [6.6.1.0$^{2,7}$.0$^{9,14}$]pentadeca-2,4,6,9,11,13-hexaene-4-carboxylate and methyl 11-bromo-15-oxatetracyclo[6.6.1.0$^{2,7}$.0$^{9,14}$]pentadeca-2,4,6,9,11,13-hexaene-4-carboxylate (INT-3; 100 mg, 0.30 mmol) was dissolved in toluene (1 ml). 1-Benzoylpiperazine (99.6 mg, 0.39 mmol) dissolved in toluene (1 ml) and THF (1.5 ml) was added and the solution was purged with Ar gas. The bromoester and piperazine solution was then combined with the palladium mixture and sodium 2-methyl-2-propanolate (40.6 mg, 0.42 mmol) was added. The reaction mixture was sealed and stirred in a heat block at 80° C. for 1.5 h. After cooling, the mixture was taken up in ethyl acetate and aqueous sodium bicarbonate solution. The phases were separated, the aqueous phase was extracted twice more with ethyl acetate and the combined organics were washed with saturated sodium chloride solution. After drying over sodium sulfate, filtration and evaporation the residue was purified by silica gel chromatography (ethyl acetate/DCM gradient) giving a mixture of (±)-methyl 12-(4-benzoylpiperazin-1-yl)-15-oxatetracyclo[6.6.1.0$^{2,7}$.0$^{9,14}$]pentadeca-2,4,6,9,11,13-hexaene-4-carboxylate and (±)-methyl 11-(4-benzoylpiperazin-1-yl)-15-oxatetracyclo-[6.6.1.0$^{2,7}$.0$^{9,14}$]pentadeca-2,4,6,9,11,13-hexaene-4-carboxylate as a faintly colored film (0.07 g, 52%).

Step 4:

Following Example 40, step 5, but substituting a mixture of (±)-methyl 11-methyl-10-phenyl-11-azatricyclo[6.2.1.0$^{2,7}$]undeca-2,4,6,9-tetraene-4-carboxylate and (±)-methyl 11-methyl-9-phenyl-11-azatricyclo[6.2.1.0$^{2,7}$]undeca-2,4,6,9-tetraene-4-carboxylate with a mixture of (±)-methyl 12-(4-benzoylpiperazin-1-yl)-15-oxatetracyclo[6.6.1.0$^{2,7}$.0$^{9,14}$]-pentadeca-2,4,6,9,11,13-hexaene-4-carboxylate and (±)-methyl 11-(4-benzoylpiperazin-1-yl)-15-oxatetracyclo [6.6.1.0$^{2,7}$.0$^{9,14}$]pentadeca-2,4,6,9,11,13-hexaene-4-carboxylate gave a mixture of (±)-12-(4-benzoylpiperazin-1-yl)-15-oxatetracyclo[6.6.1.0$^{2,7}$.0$^{9,14}$]pentadeca-2,4,6,9,11,13-hexaene-4-carboxylic acid and (±)-11-(4-benzoylpiperazin-1-yl)-15-oxatetracyclo-[6.6.1.0$^{2,7}$.0$^{9,14}$]pentadeca-2,4,6,9,11,13-hexaene-4-carboxylic acid.

Step 5:

The title compounds were prepared as in Example 40, step 6, but substituting a mixture of (±)-11-methyl-10-phenyl-11-azatricyclo[6.2.1.0$^{2,7}$]undeca-2,4,6,9-tetraene-4-carboxylic acid and (±)-11-methyl-9-phenyl-11-azatricyclo [6.2.1.0$^{2,7}$]undeca-2,4,6,9-tetraene-4-carboxylic acid with a mixture of (±)-12-(4-benzoylpiperazin-1-yl)-15-oxatetracyclo-[6.6.1.0$^{2,7}$.0$^{9,14}$]pentadeca-2,4,6,9,11,13-hexaene-4-carboxylic acid and (±)-11-(4-benzoyl-piperazin-1-yl)-15-oxatetracyclo[6.6.1.0$^{2,7}$.0$^{9,14}$]pentadeca-2,4,6,9,11,13-hexaene-4-carboxylic acid. MS: (M+H)$^+$ found for $C_{34}H_{33}N_5O_3$: 560.3.

Example 42

Synthesis of (±)-N-[(6-amino-2,4-dimethylpyridin-3-yl)methyl]-12-(2-cyano-4-fluorophenyl)-15-oxa-tetracyclo[6.6.1.0$^{2,7}$.0$^{9,14}$]pentadeca-2,4,6,9,11,13-hexaene-4-carboxamide

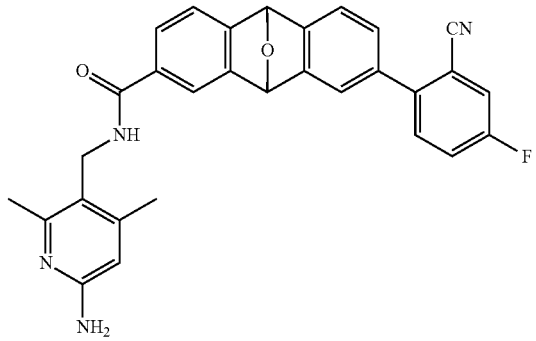 [SMILES: Cc1cc(N)nc(C)c1CNC(=O)c1ccc2c(c1)C1OC2c2ccc(-c3ccc(F)cc3C#N)cc21]

Step 1:

((2-Cyano-4-fluorophenyl)boronic acid (46 mg, 0.28 mmol), (±)-methyl 12-bromo-15-oxatetracyclo[6.6.1.0$^{2,7}$.0$^{9,14}$]pentadeca-2,4,6,9,11,13-hexaene-4-carboxylate (INT-3a; 80 mg, 0.24 mmol) and potassium carbonate (67 mg, 0.48 mmol) were dissolved in THF (1.2 ml) and water (0.6 ml). The solution was purged with Ar gas and then [1,1'-bis(di-t-butylphosphino)-ferrocene]palladium (II) dichloride (8 mg, 0.01 mmol) was added. The reaction vessel was sealed and stirred in a heat block at 60° C. After 8 h, the mixture was cooled and partitioned into ethyl acetate and sodium bicarbonate solution. The phases were separated, the aqueous phase was extracted twice more with ethyl acetate and the combined organics were washed with saturated sodium chloride solution. After drying over sodium sulfate, filtration and evaporation, the residue was purified by silica gel chromatography (ethyl acetate/hexanes gradient) to give (±)-methyl 12-(2-cyano-4-fluorophenyl)-15-oxatetracyclo[6.6.1.0$^{2,7}$.0$^{9,14}$]pentadeca-2,4,6,9,11,13-hexaene-4-carboxylate (80 mg, 89%).

Step 2:

Following Example 40, step 5, but substituting a mixture of methyl 11-methyl-10-phenyl-11-azatricyclo[6.2.1.0$^{2,7}$] undeca-2,4,6,9-tetraene-4-carboxylate and methyl 11-methyl-9-phenyl-11-azatricyclo[6.2.1.0$^{2,7}$]undeca-2,4,6,9-tetraene-4-carboxylate with (±)-methyl 12-(2-cyano-4-fluorophenyl)-15-oxatetracyclo[6.6.1.0$^{2,7}$.0$^{9,14}$]pentadeca-2,4,6,9,11,13-hexaene-4-carboxylate gave (±)-12-(2-cyano- 4-fluorophenyl)-15-oxatetracyclo[6.6.1.0²,⁷.0⁹,¹⁴]pentadeca-2,4,6,9,11,13-hexaene-4-carboxylic acid.

Step 3:

The title compound was prepared as in Example 40, step 6, but substituting a mixture of (±)-11-methyl-10-phenyl-11-azatricyclo[6.2.1.0²,⁷]undeca-2,4,6,9-tetraene-4-carboxylic acid and (±)-11-methyl-9-phenyl-11-azatricyclo[6.2.1.0²,⁷]undeca-2,4,6,9-tetraene-4-carboxylic acid with (±)-12-(2-cyano-4-fluorophenyl)-15-oxatetracyclo-[6.6.1.0²,⁷.0⁹,¹⁴]-pentadeca-2,4,6,9,11,13-hexaene-4-carboxylic acid. MS: (M+H)⁺ found for $C_{30}H_{23}FN_4O_2$: 491.1.

Example 43

Synthesis of (1R,8S)—N-[(6-amino-2,4-dimethylpyridin-3-yl)methyl]-12-(4-chloro-2,3-difluoro-phenyl)-15-oxatetracyclo[6.6.1.0²,⁷.0⁹,¹⁴]pentadeca-2,4,6,9,11,13-hexaene-4-carboxamide

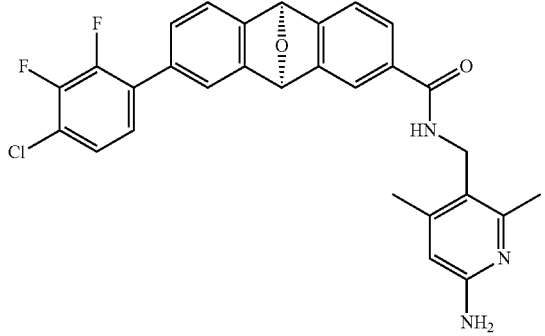 [SMILES: Cc1cc(N)nc(C)c1CNC(=O)c1ccc2c(c1)[C@@H]1O[C@H]2c2ccc(-c3ccc(Cl)c(F)c3F)cc21]

Step 1:

((4-Chloro-2,3-difluorophenyl)boronic acid (47 mg, 0.24 mmol) and methyl (1S,8R)-12-bromo-15-oxatetracyclo[6.6.1.0²,⁷.0⁹,¹⁴]pentadeca-2,4,6,9,11,13-hexaene-4-carboxylate (INT-3a1; 73.7 mg, 0.22 mmol) were dissolved in 1,4-dioxane (1.5 ml) and sodium carbonate (0.26 ml, 2.60 M aqueous solution, 0.67 mmol). The solution was purged with Ar gas and 1,1'-bis(diphenylphosphino)ferrocene]dichloropalladium(II) (16.3 mg, 0.02 mmol) was added. The reaction was stirred in a heat block at 90° C. for 4 h then cooled, diluted with ethyl acetate, filtered through Celite and rinsed through with more ethyl acetate. After evaporation, the residue was purified by silica gel chromatography (ethyl acetate/hexanes gradient) to give methyl (1R,8S)-12-(4-chloro-2,3-difluorophenyl)-15-oxatetracyclo[6.6.1.0²,⁷.0⁹,¹⁴]pentadeca-2,4,6,9,11,13-hexaene-4-carboxylate (0.08 g, 89%).

Step 2:

Following Example 40, step 5, but substituting a mixture of (±)-methyl 11-methyl-10-phenyl-11-azatricyclo[6.2.1.0²,⁷]undeca-2,4,6,9-tetraene-4-carboxylate and (±)-methyl 11-methyl-9-phenyl-11-azatricyclo[6.2.1.0²,⁷]undeca-2,4,6,9-tetraene-4-carboxylate with methyl (1R,8S)-12-(4-chloro-2,3-difluorophenyl)-15-oxatetracyclo-[6.6.1.0²,⁷.0⁹,¹⁴]pentadeca-2,4,6,9,11,13-hexaene-4-carboxylate gave (1R,8S)-12-(4-chloro-2,3-difluorophenyl)-15-oxatetracyclo[6.6.1.0²,⁷.0⁹,¹⁴]pentadeca-2,4,6,9,11,13-hexaene-4-carboxylic acid.

Step 3:

The title compound was prepared as in Example 40, step 6, but substituting a mixture of (±)-11-methyl-10-phenyl-11-azatricyclo[6.2.1.0²,⁷]undeca-2,4,6,9-tetraene-4-carboxylic acid and (±)-11-methyl-9-phenyl-11-azatricyclo[6.2.1.0²,⁷]undeca-2,4,6,9-tetraene-4-carboxylic acid with (1R,8S)-12-(4-chloro-2,3-difluorophenyl)-15-oxatetracyclo-[6.6.1.0²,⁷.0⁹,¹⁴]pentadeca-2,4,6,9,11,13-hexaene-4-carboxylic acid. MS: (M+H)⁺ found for $C_{29}H_{22}ClF_2N_3O_2$: 518.1.

Example 44

Synthesis of (1R,8S)—N-[(4-carbamimidoylphenyl)methyl]-12-(2-fluorophenyl)-15-oxatetracyclo-[6.6.1.0²,⁷.0⁹,¹⁴]pentadeca-2,4,6,9,11,13-hexaene-4-carboxamide

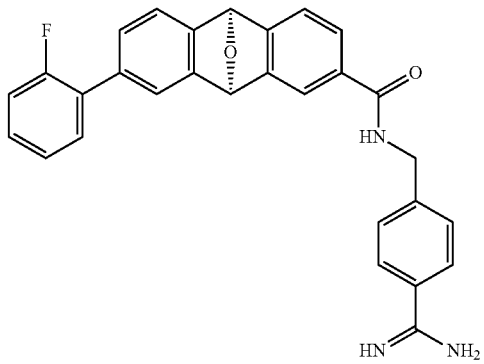 [SMILES: N=C(N)c1ccc(CNC(=O)c2ccc3c(c2)[C@@H]2O[C@H]3c3ccc(-c4ccccc4F)cc32)cc1]

Step 1:

(2-Fluorophenyl)boronic acid (27 mg, 0.19 mmol) and sodium (1S,8R)-12-bromo-15-oxatetracyclo[6.6.1.0²,⁷.0⁹,¹⁴]pentadeca-2,4,6,9,11,13-hexaene-4-carboxylate (INT-5a1; 60 mg, 0.18 mmol) were dissolved in 1,4-dioxane (1.4 ml) and sodium carbonate solution (0.2 ml, 2.6 M aq. solution, 0.53 mmol). The solution was purged with Ar gas and then 1,1'-bis(diphenyl-phosphino)ferrocene]dichloropalladium(II) (13 mg, 0.02 mmol) was added. The reaction was heated in a microwave reactor at 90° C. for 45 m. The cooled reaction was taken up in ethyl acetate and ammonium chloride solution, and the pH was adjusted to <3 with aqueous HCl. The phases were separated, the aqueous phase was extracted twice more with ethyl acetate, and the combined organics were washed with saturated sodium chloride solution. After drying over sodium sulfate, filtration and evaporation, the residue was purified by silica gel chromatography (methanol/DCM gradient) to give (1R,8S)-12-(2-fluorophenyl)-15-oxatetracyclo[6.6.1.0²,⁷.0⁹,¹⁴]-pentadeca-2,4,6,9,11,13-hexaene-4-carboxylic acid as a tan solid (59 mg, 100%).

Step 2:

The title compound was prepared as in Example 40, step 6, but substituting a mixture of (±)-11-methyl-10-phenyl-11-azatricyclo[6.2.1.0²,⁷]undeca-2,4,6,9-tetraene-4-carboxylic acid and (±)-11-methyl-9-phenyl-11-azatricyclo[6.2.1.0²,⁷]undeca-2,4,6,9-tetraene-4-carboxylic acid with (1R,8S)-12-(2-fluorophenyl)-15-oxatetracyclo-[6.6.1.0²,⁷.0⁹,¹⁴]pentadeca-2,4,6,9,11,13-hexaene-4-carboxylic acid. MS: (M+H)⁺ found for $C_{29}H_{23}FN_3O_2$: 464.2.

Example 45

Synthesis of (1R,8S)—N-[(4-carbamimidoyl-2,6-dimethylphenyl)methyl]-12-(2,4-difluoro-phenyl)-15-oxatetracyclo[6.6.1.0$^{2,7}$.0$^{9,14}$]pentadeca-2,4,6,9,11,13-hexaene-4-carboxamide

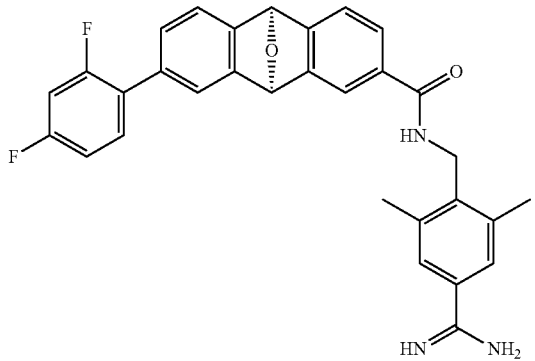 [SMILES: Cc1cc(C(=N)N)cc(C)c1CNC(=O)c1ccc2c(c1)[C@@H]1O[C@H]2c2ccc(-c3ccc(F)cc3F)cc21]

Step 1:
4-Bromo-3,5-dimethylbenzonitrile (0.5 g, 2.38 mmol) was dissolved in THF (12 ml). The solution was cooled in a dry ice/diethyl ether bath. N-butyllithium (1.05 ml 2.50 M solution in hexanes, 2.62 mmol) was added slowly over 30 m. Dry N,N-dimethylformamide (0.26 ml, 3.3 mmol) was then added slowly and the reaction allowed to warm slowly. After 1 h the reaction appeared complete (LC/MS, TLC) and by 2 h with the temperature at −30° C., the reaction was neutralized by addition of an aqueous saturated sodium chloride solution. The mixture was taken up in ethyl acetate and water, the phases were separated, the aqueous phase was extracted once more with ethyl acetate, and the combined organics were washed with more saturated sodium chloride solution. After drying over sodium sulfate, filtration and evaporation, the residue was purified by silica gel chromatography (ethyl acetate/hexanes gradient) to give 4-formyl-3,5-dimethylbenzonitrile as a white solid (0.18 g, 47%).

Step 2:
4-Formyl-3,5-dimethylbenzonitrile (0.18 g, 1.13 mmol) was dissolved in THF (12 ml) and the solution was stirred in an ice bath. Sodium borohydride (43 mg, 1.13 mmol) and then dry methanol (1.1 ml) were added. The reaction was stirred to 25° C. and after 2 h the reaction was diluted with ethyl acetate. The solution was washed with water three times, washed with saturated sodium chloride solution and dried over sodium sulfate. Filtration and evaporation gave 4-(hydroxymethyl)-3,5-dimethylbenzonitrile as a white solid (0.16 g, 89%).

Step 3:
4-(Hydroxymethyl)-3,5-dimethylbenzonitrile (0.16 g 1 mmol) was dissolved in dichloromethane (10 ml) and the solution was cooled in an ice bath. Triethylamine (0.21 ml, 1.50 mmol) was added, followed by slow addition of methanesulfonyl chloride (0.09 ml, 1.20 mmol). The reaction was stirred to 25° C., and after 2.5 h the reaction solution was washed with water and saturated sodium chloride solution. The organics were dried over sodium sulfate, filtered and evaporated to give (4-cyano-2,6-dimethylphenyl)methyl methanesulfonate as a white solid (0.2 g).

Step 4:
(4-Cyano-2,6-dimethylphenyl)methyl methanesulfonate (0.2 g 0.84 mmol) was dissolved in DMF (4 ml). Sodium azide (109 mg, 1.67 mmol) was added and the reaction was stirred in heat block at 30° C. After 2.5 h, the reaction was taken up in water and diethyl ether. The phases were separated and the aqueous phase was extracted twice more with ether. The combined organics were washed with saturated sodium chloride solution, dried over sodium sulfate, filtered and evaporated to give a crude solid of 4-(azidomethyl)-3,5-dimethyl-benzonitrile (0.37 g).

Step 5:
In a screw-cap tube, absolute ethanol (6 ml) was cooled in an ice bath. Acetyl chloride (6.1 ml, 86 mmol) was added slowly in portions. 4-(Azidomethyl)-3,5-dimethylbenzonitrile (0.16 g, 0.86 mmol) suspended in ethanol (4 ml) was added at 0° C. The tube was sealed and stirred at 4° C. for 72 h. The reaction solution was then evaporated, co-evaporated from ethanol and then taken up in ammonia/methanol solution (14 ml of 7M methanol solution). After 22 h, the solution was evaporated and the residue taken up in ethyl acetate and water. The phases were separated and the aqueous phase was extracted once more with ethyl acetate. The combined organics were washed with saturated sodium chloride solution, dried over sodium sulfate, filtered and evaporated to give a crude solid of 4-(azidomethyl)-3,5-dimethylbenzene-1-carboximidamide (0.34 g).

Step 6:
10% Palladium (44.51 mg, 0.04 mmol) on carbon was combined with 4-(azidomethyl)-3,5-dimethylbenzene-1-carboximidamide (0.17 g, 0.84 mmol) in absolute ethanol (8 ml) and flushed w/H$_2$ gas. After 4 h, the mixture was purged w/N$_2$ gas, filtered through Celite, rinsed through with more ethanol and evaporated to a crude residue of 4-(aminomethyl)-3,5-dimethylbenzene-1-carboximidamide (0.28 g).

Step 7:
Following the procedure of Example 44, Step 1, but substituting 2-fluorophenyl-boronic acid with 2,4-difluorophenylboronic acid gave (1R,8S)-12-(2,4-difluorophenyl)-15-oxatetracyclo[6.6.1.0$^{2,7}$.0$^{9,14}$]pentadeca-2,4,6,9,11,13-hexaene-4-carboxylic acid as a brownish residue.

Step 8:
(1R,8S)-12-(2,4-difluorophenyl)-15-oxatetracyclo[6.6.1.0$^{2,7}$.0$^{9,14}$]pentadeca-2,4,6,9,11,13-hexaene-4-carboxylic acid (63 mg, 0.18 mmol) was dissolved in DMF (1 ml). Ethyl bis(propan-2-yl)amine (63 ul, 0.36 mmol), hydroxybenzotriazole (37 mg, 0.27 mmol) and N-[3-(dimethylamino)propyl]-N'-ethylcarbodiimide (56 mg, 0.36 mol) were added and the solution was stirred for 5 m. Crude 4-(aminomethyl)-3,5-dimethylbenzene-1-carboximidamide (66 mg, 0.20 mmol) in DMF (0.5 ml) was then added and the mixture stirred for 14 h. The reaction mixture was taken up in water and ethyl acetate, the phases were separated and the aqueous phase was extracted twice more with ethyl acetate. The combined organics were washed with water and saturated sodium chloride solution, and dried over sodium sulfate. After filtration and evaporation the residue was purified by reverse phase chromatography (acetonitrile gradient with 0.1% aqueous formic acid, Waters XSelect CSH C18 column) to give the title compound as a white solid (28 mg, 30%). MS: (M+H)$^+$ found for $C_{31}H_{25}F_2N_3O_2$: 510.2.

Example 46

Synthesis of (1R,8S)-12-(2,4-difluorophenyl)-N-{[4-(N'-hydroxy-carbamimidoyl)phenyl]methyl)}-15-oxatetracyclo[6.6.1.0$^{2,7}$.0$^{9,14}$]pentadeca-2,4,6,9,11,13-hexaene-4-carboxamide

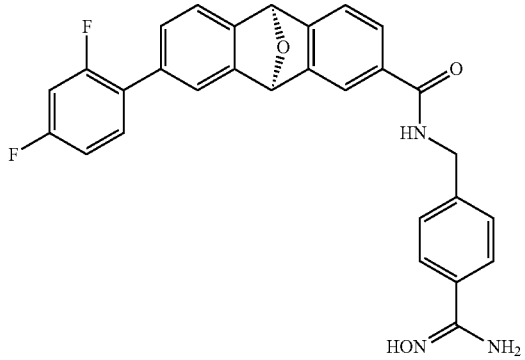

The title compound was prepared as in Example 45, step 8, but substituting 4-(amino-methyl)-3,5-dimethylbenzene-1-carboximidamide with 4-(aminomethyl)-N'-hydroxybenzene-1-carboximidamide (INT-8). MS: (M+H)$^+$ found for C$_{29}$H$_{21}$F$_2$N$_3$O$_3$: 498.2.

Example 47

Synthesis of (1R,8S)-12-(2-fluorophenyl)-N-{[4-(N'-hydroxycarbamimidoyl)phenyl]methyl}-15-oxatetracyclo[6.6.1.0$^{2,7}$.0$^{9,14}$]pentadeca-2,4,6,9,11,13-hexaene-4-carboxamide

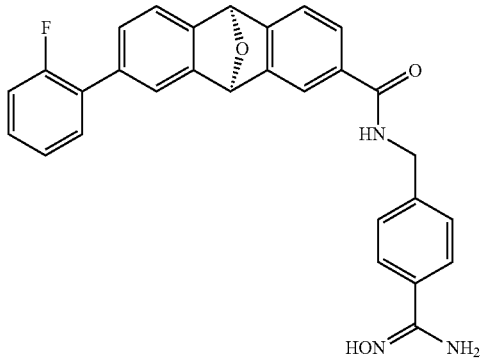

The title compound was prepared as in Example 45, Step 8, but substituting 4-(aminomethyl)-3,5-dimethylbenzene-1-carboximidamide with 4-(aminomethyl)-N'-hydroxybenzene-1-carboximidamide (INT-8), and substituting (1R,8S)-12-(2,4-difluorophenyl)-15-oxatetracyclo[6.6.1.0$^{2,7}$.0$^{9,14}$]pentadeca-2,4,6,9,11,13-hexaene-4-carboxylic acid with (1R,8S)-12-(2-fluorophenyl)-15-oxatetracyclo[6.6.1.0$^{2,7}$.0$^{9,14}$]pentadeca-2,4,6,9,11,13-hexaene-4-carboxylic acid (Example 44, Step 1). MS: (M+H)$^+$ found for C$_{29}$H$_{22}$FN$_3$O$_3$: 480.2.

Example 48

Synthesis of (1R,8S)—N-[(4-carbamimidoyl-2-methylphenyl)methyl]-12-(2,4-difluoro-phenyl)-15-oxatetracyclo[6.6.1.0$^{2,7}$.0$^{9,14}$]pentadeca-2,4,6,9,11,13-hexaene-4-carboxamide

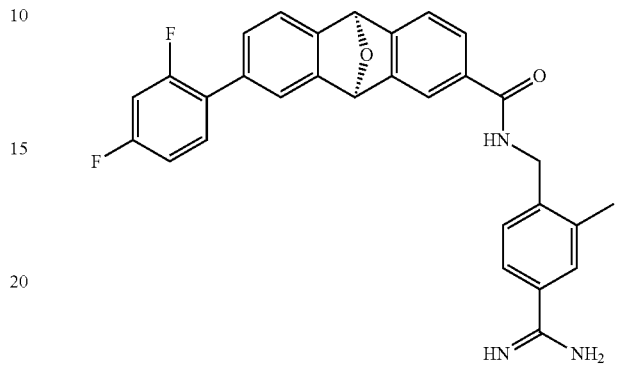

Step 1:
4-(Hydroxymethyl)-3-methylbenzonitrile (1 g, 6.79 mmol) was dissolved in dichloromethane (34 ml), and the resulting turbid solution was then cooled in an ice bath. Triethylamine (1.4 ml, 10.2 mmol) and then methanesulfonyl chloride (0.63 ml, 8.15 mmol) were added slowly. After 3 h, the reaction mixture was diluted with more DCM, washed with water and then a saturated sodium chloride solution. The organic phases was dried over sodium sulfate, filtered and evaporated to a residue of (4-cyano-2-methylphenyl)methyl methanesulfonate (1.6 g).

Step 2:
4-Cyano-2-methylphenyl)methyl methanesulfonate (1.53 g, 6.79 mmol) was dissolved in DMF (20 ml). Sodium azide (883 mg, 13.58 mmol) was added and the mixture was stirred in a heat block at 30° C. After 2 h, water and diethyl ether were added. The phases were separated, the aqueous phase was extracted twice more with ether, the combined organics were washed with water and a saturated sodium chloride solution, and then dried over sodium sulfate. Filtration and evaporation gave 4-(azidomethyl)-3-methylbenzonitrile as a yellowish liquid (1.18 g).

Step 3:
4-(Azidomethyl)-3-methylbenzonitrile (0.18 g, 1.05 mmol) was dissolved in dry methanol (3.5 ml). Triethylamine (0.44 ml 3.14 mmol) and then hydroxylamine hydrochloride (0.22 g, 3.14 mmol) were added, and the mixture was stirred in a heat block at 50° C. After 2.5 h, the reaction mixture was evaporated and taken up in ethyl acetate, saturated sodium bicarbonate and sodium chloride solutions. The phases were separated, the aqueous phase was extracted twice more with ethyl acetate. The combined organics were dried over sodium sulfate, filtered and evaporated to give 4-(azidomethyl)-N'-hydroxy-3-methylbenzene-1-carboximidamide as a colorless glass (0.22 g).

Step 4:
4-(Azidomethyl)-N'-hydroxy-3-methylbenzene-1-carboximidamide (0.10 g, 0.49 mmol) was dissolved in acetic acid (5 ml) with palladium on carbon (10%) (31 mg, 0.03 mmol). Acetic anhydride (92 ul, 0.97 mmol) was added and the vessel was charged with H$_2$ gas. After 14 h, the reaction mixture was filtered through Celite and evaporated. The resulting residue was co-evaporated from toluene to give N-[(4-carbamimidoyl-2-methylphenyl)methyl]acetamide as a white solid (0.139 g).

Step 5:

N-[(4-carbamimidoyl-2-methylphenyl)methyl]acetamide (78 mg, 0.27 mmol) was dissolved in isopropanol (3 ml) and 3M HCl (3 ml). The reaction was stirred in a heat block at 90° C. for 5 h, reduced to 65° C. for 16 h and then at 90° C. for 1 h more. The solution was then partly evaporated and freeze-dried to give [4-(azaniumylmethyl)-3-methylphenyl](imino)-methanaminium dichloride as a yellowish solid (65 mg).

Step 6:

The title compound was prepared as in Example 45, Step 8, but substituting 4-(aminomethyl)-3,5-dimethylbenzene-1-carboximidamide with [4-(azaniumylmethyl)-3-methylphenyl](imino)methanaminium dichloride. MS: (M+H)+ found for $C_{30}H_{23}F_2N_3O_2$: 496.4.

Example 49

Synthesis of (1R,8S)-12-(2,4-difluorophenyl)-N-{[4-(N'-methoxycarbamimidoyl)-2-methylphenyl]methyl}-15-oxatetracyclo[6.6.1.0$^{2,7}$.0$^{9,14}$]pentadeca-2,4,6,9,11,13-hexaene-4-carboxamide

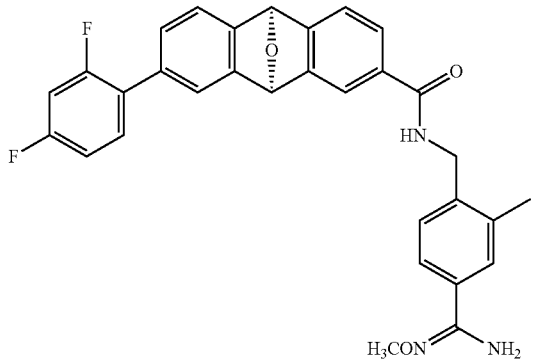

Step 1:

Absolute ethanol (22 ml) was cooled in an ice bath. Acetyl chloride (22 ml, 308 mmol) was added slowly in portions. 4-(Azidomethyl)-3-methylbenzonitrile (Example 48, Step 2; 0.53 g, 3.08 mmol) was added and the reaction sealed and stirred at 4° C. for 72 h. The reaction solution was then evaporated to dryness and co-evaporated from ethanol to a white solid. The solid was dissolved in dry methanol (6 ml), and triethylamine (1.7 ml, 12.3 mmol) and then O-methyl hydroxylamine hydrochloride (0.26 g, 3.08 mmol) were added. After 23 h, the reaction solution was evaporated and taken up in ethyl acetate and water. The phases were separated and the aqueous phase was extracted once with ethyl acetate. The combined organics were washed with a saturated sodium chloride solution and dried over sodium sulfate. Filtration and evaporation gave 4-(azidomethyl)-N'-methoxy-3-methylbenzene-1-carboximidamide as an oil (0.43 g).

Step 2:

Platinum (IV) oxide (71 mg, 0.31 mmol) was combined with 4-(azidomethyl)-N'-methoxy-3-methylbenzene-1-carboximidamide (0.43 g, 1.96 mmol) in ethanol (10 ml). The reaction vessel was charged with $H_2$ gas and stirred for 2 h. The mixture was then filtered through Celite, rinsed with ethanol and evaporated. Co-evaporation from toluene gave 4-(aminomethyl)-N'-methoxy-3-methylbenzene-1-carboximidamide as a colorless oil (0.39 g).

Step 3:

The title compound was prepared as in Example 45, Step 8, but substituting 4-(aminomethyl)-3,5-dimethylbenzene-1-carboximidamide with 4-(aminomethyl)-N'-methoxy-3-methylbenzene-1-carboximidamide. MS: (M+H)+ found for $C_{31}H_{25}F_2N_3O_3$: 526.2.

Example 50

Synthesis of (1R,8S)-12-(2,4-difluorophenyl)-N-{[4-(N'-hydroxycarbamimidoyl)-2-methylphenyl]methyl}-15-oxatetracyclo[6.6.1.0$^{2,7}$.0$^{9,14}$]pentadeca-2,4,6,9,11,13-hexaene-4-carboxamide

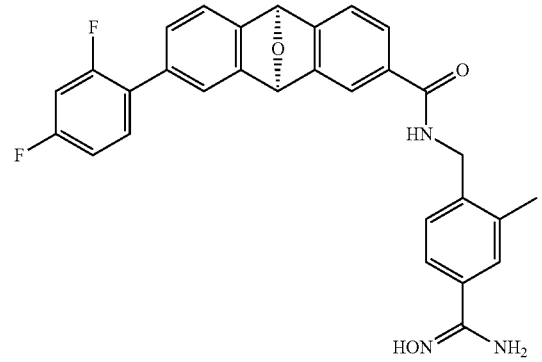

Step 1:

Platinum (IV) oxide (17.7 mg, 0.08 mmol) was combined with 4-(azidomethyl)-N'-hydroxy-3-methylbenzene-1-carboximidamide (Example 48, Step 3; 100 mg, 0.49 mmol) in ethanol (3 ml). The vessel was charged with $H_2$ gas and stirred for 1.5 h. The reaction mixture was then filtered through Celite, rinsed with ethanol, evaporated and co-evaporated from toluene to give 4-(aminomethyl)-N'-hydroxy-3-methylbenzene-1-carboximidamide as a hygroscopic solid. (90 mg). MS (ESI, pos. ion) m/z: 180.0 (M+1).

Step 2:

The title compound was prepared as in Example 44, Step 8, but substituting 4-(aminomethyl)-3,5-dimethylbenzene-1-carboximidamide with 4-(aminomethyl)-N'-hydroxy-3-methylbenzene-1-carboximidamide. MS: (M+H)+ found for $C_{30}H_{23}F_2N_3O_3$: 512.3.

Example 51

Synthesis of (1R,8S)-12-cyclopropyl-N-{[4-(N'-hydroxycarbamimidoyl)phenyl]methyl}-15-oxatetracyclo[6.6.1.0$^{2,7}$.0$^{9,14}$]pentadeca-2,4,6,9,11,13-hexaene-4-carboxamide

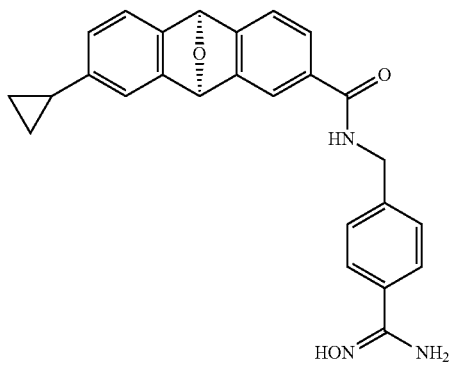

The title compound was prepared as in Example 44, Step 8, but substituting 4-(amino-methyl)-3,5-dimethylbenzene-1-carboximidamide with 4-(aminomethyl)-N'-hydroxybenzene-1-carboximidamide (INT-8), and substituting (1R,8S)-12-(2,4-difluorophenyl)-15-oxatetracyclo-[6.6.1.0$^{2,7}$.0$^{9,14}$]pentadeca-2,4,6,9,11,13-hexaene-4-carboxylic acid with (1R,8S)-12-cyclopropyl-15-oxatetracyclo[6.6.1.0$^{2,7}$.0$^{9,14}$]pentadeca-2,4,6,9,11,13-hexaene-4-carboxylic acid (Example 14, Step 1). MS: (M+H)$^+$ found for $C_{26}H_{23}N_3O_3$: 426.2.

Example 52

Synthesis of (1R,8S)-12-cyclopropyl-N-{[5-(N'-methoxycarbamimidoyl)pyridin-2-yl]-methyl}-15-oxatetracyclo[6.6.1.0$^{2,7}$.0$^{9,14}$]pentadeca-2,4,6,9,11,13-hexaene-4-carboxamide

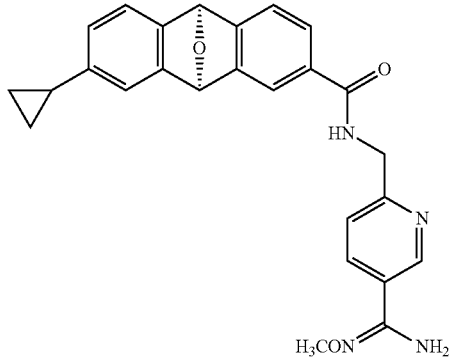

Step 1:
5-Cyano-2-methylpyridine (1.025 g, 8.68 mmol) was dissolved in carbon tetrachloride (50 ml). N-bromosuccinimide (1.7 g, 9.54 mmol) and benzoyl peroxide (75%, 140 mg, 0.43 mmol) were added, and the mixture was heated to reflux in a heat block at 86° C. After 17 h, the reaction was filtered, rinsed with DCM and evaporated. The residue was purified by silica gel chromatography (ethyl acetate/hexanes gradient) to give 6-(bromomethyl)pyridine-3-carbonitrile as a brownish oil (0.69 g, 40%).

Step 2:
Absolute ethanol (30 ml) was cooled in an ice bath. Acetyl chloride (25 ml, 350 mmol) was added slowly in portions. At 0° C., 6-(bromomethyl)pyridine-3-carbonitrile (0.69 g, 3.5 mmol) in ethanol was added. The vessel was sealed and stirred at 4° C. for 65 h. The reaction mixture was evaporated to a slight yellowish solid, a mixture of products which was used directly in the next step.

Step 3:
The crude mixture from Step 2 was dissolved in dry methanol (7 ml) and triethylamine (1 ml), and was cooled in an ice bath. O-methyl hydroxylamine hydrochloride (0.29 g, 3.5 mmol) was added and the reaction was stirred to 25° C. After 15 h, the reaction mixture was evaporated. The residue was taken up in ethyl acetate and water, the phases were separated and the aqueous phase was extracted once with ethyl acetate. The combined organics were washed with a saturated sodium chloride solution, dried over sodium sulfate, filtered and evaporated to a solid. The solid was purified by silica gel chromatography (ethyl acetate/hexanes gradient) to give 6-(chloromethyl)-N'-methoxypyridine-3-carboximidamide as an oily residue (0.07 g, 10%).

Step 4:
6-(Chloromethyl)-N'-methoxypyridine-3-carboximidamide (65 mg; 0.33 mmol) was dissolved in DMF (1 ml). Sodium azide (42 mg, 0.65 mmol) was added and the reaction mixture was stirred at 27° C. After 18 h, the mixture was taken up in ethyl acetate and water. The phases were separated, the aqueous phase was extracted twice more with ethyl acetate, and the combined organics were washed with water and a saturated sodium chloride solution. The solution was dried over sodium sulfate, filtered, and evaporated to give 6-(azidomethyl)-N'-methoxypyridine-3-carboximidamide as a yellowish oil (0.16 g).

Step 5:
Platinum (IV) oxide (12 mg, 0.05 mmol) was combined with 6-(azidomethyl)-N'-methoxypyridine-3-carboximidamide (67 mg, 0.32 mmol) in ethanol (3 ml). The vessel was charged with H$_2$ gas and stirred for 1 h. The mixture was filtered through Celite, rinsed with ethanol and evaporated. Co-evaporation from toluene gave 6-(aminomethyl)-N'-methoxy-pyridine-3-carboximidamide as a brownish oil (60 mg).

Step 6:
The title compound was prepared as in Example 51, but substituting 4-(aminomethyl)-N'-hydroxybenzene-1-carboximidamide with 6-(aminomethyl)-N'-methoxy-pyridine-3-carboximidamide. MS: (M+H)$^+$ found for $C_{26}H_{24}N_4O_3$: 441.2.

Example 53

Synthesis of (1R,8S)—N-[(5-carbamimidoylpyridin-2-yl)methyl]-12-cyclopropyl-15-oxatetracyclo[6.6.1.0$^{2,7}$.0$^{9,14}$]pentadeca-2,4,6,9,11,13-hexaene-4-carboxamide

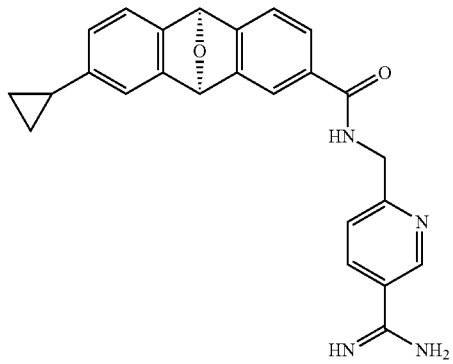 [SMILES: N=C(N)c1ccc(CNC(=O)c2ccc3c(c2)[C@@H]2O[C@H]3c3ccc(C4CC4)cc32)nc1]

413

Step 1:

6-(Bromomethyl)pyridine-3-carbonitrile (680 mg, 3.45 mmol) was dissolved in THF (70 ml). The solution was stirred in an ice bath and sodium hydride (60%, 0.17 g, 4.14 mmol) was added. Di(tert-butyl) imidodicarbonate (0.82 g, 3.8 mmol) was then added in portions and the reaction was stirred to 25° C. After 5 h, the reaction was taken up in ethyl acetate and aqueous sodium bicarbonate solution. The phases were separated and the aqueous phase was extracted once with ethyl acetate. The combined organics were washed with a saturated sodium chloride solution, dried over sodium sulfate, filtered and evaporated. The residue was purified by silica gel chromatography (ethyl acetate/hexanes gradient) to give tert-butyl N-[(tert-butoxy)carbonyl]-N-[(5-cyanopyridin-2-yl)methyl]carbamate (1.2 g).

Step 2:

Tert-butyl N-[(tert-butoxy)carbonyl]-N-[(5-cyanopyridin-2-yl)methyl]carbamate (0.19 g, 0.57 mmol) was dissolved in dry methanol (2 ml). Triethylamine (0.24 ml, 1.7 mmol) and then hydroxylamine hydrochloride (0.12 g, 1.7 mmol) were added. The reaction was stirred in a heat block at 40° C. for 5 h. Solvent was evaporated and the residue was taken up in ethyl acetate and a saturated sodium bicarbonate and sodium chloride solution. The phases were separated, the aqueous phase was extracted twice more with ethyl acetate, the combined organics were washed with a saturated sodium chloride solution and dried over sodium sulfate. After filtration and evaporation, a white solid of tert-butyl N-[(tert-butoxy)carbonyl]-N-{5-(N'-hydroxycarbamimidoyl)pyridin-2-yl]methyl}carbamate was obtained (0.22 g).

Step 3:

Tert-butyl N-[(tert-butoxy)carbonyl]-N-{5-(N'-hydroxycarbamimidoyl)pyridin-2-yl]methyl}carbamate (0.21 g, 0.57 mmol) was dissolved in acetic acid (5 ml) with palladium on carbon (10%) (37 mg, 0.03 mmol). Acetic anhydride (108 ul, 1.15 mmol) was added and the vessel was charged with $H_2$ gas. After 4 h, the mixture was purged with $N_2$ gas, filtered through Celite, rinsed with ethyl acetate and evaporated to give tert-butyl N-[(tert-butoxy)carbonyl]-N-[(5-carbamimidoylpyridin-2-yl)methyl]carbamate (0.45 g), which was used directly in the next step.

Step 4:

Tert-butyl N-[(tert-butoxy)carbonyl]-N-[(5-carbamimidoylpyridin-2-yl)methyl]-carbamate (0.20 g, 0.57 mmol) was mixed with hydrochloric acid (1.4 ml, 4 M 1,4-dioxane solution, 5.7 mmol). The mixture was diluted with DCM (1.5 ml) and more 4M HCl/dioxane (1.5 ml). After stirring for 1.5 h, the reaction was evaporated, and co-evaporated from toluene, leaving an off-white solid of [6-(azaniumylmethyl)pyridin-3-yl](imino)methanaminium dichloride (0.15 g). MS (ESI, pos. ion) m/z: 150.9 (M+1).

Step 5:

The title compound was prepared as in Example 51, but substituting 4-(aminomethyl)-N'-hydroxybenzene-1-carboximidamide with [6-(azaniumylmethyl)pyridin-3-yl](imino)methanaminium dichloride. MS: (M+H)⁺ found for $C_{25}H_{22}N_4O_2$: 411.2.

414

Example 54

Synthesis of (1R,8S)-12-(2,4-difluorophenyl)-N-{[4-(N'-methoxycarbamimidoyl)-2,6-dimethylphenyl]methyl}-15-oxatetracyclo[6.6.1.0²,⁷.0⁹,¹⁴]pentadeca-2,4,6,9,11,13-hexaene-4-carboxamide

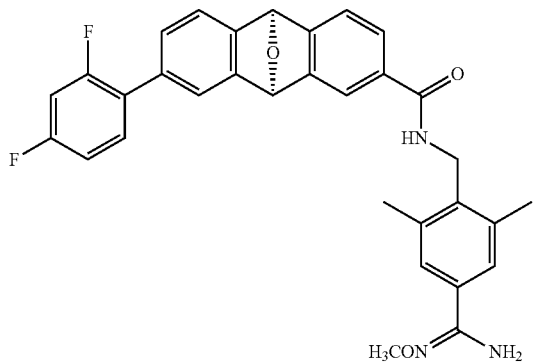

Step 1:

Into a 1-L round-bottom flask, was placed a mixture of 4-bromo-3,5-dimethylbenzonitrile (10.00 g, 47.62 mmol, 1.00 equiv), dioxane (400 mL), water (40 mL), $Cs_2CO_3$ (62.06 g, 190.48 mmol, 4.00 equiv), potassium tert-butyl N-[(difluoroboranyl)methyl]carbamate fluoride (22.57 g, 95.24 mmol, 2.00 equiv) and (2-dicyclohexylphosphino-2',4',6'-triisopropyl-1,1'-biphenyl)[2-(2'-amino-1,1'-biphenyl)]palladium(II) methanesulfonate (3rd generation XPhos pre-catalyst; 2.01 g, 2.381 mmol, 0.05 equiv). The resulting solution was stirred for 16 h at 110° C. under nitrogen then it was cooled to RT and concentrated. The residue was diluted with 500 mL of EtOAc, washed with brine, dried over anhydrous sodium sulfate and concentrated under vacuum. The residue was purified by silica gel column chromatography eluting with acetate/petroleum ether (1/4) to afford 10.70 g (86%) of tert-butyl N-[(4-cyano-2,6-dimethylphenyl)methyl]carbamate as an off-white solid.

Step 2:

Into a 500-mL round-bottom flask, was placed a mixture of tert-butyl N-[(4-cyano-2,6-dimethylphenyl)methyl]carbamate (3.50 g, 13.46 mmol, 1.00 equiv), ethanol (200 mL), TEA (6.80 g, 67.30 mmol, 5.00 equiv), O-methylhydroxylamine hydrochloride (5.59 g, 67.30 mmol, 5.00 equiv) and 2-sulfanylacetic acid (3.10 g, 33.65 mmol, 2.50 equiv). The resulting mixture was stirred for 2 days at 90° C. then it was cooled and concentrated under vacuum. The residue was diluted with 100 mL of EtOAc, washed with brine, dried over anhydrous sodium sulfate and concentrated under vacuum. The residue was purified by silica gel column chromatography eluting with ethyl acetate/petroleum ether (1/4) to afford 1.81 g (44%) of tert-butyl N-([4-N-methoxycarbamimidoyl]-2,6-dimethylphenyl]methyl)-carbamate as a light yellow solid.

Step 3:

Into a 50-mL round-bottom flask, was placed a solution of tert-butyl N-([4-[N-methoxycarbamimidoyl]-2,6-dimethylphenyl]methyl)carbamate (1.50 g, 4.88 mmol, 1.00 equiv) in dichloromethane (20 mL) followed by dioxane (5 mL) which was freshly saturated with hydrochloride (gas). The resulting mixture was stirred for 16 h at room temperature then the solids were collected by filtration to afford 1.08 g (79%) of 4-(aminomethyl)-N-methoxy-3,5-dimethylbenzene-1-carboximidamide hydrochloride as an off-white solid.

Step 4:

The title compound was prepared as in Example 45, Step 8, but substituting 4-(aminomethyl)-3,5-dimethylbenzene-1-carboximidamide with 4-(aminomethyl)-N-methoxy-3,5-dimethylbenzene-1-carboximidamide hydrochloride.

Example 55

Synthesis of (1R,8S)-12-cyclopropyl-N-{[4-(N'-methoxycarbamimidoyl)-2,6-dimethylphenyl]-methyl}-15-oxatetracyclo[6.6.1.0$^{2,7}$.0$^{9,14}$]pentadeca-2,4,6,9,11,13-hexaene-4-carboxamide

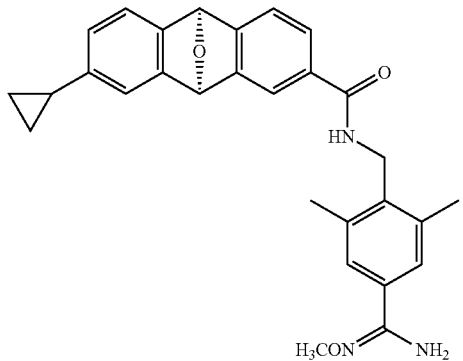

The title compound was prepared as in Example 51, but substituting 4-(amino-methyl)-N'-hydroxybenzene-1-carboximidamide with 4-(aminomethyl)-N-methoxy-3,5-dimethylbenzene-1-carboximidamide hydrochloride (Example 54, Steps 1-3). MS: (M+H)$^+$ found for $C_{29}H_{29}N_3O_3$: 468.5.

Example 56

Synthesis of (1R,8S)—N-[(4-carbamimidoyl-2,6-dimethylphenyl)methyl]-12-cyclopropyl-15-oxatetracyclo[6.6.1.0$^{2,7}$.0$^{9,14}$]pentadeca-2,4,6,9,11,13-hexaene-4-carboxamide

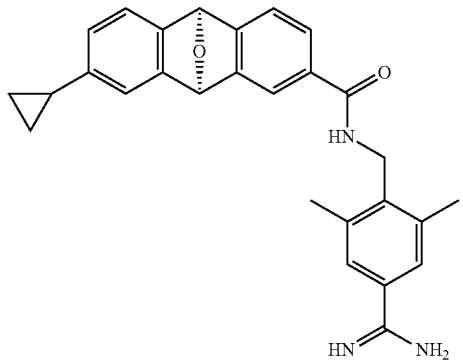 [SMILES: Cc1cc(C(=N)N)cc(C)c1CNC(=O)c1ccc2c(c1)[C@@H]1O[C@H]2c2ccc(C3CC3)cc21]

The title compound was prepared as in Example 351, but substituting 4-(amino-methyl)-N'-hydroxybenzene-1-carboximidamide with [4-(azaniumylmethyl)-3,5-dimethylphenyl](imino)methanaminium dichloride (Example 45, Step 1-6). MS: (M+H)$^+$ found for $C_{28}H_{27}N_3O_2$: 438.2.

Example 57

Synthesis of (1R,8S)—N-[(6-amino-2,4-dimethylpyridin-3-yl)methyl]-12-(4-chloro-2-cyanophenyl)-15-oxatetracyclo[6.6.1.0$^{2,7}$.0$^{9,14}$]pentadeca-2,4,6,9,11,13-hexaene-4-carboxamide

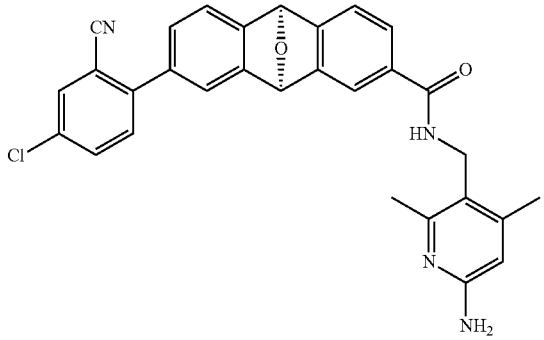 [SMILES: Cc1cc(N)nc(C)c1CNC(=O)c1ccc2c(c1)[C@@H]1O[C@H]2c2ccc(-c3ccc(Cl)cc3C#N)cc21]

Step 1:

A stirred suspension of methyl (1S,8R)-12-bromo-15-oxatetracyclo-[6.6.1.0$^{2,7}$.0$^{9,14}$]pentadeca-2,4,6,9,11,13-hexaene-4-carboxylate (85.00 mg; 0.26 mmol), (4-chloro-2-cyanophenyl)boronic acid (55.87 mg; 0.31 mmol), cesium carbonate (209.07 mg; 0.64 mmol) and 1,1'-bis(diphenylphosphino)ferrocene]dichloropalladium(II) (18.78 mg; 0.03 mmol) in 1,4-dioxane (10.27 ml) and methanol (2.85 ml) was heated to 80° C. for 1 h. The reacting mixture was cooled to ambient temperature, filtered over celite and concentrated. The brown residue was purified by flash chromatography (Hexanes/EtOAc=3:1) to provide methyl (1R,8S)-12-(4-chloro-2-cyanophenyl)-15-oxatetracyclo [6.6.1.0$^{2,7}$.0$^{9,14}$]pentadeca-2,4,6,9,11,13-hexaene-4-carboxylate as a colorless foam (80 mg).

Step 2:

To a stirred solution of methyl (1R,8S)-12-(4-chloro-2-cyanophenyl)-15-oxatetracyclo[6.6.1.0$^{2,7}$.0$^{9,14}$]pentadeca-2,4,6,9,11,13-hexaene-4-carboxylate (80.00 mg; 0.21 mmol) in tetrahydrofuran (2.40 ml) and methanol (1.20 ml) was added lithium hydroxide (0.52 ml; 2.00 mol/l). The mixture was stirred at ambient temperature for 4 h. The solvent was removed under vacuum and the residue was taken in small amounts of water. The solution was acidified with 3N HCl and extracted 3 times with EtOAc. The combined organics were dried over MgSO$_4$, filtered and concentrated. The crude (1R,8S)-12-(4-chloro-2-cyanophenyl)-15-oxatetracyclo[6.6.1.0$^{2,7}$.0$^{9,14}$]pentadeca-2,4,6,9,11,13-hexaene-4-carboxylic acid was used in the next step without further purification.

Step 3:

To a stirred solution of (1R,8S)-12-(4-chloro-2-cyanophenyl)-15-oxatetracyclo-[6.6.1.0$^{2,7}$.0$^{9,14}$]pentadeca-2,4,6,9, 11,13-hexaene-4-carboxylic acid (53.00 mg; 0.14 mmol) and 5-(aminomethyl)-4,6-dimethylpyridin-2-amine (34.96 mg; 0.16 mmol) in N,N-dimethylformamide (1.42 ml) at ambient temperature was added diisopropylethylamine (0.25 ml; 1.42 mmol) followed by HATU (53.91 mg; 0.14 mmol). The reaction mix was concentrated to dryness, then dissolved in water/acetonitrile and purified by prep HPLC.

Example 58

Synthesis of (1R,8S)—N-[(1-aminoisoquinolin-5-yl)methyl]-12-(2-fluorophenyl)-5-oxatetra-cyclo[6.6.1.0$^{2,7}$.0$^{9,14}$]pentadeca-2,4,6,9,11,13-hexaene-4-carboxamide

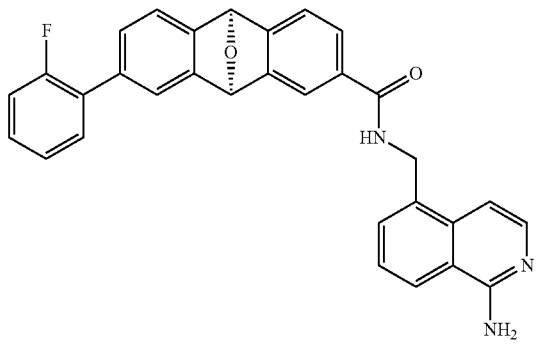 [SMILES: Nc1nccc2c(CNC(=O)c3ccc4c(c3)[C@@H]3O[C@H]4c4ccc(-c5ccccc5F)cc43)cccc12]

Step 1:

Into a 500-mL round-bottom flask purged and maintained with an inert atmosphere of nitrogen, was placed a solution of 5-bromoisoquinoline (15.3 g, 73.54 mmol, 1.00 equiv) in dichloromethane (300 mL), then 3-chlorobenzene-1-carboperoxoic acid (m-CPBA; 17.4 g, 80%/W, 80.89 mmol, 1.10 equiv) was added in portions. The resulting solution was stirred overnight at 45° C. The reaction was then cooled to RT, quenched by the addition of 200 mL of saturated aqueous $Na_2S_2O_3$ solution and the separated water layer was extracted with dichloromethane. The combined organic layer was washed with 2N aqueous sodium hydroxide aqueous solution, 200 mL of brine, dried over anhydrous sodium sulfate and concentrated under vacuum to deliver 16.5 g (100%) of 5-bromoisoquinolin-2-ium-2-olate as a yellow solid.

Step 2:

Into a 500-mL round-bottom flask purged and maintained with an inert atmosphere of nitrogen, was placed a solution of 5-bromoisoquinolin-2-ium-2-olate (16.5 g, 73.64 mmol, 1.00 equiv) and $POCl_3$ (27.1 g, 176.74 mmol, 2.40 equiv) in dichloromethane (300 mL). The resulting mixture was stirred overnight at 45° C. then it was cooled to RT and concentrated. The residue was treated cautiously with 500 mL of icy water and extracted with 3×500 mL of dichloromethane. The combined organic layer was washed with 500 mL of saturated sodium bicarbonate aqueous solution, 500 mL of brine, dried over anhydrous sodium sulfate and concentrated under vacuum to deliver 17.5 g (98%) of 5-bromo-1-chloroisoquinoline as a yellow solid.

Step 3:

Into a 500-mL round-bottom flask purged and maintained with an inert atmosphere of nitrogen, was placed a mixture of 5-bromo-1-chloroisoquinoline (17.5 g, 72.16 mmol, 1.00 equiv), $AcNH_2$ (85.8 g, 1.45 mol, 20.15 equiv) and potassium carbonate (49.0 g, 354.53 mmol, 4.91 equiv). The mixture was stirred for 3 h at 180° C. then it was cooled to RT and poured into 2000 mL of water with stirring. The solids were collected by filtration to provide 12.0 g (75%) of 5-bromoisoquinolin-1-amine as a brown solid.

Step 4:

Into a 250-mL round-bottom flask purged and maintained with an inert atmosphere of nitrogen, was placed a mixture of 5-bromoisoquinolin-1-amine (8.20 g, 36.76 mmol, 1.00 equiv), N,N-dimethylformamide (120 mL), $Zn(CN)_2$ (8.60 g, 73.50 mmol, 2.00 equiv) and $Pd(PPh_3)_4$ (8.30 g, 7.18 mmol, 0.20 equiv). The resulting mixture was stirred overnight at 130° C. The solids were separated by filtration and the filtrate was concentrated under vacuum. The residue was purified by silica gel column chromatography eluting with ethyl acetate/petroleum ether (1/1) to afford 9.40 g of 1-aminoisoquinoline-5-carbonitrile as a red solid.

Step 5:

Into a 250-mL round-bottom flask, was placed a mixture of 1-aminoisoquinoline-5-carbonitrile (3.3 g, 19.51 mmol, 1.00 equiv), methanol (100 mL), $NH_3.H_2O$ (20.0 mL) and Raney-Ni (5.60 g). The mixture was degassed, purged with $H_2$ 5 times and stirred overnight at room temperature under an atmosphere of $H_2$. After filtration through a pad of Celite, the filtrate was concentrated under vacuum to deliver 3.39 g (100%, crude) of 5-(aminomethyl)isoquinolin-1-amine as brown oil.

Step 6:

Into a 250-mL round-bottom flask, was placed a solution of 5-(aminomethyl)isoquinolin-1-amine (3.40 g, 19.63 mmol, 1.00 equiv), MeOH (100 mL) and $Boc_2O$ (5.10 g, 23.37 mmol, 1.20 equiv). The mixture was stirred for 0.5 h at room temperature. After the concentration, the residue was purified by silica gel column chromatography eluting with dichloromethane/methanol (20/1) to afford 4.70 g (88%) of tert-butyl N-[(1-aminoisoquinolin-5-yl)methyl]carbamate as a light yellow solid.

Step 7:

Into a 100-mL 3-necked round-bottom flask, was placed a solution of tert-butyl N-[(1-aminoisoquinolin-5-yl)methyl]carbamate (4.7 g, 17.20 mmol, 1.00 equiv) in dichloromethane (50 mL) with stirring at 0° C. The solution was then sparged with HCl (gas) to saturation and the resulting mixture was stirred for 1 h at 0° C. The solids were collected by filtration to provide 5.20 g of 5-(aminomethyl)isoquinolin-1-amine hydrochloride as a yellow solid.

Step 8:

To a stirred solution of (1R,8S)-12-(2-fluorophenyl)-15-oxatetracyclo-[6.6.1.0$^{2,7}$.0$^{9,14}$]pentadeca-2,4,6,9,11,13-hexaene-4-carboxylic acid (Example 44, Step 1; 60.00 mg; 0.18 mmol) and 5-(aminomethyl)isoquinolin-1-amine hydrochloride (37.86 mg; 0.18 mmol) in N,N-dimethylformamide (1.81 ml) was added diisopropylethylamine (0.32 ml; 1.81 mmol) followed by HATU (68.65 mg; 0.18 mmol) and the resulting mix was stirred at ambient temperature for 30 min. The reaction mix was concentrated and the residue was taken in acetonitrile/water and purified by prep HPLC. The fractions containing the product were partially concentrated, freeze and lyophilized to give the title compound (49.6 mg). MS: (M+H)$^+$ found for $C_{31}H_{22}FN_3O_2$: 488.1.

Example 59

Synthesis of (1R,8S)—N-[(4-carbamimidoylphenyl)methyl]-12-(4-fluorophenyl)-15-oxatetra-cyclo-[6.6.1.0$^{2,7}$.0$^{9,14}$]pentadeca-2,4,6,9,11,13-hexaene-4-carboxamide

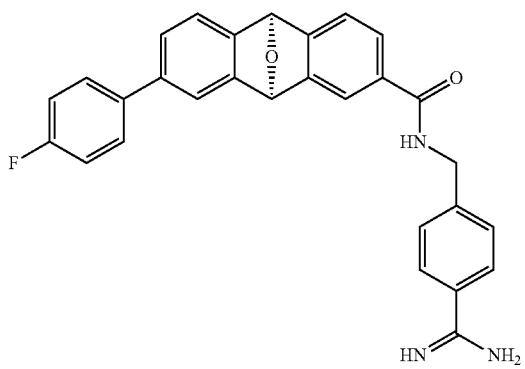

Step 1:

A stirred suspension of sodium (1S,8R)-12-bromo-15-oxatetracyclo-[6.6.1.0$^{2,7}$.0$^{9,14}$]-pentadeca-2,4,6,9,11,13-hexaene-4-carboxylate (120.00 mg; 0.35 mmol), 4-fluorophenylboronic acid (54.46 mg; 0.39 mmol), sodium carbonate (0.53 ml; 2.00 mol/l) and 1,1'-bis(diphenylphosphino)ferrocene]dichloropalladium(II) (25.89 mg; 0.04 mmol) in 1,2-dimethoxyethane (1.20 ml) was purged with nitrogen and the vial was sealed and heated to 80° C. for 60 min. The reacting mixture was cooled to r.t., filtered and concentrated. The brown residue was dissolved/suspended in water and acidified with 3N HCl. The aqueous layer was extracted three times with EtOAc and the combined organics were dried over Na$_2$SO$_4$, filtered and concentrated. The corresponding (1R,8S)-12-(4-fluorophenyl)-15-oxatetracyclo-[6.6.1.0$^{2,7}$.0$^{9,14}$]-pentadeca-2,4,6,9,11,13-hexaene-4-carboxylic acid was used in the next step without further purification.

Step 2:

To a stirred solution of (1R,8S)-12-(4-fluorophenyl)-15-oxatetracyclo-[6.6.1.0$^{2,7}$.0$^{9,14}$]pentadeca-2,4,6,9,11,13-hexaene-4-carboxylic acid (50.00 mg; 0.15 mmol) and 4-(aminomethyl)benzene-1-carboximidamide (36.76 mg; 0.17 mmol) in N,N-dimethylformamide (1.50 ml) at r.t. was added diisopropylethylamine (0.26 ml; 1.50 mmol) followed by HATU (57.21 mg; 0.15 mmol) and the reaction mixture was stirred at ambient temperature for 15 min. The reaction mixture was concentrated and the residue was taken in acetonitrile/water and purified by prep HPLC. The fractions containing the product were partially concentrated, freeze and lyophilized to give the title compound (70 mg). MS: (M+H)$^+$ found for C$_{29}$H$_{22}$FN$_3$O$_2$: 464.1.

Example 60

Synthesis of (1R,8S)—N-[(1-aminoisoquinolin-5-yl)methyl]-12-(2-cyano-4-methylphenyl)-15-oxatetracyclo[6.6.1.0$^{2,7}$.0$^{9,14}$]pentadeca-2,4,6,9,11,13-hexaene-4-carboxamide

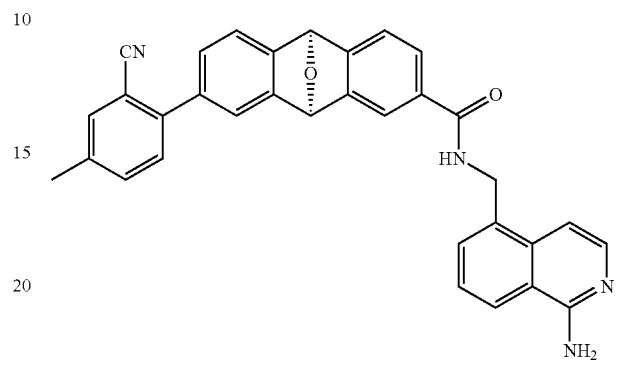

Step 1:

A stirred suspension of sodium (1S,8R)-12-bromo-15-oxatetracyclo-[6.6.1.0$^{2,7}$.0$^{9,14}$]-pentadeca-2,4,6,9,11,13-hexaene-4-carboxylate (70.00 mg; 0.21 mmol), 5-methyl-2-(4,4,5,5-tetramethyl-1,3,2-dioxaborolan-2-yl)benzonitrile (60.22 mg; 0.25 mmol), cesium carbonate (168.14 mg; 0.52 mmol) and 1,1'-bis(diphenylphosphino)ferrocene]dichloropalladium(II) (15.10 mg; 0.02 mmol) in 1,4-dioxane (8.26 ml) and methanol (2.29 ml) was stirred at ambient temperature for 1 h. The reacting mixture was filtered and concentrated. The crude was dissolved in 1 ml of water, acidified with 3N HCl and extracted 3 times with EtOAc. The combined organics were dried over Na$_2$SO$_4$, filtered and concentrated. The crude (1R,8S)-12-(2-cyano-4-methylphenyl)-15-oxatetracyclo[6.6.1.0$^{2,7}$.0$^{9,14}$]pentadeca-2,4,6,9,11,13-hexaene-4-carboxylic acid was used in the next step without further purification.

Step 2:

To a stirred solution of (1R,8S)-12-(2-cyano-4-methylphenyl)-15-oxatetracyclo[6.6.1.0$^{2,7}$.0$^{9,14}$]pentadeca-2,4,6,9,11,13-hexaene-4-carboxylic acid (50.00 mg; 0.14 mmol) and 5-(aminomethyl)isoquinolin-1-amine hydrochloride (29.67 mg; 0.14 mmol) in N,N-dimethylformamide (1.41 ml) at r.t. was added diisopropylethylamine (0.25 ml; 1.41 mmol) followed by HATU (53.80 mg; 0.14 mmol) and the mix was left stirring at ambient temperature for 30 min. The reaction mix was concentrated and the residue was taken in acetonitrile/water and purified by prep HPLC. The fractions containing the product were partially concentrated, freeze and lyophilized to give the title compound (72 mg). MS: (M+H)$^+$ found for C$_{33}$H$_{24}$N$_4$O$_2$: 509.0.

421

Example 61

Synthesis of (1S,8R)—N-[(4-carbamimidoylphenyl)methyl]-12-(5-chlorothiophen-2-yl)-15-oxatetracyclo[6.6.1.0$^{2,7}$.0$^{9,14}$]pentadeca-2,4,6,9,11,13-hexaene-4-carboxamide

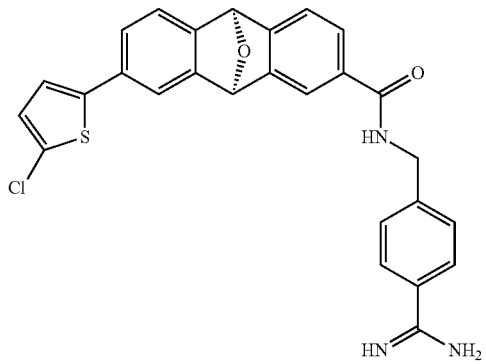 [SMILES: N=C(N)c1ccc(CNC(=O)c2ccc3c(c2)[C@@H]2O[C@H]3c3ccc(-c4ccc(Cl)s4)cc32)cc1]

Step 1:

A suspension of sodium (1S,8R)-12-bromo-15-oxatetracyclo-[6.6.1.0$^{2,7}$.0$^{9,14}$]-pentadeca-2,4,6,9,11,13-hexaene-4-carboxylate (70.00 mg; 0.21 mmol), (5-chlorothiophen-2-yl)boronic acid (40.23 mg; 0.25 mmol), sodium carbonate (0.52 ml; 2.00 mol/l; 1.03 mmol) in 1,2-dimethoxyethane (2.10 ml) was purged with nitrogen. 1,1'-bis(diphenylphosphino)ferrocene]dichloropalladium(II) (15.10 mg; 0.02 mmol) was added to the mixture and the vessel purged once again with nitrogen. The vial was sealed and heated to 80° C. for 90 min. The reacting mixture was cooled to r.t., filtered and concentrated. The crude was dissolved in 1 ml of water, acidified with 3N HCl and extracted 3 times with EtOAc. The combined organics were dried over Na$_2$SO$_4$, filtered and concentrated to give crude (1S,8R)-12-(5-chlorothiophen-2-yl)-15-oxatetracyclo[6.6.1.0$^{2,7}$.0$^{9,14}$]pentadeca-2,4,6,9,11,13-hexaene-4-carboxylic acid which was used in the next step without further purification.

Step 2:

To a stirred solution of (1S,8R)-12-(5-chlorothiophen-2-yl)-15-oxatetracyclo-[6.6.1.0$^{2,7}$.0$^{9,14}$]pentadeca-2,4,6,9,11,13-hexaene-4-carboxylic acid (70.00 mg; 0.20 mmol) and 4-(aminomethyl)benzenecarboximidamide dihydrochloride (48.20 mg; 0.22 mmol) in N,N-dimethylformamide (1.97 ml) was added diisopropylethylamine (0.34 ml; 1.97 mmol) followed by HATU (75.02 mg; 0.20 mmol) and the reaction mix stirred for 15 min at ambient temperature. The reaction mix was concentrated and the residue was taken in acetonitrile/water and purified by prep HPLC. The fractions containing the product were partially concentrated, freeze and lyophilized to give the title compound (24 mg). MS: (M+H)$^+$ found for C$_{27}$H$_{20}$ClN$_3$O$_2$S: 486.

422

Example 62

Synthesis of (1S,8R)—N-[(4-carbamimidoylphenyl)methyl]-12-(3-fluorophenoxy)-15-oxatetra-cyclo[6.6.1.0$^{2,7}$.0$^{9,14}$]pentadeca-2,4,6,9,11,13-hexaene-4-carboxamide

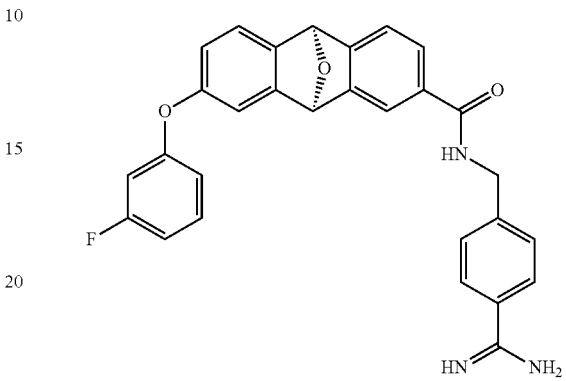

Step 1:

A flask containing a mixture of (1S,8R)-12-bromo-15-oxatetracyclo-[6.6.1.0$^{2,7}$.0$^{9,14}$]-pentadeca-2,4,6,9,11,13-hexaene-4-carboxylic acid (110.00 mg; 0.35 mmol), 3-fluorophenol (0.04 ml; 0.45 mmol), copper (I) bromide (7.46 mg; 0.05 mmol), 2,4-pentanedione (0.01 ml; 0.07 mmol) and potassium carbonate (62.23 mg; 0.45 mmol) in N,N-dimethylformamide (1.16 ml) was evacuated and back-filled with Argon and the mixture was heated to 130° C. for 48 h. The mixture was allowed to reach RT, and was directly injected onto a silica gel column for purification by flash chromatography (Hexanes/EtOAc=1:1, then DCM/MeOH=90:10) to give the corresponding (1S,8R)-12-(3-fluorophenoxy)-15-oxatetracyclo[6.6.1.0$^{2,7}$.0$^{9,14}$]pentadeca-2,4,6,9,11,13-hexaene-4-carboxylic acid (25 mg).

Step 2:

To a stirred solution of (1S,8R)-12-(3-fluorophenoxy)-15-oxatetracyclo[6.6.1.0$^{2,7}$.0$^{9,14}$]pentadeca-2,4,6,9,11,13-hexaene-4-carboxylic acid (25.00 mg; 0.07 mmol) and 4-(aminomethyl)benzene-1-carboximidamide dihydrochloride (17.54 mg; 0.08 mmol) in N,N-dimethylformamide (0.72 ml) at r.t. was added diisopropylethylamine (0.13 ml; 0.72 mmol) followed by HATU (27.29 mg; 0.07 mmol) and the reaction mix was stirred at ambient temperature for 15 minutes. The reaction mix was concentrated and the residue was taken in acetonitrile/water and purified by prep HPLC. The fractions containing the product were partially concentrated, freeze and lyophilized to give the title compound (13.7 mg). MS: (M+H)$^+$ found for C$_{29}$H$_{22}$FN$_3$O$_3$: 480.1.

Example 63

Synthesis of (1S,8R)-12-(5-chlorothiophen-2-yl)-N-{[4-(N'-hydroxycarbamimidoyl)phenyl]-methyl}-15-oxatetracyclo[6.6.1.0²,⁷.0⁹,¹⁴]pentadeca-2,4,6,9,11,13-hexaene-4-carboxamide

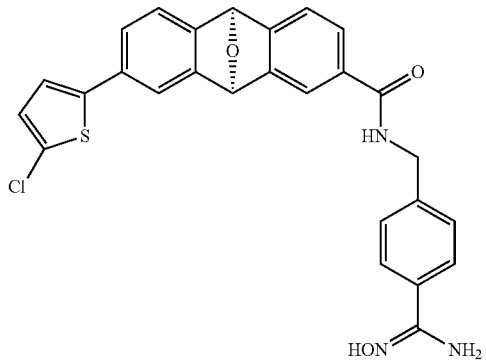

Step 1:

A suspension of sodium (1S,8R)-12-bromo-15-oxatetracyclo-[6.6.1.0²,⁷.0⁹,¹⁴]-pentadeca-2,4,6,9,11,13-hexaene-4-carboxylate, INT-5a1 (400.00 mg; 1.18 mmol), (5-chlorothiophen-2-yl)boronic acid (229.87 mg; 1.42 mmol), sodium carbonate (2.95 ml; 2.00 mol/l) in 1,2-dimethoxyethane (12.00 ml) was purged with nitrogen. 1,1'-bis(diphenylphosphino)-ferrocene]dichloropalladium(II) (86.31 mg; 0.12 mmol) was added to the reaction mix and the vessel purged once again with nitrogen. The vial was sealed and heated to 80° C. for 90 min. Additional 1.2 equivalents (5-chlorothiophen-2-yl)boronic acid were added, followed by bis(diphenylphosphino)ferrocene]dichloropalladium(II). After 1 h reaction was cooled to ambient temperature and concentrated. The crude was suspended in water, treated with 3N HCl and extracted with EtOAc. The combined organics were washed with brine and dried over Na$_2$SO$_4$. The crude (1S,8R)-12-(5-chlorothiophen-2-yl)-15-oxatetracyclo[6.6.1.0²,⁷.0⁹,¹⁴]-pentadeca-2,4,6,9,11,13-hexaene-4-carboxylic acid was used in the next step without further purification.

Step 2:

(1S,8R)-12-(5-Chlorothiophen-2-yl)-15-oxatetracyclo[6.6.1.0²,⁷.0⁹,¹⁴]-pentadeca-2,4,6,9,11,13-hexaene-4-carboxylic acid (65.00 mg; 0.18 mmol) was dissolved in N,N-dimethylformamide (1.10 ml). Diisopropylethylamine (0.25 ml; 1.47 mmol) was added to the solution followed by hydroxybenzotriazole (37.13 mg; 0.27 mmol) and N-[3-(dimethylamino)propyl]-N'-ethylcarbodiimide hydrochloride (70.24 mg; 0.37 mmol) and the reaction mix was stirred for 10 min. A solution of 4-(aminomethyl)-N'-hydroxybenzene-1-carboximidamide (INT-8) (50.17 mg; 0.21 mmol) in 1 ml of DMF which was pretreated with 2.5 eq of diisopropylethylamine was added to the reaction flask and the reaction mix was stirred for 2 h. The solvent was removed under vacuum and the residue was taken in DMSO and acetonitrile. The solids in suspension were removed by filtration and the crude filtrate purified by prep HPLC. The fractions containing the product were partially concentrated freeze and lyophilized to give the title compound (21.4 mg). MS: (M+H)$^+$ found for $C_{27}H_{20}ClN_3O_3S$: 502.

Example 64

Synthesis of (1R,8S)—N-[(4-carbamimidoyl-2-fluorophenyl)methyl]-12-(2-fluorophenyl)-15-oxatetracyclo[6.6.1.0²,⁷.0⁹,¹⁴]pentadeca-2,4,6,9,11,13-hexaene-4-carboxamide

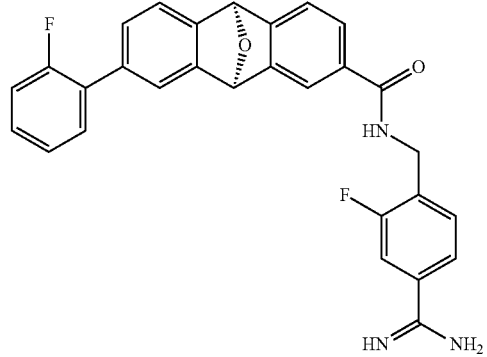 [SMILES: N=C(N)c1ccc(CNC(=O)c2ccc3c(c2)[C@@H]2O[C@H]3c3ccc(-c4ccccc4F)cc32)c(F)c1]

Step 1:

To a cooled solution of 4-(bromomethyl)-3-fluorobenzonitrile (4.00 g; 18.69 mmol in tetrahydrofuran (400.00 ml) was added sodium hydride (0.90 g; 22.43 mmol). Tert-butyl N-[(tert-butoxy)carbonyl]carbamate (4.47 g; 20.56 mmol) was added portion wise and the reaction mixture was stirred for 5 h. It was then diluted with EtOAc, washed with water and brine and dried over Na$_2$SO$_4$. The crude was purified by flash chromatography (Heptane/EtOAc=3:1) to give tert-butyl N-[(tert-butoxy)carbonyl]-N-[(4-cyano-2-fluorophenyl)methyl]carbamate (4.1 g).

Step 2:

To a solution of tert-butyl N-[(tert-butoxy)carbonyl]-N-[(4-cyano-2-fluoro-phenyl)methyl]carbamate (3.00 g; 8.56 mmol) in methanol (30.00 ml) was added hydroxylamine hydrochloride (0.89 g; 12.84 mmol) and diisopropylethylamine (2.24 ml; 12.84 mmol). The mixture was stirred at RT until complete dissolution and then heated under reflux for 16 h. The solvent was removed under vacuum and the residue was partitioned in EtOAc/water. The organic layer was isolated and washed with NaHCO$_3$ solution and brine and dried over Na$_2$SO$_4$ before being evaporated under reduced pressure to give tert-butyl N-[(tert-butoxy)carbonyl]-N-{[2-fluoro-4-(N'-hydroxycarbamimidoyl)phenyl]methyl}-carbamate (3.1 g) which was used in the next step without further purification.

Step 3:

To a solution of tert-butyl N-[(tert-butoxy)carbonyl]-N-{[2-fluoro-4-(N'-hydroxycarbamimidoyl)phenyl]methyl}carbamate (1.0 g; 2.61 mmol) in acetic acid (70.00 ml) was added acetic anhydride (0.26 ml; 2.74 mmol) followed by palladium on carbon (Pd/C) (277.56 mg; 0.26 mmol) and the mix was hydrogenated at 65 psi for 3 h. The catalyst was removed by filtration over celite and the filtrate was concentrated to give tert-butyl N-[(tert-butoxy)carbonyl]-N-[(4-carbamimidoyl-2-fluorophenyl)methyl]carbamate (870 mg) which was used in the next step without further purification.

Step 4:

4 N Hydrochloric acid (4.63 ml; 4.00 mol/l; 18.51 mmol) in dioxane was added to a suspension of tert-butyl N-[(tert-butoxy)carbonyl]-N-[(4-carbamimidoyl-2-fluorophenyl)-methyl]carbamate (850.00 mg; 2.31 mmol) and the reaction mixture was stirred at RT for 5 h. The solvent was partially removed under vacuum and the solid 4-(aminomethyl)-3-fluorobenzene-1-carboximidamide dihydrochloride that appeared was removed by filtration and dried overnight under high vacuum (420 mg).

Step 5:

(1R,8S)-12-(2-fluorophenyl)-15-oxatetracyclo[6.6.1.0$^{2,7}$.0$^{9,14}$]pentadeca-2,4,6,9,11,13-hexaene-4-carboxylic acid (Example 44, Step 1; 70.00 mg; 0.21 mmol) and 4-(aminomethyl)-3-fluorobenzene-1-carboximidamide dihydrochloride (55.63 mg; 0.23 mmol) were dissolved in N,N-dimethylformamide (0.70 ml) and the reaction mixture was cooled to −78° C. HATU (88.10 mg; 0.23 mmol) was added to the mixture followed by diisopropylethylamine (0.15 ml; 0.84 mmol) and after 5 minutes the reaction flask was removed from the bath and stirred for 20 min. The reaction mixture was cooled in an ice bath and water was added drop wise to it. The precipitate was removed by filtration and the solid was dissolved in DMSO and purified on the prep HPLC. The fractions containing the product were partially concentrated, freeze and lyophilized to give the title compound (57.3 mg). MS: (M+H)$^+$ found for $C_{30}H_{23}F_2N_3O_3$: 482.1.

Example 65

Synthesis of (1R,8S)—N-[(4-carbamimidoyl-2-fluorophenyl)methyl]-12-(2,4-difluorophenyl)-15-oxatetracyclo[6.6.1.0$^{2,7}$.0$^{9,14}$]pentadeca-2,4,6,9,11,13-hexaene-4-carboxamide

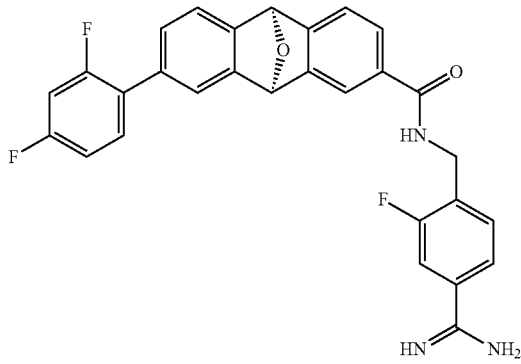 [SMILES: N=C(N)c1ccc(CNC(=O)c2ccc3c(c2)[C@@H]2O[C@H]3c3ccc(-c4ccc(F)cc4F)cc32)c(F)c1]

(1R,8S)-12-(2,4-Difluorophenyl)-15-oxatetracyclo[6.6.1.0$^{2,7}$.0$^{9,14}$]pentadeca-2,4,6,9,11,13-hexaene-4-carboxylic acid (Example 7, Steps 1-2; 70.00 mg; 0.20 mmol) and 4-(aminomethyl)-3-fluorobenzene-1-carboximidamide dihydrochloride (Example 64, Step 1-4; 57.57 mg; 0.24 mmol) were dissolved in N,N-dimethylformamide (0.70 ml) and the mixture was cooled to −78° C. HATU (83.58 mg; 0.22 mmol) was added followed by N,N-dimethylformamide (0.70 ml) and the reaction mixture was stirred 5 min. The flask was removed from the bath and was left stirred for 20 min at ambient temperature. Water was added drop wise to the reaction mixture and the precipitate formed was removed by filtration. This crude was dissolved in DMSO and purified by prep HPLC and the fractions containing the product were partially concentrated, freeze and lyophilized to give the title compound (37.2 mg). MS: (M+H)$^+$ found for $C_{29}H_{20}F_3N_3O_2$: 500.0.

Example 66

Synthesis of (1R,8S)—N-[(4-carbamimidoyl-2-fluorophenyl)methyl]-12-cyclopropyl-15-oxatetracyclo[6.6.1.0$^{2,7}$.0$^{9,14}$]pentadeca-2,4,6,9,11,13-hexaene-4-carboxamide

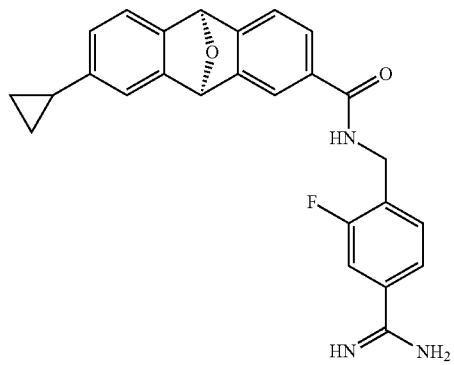 [SMILES: N=C(N)c1ccc(CNC(=O)c2ccc3c(c2)[C@@H]2O[C@H]3c3ccc(C4CC4)cc32)c(F)c1]

(1R,8S)-12-cyclopropyl-15-oxatetracyclo[6.6.1.0$^{2,7}$.0$^{9,14}$]pentadeca-2,4,6,9,11,13-hexaene-4-carboxylic acid (Example 14, Step 1; 25.70 mg; 0.09 mmol) and 4-(aminomethyl)-3-fluorobenzene-1-carboximidamide dihydrochloride (Example 64, Step 1-4; 26.61 mg; 0.11 mmol) were dissolved in N,N-dimethylformamide (0.26 ml) and the reaction mixture was cooled to 0° C. (1H-1,2,3-benzotriazol-1-yloxy)[tri(1-pyrrolidinyl)]phosphonium hexafluorophosphate (57.67 mg; 0.11 mmol) and diisopropylethylamine (0.06 ml; 0.37 mmol) were added and the reaction mix was stirred at 0° C. for 20 min. Water was added slowly to the reaction mixture and the precipitate that appeared was removed by filtration. The crude was dissolved in DMSO and purified on the prep HPLC. The fractions containing the title compound were concentrated and then suspended in acetonitrile/water, freeze and lyophilized. MS: (M+H)$^+$ found for $C_{26}H_{22}FN_3O_2$: 427.8.

Example 67

Synthesis of (1R,8S)—N-[(4-carbamimidoyl-2-fluorophenyl)methyl]-12-(4-fluorophenyl)-15-oxatetracyclo[6.6.1.0$^{2,7}$.0$^{9,14}$]pentadeca-2,4,6,9,11,13-hexaene-4-carboxamide

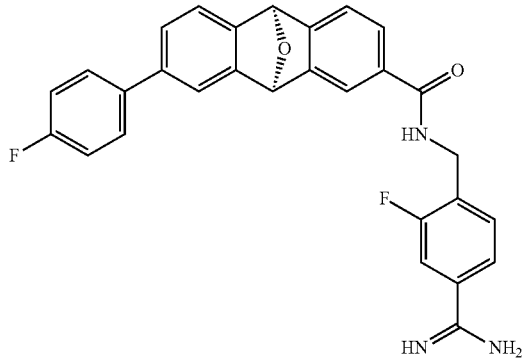 [SMILES: N=C(N)c1ccc(CNC(=O)c2ccc3c(c2)[C@@H]2O[C@H]3c3ccc(-c4ccc(F)cc4)cc32)c(F)c1]

(1R,8S)-12-(4-fluorophenyl)-15-oxatetracyclo[6.6.1.0$^{2,7}$.0$^{9,14}$]pentadeca-2,4,6,9,11,13-hexaene-4-carboxylic acid (Example 59, Step 1; 30.00 mg; 0.09 mmol) and 4-(aminomethyl)-3-fluorobenzene-1-carboximidamide dihydrochloride (Example 64, Step 1-4; 23.84 mg; 0.10 mmol) were dissolved in N,N-dimethylformamide (0.30 ml) and the reaction mixture was cooled to −78° C. HATU (37.76 mg; 0.10 mmol) was added to the reaction mixture followed by diisopropylethylamine (0.06 ml; 0.36 mmol) and after 5 minutes the reaction flask was removed from the bath and left to reach RT. After 10 min the reaction mixture was cooled in an ice bath and water was added drop wise to it. The precipitate was removed by filtration and the solid was dissolved in DMSO and purified on prep HPLC. The fractions containing the product were partially concentrated, freeze and lyophilized to give the title compound (27.10 mg). MS: (M+H)$^+$ found for $C_{29}H_{21}F_2N_3O_2$: 427.8.

Example 68

Synthesis of (1R,8S)—N-{[2-fluoro-4-(N'-methoxycarbamimidoyl)phenyl]methyl}-12-(2-fluoro-phenyl)-15-oxatetracyclo[6.6.1.0$^{2,7}$.0$^{9,14}$]pentadeca-2,4,6,9,11,13-hexaene-4-carboxamide

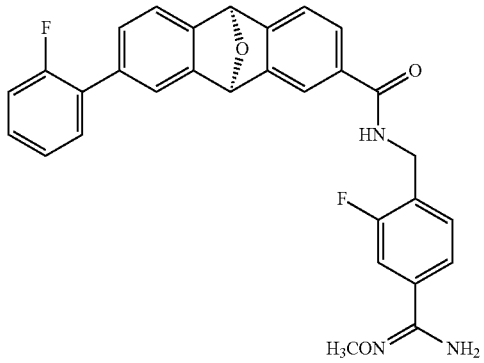

Step 1:
To a solution of tert-butyl N-[(tert-butoxy)carbonyl]-N-[(4-cyano-2-fluoro-phenyl)methyl]carbamate (Example 64, Step 1; 1.0 g; 2.85 mmol) suspended in ethanol (7.00 ml) were added triethylamine (1.39 ml; 9.99 mmol) and a 30% W/W solution of O-methylhydroxylamine hydrochloride (476.72 mg; 5.71 mmol), followed by the addition of thioglycolic acid (0.20 ml; 2.85 mmol). The resulting mixture was stirred overnight at 87° C. Approximately 0.7 eq. O-methylhydroxylamine hydrochloride were added followed by one more equivalent of triethylamine and the reaction was stirred for an additional 4 h. The solvent was removed under vacuum and the residue partitioned in EtOAc/water. The organic layer was isolated and the aqueous phase extracted 2 more times with EtOAc. The combined organics were washed with brine, filtered and concentrated. The crude was purified by flash chromatography (heptane/EtOAc=3:1) to give tert-butyl N-[(tert-butoxy)carbonyl]-N-({2-fluoro-4-[N'-methoxycarbamimidoyl]phenyl}methyl)carbamate (350 mg).

Step 2:
Hydrochloric acid (0.29 ml; 12.00 mol/l) was added drop wise to a solution of tert-butyl N-[(tert-butoxy)carbonyl]-N-({2-fluoro-4-[N'-methoxycarbamimidoyl]phenyl}methyl)carbamate (350.00 mg; 0.88 mmol) in ethanol (1.40 ml) and ethyl acetate (1.40 ml) and the suspension was heated to 35° C. for 3 h. The mixture was cooled to 0° C. and kept at that temperature for 30 min. The precipitate was removed by filtration and the crystals washed with a mixture of EtOAc and EtOH followed by EtOAc. The solid was dried under vacuum to give 4-(aminomethyl)-3-fluoro-N'-methoxybenzene-1-carboximidamide dihydrochloride (198 mg).

Step 3:
(1R,8S)-12-(2-fluorophenyl)-15-oxatetracyclo[6.6.1.0$^{2,7}$.0$^{9,14}$]pentadeca-2,4,6,9,11,13-hexaene-4-carboxylic acid (Example 44, Step 1; 75.00 mg; 0.23 mmol) was dissolved in N,N-dimethylformamide (0.75 ml). Diisopropylethylamine (0.31 ml; 1.81 mmol), hydroxybenzotriazole (45.74 mg; 0.34 mmol) and N-[3-(dimethylamino)propyl]-N'-ethylcarbodiimide hydrochloride (86.53 mg; 0.45 mmol) were added to the solution and the reaction mixture was stirred for 10 min. A solution of 4-(aminomethyl)-3-fluoro-N'-methoxybenzene-1-carboximidamide dihydrochloride (67.06 mg; 0.25 mmol) in 2 ml of DMF which was pretreated with 2.5 eq of diisorpopylethylamine was added to the reaction flask and the reaction mix was left stirring at ambient temperature for 4 h. The reaction mix was cooled to 0° C. and water was added drop wise to it and the precipitate that formed was removed by filtration. The solid was dissolved in DCM/MeOH and loaded onto silica gel and purified by flash chromatography (Heptanes/EtOAc=2:3) to give the title compound (64 mg). MS: (M+H)$^+$ found for $C_{30}H_{23}F_2N_3O_3$: 511.9.

Example 69

Synthesis of (1R,8S)—N-{[2-fluoro-4-(N'-hydroxycarbamimidoyl)phenyl]methyl}-12-(2-fluorophenyl)-15-oxatetracyclo[6.6.1.0$^{2,7}$.0$^{9,14}$]pentadeca-2,4,6,9,11,13-hexaene-4-carboxamide

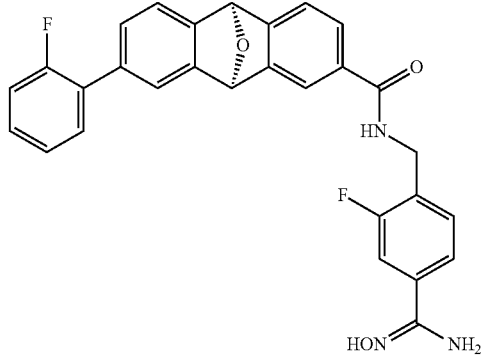

Step 1:
4 N Hydrochloric acid (6.26 ml; 4.00 mol/l) in dioxane was added to a suspension of tert-butyl N-[(tert-butoxy)carbonyl]-N-{2-fluoro-4-(N'-hydroxycarbamimidoyl)-phenyl]methyl}carbamate (Example 64, Steps 1-2; 1.2 g; 3.13 mmol) in water (2.40 ml) and the reaction mixture was stirred at RT for 5 h. The solvent was removed under vacuum and the residue was dissolved in water and concentrated once again to give 4-(aminomethyl)-3-fluoro-N'-hydroxybenzene-1-carboximidamide dihydrochloride.

Step 2:
(1R,8S)-12-(2-Fluorophenyl)-15 oxatetracyclo[6.6.1.0$^{2,7}$.0$^{9,14}$]pentadeca-2,4,6,9,11,13-hexaene-4-carboxylic acid (Example 44, Step 1; 82.00 mg; 0.25 mmol) was dissolved in N,N-dimethylformamide (0.82 ml). Diisopropylethylamine (0.34 ml; 1.97 mmol), hydroxybenzotriazole (50.01 mg; 0.37 mmol) and N-[3-(dimethylamino)propyl]-N'-ethylcarbodiimide hydrochloride (94.60 mg; 0.49 mmol) were added to the solution and the reaction mixture was stirred 10 m. A solution of 4-(aminomethyl)-3-fluoro-N'-hydroxybenzene-1-carboximidamide dihydrochloride (69.51 mg; 0.27 mmol) in 2 ml of DMF that was pretreated with 2.5 eq of diisopropylethylamine was added to the reaction flask and the reaction mixture was left stirring at ambient temperature for 1 h. The reaction mixture was cooled to 0° C. and water was added drop wise to it. The brown precipitate was removed by filtration. The crude product was dissolved in DCM/MeOH and adsorbed on silica gel. It was then purified by flash chromatography (DCM/MeOH=9:1). The fractions containing the product were concentrated and then taken in acetonitrile/water, freeze and lyophilized to the title compound (58 mg). MS: (M+H)$^+$ found for $C_{29}H_{21}F_2N_3O_3$: 498.0.

Example 70

Synthesis of (1R,8S)-12-cyclopropyl-N-{[2-fluoro-4-(N'-methoxy-carbamimidoyl)phenyl]-methyl}-15-oxatetracyclo[6.6.1.0$^{2,7}$.0$^{9,14}$]pentadeca-2,4,6,9,11,13-hexaene-4-carboxamide

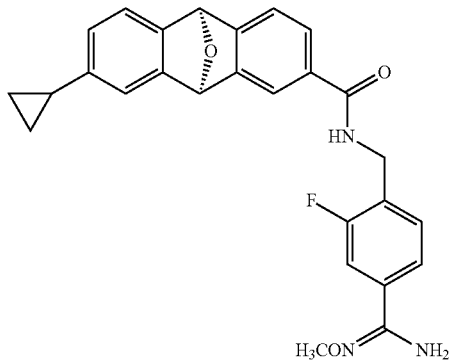

(1R,8S)-12-cyclopropyl-15-oxatetracyclo[6.6.1.0$^{2,7}$.0$^{9,14}$]pentadeca-2,4,6,9,11,13-hexaene-4-carboxylic acid (Example 14, Step 1; 48.00 mg; 0.17 mmol) and 4-(aminomethyl)-3-fluoro-N'-methoxybenzene-1-carboximidamide dihydrochloride (Example 68, Steps 1-2; 55.91 mg; 0.21 mmol) were dissolved in N,N-dimethylformamide (0.48 ml) and the mixture was cooled to 0° C. (1H-1,2,3-benzotriazol-1-yloxy)[tri(1-pyrrolidinyl)]-phosphonium hexafluorophosphate was added followed by diisopropylethylamine (0.12 ml; 0.69 mmol) and the reaction mix stirred 5 min. The flask was removed from the bath and was left to reach RT. After 10 min. water was added slowly to the reaction mix and the precipitate formed was removed by filtration. The solid was dissolved in DCM and purified by flash chromatography (Heptane/EtOAc=2:3) followed by a second purification by prep HPLC. The fractions containing the product were partially concentrated, freeze and lyophilized to give the title compound (19.2 mg). MS: (M+H)$^+$ found for $C_{27}H_{24}FN_3O_3$: 457.6.

Example 71

Synthesis of (1R,8S)-12-(2,4-difluorophenyl)-N-{[2-fluoro-4-(N'-hydroxycarbamimidoyl)phenyl]methyl}-15-oxatetracyclo[6.6.1.0$^{2,7}$.0$^{9,14}$]pentadeca-2,4,6,9,11,13-hexaene-4-carboxamide

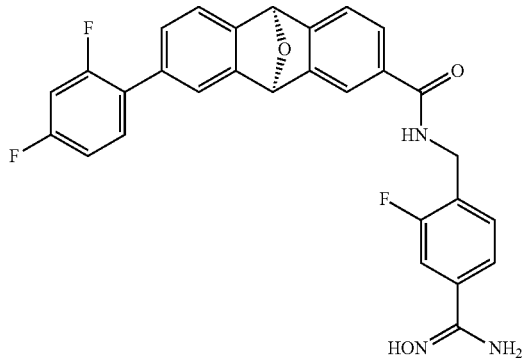

(1R,8S)-12-(2,4-Difluorophenyl)-15-oxatetracyclo[6.6.1.0$^{2,7}$.0$^{9,14}$]pentadeca-2,4,6,9,11,13-hexaene-4-carboxylic acid (Example 7, Step 1-2; 30.00 mg; 0.09 mmol) was dissolved in N,N-dimethylformamide (0.30 ml). N-[3-(Dimethylamino)propyl]-N'-ethylcarbodiimide hydrochloride (19.70 mg; 0.10 mmol), diisopropylethylamine (0.06 ml; 0.34 mmol) and hydroxybenzotriazole (13.89 mg; 0.10 mmol) were added to the reaction mix and stirred 10 min. A solution of 4-(aminomethyl)-3-fluoro-N'-hydroxybenzene-1-carboximidamide dihydrochloride (Example 69, Step 1; 26.3 mg, 0.1 mmol) in 1 ml of DMF, pretreated with 2 eq of diisopropylethylamine was added to the reaction flask and the reaction mis was left stirring at ambient temperature for 2 h. The flask was cooled to 0° C. and water was added drop wise to it. The precipitate was removed by filtration and the solid was dissolved in DCM and purified by flash chromatography (DCM/MeOH=9:1). The fractions containing the product were concentrated to dryness and then suspended in acetonitrile/water, freeze and lyophilized to give the title compound (25.8 mg). MS: (M+H)$^+$ found for $C_{29}H_{20}F_3N_3O_3$: 516.1.

Example 72

Synthesis of (1R,8S)—N-({4-[N'-ethoxycarbamimidoyl]phenyl}methyl)-12-(4-fluorophenyl)-15-oxatetracyclo[6.6.1.0$^{2,7}$.0$^{9,14}$]pentadeca-2,4,6,9,11,13-hexaene-4-carboxamide

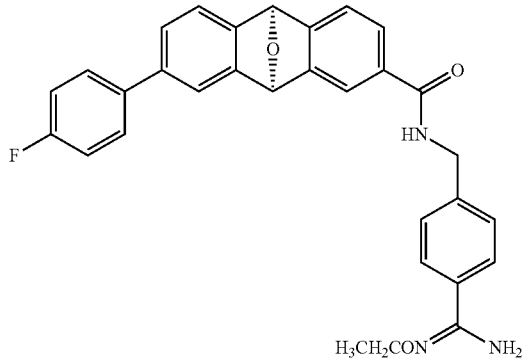

Step 1:

Tert-butyl N-[(4-cyanophenyl)methyl]carbamate (2.00 g; 8.61 mmol) was suspended in ethanol (14.00 ml). Triethylamine (4.20 ml; 30.14 mmol) and a 30% W/W solution of O-ethylhydroxylamine hydrochloride (1.68 g; 17.22 mmol) were added to the mix, followed by the addition of thioglycolic acid (0.60 ml; 8.61 mmol). The resulting mixture was stirred for 24 h at 90° C. The solvent was removed under vacuum and the residue was partitioned in EtOAc/water. The organic layer was isolated and the aqueous phase extracted 2 times; the combined organics were washed with brine, filtered and concentrated. The crude was purified by flash chromatography (Heptane/EtOAc=3:1) to give tert-butyl N-({4-[N'-ethoxy-carbamimidoyl]phenyl}methyl)carbamate (1.0 g).

Step 2:

Hydrochloric acid (1.14 ml; 12.00 mol/l; 13.64 mmol) was added drop wise to a solution tert-butyl N-({4-[N'-ethoxycarbamimidoyl]phenyl}methyl)carbamate (1.0 g; 3.41 mmol) in ethanol (4.00 ml) and ethyl acetate (4.00 ml) and the suspension was heated to 35° C. for 3 h. Additional 0.5 ml of HCl were added and the reaction mixture was left stirring overnight ambient temperature. The solvent was removed under vacuum and the remaining solid was dried under high vacuum to give 4-(aminomethyl)-N'-ethoxybenzene-1-carboximidamide dihydrochloride (907 mg).

Step 3:

(1R,8S)-12-(4-fluorophenyl)-15-oxatetracyclo[6.6.1.0$^{2,7}$.0$^{9,14}$]pentadeca-2,4,6,9,11,13-hexaene-4-carboxylic acid (Example 59, Step 1; 60.00 mg; 0.18 mmol) and 4-(aminomethyl)-N'-ethoxybenzene-1-carboximidamide dihydrochloride (57.67 mg; 0.22 mmol) were dissolved in N,N-dimethylformamide (1.81 ml). Diisopropylethylamine (0.32 ml; 1.81 mmol) and HATU (68.65 mg; 0.18 mmol) were added to the solution and the reaction mixture was stirred at ambient temperature for 45 min. The reaction mixture was cooled to 0° C. and treated by drop wise addition of water. The precipitate formed was removed by filtration and the crude solid was purified by flash chromatography (Heptane/EtOAc=1:1). The fractions containing the product were concentrated and the residue taken in acetonitrile/water freeze and lyophilized to give the title compound (51.2 mg). MS: (M+H)$^+$ found for $C_{31}H_{26}FN_3O_3$: 508.

Example 73

Synthesis of tert-butyl N-[1-amino[4-({[(1R,8S)-12-(2,4-difluorophenyl)-15-oxatetra-cyclo[6.6.1.0$^{2,7}$.0$^{9,14}$]pentadeca-2,4,6,9,11,13-hexaen-4-yl]formamido}methyl)phenyl]methylidene]carbamate

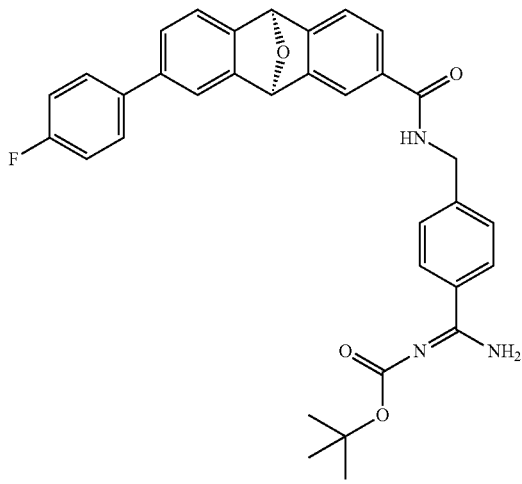 [SMILES: CC(C)(C)OC(=O)N=C(N)c1ccc(CNC(=O)c2ccc3c(c2)[C@@H]2O[C@H]3c3ccc(-c4ccc(F)cc4)cc32)cc1]

(1R,8S)—N-[(4-carbamimidoylphenyl)methyl]-12-(4-fluorophenyl)-15-oxatetracyclo-[6.6.1.0$^{2,7}$.0$^{9,14}$]pentadeca-2,4,6,9,11,13-hexaene-4-carboxamide (Example 59; 60.00 mg; 0.13 mmol) was dissolved in 1,4-dioxane (2.40 ml) and N,N-dimethylformamide (1.20 ml) and the mixture was cooled to 0° C. Sodium hydroxide (0.13 ml; 2.50 mol/l; 0.32 mmol) was added drop wise followed by di-tert-butyl dicarbonate (0.03 ml; 0.14 mmol) and when the addition was complete, the reaction flask was removed from the ice bath and left to reach ambient temperature and stirred for 45 min. The reaction flask was cooled to 0° C. and water was added slowly to the reaction mixture. The precipitate was removed by filtration and the crude was purified by flash chromatography (Heptane/EtOAc=2:3). The fractions containing the product were concentrated, suspended in acetonitrile/water, freeze and lyophilized to give the title compound (28.2 mg). MS: (M+H)$^+$ found for $C_{34}H_{30}FN_3O_4$: 562.2.

Example 74

Synthesis of (1R,8S)—N-{[2-fluoro-4-(N'-methoxy-carbamimidoyl)phenyl]methyl}-12-(4-fluoro-phenyl)-15-oxatetracyclo[6.6.1.0$^{2,7}$.0$^{9,14}$]pentadeca-2,4,6,9,11,13-hexaene-4-carboxamide

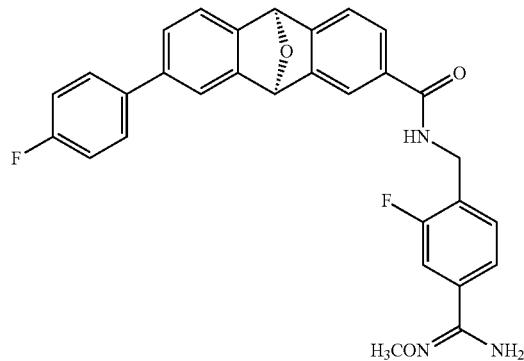

(1R,8S)-12-(2-fluorophenyl)-1 oxatetracyclo[6.6.1.0$^{2,7}$.0$^{9,14}$]pentadeca-2,4,6,9,11,13-hexaene-4-carboxylic acid (Example 59, Step 1; 50.00 mg; 0.15 mmol) and 4-(aminomethyl)-3-fluoro-N'-methoxybenzene-1-carboximidamide dihydrochloride (Example 68, Step 1-2; 48.77 mg; 0.18 mmol) were dissolved in N,N-dimethylformamide (0.50 ml) and the mixture was cooled to −78° C. HATU (62.93 mg; 0.17 mmol) was added to the mixture followed by diisopropylethylamine (0.10 ml; 0.60 mmol) and the reaction mixture was stirred 5 min. The flask was removed from the bath and stirred at ambient temperature for 20 min. Water was added slowly to the reaction mixture and the precipitate was removed by filtration. This crude material was purified by flash chromatography (Heptane/EtOAc=2:3) and the fractions containing the product were concentrated to dryness, suspended in acetonitrile/water, freeze and lyophilized to give the title compound. MS: (M+H)$^+$ found for $C_{30}H_{23}F_2N_3O_3$: 512.1.

Example 75

Synthesis of (1R,8S)—N-[(4-carbamimidoylphenyl)methyl]-12-(2,4-difluorophenyl)-15-oxatetracyclo[6.6.1.0$^{2,7}$.0$^{9,14}$]pentadeca-2,4,6,9,11,13-hexaene-4-carboxamide

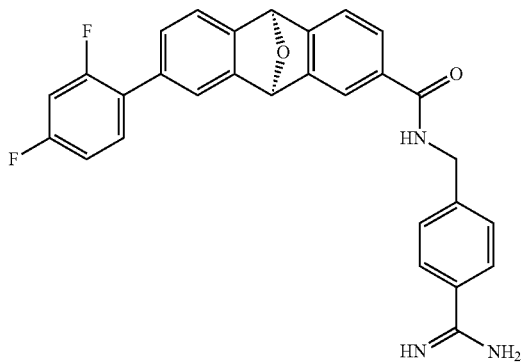 [SMILES: N=C(N)c1ccc(CNC(=O)c2ccc3c(c2)[C@@H]2O[C@H]3c3ccc(-c4ccc(F)cc4F)cc32)cc1]

Step 1:

To a 10 mL microwave reaction vial was subsequently added sodium (1S,8R)-12-bromo-15-oxatetracyclo[6.6.1.0$^{2,7}$.0$^{9,14}$]pentadeca-2,4,6,9,11,13-hexaene-4-carboxylate (INT-5a1, 330 mg, 0.97 mmol, 1.0 eq.), 2,4-difluorophenylboronic acid (230.5 mg, 1.46 mmol, 1.5 eq.), Pd(dppf)$_2$Cl$_2$.CH$_2$Cl$_2$ (63.6 mg, 0.08 mmol, 0.08 eq.) and KOAc (197 mg, 2.0 mmol, 2.1 eq.), N,N-dimethylformamide (4.0 mL) and water (0.5 mL). The resulting mixture was purged with N$_2$ for 5 min. The vial was sealed and subjected to microwave reaction condition (120° C. for 30 min). This resulting mixture was allowed to cool to rt, diluted with water and treated with 1.0 N aqueous HCl (1.0 mL), and extracted with EtOAc. The combined organic layers were washed with water and brine, and dried over MgSO$_4$. After removal of organic solvents under reduced pressure, the residue was subjected to flash chromatography on 10 g silica gel column using 0-100% EtOAc/Hexanes as eluent to provide the desired (1R,8S)-12-(2,4-difluorophenyl)-15-oxatetracyclo[6.6.1.0$^{2,7}$.0$^{9,14}$]pentadeca-2,4,6,9,11,13-hexaene-4-carboxylic acid as pale brown solid (311 mg).

Step 2:

To a rt solution of (1R,8S)-12-(2,4-difluorophenyl)-15-oxatetracyclo-[6.6.1.0$^{2,7}$.0$^{9,14}$]pentadeca-2,4,6,9,11,13-hexaene-4-carboxylic acid (150.0 mg, 0.43 mmol, 1.00 eq.) in DMF (1.65 ml) was added N,N-diisopropylethylamine (0.45 ml, 57 mmol, 6.00 eq.), 1H-1,2,3-benzotriazol-1-ol hydrate (72.13 mg, 0.47 mmol, 1.10 eq.) and N-[3-(dimethylamino)-propyl]-N'-ethylcarbodiimide hydrochloride (164.17 mg, 0.86 mmol, 2.00 eq.) subsequently. This mixture was allowed to stir at rt for 20 min followed by treatment with 4-(aminomethyl)-benzenecarboximidamide dihydrochloride (142.66 mg, 64 mmol, 1.50 eq.). Sonication of the resultant mixture for 10 min led to disappearance of the major white precipitate. The resultant solution was allowed to stir at rt for 5.0 h and the reaction was monitored with LCMS till completion. The crude reaction mixture was filtered and subjected to reverse preparative HPLC (Prep-C18, 5 µM OBD column, 19×250 mm, waters; gradient elution of 20% MeCN in water to 75% MeCN in water over a 20 min period, where both solvents contain 0.1% TFA, flow rate: 20 mL/min) to provide the title compound in the TFA salt as a white solid (110 mg, 54%). MS: (M+H)$^+$ found for C$_{29}$H$_{22}$F$_2$N$_3$O$_2$: 482.1.

Example 76

Synthesis of (1S,8R)—N-[(6-amino-2,4-dimethylpyridin-3-yl)methyl]-12-[ethyl(3-fluorophenyl)-amino]-15-oxatetracyclo[6.6.1.0$^{2,7}$.0$^{9,14}$]pentadeca-2,4,6,9,11,13-hexaene-4-carboxamide

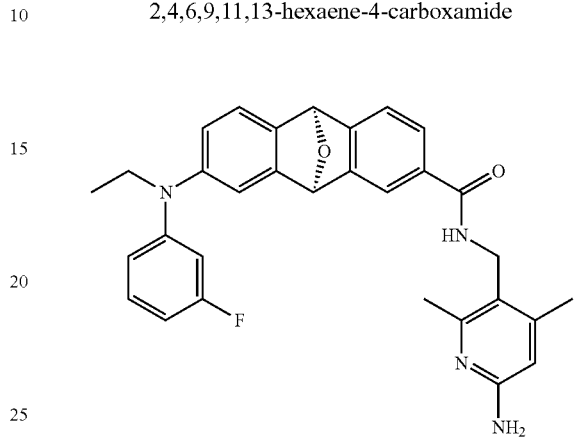

Step 1:

A mixture of methyl (1S,8R)-12-bromo-15-oxatetracyclo[6.6.1.0$^{2,7}$.0$^{9,14}$]-pentadeca-2,4,6,9,11,13-hexaene-4-carboxylate (216 mg, 0.65 mmol, 1.0 eq.,), 3-fluoroaniline (253 mg; 2.28 mmol, 3.5 eq.) and Cs$_2$CO$_3$ (745 mg, 2.28 mmol, 3.5 eq.) in toluene (5 mL) was purged with N$_2$ for 10 min. To the mixture was added Xantphos (26.2 mg; 0.05 mmol; 0.08 eq.) followed by Pd$_2$(dba)$_3$.CHCl$_3$ (54 mg, 0.05 mmol, 0.08 eq.). The mixture was purged with N$_2$ for additional 10 min and the reaction vessel was sealed. The mixture was allowed to stir at 100° C. for 3.5 h, cooled to rt, diluted with water, acidified with 1.0 N aqueous HCl to pH~7.0, and extracted with EtOAc twice. The combined organic layers were washed with water, brine, and dried over MgSO$_4$. After removal of organic solvents under reduced pressure, the residue was subjected to flash chromatography on 10 g silica gel column using 0-100% EtOAc/Hexanes as eluent to provide methyl (1S,8R)-12-[(3-fluorophenyl)amino]-15-oxatetracyclo[6.6.1.0$^{2,7}$.0$^{9,14}$]pentadeca-2,4,6,9,11,13-hexaene-4-carboxylate as colorless syrup (158 mg).

Step 2:

To a vial charged with methyl (1S,8R)-12-[(3-fluorophenyl)amino]-15-oxatetracyclo[6.6.1.0$^{2,7}$.0$^{9,14}$]pentadeca-2,4,6,9,11,13-hexaene-4-carboxylate (150.0 mg; 0.42 mmol; 1.00 eq.) and NaH (84 mg, 60% wt, 2.1 mmol; 5.0 eq.) under N$_2$ atmosphere in 0° C. bath was added DMF (3.5 mL) followed by iodoethane (194 mg, 1.25 mmol, 3.0 eq.). After stirring in the ice bath for 3.5 h, the reaction mixture was slowly poured into saturated aq. NH$_4$Cl solution under N$_2$ atmosphere, acidified with HOAc to pH-6 and then extracted with EtOAc twice. The combined organic layers were washed with water and brine, and dried over MgSO$_4$. Removal of the organic solvents provide the crude of methyl (1S,8R)-12-[ethyl(3-fluorophenyl)amino]-15-oxatetracyclo[6.6.1.0$^{2,7}$.0$^{9,14}$]pentadeca-2,4,6,9,11,13-hexaene-4-carboxylate (140 mg).

Step 3:

To a rt mixture of methyl (1S,8R)-12-[ethyl(3-fluorophenyl)amino]-15-oxatetracyclo[6.6.1.0$^{2,7}$.0$^{9,14}$]pentadeca-2,4,6,9,11,13-hexaene-4-carboxylate (140.00 mg; 0.36 mmol;

1.00 eq.) in dioxane (1.0 mL) and MeOH (1.0 mL) was added aqueous solution of LiOH (0.36 ml; 4.0 M, 1.44 mmol; 4.00 eq.). The resulting mixture was allowed to stir at 80° C. for 1.5 h, cooled to rt, treated with saturated aq. NH$_4$Cl solution followed by 0.4 mL of HOAc. The resulting mixture was extracted with 20% $^i$PrOH/CHCl$_3$. The organic layer was washed with water, brine and dried over MgSO$_4$. After removal of organic solvents under reduced pressure, the residue was subjected to flash chromatography on 10 g silica gel column using 0-100% EOAc/Hexanes as eluent to (1S,8R)-12-[ethyl(3-fluorophenyl)amino]-15-oxatetracyclo-[6.6.1.0$^{2,7}$.0$^{9,14}$]pentadeca-2,4,6,9,11,13-hexaene-4-carboxylic acid (110 mg).

Step 4:

To a flask charged with (1S,8R)-12-[ethyl(3-fluorophenyl)amino]-15-oxatetracyclo[6.6.1.0$^{2,7}$.0$^{9,14}$]pentadeca-2,4,6,9,11,13-hexaene-4-carboxylic acid (70.00 mg; 0.19 mmol; 1.00 eq.) and 1-[bis(dimethylamino)methylene]-1H-1,2,3-triazolo[4,5-b]pyridinium 3-oxid hexafluorophosphate (HATU, 141.80 mg; 0.37 mmol; 2.00 eq.) was added DMF (2.5 mL) followed by Et$_3$N (0.93 ml; 0.56 mmol; 3.00 eq.) This mixture was allowed to stir at rt for 3 h, cooled to rt, diluted with water and extracted with EtOAc thrice. The combined organic layers were washed with water and brine and dried over MgSO$_4$. After removal of organic solvents under reduced pressure, the residue was subjected to reverse preparative HPLC (Prep-C18, 5 M OBD column, 19×250 mm, waters; gradient elution of 10% MeCN in water to 95% MeCN in water over a 20 min period, where both solvents contain 0.1% TFA, flow rate: 20 mL/min) to provide the title compound as a white solid (38 mg, 39%). MS: (M+H)$^+$ found for C$_{31}$H$_{30}$FN$_4$O$_2$: 509.2.

Example 77

Synthesis of (1S,8R)—N-[(6-amino-2,4-dimethylpyridin-3-yl)methyl]-12-[(3-chlorophenyl)(methyl)amino]-15-oxatetracyclo[6.6.1.0$^{2,7}$.0$^{9,14}$]pentadeca-2,4,6,9,11,13-hexaene-4-carboxamide

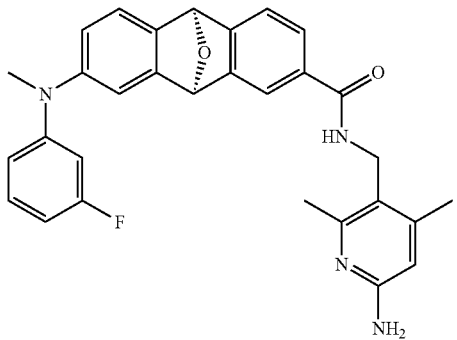

Step 1:

A mixture of methyl (1S,8R)-12-bromo-15-oxatetracyclo[6.6.1.0$^{2,7}$.0$^{9,14}$]pentadeca-2,4,6,9,11,13-hexaene-4-carboxylate (150.00 mg; 0.45 mmol; 1.00 eq., INT-3a1), 3-chloroaniline (0.25 ml; 2.26 mmol; 5.00 eq.) and cesium carbonate (516.5 mg; 1.6 mmol; 3.50 eq.) in toluene (3 mL) was purged with N$_2$ for 10 min. To the mixture was added 2-dicyclohexyl-phosphino-2',4',6'-triisopropyl-1,1'-biphenyl)[2-(2'-amino-1,1'-biphenyl)]-palladium(II) methanesulfonate (Xantphos; 18.3 mg; 0.04 mmol; 0.08 eq.) followed by Pd$_2$(dba)$_3$.CHCl$_3$ (38 mg, 0.04 mmol, 0.08 eq.). The mixture was purged with N$_2$ for additional 10 min and then allowed to reflux under N$_2$ atmosphere for 3.5 h. The resulting reaction solution was cooled to rt, diluted with water, acidified with 1.0 N aqueous HCl to pH~7.0, and extracted with EtOAc. The combined organic layers were washed with water, brine, and dried over MgSO$_4$. After removal of organic solvents under reduced pressure, the residue was subjected to flash chromatography on 10 g silica gel column using 0-100% EtOAc/Hexanes as eluent to provide methyl (1S,8R)-12-[(3-chlorophenyl)(methyl)amino]-15-oxatetracyclo[6.6.1.0$^{2,7}$.0$^{9,14}$]-pentadeca-2,4,6,9,11,13-hexaene-4-carboxylate as brown syrup (128 mg).

Step 2:

To a vial charged with (1S,8R)-12-[(3-chlorophenyl)(methyl)amino]-15-oxatetracyclo[6.6.1.0$^{2,7}$.0$^{9,14}$]pentadeca-2,4,6,9,11,13-hexaene-4-carboxylate (100.00 mg; 0.26 mmol; 1.00 eq.) and NaH (53 mg, 60% wt, 1.31 mmol; 5.00 eq.) under N$_2$ atmosphere in ice bath was added DMF (2.5 mL) followed by iodomethane (112.70 mg; 0.79 mmol; 3.00 eq.). After stirring at 0° C. for 3.0 h, the reaction mixture was slowly poured into saturated aq. NH$_4$Cl solution under N$_2$ atmosphere, acidified with HOAc to pH-6 and then extracted with EtOAc twice. The combined organic layers were washed with water and brine, and dried over MgSO$_4$. Removal of the organic solvents provide the crude of methyl (1S,8R)-12-[methyl(3-fluorophenyl)amino]-15-oxatetracyclo[6.6.1.0$^{2,7}$.0$^{9,14}$]pentadeca-2,4,6,9,11,13-hexaene-4-carboxylate (50 mg).

Step 3:

To a rt mixture of (1S,8R)-12-[methyl(3-fluorophenyl)amino]-15-oxatetracyclo[6.6.1.0$^{2,7}$.0$^{9,14}$]pentadeca-2,4,6,9,11,13-hexaene-4-carboxylate (50 mg, 0.13 mmol, 1.0 eq.) in dioxane (0.3 mL) and MeOH (0.3 mL) was added aqueous solution of LiOH (0.15 ml; 4.0 M, 0.60 mmol; 4.6 eq.). This mixture was left stirring at 80° C. for 1.5 h, cooled to rt, treated with saturated aqueous NH$_4$Cl solution followed by 0.2 mL of HOAc. The resulting mixture was extracted with 20% $^i$PrOH/CHCl$_3$ twice. The combined organic layers were washed with water, brine and dried over MgSO$_4$. Removal of organic solvents under reduced pressure provide the crude product of (1S,8R)-12-[(3-chlorophenyl)(methyl)amino]-15-oxatetracyclo[6.6.1.0$^{2,7}$.0$^{9,14}$]-pentadeca-2,4,6,9,11,13-hexaene-4-carboxylic acid (41 mg).

Step 4:

To a flask charged with (1S,8R)-12-[(3-chlorophenyl)(methyl)amino]-15-oxatetracyclo[6.6.1.0$^{2,7}$.0$^{9,14}$]pentadeca-2,4,6,9,11,13-hexaene-4-carboxylic acid (16 mg) and 1-[bis(dimethylamino)methylene]-1H-1,2,3-triazolo[4,5-b]pyridinium 3-oxid hexafluorophosphate (HATU, 32.20 mg; 0.08 mmol; 2.00 eq.) was added DMF (0.8 mL) followed by Et$_3$N (0.21 ml). This mixture was allowed to stir at rt for 5 h, cooled to rt, diluted with water and extracted with EtOAc. The combined organic layers were washed with water and brine. After removal of organic solvents under reduced pressure, the residue was subjected to reverse preparative HPLC (Prep-C18, 5 M OBD column, 19×250 mm, waters; gradient elution of 10% MeCN in water to 95% MeCN in water over a 20 min period, where both solvents contain 0.1% TFA, flow rate: 20 mL/min) to provide the title compound as a white solid (8 mg). MS: (M+H)$^+$ found for C$_{30}$H$_{28}$ClN$_4$O$_2$: 511.2.

Example 78

Synthesis of (1S,8R)—N-[(4-carbamimidoylphenyl)methyl]-12-[(3-chlorophenyl)-(methyl)amino]-15-oxatetracyclo[6.6.1.0$^{2,7}$.0$^{9,14}$]pentadeca-2,4,6,9,11,13-hexaene-4-carboxamide triflate

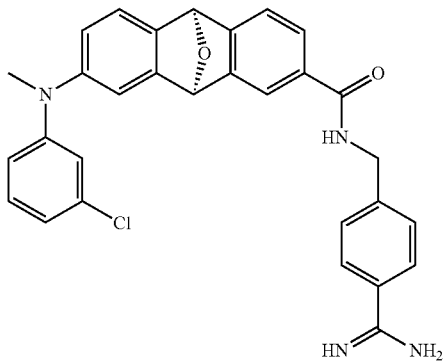 [SMILES: CN(c1cccc(Cl)c1)c1ccc2c(c1)[C@H]1O[C@@H]2c2ccc(C(=O)NCc3ccc(C(=N)N)cc3)cc21]

The title compound was made from (1S,8R)-12-[(3-chlorophenyl)(methyl)amino]-15-oxatetracyclo[6.6.1.0$^{2,7}$.0$^{9,14}$]pentadeca-2,4,6,9,11,13-hexaene-4-carboxylic acid (prepared in Step 3, Example 77) and 4-(aminomethyl)benzenecarboximidamide dihydrochloride, following the same procedure as described in Step 2, Example 59, except that the crude product was purified by reverse preparative HPLC (Prep-C18, 5 M OBD column, 19×250 mm, waters; gradient elution of 10% MeCN in water to 90% MeCN in water over a 20 min period, where both solvents contain 0.1% TFA, flow rate: 20 mL/min) to provide the title compound as TFA salt as white solid (5.1 mg, 41%). MS: (M+H)$^+$ found for C$_{30}$H$_{26}$ClN$_4$O$_2$: 509.1.

Example 79

Synthesis of (1S,8R)—N-[(4-carbamimidoylphenyl)methyl]-12-(1,1-difluoroethyl)-15-oxatetra-cyclo[6.6.1.0$^{2,7}$.0$^{9,14}$]pentadeca-2,4,6,9,13-hexaene-4-carboxamide triflate salt

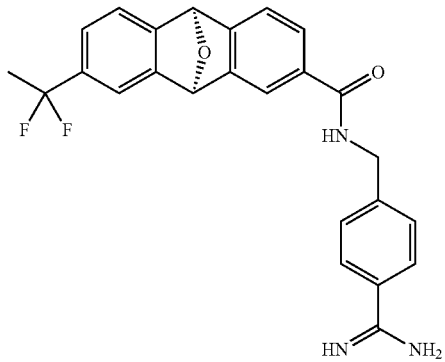 [SMILES: CC(F)(F)c1ccc2c(c1)[C@H]1O[C@@H]2c2ccc(C(=O)NCc3ccc(C(=N)N)cc3)cc21]

Step 1:

To a mixture of (1R,8S)-12-bromo-15-oxatetracyclo[6.6.1.0$^{2,7}$.0$^{9,14}$]-pentadeca-2,4,6,9,11,13-hexaene-4-carboxylic acid (INT-4a2, 1.58 g; 4.97 mmol; 1.00 eq.), methoxy-(methyl)amine hydrochloride (0.72 g; 7.46 mmol; 1.50 eq.) and HATU (2.84 g; 7.46 mmol; 1.50 eq.) in N,N-dimethylformamide (15 mL) was added Et$_3$N (3.0 mL). The resulting mixture was allowed to stir at rt for overnight. The reaction mixture was diluted with water and extracted with EtOAc. The combined organic layers were washed with water and brine. After removal of organic solvents under reduced pressure, the residue was subjected to flash chromatography on 40 g silica gel column using 0-100% EtOAc/Hexanes as eluent to provide (1R,8S)-12-bromo-N-methoxy-N-methyl-15-oxatetracyclo-[6.6.1.0$^{2,7}$.0$^{9,14}$]pentadeca-2,4,6,9,11,13-hexaene-4-carboxamide as white solid (1.56 g, 87%).

Step 2:

To a solution of (1R,8S)-12-bromo-N-methoxy-N-methyl-15-oxatetracyclo-[6.6.1.0$^{2,7}$.0$^{9,14}$]pentadeca-2,4,6,9,11,13-hexaene-4-carboxamide (1.56 g; 4.33 mmol; 1.00 eq.) in THF (10 mL) at 0° C. under N$_2$ atmosphere was added bromo(methyl)magnesium (3.8 ml; 3.4 M; 13.0 mmol; 3.00 eq.). The resulting mixture was allowed to stir in the ice bath for 35 min before being removed from the bath and allowed to stir at ambient temperature overnight. The reaction mixture was quenched with saturated aq. NH$_4$Cl solution, diluted with water and extracted with EtOAc twice. The combined organic layers were washed with water and brine. After removal of organic solvents under reduced pressure, the residue was subjected to flash chromatography on 40 g silica gel column using 0-100% EtOAc/Hexanes as eluent to provide 1-[(1R,8S)-12-bromo-15-oxatetracyclo-[6.6.1.0$^{2,7}$.0$^{9,14}$]pentadeca-2,4,6,9(14),10,12-hexaen-4-yl]ethan-1-one as colorless syrup (1.28 g, 94%).

Step 3:

To art solution of 1-[(1R,8S)-12-bromo-15-oxatetracyclo[6.6.1.0$^{2,7}$.0$^{9,14}$]-pentadeca-2,4,6,9(14),10,12-hexaen-4-yl]ethan-1-one (224.0 mg, 0.72 mmol, 1.00 eq.) in CH$_2$Cl$_2$ (1.5 mL) was added bis(2-methoxyethyl)(trifluoro-λ$^4$-sulfanyl)amine (629 mg; 2.84 mmol; 4.00 eq.) dropwise followed by MeOH (0.1 mL) and CH$_2$Cl$_2$ (0.8 mL). This mixture was left stirring at rt for 20 min then allowed to stir at 65° C. for 4 h. This mixture was then cooled to rt and additional bis(2-methoxyethyl)(trifluoro-λ$^4$-sulfanyl)amine (944 mg; 4.26 mmol; 6.00 eq.) was added. The reaction vessel was sealed and allowed to stir at 90° C. overnight. The reaction mixture was allowed to cool to rt, slowly treated with water dropwise, diluted with saturated aq. NaHCO$_3$ solution, and extracted with CH$_2$Cl$_2$ thrice. The organic layers were combined and washed with water and brine. After removal of organic solvents under reduced pressure, the residue was subjected to flash chromatography on 10 g silica gel column using 0-100% EtOAc/Hexanes as eluent to provide (1R,8S)-12-bromo-4-(1,1-difluoroethyl)-15-oxatetracyclo[6.6.1.0$^{2,7}$.0$^{9,14}$]pentadeca-2,4,6,9(14),10,12-hexaene as colorless syrup (100 mg, 42%).

Step 4:

A mixture of (1R,8S)-12-bromo-4-(1,1-difluoroethyl)-15-oxatetracyclo-[6.6.1.0$^{2,7}$.0$^{9,14}$]pentadeca-2,4,6,9(14),10,12-hexaene (75 mg; 0.22 mmol; 1.00 eq.), Xantphos (19.5 mg; 0.04 mmol; 0.15 eq.), palladium acetate (8 mg; 0.035 mmol; 0.16 eq.) and triethylamine (90 mg.) in a mixture solvent of DMF/dioxane/water (0.3 mL/0.3 mL/0.3 m L) was purged with CO for 10 min. The reaction vial was sealed and allowed to stir at 90° C. for 2 h. The reaction mixture was cooled to rt, diluted with EtOAc, washed with 1.0 N aqueous HCl, water and then brine. After removal of organic solvents under reduced pressure, the residue was subjected to flash chromatography on 4 g silica gel column using 0-100% EtOAc/Hexanes as eluent to provide (1S,8R)-12-(1,1-difluoroethyl)-15-oxatetracyclo[6.6.1.0$^{2,7}$.0$^{9,14}$]pentadeca-2,4,6,9,11,13-hexaene-4-carboxylic acid as colorless syrup (21 mg, 32%).

Step 5:

Reaction of (1S,8R)-12-(1,1-difluoroethyl)-15-oxatetracyclo[6.6.1.0$^{2,7}$.0$^{9,14}$]pentadeca-2,4,6,9,11,13-hexaene-4-carboxylic acid (12 mg, 0.04 mmol) and 4-(aminomethyl)-benzenecarboximidamide dihydrochloride (11.4 mg, 0.05 mmol) following the conditions and workup procedure as described in Step 2 for the synthesis of Example 59 provided title compound in the TFA salt form as white solid (7.5 mg, 36%). MS: (M+H)$^+$ found for $C_{25}H_{22}F_2N_3O_2$: 434.1.

Example 80

Synthesis of (1S,8R)—N-[(4-carbamimidoylphenyl)methyl]-12-(2-fluoropropan-2-yl)-15-oxatetracyclo[6.6.1.0$^{2,7}$.0$^{9,14}$]pentadeca-2,4,6,9,11,13-hexaene-4-carboxamide triflate

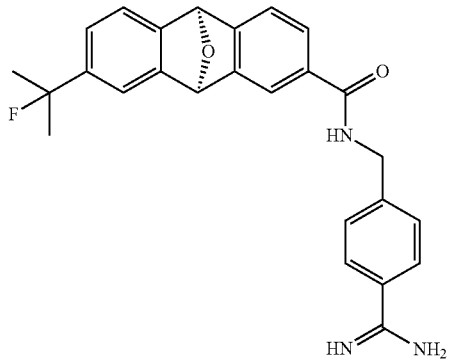 [SMILES: CC(C)(F)c1ccc2c(c1)[C@H]1O[C@@H]2c2ccc(C(=O)NCc3ccc(C(=N)N)cc3)cc21]

Step 1:

To a 0° C. solution of 1-[(1R,8S)-12-bromo-15-oxatetracyclo[6.6.1.0$^{2,7}$.0$^{9,14}$]-pentadeca-2,4,6,9(14),10,12-hexaen-4-yl]ethan-1-one (590.0 mg; 1.87 mmol; 1.00 eq., prepared in Step 2, Example 79 in THF (5 ml) under N$_2$ atmosphere was added bromo(methyl)-magnesium (1.10 ml; 3.4 m; 3.74 mmol; 2.00 eq.). The mixture was allowed to warm with the ice bath to rt and stir at rt for 1.5 hr. The reaction mixture was poured into saturated aq. NH$_4$Cl solution, diluted with water and extracted with EtOAc. The organic layers were combined. After removal of organic solvents under reduced pressure, the residue was subjected to flash chromatography on 10 g silica gel column using 0-100% EtOAc/Hexanes as eluent to provide 2-[(1R,8S)-12-bromo-15-oxatetracyclo[6.6.1.0$^{2,7}$.0$^{9,14}$]-pentadeca-2,4,6,9(14),10,12-hexaen-4-yl]propan-2-ol as colorless syrup (428 mg, 73%).

Step 2:

A mixture of 2-[(1R,8S)-12-bromo-15-oxatetracyclo[6.6.1.0$^{2,7}$.0$^{9,14}$]-pentadeca-2,4,6,9(14),10,12-hexaen-4-yl]propan-2-ol (56.00 mg; 0.17 mmol; 1.00 eq.) and bis(2-methoxyethyl)(trifluoro-λ$^4$-sulfanyl)amine (561 mg; 2.54 mmol; 15.00 eq.) was allowed to stir at 90° C. for 3.0 h. This resulting mixture was cool to rt, diluted with EtOAc, and slowly poured into saturated aq. NaHCO$_3$ solution, diluted with water and extracted with EtOAc. The organic layers were combined. After removal of organic solvents under reduced pressure, the residue was subjected to flash chromatography on 10 g silica gel column using 0-100% EtOAc/Hexanes as eluent to provide (1R,8S)-12-bromo-4-(2-fluoropropan-2-yl)-15-oxatetracyclo[6.6.1.0$^{2,7}$.0$^{9,14}$]-pentadeca-2,4,6,9(14),10,12-hexaene as colorless syrup (41 mg, 73%).

Step 3:

A mixture (1R,8S)-12-bromo-4-(2-fluoropropan-2-yl)-15-oxatetracyclo-[6.6.1.0$^{2,7}$.0$^{9,14}$]pentadeca-2,4,6,9(14),10,12-hexaene (41.0 mg; 0.12 mmol; 1.00 eq.), Xantphos (21.36 mg; 0.04 mmol; 0.30 eq.), palladium acetate (8.29 mg; 0.04 mmol; 0.30 eq.) and triethylamine (120 mg) in DMF/dioxane/water (0.3 ml/0.3 ml/0.3 ml) was purged with CO for 10 min. The reaction vial was sealed and allowed to stir at 90° C. for 4 h. The reaction mixture was cooled to rt, diluted with EtOAc, washed with 1.0 N aqueous HCl, water and then brine. After removal of organic solvents under reduced pressure, the residue was subjected to flash chromatography on 4 g silica gel column using 0-100% etoac/hexanes as eluent to provide (1S,8R)-12-(2-fluoropropan-2-yl)-15-oxatetracyclo[6.6.1.0$^{2,7}$.0$^{9,14}$]-pentadeca-2(7),3,5,9,11,13-hexaene-4-carboxylic acid (30 mg, 82%).

Step 4:

Reaction of (1S,8R)-12-(2-fluoropropan-2-yl)-15-oxatetracyclo-[6.6.1.0$^{2,7}$.0$^{9,14}$]-pentadeca-2(7),3,5,9,11,13-hexaene-4-carboxylic acid (30 mg, 0.10 mmol) and 4-(aminomethyl)benzenecarboximidamide dihydrochloride (29 mg, 0.13 mmol) following the conditions and workup procedure as described in Step 2, Example 59 provided title compound in the TFA salt form as white solid (5.8 mg, 13%). MS: (M+H)$^+$ found for $C_{26}H_{25}FN_3O_2$: 430.2.

Example 81

Synthesis of (1S,8R)-12-[(3-chlorophenyl)(methyl)amino]-N-({4-[N'-methoxycarbamimidoyl]phenyl}methyl)-15-oxatetracyclo[6.6.1.0$^{2,7}$.0$^{9,14}$]pentadeca-2,4,6,9,11,13-hexaene-4-carboxamide triflate

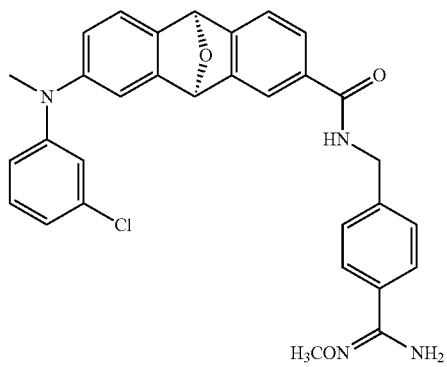

The title compound was made from (1S,8R)-12-[(3-chlorophenyl)(methyl)amino]-15-oxatetracyclo[6.6.1.0$^{2,7}$.0$^{9,14}$]pentadeca-2,4,6,9,11,13-hexaene-4-carboxylic acid (prepared in Step 3 Example 77) and 4-(aminomethyl)-N'-methoxybenzimidamide (INT-7), following the same procedure as described in Step 2, Example 63, except that the crude product was purified by reverse preparative HPLC (Prep-C18, 5 µM OBD column, 19×250 mm, waters; gradient elution of 20% MeCN in water to 75% MeCN in water over a 20 min period, where both solvents contain 0.1% TFA, flow rate: 20 mL/min) to provide the title compound in the TFA salt as a white solid (23 mg, 27%). MS: (M+H)+ found for $C_{31}H_{28}ClN_4O_3$: 539.1.

Example 82

Synthesis of (±)-N-[(6-amino-2,4-dimethylpyridin-3-yl)methyl]-10-(1-benzofuran-3-yl)tricycle-[6.2.1.0$^{2,7}$]undeca-2,4,6,9-tetraene-4-carboxamide and (±)-N-[(6-amino-2,4-dimethylpyridin-3-yl)methyl]-9-(1-benzofuran-3-yl)tricyclo[6.2.1.0$^{2,7}$]undeca-2,4,6,9-tetraene-4-carboxamide

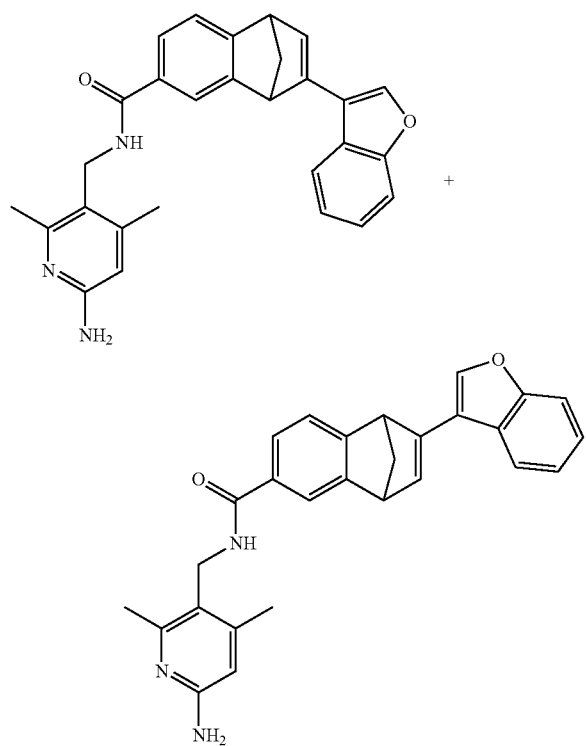 [SMILES: Cc1cc(N)nc(C)c1CNC(=O)c1ccc2c(c1)C1CC2C=C1c1coc2ccccc12 ; Cc1cc(N)nc(C)c1CNC(=O)c1ccc2c(c1)C1C=C(c3coc4ccccc34)C2C1]

Step 1:
Into a 250-mL sealed tube, was placed a mixture of cyclopenta-1,3-diene (26.4 g, 400 mmol, 1.00 equiv) and (Z)-1,4-dichlorobut-2-ene (100.0 g, 800 mmol, 2.00 equiv). The resulting mixture was stirred for 5 hours at 180° C. in an oil bath. After cooling to room temperature, the crude product was purified by fractional distillation (100° C./10 Torr) to afford 11.8 g (15%, crude product) of (±)-5,6-bis(chloromethyl)bicyclo[2.2.1]hept-2-ene as a brown oil, which was used directly for next step without further purification.

Step 2:
Into a 1000-mL round-bottom flask, was placed a solution of (±)-5,6-bis(chloromethyl)bicyclo[2.2.1]hept-2-ene (19.3 g, 101 mmol, 1.00 equiv) in tetrahydrofuran (300 mL), followed by the addition of NaBH$_4$ (5.01 g, 135.34 mmol, 1.34 equiv). BF$_3$.Et$_2$O (23.0 g, 161.6 mmol, 1.60 equiv) was then added dropwise with stirring at 0° C. and the resulting mixture was stirred for 3 hours at room temperature. Water (19.5 mL), 3 N aqueous potassium hydroxide (29.3 mL), and H$_2$O$_2$ (23.4 mL, 30%, 2.30 equiv) were then added dropwise in succession at 0° C., and the mixture was stirred at room temperature for an additional 16 hours. The reaction was then quenched by the addition of saturated aqueous Na$_2$S$_2$O$_3$, diluted with water, extracted with ethyl acetate. The organic layers were combined and concentrated under reduced pressure to afford 19.0 g of a crude mixture of (1R,2S,4R)-5,6-bis(chloromethyl)bicyclo[2.2.1]heptan-2-ol, (1S,2R,4S)-5,6-bis(chloromethyl)bicyclo[2.2.1]-heptan-2-ol and (1S,2S,4S)-5,6-bis(chloromethyl)bicyclo[2.2.1] heptan-2-ol, (1R,2R,4R)-5,6-bis(chloromethyl)bicyclo[2.2.1]heptan-2-ol as a white solid, which was used directly for next step without further purification.

Step 3:
Into a 250-mL round-bottom flask, was placed a solution of a mixture of (1R,2S,4R)-5,6-bis(chloromethyl)bicyclo[2.2.1]heptan-2-ol, (1S,2R,4S)-5,6-bis(chloromethyl)bicyclo[2.2.1]heptan-2-ol and (1S,2S,4S)-5,6-bis(chloromethyl)bicyclo[2.2.1]heptan-2-ol, (1R,2R,4R)-5,6-bis(chloromethyl)bicyclo[2.2.1]heptan-2-ol (19.0 g crude, 101 mmol, 1.00 equiv) in ethanol (150 mL), followed by the addition of potassium hydroxide (15.82 g, 282 mmol, 2.80 equiv) in portions. The resulting mixture was stirred for 16 hours at 80° C. The mixture was then cooled to RT and diluted with water and extracted with dichloromethane. The organic layers were combined and concentrated under vacuum. The crude product was purified by flash chromatography eluting with ethyl acetate/petroleum ether (1/5) to afford 5.60 g (2-step: 41%) of (1R,2S,4R)-5,6-dimethylidenebicyclo[2.2.1]-heptan-2-ol, (1S,2R,4S)-5,6-dimethylidenebicyclo[2.2.1]heptan-2-ol, (1R,2R,4R)-5,6-dimethylidenebicyclo[2.2.1]heptan-2-ol and (1S,2S,4S)-5,6-dimethylidenebicyclo[2.2.1]heptan-2-ol as a yellow oil.

Step 4:
Into a 40-mL sealed tube, was placed a mixture of (1R,2S,4R)-5,6-dimethylidenebicyclo[2.2.1]heptan-2-ol, (1S,2R,4S)-5,6-dimethylidenebicyclo[2.2.1]heptan-2-ol, (1R,2R,4R)-5,6-dimethylidenebicyclo[2.2.1]heptan-2-ol and (1S,2S,4S)-5,6-dimethylidenebicyclo[2.2.1]heptan-2-ol (1.90 g, 14.0 mmol, 1.00 equiv), methyl prop-2-ynoate (8.21 g, 97.7 mmol, 7.00 equiv) and benzene (35 mL). The resulting mixture was stirred for 2 hours at 100° C. in an oil bath. The mixture was then concentrated under vacuum to afford 3.12 g (crude) of methyl (1R,8R,10S)-10-hydroxytricyclo[6.2.1.0$^{2,7}$]undeca-2(7),4-diene-4-carboxylate, methyl (1R,8R,10R)-10-hydroxytricyclo[6.2.1.0$^{2,7}$]undeca-2(7),4-diene-4-carboxylate, methyl (1S,8S,10S)-10-hydroxytricyclo[6.2.1.0$^{2,7}$]undeca-2(7),4-diene-4-carboxylate, methyl (1S,8S,10R)-10-hydroxytricyclo[6.2.1.0$^{2,7}$]undeca-2(7),4-diene-4-carboxylate, methyl (1S,8S,9R)-9-hydroxytricyclo[6.2.1.0$^{2,7}$]undeca-2(7),4-diene-4-carboxylate, methyl (1S,8S,9S)-9-hydroxytricyclo[6.2.1.0$^{2,7}$]undeca-2(7),4-diene-4-carboxylate, methyl (1R,8R,9R)-9-hydroxytricyclo[6.2.1.0$^{2,7}$]undeca-2(7),4-diene-4-carboxylate and methyl (1R,8R,9S)-9-hydroxytricyclo[6.2.1.0$^{2,7}$]undeca-2(7),4-diene-4-carboxylate as brown oil, which was used directly for the next step without any purification.

Step 5:
Into a 100-mL round-bottom flask, was placed a solution of methyl (1R,8R,10S)-10-hydroxytricyclo[6.2.1.0$^{2,7}$]undeca-2(7),4-diene-4-carboxylate, methyl (1R,8R,10R)-10-hydroxytricyclo[6.2.1.0$^{2,7}$]undeca-2(7),4-diene-4-carboxylate, methyl (1S,8S,10S)-10-hydroxy-tricyclo[6.2.1.0$^{2,7}$]undeca-2(7),4-diene-4-carboxylate, methyl (1S,8S,10R)-10-hydroxytricyclo-[6.2.1.0$^{2,7}$]undeca-2(7),4-diene-4-carboxylate, methyl (1S,8S,9R)-9-hydroxytricyclo[6.2.1.0$^{2,7}$]-undeca-2(7),4-diene-4-carboxylate, methyl (1S,8S,9S)-9-hydroxytricyclo[6.2.1.0$^{2,7}$]undeca-2(7),4-diene-4-carboxylate, methyl (1R,8R,9R)-9-hydroxytricyclo[6.2.1.0$^{2,7}$]undeca-2(7),4-diene-4-carboxylate and methyl (1R, 8R,9S)-9-hydroxytricyclo[6.2.1.0$^{2,7}$]undeca-2(7),4-diene-4-carboxylate (3.12 g crude, 14.0 mmol, 1.00 equiv) in benzene (50 mL) followed by 2,3-dichloro-5,6-dicyano-1,4-benzoquinone (DDQ; 6.36 g, 28.02 mmol, 2.00 equiv) in portions at 0° C. The resulting mixture was stirred for 16 hours at room temperature. The reaction mixture was then quenched by the addition of 200 mL of 5% aqueous Na$_2$S$_2$O$_5$ solution and stirred for 30 minutes. The solids were separated by filtration and washed with petroleum ether (PE; 20 mL) and the filtrate was extracted with ethyl acetate. The organic layers were combined, washed with 5% Na$_2$S$_2$O$_5$ solution and saturated sodium bicarbonate solution and concentrated under vacuum. The residue was purified by flash chromatography eluting with ethyl acetate/petroleum ether (1/5) to afford 2.58 g (2-steps yield: 83%) of methyl (1R,8R,10S)-10-hydroxytricyclo[6.2.1.0$^{2,7}$]undeca-2,4,6-triene-4-carboxylate, methyl (1R,8R,10R)-10-hydroxytricyclo[6.2.1.0$^{2,7}$]undeca-2,4,6-triene-4-carboxylate, methyl (1S,8S,10S)-10-hydroxytricyclo[6.2.1.0$^{2,7}$]undeca-2,4,6-triene-4-carboxylate, methyl (1S,8S,10R)-10-hydroxytricyclo[6.2.1.0$^{2,7}$]undeca-2,4,6-triene-4-carboxylate, methyl (1S,8S,9R)-9-hydroxytricyclo[6.2.1.0$^{2,7}$]undeca-2,4,6-triene-4-carboxylate, methyl (1S,8S,9S)-9-hydroxytricyclo[6.2.1.0$^{2,7}$]undeca-2,4,6-triene-4-carboxylate, methyl (1R,8R,9R)-9-hydroxy-tricyclo[6.2.1.0$^{2,7}$]undeca-2,4,6-triene-4-carboxylate and methyl (1R,8R,9S)-9-hydroxy-tricyclo[6.2.1.0$^{2,7}$]undeca-2,4,6-triene-4-carboxylate as brown oil.

Step 6:

Into a 100-mL round-bottom flask, was placed a solution of methyl (1R,8R,10S)-10-hydroxytricyclo[6.2.1.0$^{2,7}$]undeca-2,4,6-triene-4-carboxylate, methyl (1R,8R,10R)-10-hydroxytricyclo[6.2.1.0$^{2,7}$]undeca-2,4,6-triene-4-carboxylate, methyl (1S,8S,10S)-10-hydroxy-tricyclo[6.2.1.0$^{2,7}$]undeca-2,4,6-triene-4-carboxylate, methyl (1S,8S,10R)-10-hydroxytricyclo-[6.2.1.0$^{2,7}$]undeca-2,4,6-triene-4-carboxylate, methyl (1S,8S,9R)-9-hydroxytricyclo[6.2.1.0$^{2,7}$]-undeca-2,4,6-triene-4-carboxylate, methyl (1S,8S,9S)-9-hydroxytricyclo[6.2.1.0$^{2,7}$]undeca-2,4,6-triene-4-carboxylate, methyl (1R,8R,9R)-9-hydroxytricyclo[6.2.1.0$^{2,7}$]undeca-2,4,6-triene-4-carboxylate and methyl (1R,8R,9S)-9-hydroxytricyclo[6.2.1.0$^{2,7}$]undeca-2,4,6-triene-4-carboxylate (1.50 g, 6.87 mmol, 1.00 equiv) in dichloromethane (30 mL) followed by Dess-Martin reagent (5.83 g, 13.8 mmol, 2.00 equiv) in portions at 0° C. and 0.5 mL of H$_2$O. The resulting mixture was stirred for 16 hours at 20° C. The solids were then separated by filtration and the filtrate was concentrated under vacuum. The residue was diluted with 50 mL of saturated sodium bicarbonate solution and extracted with ethyl acetate. The organic layers were combined, washed with brine, dried over anhydrous sodium sulfate and concentrated under vacuum. The residue was purified by flash chromatography eluting with ethyl acetate/petroleum ether (1/5) to afford 760 mg (51%) of (±)-methyl 10-oxotricyclo-[6.2.1.0$^{2,7}$]-undeca-2,4,6-triene-4-carboxylate and (±)-methyl 9-oxotricyclo[6.2.1.0$^{2,7}$]undeca-2,4,6-triene-4-carboxylate as yellow oil.

Step 7:

Into a 100-mL 3-necked round-bottom flask purged and maintained with an inert atmosphere of nitrogen, was placed tetrahydrofuran (50 mL) with stirring at −78° C., followed by the drop-wise addition of n-BuLi (5.12 mL, 2.5 M in hexane, 12.74 mmol, 1.10 equiv). A solution of 3-bromo-1-benzofuran (2.51 g, 12.74 mmol, 1.10 equiv) in tetrahydrofuran (10 mL) was then added drop-wise with stirring at −78° C. and the resulting mixture was stirred at −78° C. for an additional 1 h. A mixture of (±)-methyl 10-oxotricyclo[6.2.1.0$^{2,7}$]undeca-2,4,6-triene-4-carboxylate and (±)-methyl 9-oxotricyclo[6.2.1.0$^{2,7}$]undeca-2,4,6-triene-4-carboxylate (2.50 g, 11.56 mmol, 1.00 equiv) in tetrahydrofuran (10 mL) was then added dropwise and the reaction mixture was stirred for an additional 60 minutes at −78° C. The reaction was then carefully quenched by the addition of 100 mL of saturated aqueous NH$_4$Cl solution and extracted with 3×100 mL of ethyl acetate. The organic layers were combined, washed with 1×100 mL of brine, dried over anhydrous sodium sulfate and concentrated under vacuum to afford 3.71 g (96%) of methyl (1R,8R,10S)-10-(1-benzofuran-3-yl)-10-hydroxytricyclo[6.2.1.0$^{2,7}$]undeca-2,4,6-triene-4-carboxylate, methyl (1R,8R,10R)-10-(1-benzofuran-3-yl)-10-hydroxytricyclo[6.2.1.0$^{2,7}$]undeca-2,4,6-triene-4-carboxylate, methyl (1S,8S,10S)-10-(1-benzofuran-3-yl)-10-hydroxytricyclo[6.2.1.0$^{2,7}$]undeca-2,4,6-triene-4-carboxylate, methyl (1S,8S,10R)-10-(1-benzofuran-3-yl)-10-hydroxytricyclo[6.2.1.0$^{2,7}$]undeca-2,4,6-triene-4-carboxylate, methyl (1R,8R,9S)-9-(1-benzofuran-3-yl)-10-hydroxytricyclo[6.2.1.0$^{2,7}$]undeca-2,4,6-triene-4-carboxylate, methyl (1R,8R,9R)-9-(1-benzofuran-3-yl)-10-hydroxytricyclo[6.2.1.0$^{2,7}$]undeca-2,4,6-triene-4-carboxylate, methyl (1S,8S,9S)-9-(1-benzofuran-3-yl)-10-hydroxytricyclo[6.2.1.0$^{2,7}$]undeca-2,4,6-triene-4-carboxylate and methyl (1S,8S,9R)-9-(1-benzofuran-3-yl)-10-hydroxytricyclo[6.2.1.0$^{2,7}$]undeca-2,4,6-triene-4-carboxylate as a yellow solid, which was used for next step without further purification. LCMS (ES) [M+CH$_3$CN+1]$^+$ m/z 376.0.

Step 8:

Into a 50-mL round-bottom flask, was placed a mixture of methyl (1R,8R,10S)-10-(1-benzofuran-3-yl)-10-hydroxytricyclo[6.2.1.0$^{2,7}$]undeca-2,4,6-triene-4-carboxylate, methyl (1R,8R,10R)-10-(1-benzofuran-3-yl)-10-hydroxytricyclo[6.2.1.0$^{2,7}$]undeca-2,4,6-triene-4-carboxylate, methyl (1S,8S,10S)-10-(1-benzofuran-3-yl)-10-hydroxytricyclo[6.2.1.0$^{2,7}$]undeca-2,4,6-triene-4-carboxylate, methyl (1S,8S,10R)-10-(1-benzofuran-3-yl)-10-hydroxytricyclo[6.2.1.0$^{2,7}$]undeca-2,4,6-triene-4-carboxylate, methyl (1R,8R,9S)-9-(1-benzofuran-3-yl)-10-hydroxytricyclo[6.2.1.0$^{2,7}$]undeca-2,4,6-triene-4-carboxylate, methyl (1R,8R,9R)-9-(1-benzofuran-3-yl)-10-hydroxytricyclo[6.2.1.0$^{2,7}$]undeca-2,4,6-triene-4-carboxylate, methyl (1S,8S,9S)-9-(1-benzofuran-3-yl)-10-hydroxytricyclo-[6.2.1.0$^{2,7}$]undeca-2,4,6-triene-4-carboxylate and methyl (1S,8S,9R)-9-(1-benzofuran-3-yl)-10-hydroxytricyclo[6.2.1.0$^{2,7}$]undeca-2,4,6-triene-4-carboxylate (1.00 g, 2.99 mmol, 1.00 equiv), dichloromethane (20.0 mL) and TEA (906 mg, 8.95 mmol, 2.50 equiv) followed by the drop-wise addition of MsCl (682 mg, 2.00 equiv) with stirring at 0° C. The resulting mixture was stirred for 2 h at 20° C. then it was diluted with 50 mL of DCM, washed with 1×30 mL of H$_2$O, 1×30 mL of brine, dried over anhydrous sodium sulfate and concentrated under vacuum. The residue was purified by flash chromatography eluting with ethyl acetate/petroleum ether (1/3) to afford 621 mg of a 1:1 mixture of (±)-methyl 10-(1-benzofuran-3-yl)tricyclo[6.2.1.0$^{2,7}$]undeca-2,4,6,9-tetraene-4-carboxylate and (±)-methyl 9-(1-benzofuran-3-yl)tricyclo[6.2.1.0$^{2,7}$]undeca-2,4,6,9-tetraene-4-carboxylate (66%) as a yellow solid.

Step 9:

Into a 100-mL round-bottom flask, was placed a 1:1 mixture of (±)-methyl 10-(1-benzofuran-3-yl)tricyclo[6.2.1.0$^{2,7}$]undeca-2,4,6,9-tetraene-4-carboxylate and (±)-methyl 9-(1-benzofuran-3-yl)tricyclo[6.2.1.0$^{2,7}$]undeca-2,4,6,9-tetraene-4-carboxylate (300 mg, 0.95 mmol, 1.00 equiv), LiOH.H$_2$O (199 mg, 4.74 mmol, 5.00 equiv), methanol (15.0 mL) and water (5.0 mL). The resulting mixture was stirred for 2 hours at 60° C. then it was cooled to RT, diluted with 50 mL of water and the pH value of the aqueous phase was adjusted to 3 with 1 N HCl aqueous solution. The mixture was then extracted with 2×50 mL of a mixed solvents of DCM/MeOH (10/1) and the organic layer was dried and concentrated to afford 193 mg (67%) of (±)-10-(1-benzofuran-3-yl)tricyclo[6.2.1.0$^{2,7}$]undeca-2,4,6,9-tetraene-4-carboxylic acid and (±)-9-(1-benzofuran-3-yl)tricyclo[6.2.1.0$^{2,7}$]undeca-2,4,6,9-tetraene-4-carboxylic acid as yellow oil, which was used for the next step without further purification.

Step 10:

Into a 25-mL round-bottom flask, was placed 5-(aminomethyl)-4,6-dimethylpyridin-2-amine (84 mg, 0.56 mmol, 1.20 equiv), N,N-dimethylformamide (5.00 mL), (±)-10-(1-benzofuran-3-yl)tricyclo[6.2.1.0$^{2,7}$]undeca-2,4,6,9-tetraene-4-carboxylic acid and (±)-9-(1-benzofuran-3-yl)tricyclo[6.2.1.0$^{2,7}$]undeca-2,4,6,9-tetraene-4-carboxylic acid (1:1 mixture; 140 mg, 0.46 mmol, 1.00 equiv), TEA (234 mg, 2.31 mmol, 5.00 equiv) and HATU (194 mg, 0.51 mmol, 1.10 equiv). The resulting mixture was stirred for 3 hours at room temperature. The solution was then diluted with 50 mL of water and extracted with 2×50 mL of ethyl acetate. The organic layers were dried and concentrated under reduced pressure and the residue was purified by flash chromatography eluting with methanol/EtOAc (1/8). The collected fractions were concentrated and lyophilized to afford 120 mg (60%) of (±)-N-[(6-amino-2,4-dimethylpyridin-3-yl)methyl]-10-(1-benzofuran-3-yl)tricycle-[6.2.1.0$^{2,7}$]undeca-2,4,6,9-tetraene-4-carboxamide and (±)-N-[(6-amino-2,4-dimethylpyridin-3-yl)methyl]-9-(1-benzofuran-3-yl)tricyclo[6.2.1.0$^{2,7}$]-undeca-2,4,6,9-tetraene-4-carboxamide (1:1 mixture) as light yellow solids. MS: (M+H)$^+$ found for $C_{28}H_{25}N_3O_2$: 436.1.

Example 83

Synthesis of (±)-N-[(6-amino-2,4-dimethylpyridin-3-yl)methyl]-10-phenyltricyclo-[6.2.1.0$^{2,7}$]undeca-2,4,6,9-tetraene-4-carboxamide and (±)-N-[(6-amino-2,4-dimethylpyridin-3-yl)methyl]-9-phenyltricyclo[6.2.1.0$^{2,7}$]undeca-2,4,6,9-tetraene-4-carboxamide

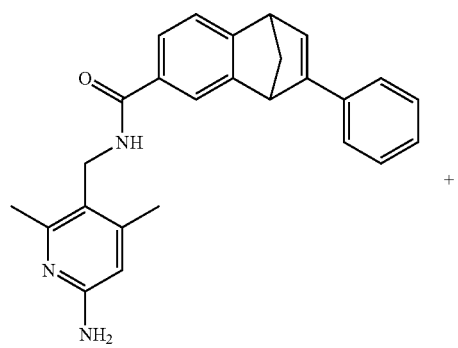

+

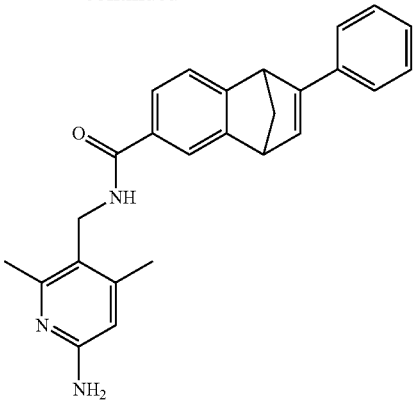

Step 1:

Into a 50-mL 3-necked round-bottom flask purged and maintained with an inert atmosphere of nitrogen, was placed tetrahydrofuran (10.0 mL) and n-BuLi (1.17 mL, 2.5 M in hexane, 2.90 mmol, 1.05 equiv) with stirring at −78° C. Bromobenzene (456 mg, 2.90 mmol, 1.05 equiv) in tetrahydrofuran (5 mL) was then added drop-wise at −78° C. abd the resulting mixture was stirred for 60 minutes at −78° C. A solution of methyl (±)-methyl 10-oxotricyclo[6.2.1.0$^{2,7}$]-undeca-2,4,6-triene-4-carboxylate and (±)-methyl 9-oxotricyclo-[6.2.1.0$^{2,7}$]undeca-2,4,6-triene-4-carboxylate (1; 1 mixture; 600 mg, 2.77 mmol, 1.00 equiv) in tetrahydrofuran (5 mL) was then added drop-wise and the resulting mixture was stirred for an additional 60 minutes at −78° C. The reaction was then quenched by the addition of 30 mL of saturated $NH_4Cl$ solution and 20 mL of $H_2O$. The aqueous phase was extracted with ethyl acetate, the organic layers were combined, washed with brine, dried over anhydrous sodium sulfate and concentrated under vacuum. The crude material was purified by flash chromatography eluting with ethyl acetate/petroleum ether (1/5) to afford 250 mg (31%) of a mixture of methyl (1R,8R,10S)-10-hydroxy-10-phenyltricyclo[6.2.1.0$^{2,7}$]undeca-2,4,6-triene-4-carboxylate, methyl (1R,8R,10R)-10-hydroxy-10-phenyltricyclo[6.2.1.0$^{2,7}$]undeca-2,4,6-triene-4-carboxylate, methyl (1S,8S,10R)-10-hydroxy-10-phenyltricyclo[6.2.1.0$^{2,7}$]undeca-2,4,6-triene-4-carboxylate, methyl (1S,8S,10S)-10-hydroxy-10-phenyltricyclo[6.2.1.0$^{2,7}$]-undeca-2,4,6-triene-4-carboxylate, methyl (1R,8R,9S)-9-hydroxy-9-phenyltricyclo-[6.2.1.0$^{2,7}$]undeca-2,4,6-triene-4-carboxylate, methyl (1R,8R,9R)-9-hydroxy-9-phenyltricyclo[6.2.1.0$^{2,7}$]undeca-2,4,6-triene-4-carboxylate, methyl (1S,8S,9R)-9-hydroxy-9-phenyltricyclo[6.2.1.0$^{2,7}$]undeca-2,4,6-triene-4-carboxylate and methyl (1S,8S,9S)-9-hydroxy-9-phenyltricyclo[6.2.1.0$^{2,7}$]undeca-2,4,6-triene-4-carboxylate as colorless oil.

Step 2:

Into a 25-mL round-bottom flask, was placed a solution of a mixture of methyl (1R,8R,10S)-10-hydroxy-10-phenyltricyclo[6.2.1.0$^{2,7}$]undeca-2,4,6-triene-4-carboxylate, methyl (1R,8R,10R)-10-hydroxy-10-phenyltricyclo[6.2.1.0$^{2,7}$]undeca-2,4,6-triene-4-carboxylate, methyl (1S,8S,10R)-10-hydroxy-10-phenyltricyclo[6.2.1.0$^{2,7}$]undeca-2,4,6-triene-4-carboxylate, methyl (1S,8S,10S)-10-hydroxy-10-phenyltricyclo[6.2.1.0$^{2,7}$]undeca-2,4,6-triene-4-carboxylate, methyl (1R,8R,9S)-9-hydroxy-9-phenyltricyclo[6.2.1.0$^{2,7}$]-undeca-2,4,6-triene-4-carboxylate, methyl (1R,8R,9R)-9-hydroxy-9-phenyltricyclo[6.2.1.0$^{2,7}$]undeca-2,4,6-triene-4-carboxylate, methyl (1S,8S,9R)-9-hydroxy-9-phenyltricyclo[6.2.1.0$^{2,7}$]undeca-2,4,6-triene-4-carboxylate and methyl

447

(1S,8S,9S)-9-hydroxy-9-phenyltricyclo[6.2.1.0$^{2,7}$]undeca-2,4,6-triene-4-carboxylate (200 mg, 0.68 mmol, 1.00 equiv) and TEA (172 mg, 1.70 mmol, 2.50 equiv) in dichloromethane (5.00 mL) with stirring at 0° C. MsCl (155 mg, 2.00 equiv) was then added drop-wise and the resulting mixture was stirred for 4 hours at 20° C. The mixture was then diluted with H$_2$O and extracted with dichloromethane. The organic layers were combined, washed with brine, dried over anhydrous sodium sulfate and concentrated under vacuum. The residue was purified by prep-TLC (PE/EtOAc=1/1) to afford 53 mg (28%) of a 1:1 mixture of (±)-methyl 10-phenyltricyclo[6.2.1.0$^{2,7}$]undeca-2,4,6,9-tetraene-4-carboxylate and (±)-methyl 9-phenyltricyclo[6.2.1.0$^{2,7}$]undeca-2,4,6,9-tetraene-4-carboxylate as brown oil.

Step 3:

Into a 25-mL round-bottom flask, was placed a 1:1 mixture of (±)-methyl 10-phenyltricyclo[6.2.1.0$^{2,7}$]undeca-2,4,6,9-tetraene-4-carboxylate and (±)-methyl 9-phenyltricyclo[6.2.1.0$^{2,7}$]undeca-2,4,6,9-tetraene-4-carboxylate (53 mg, 0.19 mmol, 1.00 equiv), methanol (3 mL), LiOH.H$_2$O (40 mg, 0.95 mmol, 5.00 equiv) and water (0.5 mL). The resulting mixture was stirred for 60 minutes at 80° C., then it was cooled to RT and concentrated under vacuum. The residue was diluted with 10 mL of H$_2$O and the pH value of the solution was adjusted to 3 with 2 N aqueous hydrogen chloride solution. The aqueous phase was extracted with 5×10 mL of a mixed solution of DCM/MeOH (10/1). The combined organic layers were dried over anhydrous sodium sulfate and concentrated under vacuum to afford 36 mg (72%) of a 1:1 mixture of (±)-10-phenyltricyclo[6.2.1.0$^{2,7}$]undeca-2,4,6,9-tetraene-4-carboxylic acid and (±)-9-phenyltricyclo[6.2.1.0$^{2,7}$]undeca-2,4,6,9-tetraene-4-carboxylic acid as yellow oil, which was used directly for next step without any further purification.

Step 4:

Into a 25-mL round-bottom flask, was placed a mixture of a 1:1 mixture of (±)-10-phenyltricyclo[6.2.1.0$^{2,7}$]undeca-2,4,6,9-tetraene-4-carboxylic acid and (±)-9-phenyltricyclo[6.2.1.0$^{2,7}$]undeca-2,4,6,9-tetraene-4-carboxylic acid (36 mg, 0.14 mmol, 1.00 equiv), N,N-dimethylformamide (3.00 mL), 5-(aminomethyl)-4,6-dimethylpyridin-2-amine (21 mg, 0.14 mmol, 1.00 equiv), DIEA (43 mg, 0.33 mmol, 2.35 equiv) and HATU (78 mg, 0.21 mmol, 1.50 equiv). The resulting mixture was stirred for 1 h at room temperature, then it was diluted with 5 mL of H$_2$O and the precipitate thus formed was collected by filtration. The crude product was subjected to reverse preparative HPLC (Prep-C18, 5 µM XBridge column, 19×150 mm, waters; gradient elution of 25% MeCN in water to 55% MeCN in water over a 8 min period, where the aqueous phase contains 10 mM NH$_4$HCO$_3$+0.5% ammonia) to provide 13.4 mg (25%) of a 1:1 mixture of (±)-N-[(6-amino-2,4-dimethylpyridin-3-yl)methyl]-10-phenyltricyclo[6.2.1.0$^{2,7}$]undeca-2,4,6,9-tetraene-4-carboxamide and (±)-N-[(6-amino-2,4-dimethylpyridin-3-yl)methyl]-9-phenyltricyclo[6.2.1.0$^{2,7}$]undeca-2,4,6,9-tetraene-4-carboxamide as a white solid. MS: (M+H)$^+$ found for C$_{26}$H$_{25}$N$_3$O: 396.1

Example 84

Synthesis of (±)-N-[(6-amino-4-methoxy-2-methylpyridin-3-yl)methyl]-12-[(1H-pyrazol-1-yl)-methyl]-15-oxatetracyclo[6.6.1.0$^{2,7}$.0$^{9,14}$]pentadeca-2,4,6,9,11,13-hexaene-4-carboxamide

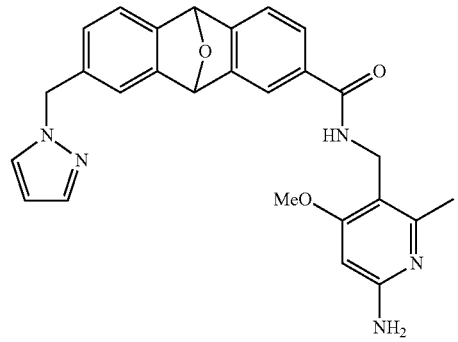 [SMILES: COc1cc(N)nc(C)c1CNC(=O)c1ccc2c(c1)C1OC2c2ccc(Cn3cccn3)cc21]

Step 1:

Into a 500-mL 3-necked round-bottom flask, was placed a mixture of 1,4-dioxane (300 mL), acetyl acetate (44.77 g, 438.54 mmol, 1.20 equiv), 2-cyanoacetic acid (37.1 g, 436.16 mmol, 1.20 equiv) and (2Z)-3-aminobut-2-enenitrile (30 g, 365.39 mmol, 1.00 equiv). The resulted solution was heated to reflux for 2 h. The reaction mixture was then cooled to room temperature with a water/ice bath and the solids were collected by filtration to afford 23.2 g (crude) of (2Z)-2-(1-aminoethylidene)-3-oxopentanedinitrile as a yellow solid. This material was used for the next step without further purification.

Step 2:

Into a 500-mL round-bottom flask, was placed a mixture of ethanol (300 mL), (2Z)-2-(1-aminoethylidene)-3-oxopentanedinitrile (23.0 g, 154.21 mmol, 1.00 equiv) and sodium ethoxide (11.0 g, 161.65 mmol, 1.05 equiv). The resulted mixture was heated to reflux for 1 h. The reaction mixture was then cooled to room temperature with a water/ice bath and concentrated under vacuum to afford 20.5 g (crude) of 6-amino-2-methyl-4-oxo-1,4-dihydropyridine-3-carbonitrile as a yellow solid. This material was used for the next step without further purification.

Step 3:

Into a 500-mL 3-necked round-bottom flask, was placed a mixture of K$_2$CO$_3$ (27.74 g, 199.26 mmol, 1.50 equiv) and 6-amino-2-methyl-4-oxo-1,4-dihydropyridine-3-carbonitrile (20 g, 134.09 mmol, 1.00 equiv) in N,N-dimethylformamide (200 mL) with stirring at 0° C., followed by the drop-wise addition of iodomethane (22.86 g, 161.06 mmol, 1.20 equiv). The resulting solution was stirred overnight at room temperature, then it was quenched by the addition of water/ice and the solids were collected by filtration to afford 13.5 g (62%) of 6-amino-4-methoxy-2-methylpyridine-3-carbonitrile as a yellow solid.

Step 4:

Into a 50-mL round-bottom flask, was placed a mixture of 6-amino-4-methoxy-2-methylpyridine-3-carbonitrile (330 mg, 2.02 mmol, 1.00 equiv), methanol (23 mL) and Raney Ni (100 mg) under N$_2$. The mixture was degassed and purged with hydrogen four times. The resulting mixture was stirred for 16 h at room temperature under a hydrogen atmosphere (balloon). The mixture was then filtered through a pad of Celite and the filtrate was concentrated under vacuum. The crude product was purified by Prep.TLC eluting with DMC/MeOH (ratio: 5/1) to afford 80 mg (24%) of 5-(aminomethyl)-4-methoxy-6-methylpyridin-2-amine as a white solid.

Step 5:

Into a 500-mL round-bottom flask, was placed a mixture of (±) sodium 12-bromo-15-oxatetracyclo[6.6.1.0$^{2,7}$.0$^{9,14}$] pentadeca-2,4,6,9,11,13-hexaene-4-carboxylate (INT-5a) (500 mg, 1.47 mmol, 1.00 equiv), dioxane (80 mL), MeOH (20 mL), trimethyl-1,3,5,2,4,6-trioxatriborinane (876 mg, 2.96 mmol, 2.00 equiv, 50% in THF), Cs$_2$CO$_3$ (1.21 g, 3.71 mmol, 2.50 equiv) and Pd(dppf)Cl$_2$ (108 mg, 0.15 mmol, 0.10 equiv). The resulting mixture was stirred for 1 hour at 80° C. then it was cooled to RT and the solids were separated by filtration and washed with MeOH. The filtrate was concentrated under vacuum to afford 1.06 g of crude (±) sodium 12-methyl-15-oxatetracyclo[6.6.1.0$^{2,7}$.0$^{9,14}$]pentadeca-2,4,6,9,11,13-hexaene-4-carboxylate as a brown solid, which was used directly for next step without further purification.

Step 6:

Into a 100-mL round-bottom flask, was placed a mixture of (±) sodium 12-methyl-15-oxatetracyclo[6.6.1.0$^{2,7}$.0$^{9,14}$] pentadeca-2,4,6,9,11,13-hexaene-4-carboxylate (1.06 g crude, 1.47 mmol, 1.00 equiv) in N,N-dimethylformamide (30 mL) with stirring at rt, followed by the drop-wise addition of iodomethane (851 mg, 6.00 mmol, 4.00 equiv). The resulting mixture was stirred for 2 hours at room temperature then it was diluted with water and extracted with ethyl acetate. The combined organic layers were washed with brine, dried over anhydrous sodium sulfate and concentrated under vacuum. The residue was purified by silica gel chromatography eluting with ethyl acetate/petroleum ether (1/5) to afford 389 mg (99% over 2 steps) of (±)-methyl 12-methyl-15-oxatetracyclo[6.6.1.0$^{2,7}$.0$^{9,14}$]pentadeca-2,4,6,9,11,13-hexaene-4-carboxylate as a yellow solid.

Step 7:

Into a 50-mL round-bottom flask, was placed a mixture of (±)-methyl 12-methyl-15-oxatetracyclo[6.6.1.0$^{2,7}$.0$^{9,14}$]pentadeca-2,4,6,9,11,13-hexaene-4-carboxylate (350 mg, 1.31 mmol, 1.00 equiv), CCl$_4$ (20 mL) and NBS (258 mg, 1.45 mmol, 1.10 equiv) with stirring at rt, followed by the addition of AIBN (22 mg, 0.13 mmol, 0.10 equiv). The resulting mixture was stirred for 3 hours at 80° C. then it was cooled to RT and the solids were separated by filtration and washed with 3×5 mL of CCl$_4$. The filtrate was concentrated under vacuum to afford 580 mg of crude (±)-methyl 12-(bromomethyl)-15-oxatetracyclo[6.6.1.0$^{2,7}$.0$^{9,14}$]pentadeca-2,4,6,9,11,13-hexaene-4-carboxylate as a yellow solid, which was used directly for next step without any further purification.

Step 8:

Into a 100-mL round-bottom flask, was placed a mixture of (±)-methyl 12-(bromomethyl)-15-oxatetracyclo[6.6.1.0$^{2,7}$.0$^{9,14}$]pentadeca-2,4,6,9,11,13-hexaene-4-carboxylate (580 mg crude, 1.31 mmol, 1.00 equiv), CH$_3$CN (20 mL), 1H-pyrazole (85 mg, 1.31 mmol, 1.00 equiv) and Cs$_2$CO$_3$ (682 mg, 2.09 mmol, 1.60 equiv). The resulting mixture was stirred for 3 hours at room temperature then the solids were separated by filtration and washed with 3×10 mL of CH$_3$CN. The filtrate was concentrated under vacuum and the residue was purified by Prep-TLC (ethyl acetate/petroleum ether=1/1) to afford 124 mg (27% yield over 2 steps) of (±)-methyl 12-(1H-pyrazol-1-ylmethyl)-15-oxatetracyclo-[6.6.1.0$^{2,7}$.0$^{9,14}$]pentadeca-2,4,6,9,11,13-hexaene-4-carboxylate as a yellow solid.

Step 9:

Into a 50-mL round-bottom flask, was placed a solution of (±)-methyl 12-(1H-pyrazol-1-ylmethyl)-15-oxatetracyclo [6.6.1.0$^{2,7}$.0$^{9,14}$]pentadeca-2,4,6,9,11,13-hexaene-4-carboxylate (78 mg, 0.23 mmol, 1.00 equiv) in methanol (6.00 mL) with stirring, followed by the addition of a solution of sodium hydroxide (47 mg, 1.18 mmol, 5.00 equiv) in water (1.00 mL). The resulting mixture was stirred for 3 hours at 60° C. then it was cooled to RT and the pH value of the solution was adjusted to 3 with aqueous 2N hydrogen chloride solution. The mixture was then concentrated under vacuum and the residue was treated with ethyl acetate. The solids were separated by filtration and washed with ethyl acetate. The filtrate was concentrated under vacuum to afford 75 mg (100%) of (±)-12-(1H-pyrazol-1-ylmethyl)-15-oxatetracyclo[6.6.1.0$^{2,7}$.0$^{9,14}$]pentadeca-2,4,6,9,11,13-hexaene-4-carboxylic acid as a yellow solid.

Step 10:

Into a 8-mL vial, was placed a mixture of (±)-12-(1H-pyrazol-1-ylmethyl)-15-oxatetracyclo[6.6.1.0$^{2,7}$.0$^{9,14}$]pentadeca-2,4,6,9,11,13-hexaene-4-carboxylic acid (83 mg, 0.26 mmol, 1.00 equiv), N,N-dimethylformamide (2.00 mL), 5-(aminomethyl)-4-methoxy-6-methylpyridin-2-amine (42 mg, 0.26 mmol, 1.00 equiv), DIEA (68 mg, 0.52 mmol, 2.00 equiv) and HATU (198 mg, 0.52 mmol, 2.00 equiv). The resulting mixture was stirred for 1 hour at room temperature then it was filtered and subjected to reverse preparative HPLC (Prep-C18, 5 μM XBridge column, 19×150 mm, waters; gradient elution of 28% MeCN in water to 40% MeCN in water over a 4 min period, 40% MeCN in water to 70% MeCN in water over an 8 min period, where the aqueous phase contained 10 mM NH$_4$HCO$_3$ and 0.5% ammonia) to provide (±)-N-[(6-amino-4-methoxy-2-methylpyridin-3-yl)methyl]-12-[(1H-pyrazol-1-yl)methyl]-15-oxatetracyclo[6.6.1.0$^{2,7}$.0$^{9,14}$]pentadeca-2,4,6,9,11,13-hexaene-4-carboxamide as a white solid (23.3 mg, 19%). MS: (M+H)$^+$ found for C$_{27}$H$_{25}$N$_5$O$_3$: 468.2.

Example 85

Synthesis of (±)-N-[(6-amino-4-methoxy-2-methylpyridin-3-yl)methyl]-12-[(4-methyl-1H-pyrazol-1-yl)methyl]-15-oxatetracyclo[6.6.1.0$^{2,7}$.0$^{9,14}$]pentadeca-2,4,6,9,11,13-hexaene-4-carboxamide

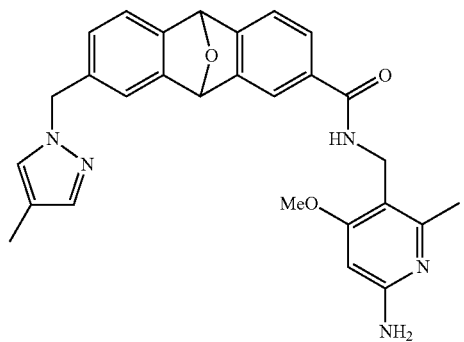

The title compound was prepared following the procedures described for Example 84 but using 4-methyl-1H- pyrazole instead of 1H-pyrazole in Step 8. MS: (M+H)+ found for $C_{28}H_{27}N_5O_3$: 482.2.

Example 86

Synthesis of (±)-N-[(6-amino-4-ethoxy-2-methyl-pyridin-3-yl)methyl]-12-(2,4-difluorophenyl)-16-oxo-15-azatetracyclo[6.6.2.0$^{2,7}$.0$^{9,14}$]hexadeca-2,4,6,9,11,13-hexaene-4-carboxamide, (±)-N-[(6-amino-4-ethoxy-2-methylpyridin-3-yl)methyl]-11-(2,4-difluorophenyl)-16-oxo-15-azatetracyclo[6.6.2.0$^{2,7}$.0$^{9,14}$]hexadeca-2,4,6,9,11,13-hexaene-4-carboxamide, (±)-N-[(6-amino-4-ethoxy-2-methylpyridin-3-yl)methyl]-12-(2,4-difluorophenyl)-16-oxo-15-azatetracyclo[6.6.2.0$^{2,7}$.0$^{9,14}$]hexadeca-2,4,6,9,11,13-hexaene-5-carboxamide and (±)-N-[(6-amino-4-ethoxy-2-methylpyridin-3-yl)methyl]-11-(2,4-difluorophenyl)-16-oxo-15-azatetracyclo[6.6.2.0$^{2,7}$.0$^{9,14}$]hexadeca-2,4,6,9,11,13-hexaene-5-carboxamide

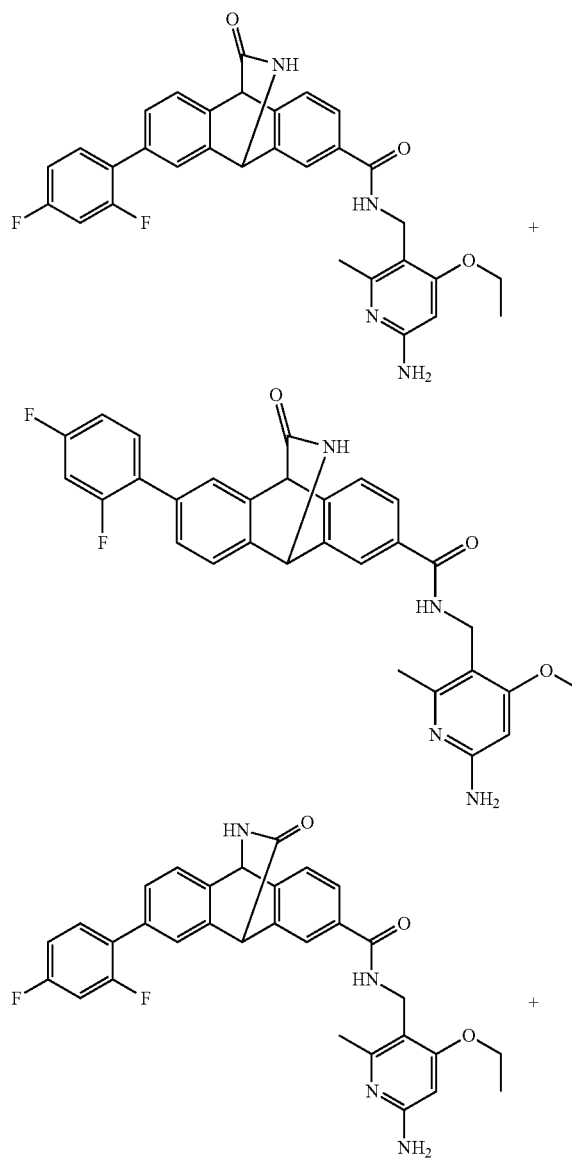

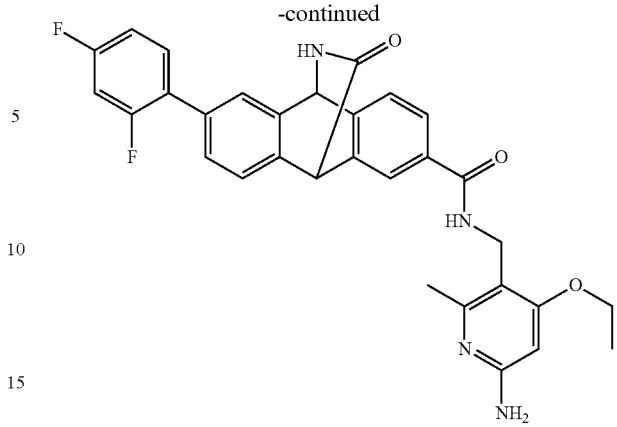

Step 1:

Into a 250-mL round-bottom flask, was placed a mixture of 7-bromoisoquinolin-3-ol (6.69 g, 29.86 mmol, 1.00 equiv), N,N-dimethylformamide (60 mL), 1-(chloromethyl)-4-methoxybenzene (7.02 g, 44.83 mmol, 1.50 equiv) and $Cs_2CO_3$ (34.23 g, 105.06 mmol, 3.50 equiv). The resulting solution was stirred for 2 h at room temperature, then the solids were separated by filtration and the filtrate was concentrated under vacuum. The residue was purified by silica gel column eluting with ethyl acetate/petroleum ether (1/1) to afford 6.0 g (crude) of 7-bromo-2-[(4-methoxyphenyl)methyl]-2,3-dihydroisoquinolin-3-one as a yellow solid.

Step 2:

Into a 100-mL round-bottom flask, was placed a solution of 7-bromo-2-[(4-methoxyphenyl) methyl]-2,3-dihydroisoquinolin-3-one (631 mg, 1.84 mmol, 1.00 equiv), dichloromethane (30 mL) and [5-(methoxycarbonyl)-2-(trimethylsilyl)phenyl](phenyl) iodanium trifluoromethanesulfonate (2.06 g, 3.68 mmol, 2.00 equiv). To the above solution was added TBAF (3.67 mL, 1.0 M in THF, 3.68 mmol, 2.00 equiv) dropwise at 0° C. and the resulting mixture was stirred for 1 h at room temperature. The suspension was then concentrated under vacuum and the residue was purified by silica gel column eluting with ethyl acetate/petroleum ether (1/2) to afford 365 mg (42%) of a mixture of (±)-methyl 12-bromo-15-[(4-methoxyphenyl)-methyl]-16-oxo-15-azatetracyclo[6.6.2.0$^{2,7}$.0$^{9,14}$]hexadeca-2,4,6,9,11,13-hexaene-4-carboxylate, (±)-methyl 11-bromo-15-[(4-methoxyphenyl)methyl]-16-oxo-15-azatetracyclo[6.6.2.0$^{2,7}$.0$^{9,14}$]-hexadeca-2,4,6,9,11,13-hexaene-5-carboxylate, (±)-methyl 11-bromo-15-[(4-methoxyphenyl)-methyl]-16-oxo-15-azatetracyclo[6.6.2.0$^{2,7}$.0$^{9,14}$]-hexadeca-2,4,6,9,11,13-hexaene-4-carboxylate and (±)-methyl 12-bromo-15-[(4-methoxyphenyl)methyl]-16-oxo-15-azatetracyclo-[6.6.2.0$^{2,7}$.0$^{9,14}$]hexadeca-2,4,6, 9,11,13-hexaene-5-carboxylate as a light yellow solid.

Step 3:

Into a 10-mL round-bottom flask, was placed a mixture of (±)-methyl 12-bromo-15-[(4-methoxyphenyl)methyl]-16-oxo-15-azatetracyclo[6.6.2.0$^{2,7}$.0$^{9,14}$]hexadeca-2,4,6,9,11,13-hexaene-4-carboxylate, (±)-methyl 11-bromo-15-[(4-methoxyphenyl)methyl]-16-oxo-15-azatetracyclo[6.6.2.0$^{2,7}$.0$^{9,14}$]hexadeca-2,4,6,9,11,13-hexaene-5-carboxylate, (±)-methyl 11-bromo-15-[(4-methoxyphenyl)methyl]-16-oxo-15-azatetracyclo[6.6.2.0$^{2,7}$.0$^{9,14}$]-hexadeca-2,4,6,9,11,13-hexaene-4-carboxylate and (±)-methyl 12-bromo-15-[(4-methoxyphenyl)methyl]-16-oxo-15-azatetracyclo[6.6.2.0$^{2,7}$.0$^{9,14}$]hexadeca-2,4,6,9,11,13-hexaene-5-carboxylate (287 mg, 0.60 mmol, 1.00 equiv), dioxane (5.00 mL), potassium carbonate (166 mg, 1.20 mmol, 2.00 equiv), (2,4-difluorophenyl)boronic acid (142 mg, 0.90 mmol, 1.50 equiv) and Pd(dppf)Cl$_2$ (44 mg, 0.06 mmol, 0.10 equiv). The resulting mixture was stirred for 4 h at 110° C. under N$_2$ then it was concentrated under vacuum. The residue was purified by silica gel column chromatography eluting with ethyl acetate/petroleum ether (1/6) to afford 210 mg (68%) of a mixture of (±)-methyl 12-(2,4-difluorophenyl)-15-[(4-methoxyphenyl)methyl]-16-oxo-15-azatetracyclo-[6.6.2.0$^{2,7}$.0$^{9,14}$]hexadeca-2,4,6,9,11,13-hexaene-4-carboxylate, (±)-methyl 11-(2,4-difluoro-phenyl)-15-[(4-methoxyphenyl)methyl]-16-oxo-15-azatetracyclo[6.6.2.0$^{2,7}$.0$^{9,14}$]hexadeca-2,4,6,9,11,13-hexaene-5-carboxylate, (±)-methyl 11-(2,4-difluorophenyl)-15-[(4-methoxy-phenyl)methyl]-16-oxo-15-azatetracyclo[6.6.2.0$^{2,7}$.0$^{9,14}$]hexadeca-2,4,6,9,11,13-hexaene-4-carboxylate and (±)-methyl 12-(2,4-difluorophenyl)-15-[(4-methoxyphenyl)methyl]-16-oxo-15-azatetracyclo-[6.6.2.0$^{2,7}$.0$^{9,14}$]hexadeca-2,4,6,9,11,13-hexaene-5-carboxylate as a yellow solid.

Step 4:

Into a 10-mL round-bottom flask, was placed a mixture of (±)-methyl 12-(2,4-difluorophenyl)-15-[(4-methoxyphenyl)methyl]-16-oxo-15-azatetracyclo[6.6.2.0$^{2,7}$.0$^{9,14}$]-hexadeca-2,4,6,9,11,13-hexaene-4-carboxylate, (±)-methyl 11-(2,4-difluorophenyl)-15-[(4-methoxyphenyl)methyl]-16-oxo-15-azatetracyclo[6.6.2.0$^{2,7}$.0$^{9,14}$]hexadeca-2,4,6,9,11,13-hexaene-5-carboxylate, (±)-methyl 11-(2,4-difluorophenyl)-15-[(4-methoxyphenyl)methyl]-16-oxo-15-azatetracyclo[6.6.2.0$^{2,7}$.0$^{9,14}$]hexadeca-2,4,6,9,11,13-hexaene-4-carboxylate and (±)-methyl 12-(2,4-difluorophenyl)-15-[(4-methoxyphenyl)methyl]-16-oxo-15-azatetracyclo-[6.6.2.0$^{2,7}$.0$^{9,14}$]hexadeca-2,4,6,9,11,13-hexaene-5-carboxylate (190 mg, 0.37 mmol, 1.00 equiv) and trifluoroacetic acid (5.00 mL). The resulting mixture was stirred for 6 h at 70° C. then it was concentrated under vacuum. The residue was purified by silica gel column chromatography eluting with dichloromethane/methanol (4/1) to afford 100 mg (69%) of a mixture of (±)-methyl 12-(2,4-difluorophenyl)-16-oxo-15-azatetracyclo[6.6.2.0$^{2,7}$.0$^{9,14}$]-hexadeca-2,4,6,9,11,13-hexaene-4-carboxylate, (±)-methyl 11-(2,4-difluorophenyl)-16-oxo-15-azatetracyclo-[6.6.2.0$^{2,7}$.0$^{9,14}$]hexadeca-2,4,6,9,11,13-hexaene-5-carboxylate, (±)-methyl 11-(2,4-difluoro-phenyl)-16-oxo-15-azatetracyclo[6.6.2.0$^{2,7}$.0$^{9,14}$]hexadeca-2,4,6,9,11,13-hexaene-4-carboxylate and (±)-methyl 12-(2,4-difluorophenyl)-16-oxo-15-azatetracyclo-[6.6.2.0$^{2,7}$.0$^{9,14}$]hexadeca-2,4,6,9,11,13-hexaene-5-carboxylate as a yellow solid.

Step 5:

Into a 10-mL round-bottom flask, was placed a mixture of (±)-methyl 12-(2,4-difluorophenyl)-16-oxo-15-azatetracyclo[6.6.2.0$^{2,7}$.0$^{9,14}$]hexadeca-2,4,6,9,11,13-hexaene-4-carboxylate, (±)-methyl 11-(2,4-difluorophenyl)-16-oxo-15-azatetracyclo[6.6.2.0$^{2,7}$.0$^{9,14}$]hexadeca-2,4,6,9,11,13-hexaene-5-carboxylate, (±)-methyl 11-(2,4-difluorophenyl)-16-oxo-15-azatetracyclo[6.6.2.0$^{2,7}$.0$^{9,14}$]hexadeca-2,4,6,9,11,13-hexaene-4-carboxylate and (±)-methyl 12-(2,4-difluorophenyl)-16-oxo-15-azatetracyclo[6.6.2.0$^{2,7}$.0$^{9,14}$]hexadeca-2,4,6,9,11,13-hexaene-5-carboxylate (98 mg, 0.25 mmol, 1.00 equiv), methanol (2 mL), water (0.50 mL) and sodium hydroxide (40 mg, 1.00 mmol, 4.00 equiv). The resulting mixture was stirred for 2 h at 40° C. then it was concentrated under vacuum. The residue was diluted with 5 mL of water; the pH value of the solution was adjusted to 3 with aqueous 2N hydrogen chloride solution and it was extracted with 2×20 mL of ethyl acetate. The organic layers was dried over anhydrous sodium sulfate and concentrated under vacuum to afford 90 mg (95%) of a mixture of (±)-12-(2,4-difluorophenyl)-16-oxo-15-azatetracyclo-[6.6.2.0$^{2,7}$.0$^{9,14}$]hexadeca-2,4,6,9,11,13-hexaene-4-carboxylic acid, (±)-11-(2,4-difluorophenyl)-16-oxo-15-azatetracyclo[6.6.2.0$^{2,7}$.0$^{9,14}$]hexadeca-2,4,6,9,11,13-hexaene-5-carboxylic acid, (±)-11-(2,4-difluorophenyl)-16-oxo-15-azatetracyclo-[6.6.2.0$^{2,7}$.0$^{9,14}$]hexadeca-2,4,6,9,11,13-hexaene-4-carboxylic acid and (±)-12-(2,4-difluorophenyl)-16-oxo-15-azatetracyclo[6.6.2.0$^{2,7}$.0$^{9,14}$]hexadeca-2,4,6,9,11,13-hexaene-5-carboxylic acid as a yellow solid.

Step 6:

Into a 10-mL round-bottom flask, was placed a solution of (±)-12-(2,4-difluorophenyl)-16-oxo-15-azatetracyclo [6.6.2.0$^{2,7}$.0$^{9,14}$]hexadeca-2,4,6,9,11,13-hexaene-4-carboxylic acid, (±)-11-(2,4-difluorophenyl)-16-oxo-15-azatetracyclo[6.6.2.0$^{2,7}$.0$^{9,14}$]hexadeca-2,4,6,9,11,13-hexaene-5-carboxylic acid, (±)-11-(2,4-difluorophenyl)-16-oxo-15-azatetracyclo[6.6.2.0$^{2,7}$.0$^{9,14}$]hexadeca-2,4,6,9,11,13-hexaene-4-carboxylic acid and (±)-12-(2,4-difluorophenyl)-16-oxo-15-azatetracyclo[6.6.2.0$^{2,7}$.0$^{9,14}$]hexadeca-2,4,6,9,11,13-hexaene-5-carboxylic acid (80 mg, 0.21 mmol, 1.00 equiv), N,N-dimethylformamide (3.00 mL), DIEA (68 mg, 0.53 mmol, 2.50 equiv), 5-(aminomethyl)-4-ethoxy-6-methylpyridin-2-amine (58 mg, 0.32 mmol, 1.50 equiv; prepared following the procedures described in Example 84, Step 1-4 but using ethyl iodide in Step 3 instead of iodomethane) and HATU (95 mg, 0.25 mmol, 1.20 equiv). The resulting solution was stirred for 2 h at room temperature then it was directly subjected to reverse preparative HPLC (Prep-C18, 5 M XBridge column, 19×150 mm, waters; gradient elution of 20% MeCN in water to 60% MeCN in water over a 4 min period and 60% MeCN in water to 85% MeCN in water over a 6 min period, where the aqueous phase contains 10 mMNH$_4$HCO$_3$+0.5% ammonia) to provide the title compounds as a yellow solid (26.5 mg, 23%). MS: (M+H)$^+$ found for C$_{31}$H$_{26}$F$_2$N$_4$O$_3$: 541.2.

Example 87

Synthesis of (±)-N-{[6-amino-2-methyl-4-(propan-2-yl)pyridin-3-yl]methyl}-12-(2,4-difluoro-phenyl)-15-oxatetracyclo[6.6.1.0$^{2,7}$.0$^{9,14}$]pentadeca-2,4,6,9,11,13-hexaene-4-carboxamide

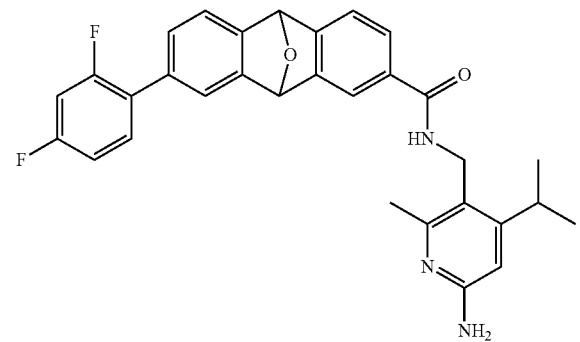 [SMILES: Cc1nc(N)cc(C(C)C)c1CNC(=O)c1ccc2c(c1)C1OC2c2ccc(-c3ccc(F)cc3F)cc21]

Step 1:

Into a 100-mL round-bottom flask purged and maintained with an inert atmosphere of nitrogen, was placed a mixture of 6-amino-2-methyl-4-oxo-1,4-dihydropyridine-3-carbonitrile (Example 84 step 2; 3.00 g, 20.1 mmol, 1.00 equiv) in phosphoryl chloride (POCl$_3$; 50 mL). The resulting mixture was stirred for 16 hours at 80° C. in an oil bath and then concentrated under vacuum. The residue was diluted with ethyl acetate and poured into saturated aqueous NaHCO₃ solution. The organic layer was separated, washed with 30 mL of brine, dried over anhydrous sodium sulfate and concentrated to dryness to give 6-amino-4-chloro-2-methylpyridine-3-carbonitrile (2.50 g, 74.2%) as a yellow solid.

Step 2:

Into a 25-mL round-bottom flask purged and maintained with an inert atmosphere of nitrogen, was placed a mixture of 6-amino-4-chloro-2-methylpyridine-3-carbonitrile (600 mg, 3.58 mmol, 1.00 equiv) in dioxane/H₂O (10 mL/1 mL), to which were added 4,4,5,5-tetramethyl-2-(prop-1-en-2-yl)-1,3,2-dioxaborolane (798 mg, 4.75 mmol, 1.50 equiv), sodium carbonate (1.14 g, 10.76 mmol, 3.00 equiv) and tetrakis(triphenylphosphine)palladium(0) (Pd(PPh₃)₄; 83 mg, 0.07 mmol, 0.02 equiv). The resulting mixture was stirred for 3 hours at 90° C. in an oil bath under N₂ then it was concentrated under vacuum. The residue was purified by flash chromatography eluting with ethyl acetate/petroleum ether (1/4) to afford 323 mg (52%) of 6-amino-2-methyl-4-(prop-1-en-2-yl)pyridine-3-carbonitrile as a yellow solid.

Step 3:

Into a 25-mL round-bottom flask (20 atm), was placed a mixture of 6-amino-2-methyl-4-(prop-1-en-2-yl)pyridine-3-carbonitrile (50 mg, 0.29 mmol, 1.00 equiv) in methanol/ammonia (4.00 mL/0.40 mL), followed by Raney Ni (20 mg). The mixture was degassed and purged with hydrogen four times and stirred for 2 days at room temperature.

The mixture was then filtered through a pad of Celite and the filtrate was concentrated under vacuum to afford 58 mg of 5-(aminomethyl)-6-methyl-4-(propan-2-yl)pyridin-2-amine as a yellow crude solid, which was used directly for next step without any purification. Step 4: Into a 25-mL round-bottom flask purged and maintained with an inert atmosphere of nitrogen, was placed a solution of (±) sodium 12-bromo-15-oxatetracyclo-[6.6.1.0²,⁷.0⁹,¹⁴]pentadeca-2,4, 6,9,11,13-hexaene-4-carboxylate (INT-5a) (80 mg, 0.24 mmol, 1.00 equiv) in dioxane/H₂O (1.0/0.2 mL), followed by the addition of (2,4-difluorophenyl)boronic acid (56 mg, 0.35 mmol, 1.50 equiv), sodium carbonate (75 mg, 0.71 mmol, 3.00 equiv) and Pd(PPh₃)₄ (27 mg, 0.02 mmol, 0.10 equiv). The resulting mixture was stirred for 16 hours at 90° C. in an oil bath under nitrogen atmosphere then it was cooled to RT, diluted with 10 mL of DCM/MeOH=10/1 and dried over anhydrous sodium sulfate. The mixture was then filtered through a pad of Celite and the filtrate was concentrated under vacuum to afford 140 mg of crude (±) sodium 12-(2,4-difluorophenyl)-15-oxatetracyclo-[6.6.1.0²,⁷.0⁹,¹⁴] pentadeca-2,4,6,9,11,13-hexaene-4-carboxylate as yellow solids, which were used directly for next step without further purification.

Step 5:

Into a 8-mL vial, was placed a mixture of 5-(aminomethyl)-6-methyl-4-(propan-2-yl)pyridin-2-amine (50 mg, 0.28 mmol, 1.00 equiv) in N,N-dimethylformamide (2.00 mL), followed by the addition of (±) sodium 12-(2,4-difluorophenyl)-15-oxatetracyclo[6.6.1.0²,⁷.0⁹,¹⁴]-pentadeca-2,4,6,9,11,13-hexaene-4-carboxylate (104 mg, 0.28 mmol, 1.00 equiv), HATU (212 mg, 0.56 mmol, 2.00 equiv) and DIEA (180 mg, 1.39 mmol, 5.00 equiv). The resulting mixture was stirred for 20 minutes at room temperature then it was filtered and directly subjected to reverse phase preparative HPLC (Prep-C18, 5 μM XBridge column, 19×150 mm, Waters; gradient elution of 20% MeCN in water to 60% MeCN in water over a 4 min period, 60% MeCN in water to 85% MeCN in water over a 6 min period, where the aqueous phase contained 10 mM NH₄HCO₃ and 0.5% ammonia) to provide 40.7 mg (29% yield over 2 steps) the title compound as a white solid. MS: (M+H)⁺ found for C₃₁H₂₇F₂N₃O₂: 512.1.

Example 88

Synthesis of (1R,8S)—N-[(6-amino-4-ethyl-2-methylpyridin-3-yl)methyl]-12-(2,4-difluoro-phenyl)-15-oxatetracyclo[6.6.1.0²,⁷.0⁹,¹⁴]pentadeca-2,4,6,9,11, 13-hexaene-4-carboxamide

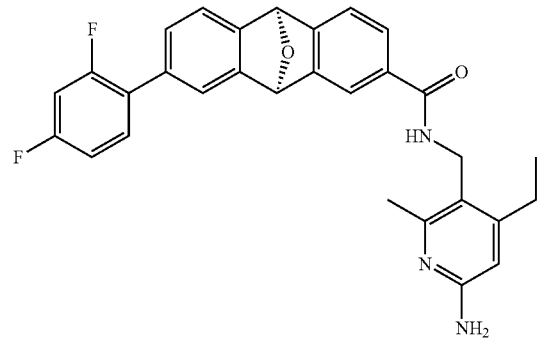 [SMILES: CCc1cc(N)nc(C)c1CNC(=O)c1ccc2c(c1)[C@@H]1O[C@H]2c2ccc(-c3ccc(F)cc3F)cc21]

Step 1:

Into a 100-mL round-bottom flask, was placed a mixture of 6-amino-4-chloro-2-methylpyridine-3-carbonitrile (Example 87 step 1; 800 mg, 4.77 mmol, 1.00 equiv), COCl₂ (200 mg, 1.54 mmol, 0.32 eq) and methanol (50 mL) with stirring at 0° C., followed by the addition of NaBH₄ (1.76 g, 47.70 mmol, 10.00 equiv) in portions. The resulting mixture was stirred for 1.5 h at 50° C. and concentrated under vacuum. The residue was purified by silica gel column chromatography eluting with dichloromethane/methanol (6/1) to afford 200 mg (24%) of 5-(aminomethyl)-4-chloro-6-methylpyridin-2-amine as a light brown solid.

Step 2:

Into a 100-mL round-bottom flask, was placed a solution of 5-(aminomethyl)-4-chloro-6-methylpyridin-2-amine (1.13 g, 6.58 mmol, 1.00 equiv), dichloromethane (30 mL), Boc₂O (5.74 g, 26.32 mmol, 4.00 equiv) and 4-dimethylaminopyridine (401 mg, 3.29 mmol, 0.50 equiv). The resulting mixture was stirred for 10 min at room temperature and concentrated under vacuum. The residue was purified by silica gel column chromatography eluting with ethyl acetate/petroleum ether (1/5) to afford 1.70 g (55%) of tert-butyl N-[5-({bis[(tert-butoxy)carbonyl]amino}methyl)-4-chloro-6-methylpyridin-2-yl]carbamate as a yellow solid.

Step 3:

Into a 50-mL round-bottom flask, was placed a mixture of tert-butyl N-[5-({bis[(tert-butoxy)carbonyl]amino}methyl)-4-chloro-6-methylpyridin-2-yl]carbamate (400 mg, 0.85 mmol, 1.00 equiv), dioxane (30 mL), water (3 mL), potassium carbonate (938 mg, 6.80 mmol, 8.00 equiv), 2-ethenyl-4,4,5,5-tetramethyl-1,3,2-dioxaborolane (393 mg, 2.55 mmol, 3.00 equiv) and Pd(PPh₃)₄ (983 mg, 0.85 mmol, 1.00 equiv). The resulting mixture was stirred for 16 h at 110° C. under an atmosphere of nitrogen and concentrated under vacuum. The residue was purified by silica gel column chromatography eluting with ethyl acetate/petroleum ether (1/3) to afford 180 mg (46%) of tert-butyl N-[5-({bis[(tert-butoxy)carbonyl]amino]methyl)-4-ethenyl-6-methylpyridin-2-yl]carbamate as a yellow solid.

Step 4:

Into a 100-mL round-bottom flask, was placed a mixture of tert-butyl N-[5-([bis[(tert-butoxy)carbonyl]amino] methyl)-4-ethenyl-6-methylpyridin-2-yl]carbamate (2.00 g, 4.32 mmol, 1.00 equiv), methanol (20.0 mL), concentrated ammonia (2.00 mL) and Raney Ni (200 mg) under $N_2$. The mixture was degassed three times and purged with hydrogen then it was stirred for 24 h at room temperature under a $H_2$ (25 atm) atmosphere. After filtration through a pad of Celite, the filtrate was concentrated under vacuum to deliver 1.80 g (80%) of tert-butyl N-[5-({bis[(tert-butoxy)carbonyl] amino}methyl)-4-ethyl-6-methylpyridin-2-yl]carbamate as a light yellow solid.

Step 5:

Into a 50-mL round-bottom flask, was placed a solution of tert-butyl N-[5-({bis[(tert-butoxy)carbonyl]amino}methy-4-ethy-6-methylpyridin-2-yl]carbamate (1.79 g, 3.87 mmol, 1.00 equiv) in dioxane (10 mL) with stirring at rt, followed by the addition of a solution of dioxane (15.0 mL) freshly saturated with HCl (gas). The resulting mixture was stirred for 0.5 h at room temperature then it was filtered to provide 807 mg (88%) of 5-(aminomethyl)-4-ethyl-6-methylpyridin-2-amine dihydrochloride as a light yellow crude solid.

Step 6:

Into a 25-mL round-bottom flask, was placed a solution of (1R,8S)-12-(2,4-difluorophenyl)-15-oxatetracyclo[6.6.1.0$^{2,7}$.0$^{9,14}$]pentadeca-2(7),3,5,9,11,13-hexaene-4-carboxylic acid (Example 7 Step 2; 95.0 mg, 0.27 mmol, 1.00 equiv) in N,N-dimethylformamide (3.00 mL), followed bu the addition of 5-(aminomethyl)-4-ethyl-6-methylpyridin-2-amine dihydrochloride (73.1 mg, 0.27 mmol, 1.00 equiv), DIEA (106 mg, 0.82 mmol, 3.00 equiv) and HATU (156 mg, 0.41 mmol, 1.50 equiv). The resulting mixture was stirred for 20 minutes at room temperature then it was filtered and subjected to reverse phase preparative HPLC (Prep-C18, 5 μM XBridge column, 19×150 mm, Waters; gradient elution of 20% MeCN in water to 30% MeCN in water over a 4 min period, 30% MeCN in water to 65% MeCN in water over a 6 min period, where the aqueous phase contained 10 mMNH$_4$HCO$_3$ and 0.5% ammonia) to provide the title compound as a white solid (35.2 mg, 26%). MS: (M+H)$^+$ found for $C_{30}H_{25}F_2N_3O_2$: 498.2.

Example 89

Synthesis of (1R,8S)—N-{[6-amino-2-methyl-4-(propan-2-yl)pyridin-3-yl]methyl}-12-(2,4-difluorophenyl)-15-oxatetracyclo[6.6.1.0$^{2,7}$.0$^{9,14}$]pentadeca-2,4,6,9,11,13-hexaene-4-carboxamide

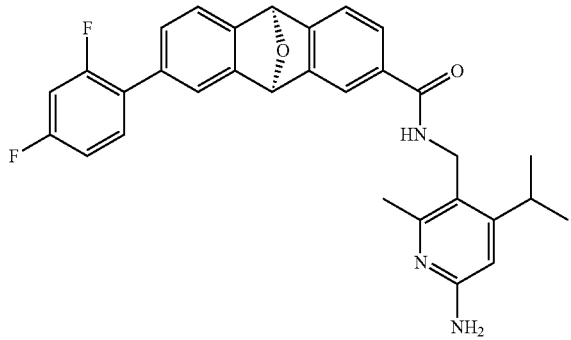

The title compound was synthesized following the procedure described for Example 88, Step 6 but using 5-(aminomethyl)-6-methyl-4-(propan-2-yl)pyridin-2-amine (Example 87, Steps 1-3) instead of 5-(aminomethyl)-4-ethyl-6-methylpyridin-2-amine dihydrochloride. MS: (M+H)$^+$ found for $C_{31}H_{27}F_2N_3O_2$: 512.1.

Example 90

Synthesis of (1R,8S)—N-[(6-amino-2,4-dimethylpyridin-3-yl)methyl]-12-benzoyl-15-oxatetracyclo [6.6.1.0$^{2,7}$.0$^{9,14}$]pentadeca-2,4,6,9,11,13-hexaene-4-carboxamide

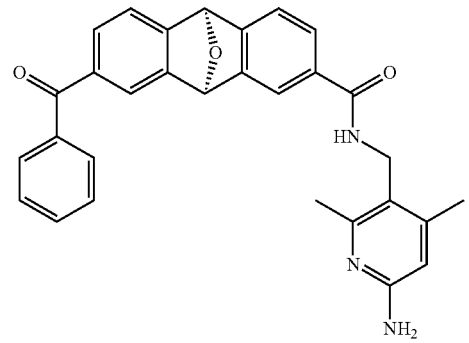 [SMILES: Cc1cc(N)nc(C)c1CNC(=O)c1ccc2c(c1)[C@@H]1O[C@H]2c2ccc(C(=O)c3ccccc3)cc21]

Step 1:

Into a 50-mL round-bottom flask, was placed a mixture of (1R,8S)-12-bromo-15-oxatetracyclo[6.6.1.0$^{2,7}$.0$^{9,14}$]pentadeca-2,4,6,9,11,13-hexaene-4-carboxylic acid (650 mg, 2.05 mmol, 1.00 equiv) and BH$_3$.THF (1M, 10 mL). The resulting solution was stirred for 1 hour at room temperature, then the solvent was removed under reduced pressure. The residue was purified by flash chromatography eluting with ethyl acetate/petroleum ether (1/1) to afford 440 mg (71%) of [(1R,8S)-12-bromo-15-oxatetracyclo[6.6.1.0$^{2,7}$.0$^{9,14}$]pentadeca-2,4,6,9,11,13-hexaen-4-yl]methanol as a white solid.

Step 2:

Into a 500-mL round-bottom flask, was placed a mixture of [(1R,8S)-12-bromo-15-oxatetracyclo[6.6.1.0$^{2,7}$.0$^{9,14}$] pentadeca-2,4,6,9,11,13-hexaen-4-yl]methanol (440 mg, 1.45 mmol, 1.00 equiv), MnO$_2$ (636 mg, 7.32 mmol, 5.00 equiv) and dichloromethane (200 mL). The resulted mixture was stirred for 20 minutes at room temperature, then the solids were separated by filtration. The filtrate was concentrated under vacuum to afford 400 mg (92%) of (1R,8S)-12-bromo-15-oxatetracyclo[6.6.1.0$^{2,7}$.0$^{9,14}$]pentadeca-2,4,6,9,11,13-hexaene-4-carbaldehyde as a yellow solid.

Step 3:

Into a 50-mL 3-necked round-bottom flask, was placed a solution of (1R,8S)-12-bromo-15-oxatetracyclo[6.6.1.0$^{2,7}$.0$^{9,14}$]pentadeca-2,4,6,9,11,13-hexaene-4-carbaldehyde (200 mg, 0.66 mmol, 1.00 equiv) in tetrahydrofuran (25 mL) at −20° C., followed by the dropwise addition of bromo(phenyl)magnesium (1.35 mL, 2.00 equiv, 1 mol/L). The resulting mixture was stirred for 1 hour at −20° C. then it was quenched by the addition of 5 mL of saturated aqueous NH$_4$Cl, diluted with H$_2$O and extracted with ethyl acetate. The organic layers were concentrated and purified by flash chromatography eluting with ethyl acetate/petroleum ether (1/5) to afford 120 mg (48%) of a 1:1 mixture of (R)-[(1R,8S)-12-bromo-15-oxatetracyclo[6.6.1.0$^{2,7}$.0$^{9,14}$]- pentadeca-22,4,6,9,11,13-hexaen-4-yl](phenyl)methanol and (S)-[(1R,8S)-12-bromo-15-oxatetracyclo[6.6.1.0$^{2,7}$.0$^{9,14}$]pentadeca-2,4,6,9,11,13-hexaen-4-yl](phenyl)methanol as a light yellow solid.

Step 4:

Into an 100-mL round-bottom flask, was placed a mixture of (R)-[(1R,8S)-12-bromo-15-oxatetracyclo[6.6.1.0$^{2,7}$.0$^{9,14}$]pentadeca-2,4,6,9,11,13-hexaen-4-yl](phenyl)methanol and (S)-[(1R,8S)-12-bromo-15-oxatetracyclo[6.6.1.0$^{2,7}$.0$^{9,14}$]pentadeca-2,4,6,9,11,13-hexaen-4-yl](phenyl)methanol (120 mg, 0.32 mmol, 1.00 equiv), MnO$_2$ (138 mg, 1.59 mmol, 5.00 equiv) and dichloromethane (30 mL). The resulting mixture was stirred for 30 minutes at room temperature then the solids were separated by filtration. The filtrate was concentrated under vacuum to afford 118 mg (100%) of (1R,8S)-4-benzoyl-12-bromo-15-oxatetracyclo[6.6.1.0$^{2,7}$.0$^{9,14}$]pentadeca-2,4,6,9,11,13-hexaene as an off-white solid.

Step 5:

Into a 50-mL pressure tank reactor, was placed a mixture of (1R,8S)-4-benzoyl-12-bromo-15-oxatetracyclo[6.6.1.0$^{2,7}$.0$^{9,14}$]pentadeca-2,4,6,9,11,13-hexaene (120 mg, 0.32 mmol, 1.00 equiv), Pd(dppf)Cl$_2$ (24 mg, 0.03 mmol, 0.10 equiv), TEA (161 mg, 1.59 mmol, 5.00 equiv) and methanol (25 mL). The resulting mixture was stirred for 16 hours at 120° C. under a CO atmosphere (20 atm). The mixture was then cooled to RT, concentrated and purified by flash chromatography eluting with ethyl acetate/petroleum ether (1/5) to afford 84 mg (74%) of methyl (1R,8S)-12-benzoyl-15-oxatetracyclo[6.6.1.0$^{2,7}$.0$^{9,14}$]pentadeca-2,4,6,9,11,13-hexaene-4-carboxylate as a white solid.

Step 6:

Into a 50-mL round-bottom flask, was placed a mixture of methyl (1R,8S)-12-benzoyl-15-oxatetracyclo[6.6.1.0$^{2,7}$.0$^{9,14}$]pentadeca-2,4,6,9,11,13-hexaene-4-carboxylate (84 mg, 0.24 mmol, 1.00 equiv), sodium hydroxide (45 mg, 1.12 mmol, 5.00 equiv) and methanol (10 mL). The resulting mixture was stirred for 2 hours at room temperature then it was diluted with 15 mL of water. The pH value of the solution was adjusted to 4 with 2N aqueous HCl solution and the resulting mixture was extracted with 30 mL of ethyl acetate. The organic layer was concentrated and dried to afford 73 mg (90%) of (1R,8S)-12-benzoyl-15-oxatetracyclo[6.6.1.0$^{2,7}$.0$^{9,14}$]pentadeca-2,4,6,9,11,13-hexaene-4-carboxylic acid as a yellow solid.

Step 7:

Into a 20-mL vial, was placed a mixture of 5-(aminomethyl)-4,6-dimethyl-pyridin-2-amine (32 mg, 0.21 mmol, 1.00 equiv), (1R,8S)-12-benzoyl-15-oxatetracyclo-[6.6.1.0$^{2,7}$.0$^{9,14}$]pentadeca-2,4,6,9,11,13-hexaene-4-carboxylic acid (72 mg, 0.21 mmol, 1.00 equiv), DIEA (136 mg, 1.05 mmol, 5.00 equiv), HATU (88 mg, 0.23 mmol, 1.10 equiv) and N,N-dimethylformamide (10 mL). The resulting mixture was stirred for 1 hour at room temperature then it was purified by Prep-HPLC (Column: SunFire Prep C18 19*150 mm, 5 µm; mobile phase: CH$_3$CN/water (a buffer of 10 mM NH$_4$HCO$_3$ and 0.05% ammonia) with a gradient of acetonitrile from 15% to 40% in 4 min, 40% to 48% in 6 min; flow rate: 20 mL/min; detector UV wavelength: 254 nm). The HPLC fractions were concentrated under vacuum and lyophilized to afford 55.8 mg (55%) of the title compound as a light yellow solid. MS: (M+H)$^+$ found for C$_{30}$H$_{25}$N$_3$O$_3$: 476 [M+H]$^+$.

Example 91

Synthesis of (1R,8S)—N-[(6-amino-2,4-dimethyl-pyridin-3-yl)methyl]-12-(3-fluorobenzoyl)-15-oxatetracyclo[6.6.1.0$^{2,7}$.0$^{9,14}$]pentadeca-2,4,6,9,11,13-hexaene-4-carboxamide

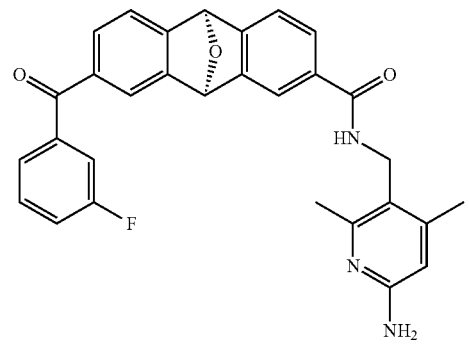

The title compound was synthesized following the procedures described for Example 90 (steps 3-7) using bromo(3-fluorophenyl)magnesium instead of bromo(phenyl)magnesium. This resulted in 62.6 mg (47%) of the title compound as a white solid. MS: (M+H)$^+$ found for C$_{30}$H$_{26}$FN$_3$O$_3$: 494.

Example 92

Synthesis of (1R,8S)—N-{[6-amino-2-methyl-4-(oxan-4-yl)pyridin-3-yl]methyl}-12-(2,4-difluorophenyl)-15-oxatetracyclo[6.6.1.0$^{2,7}$.0$^{9,14}$]pentadeca-2,4,6,9,11,13-hexaene-4-carboxamide

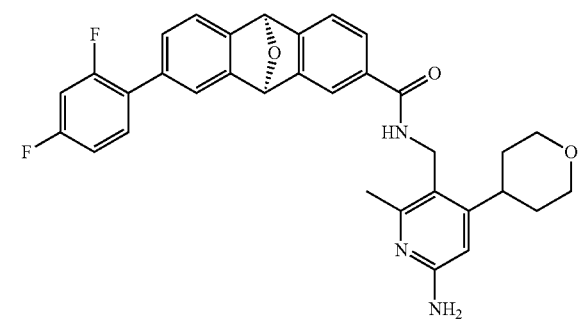 [SMILES: Cc1nc(N)cc(C2CCOCC2)c1CNC(=O)c1ccc2c(c1)[C@@H]1O[C@H]2c2ccc(-c3ccc(F)cc3F)cc21]

Step 1:

Into a 50-mL 3-necked round-bottom flask was placed a mixture of tert-butyl N-[5-([bis[(tert-butoxy)carbonyl]amino]methyl)-4-chloro-6-methylpyridin-2-yl]carbamate (Example 88, Step 2; 471 mg, 1.00 mmol, 1.00 equiv), dioxane (10.0 mL) and water (1.00 mL), 2-(3,6-dihydro-2H-pyran-4-yl)-4,4,5,5-tetramethyl-1,3,2-dioxaborolane (840 mg, 4.00 mmol, 4.00 equiv), potassium carbonate (276 mg, 2.00 mmol, 2.00 equiv) and Pd(PPh$_3$)$_4$ (116 mg, 0.10 mmol, 0.10 equiv). The resulting mixture was stirred overnight at 110° C. under N$_2$ then it was concentrated under vacuum. The residue was purified by a silica gel column chromatography eluting with ethyl acetate/petroleum ether (1/4) to afford 455 mg (88%) of tert-butyl N-[5-([bis[(tert-butoxy)

carbonyl]amino]methyl)-4-(3,6-dihydro-2H-pyran-4-yl)-6-methylpyridin-2-yl]carbamate as yellow oil.

Step 2:

Into a 50-mL 3-necked round-bottom flask, was placed a mixture of tert-butyl N-[5-([bis[(tert-butoxy)carbonyl]amino]methyl)-4-(3,6-dihydro-2H-pyran-4-yl)-6-methylpyridin-2-yl]carbamate (260 mg, 0.5 mmol, 1.00 equiv), MeOH (10.0 mL) and 10% dry palladium on C (100 mg). The resulting suspension was degassed and purged with $H_2$ several times. The mixture was then stirred for 5 h at room temperature under an atmosphere of hydrogen then it was filtered through a pad of Celite and the filter cake was washed with MeOH (20 mL). The filtrate was combined and concentrated under vacuum to afford 255 mg of tert-butyl N-[5-([bis[(tert-butoxy)carbonyl]amino]methyl)-6-methyl-4-(oxan-4-yl)pyridin-2-yl]carbamate as a white solid.

Step 3:

Into a 50-mL round-bottom flask, was placed a solution of tert-butyl N-[5-([bis[(tert-butoxy)carbonyl]amino]methyl)-6-methyl-4-(oxan-4-yl)pyridin-2-yl]carbamate (255 mg, 0.49 mmol, 1.00 equiv) in dioxane (5.00 mL) followed by the drop-wise addition of a solution of dioxane (5.00 mL) freshly saturated with HCl (gas). The resulting mixture was stirred for 2 h at room temperature and then concentrated under vacuum to afford 108 mg (100%) of 5-(aminomethyl)-6-methyl-4-(oxan-4-yl)pyridin-2-amine as yellow oil. LCMS (ES) [M+1]$^+$ m/z: 222.1.

Step 4:

Into a 10-mL round-bottom flask, was placed a solution of 5-(aminomethyl)-6-methyl-4-(oxan-4-yl)pyridin-2-amine (100 mg, 0.45 mmol, 1.00 equiv), N,N-dimethylformamide (5.00 mL), (1R,8S)-12-(2,4-difluorophenyl)-15-oxatetracyclo-[6.6.1.0$^{2,7}$.0$^{9,14}$]pentadeca-2,4,6,9,11,13-hexaene-4-carboxylic acid (Example 7 Step 2; 158 mg, 0.45 mmol, 1.00 equiv), DIEA (116 mg, 0.90 mmol, 2.00 equiv) and HATU (205 mg, 0.54 mmol, 1.20 equiv). The resulting mixture was stirred for 2 h at room temperature then it was filtered and directly subjected to reverse preparative HPLC (Prep-C18, 5 µM XBridge column, 19×150 mm, waters; gradient elution of 15% MeCN in water to 45% MeCN in water over a 4 min period, 45% MeCN in water to 75% MeCN in water over a 6 min period, where the aqueous phase contains 10 mMNH$_4$HCO$_3$+0.5% ammonia) to provide 61.8 mg (25%) of the title compound as a white solid. MS: (M+H)$^+$ found for $C_{33}H_{29}F_2N_3O_3$: 554.1

Example 93

Synthesis of 4-[(1R,8S)-12-{[(6-amino-4-cyclopropyl-2-methylpyridin-3-yl)methyl]-carbamoyl}-15-oxatetracyclo[6.6.1.0$^{2,7}$.0$^{9,14}$]pentadeca-2,4,6,9,11,13-hexaen-4-yl]-3-fluoropyridin-1-ium-1-olate

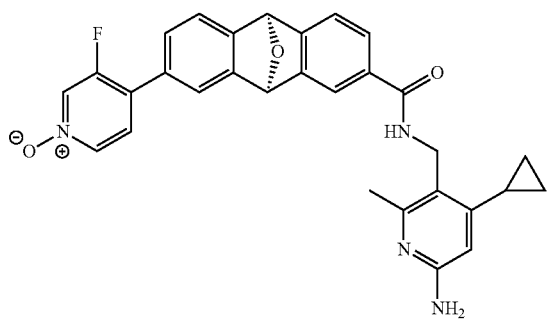 [SMILES: Cc1nc(N)cc(C2CC2)c1CNC(=O)c1ccc2c(c1)[C@@H]1O[C@H]2c2ccc(-c3cc[n+]([O-])cc3F)cc21]

Step 1:

Into a 100-mL round-bottom flask, was placed a mixture of 6-amino-4-chloro-2-methylpyridine-3-carbonitrile (Example 87 step 1, 500 mg, 2.98 mmol, 1.00 equiv), tetrahydrofuran (30.0 mL), 4-dimethylaminopyridine (36.5 mg, 0.30 mmol, 0.10 equiv) and di-tert-butyl dicarbonate (714 mg, 3.28 mmol, 1.10 equiv). The resulting mixture was stirred for 5 h at 25° C. then it was concentrated and purified by silica gel column chromatography eluting with ethyl acetate/petroleum ether (1/5) to afford 567 mg (71%) of tert-butyl N-(4-chloro-5-cyano-6-methylpyridin-2-yl)carbamate as yellow oil.

Step 2:

Into a 100-mL round-bottom flask, was placed a mixture of tert-butyl N-(4-chloro-5-cyano-6-methylpyridin-2-yl)carbamate (567 mg, 2.12 mmol, 1.00 equiv), dioxane (40.0 mL), water (4.00 mL), cyclopropyltrifluoro-[4]-borane potassium (1.25 g, 8.48 mmol, 4.00 equiv), Pd(PPh$_3$)$_4$ (535.3 mg, 0.46 mmol, 0.22 equiv) and Cs$_2$CO$_3$ (4.13 g, 12.72 mmol, 6.00 equiv). The resulting mixture was stirred for 12 h at 80° C. under nitrogen then it was concentrated under vacuum, diluted with 30 mL of ethyl acetate and washed with water. The mixture was then extracted with ethyl acetate, dried over anhydrous sodium sulfate and concentrated under vacuum. The residue was purified by silica gel column chromatography eluting with ethyl acetate/petroleum ether (1/5) to afford 250 mg (43%) of tert-butyl N-(5-cyano-4-cyclopropyl-6-methylpyridin-2-yl)carbamate as a light yellow solid.

Step 3:

Into a 100-mL round-bottom flask, was placed a mixture of tert-butyl N-(5-cyano-4-cyclopropyl-6-methylpyridin-2-yl)carbamate (150 mg, 0.55 mmol, 1.00 equiv), methanol (10.0 mL), ammonia (1.00 mL) and Raney Ni (30 mg). The mixture was degassed three times, purged with hydrogen and stirred for 4 h at 25° C. under a hydrogen atmosphere. The solids were separated by filtration and the filtrate was concentrated under vacuum to deliver 150 mg (99%) of tert-butyl N-[5-(aminomethyl)-4-cyclopropyl-6-methylpyridin-2-yl]carbamate as light yellow oil.

Step 4:

Into a 100-mL round-bottom flask, was placed a solution of tert-butyl N-[5-(aminomethyl)-4-cyclopropyl-6-methylpyridin-2-yl]carbamate (150 mg, 0.55 mmol, 1.00 equiv) in dichloromethane (6.00 mL) and trifluoroacetic acid (1.00 mL). The resulting mixture was stirred for 2 h at 25° C., then the pH was adjusted to 9 with 2N sodium hydroxide aqueous solution. The mixture was then concentrated under vacuum to deliver 160 mg (crude) of 5-(aminomethyl)-4-cyclopropyl-6-methylpyridin-2-amine as yellow oil. LC-MS (ES) [M+1]$^+$ m/z: 178.1.

Step 5:

Into a 50-mL round-bottom flask, was placed a mixture of (1S,8R)-12-bromo-15-oxatetracyclo[6.6.1.0$^{2,7}$.0$^{9,14}$]pentadeca-2,4,6,9,11,13-hexaene-4-carboxylic acid (INT4a1; 158.0 mg, 0.50 mmol, 1.00 equiv), dioxane (8.0 mL), H$_2$O (0.8 mL), (3-fluoropyridin-4-yl)boronic acid (212 mg, 1.50 mmol, 3.00 equiv), Pd(PPh$_3$)$_4$ (18.3 mg, 0.02 mmol, 0.05 equiv) and sodium carbonate (159.0 mg, 1.50 mmol, 3.00 equiv). The resulting mixture was stirred for 3 h at 80° C. then it was cooled to RT and concentrated. The crude product was purified by silica gel column chromatography eluting with DCM/MeOH (5/1) to afford 140.0 mg (84%) of (1R,8S)-12-(3-fluoropyridin-4-yl)-15-oxatetracyclo[6.6.1.0$^{2,7}$.0$^{9,14}$]pentadeca-2,4,6,9,11,13-hexaene-4-carboxylic acid as an off-white solid.

463

Step 6:

Into a 10-mL round-bottom flask, was placed a mixture of (1R,8S)-12-(3-fluoropyridin-4-yl)-15-oxatetracyclo[6.6.1.0$^{2,7}$.0$^{9,14}$]pentadeca-2,4,6,9,11,13-hexaene-4-carboxylic acid (140 mg, 0.42 mmol, 1.00 equiv), N,N-dimethylformamide (5 mL) and meta-chloro-peroxybenzoic acid (m-CPBA; 85.1 mg, 85%/W, 0.42 mmol, 2.00 equiv). The resulting mixture was stirred for 5 h at room temperature then it was diluted with of $H_2O$ and extracted with ethyl acetate. The organic layers were combined, dried over sodium sulfate and concentrated under vacuum. The residue was purified by silica gel column chromatography eluting with DCM/MeOH (5/1) to afford 130 mg (89%) of 4-[(1R,8S)-12-carboxy-15-oxatetracyclo[6.6.1.0$^{2,7}$.0$^{9,14}$]pentadeca-2,4,6,9,11,13-hexaen-4-yl]-3-fluoropyridin-1-ium-1-olate as a yellow solid.

Step 7:

Into a 25-mL round-bottom flask, was placed 4-[(1R,8S)-12-carboxy-15-oxatetracyclo[6.6.1.0$^{2,7}$.0$^{9,14}$]pentadeca-2,4,6,9,11,13-hexaen-4-yl]-3-fluoropyridin-1-ium-1-olat (62.0 mg, 0.18 mmol, 1.00 equiv), N,N-dimethylformamide (4 mL), DIEA (69 mg, 0.53 mmol, 3.00 equiv), HATU (81 mg, 0.21 mmol, 1.20 equiv) and 5-(aminomethyl)-4-cyclopropyl-6-methylpyridin-2-amine TFA salt (81.0 mg, 0.20 mmol, 1.10 equiv). The resulting mixture was stirred for 1 h at room temperature then it was filtered and directly subjected to reverse phase preparative HPLC (Prep-C18, 5 M×Bridge column, 19×150 mm, Waters; gradient elution of 10% MeCN in water to 26% MeCN in water over a 1 min period, 26% MeCN in water to 32% MeCN in water over a 6 min period, where the aqueous phase contained 10 mM $NH_4HCO_3$ and 0.05% $NH_3$—$H_2O$) to provide the title compound as an off-white solid (24.6 mg, 27%). MS: (M+H)$^+$ found for $C_{30}H_{25}FN_4O_3$: 509.1.

Example 94

Synthesis of (1R,8S)—N-[(1-amino-6-chloroisoquinolin-5-yl)methyl]-12-(2-fluorophenyl)-15-oxatetracyclo[6.6.1.0$^{2,7}$.0$^{9,14}$]pentadeca-2,4,6,9,11,13-hexaene-4-carboxamide

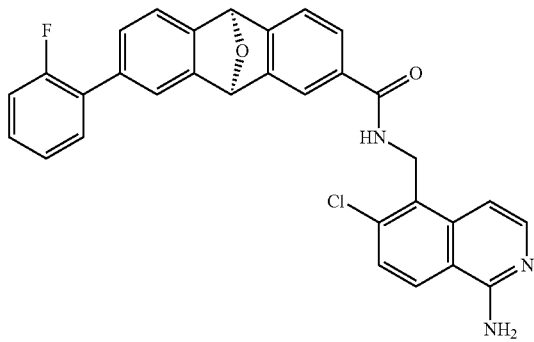

Step 1:

Into a 2-L 3-necked round-bottom flask, were placed a solution of 4-chloro-3-methylbenzoic acid (34.0 g, 199.30 mmol, 1.00 equiv), 2,2-dimethoxyethan-1-amine (21.0 g, 199.74 mmol, 1.00 equiv), DIEA (51.6 g, 399.26 mmol, 2.00 equiv) in dichloromethane (600 mL), followed by the addition of HATU (91.2 g, 239.85 mmol, 1.20 equiv) in portions. The resulting mixture was stirred for 5 h at room temperature then it was washed with 3×300 mL of $H_2O$, dried over anhydrous sodium sulfate and concentrated under vacuum. The residue was purified by silica gel column eluting with ethyl acetate/petroleum ether (1/4) to afford 42.1 g (82%) of 4-chloro-N-(2,2-dimethoxyethyl)-3-methylbenzamide as a yellow solid.

Step 2:

Into a 500-mL 3-necked round-bottom flask, was placed sulfuric acid (150 mL) with stirring at 0° C., followed by the addition of 4-chloro-N-(2,2-dimethoxyethyl)-3-methylbenzamide (20.0 g, 77.61 mmol, 1.00 equiv) in portions. The resulting mixture was stirred at 120° C. for 16 h then it was cooled to room temperature, poured into 1000 mL of iced-water slowly, and extracted with ethyl acetate. The organic layers were combined, washed with 500 mL of brine, dried over anhydrous sodium sulfate and concentrated under vacuum. The residue was purified by silica gel column eluting with dichloromethane/ethyl acetate (1/1) to afford 13.6 g (91%) of a mixture of 6-chloro-5-methylisoquinolin-1-ol and 6-chloro-7-methylisoquinolin-1-ol as a yellow solid.

Step 3:

Into a 500-mL 3-necked round-bottom flask, were placed a mixture of 6-chloro-5-methylisoquinolin-1-ol and 6-chloro-7-methylisoquinolin-1-ol (9.65 g, 49.84 mmol, 1.00 equiv) in $POCl_3$ (120 mL). The resulting mixture was stirred for 5 h at 100° C. and then concentrated under vacuum. The residue was diluted with DCM, washed with sat. aq. $NaHCO_3$, brine and concentrated. The crude product was purified by silica gel column eluting with ethyl acetate/petroleum ether (1/8) o afford 9.45 g (89%) mixture of 1,6-dichloro-5-methylisoquinoline and 1,6-dichloro-7-methylisoquinoline as a yellow solid.

Step 4:

Into a 500-mL 3-necked round-bottom flask, were placed a mixture of 1,6-dichloro-5-methylisoquinoline and 1,6-dichloro-7-methylisoquinoline (6.33 g, 29.85 mmol, 1.00 equiv), (2,4-dimethoxyphenyl)methanamine (15.03 g, 89.89 mmol, 3.00 equiv) and DMSO (200 mL). The resulting solution was stirred overnight at 120° C. then it was diluted with 500 mL of water and extracted with ethyl acetate. The combined organic layer was washed with brine, dried over anhydrous sodium sulfate and concentrated under vacuum. The residue was purified by silica gel column eluting with ethyl acetate/petroleum ether (1/4) to afford 8.7 g (85%) of a mixture of 6-chloro-N-[(4-methoxyphenyl)methyl]-5-methylisoquinolin-1-amine and 6-chloro-N-[(4-methoxyphenyl)methyl]-7-methylisoquinolin-1-amine as a yellow solid.

Step 5:

Into a 500-mL 3-necked round-bottom flask, were placed a solution of 6-chloro-N-[(4-methoxyphenyl)methyl]-5-methylisoquinolin-1-amine and 6-chloro-N-[(4-methoxyphenyl)-methyl]-7-methylisoquinolin-1-amine (10.0 g, 29.17 mmol, 1.00 equiv), dichloromethane (100 mL) and TFA (10 mL). The resulting solution was stirred for 3 h at room temperature and then it was concentrated under vacuum to afford 9.61 g (crude) of a mixture of 6-chloro-5-methylisoquinolin-1-amine and 6-chloro-7-methylisoquinolin-1-amine as a yellow solid.

Step 6:

Into a 1-L round-bottom flask, were placed a solution of 6-chloro-5-methylisoquinolin-1-amine and 6-chloro-7-methylisoquinolin-1-amine (11.52 g, 59.80 mmol, 1.00 equiv), dichloromethane (250 mL), Boc$_2$O (52.32 g, 239.73 mmol, 4.00 equiv) and 4-dimethylaminopyridine (730 mg, 5.98 mmol, 0.10 equiv). The resulting mixture was stirred for 3 h at room temperature then it was concentrated. The residue was purified by silica gel column chromatography eluting with ethyl acetate/petroleum ether (1/4) to afford 8.90 g (38%) of a mixture of tert-butyl N-[(tert-butoxy)carbonyl]-N-(6-chloro-5-methylisoquinolin-1-yl)carbamate and tert-butyl N-[(tert-butoxy)carbonyl]-N-(6-chloro-7-methylisoquinolin-1-yl)carbamate as a yellow solid.

Step 7:

Into a 250-mL 3-necked round-bottom flask, were placed a mixture of tert-butyl N-[(tert-butoxy)carbonyl]-N-(6-chloro-5-methylisoquinolin-1-yl)carbamate and tert-butyl N-[(tert-butoxy)carbonyl]-N-(6-chloro-7-methylisoquinolin-1-yl)carbamate (2.00 g, 5.09 mmol, 1.00 equiv), $CCl_4$ (40 mL), NBS (1.09 g, 6.12 mmol, 1.20 equiv) and benzoyl peroxide (BPO; 370 mg, 1.44 mmol, 0.30 equiv). The resulting mixture was stirred overnight at 90° C. then it was cooled to RT and concentrated. The residue was purified by silica gel column chromatography eluting with ethyl acetate/petroleum ether (1/4) to afford 1.60 g (67%) of a mixture of tert-butyl N-[5-(bromomethyl)-6-chloroisoquinolin-1-yl]-N-[(tert-butoxy)carbonyl]carbamate and tert-butyl N-[7-(bromomethyl)-6-chloroisoquinolin-1-yl]-N-[(tert-butoxy)carbonyl]carbamate as a yellow oil.

Step 8:

Into a 500-mL 3-necked round-bottom flask, were placed a solution of concentrated ammonia (100 mL) and dioxane (50 mL). This was followed by the addition of a solution of tert-butyl N-[5-(bromomethyl)-6-chloroisoquinolin-1-yl]-N-[(tert-butoxy)carbonyl]-carbamate and tert-butyl N-[7-(bromomethyl)-6-chloroisoquinolin-1-yl]-N-[(tert-butoxy)-carbonyl]carbamate (1.60 g, 3.39 mmol, 1.00 equiv) in dioxane (50 mL) dropwise with stirring at room temperature. The resulting mixture was stirred for 4 h at RT and then concentrated under vacuum. The residue was purified by silica gel column chromatography eluting with dichloromethane/methanol (30/1) to afford 480 mg (35%) of a mixture of tert-butyl N-[5-(aminomethyl)-6-chloroisoquinolin-1-yl]-N-[(tert-butoxy)carbonyl]carbamate and tert-butyl N-[7-(aminomethyl)-6-chloroisoquinolin-1-yl]-N-[(tert-butoxy)carbonyl]carbamate as a yellow solid.

Step 9:

Into a 25-mL round-bottom flask, was placed a solution of tert-butyl N-[5-(aminomethyl)-6-chloroisoquinolin-1-yl]-N-[(tert-butoxy)carbonyl]carbamate and tert-butyl N-[7-(aminomethyl)-6-chloroisoquinolin-1-yl]-N-[(tert-butoxy)carbonyl]carbamate (190 mg, 0.47 mmol, 1.00 equiv) in dioxane (5 mL) saturated with HCl gas. The resulting mixture was stirred for 3 h at room temperature then the solids were collected by filtration to afford 90 mg (69%) of a mixture of 5-(aminomethyl)-6-chloroisoquinolin-1-amine dihydrochloride and 7-(aminomethyl)-6-chloroisoquinolin-1-amine dihydrochloride as a yellow solid.

Step 10:

Into a 50-mL 3-necked round-bottom flask purged and maintained with an inert atmosphere of nitrogen, were placed a mixture of (1S,8R)-12-bromo-15-oxatetracyclo[$6.6.1.0^{2,7}.0^{9,14}$]pentadeca-2,4,6,9,11,13-hexaene-4-carboxylic acid (INT-4a1; 158 mg, 0.50 mmol, 1.00 equiv), dioxane (5 mL), water (0.5 mL), (2-fluorophenyl)boronic acid (84 mg, 0.60 mmol, 1.20 equiv), potassium carbonate (138 mg, 1.00 mmol, 2.00 equiv) and $Pd(PPh_3)_4$ (12 mg, 0.01 mmol, 0.02 equiv). The resulting mixture was stirred for 16 h at 100° C. then it was cooled to RT, diluted with 50 mL of DCM and 10 mL of MeOH, dried over anhydrous sodium sulfate and filtered. The filtrate was concentrated under vacuum to afford 175 mg (crude) of (1R,8S)-12-(2-fluorophenyl)-15-oxatetracyclo[$6.6.1.0^{2,7}.0^{9,14}$]pentadeca-2,4,6,9,11,13-hexaene-4-carboxylic acid as an off-white solid.

Step 11:

Into a 25-mL round-bottom flask, were placed a solution of (1R,8S)-12-(2-fluorophenyl)-15-oxatetracyclo[$6.6.1.0^{2,7}.0^{9,14}$]pentadeca-2,4,6,9,11,13-hexaene-4-carboxylic acid (66 mg, 0.20 mmol, 1.00 equiv), N,N-dimethylformamide (5 mL), a mixture of 5-(aminomethyl)-6-chloroisoquinolin-1-amine dihydrochloride and 7-(aminomethyl)-6-chloroisoquinolin-1-amine dihydrochloride (67 mg, 0.24 mmol, 1.20 equiv), DIEA (129 mg, 1.00 mmol, 5.00 equiv) and HATU (91 mg, 0.24 mmol, 1.20 equiv). The resulting mixture was stirred for 3 h at room temperature then the solids were separated by filtration. The filtrate was purified by Prep-HPLC (Column: Waters×Bridge RP18 19*150 mm, 5 um; mobile phase: $CH_3CN$ and $H_2O$ (it is a buffer of 10 mM $NH_4HCO_3$+0.05% ammonia) with 51% acetonitrile in 8 min, flow rate: 20 mL/min; detector UV wavelength: 220 nm) to afford 19.6 mg (19%) of (1R,8S)—N-[(1-amino-6-chloroisoquinolin-5-yl)methyl]-12-(2-fluorophenyl)-15-oxatetracyclo[$6.6.1.0^{2,7}.0^{9,14}$]pentadeca-2,4,6,9,11,13-hexaene-4-carboxamide as a white solid. MS: (M+H)$^+$ found for $C_{31}H_{21}ClFN_3O_2$: 522.

Example 95

Synthesis of (1R,8S)—N-[(1-amino-6-methylisoquinolin-5-yl)methyl]-12-(2-fluoro-phenyl)-15-oxatetracyclo[$6.6.1.0^{2,7}.0^{9,14}$]pentadeca-2,4,6,9,11,13-hexaene-4-carboxamide

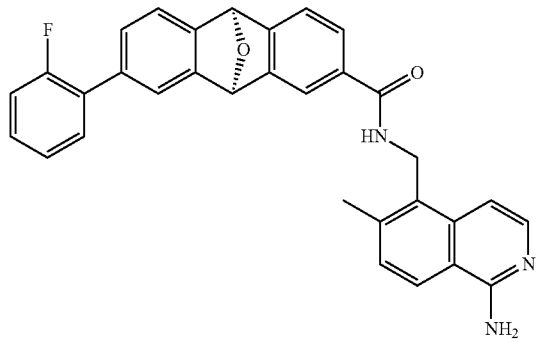

Step 1:

Into a 50-mL 3-necked round-bottom flask, were placed tert-butyl N-[5-(bromomethyl)-6-chloroisoquinolin-1-yl]-N-[(tert-butoxy)carbonyl]carbamate and tert-butyl N-[7-(bromomethyl)-6-chloroisoquinolin-1-yl]-N-[(tert-butoxy)carbonyl]carbamate (Example 94, Step 7; 470 mg, 1.00 mmol, 1.00 equiv), N,N-dimethylformamide (15 mL), tert-butyl N-[(tert-butoxy)carbonyl]carbamate (434 mg, 2.00 mmol, 2.00 equiv), $Cs_2CO_3$ (1.3 g, 3.99 mmol, 4.00 equiv) and LiI (67 mg, 0.50 equiv). The resulting mixture was stirred for 3 h at room temperature then it was diluted with 50 mL of water, extracted with ethyl acetate. The organic layers were combined, washed with 3×50 mL of brine, dried over anhydrous sodium sulfate and concentrated under vacuum. The residue was purified by silica gel column chromatography eluting with ethyl acetate/petroleum ether (1/4) to afford 330 mg (54%) mixture of tert-butyl N-[(1-{bis[(tert-butoxy)carbonyl]amino}-6-chloroisoquinolin-5-yl)methyl]-N-[(tert-butoxy)-carbonyl]-carbamate and tert-butyl N-[(1-{bis[(tert-butoxy)carbonyl]amino}-6-chloroisoquinolin-7-yl)methyl]-N-[(tert-butoxy)carbonyl]carbamate as a yellow solid.

Step 2:

Into a 50-mL 3-necked round-bottom flask purged and maintained with an inert atmosphere of nitrogen, were placed a mixture of tert-butyl N-[(1-{bis[(tert-butoxy)carbonyl]-amino}-6-chloroisoquinolin-5-yl)methyl]-N-[(tert-butoxy)carbonyl]-carbamate and tert-butyl N-[(1-{bis[(tert-butoxy)carbonyl]amino}-6-chloroisoquinolin-7-yl)methyl]-N-[(tert-butoxy)-carbonyl]carbamate (243 mg, 0.40 mmol, 1.00 equiv), dioxane (5 mL) and water (0.5 mL), trimethyl-1,3,5,2,4,6-trioxatriborinane (528 mg, 4.21 mmol, 5.00 equiv), $Pd_2(dba)_3 \cdot CH_2Cl_2$ (41 mg, 0.04 mmol, 0.10 equiv), $Cs_2CO_3$ (261 mg, 0.80 mmol, 2.00 equiv), and tricyclohexyl phosphine ($PCy_3$; 22 mg, 0.20 equiv). The resulting mixture was stirred overnight at 100° C. then it was cooled to RT and concentrated. The residue was directly purified by silica gel column chromatography eluting with ethyl acetate/petroleum ether (1/4) to afford 190 mg (81%) of tert-butyl N-[(1-{bis[(tert-butoxy)carbonyl]amino}-6-methylisoquinolin-5-yl)methyl]-N-[(tert-butoxy)carbonyl]carbamate and tert-butyl N-[(1-{bis[(tert-butoxy)carbonyl]amino}-6-methylisoquinolin-7-yl)methyl]-N-[(tert-butoxy)carbonyl]carbamate as a brown oil.

Step 3:

Into a 25-mL round-bottom flask, was placed a solution of tert-butyl N-[(1-{bis[(tert-butoxy)carbonyl]amino}-6-methylisoquinolin-5-yl)methyl]-N-[(tert-butoxy)carbonyl]-carbamate and tert-butyl N-[(1-{bis[(tert-butoxy)carbonyl]amino}-6-methylisoquinolin-7-yl)methyl]-N-[(tert-butoxy)carbonyl]carbamate (352 mg, 0.60 mmol, 1.00 equiv) in dioxane (5 mL) saturated with HCl gas. The resulting solution was stirred for 5 h at room temperature then the solids were collected by filtration to afford 150 mg (96%) mixture of 5-(aminomethyl)-6-methylisoquinolin-1-amine dihydrochloride and 7-(aminomethyl)-6-methylisoquinolin-1-amine dihydrochloride as a gray solid.

Step 4:

Into a 25-mL round-bottom flask, were placed 5-(aminomethyl)-6-methylisoquinolin-1-amine dihydrochloride and 7-(aminomethyl)-6-methylisoquinolin-1-amine dihydrochloride (62 mg, 0.24 mmol, 1.20 equiv), N,N-dimethylformamide (5 mL), (1R,8S)-12-(2-fluorophenyl)-15-oxatetracyclo[6.6.1.0$^{2,7}$.0$^{9,14}$]pentadeca-2,4,6,9,11,13-hexaene-4-carboxylic acid (Example 94, Step 10; 66 mg, 0.20 mmol, 1.00 equiv), DIEA (129 mg, 1.00 mmol, 5.00 equiv) and HATU (91 mg, 0.24 mmol, 1.20 equiv). The resulting mixture was stirred for 3 h at room temperature then the solids were separated by filtration. The filtrate was purified by Prep-HPLC (Column: Waters×Bridge RP18 19*150 mm, 5 um; mobile phase: $CH_3CN$/water (a buffer of 10 mM $NH_4HCO_3$+0.05% ammonia) with a gradient of acetonitrile from 46% to 50% in 8 min, flow rate: 20 mL/min; detector UV wavelength: 254 nm) to afford 25.8 mg (26%) of the title compound as a white solid. MS: (M+H)$^+$ found for $C_{32}H_{24}FN_3O_2$: 502.

Example 96

Synthesis of (±)-N-[(6-amino-2,4-dimethylpyridin-3-yl)methyl]-11,12-dimethyl-15-oxatetracyclo[6.6.1.0$^{2,7}$.0$^{9,14}$]pentadeca-2,4,6,9(14),10,12-hexaene-4-carboxamide

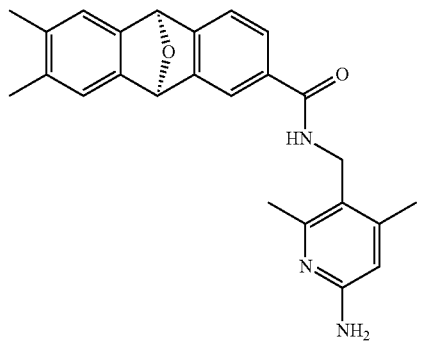

Step 1:

Into a 1-L 3-necked round-bottom flask, was placed a mixture of 1,2,4,5-tetrabromobenzene (100.0 g, 254.00 mmol, 1.00 equiv), toluene (500 mL) and furan (35.4 g, 2.00 equiv) with stirring at –30° C., followed by the drop-wise addition of n-BuLi (112 mL, 2.5 M in hexane, 279.40 mmol, 1.10 equiv). The resulting mixture was allowed to warm up to room temperature and stirred for 30 min. then it was quenched by the addition of water (20 mL). The mixture was then washed with 500 mL of $H_2O$. The water layer was extracted with 3×300 mL of ethyl acetate. The combined organic layers were dried over anhydrous sodium sulfate, concentrated under vacuum and purified by silica gel column chromatography eluting with ethyl acetate/petroleum ether (1/10) to afford 38.5 g (50%) of 4,5-dibromo-11-oxatricyclo[6.2.1.0$^{2,7}$]-undeca-2,4,6,9-tetraene as a yellow solid.

Step 2:

Into a 1000-mL 3-necked round-bottom flask purged and maintained with an inert atmosphere of nitrogen, was placed a solution of 4,5-dibromo-11-oxatricyclo[6.2.1.0$^{2,7}$]-undeca-2,4,6,9-tetraene (10.0 g, 33.12 mmol, 1.00 equiv) in chloroform (150 mL) with stirring at 0° C., followed by the drop-wise addition of bis(pyridin-2-yl)-1,2,4,5-tetrazine (9.40 g, 39.79 mmol, 1.20 equiv) in chloroform (100 mL). The resulting mixture was then stirred for 1 h at 50° C. to deliver 5, 6-dibromo-2-benzofuran in chloroform (150 mL) as a brown liquid (crude).

This solution was cooled to 0° C. with stirring and a solution of [5-(methoxycarbonyl)-2-(trimethylsilyl)phenyl](phenyl)iodanium trifluoromethanesulfonate (18.6 g, 45.22 mmol, 1.00 equiv) in dichloromethane (200 mL) was added drop-wise, followed by TBAF (66.6 mL, 1 mol/L in THF, 66.55 mmol, 1.50 equiv) drop-wise. The resulting mixture was stirred for an additional 30 min at 0° C. then it was concentrated under vacuum. The residue was purified by silica gel column chromatography eluting with ethyl acetate/petroleum ether (1/10) to afford 4.80 g (35%) of (±)-methyl 11,12-dibromo-15-oxatetracyclo[6.6.1.0$^{2,7}$.0$^{9,14}$]-pentadeca-2(7),3,5,9,11,13-hexaene-4-carboxylate as a yellow solid.

Step 3:

Into a 10-mL round-bottom flask, was placed a mixture of (±)-methyl 11,12-dibromo-15-oxatetracyclo[6.6.1.0$^{2,7}$.0$^{9,14}$]pentadeca-2(7),3,5,9,11,13-hexaene-4-carboxylate (100 mg, 0.24 mmol, 1.00 equiv), dioxane (2 mL), water (0.2 mL), trimethyl-1,3,5,2,4,6-trioxatri-borinane (304 mg, 2.42 mmol, 10.00 equiv), K$_3$PO$_4$ (206 mg, 0.97 mmol, 4.00 equiv) and Pd(dppf)Cl$_2$ (14 mg, 0.02 mmol, 0.05 equiv). The resulting mixture was stirred for 5 h at 80° C. under N$_2$, then it was cooled to RT and concentrated. The residue was purified by silica gel column chromatography eluting with ethyl acetate/petroleum ether (1/5) to afford 45 mg (66%) of (±)-methyl 11,12-dimethyl-15-oxatetracyclo[6.6.1.0$^{2,7}$.0$^{9,14}$]pentadeca-2(7),3,5,9,11,13-hexaene-4-carboxylate as yellow solids.

Step 4:

Into a 10-mL round-bottom flask, was placed a mixture of (±)-methyl 11,12-dimethyl-15-oxatetracyclo[6.6.1.0$^{2,7}$.0$^{9,14}$]pentadeca-2(7),3,5,9,11,13-hexaene-4-carboxylate (40 mg, 0.14 mmol, 1.00 equiv), methanol (1.0 mL), water (0.5 mL), dichloromethane (1.0 mL) and 60% sodium hydroxide (in oil suspension, 11.4 mg, 0.29 mmol, 2.00 equiv). The resulting mixture was stirred for 2 h at 50° C. then it was cooled to RT, diluted with 5 mL of water and the pH value of the solution was adjusted to 6 with 2 mol/L HCl aqueous solution. The mixture was then extracted with 3×10 mL of ethyl acetate. The organic layers were dried over anhydrous sodium sulfate and concentrated under vacuum to afford 30 mg (79%) of (±)-11,12-dimethyl-15-oxatetracyclo[6.6.1.0$^{2,7}$.0$^{9,14}$]pentadeca-2(7),3,5,9,11,13-hexaene-4-carboxylic acid as a yellow solid.

Step 5:

Into a 10-mL round-bottom flask, was placed (±)-11,12-dimethyl-15-oxatetracyclo-[6.6.1.0$^{2,7}$.0$^{9,14}$]pentadeca-2(7),3,5,9,11,13-hexaene-4-carboxylic acid (30 mg, 0.11 mmol, 1.00 equiv), N,N-dimethylformamide (2 mL), 5-(aminomethyl)-4,6-dimethylpyridin-2-amine (17 mg, 0.11 mmol, 1.00 equiv), DIEA (58 mg, 0.45 mmol, 4.00 equiv) and HATU (42 mg, 0.11 mmol, 1.00 equiv). The resulting mixture was stirred for 5 h at 25° C. then the solids were separated by filtration. The filtrate was directly subjected to reverse preparative HPLC (Prep-C18, 5 M×Bridge column, 19×150 mm, waters; gradient elution of 55% MeCN in water to 65% MeCN in water over a 8 min period, where the aqueous phase contains 10 mM NH$_4$HCO$_3$+0.05% ammonia) to provide the title compound as a white solid (25.6 mg, 57%). MS: (M+H)$^+$ found for C$_{25}$H$_{25}$N$_3$O$_2$: 400.2.

Example 97

Synthesis of (±)-N-[(6-amino-2,4-dimethylpyridin-3-yl)methyl]-11,12-dicyclopropyl-15-oxatetracyclo[6.6.1.0$^{2,7}$.0$^{9,14}$]pentadeca-2,4,6,9,11,13-hexaene-4-carboxamide trifluoroacetate salt

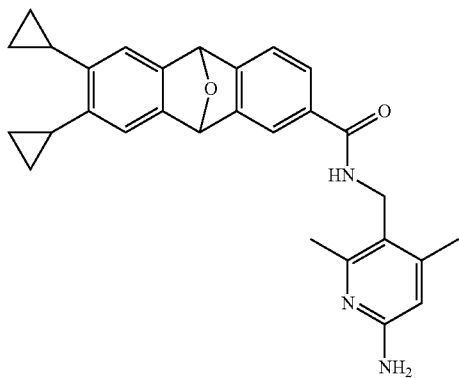 [SMILES: Cc1cc(N)nc(C)c1CNC(=O)c1ccc2c(c1)C1OC2c2cc(C3CC3)c(C3CC3)cc21]

Step 1:

Into a 100-mL round-bottom flask, was placed (±)-methyl 11,12-dibromo-15-oxatetracyclo[6.6.1.0$^{2,7}$.0$^{9,14}$]pentadeca-2(7),3,5,9,11,13-hexaene-4-carboxylate (Example 96, Steps 1-2; 700 mg, 1.71 mmol, 1.00 equiv), toluene (20 mL), water (2 mL), cyclopropylboronic acid (370 mg, 4.31 mmol, 2.50 equiv), K$_3$PO$_4$ (2.53 g, 11.92 mmol, 7.00 equiv), tricyclohexylphosphane (960 mg, 3.42 mmol, 2.00 equiv) and Pd(OAc)$_2$ (380 mg, 1.69 mmol, 1.00 equiv). The resulting mixture was stirred for 4 h at 100° C. under nitrogen then it was cooled to RT and concentrated. The residue was purified by silica gel column chromatography eluting with ethyl acetate/petroleum ether (1/5) to deliver 320 mg (56%) of (±)-methyl 11,12-dicyclopropyl-15-oxatetracyclo[6.6.1.0$^{2,7}$.0$^{9,14}$]pentadeca-2,4,6,9,11,13-hexaene-4-carboxylate as a light yellow solid.

Step 2:

Into a 50-mL round-bottom flask, was placed (±)-methyl 11,12-dicyclopropyl-15-oxatetracyclo[6.6.1.0$^{2,7}$.0$^{9,14}$]pentadeca-2,4,6,9,11,13-hexaene-4-carboxylate (300 mg, 0.90 mmol, 1.00 equiv), THF (4 mL), MeOH (4 mL), H$_2$O (4 mL) and NaOH (140 mg, 3.50 mmol, 4.00 equiv). The resulting mixture was stirred for 2 h at room temperature then it was diluted with 5 mL of water and acidified with 1 N hydrogen chloride aqueous solution to pH=4. The mixture was then extracted with ethyl acetate (3×10 mL), dried over anhydrous Na$_2$SO$_4$ and concentrated under vacuum to afford 280 mg (crude) of (±)-11,12-dicyclopropyl-15-oxatetracyclo[6.6.1.0$^{2,7}$.0$^{9,14}$]pentadeca-2,4,6,9,11,13-hexaene-4-carboxylic acid as a yellow solid.

Step 3:

Into a 10-mL round-bottom flask, was placed (±)-11,12-dicyclopropyl-15-oxatetracyclo[6.6.1.0$^{2,7}$.0$^{9,14}$]pentadeca-2,4,6,9,11,13-hexaene-4-carboxylic acid (80 mg, 0.25 mmol, 1.00 equiv), DMF (2 mL), 5-(aminomethyl)-4,6-dimethylpyridin-2-amine dihydrochloride (56 mg, 0.25 mmol, 1.00 equiv), DIEA (162 mg, 1.25 mmol, 5.00 equiv) and HATU (143 mg, 0.38 mmol, 1.50 equiv). The resulting mixture was stirred for 4 h at 25° C. then it was filtered and directly subjected to reverse phase preparative HPLC (Prep-C18, 5 M SunFire column, 19×150 mm, Waters; gradient elution of 66% MeCN in water to 78% MeCN in water over a 8 min period, where both solvents contain 0.1% TFA) to provide the title compound as a white solid (26 mg, 18%). MS: [M-TFA+1]$^+$ found for C$_{29}$H$_{29}$N$_3$O$_2$: 452.1

Example 98

Synthesis of (±)-N-[(4-carbamimidoylphenyl)methyl]-11,12-diethyl-15-oxatetra-cyclo[6.6.1.0$^{2,7}$.0$^{9,14}$]pentadeca-2,4,6,9(14),10,12-hexaene-4-carboxamide trifluoroacetate Salt

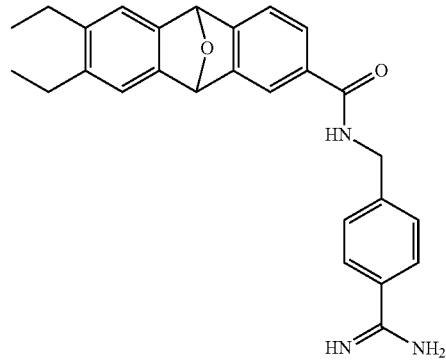 [SMILES: CCc1cc2c(cc1CC)C1OC2c2ccc(C(=O)NCc3ccc(C(=N)N)cc3)cc21]

Step 1:

Into a 50-mL round-bottom flask, was placed (±)-methyl 11,12-dibromo-15-oxatetracyclo[6.6.1.0$^{2,7}$.0$^{9,14}$]pentadeca-2(7),3,5,9,11,13-hexaene-4-carboxylate (Example 96, Steps 1-2; 500 mg, 1.22 mmol), ethylboronic acid (910 mg, 12.32 mmol, 10.00 equiv), dioxane (10 mL), H$_2$O (1 mL), K$_3$PO$_4$ (782 mg, 3.68 mmol, 3.00 equiv) and Pd(dppf)Cl$_2$ (44.9 mg, 0.06 mmol, 0.05 equiv). The resulting mixture was stirred for 12 h at 80° C. then it was cooled to RT and concentrated under vacuum. The residue was purified by silica gel column chromatography eluting with ethyl acetate/petroleum ether (1/5) to deliver 320 mg (85%) of (±)-methyl 11,12-diethyl-15-oxatetracyclo[6.6.1.0$^{2,7}$.0$^{9,14}$]pentadeca-2(7),3,5,9,11,13-hexaene-4-carboxylate as yellow oil.

Step 2:

Into a 10-mL round-bottom flask, was placed (±)-methyl 11,12-diethyl-15-oxatetracyclo[6.6.1.0$^{2,7}$.0$^{9,14}$]pentadeca-2(7),3,5,9,11,13-hexaene-4-carboxylate (308 mg, 1.00 mmol, 1.00 equiv), methanol (2 mL), dichloromethane (2 mL), water (1 mL) and NaOH (160 mg, 4.00 mmol, 4.00 equiv). The resulting mixture was stirred for 2 h at 50° C. then it was cooled to RT and the pH value of the solution was adjusted to 7 with 1 mol/L HCl aqueous solution. The mixture was then concentrated under vacuum to deliver 320 mg (crude) of (±)-11,12-diethyl-15-oxatetracyclo[6.6.1.0$^{2,7}$.0$^{9,14}$]pentadeca-2(7),3,5,9,11,13-hexaene-4-carboxylic acid as a yellow solid. The crude product was used in the next step without further purification.

Step 3:

Into a 10-mL round-bottom flask, was placed (±)-11,12-diethyl-15-oxatetracyclo[6.6.1.0$^{2,7}$.0$^{9,14}$]pentadeca-2(7),3,5,9,11,13-hexaene-4-carboxylic acid (100.0 mg, 0.34 mmol, 1.00 equiv), N,N-dimethylformamide (5 mL), DIEA (132 mg, 1.02 mmol, 3.00 equiv), HOBt (55.0 mg, 0.41 mmol, 1.20 equiv), EDC (79.0 mg, 0.51 mmol, 1.50 equiv) and 4-(aminomethyl)benzene-1-carboximidamide dihydrochloride (113.0 mg, 0.51 mmol, 1.50 equiv). The resulting mixture was stirred for 1 h at room temperature then it was filtered and directly subjected to reverse preparative HPLC (Prep-C18, 5 M×Bridge column, 19×150 mm, waters; gradient elution of 29% MeCN in water to 44% MeCN in water over a 7 min period, where both solvents contain 0.1% TFA) to provide the title compound as a white solid (71.8 mg, 39%). MS [M-TFA+1]$^+$ found for C$_{27}$H$_{27}$N$_3$O$_2$:426.2.

Example 99

Synthesis of (±)-N-[(4-carbamimidoylphenyl)methyl]-11,12-dicyclopropyl-15-oxatetracyclo-[6.6.1.0$^{2,7}$.0$^{9,14}$]pentadeca-2,4,6,9,11,13-hexaene-4-carboxamide

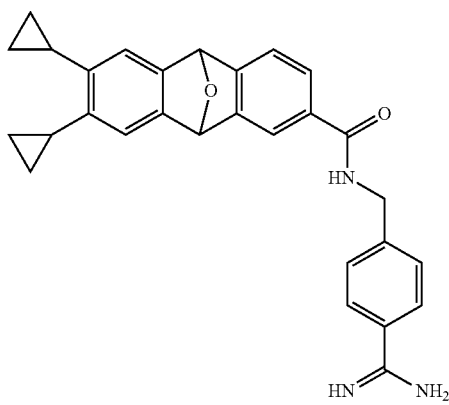 [SMILES: N=C(N)c1ccc(CNC(=O)c2ccc3c(c2)C2OC3c3cc(C4CC4)c(C4CC4)cc32)cc1]

The title compound was prepared following the procedure described in Example 97, Step 3, but using 4-(aminomethyl)benzene-1-carboximidamide dihydrochloride instead of 5-(aminomethyl)-4,6-dimethylpyridin-2-amine dihydrochloride. This provided (±)-N-[(4-carbamimidoylphenyl)methyl]-11,12-dicyclopropyl-15-oxatetracyclo[6.6.1.0$^{2,7}$.0$^{9,14}$]pentadeca-2,4,6,9,11,13-hexaene-4-carboxamide as an off-white solid (46.0 mg, 33%). MS: (M+H)$^+$ found for C$_{29}$H$_{27}$N$_3$O$_2$: 450.3.

Example 100

Synthesis of (±)-N-[(4-carbamimidoylphenyl)methyl]-11,12-dimethyl-15-oxatetracyclo-[6.6.1.0$^{2,7}$.0$^{9,14}$]pentadeca-2,4,6,9(14),10,12-hexaene-4-carboxamide trifluoroacetate Salt

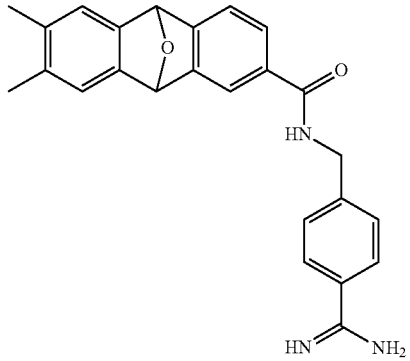 [SMILES: Cc1cc2c(cc1C)C1OC2c2ccc(C(=O)NCc3ccc(C(=N)N)cc3)cc21]

The title compound was prepared following the procedure described in Example 96, Step 5, but using 4-(aminomethyl)benzene-1-carboximidamide dihydrochloride instead of 5-(aminomethyl)-4,6-dimethylpyridin-2-amine dihydrochloride. This provided (±)-N-[(4-carbamimidoylphenyl)methyl]-11,12-dimethyl-15-oxatetracyclo[6.6.1.0$^{2,7}$.0$^{9,14}$]pentadeca-2,4,6,9(14),10,12-hexaene-4-carboxamide trifluoroacetate salt as a white solid (26.9 mg, 23%). MS [M-TFA+1]$^+$ found for C$_{25}$H$_{23}$N$_3$O$_2$: 398.2.

Example 101

Synthesis of (±)-N-[(6-amino-2,4-dimethylpyridin-3-yl)methyl]-12-(2,4-difluorophenyl)-11-ethyl-15-oxatetracyclo[6.6.1.0$^{2,7}$.0$^{9,14}$]pentadeca-2,4,6,9(14),10,12-hexaene-4-carboxamide and (±)-N-[(6-amino-2,4-dimethylpyridin-3-yl)methyl]-11-(2,4-difluorophenyl)-12-ethyl-15-oxatetracyclo[6.6.1.0$^{2,7}$.0$^{9,14}$]pentadeca-2,4,6,9(14),10,12-hexaene-4-carboxamide

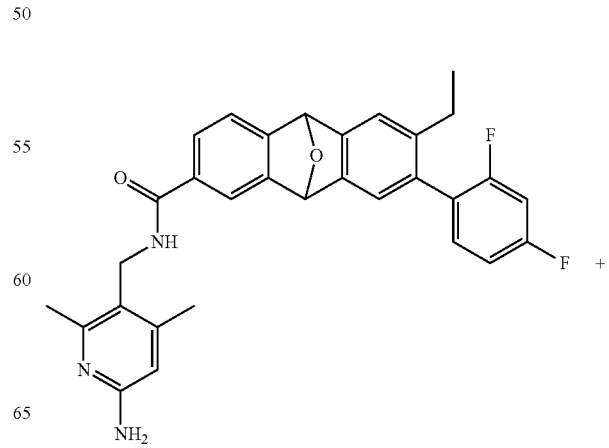

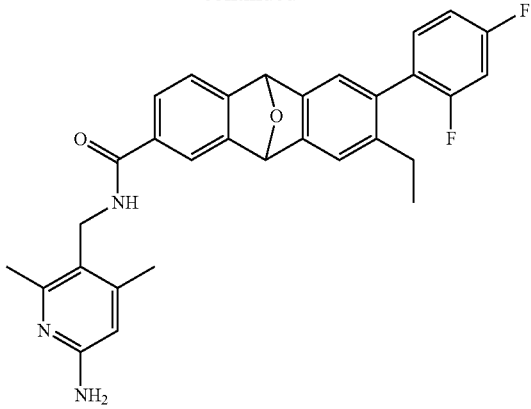

Step 1:

Into a 25-mL round-bottom flask purged and maintained with an inert atmosphere of nitrogen, was placed (±)-methyl 11,12-dibromo-15-oxatetracyclo-[6.6.1.0$^{2,7}$.0$^{9,14}$]-pentadeca-2(7),3,5,9,11,13-hexaene-4-carboxylate (Example 96, Steps 1-2; 300 mg, 0.73 mmol, 1.00 equiv), 1,4-dioxane (4 mL), water (0.5 mL), (2,4-difluorophenyl)boronic acid (115.6 mg, 0.73 mmol, 1.00 equiv), Pd(dppf)Cl$_2$.CH$_2$Cl$_2$ (60 mg, 0.08 mmol, 0.10 equiv) and K$_3$PO$_4$ (310 mg, 1.46 mmol, 2.00 equiv). The resulting mixture was degassed and purged with nitrogen 3 times, then it was stirred for 3 h at 80° C. The mixture was then concentrated under vacuum and the residue was purified by silica gel column chromatography eluting with ethyl acetate/petroleum ether (1/5) to deliver 150 mg (46.3%) of a mixture of (±)-methyl 11-bromo-12-(2,4-difluorophenyl)-15-oxatetracyclo [6.6.1.0$^{2,7}$.0$^{9,14}$]pentadeca-2(7),3,5,9,11,13-hexaene-4-carboxylate and (±)-methyl 11-(2,4-difluorophenyl)-12-bromo-15-oxatetracyclo[6.6.1.0$^{2,7}$.0$^{9,14}$]-pentadeca-2(7),3,5,9,11,13-hexaene-4-carboxylate as a white solid.

Step 2:

Into a 25-mL round-bottom flask, was placed a mixture of (±)-methyl 11-bromo-12-(2,4-difluorophenyl)-15-oxatetracyclo[6.6.1.0$^{2,7}$.0$^{9,14}$]pentadeca-2(7),3,5,9,11,13-hexaene-4-carboxylate and (±)-methyl 11-(2,4-difluorophenyl)-12-bromo-15-oxatetracyclo-[6.6.1.0$^{2,7}$.0$^{9,14}$]pentadeca-2(7),3,5,9,11,13-hexaene-4-carboxylate (150 mg, 0.34 mmol, 1.00 equiv), 2-ethenyl-4,4,5,5-tetramethyl-1,3,2-dioxaborolane (104 mg, 0.68 mmol, 2.00 equiv), dioxane (4.00 mL), water (0.50 mL), K$_3$PO$_4$ (216 mg, 1.02 mmol, 3.00 equiv) and Pd(dppf)Cl$_2$.CH$_2$Cl$_2$ (55 mg, 0.08 mmol, 0.20 equiv). This mixture was degassed, purged with nitrogen 3 times and stirred for 3 h at 80° C. The residue was purified by silica gel column chromatography eluting with ethyl acetate/petroleum ether (1/5) to deliver 110 mg (83%) a mixture of (±)-methyl 11-ethenyl-12-(2,4-difluorophenyl)-15-oxatetracyclo[6.6.1.0$^{2,7}$.0$^{9,14}$]-pentadeca-2(7),3,5,9,11,13-hexaene-4-carboxylate and (±)-methyl 11-(2,4-difluorophenyl)-12-ethenyl-15-oxatetracyclo[6.6.1.0$^{2,7}$.0$^{9,14}$]pentadeca-2(7),3,5,9,11,13-hexaene-4-carboxylate as a light yellow solid.

Step 3:

Into a 50-mL round-bottom flask, was placed a mixture of (±)-methyl 11-ethenyl-12-(2,4-difluorophenyl)-15-oxatetracyclo[6.6.1.0$^{2,7}$.0$^{9,14}$]pentadeca-2(7),3,5,9,11,13-hexaene-4-carboxylate and (±)-methyl 11-(2,4-difluorophenyl)-12-ethenyl-15-oxatetracyclo[6.6.1.0$^{2,7}$.0$^{9,14}$]-pentadeca-2(7),3,5,9,11,13-hexaene-4-carboxylate (140 mg, 0.36 mmol, 1.00 equiv), methanol (10 mL), water (5 mL) and sodium hydroxide (144 mg, 3.60 mmol, 10.00 equiv). The resulting mixture was stirred for 2 h at 60° C. then it was cooled to RT and the pH value was adjusted to 5 with 2N HCl aqueous solution. The crude reaction mixture was filtered and directly subjected to reverse preparative HPLC (SunFire Prep C18 5 m 19*150 mm; gradient elution of 19% MeCN in water to 33% MeCN in water over a 6 min period, where both solvents contain 0.1% TFA) to provide a mixture of (±)-1-ethenyl-12-(2,4-difluorophenyl)-15-oxatetracyclo[6.6.1.0$^{2,7}$.0$^{9,14}$]-pentadeca-2(7),3,5,9,11,13-hexaene-4-carboxylic acid and (±)-11-(2,4-difluorophenyl)-12-ethenyl-15-oxatetracyclo [6.6.1.0$^{2,7}$.0$^{9,14}$]pentadeca-2(7),3,5,9,11,13-hexaene-4-carboxylic acid as a white solid (110 mg, 54%).

Step 4:

Into a 25-mL round-bottom flask, was placed a mixture of (±)-1-ethenyl-12-(2,4-difluorophenyl)-15-oxatetracyclo [6.6.1.0$^{2,7}$.0$^{9,14}$]pentadeca-2(7),3,5,9,11,13-hexaene-4-carboxylic acid and (±)-11-(2,4-difluorophenyl)-12-ethenyl-15-oxatetracyclo[6.6.1.0$^{2,7}$.0$^{9,14}$]pentadeca-2(7),3,5,9,11,13-hexaene-4-carboxylic acid (110 mg, 0.29 mmol, 1.00 equiv), N,N-dimethylformamide (4.0 mL), 5-(aminomethyl)-4,6-dimethylpyridin-2-amine dihydrochloride (78 mg, 0.35 mmol, 1.20 equiv), DIEA (151 mg, 1.17 mmol, 4.00 equiv) and HATU (133.4 mg, 0.35 mmol, 1.20 equiv). The resulting mixture was stirred for 2 h at room temperature then it was concentrated. The residue was purified by silica gel column chromatography eluting with dichloromethane/methanol (5/1) to deliver 120 mg (81%) of (±)-N-[(6-amino-2,4-dimethyl-pyridin-3-yl)methyl]-12-(2,4-difluorophenyl)-11-ethenyl-15-oxatetracyclo[6.6.1.0$^{2,7}$.0$^{9,14}$]-pentadeca-2,4,6,9(14),10,12-hexaene-4-carboxamide and (±)-N-[(6-amino-2,4-dimethylpyridin-3-yl)methyl]-1-(2,4-difluorophenyl)-12-ethenyl-15-oxatetracyclo[6.6.1.0$^{2,7}$.0$^{9,14}$]pentadeca-2,4,6,9(14),10,12-hexaene-4-carboxamide as a light yellow solid.

Step 5:

Into a 100-mL round-bottom flask, was placed (±)-N-[(6-amino-2,4-dimethylpyridin-3-yl)methyl]-12-(2,4-difluorophenyl)-11-ethenyl-15-oxatetracyclo-[6.6.1.0$^{2,7}$.0$^{9,14}$]-pentadeca-2,4,6,9(14),10,12-hexaene-4-carboxamide and (±)-N-[(6-amino-2,4-dimethylpyridin-3-yl)methyl]-11-(2,4-difluorophenyl)-12-ethenyl-15-oxatetracyclo[6.6.1.0$^{2,7}$.0$^{9,14}$]pentadeca-2,4,6,9(14),10,12-hexaene-4-carboxamide (80 mg, 0.16 mmol, 1.00 equiv), methanol (50 mL) and 5% palladium on carbon (8 mg). The mixture was degassed, purged with hydrogen 3 times and stirred for 2 h at 25° C. under a hydrogen atmosphere. The solids were then separated by filtration and the filtrate was concentrated under vacuum. The residue was directly subjected to reverse preparative HPLC (Prep-C18, 5 M XBridge column, 19×150 mm, Waters; gradient elution of 52% MeCN in water to 57% MeCN in water over a 6 min period, where both solvents contain 10 mM NH$_4$HCO$_3$ and 0.05% ammonia) to provide (±)-N-[(6-amino-2,4-dimethylpyridin-3-yl)methyl]-12-(2,4-difluoro-phenyl)-11-ethyl-15-oxatetracyclo[6.6.1.0$^{2,7}$.0$^{9,14}$] pentadeca-2,4,6,9(14),10,12-hexaene-4-carboxamide and (±)-N-[(6-amino-2,4-dimethylpyridin-3-yl)methyl]-11-(2,4-difluorophenyl)-12-ethyl-15-oxatetracyclo[6.6.1.0$^{2,7}$.0$^{9,14}$] pentadeca-2,4,6,9(14),10,12-hexaene-4-carboxamide as a white solid (17.3 mg, 21.5%). MS: (M+H)$^+$ found for C$_{31}$H$_{27}$F$_2$N$_3$O$_2$: 512.0.

Example 102

Synthesis of (±)-N-[(6-amino-2,4-dimethylpyridin-3-yl)methyl]-12-(4-fluorophenyl)-8-methyl-15-oxatetracyclo[6.6.1.0$^{2,7}$.0$^{9,14}$]pentadeca-2,4,6,9,11,13-hexaene-4-carboxamide, (±)-N-[(6-amino-2,4-dimethylpyridin-3-yl)methyl]-11-(4-fluorophenyl)-8-methyl-15-oxatetra-cyclo[6.6.1.0$^{2,7}$.0$^{9,14}$]pentadeca-2,4,6,9,11,13-hexaene-4-carboxamide, (±)-N-[(6-amino-2,4-dimethylpyridin-3-yl)methyl]-12-(4-fluorophenyl)-1-methyl-15-oxatetracyclo-[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(4-fluorophenyl)-1-methyl-15-oxatetracyclo-[6.6.1.0$^{2,7}$.0$^{9,14}$]pentadeca-2,4,6,9,11,13-hexaene-4-carboxamide triflate salt

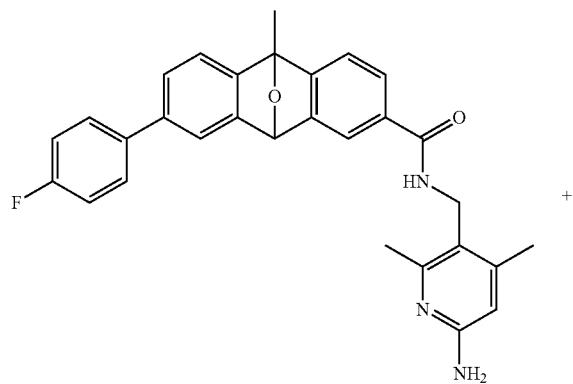

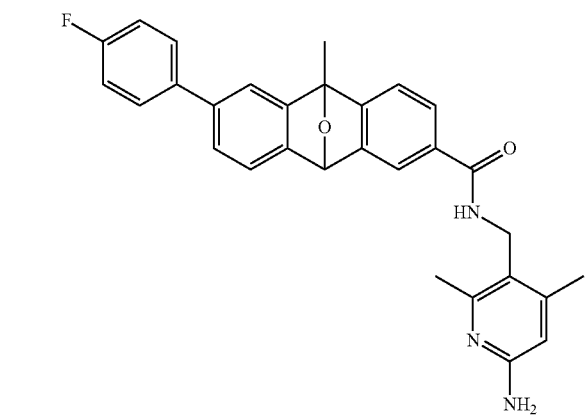

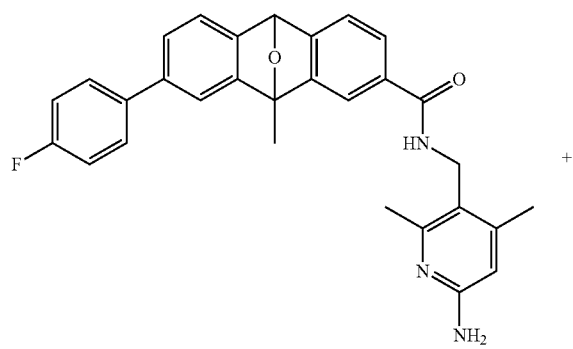

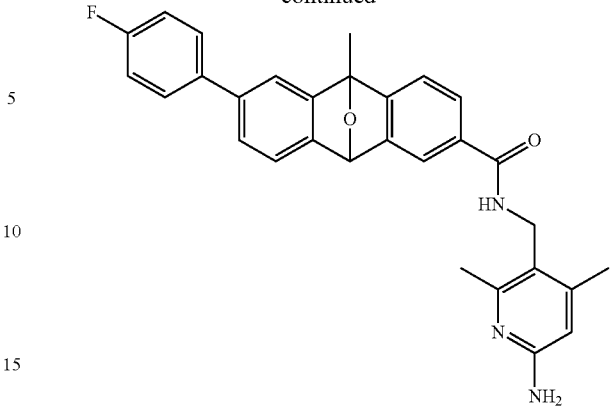

Step 1:

Into a 100-mL 3-necked round-bottom flask, was placed a mixture of 1,2,4-tribromobenzene (5.20 g, 16.52 mmol, 1.00 equiv) and 2-methylfuran (4.18 g, 50.91 mmol, 3.00 equiv) in toluene (30 mL) with stirring at −30° C., followed by the drop-wise addition of n-BuLi (7.48 mL, 1.10 equiv). The resulting mixture was stirred for 30 min at −30° C. then it was quenched by the addition of 50 mL of H$_2$O, cooled to RT and extracted with 3×50 mL of ethyl acetate. The organic layer was washed with 200 mL of H$_2$O, dried over anhydrous sodium sulfate and concentrated under vacuum. The residue was purified by a silica gel column chromatography eluting with ethyl acetate/petroleum ether (1:3) to deliver 2.10 g (54%) of a mixture of (±)-4-bromo-1-methyl-11-oxatricyclo[6.2.1.0$^{2,7}$]undeca-2,4,6,9-tetraene and (±)-5-bromo-1-methyl-11-oxatricyclo[6.2.1.0$^{2,7}$]undeca-2,4,6,9-tetraene as a light yellow solid.

Step 2:

Into a 100-mL 3-necked round-bottom flask, was placed a solution of (±)-4-bromo-1-methyl-11-oxatricyclo[6.2.1.0$^{2,7}$]undeca-2,4,6,9-tetraene and (±)-5-bromo-1-methyl-11-oxatricyclo[6.2.1.0$^{2,7}$]undeca-2,4,6,9-tetraene (2.10 g, 8.86 mmol, 1.00 equiv) in chloroform (30 mL) with stirring at rt, followed by the slow addition of a solution of bis(pyridin-2-yl)-1,2,4,5-tetrazine (2.40 g, 10.16 mmol, 1.10 equiv) in chloroform (20 mL). The resulting mixture was stirred for 1 h at 50° C. to deliver the mixture of corresponding isobenzofurans intermediate (50 mL) as a red solution. To this solution into a 100-mL 3-necked round-bottom flask at 0° C. was added a solution of [5-(methoxycarbonyl)-2-(trimethylsilyl)phenyl](phenyl)iodanium trifluoromethanesulfonate (5.60 g, 9.99 mmol, 1.00 equiv) in dichloromethane (40 mL), followed by TBAF (5.23 g, 20.00 mmol, 2.00 equiv). The resulting mixture was stirred for 30 min at 0° C. then it was concentrated under vacuum. The residue was purified by silica gel column chromatography eluting with ethyl acetate/petroleum ether (1:3) to deliver 900 mg (26%) of (±)-methyl 12-bromo-8-methyl-15-oxatetracyclo[6.6.1.0$^{2,7}$.0$^{9,14}$]pentadeca-2(7),3,5,9,11,13-hexaene-4-carboxylate, (±)-methyl 11-bromo-8-methyl-15-oxatetracyclo[6.6.1.0$^{2,7}$.0$^{9,14}$]pentadeca-2(7),3,5,9,11,13-hexaene-4-carboxylate, (±)-methyl 12-bromo-1-methyl-15-oxatetracyclo-[6.6.1.0$^{2,7}$.0$^{9,14}$]pentadeca-2(7),3,5,9,11,13-hexaene-4-carboxylate and (±)-methyl 11-bromo-1-methyl-15-oxatetracyclo[6.6.1.0$^{2,7}$.0$^{9,14}$]pentadeca-2(7),3,5,9,11,13-hexaene-4-carboxylate as a light yellow solid.

Step 3:

Into a 50-mL round-bottom flask, was placed a mixture of (±)-methyl 12-bromo-8-methyl-15-oxatetracyclo[6.6.

1.0²,⁷.0⁹,¹⁴]pentadeca-2(7),3,5,9,11,13-hexaene-4-carboxylate, (±)-methyl 11-bromo-8-methyl-15-oxatetracyclo[6.6.1.0²,⁷.0⁹,¹⁴]pentadeca-2(7),3,5,9,11,13-hexaene-4-carboxylate, (±)-methyl 12-bromo-1-methyl-15-oxatetracyclo[6.6.1.0²,⁷.0⁹,¹⁴]-pentadeca-2(7),3,5,9,11,13-hexaene-4-carboxylate and (±)-methyl 11-bromo-1-methyl-15-oxatetracyclo[6.6.1.0²,⁷.0⁹,¹⁴]pentadeca-2(7),3,5,9,11,13-hexaene-4-carboxylate (500.0 mg, 1.45 mmol, 1.00 equiv), dioxane/H₂O (5/0.5 mL), (4-fluorophenyl)boronic acid (665.0 mg, 4.75 mmol, 1.50 equiv), sodium carbonate (461.0 mg, 4.35 mmol, 3.00 equiv) and Pd(dppf)Cl₂ (53.0 mg, 0.07 mmol, 0.05 equiv) with stirring under N₂. The resulting mixture was stirred for 3 h at 90° C. then it was cooled to RT and concentrated under vacuum. The residue was purified by silica gel column chromatography eluting with ethyl acetate/petroleum ether (1:5) to afford 410.0 mg (79%) of a mixture of (±)-methyl 12-(4-fluorophenyl)-8-methyl-15-oxatetracyclo-[6.6.1.0²,⁷.0⁹,¹⁴]pentadeca-2(7),3,5,9,11,13-hexaene-4-carboxylate, (±)-methyl 11-(4-fluorophenyl)-8-methyl-15-oxatetracyclo[6.6.1.0²,⁷.0⁹,¹⁴]pentadeca-2(7),3,5,9,11,13-hexaene-4-carboxylate, (±)-methyl 12-(4-fluorophenyl)-1-methyl-15-oxatetracyclo[6.6.1.0²,⁷.0⁹,¹⁴]-pentadeca-2(7),3,5,9,11,13-hexaene-4-carboxylate and (±)-methyl 11-(4-fluorophenyl)-1-methyl-15-oxatetracyclo[6.6.1.0²,⁷.0⁹,¹⁴]pentadeca-2(7),3,5,9,11,13-hexaene-4-carboxylate as a light yellow solid.

Step 4:

Into a 25-mL round-bottom flask, was placed a mixture of (±)-methyl 12-(4-fluorophenyl)-8-methyl-15-oxatetracyclo[6.6.1.0²,⁷.0⁹,¹⁴]pentadeca-2(7),3,5,9,11,13-hexaene-4-carboxylate, (±)-methyl 11-(4-fluorophenyl)-8-methyl-15-oxatetracyclo[6.6.1.0²,⁷.0⁹,¹⁴]-pentadeca-2(7),3,5,9,11,13-hexaene-4-carboxylate, (±)-methyl 12-(4-fluorophenyl)-1-methyl-15-oxatetracyclo[6.6.1.0²,⁷.0⁹,¹⁴]pentadeca-2(7),3,5,9,11,13-hexaene-4-carboxylate and (±)-methyl 11-(4-fluorophenyl)-1-methyl-15-oxatetracyclo[6.6.1.0²,⁷.0⁹,¹⁴]pentadeca-2(7),3,5,9,11,13-hexaene-4-carboxylate (410.0 mg, 1.14 mmol, 1.00 equiv), methanol/H₂O (5/1 mL) and sodium hydroxide (142.8 mg, 3.57 mmol, 3.00 equiv). The resulting mixture was stirred for 2 h at room temperature then the pH value of the solution was adjusted to 7 with 1N hydrogen chloride aqueous solution. The mixture was then concentrated under vacuum to deliver 430.0 mg (crude) of a mixture of (±)-12-(4-fluorophenyl)-8-methyl-15-oxatetracyclo[6.6.1.0²,⁷.0⁹,¹⁴]pentadeca-2(7),3,5,9,11,13-hexaene-4-carboxylic acid, (±)-11-(4-fluorophenyl)-8-methyl-15-oxatetracyclo-[6.6.1.0²,⁷.0⁹,¹⁴]pentadeca-2(7),3,5,9,11,13-hexaene-4-carboxylic acid, (±)-12-(4-fluorophenyl)-1-methyl-15-oxatetracyclo-[6.6.1.0²,⁷.0⁹,¹⁴]pentadeca-2(7),3,5,9,11,13-hexaene-4-carboxylic acid and (±)-11-(4-fluorophenyl)-1-methyl-15-oxatetracyclo[6.6.1.0²,⁷.0⁹,¹⁴]pentadeca-2(7),3,5,9,11,13-hexaene-4-carboxylic acid as a yellow solid.

Step 5:

Into a 8-mL vial, was placed a mixture of (±)-12-(4-fluorophenyl)-8-methyl-15-oxatetracyclo[6.6.1.0²,⁷.0⁹,¹⁴]pentadeca-2(7),3,5,9,11,13-hexaene-4-carboxylic acid, (±)-11-(4-fluorophenyl)-8-methyl-15-oxatetracyclo[6.6.1.0²,⁷.0⁹,¹⁴]pentadeca-2(7),3,5,9,11,13-hexaene-4-carboxylic acid, (±)-12-(4-fluorophenyl)-1-methyl-15-oxatetracyclo-[6.6.1.0²,⁷.0⁹,¹⁴]pentadeca-2(7),3,5,9,11,13-hexaene-4-carboxylic acid and (±)-11-(4-fluorophenyl)-1-methyl-15-oxatetracyclo[6.6.1.0²,⁷.0⁹,¹⁴]pentadeca-2(7),3,5,9,11,13-hexaene-4-carboxylic acid (100.0 mg, 0.29 mmol, 1.00 equiv), N,N-dimethylformamide (4.0 mL), 5-(aminomethyl)-4,6-dimethyl-pyridin-2-amine dihydrochloride (65.6 mg, 0.29 mmol, 1.00 equiv), HATU (133.3 mg, 0.35 mmol, 1.20 equiv) and DIEA (261.8 mg, 2.03 mmol, 7.00 equiv). The resulting mixture was stirred for 2 h at room temperature then it was filtered and directly subjected to reverse preparative HPLC (SunFire Prep C18 Column, 19*150 mm, Waters; gradient elution of 36% MeCN in water to 51% MeCN in water over a 7 min period, where both solvents contain 0.1% TFA) to provide the title compounds as a light yellow solid (33.0 mg, 19%). MS: (M+H)⁺ found for C₃₀H₂₆FN₃O₂: 480.2.

Example 103

Synthesis of (±)-N-[(6-amino-2,4-dimethylpyridin-3-yl)methyl]-12-(4-fluorophenyl)-10-methyl-15-oxatetracyclo[6.6.1.0²,⁷.0⁹,¹⁴]pentadeca-2,4,6,9(14),10,12-hexaene-4-carboxamide and (±)-N-[(6-amino-2,4-dimethylpyridin-3-yl)methyl]-11-(4-fluorophenyl)-13-methyl-15-oxatetracyclo[6.6.1.0²,⁷.0⁹,¹⁴]pentadeca-2,4,6,9(14),10,12-hexaene-4-carboxamide

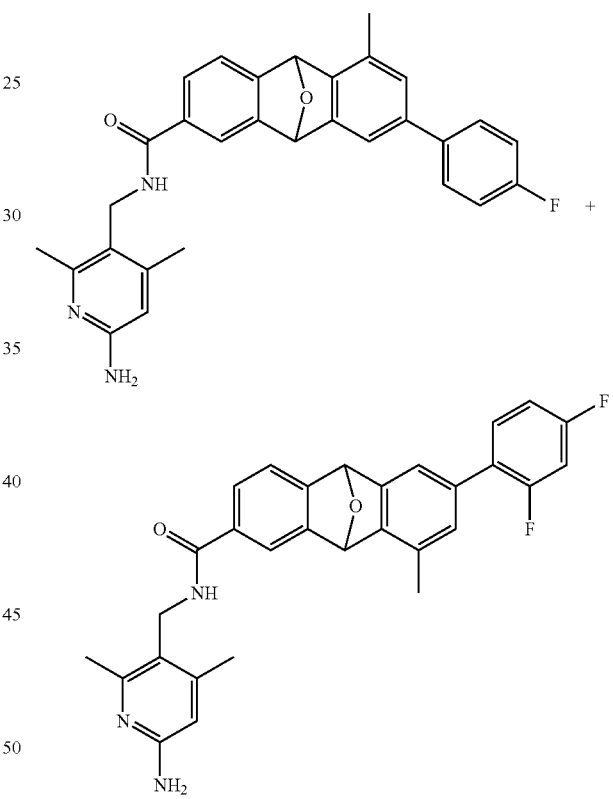

Step 1:

Into a 250-mL 3-necked round-bottom flask purged and maintained with an inert atmosphere of nitrogen, was placed a mixture of 1,5-dichloro-2-iodo-3-methylbenzene (5.00 g, 17.43 mmol, 1.00 equiv), toluene (50 mL) and furan (2.40 g, 34.67 mmol, 2.00 equiv) followed by the drop-wise addition of n-BuLi (19.2 mL, 1.10 equiv) with stirring at −30° C. The mixture was then quenched by the addition of 10.0 mL of water, cooled to RT and concentrated under vacuum. The residue was purified by a silica gel column chromatography eluting with ethyl acetate/petroleum ether (1/5) to afford 3.10 g (92%) of (±)-5-chloro-3-methyl-11-oxatricyclo-[6.2.1.0²,⁷]undeca-2,4,6,9-tetraene as yellow oil.

Step 2:

Into a 50-mL 3-necked round-bottom flask purged and maintained with an inert atmosphere of nitrogen, was placed a solution of (±)-5-chloro-3-methyl-11-oxatricyclo-[6.2.1.0$^{2,7}$]undeca-2,4,6,9-tetraene (500 mg, 2.60 mmol, 1.00 equiv) in chloroform (10 mL) with stirring at 0° C., followed by the drop-wise addition of bis(pyridin-2-yl)-1,2,4,5-tetrazine (674 mg, 2.85 mmol, 1.10 equiv) in chloroform (10.0 mL). The resulting mixture was stirred for 1 h at 50° C. then it was cooled to RT to deliver 6-chloro-4-methyl-2-benzofuran in chloroform (20 mL) as a yellow liquid, which was used in the next step directly.

To this solution was added dichloromethane (10 mL) with stirring at 0° C., and a solution of [5-(methoxycarbonyl)-2-(trimethylsilyl)phenyl](phenyl)iodanium trifluoromethanesulfonate (840.0 mg, 1.50 mmol, 0.50 equiv) in dichloromethane (10 mL) drop-wise, followed by the drop-wise addition of TBAF (3.6 mL, 1.20 equiv) with stirring at 0° C. The mixture was stirred for 30 min at 0° C. then it was diluted with 10 mL of DCM, washed with H$_2$O and concentrated under vacuum. The residue was purified by silica gel column chromatography eluting with ethyl acetate/petroleum ether (1/5) to afford 220.0 mg (24%) of a mixture of (±)-methyl 12-chloro-10-methyl-15-oxatetracyclo[6.6.1.0$^{2,7}$.0$^{9,14}$]-pentadeca-2(7),3,5,9,11,13-hexaene-4-carboxylate and (±)-methyl 11-chloro-13-methyl-15-oxatetracyclo[6.6.1.0$^{2,7}$.0$^{9,14}$]-pentadeca-2(7),3,5,9,11,13-hexaene-4-carboxylate as an off-white solid.

Step 3:

Into a 10-mL round-bottom flask purged and maintained with an inert atmosphere of nitrogen, was placed a mixture of (±)-methyl 12-chloro-10-methyl-15-oxatetracyclo[6.6.1.0$^{2,7}$.0$^{9,14}$]pentadeca-2(7),3,5,9,11,13-hexaene-4-carboxylate and (±)-methyl 11-chloro-13-methyl-15-oxatetracyclo[6.6.1.0$^{2,7}$.0$^{9,14}$]pentadeca-2(7),3,5,9,11,13-hexaene-4-carboxylate (300.0 mg, 1.00 mmol, 1.00 equiv), (4-fluorophenyl)boronic acid (210.0 mg, 1.50 mmol, 1.50 equiv), K$_3$PO$_4$ (636.0 mg, 3.00 mmol, 3.00 equiv), dioxane/H$_2$O (3 mL) and 3$^{rd}$ generation XPhos (4.0 mg, 0.05 equiv). The resulting mixture was stirred for 2.5 h at 100° C. under nitrogen atmosphere then it was cooled to RT and concentrated. The residue was purified by silica gel column chromatography eluting with ethyl acetate/petroleum ether (1/5) to afford 280.0 mg (78%) of a mixture of (±)-methyl 12-(4-fluorophenyl)-10-methyl-15-oxatetracyclo[6.6.1.0$^{2,7}$.0$^{9,14}$]pentadeca-2(7),3,5,9,11,13-hexaene-4-carboxylate and (±)-methyl 11-(4-fluorophenyl)-13-methyl-15-oxatetracyclo[6.6.1.0$^{2,7}$.0$^{9,14}$]pentadeca-2(7),3,5,9,11,13-hexaene-4-carboxylate as an off-white solid.

Step 4:

Into a 10-mL round-bottom flask, was placed a mixture of (±)-methyl 12-(4-fluorophenyl)-10-methyl-15-oxatetracyclo[6.6.1.0$^{2,7}$.0$^{9,14}$]pentadeca-2(7),3,5,9,11,13-hexaene-4-carboxylate and (±)-methyl 11-(4-fluorophenyl)-13-methyl-15-oxatetracyclo[6.6.1.0$^{2,7}$.0$^{9,14}$]-pentadeca-2(7),3,5,9,11,13-hexaene-4-carboxylate (360 mg, 1.00 mmol, 1.00 equiv), methanol (8.00 mL), water (2.00 mL) and sodium hydroxide (80 mg, 2.00 mmol, 2.00 equiv). The resulting mixture was stirred for 3 h at 50° C., then it was cooled to RT and the pH value of the solution was adjusted to 6 with 6N hydrogen chloride aqueous solution. The mixture was then diluted with 10 mL of H$_2$O and extracted with 3×10 mL of ethyl acetate, the organic layers were combined, dried and concentrated under vacuum to afford 320.0 mg (92%) of a mixture of (±)-12-(4-fluorophenyl)-10-methyl-15-oxatetracyclo[6.6.1.0$^{2,7}$.0$^{9,14}$]pentadeca-2(7),3,5,9,11,13-hexaene-4-carboxylic acid and (±)-11-(4-fluorophenyl)-13-methyl-15-oxatetracyclo-[6.6.1.0$^{2,7}$.0$^{9,14}$]pentadeca-2(7),3,5,9,11,13-hexaene-4-carboxylic acid as a white solid.

Step 5:

Into a 10-mL round-bottom flask, was placed a mixture of (±)-12-(4-fluoro-phenyl)-10-methyl-15-oxatetracyclo [6.6.1.0$^{2,7}$.0$^{9,14}$]pentadeca-2(7),3,5,9,11,13-hexaene-4-carboxylic acid and (±)-11-(4-fluorophenyl)-13-methyl-15-oxatetracyclo[6.6.1.0$^{2,7}$.0$^{9,14}$]pentadeca-2(7),3,5,9,11,13-hexaene-4-carboxylic acid (34.6 mg, 0.10 mmol, 1.00 equiv), 5-(aminomethyl)-4,6-dimethylpyridin-2-amine (22.4 mg, 0.10 mmol, 1.00 equiv), N,N-dimethylformamide (2 mL), HATU (38.0 mg, 0.10 mmol, 1.00 equiv) and DIEA (64.5 mg, 0.50 mmol, 5.00 equiv). The resulting mixture was stirred for 2 h at 20° C., the solids were then separated by filtration and the filtrate was directly subjected to reverse preparative HPLC (Prep-C18, 5 mM XBridge column, 19×150 mm, Waters; gradient elution of 35% MeCN in water to 43% MeCN in water over a 7 min period, where the aqueous phase contains 10 mM NH$_4$HCO$_3$+0.5% ammonia) to provide a mixture of the title compounds as a white solid (29.9 mg, 62%). MS: (M+H)$^+$ found for C$_{30}$H$_{26}$FN$_3$O$_2$: 480.2

Example 104

Synthesis of (±)-11,12-dicyclopropyl-N-({4-[N'-methoxycarbamimidoyl]phenyl}methyl)-15-oxatetracyclo[6.6.1.0$^{2,7}$.0$^{9,14}$]pentadeca-2,4,6,9,11,13-hexaene-4-carboxamide

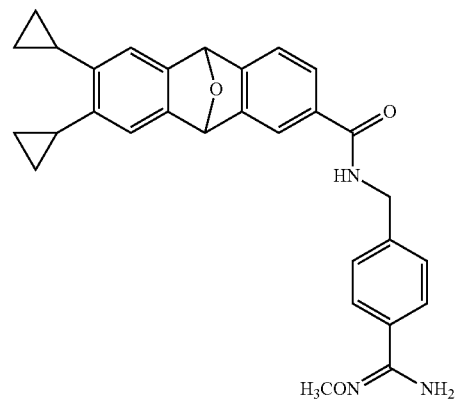

The title compound was prepared following the procedure described in Example 97, Step 3, but using 4-(aminomethyl)-N'-methoxybenzimidamide dihydrochloride (INT-7) instead of 5-(aminomethyl)-4,6-dimethylpyridin-2-amine dihydrochloride. MS: (M+H)$^+$ found for C$_{30}$H$_{29}$N$_3$O$_3$: 480.1.

Example 105

Synthesis of (±)-11,12-diethyl-N-({4-[N'-methoxycarbamimidoyl]phenyl}methyl)-15-oxatetracyclo[6.6.1.0$^{2,7}$.0$^{9,14}$]pentadeca-2,4,6,9,11,13-hexaene-4-carboxamide

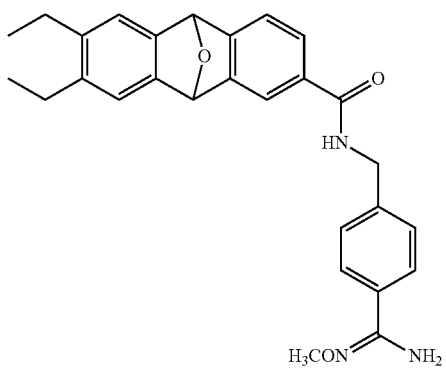

The title compound was prepared following the procedure described in Example 98, Step 3, but using 4-(aminomethyl)-N'-methoxybenzimidamide dihydrochloride (INT-7) instead of 4-(aminomethyl)benzene-1-carboximidamide dihydrochloride. MS: (M+H)$^+$ found for $C_{28}H_{29}N_3O_3$: 456.0.

Example 106

Synthesis of (±)-11,12-dimethyl-N-({4-[N'-methoxycarbamimidoyl]phenyl}methyl)-15-oxatetracyclo[6.6.1.0$^{2,7}$.0$^{9,14}$]pentadeca-2,4,6,9,11,13-hexaene-4-carboxamide

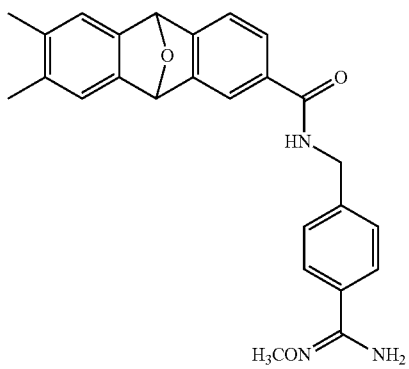

The title compound was prepared following the procedure described in Example 96, Step 5, but using 4-(aminomethyl)-N'-methoxybenzimidamide dihydrochloride (INT-7) instead of 5-(aminomethyl)-4,6-dimethylpyridin-2-amine. MS: (M+H)$^+$ found for $C_{26}H_{25}N_3O_3$: 482.2.

Example 107

Synthesis of (1R,8S)—N-[(4-carbamimidoylphenyl)methyl]-11,12-diethyl-15-oxatetracyclo[6.6.1.0$^{2,7}$.0$^{9,14}$]pentadeca-2,4,6,9(14),10,12-hexaene-4-carboxamide formate salt

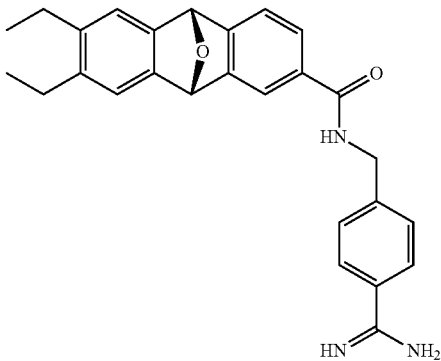 [SMILES: CCc1cc2c(cc1CC)[C@H]1O[C@@H]2c2cc(C(=O)NCc3ccc(C(=N)N)cc3)ccc21]

Step 1:

(±)-11,12-Diethyl-15-oxatetracyclo[6.6.1.0$^{2,7}$.0$^{9,14}$]pentadeca-2(7),3,5,9,11,13-hexaene-4-carboxylic acid (Example 98, steps 1-2; 2.40 g, 8.15 mmol, 1.00 equiv) was subjected to chiral purification by Chiral-Prep-HPLC using the following conditions (SHIMADZU LC-20AT): Column: DAICEL CHIRALPAK IA-H 20*250 mm 5 um; mobile phase: Phase A: n-hexane (with 0.1% TFA), Phase B: ethanol; Detector, 230 nm to provide 900 mg (37.5%) of (1R,8S)-11,12-diethyl-15-oxatetracyclo[6.6.1.0$^{2,7}$.0$^{9,14}$]-pentadeca-2(7),3,5,9,11,13-hexaene-4-carboxylic acid as a yellow solid. LC-MS (ES) [M+1]+m/z: 295.2 and 940 mg (39%) of (1S,8R)-11,12-diethyl-15-oxatetracyclo[6.6.1.0$^{2,7}$.0$^{9,14}$]-pentadeca-2(7),3,5,9,11,13-hexaene-4-carboxylic acid as a yellow solid. LC-MS (ES) [M+1]$^+$ m/z: 295.2.

Step 2:

Into a 8-mL vial, was placed a mixture of (1R,8S)-11,12-diethyl-15-oxatetracyclo[6.6.1.0$^{2,7}$.0$^{9,14}$]pentadeca-2(7),3,5,9,11,13-hexaene-4-carboxylic acid (100 mg, 0.34 mmol, 1.00 equiv), N,N-dimethylformamide (5 mL), 4-(aminomethyl)benzene-1-carboximidamide dihydrochloride (90.2 mg, 0.41 mmol, 1.20 equiv), HATU (155.8 mg, 0.41 mmol, 1.20 equiv) and DIEA (131.6 mg, 1.02 mmol, 3.00 equiv). The resulting mixture was stirred for 1 h at room temperature then the solids were separated by filtration and the filtrate was directly subjected to reverse preparative HPLC (SunFire Prep-C18, 5 mM XBridge column, 19×150 mm, waters; gradient elution of 33% MeCN in water to 48% MeCN in water over a 6 min period, where both solvents contain 0.05% TFA) to provide the title compound as a white solid (35.4 mg, 22%). MS: [M-FA+1]$^+$ found for $C_{27}H_{27}N_3O_2$: 474.3.

Example 108

Synthesis of (1R,8S)-11,12-diethyl-N-({4-[N'-hydroxycarbamimidoyl]-phenyl}methyl)-15-oxatetracyclo[6.6.1.0$^{2,7}$.0$^{9,14}$]pentadeca-2,4,6,9(14),10,12-hexaene-4-carboxamide trifluoroacetate salt

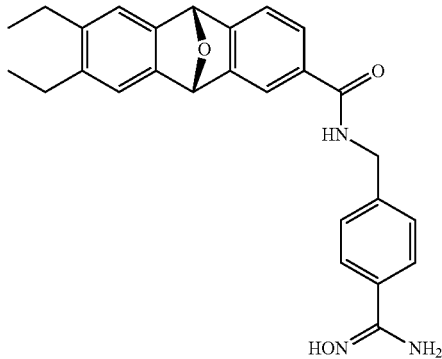

Into a 8-mL vial, was placed (1R,8S)-11,12-diethyl-15-oxatetracyclo[6.6.1.0$^{2,7}$.0$^{9,14}$]-pentadeca-2(7),3,5,9,11,13-hexaene-4-carboxylic acid (Example 107, Step 1; 100 mg, 0.34 mmol, 1.00 equiv), N,N-dimethylformamide (5 mL), 4-(aminomethyl)-N-hydroxybenzene-1-carboximidamide dihydrochloride (68 mg, 0.29 mmol, 1.20 equiv), HOBT (55 mg, 0.41 mmol, 1.20 equiv), EDCI (79 mg, 0.41 mmol, 1.20 equiv) and DIEA (132 mg, 1.02 mmol, 3.00 equiv). The resulting mixture was stirred for 4 h at 50° C. then it was cooled to RT, filtered and directly subjected to reverse preparative HPLC (Atlantis Prep T3 OBD Column, 19×150 mm, waters; gradient elution of 38% MeCN in water to 56% MeCN in water over a 8 min period, where both solvents contain 0.05% TFA) to provide the title compound as an off-white solid (23.4 mg, 12%). MS: [M-TFA+1]$^+$ found for $C_{27}H_{27}N_3O_3$: 442.2.

Example 109

Synthesis of (1S,8R)—N-[(4-carbamimidoylphenyl)methyl]-11,12-diethyl-15-oxatetracyclo[6.6.1.0$^{2,7}$.0$^{9,14}$]pentadeca-2,4,6,9(14),10,12-hexaene-4-carboxamide trifluoroacetate salt

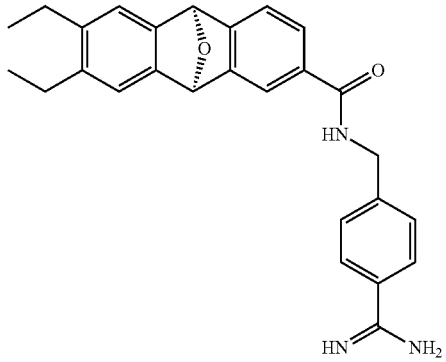

Into a 8-mL vial, was placed a mixture of (1S,8R)-11,12-diethyl-15-oxatetracyclo-[6.6.1.0$^{2,7}$.0$^{9,14}$]pentadeca-2(7),3,5,9,11,13-hexaene-4-carboxylic acid (Example 107, step 1) (100.0 mg, 0.34 mmol, 1.00 equiv), N,N-dimethylformamide (5 mL), 4-(aminomethyl)benzene-1-carboximidamide dihydrochloride (90.2 mg, 0.41 mmol, 1.20 equiv), HATU (155.8 mg, 0.41 mmol, 1.20 equiv) and DIEA (131.6 mg, 1.02 mmol, 3.00 equiv). The resulting mixture was stirred for 1 h at room temperature then it was filtered and directly subjected to reverse preparative HPLC (SunFire Prep-C18, 5 mM XBridge column, 19×150 mm, Waters; gradient elution of 33% MeCN in water to 48% MeCN in water over a 6 min period, where both solvents contain 0.05% TFA) to provide the title compound as an off-white solid (56.6 mg, 31%). MS: [M-TFA+1]$^+$ found for $C_{27}H_{27}N_3O_2$: 442.2.

Example 110

Synthesis of (1S,8R)-11,12-diethyl-N-({4-[N'-hydroxycarbamimidoyl]-phenyl}methyl)-15-oxatetracyclo[6.6.1.0$^{2,7}$.0$^{9,14}$]pentadeca-2,4,6,9(14),10,12-hexaene-4-carboxamide trifluoroacetate salt

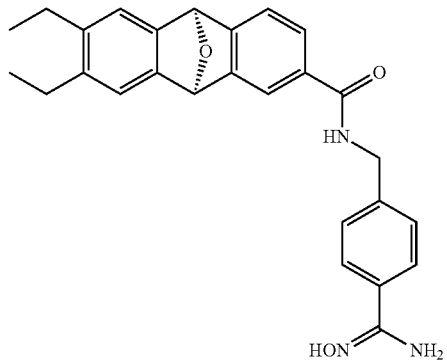

Into a 8-mL vial, was placed (1S,8R)-11,12-diethyl-15-oxatetracyclo[6.6.1.0$^{2,7}$.0$^{9,14}$]-pentadeca-2(7),3,5,9,11,13-hexaene-4-carboxylic acid (Example 107, Step 1; 100 mg, 0.34 mmol, 1.00 equiv), N,N-dimethylformamide (5 mL), 4-(aminomethyl)-N-hydroxybenzene-1-carboximidamide dihydrochloride 68 mg, 0.29 mmol, 1.20 equiv), HOBT (55 mg, 0.41 mmol, 1.20 equiv), EDCI (79 mg, 0.41 mmol, 1.20 equiv) and DIEA (132 mg, 1.02 mmol, 3.00 equiv). The resulting mixture was stirred for 4 h at 50° C. then it was cooled to RT, filtered and directly subjected to reverse preparative HPLC (Atlantis Prep T3 OBD Column, 19×150 mm, Waters; gradient elution of 38% MeCN in water to 56% MeCN in water over a 8 min period, where both solvents contain 0.05% TFA) to provide the title compound as an off-white solid (13.2 mg, 7%). MS: [M-TFA+1]$^+$ found for $C_{27}H_{27}N_3O_3$: 442.2.

Example 111

Synthesis of (1S,8R)-11,12-diethyl-N-({4N'-methoxycarbamimidoyl]phenyl}methyl)-15-oxatetracyclo[6.6.1.0$^{2,7}$.0$^{9,14}$]pentadeca-2,4, 6,9(14),10, 12-hexaene-4-carboxamide trifluoroacetate salt

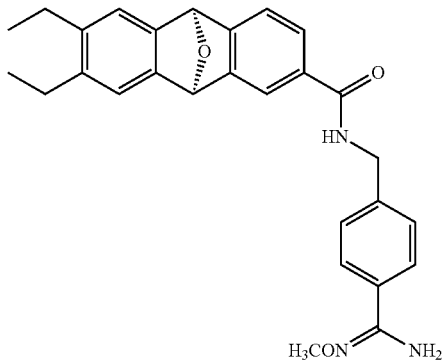

Into a 50-mL round-bottom flask, was placed a mixture of (1S,8R)-11,12-diethyl-15-oxatetracyclo[6.6.1.0$^{2,7}$.0$^{9,14}$]pentadeca-2(7),3,5,9,11,13-hexaene-4-carboxylic acid (Example 107, Step 1; 785 mg, 2.67 mmol, 1.00 equiv), N,N-dimethylformamide (20 mL), 4-(aminomethyl)-N'-methoxybenzimidamide dihydrochloride (INT-7; 573 mg, 2.27 mmol, 1.20 equiv), HATU (1.22 g, 3.21 mmol, 1.20 equiv) and DIEA (1.03 g, 7.97 mmol, 3.00 equiv). The resulting mixture was stirred for 1 h at room temperature then it was filtered and directly subjected to reverse preparative HPLC (Atlantis Prep T3 OBD Column, 19×150 mm, Waters; gradient elution of 38% MeCN in water to 56% MeCN in water over a 8 min period, where both solvents contain 0.05% TFA) to provide the title compound as a light yellow solid (1.060 g, 70%). MS: [M-TFA+1]$^+$ found for $C_{28}H_{29}N_3O_3$: 456.3.

Example 112

Synthesis of (1S,8R)—N-[(4-carbamimidoylphenyl)methyl]-11,12-dicyclopropyl-15-oxatetracyclo [6.6.1.0$^{2,7}$.0$^{9,14}$]pentadeca-2,4,6,9,11,13-hexaene-4-carboxamide trifluoroacetate Salt

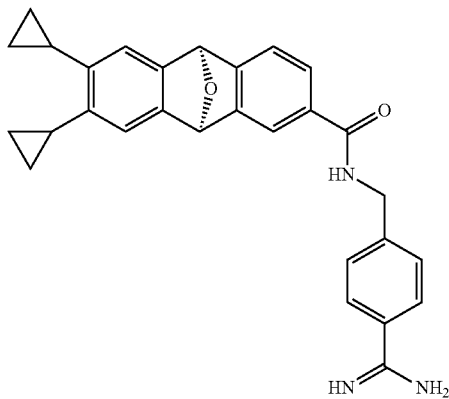 [SMILES: N=C(N)c1ccc(CNC(=O)c2ccc3c(c2)[C@@H]2O[C@H]3c3cc(C4CC4)c(C4CC4)cc32)cc1]

Step 1:
(±)-11,12-dicyclopropyl-15-oxatetracyclo[6.6.1.0$^{2,7}$.0$^{9,14}$]pentadeca-2(7),3,5,9,11,13-hexaene-4-carboxylic acid (Example 97, Steps 1-2; 300 mg) was separated by Chiral Prep-HPLC using the following conditions. Column: chiralPAK-AD-3; mobile phase: A: n-Hexane (0.1% TFA), B: isopropanol; gradient elution of 20% B to 100% B in 10 min to deliver 128 mg (43%) of (1S,8R)-11,12-dicyclopropyl-15-oxatetracyclo[6.6.1.0$^{2,7}$.0$^{9,14}$]-pentadeca-2(7),3,5,9,11, 13-hexaene-4-carboxylic acid as a yellow solid and 135 mg (45%) of (1R,8S)-11,12-dicyclopropyl-15-oxatetracyclo [6.6.1.0$^{2,7}$.0$^{9,14}$]pentadeca-2(7),3,5,9,11,13-hexaene-4-carboxylic acid as a yellow solid. LCMS (ES) [M+1]$^+$ m/z 319.1.

Step 2:
Into a 50-mL round-bottom flask, was placed a mixture of (1S,8R)-11,12-dicyclopropyl-15-oxatetracyclo[6.6.1. 0$^{2,7}$.0$^{9,14}$]pentadeca-2(7),3,5,9,11,13-hexaene-4-carboxylic acid (100 mg, 0.31 mmol, 1.00 equiv), DMF (8 mL), 4-(aminomethyl)benzene-1-carboximidamide dihydrochloride (84 mg, 0.38 mmol, 1.20 equiv), DIEA (202 mg, 1.56 mmol, 5.00 equiv) and HATU (180 mg, 0.47 mmol, 1.50 equiv). The resulting mixture was stirred for 4 h at 25° C. then it was filtered and directly subjected to reverse phase preparative HPLC (Prep-C18, 5 M XBridge column, 19×150 mm, Waters; gradient elution of 30% MeCN in water to 40% MeCN in water over a 10 min period, where both solvents contain 0.1% TFA) to provide the title compound as a light yellow solid (44.8 mg, 25%). MS: [M-TFA+1]$^+$ found for $C_{29}H_{27}N_3O_2$: 450.2.

Example 113

Synthesis of (1S,8R)-11,12-dicyclopropyl-N-({4-[N'-hydroxycarbamimidoyl]-phenyl}methyl)-15-oxatetracyclo[6.6.1.0$^{2,7}$.0$^{9,14}$]pentadeca-2,4,6,9,11, 13-hexaene-4-carboxamide trifluoroacetate Salt

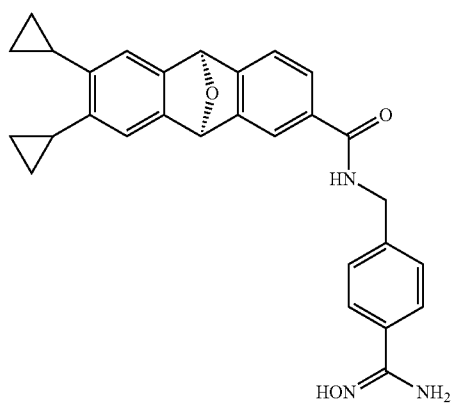

Into a 8-mL vial, was placed a mixture of (1S,8R)-11,12-dicyclopropyl-15-oxatetracyclo[6.6.1.0$^{2,7}$.0$^{9,14}$]pentadeca-2 (7),3,5,9,11,13-hexaene-4-carboxylic acid (Example 112, Step 1; 105 mg, 0.33 mmol, 1.00 equiv), N,N-dimethylformamide (5 mL), 4-(aminomethyl)-N-hydroxybenzene-1-carboximidamide dihydrochloride (95 mg, 0.40 mmol, 1.20 equiv), DIEA (170 mg, 1.32 mmol, 4.00 equiv), EDCI (76.4 mg, 0.40 mmol, 1.20 equiv) and HOBT (54 mg, 0.40 mmol, 1.20 equiv). The resulting mixture was stirred for 5 h at 50° C. then it was cooled to RT, filtered and directly subjected to reverse phase preparative HPLC (Prep-C18, 5 mM XBridge column, 19×150 mm, Waters; SunFire gradient elution of 8% MeCN in water to 15% MeCN in water over a 1 min period, then 15% MeCN in water to 18% MeCN in water over a 7 min period, where both solvents contain 0.1% TFA) to provide the title compound as an off-white solid (11.0 mg, 6%). MS: [M-TFA+1]$^+$ found for $C_{29}H_{27}N_3O_3$: 466.5.

Example 114

Synthesis of (1S,8R)-11,12-dicyclopropyl-N-({4-[N'-methoxycarbamimidoyl]-phenyl}methyl)-15-oxatetracyclo[6.6.1.0$^{2,7}$.0$^{9,14}$]pentadeca-2,4,6,9,11,13-hexaene-4-carboxamide

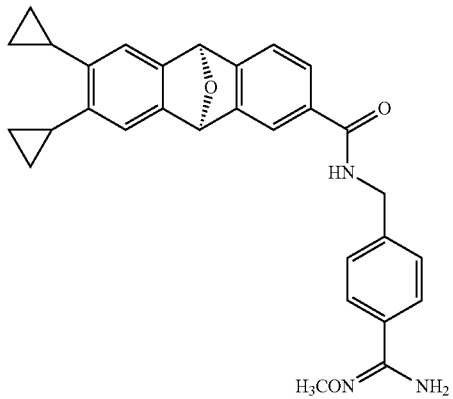

Into a 50-mL round-bottom flask, was placed a mixture of (1S,8R)-11,12-dicyclopropyl-15-oxatetracyclo[6.6.1.0$^{2,7}$.0$^{9,14}$]pentadeca-2(7),3,5,9,11,13-hexaene-4-carboxylic acid (Example 112, Step 1; 900 mg, 2.83 mmol, 1.00 equiv), N,N-dimethylformamide (30 mL), 4-(aminomethyl)-N'-methoxybenzimidamide dihydrochloride (INT-7; 853 mg, 3.38 mmol, 1.20 equiv), HATU (1.29 g, 3.39 mmol, 1.20 equiv) and DIEA (1.46 g, 11.30 mmol, 4.00 equiv). The resulting mixture was stirred for 1 h at room temperature then it was diluted with 20 mL of H$_2$O and extracted with 3×20 mL of ethyl acetate. The organic layers were washed with 50 mL of H$_2$O and 50 mL of brine, dried over anhydrous sodium sulfate and concentrated under vacuum. The residue was purified by silica gel column chromatography eluting with dichloromethane/methanol (10:1) to afford 647.1 mg (48%) of the title compound as an off-white solid. MS: [M-TFA+1]$^+$ found for $C_{30}H_{29}N_3O_3$: 480.4.

Biological Assays

Example 1

In Vitro Plasma Kallikrein Inhibition Assay

Materials

The chromogenic substrate D-Pro-Phe-Arg-pNa, 2HCl (BIOPHEN CS-31(02) from Hyphen BioMed, Neuville-Sur-oise, France) was dissolved in 5 mL deionized water and stored at 4° C. Concentration was determined in the spectrophotometer at 342 nm using an extinction coefficient of 8270. All other chemicals were of analytical grade.

Human plasma kallikrein was purchased from Enzyme Research Labs (South Bend, Ind., USA, batch HPKa 2830). A stock solution of 7 μM in 50% glycerol was stored at −20° C.

Enzyme reactions were conducted in "assay buffer" comprised of 20 mM HEPES at pH 7.4, 150 mM NaCl, 0.1% PEG-8000 and 0.01% Triton X-100.

Both enzyme and substrate were diluted in assay buffer. The compound solutions as well as the enzyme and the substrate solutions were transferred to 96-well plates (Clear, UV-Star, Flat-bottom, Half-Area plates; cat. No. 675801 Greiner Bio-one, purchased from VWR International, Arlington Heights, Ill., USA) using a Rainin LTS 96-channel pipettor (Rainin, Columbus, Ohio, USA). Plate measurements were conducted using a SPECTROStar Nano reader (BMG Labtech, San Francisco, Calif., USA). The SPECTROStar Nano is a spectrophotometer and absorbance was measured at 405 nm. We used discrete wavelength, precise, kinetic reads of 15 cycles with a 60 sec cycle time.

Determination of IC$_{50}$ Values

For the determination of IC$_{50}$ values, the assays were performed at room temperature in 96-well plates with a total assay volume of 85 μL per well. The test compound was dissolved in 100% DMSO. The compounds were serially diluted in DMSO in a 7 point dose response. For the assays, 66.5 μL of protease solution (protease in assay buffer) was added per well followed by the addition of 8.5 μL of compound in 100% DMSO. The final assay concentration of the human plasma kallikrein was 250 pM. After 30 min. incubation at room temperature on an orbital shaker, the reactions were started by the addition of 10 μL substrate solution (in assay buffer, final assay concentration was 600 uM). After the addition of the substrate solution the final DMSO concentration was 10%. The plate was placed again on the shaker for 5 sec, spun at 2000 rpm for 5 sec and read on the spectrophotometer. The effect of the compound on the enzymatic activity was obtained from the linear part of the progress curves and determined after 15 minutes. The IC$_{50}$ value was calculated from the plot of rate vs. inhibitor concentration by a 4 parameter logistic equation:

$$y=A+((B-A)/(1=((C/x)^D)))$$

where y is the rate at the inhibitor concentration, x. A is the minimum y value at the highest inhibitor concentration and B is the y value in the absence of inhibitor, C is the IC$_{50}$ value and D is the slope factor. The curve fitting was conducted with the non-linear regression routine of the analysis software XLfit (IDBS, version 5.3.1).

Example 2

Kallikrein Chromogenic Assay

A 5.1 mM solution of the chromogenic substrate D-Pro-Phe-Arg-pNA, 2HCl (BIOPHEN CS-31-02) from Hyphen BioMed (Neuville-Sur-oise, France) was prepared by dissolving 25 mg of the chromogenic substrate D-Pro-Phe-Arg-pNA, 2HCl in about 5 ml deionized water a. The concentration was determined by an absorbance measurement at 342 nm (ϵ=8270 l/M cm). The solution was stored in the freezer.

Human plasma kallikrein was obtained from Molecular Innovations (Novi, USA). The purchased stock was diluted to 7 M in 50% glycerol and stored at −20° C. The test compounds were provided as 10 mM solutions in DMSO and were serially diluted in the appropriate concentration range in a polypropylene plate with one well as DMSO control.

The reaction buffer contained 26 mM HEPES, 195 mM NaCl, 0.13% PEG8000, 0.013% Triton X-100 pH 7.4. The assays were performed in UV-Star, flat-bottom, half-area plates 96 well plates (Greiner 675801). For the assay, 65 μL of 325 pM kallikrein solution in reaction buffer was added add to each well of the assay plate and 10 μL of a test compound was added. After 30 min incubation on a shaker, 10 μL of D-Pro-Phe-Arg-pNA, 2HCl solution was added. After mixing with the pipette, air bubbles were removed by centrifugation and the reaction was read on the Envision plate reader (Perkin Elmer, MA, USA) for 10 minutes at 405 nm.

For $IC_{50}$ determination the rates of hydrolysis were plotted against inhibitor concentration and analyzed by regression to a logistic curve.

Formulation Examples

The following are representative pharmaceutical formulations containing a compound of the present disclosure.

Tablet Formulation

The following ingredients are mixed intimately and pressed into single scored tablets.

| Ingredient | Quantity per tablet mg |
| --- | --- |
| compound of this disclosure | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule mg |
| --- | --- |
| compound of this disclosure | 200 |
| lactose spray dried | 148 |
| magnesium stearate | 2 |

Injectable Formulation

Compound of the disclosure (e.g., compound 1) in 2% HPMC, 1% Tween 80 in DI water, pH 2.2 with MSA, q.s. to at least 20 mg/mL.

Inhalation Composition

To prepare a pharmaceutical composition for inhalation delivery, 20 mg of a compound disclosed herein is mixed with 50 mg of anhydrous citric acid and 100 mL of 0.9% sodium chloride solution. The mixture is incorporated into an inhalation delivery unit, such as a nebulizer, which is suitable for inhalation administration.

Topical Gel Composition

To prepare a pharmaceutical topical gel composition, 100 mg of a compound disclosed herein is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

Ophthalmic Solution Composition

To prepare a pharmaceutical ophthalmic solution composition, 100 mg of a compound disclosed herein is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

Nasal Spray Solution

To prepare a pharmaceutical nasal spray solution, 10 g of a compound disclosed herein is mixed with 30 mL of a 0.05M phosphate buffer solution (pH 4.4). The solution is placed in a nasal administrator designed to deliver 100 μL of spray for each application.

What is claimed:
1. A compound of formula (I):

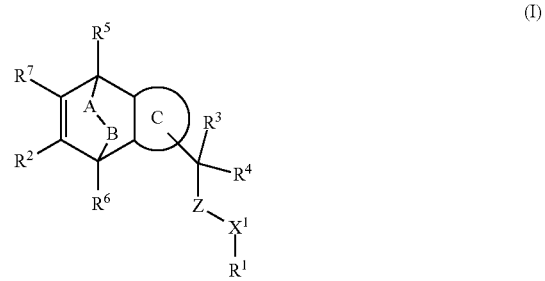

wherein:
one of A and B is O and the other of A and B is a bond;
ring C is phenyl, wherein ring C, in addition to $-CR^3R^4-Z-X^1-R^1$, is optionally substituted with one or two substituents independently selected from $C_1$-$C_6$alkyl, $C_1$-$C_6$alkoxy, hydroxy, halo, halo$C_1$-$C_6$alkyl, halo$C_1$-$C_6$alkoxy, amino, $C_1$-$C_6$alkyl-amino, di$C_1$-$C_6$alkylamino, and cyano;
$R^3$ and $R^4$ are independently hydrogen, fluoro, or $C_1$-$C_6$alkyl; or $R^3$ and $R^4$ together with the carbon they are attached form C=O, C=NR$^{12}$ (wherein R$^{12}$ is hydrogen, $C_1$-$C_6$alkyl, $C_1$-$C_6$alkoxy, or hydroxy), or $C_3$-$C_6$cycloalkyl, provided that when $R^3$ and $R^4$ together form C=NR$^{12}$, then Z is NR$^{13}$;
Z is a bond, NR$^{13}$, or CR$^{14}$R$^{15}$ wherein R$^{13}$, R$^{14}$, and R$^{15}$ are independently hydrogen or $C_1$-$C_6$alkyl;
$X^1$ is bond, —C=NR$^8$, CR$^{16}$R$^{17}$, O, or S(O)$_q$, wherein q is 0, 1, or 2, R$^8$ is hydrogen OH, $C_1$-$C_6$alkoxy, $C_1$-$C_6$alkyl, or $C_3$-$C_8$cycloalkyl, and R$^{16}$ and R$^{17}$ are independently hydrogen, deuterium, or $C_1$-$C_6$alkyl, or R$^{16}$ and R$^{17}$ together with the carbon atom they are attached form $C_3$-$C_6$cycloalkyl, C=NH, or C=O, provided that when $R^3$ and $R^4$ together form C=O, then $X^1$ is not O;

$R^1$ is mono or bicyclic aryl, mono or bicyclic heteroaryl, $C_3$-$C_6$cycloalkyl, monocyclic heterocyclyl, or fused heterocyclyl, wherein each of the aforementioned ring(s) is optionally substituted with $R^e$, $R^f$ or $R^g$ independently selected from $C_1$-$C_6$alkyl, $C_2$-$C_6$alkenyl, $C_3$-$C_6$cyclo-alkyl, $C_1$-$C_6$alkoxy, hydroxy, halo, halo$C_1$-$C_6$alkyl, halo$C_1$-$C_6$alkoxy, amino, $C_1$-$C_6$alkylamino, di$C_1$-$C_6$alkylamino, amino$C_1$-$C_6$alkyl, aminocarbonyl, amidino$C_1$-$C_6$alkyl, —C(=N$R^h$)NH$R^i$ (wherein $R^h$ and $R^i$ are independently hydrogen, hydroxy, $C_1$-$C_6$alkoxy, benzyloxy, acyl, —C(O)O$C_1$-$C_6$alkyl, a natural or an unnatural amino acid residue, a dipeptidic residue, —CO(ethylene)$SO_2R^u$ ((wherein $R^u$ is $C_1$-$C_6$alkyl, optionally substituted monocyclic heteroaryl, optionally substituted phenyl, or optionally substituted monocyclic heterocyclyl), or —CO(CH$_2$)$_{2-3}$O$R^v$ (wherein $R^v$ is hydrogen, $C_1$-$C_6$alkoxy$C_{1-3}$alkyl, or optionally substituted monocyclic heterocyclyl)), cyano, monocyclic heteroaryl (wherein the monocyclic heteroaryl is optionally substituted with one, two or three substituents independently selected from $C_1$-$C_6$alkyl, $C_3$-$C_6$cycloalkyl, $C_1$-$C_6$alkoxy, hydroxy, halo, halo$C_1$-$C_6$alkyl, halo$C_1$-$C_6$alkoxy, amino, $C_1$-$C_6$alkylamino, di$C_1$-$C_6$alkylamino, and cyano) and monocyclic heterocyclyl (wherein the monocyclic heterocyclyl is optionally substituted with one, two or three substituents independently selected from $C_1$-$C_6$alkyl, $C_3$-$C_6$cycloalkyl, $C_1$-$C_6$alkoxy, hydroxy, halo, halo$C_1$-$C_6$alkyl, halo$C_1$-$C_6$alkoxy, amino, $C_1$-$C_6$alkylamino, and di$C_1$-$C_6$alkylamino);

$R^5$ and $R^6$ are hydrogen;

$R^2$ and $R^7$ together with the atoms they are attached form ring D:

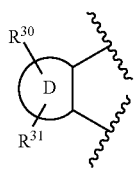

wherein ring D is phenyl; and $R^{30}$ is $C_3$-$C_6$cycloalkyl, mono or bicyclic aryl, mono or bicyclic heteroaryl, monocyclic heterocyclyl, fused heterocyclyl, spiro heterocycloamino or bridged heterocycloamino, and wherein each of the aforementioned ring in $R^{30}$, whether by itself or part of another group, is optionally substituted with $R^m$, $R^n$ or $R^o$ independently selected from $C_1$-$C_6$alkyl, $C_2$-$C_6$alkenyl, $C_3$-$C_6$cycloalkyl, $C_3$-$C_6$cycloalkyl$C_{1-6}$alkoxy, $C_3$-$C_6$cycloalkyl$C_{1-6}$alkoxy, $C_1$-$C_6$alkoxy, hydroxy, halo, halo$C_1$-$C_6$alkyl, halo$C_1$-$C_6$alkoxy, $C_1$-$C_6$alkylthio, $C_1$-$C_6$alkyl-sulfonyl, amino, $C_1$-$C_6$alkylamino, di$C_1$-$C_6$alkylamino, aminocarbonyl, acyl, amino$C_1$-$C_6$alkyl, cyano, monocyclic heteroaryl (wherein the monocyclic heteroaryl is optionally substituted with one, two or three substituents independently selected from $C_1$-$C_6$alkyl, $C_3$-$C_6$cycloalkyl, $C_1$-$C_6$alkoxy, hydroxy, halo, halo$C_1$-$C_6$alkyl, halo$C_1$-$C_6$alkoxy, amino, $C_1$-$C_6$alkylamino, di$C_1$-$C_6$alkylamino, and cyano), and monocyclic heterocyclyl (wherein the monocyclic heterocyclyl is optionally substituted with one, two or three substituents independently selected from $C_1$-$C_6$alkyl, $C_3$-$C_6$cycloalkyl, $C_1$-$C_6$alkoxy, hydroxy, halo, halo$C_1$-$C_6$alkyl, halo$C_1$-$C_6$alkoxy, amino, $C_1$-$C_6$alkylamino, and di$C_1$-$C_6$alkylamino);

$R^{31}$ is hydrogen; or a pharmaceutically acceptable salt thereof.

2. The compound of claim 1, or a pharmaceutically acceptable salt thereof, wherein ring C is phenyl optionally substituted, in addition to —CR$^3$R$^4$—Z—X$^1$—R$^1$, with a substituent selected from $C_1$-$C_6$alkyl, $C_1$-$C_6$alkoxy, hydroxy, and halo.

3. The compound of claim 2, or a pharmaceutically acceptable salt thereof, having structure (I'')

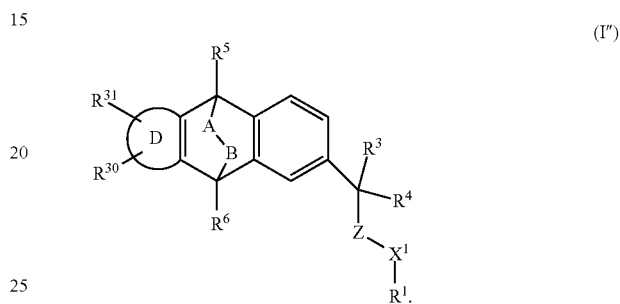

(I'')

4. The compound of claim 3, or a pharmaceutically acceptable salt thereof, wherein $R^3$ and $R^4$ together with the carbon atom to which they are attached form C=O.

5. The compound of claim 3, or a pharmaceutically acceptable salt thereof, wherein Z is NR$^{13}$, and X$^1$ is CR$^{16}$R$^{17}$ where R$^{16}$ and R$^{17}$ are independently hydrogen, deuterium, or $C_1$-$C_6$alkyl.

6. The compound of claim 3, or a pharmaceutically acceptable salt thereof, wherein —(CR$^3$R$^4$)—Z—X$^1$— is —CONHCH$_2$—.

7. The compound of claim 6, or a pharmaceutically acceptable salt thereof, wherein R$^1$ is phenyl optionally substituted with R$^e$, R$^f$, or R$^g$ independently selected from methyl, ethyl, isopropyl, n-propyl, cyclopropyl, methoxy, ethoxy, hydroxy, trifluoromethyl, trifluoromethoxy, difluoromethyl, difluoromethoxy, fluoro, chloro, amino, aminomethyl, —CONH$_2$, —CONHCH$_3$, tetrahydropyran-4-yl, 3,6-dihydro-2H-pyran-4-yl, 2,4-dihydrofuran-3-yl, tetrazol-1-yl, amidino$C_1$-$C_6$alkyl, —C(=NR$^h$)NHR$^i$ (where R$^h$ and R$^i$ are independently hydrogen, hydroxy, $C_1$-$C_6$alkoxy, acyl, —C(O)O$C_1$-$C_6$alkyl, a natural or an unnatural amino acid residue, —CO(ethylene)$SO_2R^u$ (where R$^u$ is $C_1$-$C_6$alkyl, optionally substituted monocyclic heteroaryl, optionally substituted phenyl, or optionally substituted monocyclic heterocyclyl), or —CO(CH$_2$)$_{2-3}$OR$^v$ (where R$^v$ is hydrogen, $C_1$-$C_6$alkoxy$C_{1-3}$alkyl, or optionally substituted monocyclic heterocyclyl)), cyano, and 1,2,4-oxadiazol-5(4H)-one-3-yl.

8. The compound of claim 6, or a pharmaceutically acceptable salt thereof, wherein R$^1$ is phenyl optionally substituted with R$^e$ and R$^f$ independently selected from methyl, ethyl, isopropyl, n-propyl, cyclopropyl, methoxy, ethoxy, hydroxy, trifluoromethyl, trifluoromethoxy, difluoromethyl, difluoromethoxy, fluoro, chloro, —CONH$_2$, —CONHCH$_3$, tetrahydropyran-4-yl, 3,6-dihydro-2H-pyran-4-yl,2,4-dihydrofuran-3-yl, tetrazol-1-yl, and cyano wherein R$^e$ and R$^f$ are attached to the carbon atoms of the phenyl ring that are ortho to the carbon of the phenyl ring attached to X$^1$, and is substituted with R$^g$ wherein R$^g$ is amino, aminomethyl, —C(=NR$^h$)NHR$^i$ (where R$^h$ and R$^i$ are independently hydrogen, hydroxy, methoxy, ethoxy, methylcarbonyl, methoxycarbonyl, ethoxycarbonyl, a natural or an unnatural amino acid residue, —CO(ethylene)SO$_2$R$^u$ (where R$^u$ is C$_1$-C$_6$alkyl, optionally substituted monocyclic heteroaryl, optionally substituted phenyl, or optionally substituted monocyclic heterocyclyl), or —CO(CH$_2$)$_{2-3}$OR$^v$ (where R$^v$ is hydrogen, C$_1$-C$_6$alkoxyC$_{1-3}$alkyl, or optionally substituted monocyclic heterocyclyl)), and 1,2,4-oxadiazol-5(4H)-one-3-yl and wherein R$^g$ is located at the carbon of the phenyl ring that is para to the carbon of the phenyl ring attached to X$^1$.

9. The compound of claim 6, or a pharmaceutically acceptable salt thereof, wherein R$^1$ is mono or bicyclic heteroaryl optionally substituted with R$^e$, R$^f$ or R$^g$ independently selected from C$_1$-C$_6$alkyl, C$_2$-C$_6$alkenyl, C$_3$-C$_6$cycloalkyl, C$_1$-C$_6$alkoxy, hydroxy, halo, haloC$_1$-C$_6$alkyl, haloC$_1$-C$_6$alkoxy, amino, C$_1$-C$_6$alkylamino, diC$_1$-C$_6$alkylamino, aminoC$_1$-C$_6$alkyl, aminocarbonyl, amidinoC$_1$-C$_6$alkyl, —C(=NR$^h$)NHR$^i$ (where R$^h$ and R$^i$ are independently hydrogen, hydroxy, C$_1$-C$_6$alkoxy, acyl, —C(O)OC$_1$-C$_6$alkyl, a natural or an unnatural amino acid residue, a dipeptidic residue, —CO(ethylene)SO$_2$R$^u$ (where R$^u$ is C$_1$-C$_6$alkyl, optionally substituted monocyclic heteroaryl, optionally substituted phenyl, or optionally substituted monocyclic heterocyclyl), or —CO(CH$_2$)$_{2-3}$OR$^v$ (where R$^v$ is hydrogen, C$_1$-C$_6$alkoxyC$_{1-3}$alkyl, or optionally substituted monocyclic heterocyclyl)), cyano, monocyclic heteroaryl (wherein the monocyclic heteroaryl is optionally substituted with one, two or three substituents independently selected from C$_1$-C$_6$alkyl, C$_3$-C$_6$cycloalkyl, C$_1$-C$_6$alkoxy, hydroxy, halo, haloC$_1$-C$_6$alkyl, haloC$_1$-C$_6$alkoxy, amino, C$_1$-C$_6$alkylamino, diC$_1$-C$_6$alkylamino, and cyano), and monocyclic heterocyclyl (wherein the monocyclic heterocyclyl is optionally substituted with one, two or three substituents independently selected from C$_1$-C$_6$alkyl, C$_3$-C$_6$cycloalkyl, C$_1$-C$_6$alkoxy, hydroxy, halo, haloC$_1$-C$_6$alkyl, haloC$_1$-C$_6$alkoxy, amino, C$_1$-C$_6$alkylamino, and diC$_1$-C$_6$alkylamino).

10. The compound of claim 6, or a pharmaceutically acceptable salt thereof, wherein R$^1$ is pyridinyl, pyrimidinyl, pyazinyl, pyridazinyl, isoquinolinyl, benzypyrazolyl, or benzisoxazolyl, optionally substituted with R$^e$, R$^f$, or R$^g$ independently selected from methyl, ethyl, isopropyl, n-propyl, cyclopropyl, methoxy, ethoxy, hydroxy, trifluoromethyl, trifluoromethoxy, difluoromethyl, difluoromethoxy, fluoro, chloro, amino, aminomethyl, —CONH$_2$, —CONHCH$_3$, tetrahydropyran-4-yl, 3,6-dihydro-2H-pyran4-yl, 2,4-dihydrofuran-3-yl, tetrazol-1-yl, amidinoC$_1$-C$_6$alkyl, —C(=NR$^h$)NHR$^i$ (where R$^h$ and R$^i$ are independently hydrogen, hydroxy, C$_1$-C$_6$alkoxy, acyl, —C(O)OC$_1$-C$_6$alkyl, a natural or an unnatural amino acid residue, —CO(ethylene)SO$_2$R$^u$ (where R$^u$ is C$_1$-C$_6$alkyl, optionally substituted monocyclic heteroaryl, optionally substituted phenyl, or optionally substituted monocyclic heterocyclyl), or —CO(CH$_2$)$_{2-3}$OR$^v$ (where R$^v$ is hydrogen, C$_1$-C$_6$alkoxyC$_{1-3}$alkyl, or optionally substituted monocyclic heterocyclyl)), cyano, and 1,2,4-oxadiazol-5(4H)-one-3-yl.

11. The compound of claim 6, or a pharmaceutically acceptable salt thereof, wherein R$^1$ is pyridin-3-yl optionally substituted with R$^e$ and R$^f$ independently selected from methyl, ethyl, isopropyl, n-propyl, cyclopropyl, methoxy, ethoxy, hydroxy, trifluoromethyl, trifluoromethoxy, difluoromethyl, difluoromethoxy, fluoro, chloro, —CONH$_2$, —CONHCH$_3$, tetrahydropyran-4-yl, 3,6-dihydro-2H-pyran-4-yl, 2,4-dihydrofuran-3-yl, tetrazol-1-yl, and cyano and wherein R$^e$ and R$^f$ are attached to the C-2 and C-4 position of the pyridine-3-yl ring, and is substituted with R$^9$ wherein R$^9$ is amino, aminomethyl, —C(=NR$^h$)NHR$^i$ (where R$^h$ and R$^i$ are independently hydrogen, hydroxy, methoxy, ethoxy, methylcarbonyl, methoxycarbonyl, ethoxycarbonyl, a natural or an unnatural amino acid residue, —CO(ethylene)SO$_2$R$^u$ (where R$^u$ is C$_1$-C$_6$alkyl, optionally substituted monocyclic heteroaryl, optionally substituted phenyl, or optionally substituted monocyclic heterocyclyl), or —CO(CH$_2$)$_{2-3}$OR$^v$ (where R$^v$ is hydrogen, C$_1$-C$_6$alkoxyC$_{1-3}$alkyl, or optionally substituted monocyclic heterocyclyl)), or 1,2,4-oxadiazol-5(4H)-one-3-yl, and R$^9$ is attached to the C-6 position of the pyridinyl ring.

12. The compound of claim 8, or a pharmaceutically acceptable salt thereof, wherein the compound has the structure below:

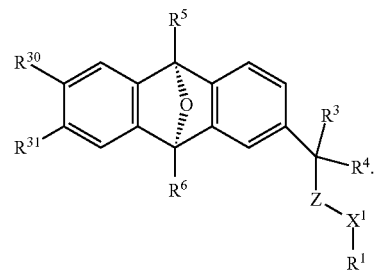

13. A compound selected from:
a mixture of (±)-N-[(6-amino-2,4-dimethylpyridin-3-yl)methyl]-12-phenyl-15-oxatetracyclo-[6.6.1.0$^{2,7}$.0$^{9,14}$]pentadeca-2,4,6,9,11,13-hexaene-4-carboxamide and N-[(6-amino-2,4-dimethyl-pyridin-3-yl)methyl]-1-phenyl-15-oxatetra-cyclo[6.6.1.0$^{2,7}$.0$^{9,14}$]-pentadeca-2,4,6,9,11,13-hexaene-4-carboxamide;
a mixture of (±)-N-[(6-amino-2,4 dimethylpyridin-3-yl)methyl]12-(4-fluorophenyl)-15-oxatetra-cyclo-[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(4-fluorophenyl)-15-oxatetracyclo-[6.6.1.0$^{2,7}$.0$^{9,14}$]-pentadeca-2,4,6,9,11,13-hexaene-4-carboxamide;
a mixture of (±)-N-[(6-amino-2,4-dimethylpyridin-3-yl)methyl]-12-(6-methoxypyridin-3-yl)-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(6-methoxypyridin-3-yl)-15-oxatetracyclo-[6.6.1.0$^{2,7}$.0$^{9,14}$]pentadeca-2,4,6,9,11,13-hexaene-4-carboxamide;
a mixture of (±)-N-[(6-amino-2,4-dimethylpyridin-3-yl)methyl]-12-(3,5-dimethyl-1,2-oxazol-4-yl)-15-oxatetracyclo[6.6.1.0$^{2,7}$.0$^{9,14}$]pentadeca-2,4,6,9,11,13-hexaene-4-dimethyl-1,2-oxazol-4-yl)-15-oxatetracyclo-[6.6.1.0$^{2,7}$.0$^{9,14}$]pentadeca-2,4,6,9,11,13-hexaene-4-carboxamide;
a mixture of (±)-N-[(6-amino-2,4-dimethylpyridin-3-yl)methyl]-12-{8-oxa-3-azabicyclo[3.2.1]octan-3-yl}-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-{8-oxa-3-azabicyclo[3.2.1]octan-3-yl}-15-oxatetracyclo[6.6.1.0$^{2,7}$.0$^{9,14}$]pentadeca-2,4,6,9,11,13-hexaene-4-carboxamide;
a mixture of (±)-N-{[4-(aminomethyl)phenyl]methyl}-12-(4-fluorophenyl)-15-oxatetracyclo-[6.6.1.0$^{2,7}$.0$^{9,14}$]-pentadeca-2,4,6,9,11,13-hexaene-4-carboxamide and (±)-N-{[4-(aminomethyl)phenyl]methyl}-11-(4-fluorophenyl)-15-oxatetracyclo-[6.6.1.0$^{2,7}$.0$^{9,14}$]-pentadeca-2,4,6,9,11,13-hexaene-4-carboxamide;

a mixture of (±)-12-(4-fluorophenyl)-N-{[5-methoxy-2-(1H-1,2,3,4-tetrazol-1-yl)phenyl]methyl}-15-oxatetracyclo[6.6.1.0$^{2,7}$.0$^{9,14}$]pentadeca-2,4,6,9,11,13-hexaene-4-carboxamide and (±)-11-(4-fluorophenyl)-N-{[5-methoxy-2-(1H-1,2,3,4-tetrazol-1-yl)phenyl]methyl}-15-oxatetracyclo[6.6.1.0$^{2,7}$.0$^{9,14}$]pentadeca-2,4,6,9,11,13-hexaene-4-carboxamide;

a mixture of (±)-N-[(6-amino-2,4-dimethylpyridin-3-yl)methyl]-12-(3-fluorophenyl)-15-oxatetracyclo-[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(3-fluorophenyl)-15-oxatetracyclo[6.6.1.0$^{2,7}$.0$^{9,14}$]-pentadeca-2,4,6,9,11,13-hexaene-4-carboxamide a mixture of (±)-N-[(6-amino-2,4-dimethylpyridin-3-yl)methyl]-12-(2-ethoxy-5-fluoropyridin-4-yl)-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(2-ethoxy-5-fluoropyridin-4-yl)-15-oxatetra-cyclo[6.6.1.0$^{2,7}$.0$^{9,14}$]pentadeca-2,4,6,9,11,13-hexaene-4-carboxamide;

a mixture of (±)-N-[(6-amino-2,4-dimethylpyridin-3-yl)methyl]-12-[5-fluoro-2-(propan-2-yloxy)pyridin-4-yl]-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-[5-fluoro-2-(propan-2-yloxy)pyridin-4-yl]-15-oxatetracyclo[6.6.1.0$^{2,7}$.0$^{9,14}$]pentadeca-2,4,6,9,11,13-hexaene-4-carboxamide;

a mixture of (±)-N-[(6-chloro-2-fluoro-3-methoxyphenyl)methyl]-12-(furan-2-yl)-15-oxatetracyclo-[6.6.1.0$^{2,7}$.0$^{9,14}$]-pentadeca-2,4,6,9,11,13-hexaene-4-carboxamide; and (±)-N-[(6-chloro-2-fluoro-3-methoxyphenyl)methyl]-11-(furan-2-yl)-15-oxatetracyclo-[6.6.1.0$^{2,7}$.0$^{9,14}$]-pentadeca-2,4,6,9,11,13-hexaene-4-carboxamide;

a mixture of (±)-N-[(6-amino-2,4-dimethylpyridin-3-yl)methyl]-12-(furan-2-yl)-15-oxatetracyclo-[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(furan-2-yl)-15-oxatetracyclo-[6.6.1.0$^{2,7}$.0$^{9,14}$]pentadeca-2,4,6,9,11,13-hexaene-4-carboxamide;

a mixture of (±)-N-[(6-chloro-2-fluoro-3-methoxyphenyl)-methyl]-12-(3-fluorophenyl)-15-oxatetracyclo-[6.6.1.0$^{2,7}$.0$^{9,14}$]pentadeca-2,4,6,9,11,13-hexaene-4-carboxamide and (±)-N-[(6-chloro-2-fluoro-3-methoxyphenyl)methyl]-11-(3-fluorophenyl)-15-oxatetracyclo-[6.6.1.0$^{2,7}$.0$^{9,14}$]pentadeca-2,4,6,9,11,13-hexaene-4-carboxamide;

a mixture of (±)-{2-[12-(4-fluorophenyl)-15-oxatetracyclo-[6.6.1.0$^{2,7}$.0$^{9,14}$]pentadeca-2,4,6,9,11,13-hexaene-4-carbonyl]-2,3-dihydro-1H-isoindol-5-yl}methanamine and (±)-{2-[11-(4-fluorophenyl)-15-oxatetracyclo[6.6.1.0$^{2,7}$.0$^{9,14}$]pentadeca-2,4,6,9,11,13-hexaene-4-carbonyl]-2,3-dihydro-1H-isoindol-5-yl}methanamine;

a mixture of (±)-N-[(6-amino-2,4-dimethylpyridin-3-yl)methyl]-12-(2-fluorophenyl)-15-oxatetracyclo-[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(2-fluoro-phenyl)-15-oxatetracyclo-[6.6.1.0$^{2,7}$.0$^{9,14}$]-pentadeca-2,4,6,9,11,13-hexaene-4-carboxamide;

(±)-N-[(6-amino-2,4-dimethylpyridin-3-yl)-methyl]-12-(2-fluorophenyl)-15-oxatetracyclo[6.6.1.0$^{2,7}$.0$^{9,14}$]pentadeca-2,4,6,9,11,13-hexaene-4-carboxamide a mixture of (±)-N-[(6-amino-2,4-dimethylpyridin-3-yl)methyl]-12-(2-methoxyphenyl)-15-oxatetra-cyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(2-methoxy-phenyl)-15-oxatetracyclo-[6.6.1.0$^{2,7}$.0$^{9,14}$]-pentadeca-2,4,6,9,11,13-hexaene-4-carboxamide;

a mixture of (±)-N-[(6-amino-2,4-dimethylpyridin-3-yl)methyl]-12-(1H-1,3-benzodiazol-4-yl)-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(1H-1,3-benzodiazol-4-yl)-15-oxatetracyclo-[6.6.1.0$^{2,7}$.0$^{9,14}$]pentadeca-2,4,6,9,11,13-hexaene-4-carboxamide;

a mixture of (±)-12-(1H-1,3-benzodiazol-4-yl)-N-[(6-chloro-2-fluoro-3-methoxyphenyl)methyl]-15-oxatetra-cyclo[6.6.1.0$^{2,7}$.0$^{9,14}$]pentadeca-2,4,6,9,11,13-hexaene-4-carboxamide and (±)-11-(1H-1,3-benzodiazol-4-yl)-N-[(6-chloro-2-fluoro-3-methoxyphenyl)methyl]-15-oxatetracyclo-[6.6.1.0$^{2,7}$.0$^{9,14}$]pentadeca-2,4,6,9,11,13-hexaene-4-carboxamide;

a mixture of (±)-N-[(6-amino-2,4-dimethylpyridin-3-yl)methyl]-12-(1,3-benzoxazol-7-yl)-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-1-(1,3-benzoxazol-7-yl)-15-oxatetracyclo-[6.6.1.0$^{2,7}$.0$^{9,14}$]pentadeca-2,4,6,9,11,13-hexaene-4-carboxamide a mixture of (±)-N-[(6-amino-2,4-dimethylpyridin-3-yl)methyl]-12-(2-oxo-1,2-dihydropyridin-1-yl)-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(2-oxo-1,2-dihydropyridin-1-yl)-15-oxatetracyclo[6.6.1.0$^{2,7}$.0$^{9,14}$]pentadeca-2,4,6,9,11,13-hexaene-4-carboxamide;

a mixture of (±)-N-[(1-aminoisoquinolin-6-yl)methyl]-12-(2-fluorophenyl)-15-oxatetracyclo[6.6.1.0$^{2,7}$.0$^{9,14}$]-pentadeca-2,4,6,9,11,13-hexaene-4-carboxamide and (±)-N-[(1-aminoisoquinolin-6-yl)methyl]-11-(2-fluorophenyl)-15-oxatetracyclo-[6.6.1.0$^{2,7}$.0$^{9,14}$]-pentadeca-2,4,6,9,11,13-hexaene-4-carboxamide;

a mixture of (±)-N-[(6-amino-2,4-dimethylpyridin-3-yl)methyl]-12-(4-fluoropyridin-3-yl)-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(4-fluoropyridin-3-yl)-15-oxatetracyclo-[6.6.1.0$^{2,7}$.0$^{9,14}$]pentadeca-2,4,6,9,11,13-hexaene-4-carboxamide;

a mixture of (±)-N-[(6-amino-2,4-dimethylpyridin-3-yl)methyl]-12-(1,3-benzoxazol-4-yl)-15-oxatetra-cyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(1,3-benzoxazol-4-yl)-15-oxatetracyclo-[6.6.1.0$^{2,7}$.0$^{9,14}$]pentadeca-2,4,6,9,11,13-hexaene-4-carboxamide;

a mixture of (±)-N-[(6-amino-2,4-dimethylpyridin-3-yl)methyl]-12-(2,6-difluorophenyl)-15-oxatetra-cyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(2,6-difluorophenyl)-15-oxatetracyclo-[6.6.1.0$^{2,7}$.0$^{9,14}$]-pentadeca-2,4,6,9,11,13-hexaene-4-carboxamide a mixture of (±)-N-[(6-amino-2,4-dimethylpyridin-3-yl)methyl]-12-(2,4-difluorophenyl)-15-oxatetra-cyclo[6.6.1.0$^{2,7}$.0$^{9,14}$]pentadeca-2,4,6,9,11,13-hexaene-4-carboxamide and (±)-N-[(6-amino-2,4- dimethylpyridin-3-yl)methyl]-11-(2,4-difluoro-phenyl)-15-oxatetracyclo-[6.6.1.0$^{2,7}$.0$^{9,14}$]-pentadeca-2,4,6,9,11,13-hexaene-4-carboxamide;

a mixture of (±)-N-[(6-amino-2,4-dimethylpyridin-3-yl)methyl]-12-(3-fluoropyridin-4-yl)-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-1-(3-fluoropyridin-4-yl)-15-oxatetracyclo-[6.6.1.0$^{2,7}$.0$^{9,14}$]pentadeca-2,4,6,9,11,13-hexaene-4-carboxamide;

a mixture of (±)-N-[(6-amino-2,4-dimethylpyridin-3-yl)methyl]-12-(3,5-difluorophenyl)-15-oxatetra-cyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-1-(3,5-difluorophenyl)-15-oxatetracyclo-[6.6.1.0$^{2,7}$.0$^{9,14}$]pentadeca-2,4,6,9,11,13-hexaene-4-carboxamide;

a mixture of (±)-N-[(6-amino-2,4-dimethylpyridin-3-yl)methyl]-12-(2,3-difluorophenyl)-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-1-(2,3-difluorophenyl)-15-oxatetracyclo-[6.6.1.0$^{2,7}$.0$^{9,14}$]pentadeca-2,4,6,9,11,13-hexaene-4-carboxamide;

a mixture of (±)-N-[(6-amino-2,4-dimethylpyridin-3-yl)methyl]-12-(2-chlorophenyl)-15-oxatetra-cyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(2-chloro-phenyl)-15-oxatetracyclo-[6.6.1.0$^{2,7}$.0$^{9,14}$]-pentadeca-2,4,6,9,11,13-hexaene-4-carboxamide;

a mixture of (±)-N-[(6-amino-2,4-dimethylpyridin-3-yl)methyl]-12-(3,4-difluorophenyl)-15-oxatetra-cyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(3,4-difluorophenyl)-15-oxatetracyclo-[6.6.1.0$^{2,7}$.0$^{9,14}$]-pentadeca-2,4,6,9,11,13-hexaene-4-carboxamide;

a mixture of (±)-N-[(6-amino-2,4-dimethylpyridin-3-yl)methyl]-12-[2-(trifluoromethyl)-phenyl]-15-oxatetra-cyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-1-[2-(trifluoromethyl)phenyl]-15-oxatetracyclo-[6.6.1.0$^{2,7}$.0$^{9,14}$]pentadeca-2,4,6,9,11,13-hexaene-4-carboxamide;

a mixture of (±)-N-[(6-amino-2,4-dimethylpyridin-3-yl)methyl]-12-(5-chloro-2-fluorophenyl)-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(5-chloro-2-fluorophenyl)-15-oxatetracyclo-[6.6.1.0$^{2,7}$.0$^{9,14}$]pentadeca-2,4,6,9,11,13-hexaene-4-carboxamide a mixture of (±)-N-[(6-amino-2,4-dimethylpyridin-3-yl)methyl]-12-(2-fluoro-5-methylphenyl)-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-1-(2-fluoro-5-methylphenyl)-15-oxatetracyclo-[6.6.1.0$^{2,7}$.0$^{9,14}$]pentadeca-2,4,6,9,11,13-hexaene-4-carboxamide;

a mixture of (±)-N-[(6-amino-2,4-dimethylpyridin-3-yl)methyl]-12-(5-chlorothiophen-2-yl)-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-1-(5-chlorothiophen-2-yl)-15-oxatetracyclo-[6.6.1.0$^{2,7}$.0$^{9,14}$]pentadeca-2,4,6,9,11,13-hexaene-4-carboxamide;

a mixture of (±)-N-[(6-amino-2,4-dimethylpyridin-3-yl)-methyl]-12-(4-benzoylpiperazin-1-yl)-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(4-benzoylpiperazin-1-yl)-15-oxatetracyclo-[6.6.1.0$^{2,7}$.0$^{9,14}$]pentadeca-2,4,6,9,11,13-hexaene-4-carboxamide;

(±)-N-[(6-amino-2,4-dimethylpyridin-3-yl)methyl]-11-(4-benzoylpiperazin-1-yl)-15-oxatetracyclo[6.6.1.0$^{2,7}$.0$^{9,14}$]pentadeca-2,4,6,9,11,13-hexaene-4-carboxamide a mixture of (±)-N-[(6-amino-2,4-dimethylpyridin-3-yl)-methyl]-12-(2-fluoro-4-methoxyphenyl)-15-oxatetra-cyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(2-fluoro-4-methoxyphenyl)-15-oxatetracyclo[6.6.1.0$^{2,7}$.0$^{9,14}$]pentadeca-2,4,6,9,11,13-hexaene-4-carboxamide;

a mixture of (±)-N-[(6-amino-2,4-dimethylpyridin-3-yl)-methyl]-12-(4-cyano-2-fluorophenyl)-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-1-(4-cyano-2-fluorophenyl)-15-oxatetracyclo-[6.6.1.0$^{2,7}$.0$^{9,14}$]pentadeca-2,4,6,9,11,13-hexaene-4-carboxamide;

a mixture of (±)-N-[(6-amino-2,4-dimethylpyridin-3-yl)-methyl]-12-(2-cyano-4-fluorophenyl)-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(2-cyano-4-fluorophenyl)-15-oxatetracyclo-[6.6.1.0$^{2,7}$.0$^{9,14}$]pentadeca-2,4,6,9,11,13-hexaene-4-carboxamide;

(±)-N-[(6-amino-2,4-dimethylpyridin-3-yl)-methyl]-12-(2-cyano-4-fluorophenyl)-15-oxatetracyclo[6.6.1.0$^{2,7}$.0$^{9,14}$]pentadeca-2,4,6,9,11,13-hexaene-4-carboxamide;

a mixture of (±)-N-[(6-amino-2,4-dimethylpyridin-3-yl)-methyl]-12-(2H-1,3-benzodioxol-4-yl)-15-oxatetracyclo[6.6.1.0$^{2,7}$.0$^{9,14}$]pentadeca-2,4,6,9,11,13-hexaene-4-carboxamide a mixture of (±)-N-[(6-amino-2,4-dimethylpyridin-3-yl)-methyl]-12-(2-carbamoylphenyl)-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(2-carbamoylphenyl)-15-oxatetracyclo-[6.6.1.0$^{2,7}$.0$^{9,14}$]pentadeca-2,4,6,9,11,13-hexaene-4-carboxamide;

a mixture of (±)-N-[(6-amino-2,4-dimethylpyridin-3-yl)-methyl]-12-(2-cyano-4-methyl-phenyl)-15-oxaetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(2-cyano-4-methylphenyl)-15-oxateracyclo-[6.6.1.0$^{2,7}$.0$^{9,14}$]pentadeca-2,4,6,9,11,13-hexaene-4-carboxamide;

(±)-N-[(6-amino-2,4-dimethylpyridin-3-yl)-methyl]-12-(2-cyano-4-methylphenyl)-15-oxatetracyclo[6.6.1.0$^{2,7}$.0$^{9,14}$]pentadeca-2,4,6,9,11,13-hexaene-4-carboxamide;

a mixture of (±)-N-[(6-amino-2,4-dimethylpyridin-3-yl)-methyl]-12-(2-cyano-4-methoxy-phenyl)-15-oxatetra-cyclo[6.6.1.0$^{2,7}$.0$^{9,14}$]pentadeca-2,4,6,9,11,13-hexaene-4-carboxamide;

a mixture of (±)-N-[(6-amino-2,4-dimethylpyridin-3-yl)methyl]-12-(pyridin-2-yl)-15-oxatetra-cyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)

methyl]-11-(pyridin-2-yl)-15-oxatetracyclo-[6.6.1.0$^{2,7}$.0$^{9,14}$]pentadeca-2,4,6,9,11,13-hexaene-4-carboxamide;

(±)-N-[(6-amino-4-methoxy-2-methylpyridin-3-yl)methyl]-12-(2,4-difluorophenyl)-15-oxatetra-cyclo[6.6.1.0$^{2,7}$.0$^{9,14}$]pentadeca-2,4,6,9,11,13-hexaene-4-carboxamide;

a mixture of (±)-N-[(6-amino-2,4-dimethylpyridin-3-yl)methyl]-12-(2,3-dihydro-1,4-benzodioxin-5-yl)-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(2,3-dihydro-1,4-benzodioxin-5-yl)-15-oxatetracyclo[6.6.1.0$^{2,7}$.0$^{9,14}$]pentadeca-2,4,6,9,11,13-hexaene-4-carboxamide;

a mixture of (±)-N-[(6-amino-2,4-dimethylpyridin-3-yl)methyl]-12-(2-cyanophenyl)-15-oxatetra-cyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(2-cyanophenyl)-15-oxatetracyclo-[6.6.1.0$^{2,7}$.0$^{9,14}$]pentadeca-2,4,6,9,11,13-hexaene-4-carboxamide;

a mixture of (±)-N-[(6-amino-2,4-dimethylpyridin-3-yl)methyl]-12-(2-cyano-6-methylphenyl)-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(2-cyano-6-methylphenyl)-15-oxatetra-cyclo[6.6.1.0$^{2,7}$.0$^{9,14}$]pentadeca-2,4,6,9,11,13-hexaene-4-carboxamide;

a mixture of (±)-N-[(6-amino-2,4-dimethylpyridin-3-yl)methyl]-12-[6-(cyclopropylmethoxy)pyridin-3-yl]-15-oxatetracyclo[6.6.1.0$^{2,7}$.0$^{9,14}$]pentadeca-2,4,6,9,11,13-hexaene-4-carboxamide (±)-N-[(6-amino-2,4-dimethylpyridin-3-yl)methyl]-11-[6-(cyclopropylmethoxy)pyridin-3-yl]-15-oxatetra-cyclo[6.6.1.0$^{2,7}$.0$^{9,14}$]pentadeca-2,4,6,9,11,13-hexaene-4-carboxamide;

a mixture of (±)-N-[(6-amino-2,4-dimethylpyridin-3-yl)methyl]-12-(6-methoxy-4-methylpyridin-3-yl)-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(6-methoxy-4-methylpyridin-3-yl)-15-oxatetra-cyclo[6.6.1.0$^{2,7}$.0$^{9,14}$]pentadeca-2,4,6,9,11,13-hexaene-4-carboxamide;

a mixture of (±)-N-[(6-amino-2,4-dimethylpyridin-3-yl)methyl]-12-(pyrimidin-2-yl)-15-oxatetra-cyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-1-(pyrimidin-2-yl)-15-oxatetracyclo-[6.6.1.0$^{2,7}$.0$^{9,14}$]pentadeca-2,4,6,9,11,13-hexaene-4-carboxamide;

a mixture of (±)-N-[(6-amino-2,4-dimethylpyridin-3-yl)methyl]-12-(2-methanesulfonylphenyl)-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(2-methanesulfonylphenyl)-15-oxatetra-cyclo[6.6.1.0$^{2,7}$.0$^{9,14}$]pentadeca-2,4,6,9,11,13-hexaene-4-carboxamide;

a mixture of (±)-N-[(6-amino-4-ethoxy-2-methylpyridin-3-yl)-methyl]-12-(2,4-difluorophenyl)-15-oxatetracyclo[6.6.1.0$^{2,7}$.0$^{9,14}$]pentadeca-2,4,6,9,11,13-hexaene-4-carboxamide and (±)-N-[(6-amino-4-ethoxy-2-methylpyridin-3-yl)methyl]-11-(2,4-difluorophenyl)-15-oxatetracyclo-[6.6.1.0$^{2,7}$.0$^{9,14}$]pentadeca-2,4,6,9,11,13-hexaene-4-carboxamide;

a mixture of (±)-N-[(6-amino-4-ethoxy-2-methylpyridin-3-yl)methyl]-12-(2,3-difluorophenyl)-15-oxatetra-cyclo[6.6.1.0$^{2,7}$.0$^{9,14}$]pentadeca-2,4,6,9,11,13-hexaene-4-carboxamide and (±)-N-[(6-amino-4-ethoxy-2-methylpyridin-3-yl)methyl]-11-(2,3-difluorophenyl)-15-oxatetracyclo[6.6.1.0$^{2,7}$.0$^{9,14}$]-pentadeca-2,4,6,9,11,13-hexaene-4-carboxamide;

(±)-12-(2,3-difluorophenyl)-N-[(6-fluoro-4-methyl-2,3-dihydro-1H-isoindol-5-yl)methyl]-15-oxatetracyclo[6.6.1.0$^{2,7}$.0$^{9,14}$]pentadeca-2,4,6,9,11,13-hexaene-4-carboxamide;

(1R,8S)—N-[(6-amino-2,4-dimethylpyridin-3-yl)methyl]-12-(2,4-difluorophenyl)-15-oxatetra-cyclo[6.6.1.0$^{2,7}$.0$^{9,14}$]pentadeca-2,4,6,9,11,13-hexaene-4-carboxamide;

(1S,8R)—N-[(6-amino-2,4-dimethylpyridin-3-yl)-methyl]-12-(2,4-difluorophenyl)-15-oxatetracyclo-[6.6.1.0$^{2,7}$.0$^{9,14}$]pentadeca-2,4,6,9,11,13-hexaene-4-carboxamide;

a mixture of (±)-N-[(6-amino-2,4-dimethylpyridin-3-yl)methyl]-12-(5-methylfuran-2-yl)-15-oxatetra-cyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-1-(5-methylfuran-2-yl)-15-oxatetracyclo-[6.6.1.0$^{2,7}$.0$^{9,14}$]pentadeca-2,4,6,9,11,13-hexaene-4-carboxamide;

a mixture of (±)-N-{[4-(aminomethyl)-2,6-dimethylphenyl]-methyl}-12-(2-cyano-4-fluorophenyl)-15-oxatetracyclo[6.6.1.0$^{2,7}$.0$^{9,14}$]pentadeca-2,4,6,9,11,13-hexaene-4-carboxamide and (±)-N-{[4-(aminomethyl)-2,6-dimethylphenyl]methyl}-1-(2-cyano-4-fluorophenyl)-15-oxatetracyclo-[6.6.1.0$^{2,7}$.0$^{9,14}$]pentadeca-2,4,6,9,11,13-hexaene-4-carboxamide;

a mixture of (±)-N-[(6-amino-2,4-dimethylpyridin-3-yl)-methyl]-12-{2-oxa-6-azaspiro[3.3]heptan-6-yl}-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-{2-oxa-6-azaspiro[3.3]heptan-6-yl}-15-oxatetracyclo[6.6.1.0$^{2,7}$.0$^{9,14}$]pentadeca-2,4,6,9,11,13-hexaene-4-carboxamide;

(±)-12-(2,4-difluorophenyl)-N-[(6-fluoro-4-methyl-2,3-dihydro-1H-isoindol-5-yl)methyl]-15-oxatetracyclo[6.6.1.0$^{2,7}$.0$^{9,14}$]pentadeca-2,4,6,9,11,13-hexaene-4-carboxamide;

(±)-12-(2,4-difluorophenyl)-N-[(4,6-dimethyl-2,3-dihydro-1H-isoindol-5-yl)methyl]-15-oxatetra-cyclo[6.6.1.0$^{2,7}$.0$^{9,14}$]pentadeca-2,4,6,9,11,13-hexaene-4-carboxamide;

(±)-12-(2,3-difluorophenyl)-N-[(4,6-dimethyl-2,3-dihydro-1H-isoindol-5-yl)methyl]-15-oxatetra-cyclo[6.6.1.0$^{2,7}$.0$^{9,14}$]pentadeca-2,4,6,9,11,13-hexaene-4-carboxamide;

a mixture of (±)-N-[(6-amino-2,4-dimethylpyridin-3-yl)-methyl]-12-(3-oxomorpholin-4-yl)-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-1-(3-oxomorpholin-4-yl)-15-oxatetracyclo-[6.6.1.0$^{2,7}$.0$^{9,14}$]pentadeca-2,4,6,9,11,13-hexaene-4-carboxamide;

(±)-N-[(6-amino-2,4-dimethylpyridin-3-yl)methyl]-12-[2-fluoro-4-(trifluoromethyl)-phenyl]-15-oxatetracyclo[6.6.1.0$^{2,7}$.0$^{9,14}$]-pentadeca-2,4,6,9,11,13-hexaene-4-carboxamide (±)-N-[(6-amino-2,4-dimethylpyridin-3-yl)-methyl]-12-(4-chloro-2-cyanophenyl)-15-oxatetracyclo[6.6.1.0$^{2,7}$.0$^{9,14}$]pentadeca-2,4,6,9,11,13-hexaene-4-carboxamide;

(±)-N-[(6-amino-2,4-dimethylpyridin-3-yl)-methyl]-12-(2,3,4-trifluorophenyl)-15-oxatetracyclo[6.6.1.0$^{2,7}$.0$^{9,14}$]pentadeca-2,4,6,9,11,13-hexaene-4-carboxamide;

(±)-N-[(6-amino-4-methoxy-2-methylpyridin-3-yl)methyl]-12-(2-cyano-4-methylphenyl)-15-oxatetracyclo[6.6.1.0$^{2,7}$.0$^{9,14}$]pentadeca-2,4,6,9,11,13-hexaene-4-carboxamide;

(±)-N-[(6-amino-2,4-dimethylpyridin-3-yl)-methyl]-12-(4-chloro-2,3-difluorophenyl)-15-oxatetracyclo[6.6.1.0$^{2,7}$.0$^{9,14}$]pentadeca-2,4,6,9,11,13-hexaene-4-carboxamide;

a mixture of (±)-N-[(6-amino-2,4-dimethylpyridin-3-yl)-methyl]-12-(1,3-thiazol-2-yl)-15-oxatetra-cyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-1-(1,3-thiazol-2-yl)-15-oxatetracyclo-[6.6.1.0$^{2,7}$.0$^{9,14}$]pentadeca-2,4,6,9,11,13-hexaene-4-carboxamide;

(±)-N-[(6-amino-2,4-dimethylpyridin-3-yl)-methyl]-12-(7-fluoro-2H-1,3-benzodioxol-4-yl)-15-oxatetracyclo[6.6.1.0$^{2,7}$.0$^{9,14}$]pentadeca-2,4,6,9,11,13-hexaene-4-carboxamide;

(±)-N-[(6-amino-4-methoxy-2-methylpyridin-3-yl)methyl]-12-(4-chloro-2,3-difluorophenyl)-15-oxatetracyclo[6.6.1.0$^{2,7}$.0$^{9,14}$]pentadeca-2,4,6,9,11,13-hexaene-4-carboxamide;

(±)-N-[(6-amino-2,4-dimethylpyridin-3-yl)-methyl]-12-(3-fluoropyridin-2-yl)-15-oxatetracyclo[6.6.1.0$^{2,7}$.0$^{9,14}$]pentadeca-2,4,6,9,11,13-hexaene-4-carboxamide;

(±)-N-[(6-amino-4-ethoxy-2-methylpyridin-3-yl)-methyl]-12-(2-fluoro-6-methylphenyl)-15-oxatetracyclo[6.6.1.0$^{2,7}$.0$^{9,14}$]pentadeca-2,4,6,9,11,13-hexaene-4-carboxamide;

(±)-N-[(6-amino-2,4-dimethylpyridin-3-yl)-methyl]-12-(2-fluoro-6-methylphenyl)-15-oxatetracyclo[6.6.1.0$^{2,7}$.0$^{9,14}$]pentadeca-2,4,6,9,11,13-hexaene-4-carboxamide;

(±)-N-[(6-amino-4-methoxy-2-methylpyridin-3-yl)methyl]-12-(2-fluoro-6-methylphenyl)-15-oxatetracyclo[6.6.1.0$^{2,7}$.0$^{9,14}$]pentadeca-2,4,6,9,11,13-hexaene-4-carboxamide;

(±)-N-[(6-amino-2,4-dimethylpyridin-3-yl)-methyl]-12-(3,5-difluoropyridin-2-yl)-15-oxatetracyclo[6.6.1.0$^{2,7}$.0$^{9,14}$]pentadeca-2,4,6,9,11,13-hexaene-4-carboxamide;

(±)-N-[(6-amino-2,4-dimethylpyridin-3-yl)-methyl]-12-(2,3-difluoro-4-methylphenyl)-15-oxatetracyclo[6.6.1.0$^{2,7}$.0$^{9,14}$]pentadeca-2,4,6,9,11,13-hexaene-4-carboxamide;

(±)-N-[(6-amino-2,4-dimethylpyridin-3-yl)-methyl]-12-[2,3-difluoro-4-(trifluoromethyl)-phenyl]-15-oxatetracyclo[6.6.1.0$^{2,7}$.0$^{9,14}$]-pentadeca-2,4,6,9,11,13-hexaene-4-carboxamide;

(±)-N-[(6-amino-2,4-dimethylpyridin-3-yl)-methyl]-12-[4-fluoro-3-(trifluoromethyl)-phenyl]-15-oxatetracyclo[6.6.1.0$^{2,7}$.0$^{9,14}$]pentadeca-2,4,6,9,11,13-hexaene-4-carboxamide;

(±)-N-[(6-amino-2,4-dimethylpyridin-3-yl)-methyl]-12-(1H-1,3-benzodiazol-5-yl)-15-oxatetracyclo[6.6.1.0$^{2,7}$.0$^{9,14}$]pentadeca-2,4,6,9,11,13-hexaene-4-carboxamide;

(±)-N-[(4,6-dimethyl-2,3-dihydro-1H-isoindol-5-yl)methyl]-12-(2-fluoro-6-methylphenyl)-15-oxatetracyclo[6.6.1.0$^{2,7}$.0$^{9,14}$]pentadeca-2,4,6,9,11,13-hexaene-4-carboxamide;

(±)-N-{[4-(aminomethyl)-2,6-dimethylphenyl]-methyl}-12-(4-chloro-2,3-difluorophenyl)-15-oxatetracyclo-[6.6.1.0$^{2,7}$.0$^{9,14}$]pentadeca-2,4,6,9,11,13-hexaene-4-carboxamide;

(±)-N-[(6-amino-2,4-dimethylpyridin-3-yl)-methyl]-12-(2-ethynylphenyl)-15-oxatetra-cyclo[6.6.1.0$^{2,7}$.0$^{9,14}$]pentadeca-2,4,6,9,11,13-hexaene-4-carboxamide;

(±)-12-(2,4-difluorophenyl)-N-{[5-methoxy-2-(1H-1,2,3,4-tetrazol-1-yl)phenyl]methyl}-15-oxatetracyclo[6.6.1.0$^{2,7}$.0$^{9,14}$]pentadeca-2,4,6,9,11,13-hexaene-4-carboxamide;

(±)-N-[(6-amino-2,4-dimethylpyridin-3-yl)-methyl]-12-(3-methanesulfonylphenyl)-15-oxatetracyclo[6.6.1.0$^{2,7}$.0$^{9,14}$]pentadeca-2,4,6,9,11,13-hexaene-4-carboxamide;

(±)-12-(2,4-difluorophenyl)-N-{[2-fluoro-3-methoxy-6-(1H-1,2,3,4-tetrazol-1-yl)phenyl]-methyl}-15-oxatetracyclo[6.6.1.0$^{2,7}$.0$^{9,14}$]-pentadeca-2,4,6,9,11,13-hexaene-4-carboxamide;

(1R,8R)—N-[(6-amino-2,4-dimethylpyridin-3-yl)-methyl]-11-(2-fluorophenyl)-15-oxatetracyclo-[6.6.1.0$^{2,7}$.0$^{9,14}$]pentadeca-2,4,6,9,11,13-hexaene-4-carboxamide;

(±)-N-[(4-chloro-6-methyl-2,3-dihydro-1H-isoindol-5-yl)methyl]-12-(2,4-difluorophenyl)-15-oxatetracyclo[6.6.1.0$^{2,7}$.0$^{9,14}$]pentadeca-2,4,6,9,11,13-hexaene-4-carboxamide;

(±)-N-[(6-amino-4-ethyl-2-methylpyridin-3-yl)methyl]-12-(2,4-difluorophenyl)-15-oxatetracyclo[6.6.1.0$^{2,7}$.0$^{9,14}$]pentadeca-2,4,6,9,11,13-hexaene-4-carboxamide;

(±)-N-[(6-amino-4-ethyl-2-methylpyridin-3-yl)methyl]-12-(2-cyano-4-methylphenyl)-15-oxatetracyclo[6.6.1.0$^{2,7}$.0$^{9,14}$]pentadeca-2,4,6,9,11,13-hexaene-4-carboxamide;

(±)-12-(2-cyano-4-methylphenyl)-N-[(4,6-dimethyl-2,3-dihydro-1H-isoindol-5-yl)methyl]-15-oxatetracyclo[6.6.1.0$^{2,7}$.0$^{9,14}$]pentadeca-2,4,6,9,11,13-hexaene-4-carboxamide;

(1R,8S)—N-[(6-amino-4-ethyl-2-imethylpyridin-3-yl)methyl]-12-(2,4-trifluorophenyl)-15-oxatetracyclo[6.6.1.0$^{2,7}$.0$^{9,14}$]pentadeca-2,4,6,9,11,13-hexaene-4-carboxamide;

(1R,8S)—N-[(6-amino-4-ethyl-2-imethylpyridin-3-yl)methyl]-12-(chloro-2-cyano-4-methylphenyl)-15-oxatetracyclo[6.6.1.0$^{2,7}$.0$^{9,14}$]pentadeca-2,4,6,9,11,13-hexaene-4-carboxamide;

(1R,8S)—N-[(6-amino-2,4-dimethylpyridin-3-yl)-methyl]-12-(2-cyano-4-methylphenyl)-15-oxatetracyclo[6.6.1.0$^{2,7}$.0$^{9,14}$]pentadeca-2,4,6,9,11,13-hexaene-4-carboxamide;

(±)-N-[(6-amino-2,4-dimethylpyridin-3-yl)-methyl]-12-(2,4-difluoro-6-methylphenyl)-15-oxatetracyclo[6.6.1.0$^{2,7}$.0$^{9,14}$]pentadeca-2,4,6,9,11,13-hexaene-4-carboxamide;

(±)-N-[(6-amino-4-ethyl-2-methylpyridin-3-yl)-methyl]-12-(2,4-difluoro-6-methylphenyl)-15-oxatetracyclo[6.6.1.0$^{2,7}$.0$^{9,14}$]pentadeca-2,4,6,9,11,13-hexaene-4-carboxamide;

(±)-12-(2-cyano-4-methylphenyl)-N-[(6-fluoro-4-methyl-2,3-dihydro-1H-isoindol-5-yl)methyl]-15-oxatetracyclo[6.6.1.0$^{2,7}$.0$^{9,14}$]pentadeca-2,4,6,9,11,13-hexaene-4-carboxamide;

(1R,8S)—N-[(6-amino-2,4-dimethylpyridin-3-yl)-methyl]-12-(4-chloro-2,3-difluorophenyl)-15-oxatetracyclo[6.6.1.0$^{2,7}$.0$^{9,14}$]pentadeca-2,4,6,9,11,13-hexaene-4-carboxamide;

(±)-N-[(6-amino-2,4-dimethylpyridin-3-yl)-methyl]-12-(2-chloro-4,6-difluorophenyl)-15-oxatetracyclo[6.6.1.0$^{2,7}$.0$^{9,14}$]pentadeca-2,4,6,9,11,13-hexaene-4-carboxamide;

(±)-N-{[4-(aminomethyl)-2,6-dimethylphenyl]-methyl}-12-(2,4-difluorophenyl)-15-oxatetracyclo[6.6.1.0$^{2,7}$.0$^{9,14}$]pentadeca-2,4,6,9,11,13-hexaene-4-carboxamide;

(±)-N-[(1-aminoisoquinolin-5-yl)methyl]-12-(2,4-difluorophenyl)-15-oxatetracyclo-[6.6.1.0$^{2,7}$.0$^{9,14}$]-pentadeca-2,4,6,9,11,13-hexaene-4-carboxamide;

(±)-N-[(6-amino-2,4-dimethylpyridin-3-yl)-methyl]-12-(4-oxo-1,4-dihydropyridin-1-yl)-15-oxatetracyclo[6.6.1.0$^{2,7}$.0$^{9,14}$]pentadeca-2,4,6,9,11,13-hexaene-4-carboxamide;

(±)-N-[(6-amino-4-methoxy-2-methylpyridin-3-yl)methyl]-12-(2,4-difluoro-6-methylphenyl)-15-oxatetracyclo[6.6.1.0$^{2,7}$.0$^{9,14}$]pentadeca-2,4,6,9,11,13-hexaene-4-carboxamide;

(±)-N-[(6-amino-4-ethoxy-2-methylpyridin-3-yl)-methyl]-12-(2,4-difluoro-6-methylphenyl)-15-oxatetracyclo[6.6.1.0$^{2,7}$.0$^{9,14}$]pentadeca-2,4,6,9,11,13-hexaene-4-carboxamide;

(±)-N-[(1-aminoisoquinolin-7-yl)methyl]-12-(2,4-difluorophenyl)-15-oxatetracyclo-[6.6.1.0$^{2,7}$.0$^{9,14}$]-pentadeca-2,4,6,9,11,13-hexaene-4-carboxamide;

(±)-N-[(1-aminoisoquinolin-4-yl)methyl]-12-(2,4-difluorophenyl)-15-oxatetracyclo-[6.6.1.0$^{2,7}$.0$^{9,14}$]-pentadeca-2,4,6,9,11,13-hexaene-4-carboxamide;

(±)-N-[(6-amino-2,4-dimethylpyridin-3-yl)-methyl]-2-(2-cyano-5-methylphenyl)-15-oxatetracyclo[6.6.1.0$^{2,7}$.0$^{9,14}$]pentadeca-2,4,6,9,11,13-hexaene-4-carboxamide;

(±)-N-[(6-amino-2,4-dimethylpyridin-3-yl)-methyl]-12-(2-cyano-6-methylpyridin-3-yl)-15-oxatetracyclo[6.6.1.0$^{2,7}$.0$^{9,14}$]pentadeca-2,4,6,9,11,13-hexaene-4-carboxamide;

(±)-N-[(6-amino-2,4-dimethylpyridin-3-yl)-methyl]-12-[2-cyano-3-(trifluoromethyl)-phenyl]-15-oxatetracyclo[6.6.1.0$^{2,7}$.0$^{9,14}$]pentadeca-2,4,6,9,11,13-hexaene-4-carboxamide;

(±)-N-[(6-amino-2,5-dimethylpyridin-3-yl)-methyl]-12-(2,4-difluorophenyl)-15-oxatetracyclo[6.6.1.0$^{2,7}$.0$^{9,14}$]pentadeca-2,4,6,9,11,13-hexaene-4-carboxamide;

(±)-N-[(6-amino-2,4-dimethylpyridin-3-yl)-methyl]-12-(4-methoxypyridin-3-yl)-15-oxatetracyclo[6.6.1.0$^{2,7}$.0$^{9,14}$]pentadeca-2,4,6,9,11,13-hexaene-4-carboxamide;

(±)-N-[(2-aminopyridin-4-yl)methyl]-12-(2,4-difluorophenyl)-15-oxatetracyclo-[6.6.1.0$^{2,7}$.0$^{9,14}$]-pentadeca-2,4,6,9,11,13-hexaene-4-carboxamide;

(±)-N-[(6-amino-2,4-dimethylpyridin-3-yl)-methyl]-12-(2,4,5-trifluorophenyl)-15-oxatetra-cyclo[6.6.1.0$^{2,7}$.0$^{9,14}$]pentadeca-2,4,6,9,11,13-hexaene-4-carboxamide;

(±)-N-[(4-carbamimidoylphenyl)methyl]-12-(2,4-difluorophenyl)-15-oxatetracyclo-[6.6.1.0$^{2,7}$.0$^{9,14}$]-pentadeca-2,4,6,9,11,13-hexaene-4-carboxamide;

a mixture of (±)-N-[(4-carbamimidoylphenyl)methyl]-11-(2,4-difluorophenyl)-15-oxa-4-azatetracyclo-[6.6.1.0$^{2,7}$.0$^{9,14}$]pentadeca-2(7),3,5,9,11,13-hexaene-5-carboxamide and (±)-N-[(4-carbamimidoylphenyl)methyl]-12-(2,4-difluorophenyl)-15-oxa-4-azatetracyclo-[6.6.1.0$^{2,7}$.0$^{9,14}$]pentadeca-2(7),3,5,9,11,13-hexaene-5-carboxamide;

(±)-N-[(6-amino-2-methyl-4-propylpyridin-3-yl)methyl]-12-(2,4-difluorophenyl)-15-oxatetracyclo[6.6.1.0$^{2,7}$.0$^{9,14}$]pentadeca-2,4,6,9,11,13-hexaene-4-carboxamide (±)-N-{[6-amino-2-methyl-4-(propan-2-yl)pyridin-3-yl]methyl}-12-(2,4-difluorophenyl)-15-oxatetra-cyclo[6.6.1.0$^{2,7}$.0$^{9,14}$]pentadeca-2,4,6,9,11,13-hexaene-4-carboxamide;

(1R,8S)—N-[(6-amino-2,4-dimethylpyridin-3-yl)-methyl]-12-(4-chloro-2-fluorophenyl)-15-oxatetracyclo[6.6.1.0$^{2,7}$.0$^{9,14}$]pentadeca-2,4,6,9,11,13-hexaene-4-carboxamide;

(1R,8S)—N-[(1-aminoisoquinolin-5-yl)methyl]-12-(2-fluorophenyl)-15-oxatetracyclo-[6.6.1.0$^{2,7}$.0$^{9,14}$]pentadeca-2,4,6,9,11,13-hexaene-4-carboxamide;

(1R,8S)—N-[(6-amino-2,4-dimethylpyridin-3-yl)-methyl]-12-(2-chloro-4-fluorophenyl)-15-oxatetracyclo[6.6.1.0$^{2,7}$.0$^{9,14}$]pentadeca-2,4,6,9,11,13-hexaene-4-carboxamide;

(1R,8S)—N-[(6-amino-2,4-dimethylpyridin-3-yl)-methyl]-12-(2-fluoro-6-methoxypyridin-3-yl)-15-oxatetracyclo[6.6.1.0$^{2,7}$.0$^{9,14}$]pentadeca-2,4,6,9,11,13-hexaene-4-carboxamide;

(±)-N-[(6-amino-4-cyclopropyl-2-methylpyridin-3-yl)methyl]-12-(2,4-difluorophenyl)-15-oxatetracyclo[6.6.1.0$^{2,7}$.0$^{9,14}$]pentadeca-2,4,6,9,11,13-hexaene-4-carboxamide;

(1R,8S)—N-[(2-amino-4,6-dimethylpyrimidin-5-yl)methyl]-12-(2,4-difluorophenyl)-15-oxatetracyclo[6.6.1.0$^{2,7}$.0$^{9,14}$]pentadeca-2,4,6,9,11,13-hexaene-4-carboxamide;

(1R,8S)—N-[(6-amino-4-ethyl-2-methylpyridin-3-yl)methyl]-12-(2,4-difluorophenyl)-15-oxatetracyclo[6.6.1.0$^{2,7}$.0$^{9,14}$]pentadeca-2,4,6,9,11,13-hexaene-4-carboxamide;

(1S,8R)—N-[(6-amino-2,4-dimethylpyridin-3-yl)-methyl]-12-(2-(methyl-5-oxo-2,5-dihydro-1H-pyrazol-1-yl)-5-oxatetracyclo[6.6.1.0$^{2,7}$.0$^{9,14}$]pentadeca-2,4,6,9,11,13-hexaene-4-carboxamide;

(1R,8S)—N-[(4-carbamimidoylphenyl)methyl]-12-(2-fluorophenyl)-15-oxatetracyclo-[6.6.1.0$^{2,7}$.0$^{9,14}$]pentadeca-2,4,6,9,11,13-hexaene-4-carboxamide;

(±)-N-[(4-carbamimidoylphenyl)methyl]-12-phenyl-15-oxatetracyclo[6.6.1.0$^{2,7}$.0$^{9,14}$]-pentadeca-2,4,6,9,11,13-hexaene-4-carboxamide;

(1R,8S)—N-[(6-amino-4-chloro-2-methylpyridin-3-yl)methyl]-12-(2,4-difluorophenyl)-15-oxatetracyclo[6.6.1.0$^{2,7}$.0$^{9,14}$]pentadeca-2,4,6,9,11,13-hexaene-4-carboxamide;

2-[(1R,8S)-12-{[(6-amino-2,4-dimethylpyridin-3-yl)methyl]carbamoyl}-15-oxatetracyclo-[6.6.1.0$^{2,7}$.0$^{9,14}$]pentadeca-2,4,6,9,11,13-hexaen-4-yl]pyridin-1-ium-1-olate;

(±)-12-(2,4-difluorophenyl)-N-({3-fluoro-4-[N'-hydroxycarbamimidoyl]phenyl}methyl)-15-oxatetracyclo[6.6.1.0$^{2,7}$.0$^{9,14}$]pentadeca-2,4,6,9,11,13-hexaene-4-carboxamide (±)-N-[(4-carbamimidoyl-3-fluorophenyl)methyl]-12-(2,4-difluorophenyl)-15-oxatetracyclo-[6.6.1.0$^{2,7}$.0$^{9,14}$]pentadeca-2,4,6,9,11,13-hexaene-4-carboxamide;

(1R,8S)—N-[(4-carbamimidoyl-2,6-dimethyl-phenyl)methyl]-12-(2,4-difluorophenyl)-15-oxatetracyclo[6.6.1.0$^{2,7}$.0$^{9,14}$]pentadeca-2,4,6,9,11,13-hexaene-4-carboxamide;

(1R,8S)—N-[(3-carbamimidoylphenyl)methyl]-12-(2-fluorophenyl)-15-oxatetracyclo-[6.6.1.0$^{2,7}$.0$^{9,14}$]pentadeca-2,4,6,9,11,13-hexaene-4-carboxamide;

(1R,8S)—N-[(4-carbamimidoylphenyl)methyl]-12-(4-fluorophenyl)-15-oxatetracyclo-[6.6.1.0$^{2,7}$.0$^{9,14}$]pentadeca-2,4,6,9,11,13-hexaene-4-carboxamide;

(1R,8S)—N-[(4-carbamimidoylphenyl)methyl]-12-(2,4-difluorophenyl)-15-oxatetracyclo-[6.6.1.0$^{2,7}$.0$^{9,14}$]pentadeca-2,4,6,9,11,13-hexaene-4-carboxamide;

(1R,8S)-12-(2,4-difluorophenyl)-N-{[4-(N'-hydroxycarbamimidoyl)phenyl]methyl}-15-oxatetracyclo[6.6.1.0$^{2,7}$.0$^{9,14}$]pentadeca-2,4,6,9,11,13-hexaene-4-carboxamide;

(1R,8S)-12-(2-fluorophenyl)-N-{[4-(N'-hydroxycarbamimidoyl)phenyl]methyl}-15-oxatetracyclo[6.6.1.0$^{2,7}$.0$^{9,14}$]pentadeca-2,4,6,9,11,13-hexaene-4-carboxamide;

(1R,8S)—N-[(3-amino-1,2-benzoxazol-6-yl)-methyl]-12-(2,4-difluorophenyl)-15-oxatetracyclo[6.6.1.0$^{2,7}$.0$^{9,14}$]pentadeca-2,4,6,9,11,13-hexaene-4-carboxamide;

(1R,8S)—N-[(3-amino-1H-indazol-6-yl)methyl]-12-(2,4-difluorophenyl)-15-oxatetracyclo-[6.6.1.0$^{2,7}$.0$^{9,14}$]pentadeca-2,4,6,9,11,13-hexaene-4-carboxamide;

(1R,8S)—N-{[6-amino-2-methyl-4-(propan-2-yl)-pyridin-3-yl]methyl}-12-(2,4-difluorophenyl)-15-oxatetracyclo[6.6.1.0$^{2,7}$.0$^{9,14}$]pentadeca-2,4,6,9,11,13-hexaene-4-carboxamide;

(1R,8S)—N-[(4-carbamimidoyl-3-fluorophenyl)-methyl]-12-(2,4-difluorophenyl)-15-oxatetracyclo[6.6.1.0$^{2,7}$.0$^{9,14}$]pentadeca-2,4,6,9,11,13-hexaene-4-carboxamide;

(1R,8S)—N-[(6-amino-2,4-dimethylpyridin-3-yl)-methyl]-12-(2-methylpyridin-3-yl)-15-oxatetracyclo[6.6.1.0$^{2,7}$.0,$^{9,14}$]pentadeca-2,4,6,9,11,13-hexaene-4-carboxamide;

(1R,8S)—N-[(6-amino-2,4-dimethylpyridin-3-yl)methyl]-12-(2-methoxypyridin-3-yl)-15-oxatetracyclo[6.6.1.0$^{2,7}$.0$^{9,14}$]pentadeca-2,4,6,9,11,13-hexaene-4-carboxamide;

2-[(1R,8S)-12-{[(6-amino-2,4-dimethylpyridin-3-yl)methyl]carbamoyl}-15-oxatetracyclo-[6.6.1.0$^{2,7}$.0$^{9,14}$]pentadeca-2,4,6,9,11,13-hexaen-4-yl]-5-fluoropyridin-1-ium-1-olate;

(1R,8S)—N-[(6-amino-2,4-dimethylpyridin-3-yl)methyl]-12-(4-methylpyridin-3-yl)-15-oxatetracyclo[6.6.1.0$^{2,7}$.0$^{9,14}$]pentadeca-2,4,6,9,11,13-hexaene-4-carboxamide;

(1R,8S)—N-[(1-aminoisoquinolin-5-yl)methyl]-12-(2-cyano-4-methylphenyl)-15-oxatetracyclo-[6.6.1.0$^{2,7}$.0$^{9,14}$]pentadeca-2,4,6,9,11,13-hexaene-4-carboxamide;

(1S,8R)—N-[(4-carbamimidoylphenyl)methyl]-12-(5-chlorothiophen-2-yl)-15-oxatetracyclo-[6.6.1.0$^{2,7}$.0$^{9,14}$]pentadeca-2,4,6,9,11,13-hexaene-4-carboxamide;

(1R,8S)—N-[(6-amino-4-ethenyl-2-methylpyridin-3-yl)methyl]-12-(2,4-difluorophenyl)-15-oxatetracyclo[6.6.1.0$^{2,7}$.0$^{9,14}$]pentadeca-2,4,6,9,11,13-hexaene-4-carboxamide;

(1R,8S)—N-(4-aminobenzenecarboximidoyl)-12-(2,4-difluorophenyl)-15-oxatetracyclo-[6.6.1.0$^{2,7}$.0$^{9,14}$]pentadeca-2,4,6,9,11,13-hexaene-4-carboxamide;

(1R,8S)—N-{[6-amino-4-(3,6-dihydro-2H-pyran-4-yl)-2-methylpyridin-3-yl]methyl}-12-(2,4-difluorophenyl)-15-oxatetracyclo[6.6.1.0$^{2,7}$.0$^{9,14}$]-pentadeca-2,4,6,9,11,13-hexaene-4-carboxamide;

(1R,8S)—N-[(4-carbamimidoylphenyl)methyl]-12-(5-methylfuran-2-yl)-15-oxatetracyclo-[6.6.1.0$^{2,7}$.0$^{9,14}$]pentadeca-2,4,6,9,11,13-hexaene-4-carboxamide;

(1R,8S)-12-(2,4-difluorophenyl)-N-{[4-(N'-methoxycarbamimidoyl)phenyl]methyl}-15-oxatetracyclo[6.6.1.0$^{2,7}$.0$^{9,14}$]pentadeca-2,4,6,9,11,13-hexaene-4-carboxamide;

(1R,8S)—N-{[6-amino-2-methyl-4-(prop-1-en-2-yl)pyridin-3-yl]methyl}-12-(2,4-difluorophenyl)-15-oxatetracyclo[6.6.1.0$^{2,7}$.0$^{9,14}$]pentadeca-2,4,6,9,11,13-hexaene-4-carboxamide;

(1S,8R)—N-[(4-carbamimidoylphenyl)methyl]-12-{8-oxa-3-azabicyclo[3.2.1]octan-3-yl}-5-oxatetracyclo[6.6.1.0$^{2,7}$.0$^{9,14}$]pentadeca-2,4,6,9,11,13-hexaene-4-carboxamide;

(1S,8R)—N-[(4-carbamimidoylphenyl)methyl]-12-(pyrrolidin-1-yl)-15-oxatetracyclo-[6.6.1.0$^{2,7}$.0$^{9,14}$]pentadeca-2,4,6,9,11,13-hexaene-4-carboxamide;

(1R,8S)—N-[(3-amino-1,2-benzoxazol-7-yl)-methyl]-12-(2-fluorophenyl)-15-oxatetracyclo-[6.6.1.0$^{2,7}$.0$^{9,14}$]pentadeca-2,4,6,9,11,13-hexaene-4-carboxamide;

(1R,8S)-12-(2-fluorophenyl)-N-{[4-(N'-methoxy-carbamimidoyl)phenyl]methyl}-15-oxatetracyclo-[6.6.1.0$^{2,7}$.0$^{9,14}$]pentadeca-2,4,6,9,11,13-hexaene-4-carboxamide;

(1R,8S)-12-(4-fluorophenyl)-N-{[4-(N'-methoxy-carbamimidoyl)phenyl]methyl}-15-oxatetracyclo-[6.6.1.0$^{2,7}$.0$^{9,14}$]pentadeca-2,4,6,9,11,13-hexaene-4-carboxamide;

(1R,8S)—N-[(6-amino-4,5-dimethylpyridin-3-yl)methyl]-12-(2-fluorophenyl)-15-oxatetra-cyclo-[6.6.1.0$^{2,7}$.0$^{9,14}$]pentadeca-2,4,6,9,11,13-hexaene-4-carboxamide;

(1R,8S)—N-(4-carbamimidoylphenyl)-12-(2,4-difluorophenyl)-15-oxatetracyclo-[6.6.1.0$^{2,7}$.0$^{9,14}$]-pentadeca-2,4,6,9,11,13-hexaene-4-carboxamide;

(1R,8S)—N-(3-amino-1,2-benzoxazol-5-yl)-12-(2,4-difluorophenyl)-15-oxatetracyclo-[6.6.1.0$^{2,7}$.0$^{9,14}$]pentadeca-2,4,6,9,11,13-hexaene-4-carboxamide;

(1R,8S)—N-{[6-amino-2-methyl-4-(trifluoro-methyl)pyridin-3-yl]methyl}-12-(2,4-difluorophenyl)-15-oxatetracyclo[6.6.1.0$^{2,7}$.0$^{9,14}$]-pentadeca-2,4,6,9,11,13-hexaene-4-carboxamide;

(1R,8S)—N-{[6-amino-2-methyl-4-(oxan-4-yl)pyridin-3-yl]methyl}-12-(2,4-difluorophenyl)-15-oxatetracyclo[6.6.1.0$^{2,7}$.0$^{9,14}$]pentadeca-2,4,6,9,11,13-hexaene-4-carboxamide;

(1R,8S)—N-[(6-amino-2,4-diethylpyridin-3-yl)methyl]-12-(2,4-difluorophenyl)-15-oxatetracyclo[6.6.1.0$^{2,7}$.0$^{9,14}$]pentadeca-2,4,6,9,11,13-hexaene-4-carboxamide;

(1S,8R)-12-(5-chlorothiophen-2-yl)-N-({4-[N'-methoxycarbamimidoyl]phenyl}methyl)-15-oxatetracyclo[6.6.1.0$^{2,7}$.0$^{9,14}$]pentadeca-2,4,6,9,11,13-hexaene-4-carboxamide;

(1R,8S)—N-[(6-amino-2,4-dimethylpyridin-3-yl)methyl]-12-{imidazo[1,2-a]pyridin-2-yl}-15-oxatetracyclo[6.6.1.0$^{2,7}$.0$^{9,14}$]pentadeca-2,4,6,9,11,13-hexaene-4-carboxamide;

(1R,8S)-12-(2-fluorophenyl)-N-[(4-methoxy-phenyl)methyl]-15-oxatetracyclo-[6.6.1.0$^{2,7}$.0$^{9,14}$]-pentadeca-2,4,6,9,11,13-hexaene-4-carboxamide;

(1R,8S)—N-({2,6-difluoro-4-[N'-methoxy-carbamimidoyl]phenyl}methyl)-12-(2,4-difluorophenyl)-5-oxatetracyclo[6.6.1.0$^{2,7}$.0$^{9,14}$]-pentadeca-2,4,6,9,11,13-hexaene-4-carboxamide;

(1R,8S)—N-[(4-carbamimidoyl-2,6-difluoro-phenyl)methyl]-12-(2,4-difluorophenyl)-[15-oxatetracyclo[6.6.1.0$^{2,7}$.0$^{9,14}$]pentadeca-2,4,6,9,11,13-hexaene-4-carboxamide;

(1R,8S)—N-[(6-amino-2,4-dicyclopropylpyridin-3-yl)methyl]-12-(2,4-difluorophenyl)-15-oxatetracyclo[6.6.1.0$^{2,7}$.0$^{9,14}$]pentadeca-2,4,6,9,11,13-hexaene-4-carboxamide;

(1R,8S)—N-(3-carbamimidoylphenyl)-methyl]-12-(2,4-difluorophenyl)-15-oxatetracyclo-[6.6.1.0$^{2,7}$.0$^{9,14}$]pentadeca-2,4,6,9,11,13-hexaene-4-carboxamide;

(1R,8S)—N-[(4-carbamimidoylphenyl)methyl]-12-cyclopropyl-15-oxatetracyclo-[6.6.1.0$^{2,7}$.0$^{9,14}$]pentadeca-2,4,6,9,11,13-hexaene-4-carboxamide;

(1R,8S)—N-[(6-chloro-2-fluoro-3-methoxyphenyl)-methyl]-12-(2,4-difluorophenyl)-15-oxatetracyclo[6.6.1.0$^{2,7}$.0$^{9,14}$]pentadeca-2,4,6,9,11,13-hexaene-4-carboximidamide;

4-[(1R,8S)-12-({[6-amino-2-methyl-4-(propan-2-yl)pyridin-3-yl]methyl}carbamoyl)-15-oxatetracyclo[6.6.1.0$^{2,7}$.0$^{9,14}$]pentadeca-2,4,6,9,11,13-hexaen-4-yl]-3-fluoropyridin-1-ium-1-olate (1R,8S)—N-({2,6-difluoro-4-[N'-hydroxy-carbamimidoyl]phenyl}methyl)-12-(2,4-difluorophenyl)-15-oxatetracyclo[6.6.1.0$^{2,7}$.0$^{9,14}$]-pentadeca-2,4,6,9,11,13-hexaene-4-carboxamide;

(1R,8S)—N-{[6-amino-4-(2,5-dihydrofuran-3-yl)-2-methylpyridin-3-yl]methyl}-12-(2,4-difluoro-phenyl)-15-oxatetracyclo[6.6.1.0$^{2,7}$.0$^{9,14}$]-pentadeca-2,4,6,9,11,13-hexaene-4-carboxamide;

(1R,8S)—N-[(6-carbamimidoylpyridin-3-yl)-methyl]-12-(2,4-difluorophenyl)-15-oxatetracyclo[6.6.1.0$^{2,7}$.0$^{9,14}$]pentadeca-2,4,6,9,11,13-hexaene-4-carboxamide;

ethyl N-[amino[4-({[(1R,8S)-12-(2,4-difluoro-phenyl)-15-oxatetracyclo[6.6.1.0$^{2,7}$.0$^{9,14}$]-pentadeca-2,4,6,9,11,13-hexaen-4-yl]formamido}-methyl)-3,5-difluorophenyl]-methylidene]-carbamate;

(1R,8S)-12-(2,4-difluorophenyl)-N-{[4-(5-oxo-4,5-dihydro-1,2,4-oxadiazol-3-yl)phenyl]methyl}-15-oxatetracyclo[6.6.1.0$^{2,7}$.0$^{9,14}$]pentadeca-2,4,6,9,11,13-hexaene-4-carboxamide;

(1R,8S)-12-cyclopropyl-N-({4-[N'-methoxy-carbamimidoyl]phenyl}methyl)-15-oxatetracyclo[6.6.1.0$^{2,7}$.0$^{9,14}$]pentadeca-2,4,6,9,11,13-hexaene-4-carboxamide;

ethyl N-[amino[4-({[(1R,8S)-12-(2,4-difluorophenyl)-15-oxatetracyclo[6.6.1.0$^{2,7}$.0$^{9,14}$]-pentadeca-2,4,6,9,11,13-hexaen-4-yl]formamido}-methyl)phenyl]methylidene]carbamate;

(1S,8R)—N-({2,6-difluoro-4-[N'-methoxy-carbamimidoyl]phenyl}methyl)-12-(1,3-thiazol-2-yl)-15-oxatetracyclo[6.6.1.0$^{2,7}$.0$^{9,14}$]pentadeca-2,4,6,9,11,13-hexaene-4-carboxamide;

(1S,8R)—N-[(4-carbamimidoyl-2,6-difluoro-phenyl)methyl]-12-(1,3-thiazol-2-yl)-15-oxatetracyclo[6.6.1.0$^{2,7}$.0$^{9,14}$]pentadeca-2,4,6,9,11,13-hexaene-4-carboxamide;

(1S,8R)-12-(5-chlorothiophen-2-yl)-N-{[4-(N'-hydroxy-carbamimidoyl)phenyl]methyl}-15-oxatetracyclo[6.6.1.0$^{2,7}$.0$^{9,14}$]pentadeca-2,4,6,9,11,13-hexaene-4-carboxamide;

4-[(1R,8S)-12-{[(6-amino-4-cyclopropyl-2-methylpyridin-3-yl)methyl]carbamoyl}-15-oxatetracyclo[6.6.1.0$^{2,7}$.0$^{9,14}$]pentadeca-2,4,6,9,11,13-hexaen-4-yl]-3-fluoropyridin-1-ium-1-olate;

(1R,8S)—N-[(4-carbamimidoyl-2,6-difluoro-phenyl)methyl]-12-cyclopropyl-15-oxatetracyclo[6.6.1.0$^{2,7}$.0$^{9,14}$]pentadeca-2,4,6,9,11,13-hexaene-4-carboxamide;

(1R,8S)—N-[(6-amino-2,4-dimethylpyridin-3-yl)methyl]-12-(2,4-difluorophenyl)-15-oxatetracyclo[6.6.1.0$^{2,7}$.0$^{9,14}$]pentadeca-2,4,6,9,11,13-hexaene-4-carboximidamide;

(1R,8S)—N-(3-cyano-4-fluorophenyl)-12-(2,4-difluorophenyl)-15-oxatetracyclo-[6.6.1.0$^{2,7}$.0$^{9,14}$]-pentadeca-2,4,6,9,11,13-hexaene-4-carboximidamide;

(1S,8R)—N-[(4-carbamimidoyl-2,6-difluoro-phenyl)methyl]-12-(1H-pyrazol-1-yl)-15-oxatetracyclo[6.6.1.0$^{2,7}$.0$^{9,14}$]pentadeca-2,4,6,9,11,13-hexaene-4-carboxamide;

(1R,8S)—N-(3-aminophenyl)-12-(2,4-difluoro-phenyl)-15-oxatetracyclo[6.6.1.0$^{2,7}$.0$^{9,14}$]-pentadeca-2,4,6,9,11,13-hexaene-4-carboxamide;

(1R,8S)—N-(4-aminophenyl)-12-(2,4-difluoro-phenyl)-15-oxatetracyclo[6.6.1.0$^{2,7}$.0$^{9,14}$]-pentadeca-2,4,6,9,11,13-hexaene-4-carboxamide;

2-[(1R,8S)-12-({[6-amino-2-methyl-4-(propan-2-yl)pyridin-3-yl]methyl}carbamoyl)-15-oxatetracyclo[6.6.1.0$^{2,7}$.0$^{9,14}$]pentadeca-2,4,6,9,11,13-hexaen-4-yl]-3-fluoropyridin-1-ium-1-olate;

(1R,8S)—N-[(4-carbamimidoyl-2-fluorophenyl)-methyl]-12-(2-fluorophenyl)-15-oxatetracyclo[6.6.1.0$^{2,7}$.0$^{9,14}$]pentadeca-2,4,6,9,11,13-hexaene-4-carboxamide;

(1R,8S)—N-[(4-carbamimidoyl-2-fluorophenyl)-methyl]-12-(2,4-difluorophenyl)-15-oxatetracyclo[6.6.1.0$^{2,7}$.0$^{9,14}$]pentadeca-2,4,6,9,11,13-hexaene-4-carboxamide;

(1R,8S)—N-[(3-carbamoylphenyl)methyl]-12-(2,4-difluorophenyl)-15-oxatetracyclo-[6.6.1.0$^{2,7}$.0$^{9,14}$]-pentadeca-2,4,6,9,11,13-hexaene-4-carboxamide;

2-[(1R,8S)-12-({[6-amino-2-methyl-4-(propan-2-yl)pyridin-3-yl]methyl}carbamoyl)-15-oxatetracyclo[6.6.1.0$^{2,7}$.0$^{9,14}$]pentadeca-2,4,6,9,11,13-hexaen-4-yl]-5-fluoropyridin-1-ium-1-olate;

(1R,8S)—N-[(1-amino-6-chloroisoquinolin-5-yl)methyl]-12-(2-fluorophenyl)-15-oxatetracyclo[6.6.1.0$^{2,7}$.0$^{9,14}$]pentadeca-2,4,6,9,11,13-hexaene-4-carboxamide;

(1R,8S)—N-[(1-amino-6-chloroisoquinolin-7-yl)methyl]-12-(2-fluorophenyl)-15-oxatetracyclo[6.6.1.0$^{2,7}$.0$^{9,14}$]pentadeca-2,4,6,9,11,13-hexaene-4-carboxamide;

(1S,8R)—N-[(4-carbamimidoyl-2,6-difluoro-phenyl)methyl]-12-(2H-1,2,3-triazol-2-yl)-15-oxatetracyclo[6.6.1.0$^{2,7}$.0$^{9,14}$]pentadeca-2,4,6,9,11,13-hexaene-4-carboxamide;

(1R,8S)—N-[(1-amino-6-methylisoquinolin-5-yl)methyl]-12-(2-fluorophenyl)-15-oxatetracyclo[6.6.1.0$^{2,7}$.0$^{9,14}$]pentadeca-2,4,6,9,11,13-hexaene-4-carboxamide;

(1R,8S)—N-[(1-amino-6-methylisoquinolin-7-yl)methyl]-12-(2-fluorophenyl)-15-oxatetracyclo[6.6.1.0$^{2,7}$.0$^{9,14}$]pentadeca-2,4,6,9,11,13-hexaene-4-carboxamide;

(1R,8S)—N-[(4-carbamimidoyl-2-fluorophenyl)-methyl]-12-cyclopropyl-15-oxatetracyclo-[6.6.1.0$^{2,7}$.0$^{9,14}$]pentadeca-2,4,6,9,11,13-hexaene-4-carboxamide;

(1R,8S)—N-(6-aminopyridin-3-yl)-12-(2,4-difluorophenyl)-15-oxatetracyclo-[6.6.1.0$^{2,7}$.0$^{9,14}$]-pentadeca-2,4,6,9,11,13-hexaene-4-carboxamide;

(1S,8R)—N-[(4-carbamimidoylphenyl)methyl]-12-(1H-pyrazol-1-yl)-15-oxatetracyclo-[6.6.1.0$^{2,7}$.0$^{9,14}$]pentadeca-2,4,6,9,11,13-hexaene-4-carboxamide;

(1R,8S)—N-[(4-carbamimidoyl-2-methylphenyl)-methyl]-12-(2,4-difluorophenyl)-15-oxatetracyclo[6.6.1.0$^{2,7}$.0$^{9,14}$]pentadeca-2,4,6,9,11,13-hexaene-4-carboxamide;

(1S,8R)—N-[(4-carbamimidoylphenyl)methyl]-12-(3,3-difluoroazetidin-1-yl)-15-oxatetracyclo-[6.6.1.0$^{2,7}$.0$^{9,14}$]pentadeca-2,4,6,9,11,13-hexaene-4-carboxamide;

(1R,8S)—N-(4-aminopyridin-2-yl)-12-(2,4-difluorophenyl)-15-oxatetracyclo-[6.6.1.0$^{2,7}$.0$^{9,14}$]-pentadeca-2,4,6,9,11,13-hexaene-4-carboxamide;

a mixture of (±)-N-[(6-amino-2,4-dimethylpyridin-3-yl)methyl]-12-(2,4-difluorophenyl)-11-methyl-15-oxatetracyclo[6.6.1.0$^{2,7}$.0$^{9,14}$]pentadeca-2,4,6,9(14),10,12-hexaene-4-carboxamide and (±)-N-[(6-amino-2,4-dimethylpyridin-3-yl)methyl]-11-(2,4-difluorophenyl)-12-methyl-15-oxatetracyclo[6.6.1.0$^{2,7}$.0$^{9,14}$]pentadeca-2,4,6,9(14),10,12-hexaene-4-carboxamide;

(±)-N-[(6-amino-2,4-dimethylpyridin-3-yl)-methyl]-11,12-dicyclopropyl-15-oxatetracyclo[6.6.1.0$^{2,7}$.0$^{9,14}$]pentadeca-2,4,6,9,11,13-hexaene-4-carboxamide;

(1S,8R)—N-[(4-carbamimidoyl-2-methylphenyl)-methyl]-12-(1H-pyrazol-1-yl)-15-oxatetracyclo[6.6.1.0$^{2,7}$.0$^{9,14}$]pentadeca-2,4,6,9,11,13-hexaene-4-carboxamide;

(1R,8S)-12-(2,4-difluorophenyl)-N-[(piperidin-4-yl)methyl]-15-oxatetracyclo-6.6.1.0$^{2,7}$.0$^{9,14}$]-pentadeca-2,4,6,9,11,13-hexaene-4-carboxamide;

(±)-N-[(6-amino-2,4-dimethylpyridin-3-yl)-methyl]-11,12-diphenyl-15-oxatetracyclo-[6.6.1.0$^{2,7}$.0$^{9,14}$]pentadeca-2,4,6,9,11,13-hexaene-4-carboxamide;

(±)-N-[(4-carbamimidoylphenyl)methyl]-11,12-dicyclopropyl-15-oxatetracyclo-[6.6.1.0$^{2,7}$.0$^{9,14}$]-pentadeca-2,4,6,9,11,13-hexaene-4-carboxamide;

(1R,8S)—N-[(azetidin-3-yl)methyl]-12-(2,4-difluorophenyl)-15-oxatetracyclo-[6.6.1.0$^{2,7}$.0$^{9,14}$]-pentadeca-2,4,6,9,11,13-hexaene-4-carboxamide;

(1R,8S)-12-(2,4-difluorophenyl)-N-[(3R)-pyrrolidin-3-yl]-15-oxatetracyclo-[6.6.1.0$^{2,7}$.0$^{9,14}$]-pentadeca-2,4,6,9,11,13-hexaene-4-carboxamide;

(1R,8S)-12-(2,4-difluorophenyl)-N-[(3S)-pyrrolidin-3-yl]-15-oxatetracyclo-[6.6.1.0$^{2,7}$.0$^{9,14}$]-pentadeca-2,4,6,9,11,13-hexaene-4-carboxamide;

(1R,8S)—N-[(5-carbamimidoylpyridin-2-yl)methyl]-12-cyclopropyl-15-oxatetracyclo-[6.6.1.0$^{2,7}$.0$^{9,14}$]pentadeca-2,4,6,9,11,13-hexaene-4-carboxamide;

(1R,8S)—N-[(4-carbamimidoyl-2-fluorophenyl)-methyl]-12-(4-fluorophenyl)-15-oxatetracyclo[6.6.1.0$^{2,7}$.0$^{9,14}$]pentadeca-2,4,6,9,11,13-hexaene-4-carboxamide;

(1R,8S)-12-(2,4-difluorophenyl)-N-{[4-(N'-methoxycarbamimidoyl)-2,6-dimethylphenyl]-methyl}-15-oxatetracyclo[6.6.1.0$^{2,7}$.0$^{9,14}$]-pentadeca-2,4,6,9,11,13-hexaene-4-carboxamide;

(1R,8S)—N-[(4-carbamimidoyl-2,6-dimethyl-phenyl)methyl]-12-cyclopropyl-15-oxatetracyclo[6.6.1.0$^{2,7}$.0$^{9,14}$]pentadeca-2,4,6,9,11,13-hexaene-4-carboxamide;

(1R,8S)—N-[(5-carbamimidoylpyridin-2-yl)-methyl]-12-(2,4-difluorophenyl)-15-oxatetracyclo[6.6.1.0$^{2,7}$.0$^{9,14}$]pentadeca-2,4,6,9,11,13-hexaene-4-carboxamide;

(1S,8R)—N-[(4-carbamimidoyl-2,6-difluoro-phenyl)methyl]-12-(1,1-dioxo-1λ$^6$-thiomorpholin-4-yl)-15-oxatetracyclo-[6.6.1.0$^{2,7}$.0$^{9,14}$]pentadeca-2,4,6,9,11,13-hexaene-4-carboxamide;

(1S,8R)—N-[(4-carbamimidoylphenyl)methyl]-12-(1,1-dioxo-1λ$^6$-thiomorpholin-4-yl)-15-oxatetracyclo[6.6.1.0$^{2,7}$.0$^{9,14}$]pentadeca-2,4,6,9,11,13-hexaene-4-carboxamide;

(1R,8S)—N-[(4-carbamimidoyl-3-methoxyphenyl)-methyl]-12-(2,4-difluorophenyl)-15-oxatetracyclo[6.6.1.0$^{2,7}$.0$^{9,14}$]pentadeca-2,4,6,9,11,13-hexaene-4-carboxamide;

a mixture of (±)-N-[(6-amino-2,4-dimethylpyridin-3-yl)methyl]-12-(4-fluorophenyl)-1,8-dimethyl-15-oxatetracyclo[6.6.1.0$^{2,7}$.0$^{9,14}$]pentadeca-2,4,6,9,11,13-hexaene-4-carboxamide and (±)-N-[(6-amino-2,4-dimethylpyridin-3-yl)methyl]-11-(4-fluorophenyl)-1,8-dimethyl-15-oxatetracyclo[6.6.1.0$^{2,7}$.0$^{9,14}$]pentadeca-2,4,6,9,11,13-hexaene-4-carboxamide;

(1R,8S)—N-(azepan-4-yl)-12-(2,4-difluorophenyl)-15-oxatetracyclo[6.6.1.0$^{2,7}$.0$^{9,14}$]-pentadeca-2,4,6,9,11,13-hexaene-4-carboxamide;

(1R,8S)-12-(2,4-difluorophenyl)-N-(piperidin-4-yl)-15-oxatetracyclo[6.6.1.0$^{2,7}$.0$^{9,14}$]-pentadeca-2,4,6,9,11,13-hexaene-4-carboxamide;

(1R,8S)—N-(2-aminopyridin-4-yl)-12-(2,4-difluorophenyl)-15-oxatetracyclo-[6.6.1.0$^{2,7}$.0$^{9,14}$]-pentadeca-2,4,6,9,11,13-hexaene-4-carboxamide;

methyl N-[1-amino[4-({[(1R,8S)-12-(2,4-difluorophenyl)-15-oxatetracyclo-[6.6.1.0$^{2,7}$.0$^{9,14}$]-pentadeca-2,4,6,9,11,13-hexaen-4-yl]formamido}-methyl)phenyl]-methylidene]carbamate;

hexyl N-[1-amino[4-({[(1R,8S)-12-(2,4-difluorophenyl)-15-oxatetracyclo[6.6.1.0$^{2,7}$.0$^{9,14}$]-pentadeca-2,4,6,9,11,13-hexaen-4-yl]formamido}-methyl)phenyl]methylidene]carbamate;

(1R,8S)-12-cyclopropyl-N-({2,6-difluoro-4-[N'-methoxycarbamimidoyl]phenyl}methyl)-15-oxatetracyclo[6.6.1.0$^{2,7}$.0$^{9,14}$]pentadeca-2,4,6,9,11,13-hexaene-4-carboxamide;

methyl N-[(1)-amino[4-({[(1R,8S)-12-cyclopropyl-15-oxatetracyclo[6.6.1.0$^{2,7}$.0$^{9,14}$]-pentadeca-2,4,6,9,11,13-hexaen-4-yl]formamido}methyl)phenyl]methylidene]carbamate methyl N-[1-amino[4-({[(1R,8S)-12-cyclopropyl-15-oxatetracyclo[6.6.1.0$^{2,7}$.0$^{9,14}$]-pentadeca-2,4,6,9,11,13-hexaen-4-yl]formamido}-methyl)-3,5-difluorophenyl]-methylidene]-carbamate;

propyl N-[1-amino[4-({[(1R,8S)-12-(2,4-difluorophenyl)-15-oxatetracyclo[6.6.1.0$^{2,7}$.0$^{9,14}$]-pentadeca-2,4,6,9,11,13-hexaen-4-yl]formamido}-methyl)phenyl]methylidene]carbamate;

(1S,8R)—N-({2,6-difluoro-4-[N'-methoxycarbamimidoyl]phenyl}methyl)-12-(1H-pyrazol-1-yl)-15-oxatetracyclo[6.6.1.0$^{2,7}$.0$^{9,14}$]-pentadeca-2,4,6,9,11,13-hexaene-4-carboxamide;

(1R,8S)—N-{[2-fluoro-4-(N'-hydroxy-carbamimidoyl)phenyl]methyl}-12-(2-fluorophenyl)-15-oxatetracyclo[6.6.1.0$^{2,7}$.0$^{9,14}$]-pentadeca-2,4,6,9,11,13-hexaene-4-carboxamide;

(1R,8S)—N-{[2-fluoro-4-(N'-methoxy-carbamimidoyl)phenyl]methyl}-12-(2-fluorophenyl)-15-oxatetracyclo[6.6.1.0$^{2,7}$.0$^{9,14}$]-pentadeca-2,4,6,9,11,13-hexaene-4-carboxamide;

(1R,8S)—N-({4-[(1)-amino({[benzoyl]-imino})methyl]phenyl}methyl)-12-(2,4-difluorophenyl)-15-oxatetracyclo-[6.6.1.0$^{2,7}$.0$^{9,14}$]pentadeca-2,4,6,9,11,13-hexaene-4-carboxamide;

(1R,8S)-12-(2,4-difluorophenyl)-N-{[4-(5,5-dimethyl-4,6-dioxo-1,4,5,6-tetrahydropyrimidin-2-yl)phenyl]methyl}-15-oxatetracyclo-[6.6.1.0$^{2,7}$.0$^{9,14}$]pentadeca-2,4,6,9,11,13-hexaene-4-carboxamide;

(1R,8S)-12-cyclopropyl-N-{[2-fluoro-4-(N'-methoxycarbamimidoyl)phenyl]methyl}-15-oxatetracyclo[6.6.1.0$^{2,7}$.0$^{9,14}$]pentadeca-2,4,6,9,11,13-hexaene-4-carboxamide;

(1R,8S)-12-(2,4-difluorophenyl)-N-{[2-fluoro-4-(N'-hydroxycarbamimidoyl)phenyl]-methyl}-15-oxatetracyclo[6.6.1.0$^{2,7}$.0$^{9,14}$]pentadeca-2,4,6,9,11,13-hexaene-4-carboxamide;

(1S,8R)—N-({4-[N'-methoxycarbamimidoyl]-phenyl}methyl)-12-(1H-pyrazol-1-yl)-15-oxatetracyclo[6.6.1.0$^{2,7}$.0$^{9,14}$]pentadeca-2,4,6,9,11,13-hexaene-4-carboxamide;

(1R,8S)-12-(2,4-difluorophenyl)-N-{[4-(N'-methoxycarbamimidoyl)-2-methylphenyl]-methyl}-15-oxatetracyclo[6.6.1.0$^{2,7}$.0$^{9,14}$]pentadeca-2,4,6,9,11,13-hexaene-4-carboxamide;

(1R,8S)-12-(2,4-difluorophenyl)-N-{[4-(N,N'-dihydroxycarbamimidoyl)phenyl]methyl}-15-oxatetracyclo[6.6.1.0$^{2,7}$.0$^{9,14}$]pentadeca-2,4,6,9,11,13-hexaene-4-carboxamide;

(1R,8S)-12-(2,4-difluorophenyl)-N-{[4-(N'-hydroxycarbamimidoyl)-2-methylphenyl]-methyl}-15-oxatetracyclo[6.6.1.0$^{2,7}$.0$^{9,14}$]pentadeca-2,4,6,9,11,13-hexaene-4-carboxamide;

(1R,8S)—N-({4-[N'-(benzyloxy)carbamimidoyl]-phenyl}methyl)-12-(2,4-difluorophenyl)-15-oxatetracyclo[6.6.1.0$^{2,7}$.0$^{9,14}$]pentadeca-2,4,6,9,11,13-hexaene-4-carboxamide;

tert-butyl N-[1-amino[4-({[(1R,8S)-12-(2,4-difluorophenyl)-15-oxatetracyclo-[6.6.1.0$^{2,7}$.0$^{9,14}$]pentadeca-2,4,6,9,11,13-hexaen-4-yl]formamido}methyl)phenyl]-methylidene]carbamate;

(1S,8R)—N-[(4-carbamimidoylphenyl)methyl]-12-(3,3-difluoroazetidin-1-yl)-15-oxatetracyclo-[6.6.1.0$^{2,7}$.0$^{9,14}$]pentadeca-2,4,6,9,11,13-hexaene-4-carboxamide;

(±)-11,12-dicyclopropyl-N-({4-[N'-methoxy-carbamimidoyl]phenyl}methyl)-15-oxatetracyclo-[6.6.1.0$^{2,7}$.0$^{9,14}$]pentadeca-2,4,6,9,11,13-hexaene-4-carboxamide;

(1S,8R)—N-({4-[N'-methoxycarbamimidoyl]-2-methylphenyl}methyl)-12-(1H-pyrazol-1-yl)-15-oxatetracyclo[6.6.1.0$^{2,7}$.0$^{9,14}$]pentadeca-2,4,6,9,11,13-hexaene-4-carboxamide;

(1R,8S)-12-cyclopropyl-N-{[4-(N-ethoxy-carbamimidoyl)phenyl]methyl}-15-oxatetracyclo[6.6.1.0$^{2,7}$.0$^{9,14}$]pentadeca-2,4,6,9,11,13-hexaene-4-carboxamide;

(1R,8S)-12-(2,4-difluorophenyl)-N-{[4-(N'-ethoxycarbamimidoyl)phenyl]methyl}-15-oxatetracyclo[6.6.1.0$^{2,7}$.0$^{9,14}$]pentadeca-2,4,6,9,11,13-hexaene-4-carboxamide;

(1S,8R)-12-(3,3-difluoroazetidin-1-yl)-N-({4-[N'-methoxycarbamimidoyl]phenyl}methyl)-15-oxatetracyclo[6.6.1.0$^{2,7}$.0$^{9,14}$]pentadeca-2,4,6,9,11,13-hexaene-4-carboxamide;

(1R,8S)-12-cyclopropyl-N-{[4-(N'-hydroxy-carbamimidoyl)phenyl]methyl}-15-oxatetracyclo[6.6.1.0$^{2,7}$.0$^{9,14}$]pentadeca-2,4,6,9,11,13-hexaene-4-carboxamide;

(1R,8S)-12-cyclopropyl-N-{[5-(N'-methoxy-carbamimidoyl)pyridin-2-yl]methyl}-15-oxatetracyclo[6.6.1.0$^{2,7}$.0$^{9,14}$]pentadeca-2,4,6,9,11,13-hexaene-4-carboxamide;

(1R,8S)—N-({4-[N'-ethoxycarbamimidoyl]-phenyl}methyl)-12-(4-fluorophenyl)-15-oxatetracyclo[6.6.1.0$^{2,7}$.0$^{9,14}$]pentadeca-2,4,6,9,11,13-hexaene-4-carboxamide;

tert-butyl N-[1-amino[4-({[(1R,8S)-12-(4-fluorophenyl)-15-oxatetracyclo[6.6.1.0$^{2,7}$.0$^{9,14}$]-pentadeca-2,4,6,9,11,13-hexaen-4-yl]formamido}-methyl)phenyl]methylidene]carbamate;

(1R,8S)—N-{[2-fluoro-4-(N'-methoxy-carbamimidoyl)phenyl]methyl}-12-(4-fluorophenyl)-15-oxatetracyclo[6.6.1.0$^{2,7}$.0$^{9,14}$]-pentadeca-2,4,6,9,11,13-hexaene-4-carboxamide;

(1R,8S)-12-cyclopropyl-N-{[4-(N'-methoxy-carbamimidoyl)-2,6-dimethylphenyl]methyl}-15-oxatetracyclo[6.6.1.0$^{2,7}$.0$^{9,14}$]pentadeca-2,4,6,9,11,13-hexaene-4-carboxamide;

(1R,8S)-12-(2,4-difluorophenyl)-N-({4-[N'-(propan-2-yloxy)carbamimidoyl]phenyl}-methyl)-15-oxatetracyclo[6.6.1.0$^{2,7}$.0$^{9,14}$]pentadeca-2,4,6,9,11,13-hexaene-4-carboxamide;

(1R,8S)-12-(2,4-difluorophenyl)-N-{[6-(N'-methoxycarbamimidoyl)pyridin-3-yl]methyl}-15-oxatetracyclo[6.6.1.0$^{2,7}$.0$^{9,14}$]pentadeca-2,4,6,9,11,13-hexaene-4-carboxamide;

N-[(6-amino-2,4-dimethylpyridin-3-yl)methyl]-6-fluoro-11-(4-fluorophenyl)-13-methyl-15-oxatetracyclo[6.6.1.0$^{2,7}$.0$^{9,14}$]pentadeca-2,4,6,9(14),10,12-hexaene-4-carboxamide;

(1R,8S)—N-[(4-carbamimidoylphenyl)methyl]-11,12-dicyclopropyl-15-oxatetracyclo-[6.6.1.0$^{2,7}$.0$^{9,14}$]pentadeca-2,4,6,9,11,13-hexaene-4-carboxamide;

(1S,8R)—N-[(4-carbamimidoylphenyl)methyl]-11,12-dicyclopropyl-15-oxatetracyclo-[6.6.1.0$^{2,7}$.0$^{9,14}$]pentadeca-2,4,6,9,11,13-hexaene-4-carboxamide;

(1S,8R)-11,12-dicyclopropyl-N-({4-[N'-hydroxycarbamimidoyl]phenyl}methyl)-15-oxatetracyclo[6.6.1.0$^{2,7}$.0$^{9,14}$]pentadeca-2,4,6,9,11,13-hexaene-4-carboxamide;

(1R,8S)-11,12-dicyclopropyl-N-({4-[N'-hydroxycarbamimidoyl]phenyl}methyl)-15-oxatetracyclo[6.6.1.0$^{2,7}$.0$^{9,14}$]pentadeca-2,4,6,9,11,13-hexaene-4-carboxamide;

(±)-N-[(6-amino-2,4-dimethylpyridin-3-yl)-methyl]-6-fluoro-12-(4-fluorophenyl)-15-oxatetracyclo[6.6.1.0$^{2,7}$.0$^{9,14}$]pentadeca-2(7),3,5,9,11,13-hexaene-4-carboxamide;

(±)-N-[(6-amino-2,4-dimethylpyridin-3-yl)-methyl]-6-fluoro-11-(4-fluorophenyl)-15-oxatetracyclo[6.6.1.0$^{2,7}$.0$^{9,14}$]pentadeca-2(7),3,5,9,11,13-hexaene-4-carboxamide;

a mixture of (±)-N-[(4-carbamimidoylphenyl)methyl]-11-(2,4-difluorophenyl)-15-oxa-4-azatetracyclo-[6.6.1.0$^{2,7}$.0$^{9,14}$]pentadeca-2(7),3,5,9,11,13-hexaene-5-carboxamide and (±)-N-[(4-carbamimidoylphenyl)methyl]-12-(2,4-difluorophenyl)-15-oxa-4-azatetracyclo-[6.6.1.0$^{2,7}$.0$^{9,14}$]pentadeca-2(7),3,5,9,11,13-hexaene-5-carboxamide;

(1S,8R)-11,12-dicyclopropyl-N-({4-[N'-methoxycarbamimidoyl]phenyl}methyl)-15-oxatetracyclo[6.6.1.0$^{2,7}$.0$^{9,14}$]pentadeca-2,4,6,9,11,13-hexaene-4-carboxamide;

a mixture of (±)-N-[(6-amino-2,4-dimethylpyridin-3-yl)methyl]-5-fluoro-12-(4-fluorophenyl)-15-oxatetracyclo[6.6.1.0$^{2,7}$.0$^{9,14}$]pentadeca-2(7),3,5,9,11,13-hexaene-4-carboxamide and (±)-N-[(6-amino-2,4-dimethylpyridin-3-yl)methyl]-5-fluoro-11-(4-fluorophenyl)-15-oxatetracyclo[6.6.1.0$^{2,7}$.0$^{9,14}$]pentadeca-2(7),3,5,9,11,13-hexaene-4-carboxamide;

(±)-N-[(6-amino-2,4-dimethylpyridin-3-yl)-methyl]-6-fluoro-11-(4-fluorophenyl)-15-oxatetracyclo[6.6.1.0$^{2,7}$.0$^{9,14}$]pentadeca-2(7),3,5,9,11,13-hexaene-4-carboxamide; and a mixture of (±)-N-[(4-carbamimidoylphenyl)methyl]-11-(2,4-difluorophenyl)-15-oxa-4-azatetracyclo-[6.6.1.0$^{2,7}$.0$^{9,14}$]pentadeca-2(7),3,5,9,11,13-hexaene-5-car boxamide and (±)-N-[(4-carbamimidoylphenyl)methyl]-12-(2,4-difluorophenyl)-15-oxa-4-azatetracyclo-[6.6.1.0$^{2,7}$.0$^{9,14}$]pentadeca-2(7),3,5,9,11,13-hexaene-5-carboxamide;

or an individual regioisomer thereof;

or an individual stereoisomer of any of the foregoing compounds;

or an E or Z isomer thereof of any of the foregoing compounds;

or a pharmaceutically acceptable salt of any of the foregoing compounds.

14. A compound selected from:

(1R,8S)—N-[(4-carbamimidoylphenyl)methyl]-12-(2-fluorophenyl)-15-oxatetracyclo-[6.6.1.0$^{2,7}$.0$^{9,14}$]pentadeca-2,4,6,9,11,13-hexaene-4-carboxamide;

(1R,8S)—N-[(4-carbamimidoylphenyl)methyl]-12-(4-fluorophenyl)-15-oxatetracyclo-[6.6.1.0$^{2,7}$.0$^{9,14}$]pentadeca-2,4,6,9,11,13-hexaene-4-carboxamide;

(1R,8S)—N-[(4-carbamimidoylphenyl)methyl]-12-(2,4-difluorophenyl)-15-oxatetracyclo-[6.6.1.0$^{2,7}$.0$^{9,14}$]pentadeca-2,4,6,9,11,13-hexaene-4-carboxamide;

(1R,8S)-12-(2,4-difluorophenyl)-N-{[4-(N'-hydroxycarbamimidoyl)phenyl]methyl}-15-oxatetracyclo [6.6.1.0$^{2,7}$.0$^{9,14}$]pentadeca-2,4,6,9,11,13-hexaene-4-carboxamide;

(1R,8S)-12-(2-fluorophenyl)-N-{[4-(N'-hydroxycarbamimidoyl)phenyl]methyl}-15-oxatetracyclo[6.6.1.0$^{2,7}$.0$^{9,14}$]pentadeca-2,4,6,9,11,13-hexaene-4-carboxamide;

(1R,8S)-12-(2,4-difluorophenyl)-N-{[4-(N'-methoxycarbamimidoyl)phenyl]methyl}-15-oxatetracyclo [6.6.1.0$^{2,7}$.0$^{9,14}$]pentadeca-2,4,6,9,11,13-hexaene-4-carboxamide;

(1R,8S)-12-(2-fluorophenyl)-N-{[4-(N'-methoxycarbamimidoyl)phenyl]methyl}-15-oxatetracyclo[6.6.1.0$^{2,7}$.0$^{9,14}$]pentadeca-2,4,6,9,11,13-hexaene-4-carboxamide;

(1R,8S)-12-(4-fluorophenyl)-N-{[4-(N'-methoxycarbamimidoyl)phenyl]methyl}-15-oxatetracyclo[6.6.1.0$^{2,7}$.0$^{9,14}$]pentadeca-2,4,6,9,11,13-hexaene-4-carboxamide;

(1R,8S)—N-[(4-carbamimidoyl-2-fluorophenyl)methyl]-12-(2-fluorophenyl)-15-oxatetra-cyclo[6.6.1.0$^{2,7}$.0$^{9,14}$]pentadeca-2,4,6,9,11,13-hexaene-4-carboxamide;

(1R,8S)—N-[(4-carbamimidoyl-2-fluorophenyl)methyl]-12-(4-fluorophenyl)-15-oxatetra-cyclo[6.6.1.0$^{2,7}$.0$^{9,14}$]pentadeca-2,4,6,9,11,13-hexaene-4-carboxamide;

(1R,8S)—N-{[2-fluoro-4-(N'-hydroxycarbamimidoyl)phenyl]methyl}-12-(2-fluoro-phenyl)-15-oxatetracyclo[6.6.1.0$^{2,7}$.0$^{9,14}$]pentadeca-2,4,6,9,11,13-hexaene-4-carboxamide;

(1R,8S)—N-{[2-fluoro-4-(N'-methoxycarbamimidoyl)phenyl]methyl}-12-(2-fluoro-phenyl)-15-oxatetracyclo[6.6.1.0$^{2,7}$.0$^{9,14}$]pentadeca-2,4,6,9,11,13-hexaene-4-carboxamide;

(1R,8S)-12-(2,4-difluorophenyl)-N-{[4-(N'-ethoxycarbamimidoyl)phenyl]methyl}-15-oxatetracyclo [6.6.1.0$^{2,7}$.0$^{9,14}$]pentadeca-2,4,6,9,11,13-hexaene-4-carboxamide;

(1R,8S)—N-({4-[N'-ethoxycarbamimidoyl]phenyl}methyl)-12-(4-fluorophenyl)-15-oxatetracyclo [6.6.1.0$^{2,7}$.0$^{9,14}$]pentadeca-2,4,6,9,11,13-hexaene-4-carboxamide;

tert-butyl N-[1-amino[4-({[(1R,8S)-12-(4-fluorophenyl)-15-oxatetracyclo-[6.6.1.0$^{2,7}$.0$^{9,14}$]-pentadeca-2,4,6,9,11,13-hexaen-4-yl]formamido}methyl)phenyl]-methylidene]carbamate; and (1R,8S)—N-{[2-fluoro-4-(N'-methoxycarbamimidoyl)phenyl]methyl}-12-(4-fluoro-phenyl)-15-oxatetracyclo[6.6.1.0$^{2,7}$.0$^{9,14}$]pentadeca-2,4,6,9,11,13-hexaene-4-carboxamide;

or an E or Z isomer thereof;

or a pharmaceutically acceptable salt of any of the foregoing compounds.

15. The compound of claim 13 selected from:

(1S,8R)-11,12-dicyclopropyl-N-({4-[N'-methoxycarbamimidoyl]phenyl}methyl)-15-oxatetra-cyclo[6.6.1.0$^{2,7}$.0$^{9,14}$]pentadeca-2,4,6,9,11,13-hexaene-4-carboxamide;

(1S,8R)-11,12-dicyclopropyl-N-({4-[N'-hydroxycarbamimidoyl]phenyl}methyl)-15-oxatetra-cyclo[6.6.1.0$^{2,7}$.0$^{9,14}$]pentadeca-2,4,6,9,11,13-hexaene-4-carboxamide;

(1S,8R)—N-[(4-carbamimidoylphenyl)methyl]-11,12-dicyclopropyl-15-oxatetracyclo-[6.6.1.0$^{2,7}$.0$^{9,14}$]pentadeca-2,4,6,9,11,13-hexaene-4-carboxamide;

(1R,8S)-12-cyclopropyl-N-{[4-(N'-hydroxycarbamimidoyl)phenyl]methyl}-15-oxatetra-cyclo[6.6.1.0$^{2,7}$.0$^{9,14}$]pentadeca-2,4,6,9,11,13-hexaene-4-carboxamide;

(1R,8S)-12-cyclopropyl-N-{[4-(N-ethoxycarbamimidoyl)phenyl]methyl}-15-oxatetra-cyclo[6.6.1.0$^{2,7}$.0$^{9,14}$]pentadeca-2,4,6,9,11,13-hexaene-4-carboxamide;

methyl N-[1-amino[4-({[(1R,8S)-12-cyclopropyl-15-oxatetracyclo-[6.6.1.0$^{2,7}$.0$^{9,14}$]-pentadeca-2,4,6,9,11,13-hexaen-4-yl]formamido}methyl)-phenyl]methylidene]carbamate;

(1R,8S)-12-cyclopropyl-N-({4-[N'-methoxycarbamimidoyl]phenyl}methyl)-15-oxatetra-cyclo[6.6.1.0$^{2,7}$.0$^{9,14}$]pentadeca-2,4,6,9,11,13-hexaene-4-carboxamide; and (1R,8S)—N-[(4-carbamimidoylphenyl)methyl]-12-cyclopropyl-15-oxatetracyclo-[6.6.1.0$^{2,7}$.0$^{9,14}$]pentadeca-2,4,6,9,11,13-hexaene-4-carboxamide; or an E or Z isomer thereof;

or a pharmaceutically acceptable salt of any of the foregoing compounds.

16. A pharmaceutical composition comprising a compound of claim 1, or a pharmaceutically acceptable salt thereof, and at least one pharmaceutically acceptable excipient.

* * * * *

UNITED STATES PATENT AND TRADEMARK OFFICE
CERTIFICATE OF CORRECTION

PATENT NO. : 9,815,853 B2
APPLICATION NO. : 15/177641
DATED : November 14, 2017
INVENTOR(S) : Zhe Li et al.

It is certified that error appears in the above-identified patent and that said Letters Patent is hereby corrected as shown below:

In the Specification

Column 2, Line 12 (Approx.), change "$C_3$-$C_6$cycloalkyl," to --$C_3$-$C_8$cycloalkyl,--.

Column 4, Line 9, change "$C_3$-$C_6$cycloalkyoxy," to --$C_3$-$C_6$cycloalkyloxy,--.

Column 4, Line 61, change ""$C_1$-$C_6$lkylsulfonynl"" to --"$C_1$-$C_6$alkylsulfonyl"--.

Column 5, Line 20, change "S(O)," to --S(O)n,--.

Column 6, Lines 37-38, change "moncyclic" to --monocyclic--.

Column 7, Line 55, change "tetrahydro-pyranyl," to --tetrahydropyranyl,--.

Column 7, Lines 60-61, change "tetraydrofuranylmethyl," to --tetrahydrofuranylmethyl,--.

Column 8, Line 47, change "diasteromeric" to --diastereomeric--.

Column 9, Line 29, change "S(O)," to --S(O)n,--.

Column 11, Line 62, change "angiodema," to --angioedema,--.

Column 12, Line 7, change "(Al)" to --(A1)--.

Column 14, Lines 35-36, change "substitutedalkoxy-$NR^{300}C(O)$—" to --substituted alkoxy-$NR^{300}C(O)$— --.

Column 16, Line 64, change "—$C(=NR^{35})NR^{330}R^{340}$" to -- —$C(=NR^{350})NR^{330}R^{340}$--.

Column 18, Lines 40-41 (Approx.), change "adamentyl," to --adamantyl,--.

Signed and Sealed this
Twenty-first Day of May, 2019

Andrei Iancu
*Director of the United States Patent and Trademark Office*

CERTIFICATE OF CORRECTION (continued)
U.S. Pat. No. 9,815,853 B2

Column 20, Line 53, change "difluromethyl," to --difluoromethyl,--.

Column 21, Line 2, change "difluromethyl," to --difluoromethyl,--.

Column 21, Line 36, change "difluromethyl," to --difluoromethyl,--.

Column 21, Line 45, change "ring=N—" to --ring =N— --.

Column 21, Lines 56-57, change "fluoroenylmethyl" to --fluorenylmethyl--.

Column 21, Lines 57-58, change "10,10,10,10,10" to --10,10,10,10--.

Column 21, Line 65, change "eneamines" to --enamines--.

Column 22, Line 31, change "$C_1$-$C_5$alkyl;" to --$C_1$-$C_8$alkyl;--.

Column 27, Line 6, after " 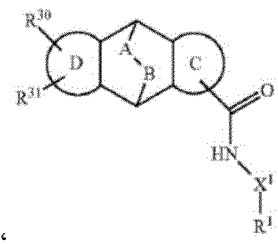 " delete "or".

Column 29, Lines 1-12, change " 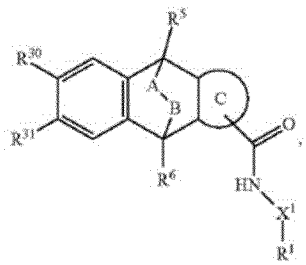 " to -- 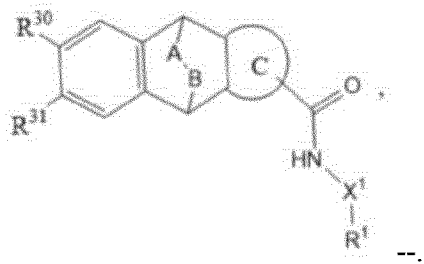 --.

Column 29, Lines 12-24, change " 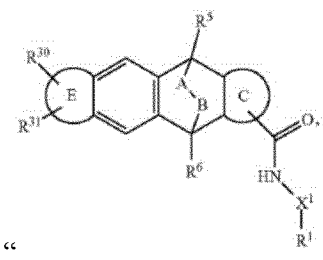 ," to -- 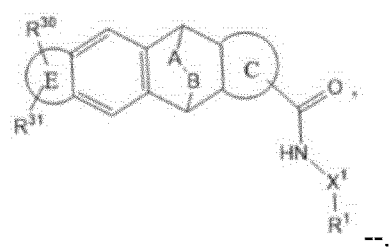 --.

Column 40, Line 10 (Approx.), change "$C_3$-$C_8$cycloalkyl" to --$C_3$-$C_5$cycloalkyl--.

Column 45, Line 6 (Approx.), Change "R)" to --$R^7$)--.

Column 48, Lines 1-9 (Approx.), change "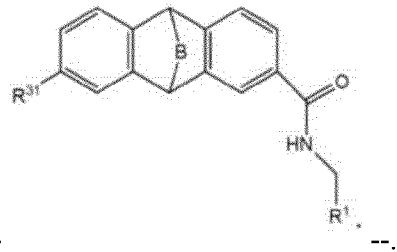"
to -- 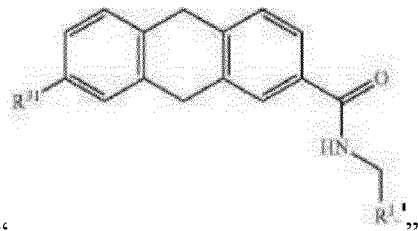 --.
Column 48, Lines 16-22 (Approx.), change "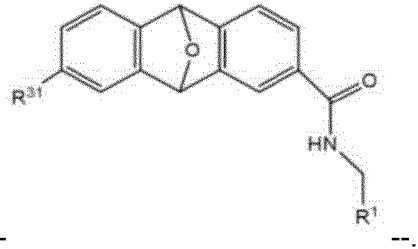"
to -- 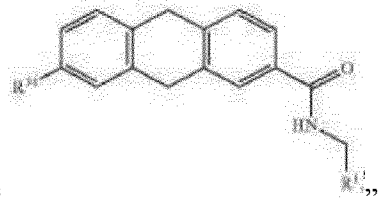 --.
Column 48, Line 49 (Approx.), after "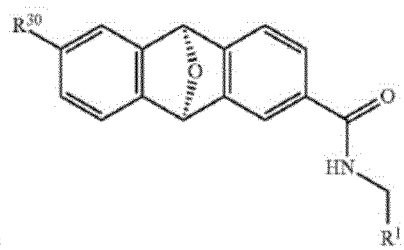" insert --.--.
Column 49, Lines 21-28 (Approx.), change "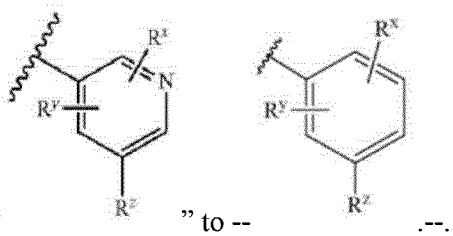" to -- --.

Column 49, Line 54 (Approx.), after " 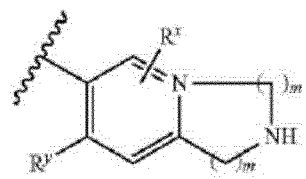 " insert --,--.

Column 49, Line 59 (Approx.), after " 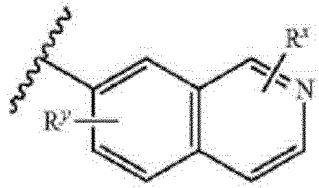 " insert --,--.

Column 50, Lines 1-9 (Approx.), change " 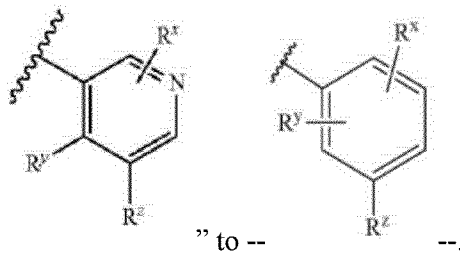 " to -- --.

Column 51, Line 27 (Approx.), change "$C_3$-$C_8$cycloalkyl" to --$C_3$-$C_5$cycloalkyl--.

Column 64, Lines 1-8 (Approx.), change " 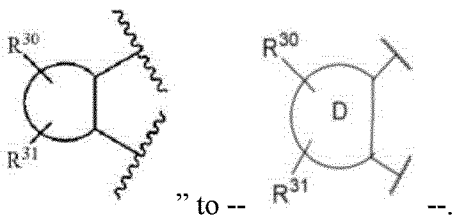 " to -- --.

Column 67, Lines 42-43, change "3,6-dihydro-2H-pyran-4-yl,2,4-dihydrofuran-3-yl," to --3,6-dihydro-2H-pyran-4-yl, 2,4-dihydrofuran-3-yl,--.

Column 68, Lines 50-51, change "pyazinyl," to --pyrazinyl,--.

Column 68, Line 57, change "3,6-dihydro-2H-pyran4-yl," to --3,6-dihydro-2H-pyran-4-yl,--.

Column 69, Line 2, change "pyazinyl," to --pyrazinyl,--.

Column 69, Line 8 (Approx.), change "3,6-dihydro-2H-pyran4-yl," to --3,6-dihydro-2H-pyran-4-yl,--.

Column 69, Line 28 (Approx.), change "C4" to --C-4--.

Column 72, Line 58, change "3-methyl-2-oxo-1,3-diazinan-1-yl)methyl," to --3-methyl-2-oxo-1,3-(diazinan-1-yl)methyl,--.

Columns 139-140, Line 7 (Approx.)(TABLE 1-continued), change "aminol-15-" to --amino]-15- --.

Columns 161-162, Lines 17-25 (Approx.) (TABLE 1-continued), change

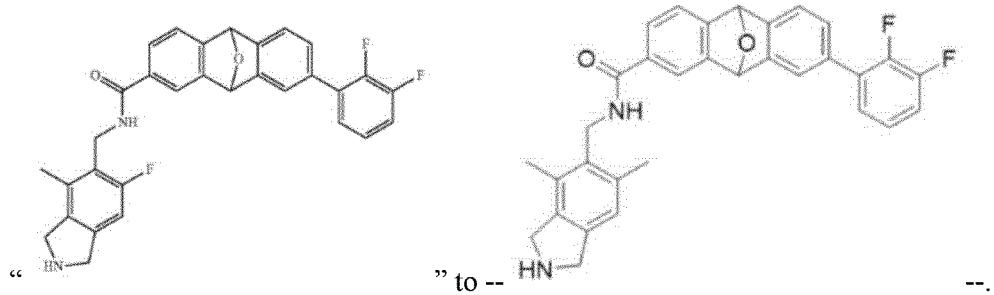

" to -- --.

Columns 169-170, Line 9 (Approx.) (TABLE 1-continued), change "pentadeca-+nl2," to --pentadeca-2,--.

Columns 179-180, Line 24 (Approx.) (TABLE 1-continued), change "87" to --8.7--.

Columns 233-234, Line 9 (Approx.) (TABLE 1-continued), change "(1S, 8R)" to --(1S,8R)--.

Column 331, Line 63, change "carboxamide" to --carboxamide,--.

Column 333, Line 30 (Approx.), change "11, 12" to --11,12--.

Column 333, Lines 44-45, change "oxatetracycl[" to --oxatetracyclo[--.

Column 333, Lines 47-48, change "oxatetracycl[" to --oxatetracyclo[--.

Column 333, Line 56, change "(14), 10, 12" to --(14),10,12--.

Column 335, Line 31, change "(14), 10, 12" to --(14),10,12--.

Column 336, Lines 5-15, change " 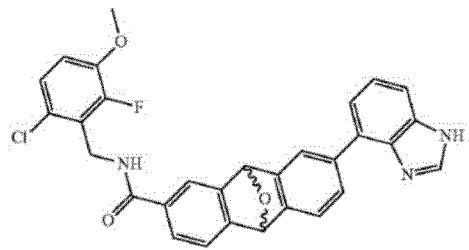 "

to -- 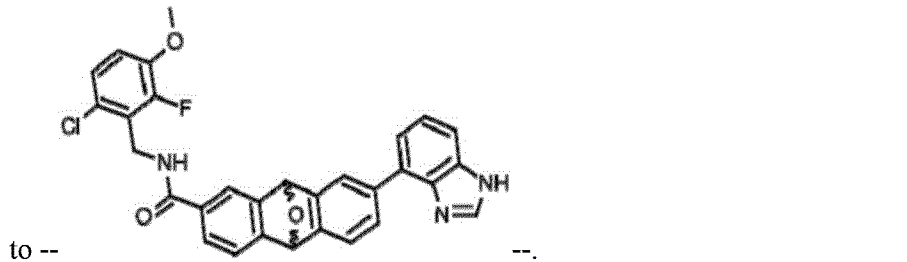 --.

CERTIFICATE OF CORRECTION (continued)
U.S. Pat. No. 9,815,853 B2

Column 336, Line 34, change "diasteroisomers" to --diastereoisomers--.

Column 339, Lines 30-31, change "5-yl-methoxy)" to --5-ylmethoxy)--.

Column 340, Lines 64-65, change "tetrahydrofuan" to --tetrahydrofuran--.

Column 341, Line 14, change "(trifluoromnethyl)" to --(trifluoromethyl)--.

Column 341, Line 51, change "tetrahvdroisoquinoline," to --tetrahydroisoquinoline,--.

Column 342, Line 20 (Approx.), change "hydroxybenzotriazol" to --hydroxybenzotriazole--.

Column 343, Line 43, change "means±10%" to --means ±10%--.

Column 345, Line 16, change "Creutzfeld-Jacob" to --Creutzfeldt–Jakob--.

Column 347, Line 10 (Approx.), change "~30°" to -- -30°--.

Column 347, Line 19 (Approx.), change "o" to --to--.

Column 348, Line 27, change "(phenyl)iodonium" to --(phenyl)-iodonium--.

Column 352, Line 32, change "methyl)isobenzofuran" to --methyl)-isobenzofuran--.

Column 356, Line 21 (Approx.), after "180.1" insert --.--.

Column 357, Lines 39-47, delete "Step 3: Into a 1-L round-bottom flask, was placed a solution of ammonia (300 mL) and dioxane (300 mL) and 5-bromo-2-(chloromethyl)-1,3-difluorobenzene (46.0 g, 190.08 mmol, 1.00 equiv) in dioxane (50 mL) was added dropwise with stirring over 1 h. The resulting mixture was stirred for 16 h at room temperature then it was concentrated under vacuum to afford 47.0 g of (4-bromo-2,6 difluorophenyl)methanamine as a white crude solid." and insert --Step 3: Into a 1-L round-bottom flask, was placed a solution of ammonia (300 mL) and dioxane (300 mL) and 5-bromo-2-(chloromethyl)-1,3-difluorobenzene (46.0 g, 190.08 mmol, 1.00 equiv) in dioxane (50 mL) was added dropwise with stirring over 1 h. The resulting mixture was stirred for 16 h at room temperature then it was concentrated under vacuum to afford 47.0 g of (4-bromo-2,6-difluorophenyl)methanamine as a white crude solid.-- on Column 357, Line 40 as a new paragraph.

Column 357, Line 67, change "(dppf," to --(dppf;--.

Column 358, Line 11, change "tert-utyl" to --tert-butyl--.

Column 358, Line 32, change "273.02." to --273.02;--.

Column 359, Line 18, change "257.03." to --257.03;--.

Column 359, Line 67, change "215.09." to --215.09;--.

Column 360, Line 9 (Approx.), change "11, 13" to --11,13--.

Column 360, Line 26, change "phenyl)(phenyl)" to --phenyl)-(phenyl)--.

Column 362, Line 62, change "yl))" to --yl)--.

Column 365, Line 10, change "4, 6," to --4,6,--.

Column 367, Line 67, after "484.2" insert --.--.

Column 368, Line 33, change "difluoropheny-lboronic" to --difluorophenylboronic--.

Column 368, Line 67, after "484.2" insert --.--.

Column 374, Line 62, change "(dimethylamino)methylene]" to --(dimethylamino)-methylene]--.

Column 378, Line 26 (Approx.), change "-1-" to -- -11- --.

Column 382, Line 39, change "dimethylformamide" to --dimethyl-formamide--.

Column 383, Line 35, change "an" to --and--.

Column 386, Line 66 (Approx.), after "440.1" insert --.--.

Column 387, Line 42 (Approx.), change "methoxycarbamimidoyl)phenyl]" to --methoxycarbamimidoyl)-phenyl]--.

Column 387, Line 43 (Approx.), change "methyl})" to --methyl}- --.

Column 388, Line 67 (Approx.), change "acd" to --acid--.

Column 391, Line 14, change "8 S)" to --8S)--.

Column 391, Line 67, change "Ater" to --After--.

Column 399, Line 53, change "[6.2.1.0$^{2,7}$]undeca" to --[6.2.1.0$^{2,7}$]-undeca--.

Column 400, Line 12 (Approx.), change "amine (27" to --amine; (27--.

Column 407, Line 5 (Approx.), change "carbamimidoyl)phenyl]" to --carbamimidoyl)-phenyl]--.

Column 407, Line 37 (Approx.), change "hydroxycarbamimidoyl)phenyl]" to --hydroxycarbamimidoyl)-phenyl]--.

Column 409, Line 25, change "methylphenyl]" to --methyl-phenyl]--.

CERTIFICATE OF CORRECTION (continued)
U.S. Pat. No. 9,815,853 B2

Column 414, Line 30 (Approx.), change "[(difluoroboranyl)methyl]" to --[(difluoroboranyl)-methyl]--.

Column 416, Line 35, change "mmol)" to --mmol;)--.

Column 417, Line 7 (Approx.), change "-5-" to -- -15- --.

Column 418, Line 34, change "(aminomethyl)isoquinolin" to --(aminomethyl)-isoquinolin--.

Column 420, Line 39 (Approx.), change "(diphenylphosphino)ferrocene]" to --(diphenylphosphino)-ferrocene]--.

Column 421, Lines 40-41, change "(diphenylphosphino)ferrocene]" to --(diphenylphosphino)-ferrocene]--.

Column 428, Line 21, change "diisorpopylethylamine" to --diisopropylethylamine--.

Column 430, Line 34, change "mis" to --mix--.

Column 432, Line 49 (Approx.), change "1 oxatetracyclo" to --1-oxatetracyclo--.

Column 433, Line 45, change "[6.6.1.0$^{2,7}$.0$^{9,14}$]pentadeca" to --[6.6.1.0$^{2,7}$.0$^{9,14}$]-pentadeca--.

Column 435, Line 27, change "5 M" to --5 μM--.

Column 435, Line 37 (Approx.), change "chlorophenyl)(methyl)" to --chlorophenyl)-(methyl)--.

Column 435, Line 59, change "[6.6.1.0$^{2,7}$.0$^{9,14}$]pentadeca" to --[6.6.1.0$^{2,7}$.0$^{9,14}$]-pentadeca--.

Column 436, Line 62, change "5 M" to --5 μM--.

Column 437, Line 4 (Approx.), change "(methyl)amino]" to --methyl)-amino]--.

Column 437, Line 32 (Approx.), "5 M" to --5 μM--.

Column 437, Line 43 (Approx.), change "9,13" to --9,11,13--.

Column 438, Line 33, change "art" to --a rt--.

Column 439, Line 6, change "[6.6.1.0$^{2,7}$.0$^{9,14}$]pentadeca" to --[6.6.1.0$^{2,7}$.0$^{9,14}$]-pentadeca--.

Column 440, Line 34 (Approx.), change "methoxycarbamimidoyl]" to --methoxy-carbamimidoyl]--.

Column 442, Line 7, change "(chloromethyl)bicyclo" to --(chloromethyl)-bicyclo--.

Column 442, Lines 15-16, change "(chloromethyl)bicyclo" to --(chloromethyl)-bicyclo--.

CERTIFICATE OF CORRECTION (continued)
U.S. Pat. No. 9,815,853 B2

Column 446, Line 24 (Approx.), change "abd" to --and--.

Column 447, Line 67 (Approx.), after "396.1" insert --.--.

Column 454, Lines 30-31, change "5 M" to --5 µM--.

Column 455, Lines 31-35, delete "The mixture was then filtered through a pad of Celite and the filtrate was concentrated under vacuum to afford 58 mg of 5-(aminomethyl)-6-methyl-4-(propan-2-yl)pyridin-2-amine as a yellow crude solid, which was used directly for next step without any purification." and insert the same on Column 455, Line 30 as a continuation of the same paragraph.

Column 455, Lines 35-53, delete "Step 4: Into a 25-mL round-bottom flask purged and maintained with an inert atmosphere of nitrogen, was placed a solution of (±) sodium 12-bromo-15-oxatetracyclo-[6.6.1.0$^{2,7}$.0$^{9,14}$]pentadeca-2,4,6,9,11,13-hexaene-4-carboxylate (INT-5a) (80 mg, 0.24 mmol, 1.00 equiv) in dioxane/H$_2$O (1.0/0.2 mL), followed by the addition of (2,4 difluorophenyl)boronic acid (56 mg, 0.35 mmol, 1.50 equiv), sodium carbonate (75 mg, 0.71 mmol, 3.00 equiv) and Pd(PPh$_3$)$_4$ (27 mg, 0.02 mmol, 0.10 equiv). The resulting mixture was stirred for 16 hours at 90° C. in an oil bath under nitrogen atmosphere then it was cooled to RT, diluted with 10 mL of DCM/MeOH=10/1 and dried over anhydrous sodium sulfate. The mixture was then filtered through a pad of Celite and the filtrate was concentrated under vacuum to afford 140 mg of crude (±) sodium 12-(2,4-difluorophenyl)-15-oxatetracyclo-[6.6.1.0$^{2,7}$.0$^{9,14}$]pentadeca-2,4,6,9,11,13-hexaene-4-carboxylate as yellow solids, which were used directly for next step without further purification." and insert --Step 4: Into a 25-mL round-bottom flask purged and maintained with an inert atmosphere of nitrogen, was placed a solution of (±) sodium 12-bromo-15-oxatetracyclo-[6.6.1.0$^{2,7}$.0$^{9,14}$]pentadeca-2,4,6,9,11,13-hexaene-4-carboxylate (INT-5a) (80 mg, 0.24 mmol, 1.00 equiv) in dioxane/H$_2$O (1.0/0.2 mL), followed by the addition of (2,4-difluorophenyl)boronic acid (56 mg, 0.35 mmol, 1.50 equiv), sodium carbonate (75 mg, 0.71 mmol, 3.00 equiv) and Pd(PPh$_3$)$_4$ (27 mg, 0.02 mmol, 0.10 equiv). The resulting mixture was stirred for 16 hours at 90° C. in an oil bath under nitrogen atmosphere then it was cooled to RT, diluted with 10 mL of DCM/MeOH=10/1 and dried over anhydrous sodium sulfate. The mixture was then filtered through a pad of Celite and the filtrate was concentrated under vacuum to afford 140 mg of crude (±) sodium 12-(2,4-difluorophenyl)-15-oxatetracyclo-[6.6.1.0$^{2,7}$.0$^{9,14}$]pentadeca-2,4,6,9,11,13-hexaene-4-carboxylate as yellow solids, which were used directly for next step without further purification.-- on Column 455, Line 36 as a new paragraph.

Column 455, Line 41, change "difluorophenyl)boronic" to --difluorophenyl)-boronic--.

Column 457, Lines 17-18, change "methy-4-ethy" to --methyl)-4-ethyl--.

Column 457, Line 29 (Approx.), change "bu" to --by--.

Column 459, Line 32 (Approx.), change "[6.6.1.0$^{2,7}$.0$^{9,14}$]pentadeca" to --[6.6.1.0$^{2,7}$.0$^{9,14}$]-pentadeca--.

Column 461, Line 43, after "554.1" insert --.--.

Column 463, Line 20, change "-1-olat" to -- -1-olate--.

CERTIFICATE OF CORRECTION (continued)
U.S. Pat. No. 9,815,853 B2

Column 463, Line 32, change "NH$_3$—H$_2$O)" to --NH$_3$.H$_2$O)--.

Column 469, Line 5 (Approx.), change "trioxatri-borinane" to --trioxatriborinane--.

Column 469, Line 37 (Approx.), change "5 M" to --5 µM--.

Column 470, Line 41, change "5 M" to --5 µM--.

Column 470, Line 45, after "452.1" insert --.--.

Column 473, Line 26 (Approx.), change "(2,4-difluorophenyl)boronic" to --(2,4-difluorophenyl)-boronic--.

Column 474, Line 8 (Approx.), change "5 m" to --5 µm--.

Column 474, Line 23, change "[6.6.1.0$^{2,7}$.0$^{9,14}$]pentadeca" to --[6.6.1.0$^{2,7}$.0$^{9,14}$]-pentadeca--.

Column 474, Line 38 (Approx.), change "-1-(2,4" to -- -11-(2,4--.

Column 474, Line 55 (Approx.), change "5 M" to --5 µM--.

Column 480, Line 31 (Approx.), after "480.2" insert --.--.

Column 485, Line 5, change "4, 6," to --4,6,--.

Column 486, Lines 5-6, change "chiralPAK" to --CHIRALPAK--.

Column 486, Line 26 (Approx.), change "5 M" to --5 µM--.

Column 488, Line 66, change "7 M" to --7 µM--.

In the Claims

Column 490, Line 53, in Claim 1, change "C$_1$-C$_6$alkyl;" to --C$_1$-C$_6$alkyl,--.

Column 490, Line 58, in Claim 1, change "CR$^{14}$R$^{15}$" to --CR$^{14}$R$^{15}$,--.

Column 490, Line 61, in Claim 1, after "hydrogen" insert --,--.

Column 490, Line 64, in Claim 1, after "carbon" delete "atom".

Column 491, Line 6, in Claim 1, change "C$_3$-C$_6$cyclo-alkyl," to --C$_3$-C$_6$cycloalkyl,"--.

Column 491, Line 17 (Approx.), in Claim 1, change "(wherein" to --(where--.

Column 491, Line 25 (Approx.), in Claim 1, change "cyano)" to --cyano),--.

Column 492, Lines 61-62, in Claim 8, change "3,6-dihydro-2H-pyran-4-yl,2,4-dihydrofuran-3-yl," to --3,6-dihydro-2H-pyran-4-yl, 2,4-dihydrofuran-3-yl,--.

Column 493, Line 40, in Claim 10, change "pyazinyl," to --pyrazinyl,--.

Column 493, Line 46, in Claim 10, change "3,6-dihydro-2H-pyran4-yl," to --3,6-dihydro-2H-pyran-4-yl,--.

Column 493, Line 53, in Claim 10, change "—CO(CH$_2$)$_{2-3}$OR" to -- —CO(CH$_2$)$_{2-3}$OR$^v$--.

Column 493, Line 66, in Claim 11, change "R$^{9}$" to --R$^g$--.

Column 493, Line 67, in Claim 11, change "R$^{9}$" to --R$^g$--.

Column 494, Line 9 (Approx.), in Claim 11, change "R$^{9}$" to --R$^g$--.

Column 494, Line 35, in Claim 13, change "2,4 dimethylpyridin-3-yl)" to --2,4-dimethylpyridin-3-yl)--.

Column 495, Line 15 (Approx.), in Claim 13, change "carboxamide" to --carboxamide;--.

Column 495, Line 67, in Claim 13, change "carboxamide" to --carboxamide;--.

Column 496, Line 29, in Claim 13, change "carboxamide" to --carboxamide;--.

Column 496, Line 63, in Claim 13, change "carboxamide" to --carboxamide;--.

Column 497, Line 53, in Claim 13, change "carboxamide" to --carboxamide;--.

Column 498, Lines 11-12 (Approx.), in Claim 13, change "carboxamide" to --carboxamide;--.

Column 498, Line 41, in Claim 13, change "carboxamide" to --carboxamide;--.

Column 504, Line 35, in Claim 13, change "[6.6.1.0$^{2,7}$.0$^{9,14}$]pentadeca" to --[6.6.1.0$^{2,7}$.0$^{9,14}$]-pentadeca--.

Column 510, Line 34 (Approx.), in Claim 13, change "carboxamide" to --carboxamide;--.